US007585963B2

(12) United States Patent
Leavitt et al.

(10) Patent No.: US 7,585,963 B2
(45) Date of Patent: Sep. 8, 2009

(54) CHICKEN OVALBUMIN NUCLEOTIDE SEQUENCE

(75) Inventors: Markley C. Leavitt, Watkinsville, GA (US); Jeff Rapp, Athens, GA (US); Robert Ivarie, Watkinsville, GA (US); Arthur Karnuah, Athens, GA (US)

(73) Assignees: Synageva BioPharma Corp., Waltham, MA (US); University of Georgia Research Foundation, Inc., Athens, GA (US)

( * ) Notice: Subject to any disclaimer, the term of this patent is extended or adjusted under 35 U.S.C. 154(b) by 625 days.

(21) Appl. No.: 10/733,042

(22) Filed: Dec. 11, 2003

(65) Prior Publication Data

US 2006/0130170 A1 Jun. 15, 2006

Related U.S. Application Data

(60) Provisional application No. 60/462,953, filed on Apr. 15, 2003, provisional application No. 60/465,215, filed on Apr. 24, 2003, provisional application No. 60/469,488, filed on May 9, 2003.

(51) Int. Cl.
*C01H 21/04* (2006.01)
*C12N 15/00* (2006.01)
*C12N 5/00* (2006.01)

(52) U.S. Cl. .................. 536/24.1; 435/320.1; 435/325; 800/3; 800/18

(58) Field of Classification Search .............. 435/320.1, 435/325; 800/18, 3; 536/24.1
See application file for complete search history.

(56) References Cited

FOREIGN PATENT DOCUMENTS

WO WO 02/079447 10/2002

OTHER PUBLICATIONS

Woo (PNAS, Aug. 1978, vol. 75, No. 8, p. 3688-3692).*
Woo (Biochem., 1981, vol. 20, p. 6437-6446).*
Schreiber (AC159826, submitted 2001).*
"Quantitation of Parameters that Determine the Rate of Ovalbumin Synthesis," Palmiter, Richard D., Cell, 4:189-197 (1975).
"Transcriptional Regulation of the Ovalbumin and Conalbumin Genes by Steroid Hormones in Chick Oviduct," McKnight et al, Journal of Biological Chemistry, 254:9050-9058 (1979).
"Effect of estrogen on gene expression in chicken oviduct: Evidence for transcriptional control of ovalbumin gene," Swaneck et al, Proc. Natl. Acad. Sci. USA, 76:1049-1053 (1979).
"The Ovalbumin gene region: common features in the organisation of three genes expressed in chicken oviduct under hormonal control," Royal et al, Nature, 279:125-132 (1979).
"Deoxyribonuclease I Sensitivity of the Nontranscribed Sequences Flanking the 5' and 3' Ends of the Ovomucoid Gene and the Ovalbumin and Its Related X and Y Genes in Hen Oviduct Nuclei," Lawson et al, Biochemistry, 19: 4404-4411 (1980).
"Complete Nucleotide Sequence of the Chicken Chromosomal Ovalbumin Gene and its Biological Significance," Woo et al, Biochemistry, 20:6437-6446 (1981).
"Differential Hormonal Responsiveness of the Ovalbumin Gene and Its Pseudogenes in the Chick Oviduct," Colbert et al, Biochemistry, 19:5586-5592 (1980).
"Identification and Sequence Analysis of the 5' Domain of the X and Y Pseudo-ovalbumin Genes," Knoll et al, Journal of Biological Chemistry, 256:7949-7953 (1981).
"The Ovalbumin Gene Family: Hormonal Control of X and Y Gene Transcription and mRNA Accumulation," LeMeur et al, Cell, 23:561-571 (1981).
"Definition of 5' and 3' Structural Boundaries of the Chromatin Domain Containing the Ovalbumin Multigene Family," Lawson et al, Journal of Biological Chemistry, 257:1501-1507 (1982).
"Higher-order structural determinants for expression of the ovalbumin gene family," Stumph et al, Molecular Biology of egg maturation, pp. 80-95 (1983).
"Chromatin Structure of the Ovalbumin Gene Family in the Chicken Oviduct," Anderson et al, Biochemistry, 22:21-30 (1983).
"Characterization of Deoxyribonucleic Acid Sequences at the 5' and 3' Borders of the 100 Kilobase Pair Ovalbumin Gene Domain," Stumph et al, Biochemistry, 22:306-315 (1983).
"A close association between sites of Dnase I hypersensitivity and sites of enhanced cleavage by micrococcal nuclease in the 5'-flanking region of the actively transcribed ovalbumin gene," Kaye et al, EMBO Journal, 3:1137-1144 (1984).
"Steroid hormone dependence of four Dnase I-hypersensitive regions located within the 7000-bp 5'-flanking segment of the ovalbumin gene," Kaye et al, EMBO Journal, 5:277-285 (1986).
"Identification of Two Factors Required for Transcription of the Ovalbumin Gene," Sagami et al, Mol. Cell. Biol., 6:4259-4267 (1986).
"The chicken ovalbumin promoter is under negative control which is relieved by steroid hormones," Gaub et al, EMBO Journal, 6:2313-2320 (1987).
"Positive and Negative Regulatory Elements Control the Steroid-Responsive Ovalbumin Promoter," Sanders et al, Biochemistry, 27:6550-6557 (1988).

(Continued)

*Primary Examiner*—Michael C. Wilson
(74) *Attorney, Agent, or Firm*—Kyle D. Yesland

(57) ABSTRACT

The present invention provides isolated and recombinant avian nucleic acid molecules comprising at least one avian MAR and an avian nucleic acid sequence encoding an ovalbumin transcriptional regulatory region. The isolated nucleic acid of the present invention is useful for reducing chromosomal positional effects upon the transcription of a transgene operably linked to the ovalbumin transcriptional regulatory region and transfected into a recipient avian cell The recombinant nucleic acid molecules of the present invention may further comprise a polyadenylation signal sequence or an avian 3' domain, and optionally, an internal ribosome entry site for expression of an operably linked heterologous nucleic acid insert in a transfected avian cell.

18 Claims, 79 Drawing Sheets

OTHER PUBLICATIONS

"The Steroid-dependent Regulatory Element in the Ovalbumin Gene Does Not Function as a Typical Steroid Response Element," Schweers et al, Journal of Biological Chemistry,. 265:7590-7595 (1990).

"A Far Upstream Estrogen Response Element of the Ovalbumin Gene Contains Several Half-Palindromic 5'-TGACC-3' Motifs Acting Synergistically," Kato et al, Cell, 68:731-742 (1992).

"A Protein with a Binding Specificity Similar to NF-κb Binds to a Steroid-dependent Regulatory Element in the Ovalbumin Gene," Schweers et al, Journal of Biological Chemistry, 266:10490-10497 (1991).

"A Complex Array of Double-stranded and Single-stranded DNA-binding Proteins Mediates Induction of the Ovalbumin Gene by Steroid Hormones," Nordstrom et al, Journal of Biological Chemistry, 268:13193-13202 (1993).

"Repression of the Ovalbumin Gene Involves Multiple Negative Elements Including a Ubiquitous Transcriptional Silencer," Haecker et al, Molecular Endocrinology, 9:1113-1126 (1995).

"Regulation of the Chicken Ovalbumin Gene by Estrogen and Corticosterone Requires a Novel DNA Element That Binds a Labile Protein, Chirp-I," Dean et al, Molecular & Cellular Biology, 16:2015-2024 (1996).

"A Winged-Helix Family Member Is Involved in a Steroid Hormone-Triggered Regulatory Circuit," Dean et al, Endocrinology, 139:4967-4975 (1998).

"Multiple Promoter Elements Including a Novel Repressor Site Modulate Expression of the Chick Ovalbumin Gene," Sensenbaugh et al, DNA & Cell Biology, 18:147-156 (1999).

"Identification of the Novel Play δEF1 in Estrogen Transcriptional Cascades," Chamberlain et al, Molecular & Cellular Biology, 19:1-7 (1999).

"The Chicken Lysozyme Chromatin Domain Contains a Second; Widely Expressed Gene," Suyinn Chong, Arthur D. Riggs and Constanze Bonifer, Department of Biology, Beckman Research Institute of the City of Hope, Duarte, CA 91010, USAA and Molecular Medicine Unit, St. James' University Hospital, University of Leeds, Leeds LS9 7TF, UK.

* cited by examiner

SEQ ID NO: 1

```
   1 TGCAAGCTTG CAAGTTTTAC TGTCTCATAT GGTTCACATA CCATTCATTT
  51 AGCGTGGCCT CACAACCAAC TTGGGAACCA CTGCCCTAAG TAACAATACC
 101 TCACATATCC ATAGGATCTT CAACACCATT CTGCTTAAAA TTCAAATCCC
 151 TTTCATTAAA ATAGAAGATA TTTAGATACA AGATAAATAG AGCATATGTT
 201 TGTATGTGGT CATCTTCAGT TCTAGAAACA GTTTCTTCTC TCTTATGCAA
 251 CTGAAAGTAG CTTAGTTTCC ACAGCCCCGT GCAGAGCAAT ACGGTTGTAC
 301 TGCTCTCAAA GAAGTACCAA CACAACATGC ATCAGCAGAG TTGCACAAGA
 351 CTACTGAAAT AAAATTTGCT TAGCTGCTAG TGAAAACATA AGTATCCTTG
 401 CTTGTAAACA AAAGCATAAG TCATTTCACA CACCTCCATT TGCAGGGCTT
                             Q gene exon 5
 451 CAGCTAATCC TCGAAGAGCA AACTTGGTCG GAGAATAGGC TGTATAACCA
 501 AAAAGGCCTA ATTGCCCAGC CTGAGATGAT ACAAACACAA TCCTTCCCAT
 551 CCGTCGTTCC TTCATGGTAG AGATGACTGC ACGACTCGGG TAAACACTAC
 601 CTAGATAATT GACTGCCATT AATCTCTGTG GGAAAAAAAA AAGATATTAA
 651 AATGGTATTT CAGTCACTGA TTCAGAATTC TTCAGATGTT TAGTTTTATT
 701 TCTCCAAAAT CCCTACTGAG GCTTGCTTTA ACATCAAACT CCACTACATT
 751 TCTATCAGCG AGCAAAGTAA ACAATTGTTT TCTACTGTAT TTGTTTCATA
 801 AACGTTCCAT AGCAAAGAAT CTCACCGTAA GACAAAAAGA AATGCACTGT
 851 ATATACAAGT GTTAATGGCA TTGAGGATAC TAATGATGTG AGCTATTATG
 901 GCTTTCACAA AGAAAAAAGG GCAAATTACA AAAAAAACTG ACTTGAACAG
 951 TGTCTAGGAA GCAATCCATT TATACAAGAA GTACAAAAAC ATTGAAGTGA
1001 AAGTTTAAAG GGCTTCCTAA AAAAAAGAAA GAGGAAAAAT TCTATGTATA
1051 TATGCACAAG CTCTCATCTT GGCAGGTAAG ATTAATTCCT GTTTCAATCT
1101 CCTGAAGACC TAAAACACAA CTGGTGGCCT ACACAAGCAA TAAAACAGAT
1151 TATTTACCCT TACTGTTACA CTTACTATAA CATTATGCCT ATTCAGTATC
1201 ACGTGCATTT TCAGATGGCT CTGTGATGAA GTGAGAATCA AAGTAACCAG
1251 AAAGTAGAGA GGCTGTTTGG TTTTTTTTAA TGTATTTTGG TTTGGGTTTT
1301 ACTGTTGTTC CTTTCTTTCC ACCAAGCTGC ACCAAGTTAC CAACAGTTTA
1351 CATACCGCAG AGTTGAATGC TGACAAGATG GATTCTTCTT TAACAGATTC
1401 AAAATATGGG AAAAAGACCC ACACATCTTC ACCAGGAAAA AAGAGCCCAA
1451 TTCAGTGTCT TTCACAGCGT GTTAAATAAA AGCACACATC AACCTTCCTT
1501 TCCATCTTGA GGTCCTTCCC TATCCCAGGT GGGGAATTCA CTGTTCTGAA
1551 TTGTCCATGG ACCAATAATC AGGTAAAAAA ATAAGTTGCA ATCCTTGCAA
1601 ATCTAAAAAT GCATACAAAG ACCACCACTA ACGAAATATA TTGCTACTCA
1651 CACAGTCCGG AAAGACACAG TAAAATAATC TATTCCTTAG AACAGCGGAA
1701 TGACAAATTA CTTGCAATGA AATAAAGCAT GATCACTCAC TTCAAAAGAA
                             Q gene exon 4
1751 TTTACTTCAA TATCCTCAAA TTTTCCTGTA ACTGATGTTC CTGCACAGTT
1801 GACAAGCAGG TCAACTGGTC CCAGCTTCTC CTGAGCCTGC AAGAGGACAG
1851 AAATTAAGCT CTCCAGCAGG AAAAAAAGCA TTCATATAGC ATAGTGTCAT
                                          Q gene exon 3
1901 CATTAAATAT ACTGCCACTT GAAACACATC GTACAGAGAT GACCTTAATA
1951 CATACGCTGG TGGAACAGTT GCTTCTCACC TGTTTTAGAA CGTTCTCCAC
2001 CTGTTCATAG TCTTTAGATA CATCAACAGA AATACACAGC ACAACCTAAA
2051 AATGGAAAAT GAAAGAACAT ATTATAACCT CAGTCCAAGA ATGGTTGGCC
2101 CCAAGTCTTA CAAAAGAAAC TGCACACTGC TTCATGAGGT CATATTAGGG
2151 ACAAAATTAG AAAAAAACAA GACTAAAAAA AACTGATTAG TGGCACAGAG
2201 CTAAATATGC CTAAAAAGTG ATTTAACGTT TACTCTTTGT CTGGGAACAA
2251 GAGGTTATGG ATCTTAGTTT GAACGATACA GGAAAATGAA AATAGACACT
2301 GGCCCAGGGG AGAATAAATA AATAAATAGT AAAAAAAAGA GAGACAGCAA
2351 TGTCTTAATT TTTGTTGCAG CTGGAACGTA GGTATTGATT TTCTTTAAAA
2401 CTGCTGATTA CATTTAGCAA CTTGATCTCA GAATCTAAGT TTTGAAGCAC
```

*Fig. 1-1*

```
2451 CTTCCAGTCA ACTTCCAGCC AAAGGAAGCA CTGACTTTGG GGTATCACCA
2501 ACTGTAAGAT CACTGCCAAC TCCAGCTTGG CCGGGGATTT ACAAAGAGAT
2551 TATCCCCTCT GCTAAACAAC TATCAAGGTT CTGAGGCAAC TCAGTATCTT
2601 GAAAGGAGAA GCAATCACAT ACCACAATAG AAGTAGAGAC TCCTGTATTC
2651 TCATTCTGAT TTCTACGTCT TACTTTGTCC AATTCCCTTA AAGCTGGTTT
2701 GAGGTGAAAT AAAGTCATCA CCGGATTCTA ACAAGCGTCA TCAGGGTCAC
2751 TTGTCATGAA GCACGCCAAC AAAAATGAAG AAAAGCTTAC CAAAGTGTAA
2801 CTAACTGCTT TGGCAGCTAG TCATTTGTCA GTTTTGCCTC TGGTCAGACT
2851 GCAACACTTC CCAGCTACAT AAACAGAATC TGCTTGCCAT TCCTGTGCAG
2901 CAGGTTGGCT ATTCCTGCCT TCCAGCACTG TGCATAGCTG GACATCGGAG
2951 TAAACTTGTG GTGCAAGTTA ATGGTTGGCC AGCAAGCATC TCCCCTTAGG
3001 GCATTTTTAG ATTTAGAAA TATTTATCTT TTACATAAGT TTGAGAACAA
3051 AAATAACAGC TGAGCTAAGA TAACACTGAT TTACTATCTG GATGTCTTTA
3101 CAAGATCAGC AAGGTTAAAA ATCACAGTTC CATACGAAAA TTGGACATCG
3151 GACCACAGAT CAGTTAATCA TACTGAGAAC AATATACTCA GGAACTACTA
3201 AAGCTTGTAT TGGCTACCAG CACATTATAC AATTCATCTT TTTGCTTCTA
3251 TTATTGTATT TCCTTTCTGC TACATTAAGT TGATTACCTC CAGTCCAGAG
3301 CATGCACTGT GAATGTGGTC CTAATAAACA GACTATGCTG CCAGGAAGTC
3351 TAATATCCTC ATTCCAGTTT CTCGTCTTTT GTTCTAATAG CGCATTATCT
3401 GACCATTCCT AAAGCATTCG TTTCTCAATA AAAGCTCAAC TCCACTCCCA
3451 GTGAAGTAAC TAGGAATATT CCATACTGAG AAAGTGATTT TAACCATTTT
3501 CCAAAAAAAT TATGGGCAAG CATTTCATTT CACTGCATCC CTTTATTTGT
3551 AAAGGCTGCA CTGTCAGCAT TCTAAATAAA TCACATACAA ATGTATTTCA
3601 GAGAACACGT GCCAAATCCA ACACCTAAAG GTACGTTGAC ACCAGAATCC
3651 TGGTTCTCAA TGCAACTTAG TTTGACATAT ATATACATGA GCAGAATGCA
3701 CAGCATATAA TCATGTAAAA ACTGGTATTT CCTCTGGATT TTTGCTCCCT
3751 AGCTTGGCAT CTTGCAAATG TAACAGCCTC TGTGGTCTGG CAACCCATCC
3801 CAGACAACTC TATACTTTCA GCAATCTTCT TGTACAGCCT CTGTCTCTTT
3851 CGCTGCCCTC ATTTGTCAGC TTCTTATCTG CCGTTCTTCT TCTATTTGTG
3901 TTCTTTGAAT TTAGAACAGG CAGACTTCCC TGTGACAATG ACTACAACTC
3951 AACAGTAGGT ACACGAGGGC ACTCCCACTA CAGCCAGATG AAGTATGGAC
4001 AAGTCTAAAT TTGCTACTGC TAAAACAATC CTGTTTAGCT CACACTGAAG
4051 CTTGTTCAGT CTTGAACTTA CTGAAATTTT AACTGAAACT CTTGCAGACA
4101 CATACCTAGT ACTCTTCTTA AGAAAACAGA AATGTAAGTC CACATCTGTC
4151 AAGCTTGGAC AGATTTTTAA CAAGAGCATT GTGACAGTGT TTGACAAAGG
4201 ATCAAAGTCA TTGTCAACCC TGGGAAGAGA CTAGAGCAAC TAAAGGGAAA
4251 CCCTTACTGG GGTTTATTTG TTTTTAAAAG GGGACAAAAC GTTGCTCCTC
4301 CTCACCTCAC ATGACTTCAT ATTTCAAGAT AAATTTGATC TGAGTAAGGC
4351 AACATGCACA GAAAGAAAGA TCACCTTGAA CCATTTGACA GGAATGAGCA
4401 AAGACAGAAT CTTGCTGAGT GTTCTTGATA TCTTCATTTA CATCGGCTAG
4451 TACTAACATT GCTTCCAAAT ATCCATCTTT CTCCACTGCT TCTTTTCAGG
4501 AGAATATCCA ACTTATCCAT TCACCAGATT ATTATACACC CAATAGACAC
4551 CAAATCCCTT ATCACAAACA AATTGCTTGC ACTTGTAATA AAGAAAATAA
4601 GAACCAACTA CTGGAGCACA AGAGAGAGGA AATCAAAGAT GCGATGGTCT
4651 CAATGCTGTT TCCCGTCTCT TTTGGATTAT GAGTATTAAG AAAAAAAAGT
4701 TGTAGTATTT CATCTTGAAG CTGTGTTTTT TTGAACACAG AAAGCTGCCC
4751 TATTTTAAAA CATAGCACCC CAGCAAGCAT TAATGCACTC AAACAGTGCA
4801 TTAAGCGTGA ATACATTATT TATTTACCAA AGTACCTCCA GTGTTTAGAA
4851 ACCTCAGTGC TTTGCCAGGA AAACAGCAAT ACACAGCACA ACATAGGGAA
4901 TGAAATCTGA AAATAAGTAC CTAAAATTTA TTCCCCATTA CAATTGCTGC
4951 ATTTACGATC TCTCGAAGAG AAACTTGAAA AAAGTAGGTT ATTCTCCTCA
5001 ATCTTGAACA ATACAAACAC TTATCAAGTG ACAGCAAATT GCAGCTATCA
5051 AAAAAAACTC TAATACACCT ACAGGTGAAG ATACCAATCT TTTTCTCTGG
5101 GAAAAAAAGT TAGCATACTA ACCAGGCAAC ATCAAATGTA GCTGAGTTTG
```

*Fig. 1-2*

```
5151 GAACATCACA CGTAGACAGA TTGGAATTTT TTGAATTCAA GTGAGGCCTC
5201 ACCTATTTTT AATCAAACAG TTTGGTTTTA AAAACCAGAC TACTGAAGCT
5251 ATGTTGAAGC GACTACCTTG AAACACAACA GTTATAGGTA GCAGCGATCT
                            Q gene exon 2
5301 TACCTGCTTG TCATTAACAG AGTACTTTTC TATTTCCTTC TTTGTCTGTA
5351 ACAGCTTGTT CTGAAACGGA TAATAAGAAC AGCTAAAGCA CCGCAGTTAT
5401 GAGAACACAT TTGTCTTCAG TATTTCGAGA AGCCCTAGAA ACACTCTCTA
5451 AAAACAAGAA CATTATCATC AGCTAGCGAT AACGCTTTAC TATGTTCATC
5501 TTAGAGGTTT ATGAACGTAC AAAACATCAA CTCCATGCCA TAGCAATGGA
5551 AGAGTTTTAA GGCAAGCTCA TCACAAACTG CATGTTAGAT TACACTACTT
5601 ACAAAGGCAG CCATCTCTAC TCTGCAAATA CATCACATTT AAATTATTAG
5651 GATCACCTTA AAGCATACAG TGGAAAAAAA ACCAATGAGT AATTATCAAT
5701 TCCCAAATTA CTCCTCAACC ATACCAATTT CATTAATATA AGGTAGCCAG
                                       Q gene exon 1
5751 CAAAAATACA AATACGCTTA CCTCATCTCT TGCAATCAGT GTTATGAAAG
5801 CTCCTTGCTT ATAACATTCA ATAGCAATAC ATTTTCCAAT TCCACTGGAG
5851 CCTCCAGTAA CCTGGAAGTT ATTTGAAAAG TCAGTTAGTC CGTTATTCTC
5901 ATCCCTACCC CTGTATCATA ACAAGTCAAA TCAAAACTCT AAAAGTGTAC
5951 TGAGATTCAA ATATCACCCA GTGAAGTATG AACACATGAG ATATACAAAA
6001 GTTTCTTTAC TTACTGAGTA CGAATGGAAA AATGAAATCT AACTACCTTG
6051 TCAGGCAACT CTCTCTGTCC CAAAAACCAG CTTTACCTTA ATGGTATTTT
6101 TTCCATATTT CTTATGTCAG GCTCACTTAG ACCCACTCTC ACGTGCCTTT
6151 GATTAACTTA TTTTTGAAGT ACGGTAATAG TTATAAGTTT GCAATCACTA
6201 TTAACATTAA GAACGCAATT ACATCCTGTC CCTCCATGCC AGGCTACAAT
6251 AAAATGCATA AAAAGAGCAA TCATAGCTTG TCTGCCAAAA ACACCGTGTA
6301 AACAAACACA ATTTAAAAAG TTATCTTCTT TCTTATTAAA TAAACATCCT
6351 TAATTTGACA GCTGGCCCCC TGCAGAGCAC GTCTCACAGT TCACATCTGG
6401 ATGCTGAACT GCCTCAATGC CCTTCTGTGG GGATCCCAGT TCTAAGCCTC
6451 CATAAGCCTT TCCTTCTTCC TCTAAACCAT AACTCTCAGT GGTCTCCCAT
6501 GCAAACGGGA AATAAACAGT TTGCCTGCAG ACAAATGCAA GGCGATGGCT
6551 ACAACCCCCC ACTAATAAAC AGGTTAAAGT CACCTGAACA CCCCCCTCTC
6601 TACCCTCCAG AAAAATCTAT TTGTGAACTC CATTTAAAAC AAAACATAGA
6651 TGGTGACCCA ACTGCTCTTC TTCTTATCGC AAATAAAACT GTCATCCTGA
6701 TACTGACTTT TGGTGATTTG TTCATTTAAA CCCAGCCTCA GTTTGTACGT
6751 GCCTTCAGTC CTTAAACACA CAGAGTTGTA TTTTCCTTGT ATGGCCAAAT
6801 GTGTTGAATT TTCTCCTAAG AGCGTATCAC TGAGAAAAGA TTGGAATGTT
6851 TCATTGATGA AGGGAGTTCT GAAATACAGG CTTAAATATT TGAGAAAGAG
6901 ATTCATATTC CTCTGGAAGT TGTCATTTCT GTTCTTTATC AAGACTTCAG
6951 AGAAAGTAAG GTATCACCTC TATTTCAACT ATGAGAAATG GAATGCACTG
7001 AGCCAATCAG TGGAAGAGCA AAGGCTTCCA GTCTCATCTG CACGTGCCTT
7051 TGTTTTGTTT TCAGGCTCAC TACCCTCAAA ATTCTTTCAT ATTCCTGGGG
7101 GCAGTAAAGT CAAAAGAGTT AGAAGTACGC TCCCATGAGT CACCAAGCTC
7151 TTCTTTCTTA CGAGTGTTTC ATCACAAACC TTCAAAGAAA ACAGCTCAGT
7201 ACACAAAGGG TGATCATGTA ACCTCAGCAA ACTTATTTTC AACAGATTCC
7251 ACAGTTTTTG TCTAATTTGT CTGCTGTCAC CAGTGGGTCA AGAACTTAGA
7301 AAGACTAACT TCAACTTAAA CAGAGTTTCA TAGACTTCCC CTATTAGAGA
7351 AAGTCGCTTC AAAGCAGCTT CTAATCGACT CTTTACTACG CTAACCTTTG
7401 TGAATGACTT TAAGATGCAC GTTCTGTTCC GGAGATGTTT AATGCTGTTG
7451 CATTCTGAAT AAAGGATGGC TGCTTCCTAA GCAAATTAAG TCTGTAAGAA
7501 CGAGTGTTAA CGTTTGGGAA CCCTAGCATC ATTTAATTCT TCACAACAGA
7551 AAGAAGTTAA ATTTTTAGTT CATTCCCAAA GCACTTTTGA AGATTCCAAT
7601 ACATCTCTAG AAGGATTAGG AGATTCAGTT TGATGTATTC AGGCAAACCT
7651 CAGTTCCAGA GCACTCATGA GCTGCCTTTA CAGATTTTCA GCAGCAGCTG
7701 GTACATCAGC ACAGGAACTA ATGAATGCAT GTGGAAGACT GCTCCAATTC
```

*Fig. 1-3*

7751 CCATTTTTGG CACAGCACTG AGGCACAGCT GATTGCTACC TGTACAAATT
7801 GCTAAGTGTC ATGAACAGGT CAACTACAGC AGTGTTTGAA GGTGAAGGTG
7851 GCATAATGCC TATGGCTTGT TAGACAACGT TAACGTTCAC TTCGGAAAGA
7901 CAAGGTCTGA AGTCAAGCAA GAAAGGGAAG TTTTTATTTG CAGTCATACC
7951 CAAGAACGCT AGATAGGGCT CATGTCAGAT TGGTCAGTGA CAAAAAGCAG
8001 AATCAGTTAG CTAGGAACTT CAGCATTTAG GTGGAAGGCT GTTACTAATA
8051 CGTTGGAGGT TGTTACTAAC ATGCACCACG AGATGCAATG TAACAGTAAA
8101 GAAACAGAAC AACTCATCGA TCAATGAGTA AGCACAATTC CAAATCATCA
8151 CAACTATCAT CAGAAGCGAT CAAAATGAAG ACTTGATATG CTCTTTCCAA
8201 CAGGGCTTGC TAGCTTTCAC TGAGCAGCAG CACAGGATGC AAGCTGGCTT
8251 CTTGCTTTTA GACAGTACTC TAACAGTAGG CATTCAGTTC CACTGAAACA
8301 GAACATCCCC GTAACTTGCT CCAATTGGCT GGTGTGCCTG ACTGGACTCC
8351 AAATGACCTC TTCCTGAACC ACCCATGTGC ATTTAAGCCA CAGGTCACGC
8401 TGCTCCCAAT GCAAGAGCTA CAAAGCTGAG ACACGGAGAT GGGTCAACTC
8451 CAGGAACACC CAAAGCCTGC TGTCCTTATC TGATGGGCTC TGCAGGGAAA
8501 TGCTGAAACT ACTCCTAGTC CTGAGATGGC CCTTACACCT GTGGCTTGGG
8551 CATACTGAAG CTTAACTATG TCCAAGTTAA AGGCCCTGCT CAAACTGAAA
8601 GGAAGACAAT CACAGGCAGC AAATATCCTT ACATTCCTGG CATAGTTAGC
8651 CTATGAAAGC AAAAATACAT TTAAAAGCAT TTTGTTTTAC TAAATAAGCA
8701 AAAACTGATG CTTGAGTCAA CCTGATAGCT GTGAAGTCCT TCCTATTTAA
8751 CAGTGCCCAC TGAGATTACC AAAACACACA GCAGATATGG AACAGGAAAA
8801 CACCCCCACA AGATTAGATC AGTAATTTGG AGTTCTGTGG AGCTCCATTC
8851 CTCTCTAAGC AGAAGAGACA CCTGTGGTCT CGGTCCCACT CTAAAGCATA
8901 CCTCATGTCA CACAGCAAGT GACTCCAGGA GAGGACAGGA GGGAAAAAAA
8951 CCCCAACAAA AAAACAACCA CACATTTTCT GCCTCAGATT TCTGTCCTTG
9001 TACCTCAAAC ACCTAGCTCT ATTAACCATT ACAACTGTTA GGAGCAGAGA
9051 GAAATAGATT CTACAAATGA TTAAGTAGGG TGTGAAAAAA TGCTGATTTA
9101 AATTGAGAAT TCAACAAGTA ACTGCTAGGA AACAATATAC ACAGTAGCGT
9151 CCAAACACAT TCAATGACCC TCTTTAAGAA ATACTACAGG TATTCTCCTG
9201 CACATATGAA GGGGGAATTA TACATACAGA TCACACAAAC AGATTTTGAC
9251 TTTTTCTGTG AAAACACTTC AAGGAAGTTC TTAACAGTGC TACGGTCCTG
9301 AATATTTTCA TGACACCTTC TGATAATTTC AGTAGCAGAG AACACTCACT
9351 CCCATTATAC GATGCAAGAA TTCACCTTGC ACATGTGATG TGTACAGCCT
9401 TCACAAGTAC AGTTTCTAAT TTACAAAACT ATCATCCAAT GTTTTTCCTT
9451 ACACAATTCA CCCAAACATT TGAAACCCAA ACATGCAAGT CTAACAGCAT
9501 CAGGGTTATT AGCAGCACCT ACATATCAAA AAAACTAAAA CTCTGAAACA
9551 ACTGCTCCAT GTTTCATGTG TTTGCACAAA TGCTTTCAGA GCATAACTGA
9601 AGCCATAGTC AAACAAGTGC TTCTGCCAGA AGCAATGCCA CTGAAGCTGA
9651 TCACCCACAG ATTTGTACCC TGATGCCAAT AAATACCTAC AGCCTTTCCT

CR1-GG

9701 TCTATTGGGA TATGAACACA GTTAATCCTC CAGAAGGTGG TGACGCACTG
9751 GAACAGGTTG CCCAAGGAAG TTGTAGATGC CCCATCCCTG GAGGCATTCA
9801 AGGCCAGGCT GGATGTGGCT CTGGGCAGAC TGGCCTACTG GTTGGCGACC
9851 CTGCACACAG CAGGGGGGTT GAAACTAGAT GCTCATTGTG GTCCATTTCA
9901 ACCCAGGCCA TTCTATAATC CTACGAATAG TCATTTTGAG ACCATCACTT
9951 ATGTCAAATT CAGGTTACGT GGCTAATACA ATTAGCAGTA GTGGCTGTGA
10001 GGGAAGATTT CTCCAACAAG ATTATTCTTT GTCATTTTCA TTGTGAGCCA
10051 ACTGAAGTGG CTCTTTGAAA AAAGAAGAAC CAGCAGAGTA GCTTTGGAAA
10101 AAGCGTAACG ACACAAAGAA AAGACAACAC TCGGGATAAT CAGATTAAAA
10151 ACAAACAGGT GGACAATACT CTGGGATAGA ATACACTGAA CATTTTGTTG
10201 CTTACTATTC TGTTTCCACG CAAGCACTGC AGTACCCTTA CCCTGCTTCA
10251 CCTTTGCTTT TACACAGTAC AGAAGGATTC CTGCTTAGCA AGAGTTACCG
10301 CTGTGGGAAG AACCTCAGAG AGCCTTCACT CACGCTCTAC TATCTCCAGC
10351 AGGACATGAT GCTGTAAAGC CAGTTACAAT ACCCAGCAAT ACCTATTGCA

*Fig. 1-4*

```
10401 TCAAGTAATT TGGGAACACT GTTGCAACTT GGACAGCTCC AAGCCGGGAC
10451 AGCTCTATCC GCAAAGAGCA GCCCTAAAAC AAATAGGCAG ATAAAAATGA
10501 ACACAAACAA ACAAGGCACC ACACAGAGCT CAAAAAAATC CCAAATGCCA
10551 AGCAGCTGTC AATTCCCTCG CACCTCAGAG GTCTAACTTC TGCATTACAC
10601 CCAAGTCCTG TAGTAACCAA GTCCTGTAGG CAGCCTGCAT GCCCTACTCA
10651 CCCCCCAAAA GCAGATTCAG CAAGCAAACA GCACAGCTCC TCTACACGGA
10701 GCACACCACG GGTAACTACA GCTAAGTCCC CAGAGCTGAC TGAAGGACCA
                                   CpG island
10751 CAGCCGCCCC GACCCGCTCT CACGCACCCA CATGCTCCAC ACACACCTGC
10801 AGGCCCCTGG CTGCTGCTCC CCATCACGCA CCCGCCCAGC TTTCAGCGGT
10851 ACGCTCCTGG GGAACCGTTC AAAAGCTATA TTTTCCCGAA TAAACCCTCC
10901 CAAAGGCTCG CTCCTACACA GCTGATTACA GACAAGCCAA ACGTCGCTCG
10951 TGGACACGGA TACCCGCGCT GAGTGCCGCC TGACCGCTTC CCTTCGCGTC
11001 AGCCCGCCCG TTTCCTCAGC ACGGGTCGCC TTTCAGCCCG TGCCTTCCAC
11051 CCTCGTGAGG AGGGCCGCAC TCCAGCACCT CGGCAGATGC AGCGGGGCCT
11101 TCCCCGGGAC ACGGCGGCCG CGGCCTCCCC GCTCCCTCCT CCCGCCCAGC
11151 GCCGGCAGCG GACCGCTCCC CCGCGGTCGG TCAGCCAGCA GCGGCCGGGA
11201 TCGGGGTGGG GAGGGGGAGG CGAGAGGCCT CGTTCGACTC ACCACGACGT
11251 GTGCGCCGGG CAGCTTGAGG GGCTTGGGGC TGATGAGCGG CGACACCATG
11301 TAGAGGAGAA GGACGATGGC CACGATGAAG GCGGCCGCCA GGAGCAGCAT
11351 GGCTCGGGCC GGGCTTGCCG CTGGGGAGGG GGCGGCGGGC GGTGACAAGG
11401 CCCCTGGGGC TGCGGGAGGC GCCGAGCGCG GCGCGGCCCG GCGCGGCACG
11451 GACAGCGGGA GTAGAACCGG TGCCCGCCTG CGCCGCGGCG CCACGGGGCC
11501 ACAGGGGAGG GGAGGAGGA AGAGGAGGAG GGAGGAGGAG AACACGGCCG
11551 CCACTCCGCG CCCTGATTGG CTGGTGGGCG GGGCGGGCGC GGCCTCGCGA
11601 GCGGGGATTG GCCAGTGAGC GACGGGAAGG AGCTGGCGGA TTGGCCGAGA
11651 GGCGGGACGG CGCTCGGAGA TTGGAGCCGC AGGCTGTTTG CAGGGTCACC
11701 GTTGGAGGCA AAGGGCGGCG GAGAAGAGAG AGTTCCTCCG GAGAAGACGG
11751 GGTGCGGGAC GGCGCCCCCT ACGGTCCCCG CCTAGGGCGG GTGAGGCGAG
11801 GAGTGAGGTA GGCCCCGCCC CTTCTCGTCA CGTGGGGCTT CCCGCCGAAA
11851 GGAGGGGGCG TGGCTCCGTG AGGTGAGAGA CGGGAGGCTG CGGGCGGCGT
11901 TCACGCTCTG GAACGCGAGG GCAGCTGTTT GTGGGGAAAA AAATGTGTAG
11951 AAGCGTGGTT TCAAAGCATA ATAATAAAAG ATTAACTAAA ACGAAAACGT
12001 CTTGCAGCTC AAATAAAATG ATTCCGTGCC TACGTTCAAT ATTTCCTTCG
12051 CTGTTTATGA CTGAAAGGAA CTCCCTGAAA TGATTTATGT TGTAAACGCT
12101 GTGCAGCCTC TGACTTGTAG AAGGGAGTTT GCAGCGTACG CGGCTTTACG
12151 GCCTCGGAGA GATTACGATT ACGGGCGAGA GGGCGTGCGG AAGGGTGTGA
12201 AGATAATGCA GGAGATGAGA TTGGAGCGGG GAGTAGGCGG AAATGGGAGC
12251 AGGGCTGCGG GCAGGGATTA GGCAGTCGTC AAGGGGAGAG CAAAGAATCT
12301 GGAACAAAAG AATCCAGGAA TTAGTTCTGG AATGGGATTG AGCCGGGATC
12351 GGGCTTCGGT GACGCTTTGA GAGTGGTGCT GTGGGGTGGA GGTGTGAGGA
12401 AATGAGAGGA AGAAAGAGCG CGTGCTGAGG TAACAGCTGC CACGGCAAGG
12451 GTGGGGAGAG AGCTGACAAA GTGGTGTGTC CAAGGAAAGG CGGTGTGGAA
12501 TCGTAGGCAT CCTTAAGGCT GGAAAGGGTC ACCAAGTCCA AGCACCAAGT
12551 CCAACTAGCA GAAGTTGGTG TAGGATATGG ACTAGGAACG CTGCAAGCAC
12601 AGATACCGAC TTCATTCTTT GCATACAGGG CAGTGTATGT GTTATCTTTT
12651 GTAGAATATT AATTAAACAC AAAGGAGGAG ATTGATAATG TAATAGAGCC
12701 TATTTATAGT TATCTAGTGC AGAATATGGC GAGACTTGAA AAGCCCAAAT
12751 GTCAGCAGCA TGGAGATAAA GCAGACGGAG ATAAATCCAT CTTTCACAAT
12801 GCGATATCGC TTTCAGAATC AACATGAGGC AAGGGCATGG ATAAAAACAA
12851 TCATCTGCAG TTAATTTCTA GTAAAATGAA GGTTAAACAT GTTGGTAGGG
12901 GGCCTCTAAA AACCTCAAAT GCATGATATG CTCCTGATTG GTCACAGTTA
12951 GGATCACATA TTACTAAATA TTTGAGAAGC CCTTGTAGAT TAACGAGGAA
13001 TCCCCTCGGT GAATTTTATG CAGAAATCCA TACTGTCTTT TCCTTTTAGC
```

*Fig. 1-5*

```
13051 TAAGTGGCCA CTTTACAACC GTGTGATTGA CAATCCAGGT AGCGTCCACT
13101 CACATTTTGT TCCTGGGGCA GTGAAGTGTC ATGAATTTAT CTCCAAGAAA
13151 AACATTCAAA AGTGAAGACC TTGTGAACTG CTTATAACTC ACCAATGTAT
13201 CGCCACAGCA GTAGGTTTTT GACTCTTTTT AGGTATGCCA GCAGGCACTG
13251 AAGTTTGCCC TCCTGAGCTG TCTGCTGTCT GGTTTGTATT TGTCTCATGT
13301 GACCTCATTC ACTGAGGAAG TGCGTTCCTG ACACACGGGA ATGGTTTGCT
13351 ACGAAACTCT TTTCTCAGTG ACTGTGGAAC TGGAAATTGA ACCCTAAAAA
13401 AAAAAAGTGT TGAAGCCCTC CAGTCCAAAC TTTGGTTGTA CATAAAGCAG
13451 TATTTAATTA ATCTGACCTT GATTAACAAC ATCAAAAAGT GTAATTTTGA
13501 AGCACAAACT GACCAAGGTA TGTATGTACC TTCGGGATGG GTAAGAAAAT
13551 AAAAAGGTTA ACACATGCTA ATTGCTTTGC TAATTAATCC TTAGAAGCAG
13601 CTTCAACACA ACAGCGATGT GTTTAGAGAA GAAAATCAAA TACAGGTAGA
13651 TTAAAGCGTC CAAACTATAG GACCAGCTGT GGTTTTCTGC TTCCTCAGTT
13701 CTGTTCATAT AATCTTTCAA CAGACGTTTG CAGTAACAAT GTTGTGGGTT
13751 GAGATAAATC AGTATGAACA AAGCATGGCA ACCGAAGTAA GAAAGTAGTC
13801 ATTTAAACAC GGAAACAAAT GTATGAATTG ATAATATTAC AACACAAGTG
13851 ACTGATACTA GAGGTGTCCT TTTGATCTTC TTGTTCCCAA AGCATACAAG
13901 GTACACACAG AAGAGACACA GGCTGTGTTA AGATGCCATT AAGAGAAGGC
13951 ATAAAGGTTT GACAGAGCAG GTAGTGAGGT TGCAGCCTGG ACAGACTTTC
14001 TTATTGCACT TGAGTACTCA TCTGCTGGAT TTTCTGGTTG TGTCATATTC
14051 ACGTTAGGGA GAGAGGAGGG AAAAAGAGCA GGATGCGTAG GCTACTCAGT
14101 GATTAAACAA AAAAAAAAAG CTGGAAACTT CTTCATGTGA TTTCCATCCA
14151 GTCAGTCCTT CTGCTTTTAG AGAAAGCAGC ATGAAGGAAA AACTTCAGTA
14201 GCCAAGGAGA ACAACTTTTT CCTTCTGTTT TCCTGAATTA ACTTACTTTC
14251 CTCTCCAACC TTCTCCCTTT TGTGTAGCAA GCATAGGTGT TCTATGCTCA
14301 TTTCTTAAGA GGTCTGTTGC AGTAATCATC ATAAGACATC AAAGGCATGT
14351 TGGCAGTTCT TGGATTCCTG CAAAGCTTCA AGATTTAGAA TGATGGCAGT
14401 CTAGGTGAGT TGTTCCTGGT CAACAAGCTG TCTTGATCCC GTGTCCCAAA
14451 TGAGAAGAGC TAATAGGGAC ATAAGAACTG AAATCAGAAA AGGATTTACA
14501 TAACATGCTG GCAGTAGAGG AGAATTGGGC AAGAAATAAT GATCTGCACA
14551 TGGTAGTGAC TAAAGCAGTG TGACTGAAAT ACTTATCACA CCCAGCTGCT
14601 TGCCTTGCTG TTCTTCCCCA AACAAACAAG CAAATCCCTT GTAGCTGAAC
14651 AATAGCTTCT TTACTGGTCC ATCACGCTGG AGAGATCATC AGCTACCCCA
14701 TGCATAGCAG GGTGAAACAG CTCCCAGAGC ACTGTGCAGG TCAAAGTACT
14751 ATATGTACCC TGTCTGCTGG AGTGCTATCA CGGTGATCTT CTGGGTATTC
14801 CTAGAAGGAG ATTTCCTGTA CTCCCAAGCT CAACGTATCA TCCAGAAAGT
14851 GCTCGCCTGC AGCAGGGACG GGTTCTGGCG ATCTCTGCAG CTTCCAGCTA
14901 TGCCGCATGC CCTTATCGCA ATGAACTCAG GCTGGGCTGA TGGCCCAGGT
14951 GCTGGAGGCT GCCAGCACGC AGGCAGGAGG TGGTTATAGC AGCTCAGGCT
15001 CAGGTCAAAC CAAGGCTTCT TGCTGGGGCA GAGGGGACTG ACTCTGTGGT
15051 GCAAAAGCAG GTAGTATATA TATATGTATA TATATACAAA GCCCAGCTAC
15101 CAGCTGAGAG TCCCAAGGCT GCTGCAGTAG TTTTGCAATG AGCACACAGG
15151 AAACAAGAAG ATCGCTGAGA ACACTGCTGA AATCAGATTT CTGTCTTCAC
15201 ACAGGTCAAG CTGATTTAAC TGTTTAATGT AATTGCTGCA GTTGCTTGGA
15251 AAAAAAAAGA AATAGTAAAA CCATGTCCAA AATGAACCAT TCATAACTGG
15301 TGGCCCATTA TGTGTCACAG CCGATGTTGT GCTGAATAAA TAACTGTACA
15351 GGTATTTTAT ATATTGAGCA ACATATTTAT TGAAACAAAA ATAATTTACC
15401 TCAAACCAGC GGTAAAAGGA AGTCTTTACT GTCTAATTTA AATAGGCATA
15451 AGTTAAACTC GGGACTGAGA TGATCTTGAA TTTCATTTGG TGCCCATGGT
15501 TCTTTTTATG TGGTACACCT GCTTACACTT ACCATCACAC TGGAGCAGTT
15551 TGCTTTTGCC ACCCGAATGT CAGACACTGC TATAGATTTA CAGTAGCTTG
15601 GGGGGGCTGC AGGTTGGAAG AGGGGGTTGA GGCCTCATCA AGTGCCATGG
15651 CAAAACACCC TCAAGTAAGC ACGGCTGGAA GCAGGAAGGA TGAGGGAATG
15701 AGCTGCCATT TCCTTTGCGC TGGAAGGATC ACTGCTAAAA CTTGTAAATA
```

*Fig. 1-6*

```
15751 TCTGTTAGAA ACAAACAGGG ACGTTCACTT TGTCCTGTGA TGCAAGAGCA
15801 CCCATTCTGA ATTTTTATCT CCTGCAAAGT TGTATTTAAG CTGATGTTTA
15851 CCGTGGACGT TCGTGTTACA AGATAGCCTT TGATACTATC AATAACAAGT
15901 CCTCTTTGAT GAAGTAAAGC TACAGAGTCA CAAAGCATGC ACTTGTCTGA
15951 CCCTTTGCCT GGCTGCCTGT CCAACCACGT TGCACCACTA CACCCAGCCC
16001 CACGAGACCT GCTCCAGGGC CAAGGGAATT GAGCACTTAA GGGAAAGTGC
16051 TTTGTACAAA ACATGGCGCT TATGAGTTTG AAAACGTAGA TCCACCAAAA
16101 CCTCCTCAGG CACGATGAGT ATATTTTTTC TCCACTACTT ACAGCGCTGT
16151 GAATTCTAGT TAAGGGCGTT TTGATTCCTA AAGAATTTTT CCTTCTAATC
16201 ATAGACGTAC TCCAGTCCTT ATTCCAGAAG GCTTACTCCT TGTATTTTGA
16251 AGGTCTTATC CTGAAATTGG GATGCAGAGC CATTCTGAAA ATGACAGTAT
16301 TTTAAGACTT TGCTGCACTT ACTCTGGCTT CCCACATACC TTCCTCTTGC
16351 AACCTTCCAC CTCCCAGAAC TGCAGCCCAG CCTATCCTCC TCTGCCAGAA
16401 AATCGGATCC CACAGGCCCT ATCTCACACC TCCCGGTTCC CCATCCTCAT
16451 GGCAGCTGCC CTCTTTCCCA AGGCACTCTA TGGAGCAGCA GAACTGCTGA
16501 GTGCACAGGG CAAAGATCTG CCGTTCCGAG AGAGCAGAGA AGCATCGCTC
16551 GGGAATCACT GCACTGCTGC AGCACTATTG TATTCTGCCT TTATTCAGAG
16601 GCAGTCCTTC ACCTATGAAT ATCACTACTA CCTTACTGAA TATATATTTT
16651 CAGGAATATT TTCACTTTTT AGCCAGATAG GAAGCGGATT TTGTAATTAC
16701 CCTTCCAGCA ACTTACAGCC AATTACTGTC TCTCCTCCTG ATTCCTGTCC
16751 AGCAATTTGG TTGCAGTTAT TGCTTCTCCA GAGCGGGCAG AATTTTTTGC
16801 TTTAGGAAAT GTACACCTCG AGGTAATCTT TGAAGAGTGA CAGGTTCTAA
16851 AGTTCACAAG TTTGATCTGC TTTGGGATTA AGCTACCTGC TAAACTACCA
16901 CACGCCATCC AGTCAAGCCA TTTCTATTAT GTGCGTATGG CTGATTCTTA
16951 TCACAAAAGA TCAAGTTAAT GATTTGCAGT CTTCGGCAAG CCTCTGGTTT
17001 CTTTGAACTT GCTTTTTGTA AGCGATATTC TCGGGTACTT TTTGTGCTTG
17051 TGAAGCTACT GCAGTGCTCT GGAGATTTTC TTTGTGCTCC TGGCTGTCAG
17101 AGTTATCCAT TTCTAGGCCT GCTTGGCCAT CCCCATAGCA CGGGGAGAAC
17151 CGTACTTTCC CATTGCCCTT GTACCTGCAC TTGTAAAAAC GCTAGAGGAA
17201 CTGAAATTAC TTCAAGTTCG TGCCCTGTCC TCTTTCAAAG CCATTCTGAG
17251 AACTTTCTTT GCACAACCTT TTTACAAGAG TTAAATCCGT TTCTAGTTCC
17301 AGGCAACACA CTTGTCATAC ACAGCGCTGG CAAGGGACTG CTGTTTATTT
17351 CTTGCTTGGA TGCAATTACA CAGCCATGTG CCCTTGTTTT CAGTCCCTGA
17401 TCCATTATCT TTGGCATTTA CTGCAAAGAA GCTGCTGTTA CGCAATGGAA
17451 ATTTAGATGA TCTCTTTTTC TTAGCTTACT TCTCCTCTAA CCCAAGAAAT
17501 GAGTACAGTA TAGCCTGCTG AATGCAAGGA AACCTGCACC TGCAAACTTT
17551 TCTCCCCACT GCGTCACTAC CAAATATGTC AGAGTTGCTT GTACTTCTTA
17601 AGTCTGTTTC CATCCCCTAA TGGCACGAAC CGTTGCCCTC CTGTTGTCAG
17651 ACTGCAAAAA GGCCAGCTTG TACAGATTTG CCCTGTAGGT TTGAATGGAA
17701 GAAGGGAAAA AAATCAGAGA AACTGCCAGC TTTTGTTCTG CCGCTTGTAA
17751 GCTTGCTTTG GTAGAAAAGT TGAAGAAATA GGAACATGCT TTGAAATAGG
17801 ATTTTAAAAG GAATCAGCTT CTTATCTTCC CTTTGGGAAA AAATAGTGTG
17851 AAGGACAGAA TAAATCAGAC GGAAAAAGAA AGAAATTGAC GTAAGAGAAC
17901 TAGTCGGGCA GAAAGGAGGA GGTGGAAAAT ACCCAAAAGC AGCAGGAAAG
17951 AGGGAGGCAC AGGTTGCCAA TTAACACTTC GATCAAAGGA AAGGCCCGAT
18001 CAAAACCTTT TTCCTCCTCT AAGAAGCATC ACCCCTTCCC ACTGCTTACT
18051 GCAATGAAGC GAGCTTTTAG ACTAAGACTC AAGAGAATAA CCCCAATACC
18101 AGTAAAGCCT GCAGAACTTG TTTTTTTCAT AGCTGACACC ACAGACAAAC
18151 AAACAAATAA ATAAATAGTA GCGCAGAGCA TCAGCACCGT GGCAGTCATT
18201 CCAGCAATCA CTTCCCCACC GTGCTCTCCT ATAGGAGAGC TGCAGCACAG
18251 GTCAGCGTCT CCCAACCCGT GCACTTCTTC ACGGACAGAT TTGCATCATG
18301 CAGACCCTCA GATTGCCCAG GAAGAACAGA ACTGCAATGC CCAGAAAGAG
18351 TGTGGAAGCT CTGAGAATTT ATCTGCCTGC TGGACAGAGC CCATCTACAC
18401 CTGGAACAAG CGGGCACCTC TCTGTGCTAC CAGTGCTGGG TAAAGAAAGC
```

Fig. 1-7

18451 TGTGCAGCAG CTCCTCCCTG AACACTGGCT ACGTTGTGAC ATCAGCCCTG
18501 TGGTTCCTGT GGCAGCTCCT GCGCTTCTGC AACTACATGA GTCTAGCTGG
18551 CAGGCCACCT GCTTGTTTCC ATATCAGCAG CAGCCACGTG CACCATGTGC
18601 ACCATGTGCA GGGGGCCTCC AGGCAGGTAA AAAAAACAAA CAAACAAAAA
18651 CATCTCTTAA TTACAGGGGC AGAGCAGGGC TGGATACGAA CAAACAAAAC
18701 CATACCAAAA CAAGCACACG TGTAAAGAGG AAAAAAAAAT AAAATAAATC
18751 ACAGCTTTGC AGTTTGTCTG TCTTCAGAGC AAATCAAGGC TGTGATTAAT
18801 TCGTTACACA TCAGAACTCC AAGCAGGCTC AAGCTGAGCC GTTGCAACTG
18851 GCATTATGAA TGGCACACTT GAAAAACAGC CAGGTTGCTT TCCAGATTCA

CR1-GG

18901 TGGAATCATA TCATAGAATC ATAGAACGGC CTGGGTTGAA AAGGACCACA
18951 ATGATCATCG AGTTTCAACC CCCCTGCTAC GTGCAGGGTC GCCAACCACC
19001 AGACCAGGCT GCCCAGAGCC ACATCCAGCC TGGCCTTGAA TGCCTCCAGG
19051 GATGGGGCAT CCACAACCTC CTTGGGCAAC CTGTTCCAAG ATGTTAGCTT
19101 CTCTAACATC TTACCACAAC ATAATAATGA AAGAATATTT AAAAAATCCG
19151 TGATGGGTAG GAACTTCCTG GCTGCAGCCT GTGCTCCAGC CCTCAGGTGG
19201 TGGAAGGAAA TAATCATTTC TAGTTGGAAT TTTCATTTTC TTTTTTTTTT
19251 CCTCAGCTTT CAAGTAGGCA AACAATTCAC TTGTCTTCCA GAGCTCAAAT
19301 CACTGCTGTA AGTAACAGTT TTCATTTGTC ATTTTTATTT CCTCTGTGAG
19351 ATGGTGATAT TTATAGCAAC ATTCTCGGTC CCTTGCTTGG ATGACTTGTG
19401 ATTGCTACGG TTCTTGTAAC AGCATTGCCA GAACAGTAGC AAAAGGCAAC
19451 TGCTCCAGCA CCGGTTTTTG TAAGCCATTA CCTGTAGACA CTCATCTGCC
19501 TACAGTAGTA TGAGTCAGTG GAAATTACTG TTTATAGTTT ACAGACCACA
19551 TGTGACACCG AGCATGTTTG AAAGCAAAGT CCCTGCCTTG AATAGCTGAG
19601 ATTTAAATTA GCTGAGGCAG CAGAGGAGGA GGGAGGGCAA GCAAAAGCAG
19651 GTCTTGCCAA TCCATGGCAT GGTGCCTAGT GATAGGTCAC CAAGCAGGAA
19701 AGAAAACCCA ACCCTGGCTT CATTATCAAC ATCAGGCCTA TGCTCAGGTG
19751 CCCGTGACTT ATTTCCTGAG AAGTCTCAAA ACACGACCAA CACCTGTTTG
19801 AACTCCTATA AGAGAGCTTA GCGCCTGCTA TGATGCAGGT AGGATACTGA
19851 TGTTTATTTT CATTACTAGT GCGTGACACA TCCAAAGAAA TTAGCTGTAA
19901 AATGTCTAGT ATTCCTGCAA AAGAACGTAA CAGATCCTGC ACGTGGCAGG
19951 TACCATGCAC AGATGGCACC AACGGATGGA TGCTGGCTTC CTCACACGTT
20001 GAGTTGTTGT GGAGTTGCTC TGATGAAGGG GAGCAGCATT TGTGAGCATT
20051 CATTCATGGA GCTGGAGTCT CCTAAGCAAG GTAACGAATG CAAAGGTGGG

CR1-GG

20101 AGTGTTCAAG TGGCCTAGGC AGGCTTGGGC AGTGAGCCCA GGTGAACCTC
20151 ATGAAGTCCA ACAGAACCAA ATGCAAGATC TGGCCTCTGC ATTGAGGCAG
20201 CTCCCACTAC CAATACAAGC TGGGAAAGGA CTGAGTGCAG CCCTGCTGAG
20251 GAAGACCTGG GGGGTATTGG TGGTTGGGAA GCTGGACATG AGCCAGCAAT
20301 GTACCCTCAC AGCCCAGAAA GCCGACTGTA TCCTGGGCTG CATCAAAAGT
20351 AGTGTGGCCA GCACAGCAAG GGAGGTGCTC CTGCCCCTCT ACTCTGTGCT
20401 GGTGAGGCCT CACCTGGAGT ACTGCATCCA GATGCGGAGT CCTCAGTACA
20451 GGAGAGACAT GGACCTGTTG GAGCGCATCC AGAAGAGGAC CACAGAAATG
20501 TTCTATGGAA TGGGACACCT CTCTTACAAG AACAGGCTGA GAGAGCTGGG
20551 GCTGTTCAGC CTGGAGAAGA GAAGGCTGTG AGTTGACCTG ATAGCAACCT
20601 GGCAGTATCT AAAGGGCAGC TACAGGAAAG AAGGGAACAG ACTTTTTAAG
20651 CAGGGTCTGG TGTGATAGGA GAAGGGGAAA TGGTTTCAAG CTCAAAGAGG
20701 GAAGATTTAA GTTAGATATA AGGATAAAAT TTTTTACAGT GAGGATGGTG
20751 AGGCACTGGA ACCCAGCGTT GTGGTTGAAG CCCTGACCCC TGAGACTTTC
20801 AAGGCGAGGC TGGCTCAGGC CCTGGGCACC CTGATCTAGC TGTGGTGTCC
20851 CTACGCACTG CAGGGGAGTT GAACTAGATG GCCTTCAGAG GTCCCTTCCA
20901 ACTGCAAAGA TTCTGTGATT CTAGTAAACA GAAAGCGTAC AGAACAGTGA
20951 CCTAGTCAAA AATTGACTAT CGGAAGGGCG TGTGGGTAGA GGTAGGCAGG
21001 CAAAACTGTA ATTAGGTCAA AGAAAAATGA CAGGACAAGC TTATCTAATA

*Fig. 1-8*

```
21051 TTTGGGATGT CAGTAGCCAA ATGCCAGTAC AGAGGATGAA CAGCAACCAT
21101 TAAGAATTTT TTACACAGGT AATTCTGACA ACAGAGAATT TGGGGAGTAA
21151 TAATTGAAAT ATTATTGGTA AAACGGTATT TTTAAAGAAA AATCAAGGTG
21201 AGAGCACAAT AGCTACAACA TAGACTACCC GCTCAAGAAT AGAAGGAGCA
21251 ATGTTTTGAT AATAATAAAG TAGCTGTTGG AAAAGCAGCA AAATTGGAAG
21301 CAAACAGTCC ATCAAGTGCT TGCAATAGGT TATGTAAGTT GTGTGAATGG
21351 CTCTAAGTCA GCCATGATTA CTAGGATGAA TCTGGTTAAG ACAAACATGT
21401 ATGGAAGCCA ACCATGAAAC CACGGTCATC ATTCTGGAGG AAGGAAGAAT
21451 TATGCAGCAA AATCAAGGCA TTCCTGCATA TTTCAATAAT TCAGAGCTAT
21501 TAAAAAGCTC CCTGTCACGA TAATCTTCAG AAATAATGTG AAAAAAATAC
21551 ATAGCGGAGC AAATTTTCAT TAGGAAGACA ACTAAATAAA CACAAAAAGT
21601 AGATCAAACA ATGGCTCAAC AGAATATTTA AAGCAGTTTC TTTGCTTCAG
21651 CTGCCAAAGA GCAAACTACG ATCAGGTGCA GCTGACTGAT AGGAGCACAA
21701 AAGCTGATTC AAGGGTATCT GCCCAGACGA CGTGTCGACA TGTTCTGCTC
21751 CACTCATTAA AACAAAAGCA GTCAACTCAA CTCTGAAGGC TAGTAGTTGA
21801 ATAATAATAA TAAAATCAAA ACCAAACAAA CCTTACCAAT CTCTAAGACA
21851 GACAAAACCA GTACTTAAAC CAGGGAAGGG ACAGAACTCT GGATTCAGAG
21901 ATTAATCAGG TGACGTGGGC AAAGATACAG CCAGAGAATT TAATGAGTTT
21951 TTCTAACTCT ATGAAAATAT GTGTTGAGAA AATCCACTGT TAGTCAATGG
22001 GAAGAAACAT CTGTGAAGAA CAAAGCAAGC AAGCACAGAC ACAACTGATT
22051 TAAAAACTAT TTTACCCACA GAACATAATT TTTCATACTG CAGTCAGAGG
22101 TAGCAATAGC ACTAGAAGTT AGGAAAAAAA CGTAGGCCAA GTAGTCAAAG
22151 ACTAGTCACA GCTGGCAGCA TGAAAGATAT GCAAGTAATT TATCCAGTGC
22201 TTAGAGGCTG TGGTTATATA AAGCAAATAT AACCTTTAAT CAACTATAAA
22251 CCAGGCAGCA TTGTTTAGAG TACATAGGTT GCTCTGAAAG TAACGCCTCC
22301 TATTTATTTC CACAGAAACT ACAACTGATA CGAAGAGCAT AACAACACTG
22351 ATAGAGCATA TTCCCAGCTA CAAAACACTA CTTTTCAACT CAGTCATCAC
22401 GATTAGCTCT GCATTTTTGC CAGCGATGAG TGAGAGCCTG CATGCTACGC
22451 GCACAGAAAT CTGCACCAGT GGAGGTGCCC CACCGTCACT GGTGCTGAAA
22501 TGCACCACCC ACTGCCTCAC CGCGCTCACA TCCACTGCTT GGTCTCCATA
22551 AATATTCAGC AAGCATTGAT GAATGTCAAG AGGTGTAATT TTTTCTGTGT
22601 GGAGGAATTC AGTGACACCT CTGCTTCATT TGCGCTTCCA GCCAAATGCC
22651 ATTCTGTCAT GCTGCCTCTC TGCTGCCATC TGTCGCACAG CCAGAGCACA
22701 TAATGGAATA CTGGTAGGAA GGTTCAACCA CTACCGCCAT ACCACCAATG
22751 ACACCTTGGG CTGATGATAT ACTAAAATAA ATACTACCTT TGGGGTAGCA
22801 CTCATAGTTT AGGTTAACCC TGAAAACTGA AGTAAATGAC ACCTCCCCCT
22851 ACCTCCCGCA GCCATTTAGC TACATCTTCT GGGATAACTT AGCTAGGAAT
22901 CTGTGATAAT ATTTCAACTT ATCCTCATTG TAGAAAAACA GCAGAACAAA
22951 AGGTTATCCT TAGAGCTGCA GTTCTAACCG GCAGTGTTTA TTTGGAATAT
23001 TTCTAAAAAC AACTTGAAAC ACCAAACATT AATGTTTCCA TTTCCATGAG
23051 CAAGTAGCGA GATGCAAGTT TAAAACATAC AGTATATTTT TCTACGTTAA
23101 AGATAAGGGA TTACACAGTT AGGTTTAGGG AAACCCATAG GACAAACTGA
23151 CCTACGACAA CAACAAAGAA ACGCATTTCC TGAGAATTTT AAGATTGCCA
23201 TAAGGACTGT CATATAGGAC TGTTATAAAG GTCAATTAAC AAGTAATTCA
23251 GGCAGTAGCT TCAATCCTCC AGGTGAGAGC CCTGCCAGTG CGTGGCTCGC
23301 TTCTGAAGTG TTCACCAGAG GCAACAGAGC AAAGAATCCT GCTGCAACTA
23351 AGATCAAGTT TACAAACCAC AGTAACTTGC ATCTACACTT GAATTTCCCC
23401 CGCTTGCCCA CAAAGGTCCA CAAAAAGATT TGCAGCCCCC TGAATCACAT
23451 TCACATTTTC CAGTGCGAGA CCGAAGTAAA GCTGCAAAAC TGAATGACTT
23501 TGGAAAGAAC ATTTCATTAT GTTAGCAAAC AAAAGCTCAG CACCTTGCAG
23551 ATCAAAGAAT TTGTATTTAA GTGTTTTGTT TAGCTGTCAA ACGTAGAAAC
23601 AAAAGTCTAA ACAAAAGTGA TAGTTTTGAA AGTAACACTG AAGAAATACT
23651 CAAGAACATA ACTGATGTTG TACATTTTAC TTCATTTAAG TACAGCAAAT
23701 TTCACCCATC CTATGATTTA TCGAGTACGC AAAATATGTA CATAGAGGAA
```

*Fig. 1-9*

```
23751 ACCAAAACCC ATAAAAAGAC AATCATCTAT GTGCATATGC GCATGTAACA
23801 TATGCACATG AAATGTGCAA TTTTCTTTTA ATGCAAGTTA AACAAAGCAT
23851 ATGCACAACA GAGTTGCACA ACCATTACAG AACAGAGTGT TCTGGGTATC
23901 CTCATGATGT TTCGCATCTA CAGCCAGTGC AAACTTACAA GGCACAAACT
23951 CAGTGCTGAC ACCGTAGTGT TGTAAGTTCA GGCACATTTC AATTTGTAGT
24001 TCTTAAAGAT AATAATCAAC AGAAGTGCTA CTTCTGTACT AAAGTGCCAG
24051 CCTCTTCCCA AAGATTAAGC ATTAAGTTGA TGTAACCTGT ACACAGTAAT
24101 GATCAGCGGC GTTCGGATTT AACCTAACCT ATCACTGCAA GGTCTGTGGC
24151 TATATCGTGC TATGCGCTCC ACACCTCTGA GGGTATGCTG CTTCCCAAAA
24201 TGCCTCCCTC ACACTCTTCA AAGACTACCC ATACCTCGCC AGCCTTGACG
24251 CGTGGACTCT TACAGGTTAC TACTCAATGC TTTTTCCTAA CCTTAGCCAA
24301 ACCTCTGATA AAACCAGACT TAAAAAATCA GCCATCGGGA AATCTTTCGC
24351 ACACTTGCAT TTAACAAACC TTTGCTCAAT TGCATAGTGA CATGTGTATC
24401 AGCTAGGAAA GAATTAAAAA CAAAAGCTTG CTGCTTAAGG CAAAAATTTT
24451 TAACACAGCA CAGCAGAAAA AGCCAAATAC CGGGTTCATC AGTATTTAAA
24501 CAAAGCACTG GCTCATACAG TCTTCTCCTC ACAGTGTTTT CTTCCTTACT
24551 TTCACAGCAA ACACACACAG TATGCTCAAT TAGCAAATTT TGTTGCATTT
24601 CTCTAAACGG AGTGATTAAC ACATAGGCTG ACTGCTACTG AAAACACCTG
24651 ACAAATCGCT TCTCTTGCAC CCTCAAAAAA GGGTTTCTTT TTGAGCCTAC
24701 CAGAAGTTGA AAACCCGCTT GCGCCCAGGT CTAATATAAC AGCTAAAACT
24751 GATCATTTAA AAATTACAAA TATTTACCAT GAGTTGCCAC ATCACTCTGC
24801 TAAAATTGTG TTTTCCGTAT TATTTTCCAA TAGAAGACAT TTAATAGACA
24851 TCTGAAGAAA ACAATACAAT ATAAAAGCGT AAGGGTCTTT GCAAACAGAT
24901 CTTCTATTCC TTCTGCAAAG TAAGAAAGGA GAGAGTTTAT TGGCATTTAT
24951 TTGCAGTGCC ATCGATAAAG ACACGAGAAT ACTTAAGAAA GCAAAAAGTT
                                         R gene exon 9
25001 CTAGTGATCC ACAGACATCT TTGGCTTAGC CTTCCTGACC AAAGTCTTCT
25051 GTAAACTTCT TTAACTTCTC CAGGTCCTGC TCATTAACTG TTGGCTTTGT
25101 GCTAGCTAGC GACCTGAGCA TATCGGCCTG TGAGAAAGAA AGCAAGAAAA
25151 CATGCATTCA GAAAACGTAC CGCTGCTAAC AGTATTGCTG TGAAGAAAAG
25201 TAAGCTTTGA AAAGCCTTTT AAAACAAGTT GACTGTAGGA ACTCTTATTG
25251 AAACAAAACT TCGAGTAAGC CTGAACATTT CTGCACGTGG ACCACTTTTT
25301 AACCTCCTGA CGATAGACAA TTAGTGAGTT TTTACAGGAC TTAAGCCACA
25351 ATCTGAGGTT CAGCTTTAAA ACAATTCATC CATTCAACAA GTGTTATCTA
25401 CCACTGCTTA CTGCAACAAA CTGAGCTTCC CATCTTACAG ATTCGTATTC
25451 CAATTCACTT TTAAGGACAT CAGGTTGAAG TGGAAAACCA TCACACGTTC
25501 CCACATATTC CAATGCCCAC CAACACAGAA TACTTCATCA TTGATCTCCA
25551 GCAAAGTTTT ACTGCTCATG ACTGCTAACT TCTGTTTCTT CAGCTCAGTC
25601 AGTTTTGTAT ATTTACATTT GGCTACTAGA AAATGGAGTT CAGAAAAAAA
25651 AACCACAGAG GTATGAACTC AAATTCAGCA GTTAAGAAAC CTTATTAAAA
25701 AAAAACGTAT ATAAAAAGTC CTGGCCAAAG GCAAAGCGAG GAGCTGCTCA
25751 ACACCTCACG TTACTATAAA AGCACAGGGT TAAGTTAAAG TCAGCATCAT
25801 GATTTTCTAG GCTTTCTCAT CTCATCGTAC TACAGACATC CTACTTAGAA
25851 AGAATTCAAG TCTGATCTTT TTAATGACAA GAACTGATTC TGGACTCTGA
25901 AATAAGTCCC TGTGCAACTG TAGCACATCA GAGTCTACCT TCCATTAGAA
25951 GCACTGAAGG AATTGTATTT AATTCCAGGA AAGACTGATG AAAAATCCAC
26001 TTAGTTTACA CAGGCAGAAG TTTTAAGGCA GGCCTGCACT TGCTTGCATC
26051 TTTTCATGCC TCCTCCATGT GCAAATATGC AGATATTTCT CTCCTCAAAC
26101 TAGTGATGGT TACATGTGCA AAGCAGTGCA CTCTACTTTA GAGGGTTTTT
26151 GATCCCTATG CAACACACCT TCCTTTCATT CATTACAGAA ACGTTTGCAC
26201 ACAGGAATGG CCATCAGCAC AGATCTGATA TCGAGTCCTT CCTTCAGACA
26251 ATGCAATTAC ATTCAGAACC TTTTGCTGCT TGAGGGTAAA ATATACGAGT
26301 GCTCAATGAT TTGTAACCTT TTAAACAATG TATTTAAACT TCAATTTCTC
26351 TCAAATATGA TGTTTTGGTC TGTAGACAGA AGCAAATATT TTAACATATA
```

*Fig. 1-10*

```
26401 CAAAAAATTC CAGCTGAATG TTAGCAAGAG CTGGCTGCAT CATCTGTGAT
26451 GAAGTATAAT CCAAACTACC ATTGCATCCA CCAGCTTTTT ACATTGCATT
26501 GGTTATGCTT GCATTTCTTT TGTGGGCAAA ATTTACCTAC AGCATGTTAT
26551 TCCCAGTTTA CACTGAATAT AATTTCCCAC TTCTCGATGT CAATAATAAT
26601 GCTACAGAGC AACAGGAAAG TAACATATCG TGGGGCAGGG ATTCTGAAGG
26651 TTTTAAATGA ATAAAAGAAA AATTAAAGAA GGGAGGAAGA TTCAGGTGCT
26701 GTCTATACTG CATGCCACTA GACAATAATA AATGCTTATC AGGGATGGAG
26751 AGCTGGCTCG CTGATAAGCA TGTTGTATTG TCATGCTGTG TGTTGCGATT
26801 AAAATGTCAT CCAGTATGTC CAAGCATGTC TAAAAACAAA GGGCTCAGCC
26851 AATTGCCTTG CATGCTGGCT CTAAAATGTC TTGAGTATTT TCAGGGTTCT
26901 GCAAAGCAAG AAACACCACC AAAAAATAAA AAAATAAAAA CAAATACCCA
                        R gene exon 8
26951 CCATGGAAAC TTTAGGCTCC AGTAATTTAT CCCCTGGAAC ATCCATCCAT
27001 GTCATTTCTT CAGCTTCAGG ATCACCTGGA GAGCAAGGAG TGAACAAATC
27051 TACCATGATA TTTGGATTCG TCACTGATGG TCCTTTTACC TAATAAATGA
27101 ATACATAAAT AAATAAAATA AACAAACTGA AGCTGAACAT CTTTAGAGCA
27151 AAAGCATACT CTTAATTTTC TGTACATGCC CCACCCGTTT GGAGTTGTGT
27201 AGTGAAGTGG AATTGTGTAA AGGTGCTGGC ATCGTTCACT TTGAAAACGC
27251 ACAGCAGTAG TCAGATACTT GAACTCATAC CATGTCAGAA CCAATGAGCC
27301 TTTAAGGTAG GAATGCTTGT AGAAAGCTAA TGTGCCAGGT CTACTGTTTG
27351 GAGAAGACCA CTCTCTTCTT AGTCCTCAGT CACTTTGGGA GTCCATTCAC
27401 CACTGGTTAA CATTTCTAAA AAATTCTCAG TAGTTATTAC TGACTGACCC
27451 TCAAGTTGGG CTGCCATGGG TGTCCTTTTA AGCTTCCACT CACTGCACTA
27501 AAAAGTTCCG GGCACCTTTT CTGACACAAT CTCTAACAGC ACTTGATAGA
27551 AGATGGGGCC ATCTAGTGGA GGAACAGAAA CCATCCCTTC TTCCAGATAC
27601 ATAGACAGAA CCTGAAAAGC TCCATCAGCT GCCTCTTATC TTTTTGCAAT
27651 GCATATCTCA GACCTGTAGT TCTACCATCC TTCCTTTGTC AGTCACTGAA
27701 GTATCACACA TCCCCATGAA CACAGAACAC ATGCAAAGGC GAAAAAAGAA
27751 CTGCTTTTAA CAGCAGAGAA CTGGATTTGC TGTTTCAATC TGCTTTTAAA
27801 GCACAGCGAA GAAAAGCATG GATTATAATA CTGGAAACTC AACTTGGACA
27851 AACCGCTATC AATAGGCTGG AACAAGCAAT GGGTTACAGT GAGTTACAGA
                                          CR1-GG
27901 AATTGAGCAA AACGCTACAA ACAGGAGGCA GGGGCAGATG GCGATTGGGA
27951 CAAGGGGGAA TAGTTTAAAC CAACAGAGGG GAGATGTAGG TGAGATGTTA
28001 GGAGGAAACT TCTTACTCAG AGGGCAGAGA GGCGCTGGCA CAGCTGCCCA
28051 GAGAAGCTGT GGTGCCCCAT CCCTGGAGGC GCCCAAGGCC AGGTTGGATG
28101 GGGCCCCAGG CAGCCTCAGC TGGTGGGGGG CAGCCCTCAC CATGGCATGG
28151 GGTTGGAGCT GGGTGGGCTT TGAGGTCCCT TCCAACCCCC AACCATCCCA
28201 TGATTCTATT TAACTGGGAC AAACTGCTAC TATGGAAATA GTTAATAAAG
28251 CAAAGGTTTT TCTTATAAAA ATAAGAATCT GCATCCAATT AAAGCACAAA
28301 CAAAACAAGT GGAATAGACT TGCATCAGAA CACTCAAAGC ACGGTAGGCT
28351 TTTTTTCCTT TTTGGCAAAA GAGGTAAGAA TTGCCTTTGG CTGCTCTGCA
28401 AACTGTGGTA ACTGAGATTA TTTCATTGTT CTGTGGCAGG CTGAGGCACG
28451 CCTCAGATGT CTGCAAATTT CAATGAAAGG CTAAAATGTG ACAACCCATT
28501 GGCCAGAAAT GCCATCATTG TATAAAAACA ACAATGGATA AATACTTCAG
28551 GCATCACTGC TTAAGGGAAG GAATAACCCA GAAAATCCCT GATATATCAA
28601 AATAGCCGCT TATTTTTTAA GCAAATACAG TTTACAACAG CTCAAAATAC
28651 TGTTTCAAAA TGTTCTTTGA TTTTAAACTG GGAAAAGTTC ATCAAAATAC
28701 CTACCAAATA TTCTTCCTCA CCACCAAAAT TACAGACTGC TGGCGTATTT
28751 TAACAAGTTG ATAAGGCTTC CTCACTGCAA GCACTGGAAC TTTAACAGAT
28801 CTCTTACATT CTGAACCATA TTGTATTTAA GCGTTCCTTT CCCTTGGTGT
28851 CTTAAGCTGA ATGTGTTCCT TACAATTACA TGGAGAAAAG TGCCCACCTT
28901 CAGTTCACAC TGACTCTAGC TGTTCAGCTG AGGGCTCTGG ATGAGTTACT
28951 GGTAAAAAAC TAAGAAACTG TCATCATAAC TCATGAGCAA CAACTGCTGC
```

*Fig. 1-11*

```
29001 CAACACAAGT TGCGTGTATG ACACGCAGAG CAATAAAATG AAAGCTCTGA
29051 AAGCTTCCCT TTCCAGAGTC AAAAGTCCCT GCAGATAACA AGAATCCACC
29101 TTCACCTGAA GTTTGTGAAT TTCTGTGAAA ACAAAGTCTG CAGTACAAAT
29151 GTAAACAGAT TATTTTAGTT TCGCTCTCTA AAACCAAAAC AACAGCAAGA
29201 AAAAACTAGA CAAGAAAAAT ACTATCATGT TATTTATAAA ATGTAGGCGA
29251 AACTCCAAGA TAAGCAAAAA AAAAAAAGTC TTATCTATCT ATAGTTACAC
29301 TCTTTTTAGA CATCAACTAA GTGTAAAGTA GTTTTCACTC TACAGCAGCA
29351 TCCATAAGAT GTTCCTTGCT GCCCCAGCAA TGACAACGAC CTTACTCAGC
29401 CGTCTTGCAT CTTAACTACT GTGACAAGTA ACATTAGGGG ATTCAATTTT
29451 TTACTGGAAT CTTAGGATAA TCTTAATTTT ACAGTTTGAA GGACATCCTG
29501 AGCAAACAGT TGTGCAGTTG TAATTCCTCT GTTCCCACGT AGATAAGGAA
29551 TACGTTTATT TACACACATG CGCTAGAAAA ACAATTACGT AATTTGATAT
29601 AGAAGAAGAG CACCACTGTA AGACTCCGAT TTAAGTTGAA CTCCAAACCG
29651 AATGCTTTTA ACAGCAGTTA TAGACGTGAA GATTGATTAG AGCTTGGATT
29701 ACACAACATG AATACCTAGA GATGAGGTGC ATCAACTTAT GGCAGGAGTA
29751 CTCCTTTGGT AGGTAATGAA GAACAGCATA CACACATCTG TAAGCACACG
29801 GTATTACCCC AAACCGAACT TGGCTTACTT ACAACAAGTT TTCAGATCAA
29851 GTTAATTCTC AGAGTTGAAG CAATATGAAA AACGTTTTGT TTTTACTTAC
                             R gene exon 7
29901 TTTTTTAAAG TGAGTAGCTG ATTGCACTTT TCTAACAGGT TGCATCAGTG
29951 CATCGCGTAC AATGATGCTT ATATCTGCAC CAGAATAGCC ATCGGTTCTT
30001 TTCCCAAGCT CCCGATAATC TGCTTCTGTT AGGAGATTGG GAGTCGACCC
30051 GAGGTGAAGT TTGAACATGG CAGCCCTGGC ATGGTCTTCA GGTAAAGGAA
30101 TATAAATTCG CTTCTCAAAC CTGGTTTCCA AAGATAAAA GCACTGGCTC
30151 ACGCAGGTGC ACGATGGAAA GAAGTTTATG CAAATCAGTA TATACTTTGT
30201 TTGTAAATGA AACTGCTTTT TTCTTATGTA TTATAAATGT TTAAAAATAT
30251 ATATCTCAGA TATTCTGCAG CCTGTTCTCA TAAGTAATAC CATGGCTATC
30301 ATAAGCTAAC ATCTACAATT TAACAACGAC TTCCTTTTTA TGACAGAAAG
30351 TCTCTTCAGA CTGTAGTTTC TCCAGGTTCA CTCCAGAGAA GTTTGTTTTA
30401 AAAGAAAATA ACTGAAGGAA AAGGAGTCTT TTAGTTTTTA AGTACATCTG
30451 AACAGTTTTC ATAGAATCTT AGAATCGCTA AGGTTGGAAA AGACCCACAG
                                                      CR1-L
30501 GATCATCCAG TCCAACTATT CACCCATCGC CAACGGTTCT CACTAAACCA
30551 TGTCCCTCAA CACAACATCC AAACATTCCT TGAACACCTC CAGGCTCGGT
30601 GACTCCACCA CCTCTCTGGG CAGCCCATTC CAGTGCCTGA TCACTCTTTC
30651 AGAGAAATAG TAGTGGTTTT TCACACTCAA AGAAAGAGCT GCCCGATAAC
30701 ACGTTCACAC AACCAGTTTC TAAAGTTTGT AAGTAGAGAA CGTTGTAGTT
30751 GGAAACGAAT TTGAAGTCTT ACTCTCAATA TAGTTGTTGG TAGGAATGGT
30801 TGATACTTGC GGTGCTTCCT TTGAAGCATC TGTTCTCAAA GAGAGGACGA
30851 CCTCCCATCA GGGAAATAGG ACCGACTCCA AGTTCTGTAG AACACTATTA
30901 ACTTCCTATA GGTAAGTGGG CCCAAGCCAT GAAAAATTAA TTCTGTTACT
30951 GCCACGCTCT ACAAGCTCCT TTAAGTTTTT CGGACAAGAA TGAGAGATAC
31001 TCGTTCACAC TGCAAAGAAT GACTTGAAAT GTTAAGTACC ACATTCGCCT
31051 CTTATTCCTT GTATGAAACT ACACATGCAC AGGATGGAAG CGACCTCTGG
31101 AGGCCACATG GTTTAAACTC CCCAGTCAAA GCACGGTCGA GTTGAATTAA
31151 GTACATCGAT AAAATGACAC TGTCACCAAA AAGGATTGTT TCTTTAGCCT
31201 ACAAAAATTA CCATTATACA GGTTGTATCA TCATCACAAC ATAATCACAT
31251 TTGTCACGTA ACTGTGTTTG TCCTTTGCTG CTCTGCAACT GAAAGATCCA
31301 GCTAATCAGA TACAGATACA AACGTCATCC CATTAGAGAA AGGCAGTTGA
31351 AACGTACACT GAAAGATCAC ACAAACTGTG TGACCAGTAC AGCAAAAACA
31401 ATGCTTCTGC ATTACTTAAA TTCTGTGAAA TTACTCAAGC TATCCAAGGG
31451 TTTGCTAAAG TTGAAAACGA TAGCTCTGCT GCCTCTTACC CTTCTGACTT
31501 GCTTATGTTG TACCTTGCCC CCCATGCTCA CCAGGAGACC AGTCAGCAAC
31551 GAAACACAAG TTTTTTGCTT AGTCAAGTGG AATTAGCTGA CTAAGAGATC
```

*Fig. 1-12*

```
31601 AGACAGACTA CAAGATATAC ATAAGAGAGA ACAATCCACC ACTTAAGTGA
31651 AGGGGATATT TGACTCAGTC CACCTCATGA GACATGCCTG CAAGAATCAA
31701 GTGGATCACT CACTCAAATA GCCTCAGGAT GAACCCTCAC AATAGTTGCA
31751 AATTTCTTAG CATAAACATG AATACATCAA TCATAGGCCA ACATACCTTC
                          R gene exon 6
31801 TCCTGATAGC AGAATCCAAA ACCCAGGGTA TGTTTGTTGC TCCTAAGACC
31851 AATATTCCTT CATTATCAAC ACCAACCCCT ATACCAAGGA AGAAATCATT
31901 TCACCATTTA GAAAATAAAC AGAGACTGCC TGATAATGTT TTAGAACATT
31951 TACAAAACGC AAGGGGGTAA AGCTGCACAT CTTTTCACAT GTAAGCAATG
32001 CATTTTATGC GTAGCTGAAC TCCTTTGATT CTGAAAACTA TTAAACTTAC
                          R gene exon 5
32051 CTTGCATCTG GACTAGAAAT TCCGTTTTAA TCCGTCTAGC AGCCTCGCTT
32101 TCATTTTCAC TTCTTGACCC ACATAGTGAA TCTATCTCAT CAATGAAGAT
32151 AATAGAGGGC TTGTTTTCTC TGGCAAGCTG GAATAGGTTT TTCACTAATC
32201 TTAAAAAAGG AAACAGCTGC AGTTATCTTA TTGTACACAC AAGCAAAAAC
32251 ATGCAACTTT GGATTATGAT ACAGTGACTT TGTTAAGAAA AAGCTAAAAG
32301 TAAAAAATAA AATGAATCCC ACATAAGATA TTAACAAAGC TACTCAAAGA
32351 TACAACATCC CTTCAGAACT ACTAACACAG CATTAGGCTG AGATGCTGAG
32401 TGAGATACCA CAGAATAAGG TAACTTTAGG CTTCCTAGTC TTGTTAACAC
32451 ATCTCATTGT AACATGCAGA GTGGATATAT CAAAGGCGCT CATCACTTCC
32501 AACCCATATA TGCCCATCTT TTATGTCTTC AAGATTTTGT TTGAAAACAG
32551 AATGTAGAAA AAAAACCTTC ACACAGAGGA AGAAACAACA TGTATTATCT
32601 GCAGGGCTAC TGCAACAGAT GAGCCAGAAG GTGACAAGAA TCAAAGTACC
32651 CCAACACTTC AGACCACTTT GTTGTACAAT CACAGCTGGG TTCAGAAGGG
32701 CATTGATCAC CATTGTGCTG CTAATACCTT TGTCCAAACT AGTTTTAAAA
32751 ACAGTCTTGA GTGCTGAAGC TGCTGTAGCA CAAAATACAG TGCATTATGG
32801 TACTTTTACC TGACACTGCA CTGAAGCAAA GAAACATCTA AGGTTTGCTT
32851 TAACAAGACA CATGAACCTT CCTTCCATTT AATTTCTTTA GAGTGTCCTA
32901 TCTAGCTCTG AAAAATTAAT TTCCTCTTGA TAATATTTTC CTGGAACTCT
                                      R gene exon 4
32951 GGAAACTCCA ACTTACTTCT CACTCTCTCC TAACCACTTT GAGACCAGGT
33001 CAGAGGAAGA TACTGAGAAG AATGTGGAAT TGTTCGCTTC CGTTGCAACA
33051 GCTTTTGCTA GATACGACTT TCCTGTTCCT GGAGGTCCAA ATAGAAGAAT
33101 CCCTCTCCAA GGTGTTCTCT TCCCTGCAAG AAAGAAATCA GCTATCATCA
33151 AAATGCTGTA TCAAGAGCAA GTCTATCTTT CTGATGAAGC CTCCCTAATG
33201 TACTAAGTTT TCTGTATGTA CCTAAGAAAC ACCTGTCAGA TCGATCATTT
33251 ACAGCTCAGC TGGAGCCTCT GATATAGCAG CATAATGCTC TTCTCAGACT
33301 CCGCTTACAC TACTCACTTC AACAGCAGTA TTTAGAATGG GAAATAAATG
                                    R gene exon 3
33351 CTGTAATACT GACCTGTGAA CAAGTGTGGA AATTTAATGG GCAAGATAAC
33401 TGCTTCTTTA AGAGCTTCTT TGGCACCTTC AAGGCCAGCA ACATCACTCC
33451 ATTTCACATT TGGTCGCTCC ATAACAATGG CACCTATAAG AAAAGATTGG
33501 ATAAATCACT GATACGTATT TTTCCACTGT TTGCTTACCA TATATTTGAA
33551 AAAAGAAATC CACGTGTATG TTTACATTAA ATAAAAACGA GCCATTTCCA
33601 CACAGATTTC AGCATCAAAC AGTGCTACTC AAATGGATAT TATTTCTACA
33651 GAGATTTGGC AATCTTTTTT TCTTTAACCA CAATAAACCA TCAATAAGCA
33701 GAGAGTTGTT AGAAGTTCTG CAGTGTGCAA ACTAACTCTG CAACTGCGCA
33751 GAAAACATAC CAATGGCAGA TACAGAAGAG TACACTTCCT AAAAAGAGAT
33801 CAACATGACG TACACCCTGA TGAAGCAGGC CCACTACAGT AGGATGCACA
33851 GGAAAGCATG AGCAAACACC CTGCTGTGAG CACTCAGTGT AAAAAGAAAG
33901 CCTGGAGTAG AGACCAACAT CAATCTGTAT TGCATCCAAA CCAGAAGAGG
33951 CAAAAAAGTG TCTCACTAAG TTGCAGAAAA TGTGAACAGT TCACACAAGA
34001 CGGATTACTG TGGAGAGAGT AAATATGTGC ACTTTTTATT TTCCCCAATA
34051 TGTCACCATT ACAAAGGAAA ATCATGGAAT GGTGGAGGGT GATGGAGGCC
```

Fig. 1-13

```
34101 CAGCCTGGGG CCCCAATACA TGCAGCAATG GACAGTGAGG TCACCGACCA
34151 AGCGGTTGTG ATGTCAGCAA TGGAAATGAC TGTGTCCTCG CTAGCCCTCA
34201 CTGTACAGAT TTGGGATCTG GCAGAGGCCA GCGTGTACTT GTACCTGGAC
34251 TTCTACTGAG CATAGCTGCG AGACTCGGAG CACTGAGCGA GTTGGTTGAG
34301 TTGTGCTGTG GGGCTGCTGG CAGCAGTTCT TGGTGCCCAC CCCACAGTAC
34351 CACCAACGTT TCCCCCAGCC CTGCCTGTCT CAGGCAGCTG GGGCCACACA
34401 GGGTGCACTT GTAGCAGCAG AGGTGAGTGG TGCAGGACAT GGCCTCTGCG
34451 GCGGCTGGTG GGGAAGTGGG AGGGTTTGCT GCTGAGGGAC CAGGACATCA
34501 CAGCTGCCTG CCCATGGGAC GAGTGACCAT GGCCTCTCTC TCTCTTTGCA
34551 GTTCGTAACA CCTTCTGCCT GCTGCAGTAC CTGTGAGGGG AGCAGCTTCC
34601 CGACCTCAGC TCTCCCAGCC CACCGCACAG CCCGGGGCCA TGGACGTGCC
34651 ATCTAACTGG ACCTGCCCCA TCTGCGGGCA AATTCGGGAG GATGTCACCT
34701 ATGTGACCCC CTGCAAACAC CAGCTTTGCT ACGGCTGTGC CATCTGGTGG
34751 GCAAACAAGA AGCCGAGTTG TGCCGTATGC GGGCACCAAA TCACCACCAT
34801 CCGATACTCG GTGAGGTCGG ACGACGACTA CCTCGAGTGT GCTGTCCCGC
34851 AGCCCGCAGC ACACTCTGAT GATAGCCTGC AGGATGAGCA GGGGCCTGCA
34901 GAGCCGGTGC TCATCCCACC TGAGCACAAC TTCCCTGCCG AGGTCTGGGC
34951 TGCCTTCTTC AAAGAACATC AGGGAGACCT CGAGCCCCTG CTCCACTGGC
35001 TGCAGGAGGA GATCCAGGAG GCGTCCAGCA GTGACTGGTG GGAGGTGGAA
35051 GTGGGACAGT GGACCACTGT CAACTTCCTC TGCGAGCACG GCCTGGACGA
35101 GGAGGCCTTG ATGCGGGAGC TGCAGCCGAT CACTAACGGC GATGTGCTGC
35151 CCTTTGTAAG GCAGCTCATC AGCACCGCTA CAGCCCTGTA CGGCCCAGCG
35201 ATCCGCCGCC AGCTCGACCA CCAGGAAGGC CGTGCTGCAG GACAGCGGGA
35251 GGACAGCCCC GCAGCCAGCC CCAGCACCAC CACCTCCCAT CAGGAGCCTC
35301 CTGCCTCGGG CCTGGGCCAC TCCACCAGCC CCGCAGGGCC CAGCACCGAG
35351 GAGCTGCCCG GCAGCTCTAC TGGGGGACCC GGGCACCCCA GCACCACCAC
35401 CGCGCCCTCA GCGGAGGAGT CGCAGGAGGA GCCATGGCAG GCGGTGGCAG
35451 CGGGCCCCTC CGCCCAGGGC AGGGACCGCT CGTGTGGGGG GCCCCGGCGC
35501 CCCCCGAAGA GGAAGGCCCG CAGCAGCCCC CAGGCCTCGC CCCCACCTCC
35551 CAAAAGGCGG CCCCGGCGGC GGCGCTAGGC TGGCACCGCA CTGCCGTCAG
35601 AGCACAGCGC CAGCGGGCTG GGAGGCCAAC ATCTACCTCT CGGCCTGCTG
35651 CTTGCTGGCA GAATAAACAT CAGTTAAAAC AAAGAAGAAA ATGTCTCTGT
35701 GTTATTGACA AGACTCTTGC TGTTGCTGTC CCTACCCATG CTGCTTTCTC
35751 TCTCTTCCGG TCCTAGAGGA GAGAAATGCA ACTTTATTTC CACCATCATA
35801 ATTCAGCATT CATGACAGTA CTAACAAAGC ACACATAGGC TCCAAAAAGC
35851 CGAAGATGGA CCCCTCATGT TGCTCTAATC ATAATCCAAC CACCAGGACT
35901 TGGCTAAATT CCTCTCCTAT TGCCAAGCTC TGGGCCACAG ATTACTTCGT
35951 TTGATTTTAG CTGCTGAGCT GTGGTGTCCC CCTCCCTTCA GACTTCCCGT
36001 TAGTCAGTCT GAAGATAAAA ACTCTGTTAC CAGATGACTT TTAGATGGGA
36051 CAGCTCACAT CTGAGCTAGT GACCCAGCTG CACATTTTGA AACCCTACTC
36101 AAGACAAATC CAAAAGGCAA GAGAAATCTT CCCAAATGAA TTAATGCCAA
36151 CTACCCCAAT GCTTATCTTT CTGTACTCAA GCACGGTGAA CTGTTCAGTT
36201 GCCATTTTTC TCTACAAAGG GCTTTCTATT AGTTCACAAC CAGTTTCTGC
36251 TAGCTATTTT CTTGTCACTT TCCCCTTGTG CCTTCAGAGC TCTGTGAATT
36301 GGTTGATGGC CATTTTCTAC AATGGAAAGT GTACCGCTAC TCGTGGCTAA
36351 CAAATAAAGC AAGTGACATT TGTTCACTTT TTGTCCATCT CCTTAGAGAT
36401 TTTTACTTTT CCTGCACGCC TTTCTCATCA GATAGAAAGG AATATTTTTT
36451 GCTTGCAATC TATATACAGG AATCCAGCCA CTCACTTTTA ATGCCCTCAA
36501 TACTTTTGCT AGGTTGATTA CAACTCAGTT TTTCCTGTAA CCAGGCTCCA
36551 TCACTAAATT AATTAGTAGG ACAAGTAGGA ACATGAGATT AGTTCCAAGC
36601 TATCAGTTAT GTGGACCTGG CATACTGTGG TAATTTAAAT TAGCACACTG
36651 TAAGACATTA CCCATACCAG GAAACAAATG GAACAGGACA TCGATCATGG
36701 CTTCCTCATT TTGTAGGTGT AAAAGAACAG CTGGAAGACT AAGCCAACAG
36751 AGCGCAAAAG GTCTTTAAAT ATCAAGCTAA GCCACTTCTT TTCTATGTAA
```

*Fig. 1-14*

```
36801 AAAACTACTG CTAGCTGCTA TATATTGCAT CACTGGATGT GTACAGCACG
36851 TTATTTCAAA AACACAAACA ATTATGTTAC TCAACTGAGT AACACCCCTT
36901 ATCACTGCAA CACGAGGAAA TCCCGCCTGT TGCTATGAAC AAACAAGAAT
36951 CCATCTTCCC GCCTTATCAA CTTGAGTTCA AGCCTTCCTG TGAAAATGGT
37001 CCTGCTTATA CTACGTACTT GGATGACATC TGTTACTTGG ATGACATCTA
37051 TTGCCTCTAG GCAATAATAT GTCAATGCAC ATAAGAGTAA AACTAGCACA
37101 GTCTAACAAA ATAGCTATCT GGGATCTTGC AACTACTCCC TTTGGAAAAT
37151 GTTTTCTTGA TAAATGATCC AATTTCAACA TATGCACCAC TGAATTTCAT
37201 GGCATGCAAA CCCATACTGT CATAAAGACT GTACTTCTGG ATGTAAAGAG
37251 TATATACTAG TTGAGCCACC TAAAGACAAC AAGTTAACTG GCAAAACAAA
37301 CAAACAAACA AACCCCCCAA ACAACTAGAA ATTCACTTGA CCAAAGTCAC
37351 CTCTATTTAA ATAAATGGAG GCTTCAAAGT TACCTTGAAG CTGATTCTGT
37401 AGTTTCTTTT TCTCAGGATC CTCTGACTCT CCTTCCCCAT CACTGTCATT
37451 CCTGATTTGG AAACAAGAAA TAAAACGTTG AAATACACTG AGAAACTGCT
37501 GTCCTAGGTC ACAAATCAGA AAGCAGGAAG TAGAAAAAAC ATCACTTCGA
37551 GGAATGAAAA ACCTTATGAT TTTAGATTTT TTCAGCTCTC TACAAGTTTA
37601 CATCCTTGTA GTCTTGTTTT TCTACACTAT ATTCTAACCC CCCCCTCTCA
37651 CTGCAACCAT TTCAACTTCT GTACAGACCC GAGCCCTTCC TCTTAACACA
37701 CTTCTACATG TGTTGACTCA GCCTCTAGGA AACAAAAGCA TCGTGGAAGC
37751 AGCAAAATGG CTTCACTGTA GATGCTGGCA CTTACTCCTT GTCCAGAATT
37801 GCAACTGGTC TTGGTCAATT CCATTTAGTA CTACGAAACT CTCTAGTCTT
37851 GTCAGAATAA AGGAAACTGG AAGTTAAAAG TAGAAAAAAG TAGACGAGCT
37901 AGGGGACAAA TGGAATGGAG ACGTGTAGCC TCATGTTTCC TTCTACTATA
37951 AACCAGCAGA ACACAGTACA GCTCAAAAAA ATAAAACCCA TGAAATGAGC
38001 AGACAATGAA AGAAGCTGAA AATCAGGGGA GGTTTCAAGA GACAACTGAG
38051 CAGTTCTAGC TGTTCAAGAC TACCAAAAAG GGCAACCTCA CCCAGAGACA
38101 CCATTGTGAA ACCTTTCTTC TACCCTAGCA AATACAAAAG AGGCTCTGCT
38151 TGTTCAGGTG GGCTGATTCA GCTCTCAGAT GTGCAAAGTG AAAAACAGAT
38201 GTAATAAAAG GAGAGCGGTG CATAGGCAGG AGCAAGGCAA TAGAGCGATT
38251 CAGACCATCA GAACATCAGC CTATGACAGA ACCTTGGAAC CCCTCATCAA
38301 ATGTGAGACA GATAAAACTC AGACCACAGT AATCATCCAA ACCAAACCAA
38351 CCAAATCTGG ACTTATTTTC TAGTCATTAA GTATTTTCAT GCAGAAGAAT
38401 TGTGTTACTA GGCTCACTGT CATCGAAACA AAAAGTATTA GTGTAAAACA
38451 GCTTTCATTC TTCAGTGAAT GTCCTACAGA AGCATTGAAA GATGTAGCAA
38501 ACAAGCACAA AAAAGCCCAT AATATTAACT CACATTATTT TTCCTTTTTA
38551 AGCCCACTGT CCTTCAGCAT TAGTAGTTAC CTGAAGCGAA GCACTTCAAA
38601 AACACTACTT AAAATGATCT CTGTTGAGAT CTAAGTTGAA TCTTAGAATA
                                       R gene exon 2
38651 AGCGGAGTTC AGGAAGTATT TTGCTTTACC TTCTCCCAAA ACATACCCTT
38701 TTCCATCGGC AGGACCAGAC TCTTTAACTG GCTTTGGTGC AGTTTTTTCT
38751 CTCTTTTTCA GATATTCTTT CAGTTTTTCT GCTCTGTCCA AGTATTCCGC
38801 ACATTTCACT CTAATGCTCT GTTTTGCTTT ATCACCCTGT GTTTCATCTA
38851 AGAGTGTGAA AAGAAACAAT GCGTTGTTAA CAACAAAACA CACGTGCATC
38901 ATTCAGAAAA CATCTTTATG TGTTATCAAG ATACCTCTCT CAGGGCTCAC
38951 CACGCATCCA AATGTTTCAT TTACTTATTT TTTCCCCTAT GCCATGGAAA
39001 GAAGTGACAG GAAAGAAGTT AACGCCTACA AATCAATGGT AAGTAATCAC
39051 TTTCAAATCA AATACACACC TGAACGTTGC TTTGCCTTAA AAACTTGCCT
39101 GAACACGAGT AAGGACAGTG GCACTGGAAG CTTTTTCTGT CAGTCTCTCA
39151 AACTGCTATA TAGTGTCTTA ACTACTTTTC TAAACTAAGC CATTGAGAGG
39201 CTGACTTCTT GTTTTTAGAG ACCTTTTTTT AATCTAAGAC CACTTTATTT
39251 TTCCCCGGCC TGCTAATTTT GAAAGTTGTG CACATCAAAG GAAGAAAAAA
39301 GTCACAAAAC ATCTGAAAAA ATGAGGAGTG GTCCAACAGC CACAGTTCTG
39351 TTAGTCGCTA CTGCAGTATT CCAGATCAGC AATCAAGCTT GAAAATATTA
39401 AGTTCATGCG CTACGTTCCC AAAAGTCCAT CAGTATGGTT AAAAGCATAG
```

*Fig. 1-15*

```
39451 GGAAGTAAGT GGCATGAGTT AATGAGCACA AAACAACCTG TGGATACTAC
39501 TAAGAGTTCT TACAAGAAGG GAGCAGGCAT GCAATATGCA ACTTTTGTCC
39551 TTGCTATAAT ATAACACCTC AGCCAAACTA CAGAGAGCAA GTGTCAACTG
39601 ACAACAACAG TCAGAAGTTA AACGTTGATG TCGACAGAGG AGACTACTCC
39651 GGGCAATATA AAACTTGACT TCATCACCCC ATGCATTACA CTTACATTTA
                        R gene exon 1
39701 ACAACGTGGA TTAAATACTG CACAGCATGC TGGTACAAAC GGAAGGCTTC
39751 TTCATAGTTT CCTGCTTTAT CTTCTTGTGC TGCCTTACTA GCGAGGTCTA
39801 TCGCTTTCTG TAACATAGGT AAATAATTCA AATGAGTGTT GTGTGAGTGC
39851 TTTGTGCGAT CAAAGAGGTT TTTAAGCTGC TGCTCTGACC GCTTCTTGGT
39901 GGCCAGCTTT TCTGCTCCTT GATGTTTACC CAAAAGAGCT GCTGTTATTG
39951 AAGACTTGCT GTCAGTTGTC TTCATCAAAT CCCATCGGCA TCAGTGTTGA
40001 TACTGGAAGT ACACGATTAC AAAGCAATGA AAGCAGCACC CTTTCCCTTC
40051 TGACCCAGTG CCAGGAGTTG GTTTCAAAGA CTCATTATTT GGTAAGCTTC
40101 TCATGAAGGC TTTAGGTACT TGACGTACAG AAGTGAGAAA TTCTAACCAT
40151 CTCTTCAGTG TGCATATGGG GGGGAGCTCA GTGGACAGGA AACATACCTA
40201 AATTATCACA GAAGTTCTAT CAAGGACAAT TTAGAGATGG ATTTTTATTT
40251 GTTTGTTGAG ATAATTTCAA ATACATCTGG TCGTAATCTA AGACACTACA
40301 TCGGCCTGTA GATATATTGA TATTACTGTT ATTCCTTTGA TCCCGAGTGC
40351 TTTTTATTAC ATTTCAGATT ACATTACAGA TTTTTATTAC ATCCTTGGAA
40401 CATCCGTACT GCTTCAGGAC AATTAAGAAT GACAATTCCA ATGACTAAGG
40451 CACGTATGCT TAAAAAAGCC AGAGTTGACT AACGCTACCT CGAACTTCTA
40501 CAGCCCTGTC TGCATATTTC CACCTTCTGC CAGTTTATTT CCCAAAGGCA
40551 GGGACAGCGT GCTCGTGATG ACTGTGCTAA CATCAGGGAG CAAGGTGAAG
40601 ATATTCAACC TCATCACAGG GTTTTCACTA CACACTGCTG TGCACATACT
40651 CTCAACAGTA ACCAGACGCT CTGATGCATC TCAGTCAAAA CCGAGCAGAT
40701 AAACTGCAGC CATCAGAGAA GGAGGAACAA CATTTCTCCT TCTATTGTTT
40751 TGTCTTGCCT TTTTGGAAGT AGAGATCACC TCATTGGATC CATCTGAAAT
40801 CAAGAGTAAT TTATTTCAAA ACAATCACCT GACAAGTAAG ACTATGGATC
40851 CTTTGTGACA AGTGTTGAAA ACAGAGCAAC CATCTGTTTC TTTGAAACAG
40901 AACTTGGTCT TTCCTCACTG CTGACCTCGT GCTGCCCTCT ACAAATTCAT
40951 TGTAGAGGGC AAACCATTCA AATTCAGCAC AACAAAAATA AATTCCAAGC
41001 AATAATTTCT GTTACTTTAG TGATTTAATT ACCACAGGAA CAGTCCAATG
41051 ATTCCTGGAT GCAGAACAAC AAAAACAGGG CTATGACAAA AATGACAATA
                                          CR1-GG
41101 TATCCAAACA ACAAATAAGA GTTGGACTTG ATGATCCCTG TGTATCACTT
41151 CCAACCCAGG ACATTCTATG ATGCTATGGC TCTGTGTTCT AAATGGCAAA
41201 GACCGCCTCT GTTCAATGGT AACTCTCTTA ACAGGGCATC TTAGAGCCCT
41251 GCTCCTCTGA AATACAAAAA CAAAGGTCTA CATCCTGTGC TGACTGTTTT
41301 TGGTATTTTT TCAAATAAAA ACCCAGAAAA CCATCACTTC GGTTTTAGAC
41351 TCTCAGCTCT GGTACTTTAT TACATTAGGA AGGCTCTTAG CCTGCTACTG
41401 CAATGAAAAA CACCAGTAAC AAACAGGAAA TAATTTATGA AAGTTGTATG
41451 AAATAAGGCA TAGCTGTAAC CATAAATGAG GCACAACCTG TATCTATGGG
41501 GCTATAGTTT GAGAGCTGGA TGAACACCAC CCTCAGAACG AACATCGGCT
                                                     CR1-GG
41551 TTGCTCTTCT GCTTACTCTG GGCCCTCTGA TTTCACAGAA GGGCGCAGGT
41601 TGGAAGGGAC CGTAAAGCCC ATTCAGTTCC AATCCCCCTT GCATGGTCAG
41651 GGCTACACCC CACCAGCTCA GTCCGCCCAG GGCCCCATCC AACCTGGCCT
                        MAR (0.72)
41701 TGAGCACCTT CAAGGATGGG GCACCACAGC TTCTCTGGGC AGCTGTGCCA
41751 GGGCCTCGCA ACCCTCTCTG AGTAAGGAGT TTCTTCCTAA CATCTAACTT
41801 TAATCTCCCC TCTTTTGGTT TAAAACCATA CCCCTTTGCC CTACCTCTAT
41851 CAGACCATGT AAAAAGTCAG ACTCCCTCCT GTTTATAAGC TCCCATCAAG
41901 TACTGGAAGG CTGCAGCAAG ATCTCTCCCA GCTTGGTCAC TATAAGCACT
```

*Fig. 1-16*

```
41951 ACATAGCCTT AAGCTTACAG GCATGGACAT GGTTTAAATA GGTTTAAAAC
42001 TACTTTTTGC ACAGATTATT CCTGGATCTA TTTTGAACCG GCAACACAAG
42051 CAGTTCACTC CCACAACCGA AGGCTAAAAT AAAATAAAAT AAAATAAATA
42101 ATAATTAAAA AAAAAAAAAA AAGGAATAGA GAGCAGACAA GCATTTCCAA
42151 GAGTCGTACT CTCAGCAGAA ACCCAGTCCA AACTACGCCT CCAGCTCACA
                                     CpG island
42201 GCAGGCCGCA GTCTTGCCTC AGAGGCCAAC GGGTCTTCTG GTCCCAGCCG
42251 GGCAGGTGAC TACCCGGGGT CCTCCGGCGC CTCCGAGCCC CCACCCAGGC
42301 CTGCTCGACG CCCCACCGCT GGTGTCAGCG CTTCTGCCCC CAGGCCCAGC
42351 CTGGCGCCCC ACCCCGCCGA GCCCGCCCTC CCACCCGCCG GCTGCAGCGC
42401 ACCGGGGTTC AACAGGACCC GCTCTACCTG CAAGTTGCCC GACATGGCGG
42451 GGAGCCGGGA AGGGGAAGGA CACGAGACGA CACTGGCTAC GGCCGACCGG
42501 AGCTGCCCTT CCCGCCACCG CCGCCCACCG AACCGAAAAG CCGGCCTTCG
42551 CTAGCCGCTT CCGCACCTCA GCGCCGGCCG GCCCGCTTCC GCTTCCGGGC
42601 AGCGCCCCGT ACGCGTCACT TGACGTCAGC ACGCCGCGCC TCGCCCCGCC
42651 CTATCCGAGG GGCTGAGCGC ATGCGGGCCG GGCGCCGGAA GCGGAAGTTC
42701 GTGGGTTGGC GCGCAGCAGT GGTGCTGAGG GAATGGGGGT GGTGTTAGGT
42751 CCAGCACTGA CGTAGGGGAT AGGGCTGAGA TCTGATCATG ACCTACTGTG
42801 GGGAGCCTGC TGTAGCAGAG GTTGGGCTGG ATGCTCTCCA GATGTCCCTT
42851 CCAGTCCCTG CGATTCTATG ATCATTTCTG TAAAATGTTA AATAGTCACT
42901 TATAGGGTTT TGAATAAATC ACGTTTTTTC CTCATGCCTC ACGTTTGGGA
42951 CACAAAGACA TTTTTTTCTT ACATCTCTTC TTTCTCGTAC CATTTGCTTG
43001 CTTTCAGCGG CACTGTCTTT TGCATAATCT GAGTGCAGAA TGCTTTTTAT
43051 TCACAGAACC AGCTCTTAAT AATTCCTGAC AGTCATAAGC AGTCAGGCGT
43101 TAGTCACCTG CAGCTCAGTA ATGAAACTCA ACTAACAGGT CTGCAGAGTA
43151 AGAGCAATGA CGTGACTCAG AAAGCACAGC ACATTGTAAA CAACTCTTGT
43201 AAACTTGCTA TATGGGTTTC AGACTAATGA ACTTCTGCTA AGTCGGTGCA
43251 ACAGTTGTGT TAAATTACTG TCATATCCTT CCCTATGTTA TTGTAATACT
43301 GTTGAGGAAA TGCTTCCTTA GATTCACAAT CCTCGTTTTT CTACCTGCCT
43351 CCAACTAAGC CCAGTACAGT CTGCTCTGGG ATGAAGGTAA AAGGCACAAG
43401 CACAGTCAGC CCTATATCTA GGAAGGTTGA TGTAATTTCT TCCTAAAGTC
43451 CTCTGCTTGG CAGCTTGTTT TGCTTAATGT CTTCATATGT GCACACCAGG
                              S gene exon 1
43501 CAGGATGCTG AAGGCTCGTT GTTTGGGGAT GATCAGTAAC AGCTGTTCTT
43551 CTATTGCAAA TGTGAAAGGG TACAATGTAG CAAAAATTCC TGGATGTAAT
43601 CAGGCTCTGG GAAATGAGAA GGCAAAGGAA ATGTTGGAGG TAAGAGCAGC
43651 GTTCAGGAAC CAGAATGATA TGGGTTGGAA GGGATCTTAA AGATCATAGA
43701 ATCATAGAAT CGCTAAGGTT GGAAAAGACC CACAGGATCA TCCAGTCCAA
43751 CCATTCACCC ATCACCAATG GTTCTCACTA AACCATGTCC CTCAACACAA
43801 CATCCAAATG TTCTTTGAAC ACCTCCAGGG TCGGTGATTC CACCACCTCT
                                S gene exon 2
43851 CTGGGCAGCC CATTCCAGTG CCTGACCACC CTTTCAGAGA AGTAGTATTT
43901 CCTAAAGTCC AGCCTGAACC TTCCCTGGCG CAGCTTGAAG CCATTCCCTC
43951 TAGTCCTACC ACTAGTCACA CGAGAGACGA GGCCGACCCC CAGCTCACTA
44001 CAACCTCCCT TCAGGTAGTT ATAGAGAGCA ATAAGGTCTC CCCTGAGCCT
                                  S gene exon 3
44051 CCTCTTCTCT AGACTGAACA ATCCCAGCTC CTTCAGCCGC TCCTCATAAG
44101 GTCTGTGCTT CAGACCCTTC TCCAACTTTG TTGCCCTCCT CTGGACACGC
44151 ACCAGGCTCT CGATGTCTTT CTTACAGTGA GGGGCCTAAA ACTGGACACA
44201 GTACTTGAGG TGCAGCCTCA CCAGTGCTGC GTAGAGGGGG AGTCATCTTG
44251 TTCCAACCCT GTTTTCCTGT AGGTAGTATT TCTGGCTGTG CCATCTGTAC
44301 CTATGGTTTT CAAATCTGTA ATGCTACACC TAGCTTTTAG ACCTAGGTCT
44351 AAAACAGTAC ACAAGTCACA GGCATGTTAG TAATGCCTCT CCAGTCACAC
44401 TTTGCAGTCT TCCGAAACTC CACATATAGA CATGTTTCTA TGATTGTGAA
```

*Fig. 1-17*

44451 TGAGATTAAA AAAAAAATAA ATTAATAAAT CAGAAAAGGC ACGTGTATAT
44501 TTACAGATAA CAGGCTAAAT ATTATACTTC TTAATTAAGC TTTACTATAC
44551 AGTATTCCTG TTATGTGACT TTGCAGCTAG TTTTGCCTAA GGAAATACTG
44601 GCTGAATGCT GAGTAATAAC ATCACGACAG ACTCCTGAGG AGCTAATGAA
44651 GTATTACACC AAGAGTGTAG CTTCAGTTTG AGAGACGTGT ATGGTCACAT
44701 TTTGGAATGC TTCCCATTGC TGAGTTGCTG TGTTACAATA TTCTCAAAAT
44751 CCGTGTCAGT TATTGTGTTC AACTGAGTGT AATGACAATA AAATATATTA
CR1-GG
44801 ATGACGTTAA ATGAAGATAT CATAGAATCA TAGAACATCC CAAGTTGGAA
44851 GAGACCCACA GGGATCACCA TGTCCAGCTC CTGGCTCCAC ACAGCACCAC
44901 CCAAAATTCA AAGTTGATGT CTGAGAGCGC TGTCCAAATG CTCCTTGAAC
44951 TCTGGCAGCT TGGGGCTGCC CTGGGCAGCC TGTTCCATAC CCACCACCCT
45001 CTTGTTCCCT CGGGCTCTGT CGCAGTCACA CAGAGCAGAG CTCAGCGCTG
CR1-GG
45051 CCCCTCCGCT CCCTGCGAGG AGCTGCAGCC GCCACCAGGC CTCCCCTCAG
45101 CTCCTCTGCT CTGGGCTGAA CAGACCAAGG GCTCTCAGCT GTTCCTCATA
45151 CACGTTGCCC TCCAGATCCT TCCCCATCTT TGTGGTCCTC CCTTGGACAG
45201 TCTCTAATAG TCTTATGTCC TTATATTGTG GCACCCAAAC CTGCACCCTG
45251 TGCTGGAGGT GCAACTGCAC AGCACAGAGT AGAGAGGACA ACCCTTTCCT
45301 GCACTCGATG GCAGTGCTGG GCCTGATGTA CCCCAGGGTA TAGTTGGCCC
45351 TTTGGGATGC TAGGGCACAA CGCTCAGTCA CATTCAACTG TCTGTCAACA
45401 AGTACCTATT GGCCTGCATG AGGCCTGTCT GCTAATTGGG ACTCTATTAA
45451 ATCACATCAC TGTGACACTA GGTGGCACAG GCACACATGA TCTCCATGTT
45501 CCTTAAGGCT GAGTGAATCA TGGAGAATGC TTCCTGCTAT CAGTTTTTGG
45551 CATGGAAAGA GAGGAGCCAA ACCACCGGTT GGTTCAATGC CTTGTGCCAG
45601 GAATAGGTGA ATGCATCAAT ACAATAAGTC ACGTCTACAG CACAGCCAGG
45651 CCTCATGTCA GCAATACTGC TCCACTGTGA TAGCTGAAAG TGACTATAAA
45701 TGACTAACGT TAGTGTGGGA CTTTGGTGTT AGATGACGTG AGAGCCATGC
45751 AGTGAAAGAG AATTAGTGTG GCAGAGTATC TAACAGTGCA GGTAGATAAG
45801 GCAGGAAGGA TAAGTGTAAG GAAAGATAAG GAGAAAGGCA GGAAAGTAAA
45851 ACCTCTGTTT TTCTCTAGTT TTCTACCTGG TGAAATGATG AAGAAAGATC
45901 AGTTTGACAT AGGTTAACAA AAACTGTCAG TAAGAAAGGT AGGAGTTAAG
45951 ATGCATGTTG TCCAAATCCC ACTACATTAC TTTGACCCTC TTCAGCATAT
46001 GCACAATGAG ATCACTTGCC CAAGACAGGA CCTCCAGTGG GCATGAAATC
46051 TGAAAATCAA TTATTTGCTA TTTGTGTTGC TTATCATTTC CAGATGAAAT
46101 TCTACACGAG ATAATTAGAG TGATGTCCTT GAAGATCAAC CTTTTTGTCT
46151 AATTAAGGTA TTTGCTATAG CTTCCAGATG TATTGCTTAT CTATGATAAA
46201 TATCCTTCCT AACTACAAGG CTTCTATAAT AAGAGTAACG TCCTCTATAG
46251 TAACCAGTAG AAAGTAGGTG GAAGCTGGGT GTTCTTAGAC AACCTGTGCC
46301 CATACATGGA CAAAGTGAGG AGGAGGACAC CTCCCTAAAT GACCACCAGA
46351 GACCACTGAA GACCCACATG CAAGCACAGA AGATTCAGAT GTGTTGGTGT
46401 AACCTTGTAA ACGCAGTAAT CTCGTGAATA TGTGATAGAT AGGTGTGCCT
46451 TATGTATTAG ATAGGCGAGT ATTGAGAACT TTTGGTTTAT GGATGTGGAT
46501 AGTGCTGTTA TCCATCTTGC ACCCTGAGCA TAAATAAAGC AATATCTCTT
S gene exon 4
46551 CTATAGTGCC TTGTCTTTTC ATTGTATTTC AGGAGACTTT GAAACTGACA
46601 ACAGGCATGC AGCTTGGGAG TGCTCACAGT CAGTCTGGCC ACAGTGCCTT
46651 CAAGCCTCCC CTGCACTGGG ATGTGGTGTG ACAAAAAGCA CAAACACTGC
46701 TTTTGTAGAA GACCCAGACC ACAGGCTGCA CTAGGGAACG TGTCTGCCTG
46751 GAGCACAGTG CCCTGGGGAG TGCTGCTGGT ACAGTAGTCC TGGATGAGTG
46801 GCTTCCTTCT GTAACCTTTT AATTGCACTA GAAGTACACC AGCATGGCAG
46851 AGAAGGGCTG GGTCCTAAGA GCCCTTCTTT CAAATTCACT CAGAACTCCA
46901 GATGTTTAGG CAGGGTGTTG TAGCTGTAAA GTCCAGGAAG AAAAGGTTTA
46951 AAGCTGTACT CGGCACCAGA AAGACTGGAG CCAAAATAAA GCCACATTGC

*Fig. 1-18*

```
47001 ACCCATGGCA CTATAGGCAA AGGGTAGCCT TGGGGCAAGA CTTGATGTAC
47051 TAGAAGTTGA GGAGTCCTCA GACTCTGTGT CAAGGGGATG TGCCACAACT
47101 CTACTGTGCC CCTACCTGAA GCCTGAATCA GTACAAATGT CTCACGCATG
47151 GGTTAGGCAT CCTTCTCTCA AAGCTCTTGG TCTTTGCACA CTTTCTTCTG
47201 CAGCTGCAGC AGCAGCCAAA GGAAAATTAG GTCTTGCTTT GAAAGCCAGC
47251 CCCTTCCAGC CATGACTGGT CCCTTCTCAC TCCACATCTG TGGATGATGC
47301 TCCCACAGCA GGTGGGAGAG ACAGAGGCTT TCTTGAAGAA ACCCAGCCCC
47351 TCTAGGGGAA CACTGTAAAG TCACAGGGGA GGAGACGTGG CTTTGAGACA
47401 GTGATATACT CCATGCCCCT GGCGTTCTTC CCCTGAGTGC CACTGGTGCT
47451 GCTCAGTGGT CACATGCCAC CAAAGTCTGC ATTCATCTTT AAATGCTGCT
47501 GAGAATTCAA CCTTTGATAA ATCATCTGCT TTGACAAAAT CGACATTTAA
47551 AAATTAATAT TTCCTCTTCC ATCCCCTACT TTTACAGGCT GGCTCAAGAA
47601 AATGGGAAGC TTAATGTAGA CTTGGGTCTT ACTAAACCAT TTCACTGGGA
47651 AAGACATTCA CAGTCTGTGG CAGATGGTAG CAGTATATTT TCTCTCATAG
47701 TACAGGAATG GGTCTGGTAG TACCTCTTTG GAAAGGAAAA TGTAAACTCA
47751 TACGTTTTGA GCCAAATTCC ATCAGATTTC TTAGTTTTGT TAGTTTTCAC
47801 TCCACTCCTG CTGGAAACTG AAAATATGGA AATGCTTGGA AATTTACTGT
47851 GATTTGGGTT CAGGTGTGTG TATGCAGGAA ATGTGTTACC TTCCAGAGTA
47901 AGTCAGTTTA TTCTAGAAAT GGGATGACTC CACTTTTATA CACTTGTAAT
47951 TCACAGTGAG ATTAATCCAG CCAATTGGGA AAACAGCCTT TCTTAAATTG
48001 TGAAAAACAT GCTCCACTTC TATGTATTTT TTAATATACT TCAGCATTGT
48051 GAATTTGAAG TTTTTCTTCT ACTGTTACAT GCATTCCAAC AGAATTTGTC
48101 AGGAACAAAA ATGAAATCTG AAATAATATT TTTCTTAGCT TTGCATGTGT
48151 TATCCTCAAG GGTAATCACT GTCCTAAACA ACATACTTAT GGCTGTTTCT
48201 GAGCCTTTCT TCTTCATGAA CTCATCAGAA AGGGACACTC ATATTGGCAG
48251 TCTGTATAGA GAGCCAAGGA CAAATATTTC GCCTACGTCT TCTCTGCGTA
48301 GCATTTTATA TATTAGGTCT TGCTAGTGAA TTATGACTGA ATGGAATACA
48351 GTCCCTTCAG TGATGACTTC ATTCATGATT GAATAAATGT AGCTTCAGGG
48401 CTGTATGGTT GACTTACATC ATCCAATTTT GCCATCTGCA ACAGCCAACA
48451 CCTCTACCCA TATATGAATT CAGCGAGGGA TTTTGTACTA TGTGTTGCTG
48501 GGATGTAGCA GCATTTCTCT TTGAAATGTC TTTACAGATG CAATGCCTAG
48551 CAGGCTTAAC AGCCCTACCT GCTTCAGAGA CACTGCTGTA AAAAGAAAAA
48601 GAGAAGCTTC CCAGCCAGTA TTTCATCAAG TTAAAAAAAA TCTAAAAGTT
48651 TATACTGTAC CATTTGGATT GCTGCATGTT GACATCATTT AGGATTCTGA
48701 AAACCTAAAG AAGCTTTGGA GCAACTCCTA AGTGTATGGT AGATGCTCTC
48751 ATTATGTAAG AGTGACAAAT CACTACCAGT CTTCCAAAAA TGCATGCTGA
48801 AATCAAAAAA GAAATAATGG ATCTCACAAA ACTGGATCTG CAGATCAGGT
48851 TCTACAGCCT CTGGTATGCA AGGGTTAAAG TAGAGTGATT GTTGTAGCTT
48901 GTGTCTCACA GTCAGACATA AATCTGTAAG CAGGTCCAGG TTTTGTAAAT
48951 TGTTGCTTAT CACCACATGA GCAATAAGTA ATCTGAACAC CCAATGTAAC
49001 AGATTTCTAG GAGTTAGGGC TGAAAGCATC ATGAAGTTTA TTCTTTTCTA
49051 CAGCAAAGCA GGCTCTGTGT ACCTGTCTAG CCACATTGTC TCTGACAAAA
49101 TTTATCATCA ATTCTCATCT CCATCAACTT TTAAGAATTA CAGAATTGAA
49151 GGGAGGGATT GTTGAAAGGG ATCTCTGGAG ATCATCTAGT CTTACCCCAT
49201 GATGAAGCAG GTTCCTTACA ATAGGTGGCA TAGGAAAGTG TGAGCAAACA
49251 CCCTGCTGTG AGCACTCAGT GTAAAAAGAA AGCCTGGAGT AGAGACCAAC
49301 ATCAATCTGT ATTGCATCCA AACCAGAAGA GGCAAAAAAA GTGTCTCACT
49351 AAGCTTCAGA AAGTGTAAAC AATTCACAGA AGATGGATTA TTGTGGAGAG
49401 AGTAAATGTG TGCAATTTTT ATTTTCCCCA ATATGTCACC ATTACAAAGG
49451 AAAATCATGG AATGGTGGAG GGTGATGGAG GCCTAGCCTG GGGCCCCAAT
49501 ACATGTAGCA GTGGACAGTG AGGTCACCGA CCAAGCGGTT GTGATGTCAG
49551 CAATGGAAAT GACTGTGACC TCGCTAGCCC TCACTGTACA GATTTGGGAT
49601 CTGGCAGAGG CCAGCGTGCA CTTGTGCCTG GACTCCCGTT GAGCATAGCT
49651 GCGAGACTTG GAGCAGTGAG CGAGTTGGTT GAGTTGTGCT GTGGGGCTGC
```

*Fig. 1-19*

```
49701 TGGCAGCAGT TCTTGGTGCC CACCCCACAG TACCACCAGC GTTTCCCCCA
49751 GCCCTGCCTG CCTCAGGCAG CTGGGGCCAC ACAGGGTGCA CTTGTAGCAG
49801 CAGAGGTGAG TGGTACAGTG GGGAAGTGGT GGGGAAGTGG GAGGGTTTGC
49851 TGCTGAGGGA CCAGGACATC TGGACAGCTG CCTGCCCATG GGACAGCGAG
49901 TGACCATGGC CTCTCTCTCT CTTTGCAGTT CGTAACACCT TCTGCCTGCT
49951 GCAGCACCTG TGAGGGGAGC AGTTTCCTGA CCTCAGCTCT CCCAGCCCAC
                                T gene
50001 TGCACAGCCC GGGGCCATGG ACGTGCCGTC CAACTGGACC TGCCCCATCT
50051 GCGGGCAAAG TCGGGAGGAT GTCACCTATG TGACCCCCTG CCAACACCAG
50101 CTTTGCTATG GCTGTGCCAT CTGGTGGGCA GAGAAGAAGC CGAGTTGTGC
50151 CATATGTGGG CACCAAATCA CCACTATCCG ATACTCGGTG AGGTCGGATG
50201 ACGATTACCT CGAGTGTGCT GTCCCGCAGC CCGCAGCACG CTCAGATCAC
50251 GGCCTGCAGG ACGAGCAGGG GCCTGCAGAG CCGGTGCTCA TCCCACCTGA
50301 GCACAACTTC CCCGCCGAGG TCTGGGCTGC ATTTTTTGAT GGACATCCCG
50351 AAGACCTCGA GCCCCTGCTC CACTGGCTGC AGGATGAGAT CCAGCAGTTG
50401 ACCAGAAATG GGTGGTGGGC AGTGTGTGTT GGACAGTGGA CTGTTGTAGG
50451 CCTCCTTTGT ATTTTCGGAC TGGACGAGGA GGCCTTGGTG CAGGAGCTGC
50501 AGCCATTCTC TGATGCTGAC TTGGTGCCCT TTGTAAGGCG GCTCATCAGC
50551 ACCGCTGCAG CCCTGTACGG CCCAGTGATC CGCCGCCAGC TCGACCAGCA
50601 GGAAGGCTGT GCTGCAGGAC AGCGGGAGGA CAGCCCCGCA GCCAGCCCCA
50651 GCACCACCAC CTCCCATCGG GAGCCTCCTG CCTTGCGCCC AGGCCGCTCC
50701 ACCAGTCCCG CAGGGCCCAG CACCGAGGAG CTGCCCGGCA GCTCTACTGG
50751 GGGAGCTGGG CACCCCAGCA CCACCACCGC GCCCTCAGTG GAGGAGCCGC
50801 AGGAGGAGCC ATGGCAGGCG GTGGCAGCGG GCCCCTCCAC CCAGGGCAGG
50851 GATCGCTCGT GTGGGGGGCC CCGGCGCCCC CCGAAGAGGA AGGCCCACAG
50901 CAGCCCCCAG GCCTCACCCC CGCCCCCCAA AAGGCGGCCC CGACGGCGGC
50951 GCTAGGCCGG CACCGCACTG CCGTCAGAGC ACGGCTCCAG TGGGCTGGGA
51001 GGCCAACATC TACCTCTCGG CCTGCTGCTT GCAGATAAAA TGTGGGGATT
51051 CAAGAAAGAA TATTTAGAGC ACAAGCTGCA GAACAAGATA AACAGCATGG
51101 GAAAGGAATG CTGAGGACAG AGGATGCCTC CAAGAGAGAA GAAAGTCAAG
51151 TGAGCTGCAT GATCGCTGCC TAACAATCCT AATTGGAAGA AGAGTATGTG
51201 GCTAGGAATG ACTCATAACT CTGATTGGAG AAGCGCCTGC ATGCGTGGTT
51251 AAGGAGTAGA ACAAGAGCAA GGGTGACCCT GTGGGATGTT TTGTTGACAT
51301 GTAAAGGGGG TGGGAAAGAT ACCAGAGAAA ACTTGGCAGT GTATTTAAGG
51351 GATATTAGAA TATGCAATAA ATGATTTGGA TTGCTCATAC ATCTGAGTCC
51401 GTGCCTTGGA TGCTGCAAGA AAATAAACAG AAATTCAAAA AAAAAAAAAA
51451 AAAAGGATAA GAAAATGTCT CTGTGTTATT GACAAGGCTG TGGGCGTTGC
51501 TGTCCTTTCC CATGCTGCTT TCTCCCTCTT TTTCTCCTGG AGGTGAGCAC
51551 AGACATGCAG CTTTATTTCC ATGACCATAA ATTGGCTTTC ATGACAGCAC
51601 TAAAAAAACA CACGAGGGCT CCAACAAACA GAGAAAGGAA CTTATGTTAC
51651 TCTAATAATA ATCCAATAAT CAGGGCTTCA CTAATTTCCT CTCATACTGC
51701 CAGCTCCAGG CCACAGATAA TTAAGTTTTG TTTGATTTCA GTGACTGAGC
51751 TGTGATGTCA CCCTCTCTGT AGACTTCCTA TTAGTCTGAT GTTAAAAACA
51801 CCAAAAATAT GTGCTGTAAT CCAAAGAGAA ATTATGGGTC CCATTAAATT
51851 GGTACTTTGG GTTCTACAGT CTCTGTTATG CAAGAGTTCA AGCTAAATGA
51901 TTGCTGTAGC TTGTGCACGA GTTTTGAAAA GATACCAATC TGTGAACAGA
51951 CCCAGATTTT CTTTCTGGAA TTCTCCTCCC CTGTGCAAAG GAAAGCACAT
52001 TGTTTTTTGC TCTCATCAGA GAGTACTCTG AAATGAACAT TTTTGAGTTA
52051 GACAGTGAGG AGCAGAAAAG AAATTCTATT CACATAGGTG CTTTTAAAAG
52101 CATTACCAGA TTCTTCTAGA CAAATGACAG AGGAATAACT TTTGCCATTC
52151 CATTACACAA TAGAATAACT GAACTGCAAA ACAAAGAGTC ACGCTACAGG
52201 AGTAAGTTTT GAAACTGACT TGCTTACCTC TGATGCTTCC AGCTGACTTT
52251 CTCCATTCTC ACAGTAGATT CAAAGTTCTT TTTTTTTTAA CTGTGTGACT
52301 GTAGAGAGTA GTGTTCACAA CTTAACTGCA TGCTGTGCAG TCTGAATTAG
```

*Fig. 1-20*

```
52351 AGCTGGGGGT AGGTGATAAC ACACCTCCTT CAACTGTTTT GTTTTCCTGA
52401 ACTGTGGTTT GTCTCATTAT TTTCTTCTAA ATGCTATTTT AAGCAGTAAG
52451 AGTTTAAACA TGCCTTCTGC CTGCCTTAGA ACTGCAGAAG ACCTTAAATG
52501 CAGAACTCTT ACTGTTCTTG AATTCATGGG AAGGTCTGAG GAAATGGGGC
52551 CATCCAAGAT GTCCTCCAAA CAATACGTTC CCTCATTCCA TTATGTGTAA
52601 GGTACAGTGG TGTTGTACCA GGGGGTGAGC ACTGCAGTGG TAAGTGCTGT
52651 TGGACCTGTC GTGCAAGAAT AGAAAGAAGT CCCACAACAG CCAAAGTCCA
52701 GTGGCTGGAC CAGGAGTAGC CAACTATGTG GCTGCTGTGA TTTGATCCAC
52751 ACCAGATTTC CAGGTTAGCA TTTTCCTCTT AGACCCATCC TTATTAATCC
52801 CTAAGCCTTT TAATTAGTTC TTGTATGGAA AGTAGCAGAA ACTGTATAGG
52851 AAGTCATTTA TCTTTCTCTT CATCCTAGCC ACTCTTACCA GAGTAATTTT
52901 CATCTTAAGC AGGAAGCTCT TCAAGCCAGG CTATTATTCC ATCATAAACT
52951 GTCTATAATT CTTCTACACG TATGACATTT TGTCTACATC TTCCAATATC
53001 TGTCTCACTA ACAAGCCTGT TTCTGTTTTT TATCCACAAC CCATCGAATT
53051 TGGTAGCCAT CTTTGCAGTG GGCTTTGGAT CTTGACCCAA GAAAGGAAAA
53101 CGGAAGGGTA TTTGCACTGT CACAAGTTCC TATAGACCTA ATTGCAGCTT
53151 TCCAAGTCAC TTATGCCTGT TATGTAAATG TTAACGCTAT TGTGGAGTTT
53201 ATTAACTCGC TGGATTATGC ATGAAGTATC CTCTGGAGTT TCCCCATCAA
53251 GCTTAATGGG ACCATTAGAT CTCAGAAGAA TGACGAAAGC TATTTCTCAG
53301 TAGCTTACAT ATTACCTGGG TAGATGTAAT GGGAAAGAGA AAAAGAAGCA
53351 TTCTGTTATC AATTCCTAGC ACTTTCTTTT GTTAAATATA GGCTATTTTT
53401 TTTATCATTC ACAATTTTTC CTACTTTTCC TTTTTTTATG GCCTAGTATG
53451 TTCTGTGCTT TGTTACACAA ATCTAGGGAT CCTGGGTTAG TGGTGATATG
53501 AGCTGAATCA GCTGCTGAAT GTAGGAATAG CTCACTTGCT TTCATGGGTG
53551 CTAATCAGTT TACATTAGCT GAGGTTCAGG GCCATTGTTT GTTAAGATTT
53601 ACATCTGGAT GTCAAGATGG GTTTGCAGGT ATAACTTTTA TAAGTGACTG
53651 GTGAGACAGC GACACTGTAG GGTGTTTTAC TTCGAGTAAT GCAGAAGAAT
53701 GTACACTGAT TTTGTTGCCT TTAGCAGATC TGCCAAATAC CAACTGAAGA
53751 AGCAAGAATT AACATGTTTG TTCCTCGTCT TAGTTGCATT CAGGGACAAG
53801 AAAAGCTCCA TCCTCTCCTG AAAATACACA GCTGGAGAAA ATTCAGACCA
53851 TGGAGGCAGA CCCATTTCCA GTGTCTATTT CAGCAAATAT TGACTCTAAG
53901 CTTTTATTGT CCTTTAATAT GCATATATTC ATGCTGTGAA TCTATGCTGA
53951 AGAACTCTGG GAAGGTGTGT GCCCTCACCC ACATTAATCA CCCAGACACT
54001 TCATAACTAC CTGGATTACA GGAGAAAGTG ACTCATCTAC TGATGACGCT
54051 GGATAAAAGC AAGAGGGGAA AGAAATCCCC AGTTCTCACA CCTCCCTCCT
54101 CTGCACATAG TAAGGAGGCA CTCAAGGGCA TAATGCAAAC CCAGAGCTGG
54151 AAGGGAGGCT GTGTGTCAGG GCCCAGGCCT GCTGCTGTGG GCAGCAAAGG
54201 CCATGTAATC GCTGGACATG TCAGTTCCTA CTGCTCCGAT CTGAAACCAG
54251 TTCAGAGTTA GAGGGAGAGG TCTGCTTGGT CTCTCTGCTA CTCATGGGAA
54301 AAGCACTTCT GCCAATGTGA TCTACTCTCT CTTCAAAGTT TCCACATTGC
54351 TTACGTGAGC AATCCTATCC CCATGCAGGC TTTCTTTTGG TAGGTGAGCC
54401 CCTGATAATT CGAAAATCAC ACCTACACTC AGCTAGGAGC TAACCAGATC
54451 TATAATCAAG CACAGTATGG TGTGGCTATG TAGAGGAAGC ATCTTCAATA
54501 AATGTACTGC AGTGGTAATA TGCTTTTAAT AAGGCAACTC TGTTCACATG
54551 AACAGTACTA GAGAGAAGCA CACCAGGCCC TGAAACTTCA GGGCAAACAA
54601 AGGTTTGAAA GTATCCCTGA ATTAAAATAA TTGAGGAAAG GTGACAAACC
54651 TAAGCATGTT TGGGTTTTTT TCTGAGACAA GCATCGTGTA GGTTGTTTTG
54701 AGCCCTAGTC ACAGCCTGGC AAAAGGAACC TGGTGCAGTC ACTATGGGCA
54751 CCAGAGAGGA AGGAAGAACA GTGTTGTCCC TGTCCTTGTG AGAAGGAGCT
54801 CTGAACCACA GTGCACATGT GTGGGGGTTC ACAATACTGT CTTCCTGGAA
54851 GGACTGGATG CTTCAGTGGG AAGTGATTAA TCCAAAGCAC TGTCTCTCTG
54901 CATCTGATTT ATCTGTGCCA TACCAAGGCC AGTTATGCCC AGTGCTAAGA
54951 GTTGGGAGCA ATGTCTTTAG GGAAAAGGTC AGATGCCAAA TGATCTGATT
55001 CCAGCACTTT CATTTCATCT TTCATTTCCT GTTCTCCAGG TTAAAGGCCT
```

*Fig. 1-21*

```
55051 TGTTCTCACT GAAAGCTGGC AACTGTTTGG CCGCCTGTTA TTTCAGAGTT
55101 GTTTTATCAT TATTATTATT TTCCTGATGA GATGTATATC CCAAACAAGA
55151 ACAGGCTCAA TAAAATAAAT GAATGAAATT AATTTCCTGT CTTTGATTAG
55201 AAATATTCAC TGGTGAGGCA CACTTCTACG TCAGCAGACA TGTCTGCAGA
55251 AGGCTGAGTT CTTGCTGGAC GTGTTGAAGC AGTGTGTTGC TGTGTGACAC
55301 CATCCCTCAT CCATCTCAGT GCAGATGCCT TGGGAAGAAA GAGGAAAAAA
55351 GAGAGGTCAG CTTGCTGCTG CTCAGCTTGT GTCTCTCTCA GTATAATCCT
55401 AGAATGACAC TTGATTATTC TAAGTGCTAT TGTAGTTGCA AATCATCGTG
55451 TGGTTTGTAA CTGTCAGTCT GACCTTTACT AGACATATAC TGGAAAATAT
55501 TCTTGCCTGT GACTTCTCTC TATTGCTAAA TAATGATCTA GACAGATACA
55551 CAGTGAATAC AGAAAGTTCA GTTGTATAGA CCAACTGACA GACATTGTGA
55601 TTTTACCCTT TGTTTTTTCT AAGTGTGCCG AGGAAGCAGG TTGTTGTATT
55651 GAAATAAAGG CATGCAAATA ACCTGCTACT GGCTCCCTCC AAGATCTCAG
55701 GCTTGCTGTA AAAGCCGTAG CTAGGTCAAA AGGGGTTGCA CCTTTTGTGA
55751 CTGGCAGCAT AATAAACATT CCCCAGTTTA TTCTGCTCAT TATTCCATCC
55801 CACTTGTAGC CAATTTCCTG TGTGGTCTCC AAAGCATGAA ATCTGCAATC
55851 AGACATGTCC TGAGTGTCAA TGCATTAGGG AAATAAAATA AGGAAAAAAA
55901 GACAACAGCC GTCAGTTGGA GTCTGTGAAG GAGCTGAGCT GGTTCATAGA
55951 ACTGTGTTGA GCAGCAGGAG CGTTCCTTGC CCCAAACGAG CCTGTCCAAG
56001 GGGTGGGAGG AAGGAAGCTG TTTTTCTTTT CCACTCAGCA GCGTGTAGCA
56051 ACAACGCCCT GAAGGAGTGG CAGGGTGAGC CGAGACCTGG GGCTGAGAGC
56101 AGACAGGATG ACAGGAGTGT TACCAGGTGG CTGCATCCCT CCTGCACACC
56151 GCATGGCCAG GTGGTGGCAC ATGGGGATGG CTGCTGCGTT CTGGTGCCCA
56201 GCAAGGCCTT CGCTTGTGTT TCCCCTTGGG CTGTTGAAGA CCTGAAAATG
56251 TTGGTGACCT GGAAAAGGAA GATGAAAGCT CCTCTGTTGC TTTGTCAGAA
56301 GACTGTGGCT TGTCCTTGTT ATGAAACTTT GGACTGCAAT AATGACGGTG
56351 TTTCACTTTG CACATCCCTT GTTCCTATGT TGTTTTGCCT CTGTCTTTTT
56401 TCAGAGACAG CATCATGACA GGAGATGTCC AACTCACAGG GAGCTTTAAA
56451 ACAGCTTTGA TTTTATTATT ATTATTATTA TTATTATTAT CTAGTAAAGA
56501 AAAATCCTGC TCTTCATTCT GCTATCTTTT TAACTTGATT AAAAAACAGG
56551 TTGCAATAGA TGTGTGTTGA AAATTCTTGG AGGTCAAACC AAGCAAGACT
56601 AATTCGGTGA CAGGTAAATG CAGGAGATGC ACAAGCTGAT GCAGTTAGTT
56651 AGATGTCATT CAGTCAGACT GAGGAAGATG AACTGGGAAG CCAAGCTCCA
56701 GTGCTTGTCC CTTGCAAACC TCAGGTACCT AAGGCTCAGC ATCTTCTGCT
56751 TTTCAAGTCA GCATCTTTTG CTTTACTGCT TCTTCCTGGT TGGGCCATAA
56801 GTAAGATCCA GGTAAGTGAC AGGCACTCCC ATAAATACTA ATGTGAAGAT
56851 ACATATAACA TATACATAAA ATGACTTTAG GATGTTATTT GTCTCTATAT
56901 GTGACACCTA ATATTATTTC AACATTATCT CCAACTGTAA ATTAACCCCA
56951 AATATCCATT CTCTGGGGAA GCAGGACTGC CCTGTGAGCC ACTCAGTTAC
57001 AGGAGCCCGT GTGGACTCCT TTCTTTGAAG CATGGCAATT GGTTATTTCT
57051 CTCATGGCAC TATGATCAGA AATCAGTCAT TTCTCAGCAG CAGCTGGGTC
57101 AGGCAGAAGA GTTCTGTAAG CCTACAAAAT GCCAGACCTC AGCTATCAAA
57151 GAGAAGTTAC AGAGTGGAGC GCAGTAATGT TCATGCACCT TCAGCTTTGT
57201 AATGTAGAGT TCTTTCACCT TTCCCTGCTC AGCTTTTAGA AGTAACCAGT
57251 GCACCCCCTT GTATTTGTAT TTCCAGCCTA CATGGTGATG GAGCTGGTGA
57301 TGGTGATAGG AGGTGAAGGT GGTGACCTGT GCTATCTCTG TCAAGGCAGT
57351 TGAGTTGTCA GCCACTCCCC ACCAGTGTGC ATCCAGAAGC TCCTGAACCA
57401 CTTCACAGAG GGCCGTCTTT AGTAGACTTG GGCCTGAAGG AAAGTTTGTT
57451 CCTTTGGCTC TAGATTACCT GCAGACATCT GAGAAGAGTC TGGCAGCCAA
57501 CATTATTGCA GATTTTTATC AAAATTTCTC TCATAGTGTA AGGCATAATT
57551 AGATATGTGA CAATAATTGC CCAGATGACA CATTTTTGCC AGCTGTTCTC
57601 GATGTTCTTT GAATTGCTTA AACATATCCA CACCTTAATG TTTGTTATGA
57651 ATTCACTTAT GGTAAAGCAT ACTAATTTTA TGTTCACTGT CTGGTAAATA
57701 AATGAAGTTG AACCCTACTT CATCACAGCA GAAAGGAAAA TAAGATTTCC
```

*Fig. 1-22*

```
57751 TTTGGGTAAT AATGAGTCTT TTGGAAGCAC ATATTGCTGG GATCTGATCA
57801 GGAAGCAGTG GTGTGATTTA CACTCAAAAC TGTCATTCCA GAAGTAGATA
57851 ACTCCTCAGT TGCCACTGCC ACCAAGGAGG TATCACATCA GGGAAGACAC
57901 GTACTTTGGT TTCCTAGCCC TTTCATTTGC CAGCATAGCA ATCTTGAAAG
57951 CAAGCTCAAT AACGTTTACT TTTTTTGTAG CACATCAGTA GTCTAAGGGC
58001 ATATAGGGCT GCCTGGGGTG GGTGAGGTGT GGACAGCAGC TGTGTTTGTG
58051 GGTGGCAGTT TCCTCATGAA GGTTGACTTG GACTCCAGGA AGTCCTTGTT
58101 AGTGTGGTGG GCAGCTAGAC TTCGTGATGG GAGAAGCAGT GTGGAGCAGA
58151 GTAGGCCACC TTTTCCTTGC TAAGGACTAC ATACATTTTT CAAATCAAAT
58201 AAGACTGTCA GGCTGCACCA CCACCTTTCC CTCTCCCTTT CTTCAACCCC
58251 CTCCGCATTG GATTCATCAG TAATCATGTG GCCAATGAGG CCTGAACCCA
58301 GTGGTTCCCA TTCTGGAGAT GCTGGAAAGG AGCTGTGGCT TTTTCCACCC
58351 TCCCAGCTGA AATCATCTGC TTGAGAGCAA CACGGTGAGC AGACATTTCT
58401 CTTTGAGCAC GAGCCCCACT CTGGCCTTGG GCTTTTGAGG CAACCAAGTA
58451 CACCACACAA CCCTCACAAA GACAACACTG AGACACTATC TTAACGCAGA
58501 CACAGATGCA AAGTACTGGG TTGCCATCAC ACGTTTTGGT TGCCTTCCCT
58551 GTGTGTCTTT TTCACAATTA CAATTTTTTA CGAATCACAG CAATTCCAAT
58601 GTACCTTGGA GCACTGGTTT TGCTCAGAAG CTCCTTCAGT TGCTCCTTCA
58651 CTCCTGCACC CTCTCTTTCA GAGTCTTTGC TCCCTCCTGT CTGGTGCCTA
58701 TTGTAGGGCA CTTGCTGCAG GCAACGTGCC GAGGCTGCTG TTTCCTGCTG
58751 GAGCATGTTG TTGTGTTCAG TAGCTAGGCA GGCAAAGACA ACTCAGGTGT
58801 GACTCATACT GCTCCTCCAG TTTAGGAGTT GCTTGAAGAA TGATTAAGGG
58851 AAAGAAAAAA AAAAAAAAAG AAGAAAAAAA AAGCGAGAGT GTGTGCGTAA
58901 TTAGGGCTGG GAAAGTGGGA GTGGTGTCAA TGAGCAGGCA AGCTAACAGA
58951 CTCTTCTGCT CAGCAAGGTT TCGCCACAGG TCTCTAGTTC TTCGTGTTGG
59001 ACCCATTTCA TTGATTCATT TACCAGGATT ATACCCTTGC AAAGTAAGTA
59051 CAACATTTTT TCTTCCTCTG GTACTTTGAT GCCTAACTAA CAGTTATAAA
59101 ATCTCTGCCG TGAAACGTAA TCGCATAGAG TGAGCAGGAT AAGGAAGCTT
59151 GTACAAAAAG ACAGCATGTG AAACTAAAGG TGGAAAAAAG CCTGCTCAGA
59201 CTACAACCTT CTGGTTTTGT CCCAGCATTG CTGTGTTTGT CCGTCTACAT
59251 TCCTTACCCC TGAAAAGATT CGTTGCAAAC GGTGAGTGGG GTCTGTCAGG
59301 TGAGACTGCG AAGACATTAG GAATTATTAG AATATTTAGA CTACCTGTTG
59351 GCTGTTCCCA ATGGCTTTTC CTGAATCAGA AGAGCAGGCT GTATATGATG
59401 CCATGAAAAT GCTCCATATC TCTAAGTAGG TGTAGACTGT TTGAGAAGTT
59451 TACAAAAGAA TATTCTTCTT GTTTTCCACA TGGGTTCGTA TGCTTTGCTC
59501 TGTTTGCTTT GTCTAAGCCT TGCTAGTTCA AAGGACAAGA ACTTAAGTCT
59551 ACTAATTACC TACTTGATCT TCAGTGTGCT CATCCGGTTG GAAAAATTCA
59601 CTGACTCTTG AGGCACAATA AAGGGTATTG TGGAGACTCT CTAATTCCTG
59651 GTGTGACTTT CTCAATTGTG TTGCTGATGG TGCTTTTTCC ACAACCTGAT
59701 GAACACTCTG ATCTCGCTAA AGCAAAGCAT CAGTCTGATA TTGTGTGTTC
59751 CTCAGAGAAA CATCTGTTCA GAGGAAATCA TGTCTTAGTC ACGGAGCTGT
59801 GTAACCTGCC TGGTGGAGAG CTGCCATTTG TGTAGAAGTA GGAGGAAGAG
59851 GCTCACAAGA GTTTTGTTCC TTTATATTTT GTGTTATCCA AGCAAGAGCT
59901 CCAGTAAGGT CATGTTAAAT GAGCTAGTTT GGAGGGGGAA TGCCCCACAT
59951 GTGGGTTCTT TCATATCGTT TATCTAAACT GAAGTGACTG CAGGGTGTTC
60001 ACTCACAGCT CATGAGCTGT AGCCCTAGTG CACAGCCCCA ATAGCAGCCC
60051 AGCTTGGATG GCCACCGCCC GGTCTGCCCC GGGTGCGCAC TCCTCAGGGC
60101 TCTTTAACAA AGGCAAGAAT AAAATAAATA CTTGCTCTGC TTTATCAGAT
60151 GATGCTTACC ATTCAGCTGA CGTGACTTGT CAGGTTTCCA CACAGATGTT
60201 GCCGTTCTCC TGATTAATGT TCAGAAGATA AACTACATTT AGCTTTTCTC
60251 TTAGTAAGCA AATAGCAAAC AAAGCTTTGT TTCTGTTGGT TGCATTCAGG
60301 AGTGACAAAG CAAAAATAGT GTCCTATACT ACTAAACACC TTTAAGTTAT
60351 TTTTTTTCTG CACTGATTCT AGAGCCTCTC AGCTTCCTCC TGTATCTGAA
60401 CGTGTTTCTT GAACTCTGTG GCCCCATCAC AGCTTTAAGC AAAGCTGGGT
```

*Fig. 1-23*

```
60451 GGATCACAGG CTGCATGTGC TTAGAAGGTG CCACCGTGCC GCGGGCCTCT
60501 CAGAATGCTG ACTTGTTGCT CTCCTGGGAA AGCAGGGATT CAGCCAGAAT
60551 CCAAGCAGCC CTTCTTGAAA TTTCATTTCC AATTTTGTTG ACTCCTCCCT
60601 GTGTGAGAGT TTCCTGTGAT TACTGACTCA GGAGCTGTGT CTGGTTTCTG
60651 GGACTGCTCG TGGGCACCTC ATGGGCTTTC GTCTTGAGTG GGGGCCTCAG
60701 CCCTTCTCAC TCAGCCAGAA CTTGCTGCAG TGGGGTCACT GACACAGCTT
60751 GGGGTGCTCA GGGCTTTAAA GAGGTTCAAG ACTTCGTAAT ATTTCATGCA
60801 GTAAATTCCT TTCAAGCATG TGAACGCTGT GAGCTCCTAT GTGTTGTATG
60851 TCATTAATGA ATGCAGCATT AAAAAAGAAG GCTGATCAGA TGCAGTTAAA
60901 AAAGATGGTG AGATAGAGAT TATTCTTTGC TATCCAGCCC TTATTGAAAC
60951 AGCAGGGTGA AACTGAGGGT GTTTTTTTCC CAACAAAATC CTCTGAATGT
61001 GCAATATATC AGTAGCAGCA CTAAAAGAAA GAAAGTGATA AGCCTTGCCA
61051 CTACCAGGAA TAGATTCTCT TGGCATAACA AAGGCATTGA GAAGCATCAT
61101 CAGCTACTGA GTGAACAGGA GGACTGTAAA AGGTTCACCA CGAAGTACCT
61151 CCAGGTTTCC TCACTGAAGA GGAACACAGA AACCTTGCAA AAACGATCCA
61201 GCTTGAATGG TACCAGAAAA GAATTTCTAC GTCCTGGTGC AGAATTCCAC
61251 TGGTGTAAGG AAGAAGAGAG TCATTTAAGT TTGCAAAATT TCACAATTTA
61301 TTTCCTTGCT CTGAATATTT TGCCACCCAG GAGAGTGAAG CACAGGTAGC
61351 ACATGCACAT TTTAATATCA CTGTAGGTCA TTTGCCAATA CGACTGAAAA
61401 TGCTGATGTT AGAAAGGCAG GATTGCATTT CTGGCATGAA GACAGAAAGG
61451 AACGTGAAAT GTTTTGAAGT TATTATGATT GCATATATTT TCTTAGGCGG
61501 TAAGGAAGAT TTGGAAGTCA AAATAGCATC AGGGCAGCCC TAACTGAAGA
61551 AGGATATTTT ACTCCGCTAG CAAATGAAAT ATTTTTCAGG TAGACTGCAC
61601 ACATCATTCT GGCATTGTGA GATTATGCGT GTTGTTTATC TTCACGAGAG
61651 TGGTAGATGT TGAATGACAC ATTCTTGGTT CCTTGGGTAA TTTTCCACGG
61701 TCTCCCCAGT GAGAAATGCC TGGGAAGTTG GTACTTGCCC ATTTCTTCCA
61751 TTTTTACTTC AGACAGAGAA AGTATGCATA TGGATTGTGT GCTCGTGGGC
61801 CTTAAAGTGC CCTTAAAGAG AATGAGTTCA AAGGGAAAAA TAAGGTAGGC
61851 ATCCTGTTCA GAGCAGTTTG TGTAAGGTGC ACAGAAGTGC GTGTCTGTGT
61901 TGAGCGAGTG CAGAAAGGCA TTTTAAAGGA TGATTTCACA TGTGCTCCTT
61951 TGACCTGTTG TTCCAAGTGA CTCCCTCAGC AGCAGTCCCA GGTCTTCTTA
62001 TTTGTTTTCA CTGTCTTTTG CCACCATTTT GCCCAAAGCT CCCTCCTCCT
62051 TTGATGTATG CGGAGTCCAT CGTTTCTAGC AAGCTTGACT TTTCTGGTTA
62101 TTAGTTGCTT TTATATGTGA GAAGTTGTGA CCACAGGAGT GACACAGGAA
62151 TGATGCTTGT AGTGCTGACT GGCACTGAGT TCTCACTTTT ACACCCAGAA
62201 AAACTCTGAG AACACTTCCC AAACCTCACT CTGACACCAG CTTGATTCCT
62251 GCTGACACTG TAAAATGGGA TCTCCCAGGG TAAGCTTCGT TACCAAGCAT
62301 CTTGGGACAC TGCCAGTGTC AAGGGAGATG GACAGACCCA TTCTGCTTGA
62351 AAAGCATCTT ACAGGGATCC TTTACATGTT GTAAACATCC TTCTTTTCAT
62401 TTTTATTTGG GGATAACTTT CTCTGGTGCT GTATATTTAA TTTTTTTTCC
62451 TCCTCAAGAT GAATTGCTTT CTTTGCGTTC GGAGGCAATT AGGAAATACT
62501 TTGTTGCTGA TACCAACAGT CAGAGCACTG TGTGAGGGCA CACTGCTGGG
62551 TAAGTGTGTT TTTCAAATTT GGATTTAAAA AGTCTTGATT TTATGCCATT
62601 ATCCTTTTTT CACTTAATTA GATTGTGCAT TATATTTCAG TAACCTTTTG
62651 TACAGCGTCT TTTAGCTAAA ATTAAGCCAG GTGCCTTACT AAATATATAG
62701 AACATATACC TATGTAAGTT AATGAAAACA AAGACGTGAA GGCCTTTTCT
62751 AATCAAACAG ATTTTACATG GAAATCAAAG TTTTCTCAGC TGTGTTGCAG
62801 AAAAAAAATA CCCCCCTGTT CTGTTACTCC TATAAAAACG TGTGAATACC
62851 ACAGATTATT TTGGAAATCT CTACTCTCAA CTACCAAAAC TGCCACAGCA
62901 TCTCGATACA TTGATGTCTG ATGTTCAGCC AAGTTTGGAC AGTATGACAC
62951 ATGCTCTTGA ATGCAGATTT TTGTCATTCA AAACACCATT CCAAACAGGG
63001 ATGAGAGTGA GCGGTCAGAA GCAGGTGTCC TTGCTCTGGA GACAGTTCCC
63051 TGCCCACATG TCCCCTCTTC CCTTTCCTGT CTTCTCTTAC CTAACTGCTG
63101 TCATCTGGTG AGATCTTTAC TCATCTGATG CAACCTAGAA TGCAAAAGGT
```

Fig. 1-24

```
63151 ATGAACTAGG TAAATGTTTA AGACTGCAGT ATTAAGTAGG CATTTGAGAG
63201 AAATCTCTGT CCTTAAGGTG CTTCTTGGAA GATCAGCAAA CCTCTCACCG
63251 AGGTAATGCT TCAGATAATG CTACAGACTT TCCTGTTTGC GTCTTCTGTG
63301 TCAGAGCCTG AAACGTTATT GCAAATAGAT GTCTGGATAA GAACAGAACT
63351 GTTAAAATCA CCTTGCCATG CCATATAAGT TCCAATATTT TGCCATTTTT
63401 TTTCCTGGGC AGGGAACATG TTGAAGAAAG TTTTTGAGTT CTGTTGGAAG
63451 TCTTTCCCTT TTGAAGTCCC TTGCAGTATT CATCTTTTCC TTTTCCTTCT
63501 GTCTCTTTCA ATAGACAGAG CTGCTGAGCA CCAATTTATC AGATTGTCTT
63551 TCCCCTTCTT TAGGGACATG TGATTCTGGG GATAGAAGAC AGTCAAACTC
63601 ACTGTGCCAA AGGAGTTACC GTCTTCCATA TTTGTGCTGC TCTTAAGCTC
63651 GATGCGATAT TGACTGAAAT TCTGTGGTTT CCCTTTGTTG TCTTTAATCT
63701 ACACCAATGG AGTTACACCG AAGTGCAGTT TTAGATCTAT GAAAGCAGTC
63751 TGGAAGATCG AATATTCCGT GTCATTCCCA GAACGTGGTC CAGAACATCT
63801 GTCGCTTGGC ACCACCTTTT CCATTCCTGA CTGCATAGAT CAGCTAACAG
63851 CCCTACGGCA ATTGCAGTTA CTCTGAACTG CTAGGAAAAT ATTTGCAGTC
63901 ATCATTGTAA GTGATGAGTG GGCACATAGC AGTATTTATG TAGGAGGCTA
63951 AGTACTTAGA GTTTCTAGGA TGATCTCAAC CTACAGGACC GGACAGCTTT
64001 CTGGAGAGTT CTAGCAAGGG TAAGGAGAAC AGGGAATCAC CTCTTAGAGA
64051 GAGGACATGC CACAGCTAAA GCTTTAATGA ACAATTAGAT GTGAAGCAAG
64101 AGACAGGAAA GATGATTGTG AGACTTTTAA AAGCCTATCA AAGCACTAGG
64151 AGAGCCCAAA GCATAGGCAA AGTACCTTAT AAGTTGGCAC ATCTGAAGAG
64201 TATCAATTAA AAACATATTA AATCCATATG TTATCCGATG TGATTCAATA
64251 TGTGTGGGTC ACCCTGACCA ACCCAGATTT CTCCACGTAT GTCTGGTAAT
64301 ACTGGCTCTA CGTAGCACGC AGAACTGCCA GCTGTCACTT GAAGGTAAGG
64351 GCTTCTACTG AGCCACTCGC ATTACCTTGG TTGGGCATGG ATGAGAGACT
64401 CCTCAAAAGC TGCTGGTGGT GTCTGAGACT GGGCAGGATT GGTCAGGCCT
64451 TTCTCGCCTC CCAGCGTAGG TTCAAGCTGC CCAGTCCCCA AACTGGTGTC
64501 CAGCCTCCTT CAGCAAGGAA ATCAGTGACC TGCCAGCCTC ACTGCAACAG
64551 GAGCTCACTC TGTGGGTCAT CTCTATCCTT TTCTGTTTCA GGATGACGAT
                         U gene exon 1
64601 GGATGCTCTG CAACTAGCAA ACACTGCCTT TGCTGTTGAT ATGTTCAAAA
64651 AGCTATGCGA GAAGGACAGA ACAGCCAATA TTGTGTTTGC CCCACTGTGT
64701 ACCTCCACAT CTTTGGCTCT GGCATATAAA GCTACAAAGG GTGACACTGC
64751 AGACCAAATG AAAAAGGTGA GCTGTCGGCA TCCTGCTGTG TAGCTGCAAA
64801 ATTGTCAGAG GTGGCTTTCC TATTTATTCC TCTTAATGCT GTATAGGACT
64851 GCTGGTTCCC TTGTAAGCCA GGCAGAAAAC TGTCCATCCA AAATTCCAGA
64901 ATATTTCCCC ACTCCATGGC TCCACACAAC CAAAGAGGCT GAAAATCACT
64951 AGCATAGGGA AAAAAGCTTT CTCAAGCATT TACAAGGTGG ATGGGGACAT
65001 GGCAGAGTCC TCAGCAGTTG TATTAAGGCC TTGTCTCCTT TCAGCAGGAA
65051 TGCTGATTGT GGCTGAAGGT GACTGCTGAA GTCACTGCAT TTTCTGGATA
65101 ATTGTTTAGT GATTATTCAG GACTGCCTAA GCTTAACAGG ACTGGAAATA
65151 ATTTTGCCAT TACCAAGTAA TTTTAGCAGT TCTGTCTGTG CCATTTCCCC
65201 TTTCTCCTGC CATACAGCTA AGAGGAAGAT AATGCAGTAG GAGGCAGCTC
65251 AGCTTGAGTA GTAGTTTGCC TTGCAAATAG CTCTAGATGC TCAAGGGTTT
65301 TACAGCACCA CGAAGCAGCA TCATGGTGAT GGTGCAATGA GTTTATCAAG
65351 GTTGCTCTGT GGCGGTGAGA GGCTGCACGA CTGCCTCTGT GAGAGCCAGG
65401 ATTTACACAG CCTCTTTTTA TTCCAGTGCC CACAGTCTCA GCAGTTACCT
65451 AGAGGTGAAT GAGAAGCAAA TTCAGCATGC ATTTATATGC TGATTATCAC
65501 CTGGCTCTCA GGGGCATTCC ATGTATTTGA ATACATTTTT CTTCGTTTAG
65551 CAGTTCCTCC TTGTACCTTT GGTTTCCCTG ACGGCACATT GCTGGAGCAC
65601 AGCCTCTGGC GCCTCTGCTC ATCCTACAGA TTGCAATGAG TCTATTTGCA
65651 CAGAAACAAA GTGGTATATC CACAAAGGCC TGCTGGGTGT TTTCCCAAAT
65701 AGGATTATTT TAAAAAAATA AAAATAAAAA TGATTTTTAG ATCTTATTTC
65751 TAGTTTAAAT GACACCCCAA AGCTTCCTTG TCATTTCAAA GTTCAAGCAC
```

Fig. 1-25

```
65801 TGTCTTTGCA ATGGAAGAGC TTAAAACATT AACCTGTGCT TAATTTCACT
65851 TTCACTTGTG CCTGCAATTT GCATTGAACC GTCCCACAAT AAGTGAACAT
65901 CCACATCCAC AAATAGGGTT CTGTTACACA AGTGCACTTA TGTTTCACAT
65951 TTCTCAAGGT AATTTACTGT GCCTGTAAAG ACATGGTGTG TTCAGGGAGA
66001 AAGAGCAGGA GTGAGGCTGA AAGGGAAAAG GAGGTCACTG ATGCTGGTTG
66051 GGAAAGATGA GAAGGGTTGG GCAGGCTGTT TTTAATGGAA CATGCACTCT
66101 CAGAGACCTT GCAACAGGCA GGCACCTAAA AGCAGAGAGG TTTAGGTCAT
66151 GCTAGAATAT CCTGGAACTG GGCATGTGAT TTCCCGGAGC TGGGAGGTGG
66201 GTCAGCAGCC TTACCTCTAA CTTACGTTCT GTCTGCCAAA GCTCACCTGC
66251 TTATCTGACT GATTTCTACT GAAATACCAC ATGACATCAT GTGTCAATAA
66301 TCAGAAAACC TTGCCATATG GTAAGCAGTT TTTAAAGAAG TAACCCACTT
66351 CCAGAAAGGA AACTAACTGG AACATTTATT TATCTGGCCT CTAAACTCCA
66401 GATTTTTGGA CAAGAATGTG AGTTTGATAA AAGCATGACT CCACGCTGCA
66451 GATATGTAGT TCACTAAATC ACTTTGCTAG TATGAACAGC TCTATGGAAT
66501 TCTTTGGACT GCTCACAGGA AGGAAACACA TTTGGTTAAA GTTTTGATAG
66551 GATCAAGTTT TTAGATTTAT GTGGGGATGT CAAATAAATT AATTTTTTTT
66601 TTAGTAATAA ATAAGAGTGA GAAGTCGTGT TGTTAGCTTG AACACAAAAA
66651 AGTCAAAGCT CTGGTCACAA ACAAGCATTA TTTATTGCCA AGCTGTCAGG
66701 CCTGGAGCAT GTCCAGAGAA GGACAACAAA GCTGTGAAGG GTCTGGAACA
66751 CAGATCTTAC AGGAGAGCAG CTGAGGAAAC TGGGATTGTT CAGTTTGGAG
66801 AAGGAGAGGC TCAGGGGAGA CCTTATCCCT CTCTACAACT GCATGAGAGG
66851 AGGCTGTGGT GAGCTTGGGG CTGACCTCTT CTCCCAGGTA GCATTAATAG
                            CR1-L
66901 AATGAGAGGC CGTGTCCTCA AGTTGCACCA GAGGAGGTTC AGGTTGGATA
66951 TGAGGAAATT TTTCTTTTTC TGAAAGAGCA GTGAGATATT GGAACAGGCT
67001 ACCCAGGGAG CTGTTCAAGA ACTGTGTACA TGTGGCACTG TGGGATATGG
67051 TTTAGCGGGC ACAGTGGTGG TGGGTTGACA GTTGGACTAG ATCATCCCAG
67101 AGGTCATTTC CAACCTTAAT GATACTATGA TGCTATGAGT TTTTAGATAA
67151 TAAAAAGAAA GGTGCTCAGT ATTTTATCTT GTTCATTATC AGGTGCTCCA
                       U gene exon 2
67201 TTTACAAGAC GTCAAAGATG TTTCTTTTGG GTTTCAAACG GTAACTGCAG
67251 ATGTTTCCAA ACTCACCTCT TTCTTTGCAC TGAAAATGGT CAAGCGGCTC
67301 TTTGTAGACA AGTCGCTCAG CCCTACCACA GTAAGTACTG CAGAAAAGTG
67351 CTTGAATTGC TCGACCAACC AGACTTCAAT GTTATTCAAA ATACGTTCTC
67401 TCACTATTAG CTTTTACTTG ACTAGACTCA GATGATGAAC AGCATAATAA
67451 GAGTTTGTAG GAGGATGATT GTTCTGCTTG ACCCCAAGCA ATGCAGCCAC
67501 TGCTAGAGTT GCAATTCTTT CATTAATATG TTTTAGGTCA GTAGGCGCAG
67551 TAGGTTTTGA ATGCAATATG ACTTCTATGC CACATCAAGG GCTTTGCAAT
67601 ATAAGTATGA CTGGGAAGGA TTTTAAATAA AGATGGTGGT GCAAGTGTGT
67651 CTAGTCCACA CACCCAAGTA ATTACTGCAT AAAGAGTAGT TTTCTTAATC
67701 TAACTGAGGA GGCACAAGCC TGGTTATTCA AACAACACAA GTGAGGAAAG
67751 TGTTGTTTGG CCATGAAACT TAAGGACCTT GCAAACAACT GAGAAAAATG
67801 TTGTGTTTGT TTTATCAGAG TTGCCTTTGA ATAGGGCCCC AAGCAAGGGC
67851 AACTTCAGCC TAGAAGTGAT GTTTCAGAAG ACTCACAGCC TGCTTGAATG
67901 GTGTTATAAT CAGGTTGCCT GCTTTTTGGC CCCATCCACA GCAGTGAGCA
67951 TCTCACCTGA CAAGGATAGG CACACTGTGA GCAGCCTGTG GCCTTTGTCT
68001 CATCCCTTTC TTTTGCCCAG GTGTAGACTG AAGGCTACTT TATCCTTTCA
68051 AACTCAGGCA ACATGTTCAC TCCTGCAGTA CGAAAGGTAC TTTAGCAGCC
68101 AGTATAACTG TATTGAAGAC AGTCTTGGGA GCAATCTGCT GAATGCGGCT
68151 GCGTGTCCTG GCTGTCACCT GCTGTTACTT ATTAGCTGTC CTTTGTAATA
68201 TACTCTCTGC CTACACCGTA ATGAAGCTTG GGATACTGGT TTTGTAGGCC
68251 GTGTGGAGAG TCATCTAGTG AAGAACATCT AAGGAAGGTT AGCTTTGGTA
                                    U gene exon 3
68301 CCTTGTGTCT TTCAGGACTT TGTTAACTCC ACAAAGAGGC CTTTTCCATC
```

*Fig. 1-26*

```
68351 AGAGCTGGAA CTAGTGGAGT TCAAGGAAAA AACTGAGGAA ACACGGCAGA
68401 AGATCAACAA ATCTCTCTCA GAGCTAACTG ATGGTGAGTA GGGCCTAACC
68451 TCGGGGATGC TGATTACCTC TTTGAAGAAT GATGTCTTTG TCTTCATGAC
68501 ATCTCCTAAC TATTGCTTTT AGAAGTAAAT ATACAGTGAA AGCAAAGGGA
68551 CTGCACCTAT TATTTGGATT CATGAGGATT AGCTGTGTTA GCATGTTTTA
68601 AAATCATTTA CTTTACTACT GTGGCATTTC TGGAGGCAGA CCTTACATTA
68651 GCCTTTGGCA AAGCATCTCA TTTGTTTTCA TTGGGAAAGT TTGGCTCCTG
68701 GCTGCAGAGC TTCACAAACA TCTGACATCA ATACATCAAA TCCTGGCCCC
68751 GTTCTCTAAT GGAGAGTATG TGCTGAACTC TGAATTTCAG GCTGTTAATT
68801 AGTAGCTCAT CTCAGCAGCA CAGCTGATTT TGACCACAGG TGGACATGTG
68851 TTTCTTACTT GGAAACACTC CCGTGGCAAT AGTTCTGCAG CACTTTTCCT
68901 GCAGTACCAC TGAGCCACTA AGTCACAAGA AGTGCCTCTC AGTGACCATC
68951 AAGGCTCCCA GGCAGAACCT GCCCAGTCTG TGCAGGGTAG AGGTCTGGTA
69001 CGCAGTGCCC AAGGCAGAGC TCATGTACAT GCTGTCCATA GGTAGCTCCA
69051 GGGTTGGTTG CTGCCTATTG CCCTCATGTG GTACACATAT GAAAATATGG
69101 GTGCCTGAGT TACATCTGCT CCATCCCGAG GTGACACAGG TGCCCACAGG
69151 GAAGTACTTT GCGCTGCCTG TGTGATTTGT GCATGAATGA AGACTAACAT
69201 CCACAACACT GTGGATTCAG TGCCTCATGA CAGTGTTTGA ACAGACACAA
69251 AATAAAGCAA GGGAAAGAAT TACGTTCTCT TTTTGAAATC CATGGCACTA
69301 TTTGGTTATG AACTGTAATT AGATGGTTAG CGGCATTTCT TATTCGGGTT
69351 TATTCTTATG TATCACTCCA AAAGTGAGTA GAAGCTAAAC TGGAACTTCC
69401 CTTGAAGTCT CGCTCTCCAA ATGAGAAATA TTTTTTTCAG TTCTACCTGC
69451 TGAATTTCGC TGAAGTTTCA GTACCTTCTT TAAAGTACTA AAGAAAAGCA
69501 GTAGACATAT TTTTTATTCT GTTTTATGTA AACCGAGTAA AAATGTCACT
69551 TGGAAGATCT GTCTTGATCC CAAATTCCAT TTTAAACATG GAGCTGCAGC
69601 TAAGGAACTA AATGCTTCTA TTTGGGGATT TCCCTTTATA ATTAAAACTG
69651 CTATCTGTGA GGTGCAGGGC AGAAATATTT TAATTCAGTA CAGTGTTTCC
69701 ATGTTCTGTG AAAACAGCAC ATATGTTGAT AATTTACTGT ATTAATGACC
                                       U gene exon 4
69751 AGCTTAACCA TCTTCACAGG CAAAATGGAG AATATTCTGA ATGAGGACAG
69801 TGTAAGTGAC CAGACTCAGA TCCTCCTAGT TAATGCAGCT TATTTTGTCA
69851 CAAACTGGAT GAAGAAGTTC CCAGAAGCAG AGATCAAGGA ATGTCCTTTT
69901 AAAGTCAACA AGGTACGTCC TGAAATAAAA TAGAGTACAC CTTCTACTCA
69951 GATGAATGTT TGCCAATTTT GTGCTAAGGA AATTTCAGTG AGAGCAAGTG
70001 AAAAATATTT GTTACTACTA TGGCATTCTT AGACTCTCTG TCAAAACCTA
70051 TGTGCTGTTG CAAAAGTACC TAAGCCAGTT TTCTTGTTAC GTTGCTAGTT
70101 TGAAGCTGTT GGTGAAACAA GCACTAAAGG TCACCGATAG TAGGTAATTC
70151 TTTCCTTTAA AGCACATCCC CAGTATATTG TATTAAGTAC ACCTTGTCAC
70201 ATGAAAACTG CTCCCCTTAA AGTACCAACA GCTTTCACTA GCAGTCTTAC
70251 AGCTGATATC GTTACTTACA GAAGCCAACA AATTCCATGA TGGTAATCAA
70301 TGTACCACTT TCATGCAAGC TTGCAAAGTT TCCTCTCTCA TCTTCTCTGT
70351 GAATTAAAAG GAGTGCTAGA TTGTCTCCTC TTGTGTTTTG CAGACTGAAA
                          U gene exon 5
70401 CTAAGCCAGT GCAAATGATG AATCTGGAAG CTACTTTTTG CCTGGGTTAT
70451 GTGAAAGAGT TGAATGTTGC AATCCTTGAA CTTCCATGCC TTAACAAACA
70501 TATAAGCATG CTCATTCTGC TTCCCAAAGA CATTGAAGAT GAAACGACTG
70551 GCCTGGAAAA GGTGAGAGAA AAAAACAGTA CTGAGATGAT GCTTTCCATG
70601 CACAGCTGTG TCGGTTAGCT GTGGGTAGCT TGGGTAGGGA CTGTCTTCCT
70651 TGAATTCCTT CATTGGGTTG TTGAGCTGAT TACATAGCAA ACGCTTGTGA
70701 AGAACCAGTA ATCAGAGTAT GCACATTTAG TGGAGTTTCT CTGGAAGTCT
70751 ACTCTATAGG TTAAATAATC ATTATATCAA TATAACTGAG AGTGTAAGTT
70801 AACTCTGAAT GCTACAAGCA AAAGTTGTCT TTTGGACTTT GTTTTTTTGG
70851 GGTTTGATAG GACTGATGAG TTCAGAAATG GTCTTTTTGT TCCCACTTTC
70901 TCTGGACTGC ACATTAATTT CCTTTGTTCT TTATGTCCTC AGCTGGAAAA
```

*Fig. 1-27*

U gene exon 6

70951 GGCACTCACC CCTGAGACAT TATTACAGTG GACCAATCCC AGCATGATGG
71001 CCAACACCAA AGTGAATGTG TTTCTTCCAA AGTTTAGTGT GGAAGGCGAT
71051 TATGACCTGA AGCCACTCCT GGAAAGCCTC GGCATGACAA ATGTCTTTAA
71101 TGAGAGTGCA TCAGATTTCT CTGAGATGTG TGAAACCAAA GGTGTGGTTT
71151 TGTCAAAGAT CATTCATAAA GTCTCCTTGG AAGTAAATGA ACAGGGTGGA
71201 GAGTCTCTAG AGGTACCAGG ATATCGGATT CTGCAACACA AAGATGAATT
71251 TAAAGCTGAC CATCCGTTTA TCTTTTTGTT TAGGCACAAC AAAACTCGCA
71301 ATGTGATTCT TTCAGGCAGA TTCTGTTCCC CATAAGCAGA GAATATTAAT
71351 TATGAAAAAG ACCATAAATT TATGGTGATG CATGTTCCTG TAAAGCTTGG
71401 TGTCCTGACT ATCACCTTTG AAAGGAATTC TAAGAGGTTC ATATATCAAC
71451 AGGGTAATAC AATGTACTCT ACATATGCAG CAGAACTAGT TTATTTCCTT
71501 TTATTTAATC CCCTTAAGCT GAAGGATTCC CACTGTGCAG AACACATGAT
71551 ATTTGACTAA GAAGTATTCC ATCCTCATCC ACGAGAATAT TTTGTTCCTC
71601 TGTGACATCT TTTTCCAAAA CAAAATGAAC AGAGAACCTG TTTTTGAAAG
71651 ACTAGGAGCT GGAAGAGGCT CTGGGGGAAA GAGCTGCATT CCTGTTTCAT
71701 ATCCAAAACA CCTTCCCTTG AGACTCATAC TCACTGCCTA AAGGGGGAAA
71751 ATGTGGACAT GTGGTGTGAT AGCCCTCCTC TTGTACTTGG CTGTAGTCTG
71801 GTGATCCAGG GTGCCCTGCT GGACCCTGCT AATGCACGGT GAAATAGTGC
71851 AGCTGAACAA CTCAGAGTTT GCATCTGTGA AACAGCAGCT GCAATATGGA
71901 TGCAAGAGGC AATAATAAAA CACCCAGAAG ACTCTTCAGT GTGTGCTACC
71951 TCAGTTTGTA GGTTGGGGAG GTTGCACTCT ACTGTGTGGG ATTTTTTCAC
72001 TCATTCTCCT TCAGACATGG CAGAGGTGAC CAGTTCACTG CAGCTGAGAG
72051 GAACTCTGTT GTATATATCC TGAGAAAAAG AAGGCTGTGC AGTTCTAGGA
72101 TAGAAATCAC TTGGATTAAT ATTGAAAATG CCACACTCTT CAGATACAGA
72151 TTTTCTGTCA CTTCTGGATT CAGCATTAAG GAGGCTCCAC ACGTCTACCT
72201 AACCTCTGGG ATTCAAGAAA GAAATAAAGG CTTTGACTTG AGTGAGATTA
72251 ACACTGTAAT TAGAAGTCTC CAAATTCCAT ATGAAATTAT GGTAATTAGT
72301 TTTCCTTTCT ATCTAAAGAC TGCCTGCTGC ATATGTTCAG TACTGATTTA
72351 CCTAATTACT GTTCAGAATA AAGCACTACA AAACCTGTGT CAAATGTCTG
72401 TAGCACATCC AGTGTCAGTC TGTTCTCCTT CACTCAGCTT CCAAGAGGGG
72451 ATAGGAACAG AAATTGGTAG ATTCATTCAG GACACAGTTA AAATAAATAT
72501 ATGAAGAAAT TAAATCTGTG ACTGAATTGC CCTTTTGGAC CACACGATAA
72551 TAGCTGACAA TTAAGGAGTA TAGTACTATT TGGTCAATAT ATAGAGTGAG
72601 TTCAATTATA TATCTTCAAA GAAGGGGCCA TTTTAACTGA GTATTCCCCT
72651 TGGTTCTTCA GATCTGAAAG AACCTAGAGA TTTCTAAATG GGAACATACA
72701 ACCCTTAATA CATATTCCTT TCTTCTCATA GCAGAGAACA GCACAGTGGC
72751 TATTATGGAT TTGGAGAGAG TTCTGTTTTG ATTCTTGGCG TTCCCAACCC
72801 ACATGTAGCC TTCAGTCACA AACGTTCAGG GTTTCACCAG TTGTCTTCCC
72851 TCTGTGAGTC TCTAATGCTC TCTGACTTAT CTTAATATCA GACAGTTAGT
72901 GGATACATTG GTTCACATCT TTGAAGGCAC TGAGGGGACT AACTCACCAA
72951 AACCAACAAG AGATGAGTCC CTGCAGGCAT CTGGGGGTCT CTGCTGCTCT
73001 TCATCAGGCA CTCTGATACA TAGATAGAAG AATGCTATGT GTAAGACTTA
73051 ATTTCATACT GTCTGAGAGG AGACAGCCTG CAAAGACCTT TACTAGCTCA
73101 ATAGCTTCAG TGATAAATGA GTGTCTGGAA AATGTTTTAA TGTGTCCCAT
73151 CATTGTCTGA TCTGTTTTGG AGGCTGCGGT TGGAGTTATT CAGAGCTGTC
73201 ATCACTGCGG TGTCCCCTGG TTCTCCCATT GGTCTGGGCA TTGCACGTGG
73251 GGTTGGCAGC CGATGAGCAG CTGGGCAGTC TGTACATAGG CAAGGTGGAC
73301 TGGTTGCCTA CAGTCTGTGC AGTTTCTCTG TGTTTCAGCA CTGACTCGTG
73351 GTCTAGTAAT TGCAGGTATC CAGCAAGCCA AATCACACTT CATTGCTACT
73401 GCTGTGCTGG TCTGCTAGAC TGATGAAAAT CTCTGTTAGA CTGCCTCATC
73451 TCTCTTTTTC TGCCTGGATA AGACTTATTA AAGGAGAAAA GCTGATATAT
73501 CACTCTCAGA TTTTCTAGAT CACGAAAACA TTGCAGTGCA GGAGCCATTC
73551 AATCCAGCTC ATACTCCATT TAAATGCTGA TCAGAACACT TAGTGCATCC

*Fig. 1-28*

```
73601 ACGTACGTTC CCAGAGAGCT CCTTGTTGGT GCCTTTGCCA AGGAGGGCTA
73651 TCCCATGAAA GCACACAGGA ATGCTGCCTC CGGCAGAGAC CTGTCTGTCT
73701 CCACCTTCTG ATTAACACAA AGGTACCCAA GACTATGCAA GGCAAGCTGA
73751 TATTTCAGAT AAGAAGTTGC CTCAGTTTAC AGAAGGCCAT GAAAAGCTCT
73801 GGTTCATTTT CCATATCTGC TTCTTCTCTC TGCTTTTGGA AAATAATTCT
73851 TATTTCCTAC TAGCAAGTCC AGACTAGTGT AATATTTAGT CTTGATTTGT
73901 TAAATCATCG TGAATTTTAG CTTTTACTAA TGGTATCTTA GATGATCTAA
73951 TATACTAACA CCTAGTAAGT GACTTCAGAT AAGGTGTTAG GCTTATACCA
74001 CAGCCCAGTT TGAAGGAGCT AAGTGCAGAT GGCAACCAAA CAAGCAACAA
74051 CACAAATAGG CCCAAATAGC CCATGGAGGG CCAGAAAGTA CAGCTGCAGG
74101 CAGAGCTGTG ATGTAATCCA TTTTTGTGAG CCCCTTGAAG CCAGCAGGCC
74151 AGCCTCGTGC TTTTAGTGTA ATGGACATCA TACAGCCAAA AAGGAAGGTT
74201 ATGCCATAAT CCTTGCTCCA TTCAGCAATT GGACTCGAGT GTACTAGCCC
74251 TGTTTCCTAG ACCCTTCCAG TCCTATGGAA ATTTAGAAGT CCCAATGTAA
74301 AACCTATTCA ACTTGCAGCA TGTGAGAGGA AGATATCAGA ACAGCTCCCG
74351 CTAACGTGAG AAATGCCATT ACAGGGTACT GTACTGTTCC ACCCATTCTG
74401 GCCTCTGGGC TGTGGGCAAG AAACTGCATG GGAGGACATG GGAAAACCTG
74451 TGTGGGAGCT TGCATATAGA AATGTATTTG TACTCAAAGG CGTTGGCTGT
74501 GACGGAGAAA GTGAGCATAG GTGAGGACTT GCTCAGATCA CCAAGCAACC
74551 CCACCTCACC TTTCAACACA GCATTACTAT CCAATGATGG GTAACTGGCC
74601 TGATGGAAAA AAGCAAGCCA TGGCTGGCTT TTGCAGGCAG TTGCAAACTG
74651 CAGTGTTATG CAGTCTAGCC ATCTCATAAC TTGCTTAGCT GCATAGTCAT
74701 TGCCCACTTC CTGCTCCCAG CATTTTGTAG AAGAGAACTG GTACATCTAA
74751 ATGCTTTGCA GTAGCAGGAA TTGGTTTTGG AGATGAGCAG CTGGTTTTGA
74801 AACTTGAAAA ATGCCACATA CAGGCAATTG GCCTGGCTGG AAAAGCAGTG
                                                CR1-GG
74851 CGGTTTTGAG CCTTAGGTAT GTTACATGTG CAAGTGTAGA GTCCTACACC
74901 TGGGGAGGAA TGACTGCAGG TACCAGTACA GGTTAGGGGC TGAGCTGCTG
74951 GTGAGGAGCT CTGTGGAAAA GAACCTCGGT GTTCTGGCGG GCAACAGGTT
75001 GGCCATGAGC CAGCAGTGTA CCTTTGTGGC CCAGAAGGCC AATGGTATCC
75051 TGGGGTGCAT TAAGAAGAAT GTGGTCAGCA GGTTGAGGAA GGTGATCCTC
75101 CCTCTCTGTT CTGGTGAAGC CACATCTGGA GTACTGTGTC CATTTCTGGG
75151 CTCCTCAGTT CAAAAAAGTC AGGGAGCTAC TGGAGAGAGA GTCCAGCAGA
75201 GGGCCACAAA GATGCCTGGG GTCCTGTAGC ATCTCCCTTG TGAGAAAAGA
75251 CTGAGAAACC TTGGGTTTTC CAGACTGGAG AAGATAAGGC TGAAGGGGGA
75301 TCATATCAGT GATTACAAAT ACTTAAAGGG CAGAAGCCAA GTGAATAGGG
75351 CCAGGCTCCT TTTGGTATCC TGTGACAGGA AATGGGCGAA AATTCAACAC
                                                CR1-b
75401 CAACAAGAGG AAGTACTTCT CTACTTTGAG GGTAACAGAG GACTGGAACA
75451 GGCTGCCCGG AGAGGTTGTG GAGTCTCCTT CTCTGGAAAT ATTCAAAACC
75501 TGCCTGGATG CTTTCCTGTG CAACCTACTC TAGGGAGCTT CTGTAGGAGT
75551 GAGTTGAACT CAGTAATCTC CAGAGGTCCC TTCCAACCTC TACAATTCTA
75601 TGATTCCATC CTAACGGCCT TAGAAGGGTC AGAATTTGCA CATACGGTAT
75651 AATGTTCTGA GGCAAAGCAG TGAAACAGAT TGCAAAGAAG CTCTAAGGAG
75701 ATATAGAGAG CAAATCAAAG AAATGAGTGG AGGAACGACG TCAGTGTAAA
75751 AGGGAGGGAG AAAGCACAGA GTTTGGAAGA ACGAAAGCAG TGAAAGGTAT
75801 TCAAAAATGG CACTGAAAAG TGGCTAGGAC TCACAAAAGC AGCAGAAGAA
75851 AAAATGGAGA ATGGAATGGG AAAGGCAATA GGCAGAAAGA AAGAAAAAGA
75901 TAAAGAGGCA GGAACAAATG ACTAAGAAGT CTGAAGAAAT ATGCAGAAAG
75951 GAAAAGCAAA CAACAAAGCG AATCCAAATG GAACAGAAAA AAAGTGAAAA
76001 GAAGGAAAAT ATTACTGAGG AGATCTGATA CTGTGTGCAG ATTTGTGCTT
76051 CCCATCTCTT TCTTTGCATC TCACTGCATG TTGGGGACAT AACCCCATGT
76101 GATCAGCCTC TCTTGGACTC CTATTCTTAG CTCCAGTGAT TTAAAAGAAT
76151 ACCCCCTGGG TGGGGATTCC TGTTACAGAT CAAGGAAATA CTTCTTCCTC
```

*Fig. 1-29*

76201 TCTCTAATTA AAATCCTTCC ACTCACAGAA AGCTGGCTCT GTACCTGAAT
MAR (0.81)
76251 GCGTGCCTAC TACCTGTAGG CAACATAAAG CTCATGCATT TCCTATTCAT
76301 TTGCTCTATT TCTGCAAGCA AGCTCAGCCC CAAACAAGGG ATCTCTAAAT
76351 CCTAGCAAGA ACCCTGCACA CCCCAGTGTT CAAGTCCTGA CACCACCAAA
76401 TTCAAAAGGA ACTACACACA GCACCACAGC CATGGATCTC CAGTGTTAAT
76451 GCTGTTCTCC AGCTAAGGGC GACTTGGCTT TGCAGTCAGG AGATGTTGCC
76501 AGGATGCCTC CTGTCAAACT AGTTGGGCAG CTTTGAGCGA AATGCTGTTA
76551 GCACATTGCT AGATATAGGT TTCCTGGTCT TCTGCAGGAA ACTGAAGGAT
76601 GACATTTGCA TGAAATTACA ACGTGCAGCC TTTATCAACA ATTGGCTAGA
76651 GACTGAATTT TCCCACAAGA AAGTGGAAGA AATTTAAAAT AGAGTATACA
76701 CAGGAAGGTG CTCCAGAGCT CAGCTGTTGT GTTCTTCATT TGACCTCCTT
76751 GCTCAAGAAG GTAAACATTA TTTTTCTCTT CAAAAATAAC TTGTCTTGTT
76801 GTTGTTGTTG TTTTGGCCAA ATCAGTCTAA AAGTTGGTAA ATTTCATGTT
76851 TATAGATGGG GCAAAGGGGG AAGTACTTTC ACAGGCTGGA GAGAGCAAAA
76901 GACACTGCTA AAATTTGGGT GGTCTTCACG AAGGGAGGTG GTCTTCTCTG
76951 GGGTGAGGCT GGGAATTTAG GAACACATGC CCAAAGCTAT GAATCTAAAG
77001 ATGCCTGTCT AAATTCCTCA GACTTTTGAC TGAAATTTCC CTCGGTTCTC
77051 CCTGCCTGCT TGGAGAGCTA TAACTGCCAC AGACTGAGTG GTTTATACCA
77101 CATGCAGATG CTTTGCTGCC TACATCTCCA GAAGGGTCAA AGGGCTGTTT
77151 TAGAACAGCC CAACTCACTC TAAAAAAATG GGCTTTATGA GAAGCGATGG
77201 TGCAGATCAT CTGGATAAAC TCACCCATAA ATTAATAGAA ACAGGTTAAT
77251 TTTCCTTCTT TACTCAGGTT TCCACAGCAC AAGGAAAAGC CTTGAAATGT
77301 TCACTAGACA AGAGAGGGCA CGCAACTCTT TGGTTGCGTG CTTGGGTGTT
77351 TCCTCTGTAC CCTGGTCTCT GCTGCTAGGA TTGTTTATGT TCTTAAACAA
77401 TGGCTGTATA TAATAGGAAG GGTGGAGTAT TCTTCAGATT TTGTTTTGGT
77451 AATGGGGATG CTTCACTATC AACATATTTG CTCCTGGCTT TGGCAGCGGT
77501 GTTCAAAAAT TTGCTGAGAA GTTTATGTAA CTACACATTG GCATAACAAA
77551 TAGCTTGCCA CTGTATGGCC AATGTACATC CATTCCTGTT CAAGCAGGAA
77601 TAATCAGCCT AGAAAGAAGC AGGAAAGATA CATCCTGGAG GTACCGATGC
77651 AAAATAATAG AACCAGTCAG GAAAAGCCCT TTCCTGTATA AAAACAGCAT
77701 CATGAGGGGC TAAGTTGCTT GGGAGATGGA CTTGGCAACA CTTCTCCTGA
77751 AAAGATATTT TGTGCTGAAA TGTATTGGGT TTTAATTTAA AGCACATTGC
77801 TTTGGAAATG CTTTGTGTTG CATGGGGAAG ACTCGAATTT CTGCGTTAAA
77851 GGAAATTTCA TTTTTCTTAT GTGTTGTGTC CCTTTAAACC CAAAAAGCCA
77901 CAGAAACACT TTGAAAGTTT TTGTATGAAT GGTCATGAAA AATAACTTCT
77951 ACAACCATAG GCTTTTCATG TGAGGACACT GTATTATCTG TTGTGTTCTC
78001 CTTTTCTAGG ATAGACACGT ATCATTTCCG CCAATTCTCT CTTCCTTTGC
78051 TTATGAGAAA TAAATGTATA TTAAAGCACT TAAATGAGAA GAAGAGTAAG
78101 TATGCAATTG GAATTATCAT GCAGCATCAG GGAAAACAGG TTTCTTCTTG
78151 CTTTCCCTTT CTACATATAG AACTGCCTTA CAAACCAGGC TACCACTCTT
78201 TCAGAATCTG CATTTTATTT ACTGCCTCCT CCTGTTGACT GCATAATGTA
78251 ACATACCACA TCTTTTAATT ATGATAGCTT TGAGCGCAGC TTTTCATTCT
78301 TCAGTAAGTT TTGCCTTGAT TTCATCTTTA GCCTAAAACA AGCTCTACAG
78351 AGAGAACAGA GCGTGAACAG CTATAGAAAA GGAGTATTTT TCACTTCACG
78401 GAGCCATGGA AGCAATTTGT TATCCTTACA AGACTTCTGG TATACAGTGG
78451 TATCTACGGA AGGAGGCTCT TTTCCTGGGT AGATCCCTGC TCACATATAA
78501 CAACGCCAGC AATTCCACCT CCCAGACTGT TAACAGCTAC TGAGCCATCA
78551 TGCAAAGCAT CTCCCTTCAT CAGCCATAAA ACCACAGCCC TGCTTGCTGC
78601 CTCTGCACAA TTGCTAATGT TCTGTGCAAA CAGTTTGTCT GGTGCAGAAC
78651 AACAGCTGTG ATCTTTCTGG AACACTTCTT TTGATCTTGT ATTTTCTCTC
78701 CTTCCCACTC CAAGATCTTT TAAAAGAACC ATTTCCATTT GTTGCCCAAC
78751 ATCTAGGTGT TCTCAAAGTT ACTCTGCCCT CACGGTGGCT CCAAAACTCA
78801 CCAACAAATG ATTACAGAGA TCATAAGCAT GGCTTAATGA TGTGGAATCA

*Fig. 1-30*

```
78851 TACCTACACA TACTCCCTCT CCAAATATCC ATTAAGAAAG TTCACTAAAT
78901 CCTTTGGTTC TCTAGTAAGA AAGTTCCTTC TCCAGCCCAC ATCCCTTCTC
78951 CCTCCACTGT TGCATTGCTT TTCTGGGGCA GCCCTGTAAA TAGCTCACAT
79001 GAAGCCATGG AATTGGTGGC AGTGGTTGTA CCTGGACGTC ACTCTGAAGA
79051 CAGTCTGCTG CTTTTTCTAA AGGCATGGAC ACCTCTGTAC GCCAGACGCT
79101 TGCCTTTAAG ACCTGTTTCC AGCTCTCATG CTCTCCCTCT GTGCTTGGTG
79151 GTTGGTTCTT TCCCTGTGGG TTGGGGTGGA GGTGCCTCTC TTCTGTTGAG
79201 GAAGTTCATT AGCTCCTGTT GTCTCCTCGA CGCCTTCTGA GGTCTAGACA
79251 CACCTACAAC ATGCATCCTG ACCTACATTC ACAGTAAACA ACCTCTTAGA
79301 TCCATTTTAG ATCTTTTACC AGCTGTGAAA GTGGAGCAAC ACAAACTTTA
79351 ACATGAAAGA AGTGCTGAGT TTTGTTTTCA GAAGGTTGTG AATAATAGCT
79401 AACGAGGGTG GAAGAAAAGA GAAATGATTA CTGCAATGTG TTTTTCTTGT
79451 GGTAGGATGA CTGCCCATTT ATGTTAGGCC TTCATATGAA GTACTACTGG
79501 ACTTCAGGGT GAAACAAGTG TCTTAGAATG AAACATATAT GAACTTTTTA
79551 TTTCAAGTTA GGTAAAAGGA AATAAATGCC TGCACTTGCC ACATATCAGC
79601 ACCTTCATAT GTTCAGCAAC TTGACTTTCC TGTCAATCTA TCTTAGGCTA
79651 AGCCTTTTTT CTTGTGGGCT GAGTTCATTC CCATTGTCTG GGACTTGCTG
79701 CAAGCTAAGC TGCTCGCACA GACAACTTGC TGCACCTCAG CAGAGCCATA
79751 GCAACTTCTT ACACCCTGTT AACTTTGGTG CCTGAGCCCC CACTTGTCAT
79801 ACAAAGATCC TGCCTGTCTC ACACCTGAAT GAGAGGCAGT GTGTGTTCCG
79851 CATCCTTGCA GTCAGTGCAG GACGCTGAGT AGTTCTTGTC CCAGAGCAGG
79901 CTGAAAGCTA GAGCCACCCT GACCTGAGTG CTTTCTCTCC ACACTGTGCT
79951 ATATATTTTC CCCTAAATAA AATATCTTTC TGGAACACAG GCCACAGTTA
80001 CTTATGTCTG CAAGCAGCCA AGAGCATATG CTTTGCTTTT CTTACATATT
80051 TCTGGTGTGC TGTCCAGAAC ATCCTTTGTT TGACACTAAA ATTGATGTGT
80101 GCTTTTTATG GTACAATATT TTGAGAAAAA CTTGAGTACT CCACTGCTAT
                                  MAR
80151 CCACACAACA GCTTTACAGT TATTTCCCTA AAGGACTGAT AAGGGCTTCT
80201 TAAAAGCCTT TTTTTTTTTT TTCAGATGGC ATTCTTCATG AAAAGACCAA
80251 GCTGAAACTT AGTCCCAAAT TCTTCTTACC AGAGTGGATT TAATGGCCCA
80301 TAGGAAAGGC ATCAGACTGC TGTATTTACA GTACAAGAGA AAAGAATGAG
80351 ACAGATCTTG TCCTGCCATT GAACAGGAAG CTTACAGACT TTCTGGGGCT
80401 GCTGAGCTAT TGCTTCGTTG TGAAATTGCC ATTCGTTATC CATTCTGAAT
80451 CAGTGGTTCC TATCAAATCA ATGAGGAGAC ATGAAGTATA CTGCAAACAG
80501 TGCATGTTTC CATAGGTAGT AGCATTCATA GCTGCTTACG TTCCTTCTTC
80551 ATACATGAAA ATAATTACTA GTAATTTTAC TTTCATGAAT CTGTTGTTTG
80601 AATCCTTCAC ACTGCAGCTC AGGTTACCAG ATGTGGTTAG ATGCCCGTGT
80651 AGTTTCTGTC ACCCCAATCT GTCTCTAATC ATGTTGTTAC AAGAGGAAAG
80701 AACTGATGCG ATGACACACA TTAAACTAGT TTGTAGAAGG AAATCCACGG
80751 CTGACTGATT TAAATACCAC AACCTTTTGC TTACAAATAA GAACAAGACA
80801 GACAGACCAC GGGAAACTCT TTTGGAAGGG ATCAGATACA TTGTGGGATA
80851 AGATGGAAAA ACAATTCTCT CTAAGGAATT CTCATATGGT ATGAGTATTG
80901 GGGCCCCTTT CCAGATCCTG CTGTATTCAC ATGAGTGTGA ATTAATAGAT
80951 GTGTGCAAAA TCAGCTATTT CAAACTCAGA ATTCAGCACA CTTCTACTAT
81001 TTAGCAACCG ACTATGGGAT GATTTTAGGG CGGACAGATA CTTCACAGTA
81051 TGATACAGAT AAGCAATCAG CTGATTCACA TTTCTCCTTT CCCTTTTTGC
                                         V gene exon 1
81101 TCCCAGTAAG CTGCAGGCTT CACAATGGGC TCCATTTCTA GAATGATTAT
81151 TGAGTTTTGC CTTGATCTCT ACAATAAACT CAACAGAACA GCAAAAGGCC
81201 AAAACATTGT CTTCTCTCCA ATGAGCATCT CTACCTCCCT TGGCCTGATC
81251 CTTCTAGGGG CACGAAACAA CACTGCTGCT CAGATAGAAG AAGTAAGTAC
81301 TGCTGAAATG TTCTGAGATA CTTCCACATA GCCTGCTGTT CCCCCAGTGG
81351 CAATGCTGGG CTTTGCAGCA CAACATGTGT GCTTAGGAGA CAAAGATAAA
81401 CACAAGCTCA ACTGCTGCCT TGAGAGCAGT GCTTGGTGTG CTGTGATCCC
```

*Fig. 1-31*

```
81451 TGCTCACTTA TCAACTGTGA CATTCAAACG ATTCAACATG TCTCACCTAC
81501 AGAGCACACG GAGCCTGGGG GTACAGGGTG GGCATGCAGA AGTCTGTTCC
81551 TCTGGTCACC ATGCCTTTTA CTCCCTGCAG TGCAAGCTGT ATGCTCTGAG
81601 ATCTTTTATT TCTTTTCTTA TTTGTTTCTG AGAGCAGTAA GTGACCAATA
81651 CTCCTAAGGT ATATGTGGCA TAAGGCAGTA GCTGGCTCTG GCTGTGTCCT
81701 GGTGGATCTT CATCCATTGT ATTATAATAT TGCCACAGGT CAGCTGCTGC
81751 CAAGGGAAAC TCATTCTCCT TATGAGGTTC TGAGTGACTC TTGCTTAGTT
                                                   CR1-c
81801 TAGGAAAGCA ATGGAGATCG AGTACTCTCA ACAAGGGGGA ATGGCGTCTA
81851 ACTAAAAGAG CGGAAATTTA GGTAAGATGT TAGGCATATA TTCTTTACAC
81901 AGAGGGCAAT GAGGCACCAG CACAGGCTTC CCAGAGAAGC TGTGGTGCGC
81951 CATCCCTGGA GGCGCTCAAA GCCAGGTTGG ATGGGGCCCT GGGCAACCTG
82001 ACCTGGTGGT GGCATCCCTG CCCACAGCAT GGGGTTGGGG CTGAGTGGGC
82051 TTTGAGGTCC CTTCCAACCC AAACCTTTCT ATGACAGTTA ATAAATCTAC
82101 ATCACTTATC CAGGACAGCC CAGTAAATCT TTCAAACAAG GAAAATGCCT
82151 TTATCCCAGT TAAAATTGCC ATTAATTTGA CCTCTTCAAC TGCAGGTTCT
82201 CCACGTCAGC AATGCCGCAG GAACTACAAG CCTTGAATCT GAGCTTGAAG
82251 GTGCAGTGCC CGAAAACAAG TCTGAACTAA GCCAGGAAAG AGAGTCTTCC
82301 CCCTCTCTGG TATGTCTTTT TTAGTACAAG AGTCTTTCAC TCCACAGTAG
82351 CCTATTAGTT GTAAAGCACC ACAGCCTGCC ACAGGAGGGA GTCAAGATCC
82401 CATGCACAAC GTCTGCCTGG TCTACTACGC CTGATTGAAG GTGTTCCCTT
82451 GTAATCAGCC AAGTCCTCCA TAAAGTCAAA TACAAAGCCC CCACCAGAAG
82501 GAAGATCAGG TTACAAAACT TAGATTAGCT GAATTTAAAT ATAATTACAG
82551 TGGGAGCTAG CCCTACACTG CAATCTAATG AGGATGCAAA TGAACAACCA
82601 AAGCTATACT GAGGAATACT TGTAATTGGT GTGTTTGAAA TATTCCTAGT
82651 GCAACACAGA TGGGAATCTT AACCACGAAG CGTTCCATGC ACTGCTTTTA
82701 CAACTACAAA ACCTTGGCAA AGACTATGTT TTAAGCCTGG CTAACAGCCT
82751 CTTTATCCAA CAAGGATTTG AACCGCATCA GGTAAGATAA CTGTACCTTG
82801 TAACCTCTGT GGCGCTGACC CCCAGCTTTC TGGCAACCAT ATGCTTCACT
82851 GTTGTCCCTC CATGTGTATT TTTGAGCATT GGAGGTGCTT CTTGGAGCCA
82901 TATCTCTTAG GGTTGTTGGG AAAGAGACAG AAGTATCAGC TTTCAGTGCT
82951 TCTGTTTAAA ACAAACAAAC AAACAAAGTC AAGACAACAC TCTGTAGAGC
83001 AAAAATAAAG CAGAAGACCT TTGACTTTTG GCATATCTAA CTTGAGCCAG
83051 AAGTGCGACT ACAGCAAAAA AATGGCCTAT TCAAGCTGTC TGCAAGCTGC
83101 TTCTGGGCTA TCTTTCTATT TGCAGCTTTG CATTGCTGGC TTTCCTCTTT
83151 TTCTTCTTTC TTTCTTTTTT TTTTTTTTTC CCCCTGCTGA ATGATTTGGA
83201 TACTTGAGAA TCACCCAACA CATCTTGCAT CTTCTCTAAT TTTTTTTTCT
83251 TTTCTATTTT TTTAAATTTT TATCTGGATA CCTGCATACT TCAGGTATGC
83301 AGTTTTCTGT GGGAAGACAT TGTCATCTAG AGGCAAAAAT GTATATAAAT
83351 AATAAGAAAG ACACAATAAT AATCTCTTTT TCAAAGATTA TCTGAATCAG
83401 CTTCTGATAG TTGATGTTTC CAAAGCCAAA TTTTGTCTCT TTCAGTCAAG
83451 AAGACCCTCA GAATTTCTAA AACGTTTCTG AATTGTTGAC TTCATGTTAA
83501 AGAGAATAAG CTCTGAACAG GTTTGGCTAA TTCACAATCT TTATTCTGCT
                                 V gene exon 2
83551 TTACAGAAAT ATCTAATGTG CAGTAAGGAA CTATACAGAG CAGCCCTTGA
83601 AACAGTGGAC TTCCAAAGGG CTCTTGAAGC AAGCAGGCTA AAAATTAATG
83651 ATTGGGTTGA AAGCGAGACA CAAGGTAAAA CAGAGCAAAA CTGTAGCTGT
83701 GCTATCTTCT CCCTCTTCCA GTGCTCCTTC AAAAAGAATT CAGCATATGA
83751 TAAGTCTTGT TCATGTTTCT AGGTTTCTCA TGCCCGTCAA AGATAGTTTG
83801 TTGTTCCCAA TCATTCTTTA GAGTCATCTA CCAGCTAAAC TATTTCTGAG
83851 TTAAAGATGT GTTTGTTGTC ACATACTGTC ATACTCCTAC CCACATGCCT
83901 AGCAAGATAA CTGCAACAGT ACCTCTAAGG GTTAAATAGA TTAATTGCTC
83951 CTGCAAATAG CCAACACTGC AGGTACAGTA AAGCAGAGGA CGGAAGTTAT
84001 GAGCGTCACA GTGAGACTGG GAACAGCATA GCAGAGAGAG AAGACACCTG
```

*Fig. 1-32*

```
84051 AGGACCTGGT GTTGACCTGC TCTGGTCGTA CACAGAGCAA TGCTAACAAA
84101 GATGAGTGAT GTGCCCACCA GAGAGATTTC ACTGTTACAA GTAACAACCA
84151 ACCAGCTTTT GCCCTTTACA GGCACATAGA GGTCATTGGC TTTTTTTCTG
84201 ATTAAGCTGA ACATGAAATA TGCCACTTTT ATTTTGTCAG AGATGCAACA
84251 TCAGCAGGGT GAAAACCTTA TAAATCTTCC AGCTGAACTT AAGCCAGAAC
84301 TTACTGAGGG AAATTACTGA TGGATGAATA GATTTGAAGG CTTCTGATTT
84351 CTTAATGGTC ATATCCTGAC CAAACCTGTC CTTGGGCTGA CAGAGCAGCC
84401 TGTGACTAAT GTGGGAAAGA GCTGCAAACC CCAGACCATC ATTGCTCTGT
84451 GTGCCTGTAC AAAGCCTGCG CGCTTGGGAA ATCCTACTTC ACCTCTGTAC
84501 AGAAAAAAAA AGGGTAAAGG GAAAGATGCC CTCATGTAAA CTGAAACAGA
84551 GGATTAATGG CGCTGCGCCT TTTACTGTGG ACAGGTGCCA CCTGGAACAT
84601 TCATTTTGCC ACTGATCCCA CAGTAGGCTA ATTTGATGAT CGGTGCCCCT
84651 TCCTCTCCCT AACAGGCCAG TACTAGGTAA CAGTGCTGAG AAATTTACCA
84701 TTTCTTTGCT TGTATCGTCC CTGTTCTGTG AAGAAACAAA CAGTTGGATT
84751 TCTAAGGTAC TCTAAAGCTA AGTTCACAGA CAAGTAATTG AGTCTCAATC
84801 CAGAGCCTTA ATAACAACTA ATAAACACCT GTGTTTTCCA AAATTTCCTC
                              V gene exon 3
84851 CAGGTAAAAT CAAGGAACTT TTTGCTCCAG GAGTGATTGA CTCACACACC
84901 ATTCTGGTGC TGGTGAACGT GATCTACTTC AAAGCATCCT GGGAACACAA
84951 GTTTGAGGAG AAAAATACAG TACAGAGAGA TTTTAAACTG AATCAGGTAG
85001 ATATGCATTG TATAAATCTT AGCATGATTT ACCTGAGTTA GCATGATTTA
85051 CATGAGTTGC AACGACTCAG CATTTTGTTT CAATGGCTGA CAAAACACAA
85101 AGCTTCAGCC CTGATCAGCG CTTTTGAACC TAATAGTCAC TATGGGCAGC
85151 TGTCATGGAT AGAAGCCAAT TGCAAAGATC TCATTTCACA CAGGCTCTGT
85201 GGGGCCATCC TGGCTTTTAT GCATCCCGTA CAATTCAGCG TGAGCCATGC
85251 AACAGATAGG TTAAACCAAA CCAATCAAAA AAAGAGGCCA GATATTAACA
85301 AGCCACATAT ATGAAGATGG AATTTGAAAC AGGAAAAATC CTCACAGAGT
85351 GTTTTGGTTT ATTTATAGTA TCTGCAATGT TTAAAAGGTT TTTTTTAAAA
85401 TATTTTTTTT ATTTTGATTC CTTTTTTCCA CCGTACATAT AAAATGGAAG
                                         CR1-GG
85451 TTTTCATTGC TCAACTAAGG TACAGAATCA TAGAATTACT CAGGTTGGAA
85501 AGGACCTCAA AGATCATCAA GTCCAACCGC AGCCTAACCA TAGTACCCTA
85551 ACTCTAACAA CCATCTGTTA AATCATATCT CTGAGCACCA CATCCAAACG
85601 GCTCTTAAAC ACATCCAGGG ATGGTAACTC AACCACCTCC CTGGGGAGCC
85651 TATCCCAGCG CTTAACAACC CTTTCTGTAA AGAAGTGTTT CCTAACGTCC
85701 AACCTAAACT TACCTTGGCA CAACTTGAGG CCATTTCCCC TCGTCTTGTC
85751 ACCTGTTGCC AGTGAGAAGA GACCTACCCC GCTCTCACTG TAAGCACCTT
85801 TCAGGTACTG GAAGAAAATA ATAAGGTCTT CTCTCAGCCT CCTCTTCTCC
85851 AGACTAAAAA GCCCCAGCTC CCTCAGCTTC TCCTCGTAGG ACTGATTTTC
85901 CAAGCCCTTC ACTAGCCTTG TGAAGCTGCA AAAGTTCTT TAACAACCAC
85951 ATTAATCCAA GCTCTGTACA GCTCAAGTCT AACAAATGTC TTCAAAAAAG
86001 ATGATCAAAA CCATTTTATT TCATTTAATT CAGTTTTGTC TTCATTCCAT
86051 ATGCTGTGCC TATGTTACAC TAAATAATGA AGCCGCCAAA AAAATGAACC
86101 CACAAAAAAC ACAGATTTAG CTCTGATCTG AAGTTGAAGA GCTTTGTATG
86151 GGAAAAACTG TATTCTAAGT GTTTCTTATC TATACAAACA AAAGGTCAGA
86201 AAGACATCTG TTGCTAGCCG TAGTGTTGCA CTGCCATTTA TTAAGACACG
86251 TAAGAAAGTG TAATTTTGGT CCCTTAATTT TTTTACTTGA AATATGTCTT
86301 TGAATTTGAA TACTGAAAAC TGACCTTAGG TAGGAACATT TGGAACACTG
86351 CTGCAGTCAC AGAAACTATG AGATTGGGGG AATCTGCATA TACTTTTCTT
86401 CATGCACTAA TTAATAATGT TCTCTACTAA AATTCTTCCG CTGATTTAGA
86451 AGGTAAGTAA AAACTTAGCT AATGGTGAAA TGAACCTTGA GCCTTTACAC
86501 AGGATTTGAA CAAACTCATC ACAAAAGAAA ATGAGGCTTA GAAGACCTAG
86551 AAGAACATGC CTGAGATTGC TCTTAATCTG TCTATTGCTT CCTGCCTAAA
86601 ACATCTACCT GATAAATGAC AACCTGATTC CTGCAGTGCT ATTTCTTCTC
```

Fig. 1-33

```
86651 TATCCCATTC CAAACCAGGA CTTGCAAATC CCATCAGCAT CAGCTTGTTT
86701 GGCTGGAGAG TAATGGTATT AAGCCACTTC ACTATCTGAT CAGTTGCAGG
86751 GAAATTGCTT TGTTTTATTT TGCCCCCCAG AGAATTATCT CCTTTATACA
86801 TGAATGGCAA AACTGATGTT TTACGTGTCG TTGTATGTGC AACAAAATAA
86851 AGAAAAAATG TTTAGCTTTA TAACAATTAC TGCTGCAAAC ACAGACTACT
86901 GATATTGCAC CTGAAGTTTA AACATTAAGG TCTGTATTGC TTGTGTGATC
                                       V gene exon 4
86951 ATTCCAATTT CTTTTTAAAT AGAATGAGAG AAAGCCAGTA CAGATGATGT
87001 ATCAGAAAGG CACATTTAAA CTAGGCTATA TTGAAGAGCT GGGAACTCAG
87051 GTGCTTGAAC TCCCTTACGC TCAGAAGTTG CTTAGCATGA TCATCCTGCA
87101 CCAGGAGAGA CAGCAGATGG ATCTCCCAGT GGGGCTGGAA CAGGTAAGGG
87151 TGAGGACTGC GGCTAAGCCG GACTGAAAGC TGGTTGTCTG AATTAAAGCT
87201 GGGCAAAAAT CTAAACTTGT TAATTTCCCC ATCTTCTAGA CTGAAAGCAC
                            V gene exon 5
87251 AATGACCTAT GAAAATTTAA TGCTGTGGTT CTCTTCCGAA CATATGTTTG
87301 AGATGGTGGT AGAGGTGTAC CTGCCCCGAT TCAAGCTCGA AGGCACCTTT
87351 GACCTCAATG AGGTATTAAA AGCAATGGGA ATGACTGACA TCTTCAGTGA
87401 ATCCAAAGCT GATCTTTCTG CATTGTCATC TGAGAAATCC CTGGTGTTGT
87451 CAAACATTGT CCACAAGGCT TATGTGGAAG TCAATGAGGA GGGTACTACA
87501 GCAGCAGCTG CTACAGGAGC TACCATTGTG AGGAGGTCTC TTCCCCTCAT
87551 AGAGGTGTTC ATAGCTGACC GTCCTTTCTT ATTCTTTATT AGGCACAATC
87601 CCACCAGTAC CATTCTTTTC TTTGGTAAAT TCTGCTCACC TTAAAATCAA
87651 GGCCATCTTC TAGCATTGTG AGAAAAACCT GGATGAATCA GAAATACTAT
87701 TTTTCCCCCT ACACCTTCTT ATTCCTATGA ATGATTGTAG ATCAAAGTAA
87751 TCACTGCAGC CAACCTAGCC TAGAACCATC AATTGAATGC CCTCCTGTTA
87801 TGCTCCTTGA ATGGCAAATA TTGATCTGAA TCTAAAACAG GAGTAAGTTT
87851 TCCCTTAACC TGACTGGAAA TCAAGAATAT TTTGTTTCTT CAAGGCGTAC
87901 ATACACTCCT GTATAGCCAA GTATGTCCGG CATAGCCAAG TAATGTAGTA
87951 CACTATTTGC CTGGCAAAGG TAGAATTTGT ATGCTGCTAC CTGAGGAGAA
88001 CTGTTTGTAA CAATTTTCAG TAACTGCCAG TAAAAGTGGA GTATTTTTAT
88051 TTTCTCTGTA GTTTTTGATT TCCTGCCAGG TGGGACTTGA TTAACAGAGA
88101 GGGGCTTTGG AAATGCTTTA TACTTATACA TAATCTGTAT TTGTGGCAAA
88151 TCCTTCGCAC AGTGGAGATC TCACTTTGAT AATTCCCTTT CCTGTAGCAG
88201 CAGTCACAAG CAAGCAGGAA ATACTTATTT ACAGCAAATT CACGTGTTTA
88251 CTGACAACTG TACCACCTTT CCCCCCATGA TGTATGCTGG ATCTATCCTT
88301 TTGCCATATA AAACGTTTAT GCTAGAAGCA GCTTTGGTTT CATTTATTTA
88351 TTTAGATATA AGCCTGCATC TGAAGCACCA ACTCATCAAC TGGAAGATAG
88401 ATGGAATATG ACATATACCC CTTTCACAAT CCCTTGGTTT TTTCCACATG
88451 AGTTCTGTTA GAAGCACTGT ATTTTTCCTT TTTTAAGATA ACAACAGTAG
88501 GAACACTCAT GGAAAGGACA AGATTACGCC TCATGAACAC ATCTAGTAAG
88551 AGAGTTGATT ATAACAGCAA CTGAGTATGT GGGAAGGCAA GATTTTGACC
88601 CTCGTTTTAC AGGATTTTTT GGCACTCTTT TTTGAAAATA AATCCACCCT
                                 CR1-GG
88651 TAAAGAATCA CAGCATGGTT GATGTTGCAA GGGACCTCTG GAGGACATTT
88701 TGTCCAACTG TCCTGTTCAG GCAGGGCAAC CATGTCCAGG GGGCTTTTGA
88751 GAATCCCCAA GCACAGAAAC TTCACAACCT CTCTGGACAA CCTCTTCTGA
88801 GTTCCCACAA TTTTGAATGA CACCAAAGAG AATTTTGTAT GCGCAGTGTC
88851 TGCAGGAATG GGATGTGAAA ACACACATTT CTAAAGCTTA ATTACTTACA
88901 TAGTGAAGTA ATTGGTTTTC TTCCTTGAGT TCTGCTCTCT GGTGAAGTTT
88951 AATGATCTGA GATGCATGTA TATAGATATA CAGGTCTCTC CAGCCCTGAG
89001 GAATGAAGAA AAGTTTTGAA AAGGGCAATG TAAGCAATAG AAATCACAGT
89051 CAAATATTAC CTGGAAAACT TTTTAGTCTG AGAGATAATT AGAAAAATAG
89101 AATTAGCAGC TGACTGATAG AGAGACATAA CTGTTAAGTT GCTGGTTTAA
89151 CACAAGTAAT ATCTTCCTCA CAGAGTTCTA TGTGAGGTTT AACTAACTAG
```

Fig. 1-34

```
89201 CGTTGGCAAC TTGTGCTTTG TGACCTATAA AAAGGCAAGT ATACATTAGC
89251 TATTAGTCAT ATAATTGAGT GTAAAGCTCC ATAAAGTAAT TCATGATTAG
89301 CACAGTTTAT GTACCAAAAG TTACCTGCGG CTCTTTGGAT AAGAAAGTCT
89351 AGGCATGATG TTCGAGCAAG AACAGGCAGG AGTAGGACAA TAATATTCAA
89401 ACAACTTACC CTTACTGACT AATCTGAAAG CACAGTACAA TGTAAGCAGT
89451 ACTTTTCCAG ATTGTGTCCA TGTTTCCATT CTGGAGGCTG ACAGCACAGA
89501 TTGCCTACTA AGCTATGTTT TTATTACCTC CAGGTGTCAT CACTTGGTTT
89551 TTACATACCC TGGGGAAGTT CTGAGCACCA CAACCTCAAA CATCAGTCCC
89601 ACTTCTGCAA CGACAGGAAC AGAGATTCCT GTGATGAAGC GTCGAATAAC
89651 ACAGTGTCTT GCTCCAGTTG TTGGAGGAGA TGGTTCATGA TAAATCTAGA
89701 GTGAGATTAA GACACAGATG AGGTCAAATG TCATCCAGCT AGTTTATGAC
89751 AAATTCTAAG CAGTTAAGGA ATGTGGGAAA CATGGCAAAG TTAGCAACAG
89801 TAAAGGGAGG AATTCTAGCA AACTGGCTAT AGAGCAGGGA TACTCACCCC
89851 CATGGATCTA GCAGTATCCC ATTGGTTTGC AGGAGGTTGC AGGTCAGTCA
89901 AAGACATATC ACTGATCTGC ACAGCTGCAG TTCAGTGGAG GATTGTCTCT
89951 GTTCTACCAC TGAACTCTTC AGGCTTTATC CTCTTCATTC TGCTCTCATG
90001 CACCTTCAGT TACTCAGGGC CAATGGCATG TGTGCCTCCC ATTGGGTGAT
90051 CGGCTGTTGA TCATGCAGCA ATCACACACC TGCCACCTGG CACGCTGTTC
                                              CR1-GG
90101 GGCATGTGTA CTGACTTAAT GGAAGAGACC TTTTAAGCTC ATCTAGTCCA
90151 ACTCCCCTCC ACTGAAGAGG GACACCTACA GCTAGATCAG GTTATTCAGA
90201 GCCCCGTCCA GCCTCCTCAA TGTCTCCAGG GAAGGGGCTT CTACCATATC
90251 TCTAAGCAGC ACATTCCAGT GCCCCACCAT CCTCACTGTA AAAGAATTTT
90301 TCTTTATATC CAAGCCAAAT CTCCCTTCCT TTAGTTTGAA ACTATTTCCC
90351 CTTGTCCCAT TACAACAGAT CCTACTAAAG AATCTGTCTC CTTCTTCTTA
90401 AGAGCTCCCT TGAGAAGGGA GCTCTTCTCA GGTCACCTTG GAGCCTTCTC
90451 ATATCCAGAC TGAGCAGTGC TAGTTCTCAG CCCGTCCTTG TAGGGGAAGC
90501 ATTCCATCCC TTGGATTATT TTCCTCTGGA CTCACTTCAA CGTCCATGTC
90551 TCCTCTGTAC TGAGGACTGC ACATTTGGAT GTAGTACTCT AGGAGAGGCC
90601 TCACCAGCAT AGAGCAAGGG ACAGGATCAC CTGCCTTGCC CTGCTGGCCA
90651 TGCTTCTTTT GCTGCAACCT AAGATACGGT TGACTTTCTA GGCTGCAAGG
90701 GCACACTACT GACTCACGTC CAGATGCCAT CTACCACAGT ACCCCTAAAT
90751 CCTTTTCTGG CAGGGCTATG CTCCCTCTTT TCGTATTCCA GCTTGTAAAT
                            V gene exon 6
90801 GTAGTGGGGG TTGCCATAAC CCAGGTGCAA GACCTTACCT TTGGATTTGT
90851 TGACCCTCAT GAAGTTCTCT CGGGCCCACT GCTTGAGCCT GTATGGATCC
90901 CTCTGAATGG CATCTCATCC TTCAGGAGCA TCCACTACAC CATACAGCTT
90951 GGTGTCCTTT GCAAACTTGC TGAGGGTGCA TCAAAATCCT GTTGACAATG
91001 TTACTGATGA AGACACTAAA GAGTACTGAT CCCAGTACTG ATCCCTAAGG
91051 AACACTACTG GTCACTGATC TCCATCCAGA CATTGAGCCA TTGACCACCA
91101 CTCTCTGGGT TTGATCCCGC AGCCAGTTTC TAGTCCACTA GTCAGCACAC
91151 CACTGATCAT AGCCACACTC GAAGGGGCAG TCATGCAAGC ACCACCCTGG
91201 GTATTTATTT CCCAGCACTC TAAAGCAGAG CTCTTGCTCC AGCTCATGTT
91251 ATTTTCTGTG TGGCAAGGAG TGAGATTCAT CGACTCTAGC AAATGGAACT
91301 AATGGCTCCA TGTGCCCCAG GTCTCAGCTC AGCACCAGCC AGGCCAGGGC
                                           V gene exon 7
91351 TGAGTCCCCC CACATCCAAC CCATAAGGTC CCAGAGGACT CCTACGTTTA
91401 CCAGTGGTGC ACAGAGATGA GTTTAGCCCA AGTCCACCCC TCAGCCTCAA
91451 CTCCCTTCAA CACCTCTTCA CCAAGAGGCC CAATCCATCA CTCCTTACCA
91501 GCCAAAACAT ATACTTGTTT AATACCACAG CCACAAAAGC CACGTGGTAA
91551 GGTCTGAAGA GACCAAAACT GTGGTTTGAG TAAAACAGAA GGAAAGCCTC
91601 TACTCAGTAC CCCACTTATG ACTGAGTTAC TAGGATAGGA CCTGATTCTA
91651 CAGCACCCCA ATACCCTGTA GATGTATTCC TTTAATTCTT CACACCAGAT
91701 TAAGGCTGCT GCCACCACCC ACCACAAATA AATCCTTGCT TAGGCTGATT
```

Fig. 1-35

```
91751 ATAACTTACA CCTGTGGCTT CCACAGTCAA ATGAGATTCC CAGTGCCCAC
91801 CTGCGTGTTC AACTTCCTTA AGGCAAAGCA TCTTGCAGTT AGCAGAGTGT
91851 TAAGAAATCT TCTTGTATTT CCTTTAACAC ACGTTTATCT TCCCCAGTGA
91901 TGCTGAATTT GCAAATGCTT TAGGGAAAAA TTGGCAGCAA GTCCTTACAT
91951 AATTACTGTT TAGCCTAGAA AATAACAACC GAGGTAGAAT ACTTCAGAAA
92001 GTTTCTAATT TAAGGTTTTT TTCTTGATGA GAGAAAAGTG CTATCAGAGC
92051 TGTTTAGTAA TTCCAGTCAT GCATGGGTAA CTCATTCTTC TGTGTTAGGG
92101 TTTACTGAGA GGTGAAGAAA CAAGTAGTTT CTTTTCCTTA TGAAAAAAAA
92151 AAAAAGTGGT ATTAGAAGAA CCCCATAAAA GAATGCCAAA CATTGCAGCT
92201 TATGATGTGC AATGTGTCAC TCAGTCTTAC AGATGACACA GCCTGGAAGT
92251 AAGCTTAAAA AAAATGTTTA ATTCCTAACT TCTTTTGACA CCATCTGTGC
92301 TGTGGTTTAT GACATCCATT AATAATGTTT ATCACTAAAC AACAACAGAT
92351 AGAGAGACCA GAAACTAAGG ATGCTGCTGT CATTTCCTTC TGATGCAAGG
92401 TAGAAACATC AGGAAATTAA GGCACACTGA AATATTTTGT AATATTTTGG
92451 ACTAGAAGCA AAACCAGAAA CTGAGTTGCA TTTGTCTCCT GGAGTACATT
92501 CTACAGGTAT TTAAAAAGAG ACAAAAACCA TAAATCTACT TGAATTTAAT
92551 TTGAAGTATC AAATGAAAAA GATGTACCTG ATTTTATTAT CCTCCACACT
92601 GGTCTTCTGA ACTTGACCAA TCCCACTGGT CAGTTACTGG TTTACGACTG
92651 CTCAAGCTGT TTGTAGCAAC TATGTTGTAC CACAAAATAT CTGAGCCATT
92701 ACAAAAACAGA AGAGTCATTA GGCATTTTAT CTCCAACCCA AAGCATACAT
92751 GCATGTTTTA AAATCTCAAA TTCTCCTGAC TTTAATTGTG CATATTATGT
92801 TCACCAAACC TTTTAGAACC TGCCTTGTTT TTTTTGTTCT GGTCTGTAGC
92851 TGGGAGTCAG AGAAATTCAA CTGTGATTGG AAAAATGGTT ACTGGCAAGC
92901 TATAGAGTTT CTAAGCCAGA AGGTGAAGAA ATACTACTTT TTTAACACTC
92951 TTGGCCTGGG ACTAGACTTA CAGACATGAT CAATATTGAA AGGCAATTTG
93001 GAGGTATACA TTTTAACATG TCCTCAGTCT GGAGTTAGCT GTGTGTCCAG
93051 TTTCCTCTCA GTGTGAGTCA AGCAATAGCA TTAGAAAGTT ATGCCCCAAG
93101 TCTCATCCCC TCCTATTGAA ACTTGGCACA GCACATTCAG GCTGTAAGCC
                                    V gene exon 8
93151 ACCAGGTCAC AGCCCCCTTA AAGGATTCGG CAACAGCTGT GGTTGCTATC
93201 ACATGGTGTT GATCATCGTT GGGCCCCTCA CTGTAAGAAA GACATTGAGA
93251 CCCTGGAGCG TGTCCAGAGG AGGGCAACAA AGCTGTTGAG GGGTCTGGAG
93301 CACAGGCCTT ATGAGGAACG GCTGAAGGAA CTGGGATTGT TCAGTCTAAA
93351 GAAGAGGAGG CTCAGGGGAG ACCTTATTGC TCTCTATAAC TACCTGAAGG
93401 GAGGTTGTAG TGAGCTGGGG GTCGGCCTCT TCTCTCGTGT GACTAGTGAT
                                    CR1-L
93451 AGGACTAGAG GGAATGGCTT CAAGCTGCGT CAGGGAAGGT TCAGGCTGGA
93501 TGTTAGGAAA TACTACTTCT CTGAAAGGGT GGTCAGGCAC TGGAAAGGGC
93551 TGCCCAGAGA GGTGGTGGAG TCACTGACCC TGAAGGTGTT CAAAGAGTGT
93601 TTGGATGTTG TGTTGAGGGA CATGGTTTAG TGAGAACCAT TGGTGAAGGG
93651 CGAACGAATG GTTGGACTGG ATGATCTTCT GGGTCTTTTC CTACCTTAGT
93701 GATTCCATGA TTCTATGATC ATTACACTGG ATTTGATACT CTGTGAGCAA
93751 AGGCATTGAA GTGGTACAAA AAATTCAACA TTCTGCATTA AATTGTAGAA
93801 TCTGGCAAGT GGAAATCGTT TTCTATAGGC ACAGCCACGC ACTCAGAATG
93851 TGTTTGCAAT TTGCTTGCAT TTAGTCTTCT GCAAGTAATG ACTGCTTTCT
93901 GTATGCAAAT GATTGATCCA TGTGAAAAAA TCTGCTTGTG TATCTGTGAA
93951 TCAAATGCAT TGCTTTATAA TGTGCATTTT GGATCATTTA TTTGTGGAAG
94001 TAAGTGTAAA AAACAGAGCC TGCAATTGTG CTTCTGCAGT ATACAAGGCG
94051 TTACTCAACT CCAGCTGTAC AGTCAGTCAG GCCCTGAGAT AATCTAGACT
94101 TATACTTTCC ATAGTTATTA TAATTTTGTC TCTTACTAAA TCTTTGATTC
94151 TGCTTGTTTG ATAAAGTAAC ACTCATTTTC TATATAGTAT TACAATCGCT
94201 TCTAGAAGGC ATTACATCAC TGAATTCATA GGCTTTCTGA AAAACAGATT
94251 CAGAAATCAG ATTTTCTAAC TGTATTTTTC CATGTATATG TATTGGAGAA
94301 CTAGTGAAGA ACGTGTTTAA TATACAGAAC TACAGATAAA TCCAGAAAGG
```

*Fig. 1-36*

```
94351 AGAAGCAACA CTCAAAATAA GGATGTGGCA ATCCTAAATA GGCTGTAAGC
94401 TGGCTTGAAG CATGTCCCTC CAAAAAAGCC ATCTGAGAGA AAATTTCTCA
94451 TTTACCATGC ATGTGCAAGT TTCCAAACTC TGCAGGTATT TTATTTTCTC
94501 CTTTTGCAAA TTCCCTTGCA GATGGCATTT TGCTTTGCTT GCTCTGAACT
94551 GCGTTGATGT GAGCAGTGAG GTGCTTTTCT CATGCTGAAA TACAAGAATA
94601 AAGAAGATTG AAGCACAGGT CTGTGCAGAA CATCTAGTGA ATGTATTCAG
94651 GGCATGCCAA GCACAAGCTA TTCAAATATT GCTCCCTGAA AATGCAGTCA
94701 GAGTGGACTT CATGTTTTTA AGTGGAAGTG GTACATAACT TCTGTAGTGG
94751 AGAAATCGTG TGACTCAGGG GGTGAAGGGC CTATCCTCAG TTAATCCCAT
94801 ATTCTTGTTG CAATATGGGC CTGCATCTTC CAGCACTGTC AGACTCCAGG
94851 TTTTAGCATA AGATCAGTGG AAAAAAATAT ACACAAATAT ACCCCTTGCT
94901 TCTGAAGCTC TGCCCTAATT GGGATGATTG CAAATAAATG AAAAAAAAAA
94951 AAAGGGAAAT TCAAATACTG ATGATAACTC TGCAGTTCAA CAACCAGGAC
95001 ACCTAGTAGG TGAGTTCTGG CTTCCAGTCC CTGCTGCTAG GACTATTCTT
95051 GTTTTAATGT TTAAGAGAAA ACAAGTATTC ACACATGGGT GAGTACCCTA
95101 GCAATAATGA CAGAGAACTA TTCTGCTCTA TAGCATTCTG ATAGTATGAA
95151 TCTCGCCTTA ATTCCATAGT CTTCTCTTAG TACCACGTCC CCCAGCTCCT
95201 GTTGTCTGAA TTAAGCAATC ACTGTGTGAC ACCTACGTCG GAGCTTAGCT
95251 CCATTACACT CAATGAAATC AGTTGCTGGT CTTCTGTGGA AAATATACTA
95301 TTGCGCCCTG AGCAGTGCTG AGCACAGCAC CTGTTTGCCT AATATTAATG
95351 CAGCACTCAG ACCACAACCA GCCTCAAGAC ACTCAGCAGA AGGAATATTA
95401 TGAAAACAGT AGGTGCTGCT CCTGAAGCAT AACAGCCTCC AGAGATGGAA
95451 GACAAGAAGA TGTGCTTTGG TAGTGTGTGG TGCTCATTTC CTTGTTCATG
95501 AATGATGATG GGAATGACTC TGGAAGACAC ACCAGAGGCC TCTGGTGTAT
95551 ACCCCATGCC TCCAGCCTGG GCAACTCCTC CTTGCTGCCT TTTTGACTTG
95601 TTTTGTGCAA GCCATCCATC CAGAGGTGCA GAGTGAAAAC AACCATGGAG
95651 CTCAAGAAGA GCCTCATCAG GTCCATACAC ACTTCAAACC CAGAGCAAAA
95701 CATTGGAGCC TCGGGCTCAC TGCACAGTTC TGCTGAAAAC TGTGATGAAG
95751 AGCTAGGGGT TAGAGGAAAA ATGTGCTGTA GTTATCAGTG CAGCTCCATC
95801 ATCTGTTCCG GGAGCATCAA GGCTTCCTGG AGAGAACATT ATCAGAAGGA
95851 CACAAATTAT TCAGTGAGAG GGAGAAGTGC GCCTCTGAAC GCTCTGAGTC
95901 AGATGCTTAT TTTGTGAATT TTTCTGTTTC CCTCTTCCTG TTATGCTTCC
95951 TGCAGATACT TGGCACATCC TTGAGGCGAT TCAGCAATAT ATGCTCATAT
96001 TCAGCCACAT CTACAGAGTG CCTCCTCCCT GAGAGGAGAA AAATATTTGT
96051 TTTAGGGGGT AAAACCAGAA TAGCTGTGCT TGGACCTCCT GCTCTGCTGT
96101 GGGACAAGAG AAGCTAGGCT CCTGGTAACC TCAGGAGGCA GAGGGAGGCA
96151 CATTATAATT TGGCTAAGAC TTGAAAATGC AATTTGTTGG TATATTTGGT
96201 AAATATACTG ATGGCCTAGT CCCATAAACT ACCTTCTAGA TGTGGAGTAA
96251 GTGGTTTAAA GGCATAGCTA AGAGGTTGCA GAAAAGAAAG GACCACATCC
96301 AATTTGGTAG CAACCAACAT CCAGCATTCA CAGACTCATG AGAAATACCT
96351 TTTAATTAAT TTATTTATAT TAAATAAAAA AAAAAAATCC TTTGATGACT
                                MAR (0.81)
96401 CACCCTGCTT TTCCTGTTAC TCTCAGTTGG GAAGAAAGTA ACCGCTGGGT
96451 ACATACTACT GCAATTTCAG AGCTGCAGAC TTGAAGAGCT TTCCCAAGTG
96501 CTGAGATATG CAGGAAAAAA AACCCTGTAA ATTACAGTAC CAGGCATTTA
96551 ATTTTGATTG CTAAATAAAG AAGACTCGTG ACAGTCCATG ACTACGTCTT
96601 GGAGGGCTGC AATTACATAT GAAATATAGT CTGAATTAGG AGAGTTACTG
96651 GCAGAGGCAA AGTTTGCATG CCAATTAATT GGTAAAAGGA GAGTACGCCA
96701 AACACAGGCT GTGGACTGCT CTGATGAACT GAGTATGTAA AAAATAGCCA
96751 TGTGTGTTTT TCAGTGAATA CCATGGTATA TGTCTGGTTT GAGTCAAATA
96801 TGTATTAAAA TGAAAAAAAA AAACAACAAG AACAGTGAAA TAAACAGTGC
96851 TAGCATATAT TAGCTTGTAT AATCAGACCT ATATAGTTTT CAAATAAATC
96901 TTCAAGGAGA ACAAAATGTA TAGTATGTAT GATAAGGATA AGTACTATAA
96951 AACATCATCA TGAGGAGTGC CAGTCTGACA ACAGGAAAAG GAATTCAGCG
```

*Fig. 1-37*

```
97001 TGTGAATGAA GGGGAAAGTG TGACTGAAAC AATTGTCACT CAGCTTACTA
97051 CAGCAGAAGC AATCATTTAT GATCTTAGAT TTTTTTTTAT TTTTTTTTTT
97101 AACTTGCTTC AGAGATATCT AAGTAATCTC AAAAACAGGA ACAAAATACC
97151 AACGCAAGGA AAAATTCTAT TTTCGCTTCA TATAATCTTT TCTTTTTTTT
97201 TCTAGTTGCA TTCTTACCTA AAAACAACAA CAACAAAACA TTTAAACAAT
97251 GTTTAAATGT TTACTGCTGG TTTGATTACA TCAAACCGAG TTGTTGCTGG
97301 AGATGACCAG CTATCAAGGT GCATAATGGA CTGGCAGATG TGCTTGGTCT
97351 TACCCCAGGT TGCTGTGCAA ACACAATACA CATTGACATA TAAGCTACTA
97401 TGAGTTCTGA AGGGCAGTTT AGACATTAAT TCTACTCCAG GCCAGACACG
97451 CTGACTATCT GAGTGGTTTA TAGCAAGGGA CTGGTTGACT TCAAAGTGGT
97501 TCCAAGTCAA CCACTGCCAA GTGCTTAAGA CTGTGTATGC ACAACAGAGC
97551 TGATCATCTC CAGTGCAACA AATAACATGA GAGCAAAAAG CATCTGAAAT
97601 TCTGTAAATG AGGCTGTTCT GGCCACACCT TGGCTCATTA AAAGACTTTG
97651 AGAGATGCCA GAATAGCCTC TGCTAAATGT GATGCAGATG GACAAGCTAT
97701 GGAATGAATG GGTCCAGGGC ATAAGGAAAC ATTACCCTCA AGCACTACAC
97751 AGGAGCTGCT GAACAACCAC AGGAAAGGAA ATGTGAAAAT GTGAACAGAT
97801 AAATGTTGGA AAGAGCCGCA TTTCTGCTGC TTACTATGTC CTTGATTATG
97851 CCAACATTAA GGAAGAATGG CAAACCCCGT GAATTGGTTT AGGAACAGCT
                               Y:OV-1 element
97901 CTACAATGGA CTGCCTGACG GAGGAAAAGG GCAGCAGAGT CCTTGCTGAC
97951 CTCTTTCTGG TACAAACACA GATCTGGAAC AGAGTTTAAC CAATTAGTCT
98001 TGCTTGCATT CATGCCTCTT GAATTTCAAG AGGTGCCTTT GATTTCCCCT
98051 GGCCTAACAC CCCATCTAAA ATTACAAAAC CATATTTTGT CTGCTGAGGA
98101 CTGTGCACGG ATAGCCCGTT CTGGTCAACA TACTCAGGCT GCTTCTGCAA
98151 CAAGTTTTGC ACTGGCATTC AGTGTAGAAA AAATGCAAGA CCTGTGTAGC
98201 GGCAGACTTC TCTCTGGAGA ACATGTATTG CCTCAACTAT CTTACCTGTG
98251 CAAAACTGTT GTGGTGACTG TGCTATTGCA GAGGTAGAGT GTTCAAAGAA
98301 GGCAAACGTA CTGAATGAGA GAACACATCA AAAACACCTT CATGCCCTCT
98351 TCTAGGGGAG ACAGCGAAAC AAAATGTTTA TTGAGAAAAT CTTGGACATC
98401 AGTCCAAGAG ATGAAAACAC TGTCCATATG TGCAGGGCTG GTTGTGTTCT
98451 ACAGGTCCAT GCTGCATAGA TGACCACAGA GGACAAAGAC ATTGAAACCA
98501 AGCATACAAA GGGCTGTGGG TACCCAGGAA AGTTCTTCAA GGAAGCCTTG
98551 AAGGGATGTT TGAGTACCCA CCTGACCTGT AGCTGCAACC CTGATGTAAA
98601 CATGTGAAAA TGGGAGCATA AGAGAAGACA CTACACACTG CAACAAAACC
98651 TGTGCCCTTG GGGAGGAAAA GTTTGACAAG ATAAAGTAGA AGCTATTGAA
98701 AAAGGAACAT TAAACAAGAC AGGAGGAAAG CTTCTTACTA TCTGTAGATT
98751 TCCCTACTCC CGACATGACT ACTGTCATGT TGACAGATAA AAAATACTCA
98801 TTTTGAGTGT GGAAACTGAA AGCCATTCCA GTTATCATGG TCTGCACATA
98851 CACACATGAC TGAATTTCAG CAACACAAAA CACAGTGCTT ATGATAAAGG
98901 AGCTCCCTTT TACCTTTACC AGTGGGTACC ACCACCACTG TGTACTGTCT
98951 GTCTTAATGT GCAAAAATTT GGGATTTCTA TTATTCATTC CCCTGGCCTT
99001 AACAGAAGCT GGATTTTTTT CTTTAGTGCT CATCAAGGGC ATTATTCAAT
                                               SDRE fragment
99051 AAAGAGTAAT AGCTTTTTAC AATTGACTAA TATTTGATAT TGTGCATTAT
99101 GATTGTCTAA CAGACCATGA ATGTTCCTTC AGACAGATTT GGTAGTTTAT
99151 TTACCTGTCA TAGTAAAATA GGAGGTACAG AAGATCTATG AGAATAGCCT
99201 GTGCATGTAC AATGGGCCTT GTTGCCATGA CCTATGAAGA ATGAAAATCA
99251 AAAGCTGACC ACCAATCATC CCTTGAATTC CACTGGCTGT TCAGCATTCA
99301 CTTCTGAATA TCTGAATACT CTGGAGTCTG CCTTCGCAAA GCAGCAAATA
99351 CTTTCAGACT GTTCCCTAAA TCTCTTCCTC TTACCTATTC ACACTGAGTT
99401 CTCTAATTCA TCCCAACACC TCTGCTCTGA ATTTTTTCAT AAGAAGCTTC
99451 AGCAAAATGT GCTTTCTCCT CTCAAATGTA TGCTGCAGAG CCTTTGGCTT
99501 ACAGTGGATA TAGCCCAAAT TCCAGTGAAA AACTTCAGTC TTGCCTAGGT
99551 GCAGAAATAG ATGGAGCTGT GCTTTTAACA AGTACTAACT ATAAGCTTCT
```

*Fig. 1-38*

```
 99601 TCAGTTCTCA AACTCTTTCA GCAGACCAAA ACATTTTTCA GTACAGTTTT
 99651 GTTCTTTAAA AAACTCATAA AGCTTTGTTT CTATTCTTAC ATGGAAAGCA
 99701 ATCCATTACA AAATCCTCAA AATAGAATGA CCATCCTGCA GCTGACTCTG
 99751 CTTGGAACTG CATTATTTTC TCTACATCAA GTGGTTGCCA TCCATGAGAA
 99801 GCATCCCTAT GTTTCTCTGC ACACTGCAGT AAGAGATCAC GTATATATCA
 99851 CACTTTTCCC TTCACCCATC TTGGGAGCAG TGCTACAGTA AATTGTATAA
 99901 TTACAGTGCC CCAGAGATGA GAAGAAACTG AACAGCAGGA AAGGAGACAC
 99951 AGTCTTAAAA AGAAGAATGT TTTCCAGGAA TTGATGCACT TTCTTGCACT
100001 CCTTGGTAAT ATGGGACTAC TCTTGCCTCA CCTTTAGCAG TGGGTGCTCA
100051 TTAAATGGTG AATGGTGGTG GGTCTTCTGG TTCTCCAATC ATGTCTTATT
100101 TTCTCATAAT ATTTTGGGAT CCTTAGATTC ATCTGACTGT GAGAATCACT
100151 TGATCTGATT TTTTTTTTTA ATCTGATTTT GCAGCTAAGT TTATCTGAAG
100201 TGTATTATGC TTATCCTCTT TTTTAAGGGT TTTTTTTTTT TTTAAAGTGT
100251 GTGTATTCAT TATTCGTTTG GCTCTAGTTA TCGATATGGC TCAATCAAAT
100301 TAATGTTTAA ATTCTGAAGT AGAGCATGAG ACATGCTAGA CTTGAAGTTG
100351 GTACAGCTTT ATAAGATACA AGAAAAGCCT GAATAATTAC ATTCTACTAT
100401 TAGGTTTCAC TTCACAAAAT AAATTTGGCT TTCTCCAAGT AGAGTACCAG
100451 TCTAATGTTG GCCTACTCAG TGCTTTCAAG CACAATGAAT CAAAAGGCAA
100501 TGACAAAGGG TAGTAACTCA AAGGATGACT CTTAGAAGGC TAACAGGGGG
100551 AGTGTCCGAA AGGGTACTGT ATATATCACC AAGGACTCAG AGAATCTGTT
                        X gene exon L
100601 CAGGTTCAAC TGGCAAGCTG GATTATTACG AGCCTCTTTG ATGTTTTTCT
100651 GTAAGTACTT CTCCAAATAA AATGTAACTT CTAAGTTGTA TTCTTGAATA
100701 TGGAAAAAAC AAAACAAAAC AGAAATATAT TATGTAAGAA CTTAGAGGAA
100751 AAAAGGGCCG CCTTCTATTT TATGATGTTG GCCCACCACA TCAGAGGCAG
100801 ATGGTGGTGG TATGGCAGTA GAGGTTGAAC CTTCCCACCA ACACCCCGTT
100851 ATGTGTTGTT GCTGTGTGAC AGATGGCAGC AGAGGGGCAG TCTGACAGAA
100901 TGGCGTCTCA CATGGAAGTG TGTATGAAGC AAAGGTGTGT CACTGAATTC
100951 CTCCATATGG AAAAAAATGG CACCCACTGA CATTCATCGA TGCTTGCTGA
101001 ATGTTTATGG AGACAAAACA GTGGATGTGA GCACAGCGAG GCAGTGAGTG
101051 GTGTGTTTCA GCAGTGGCGA CAGTGACAGT TGTTCACCTC CACTGGTACA
101101 GAATTTTGCC AGCAGGAAAT GCAGATTCTT GTACATTGTG GGCAAAAATG
101151 CATAGCTAGC TGTGGTGGCT ATGTTGAAAA ATAATGTTCC GTGGCTGAGA
101201 ATCTGCTCAA GGAAATAAAG TTATTGTAAT CATTATAATA ATATTATACA
101251 TGTGCTTTCT ATCTATTGTA GTTTACATGA AAATAAATAG GAGGCATTAC
101301 TTTGGTGTG ATCTGTATAC AGGACAGATA TGTAAAAAAT ATTTCTGGAA
101351 GAGAAAATTT TTGTTTTCAC AGTCTCACTC CCTGCAGAAC ACAGGTGAGG
101401 TACAGTAGGA TAATTCACAG AGCCTTGTTA GCACCAGGAA CCTCTCAGGT
101451 TATGTAGTAG ATCACATTTG CTACAAACTA TGGATATGCT ATTATTCCAA
101501 CTTAAAACTG TTTTAGAACG GGGAGGGCAC TATTCAGCTT TCTTGTTCTC
101551 GGATTAAAGA AAGAGAAGGA CTGTAGATTT CAATAATTTC CCCTAAGTCT
101601 TGACATTAAA TTGCATGTAC AAGACCTTCA CCTGGCTGAT CTGATGCAGC
101651 TTTACAGTGC ATTAAGTAAT TTAGCCAGAC TGTGTATTTA CGGTATATAG
101701 ACGTTTGTTT GTTTTTGTCA ACAACAAAAA AAAGGAATCA GCAGAGATTA
101751 AATGTCAAAA AATGAGAATA TAGAGAAGAA GCCCACTAAA GCTATAGTTT
101801 GGCATCTAAG CAACTGGCTA GATTTACAAA GAGATTCACT CTATAAATTA
101851 CAGGACAGCA ACCTCCAATT TTATGGCCAG TTGTACAAAG AAGCAGTTTG
101901 AAACAAGCTA AGACTATTGT GGTTTGACTA CATTTGATTG AAATATCCAG
101951 AGTATGGTCC AGAGTAGACA CAGAAGAAAT GAAATGTGTT TACATTGTCT
102001 CAAAAATCAT TCAGAGTTCT CTGGATGGCT ATAGGGAAAC TCATCTAGTC
102051 CACACTGTAT TCATCATACT GAAGCACAGA TGAAACTATC TATTTCCTAA
102101 AGGGCAAGTA CAAGATAGTG TTTTTATAAT GAACCAGTAC CTTTCTGAAG
102151 GAAAGTAAAC ATGCATTTGG GAAACAATGG GTCAGTCTTT ACAATATTTC
102201 TAATGATCAC AGAATTTTTA GGCTTTACAT TATTGTTTCA GCATCACAGA
```

*Fig. 1-39*

```
102251 AACAGCAATG AACAAGCAGC TTCTGGGCTA CAGGAAGTAC TTTTTACTAC
102301 AAGTGCCACA CGTCAACACC ACACAGTAAT AATCCTGTTT CTTTTAGACA
                          X gene exon 1
102351 ACACCGATTT CAGGATGGGC TCCATCAGTG CAGCAAATGC AGAATTTTGT
102401 TTTGATGTAT TCAATGAGCT GAAAGTCCAG CACACAAATG AGAACATCTT
102451 GTATTCCCCC TTGAGCATCA TTGTAGCCTT GGCCATGGTC TATATGGGAG
102501 CAAGAGGCAA CACTGAGTAC CAGATGGAGA AGGTAAGTTA TGCAAGTAAA
102551 TACAAGCTCA TTTTGATCCT GGTTAACAGA ACAAGTTATC CATGAAGATC
102601 TTTGAGACTT TCTCCCCTTA AGGGGCCAGC TGCTGTACAT TTGCCACTGG
102651 ATTTGAACTT GGCTAGCAGA AGGACATTGA GCCATGAGGT TTGGATCTGG
102701 AACTAACTTT TCACTTATTG CTTTTCACTA CAAAGGGTAA CAACAGTTTC
102751 TACTAAGGAG GAGATCTCCT GCTTCAGTTT ATATTATCTC ACAAACCTGA
102801 CTCCTTCCAG ATAAAATGAA CAAATTTTCA TGTATAAAAG ATGAAACACT
102851 CAGAAATCAG GAGTCACAGT TCTAAGTACA GTATGGGTGT AGCTGGTTTC
102901 TGGATGGAAA AATAAGTGAA CTAATTGGAA GATCCTATCA AAAAATGTTC
102951 AGAGCAGCAC ATGCAGTAAA AAAACAAACA AACAAACAAA CAAAAAAAAA
103001 CCACACAAAT TTCAACCTCG AATGAAACTT CTCAGTTCAG CCATTGGTTA
103051 TTTCAAGCCC AGAATTTGAA CACAAAATCC AGAGACTCTC AGTGAACTTT
103101 GCATACTTCA TTTCTTCTTC TGCTACTTCC ATTTGCAGGC TCTTCACTTT
                          X gene exon 2
103151 GACAGCATTG CAGGACTTGG AGGAAGCACT CAGACAAAGG TACAGAAACC
103201 TAAGGTACAT TATTTTTCTC TCACATTCAC TTTTTTTTTT TTTCCTGAAA
103251 ACTTAAAACT GTTCTGACTG TGCTTCCAAT AGGTCCAGCC CCTTCCCAAA
103301 CCCTAGCTAA TGCTCTCAAC ACATGATATG CAAATGAAAA ACTAAAATTT
103351 GTTCTAAAAA AAAAAAAAAT AATGACAAAA AGAAGGCTCA TTTCACATGT
103401 TGCACCAGAA AAAGTGATAG GATAGTTGAA GGACATTTTG AGCACCAGGA
103451 TACCTTCCTA CATTGATAAG AACTTGCACA CTTGTAGGGC TTGCTGGAGG
103501 ACCACACATG AACCATGTGT GCTTTTCTCC TTGGTCACTT GATACATTTG
103551 GAAAGATAAC ACAAGCCATG CTCCCAGGGC TGTCCTCATC CACTTGGGTT
103601 CTCCAAGCAC AATGTGGGGC TTGTAAAGGA CAAGAAGATT TTTCCGTTTC
103651 CTTTTCTTTT TCCTTTCCCC CTTTCACTTT TTCCTTTCCC CCTCACTTTC
103701 TCTCTCCTTT TCCCACTTCC CTCTTTCCTT TACATTTCCC ACTCTCCTCT
103751 CCTCTCCTCT CCACTCCACT CCACTCCTCT CCTCTCCTCT CCTCTCCTCT
103801 CCTCTCCTCT CCTCTCCTCT CCTCTCCTCT CCTCTCCTCT CCTCTCCTCT
103851 CCTCTCCTCT CCTCTCCTCT CCTCTCCTCT CCTCTCCTCT CCTCTCCTCT
103901 CCTCTCCTCT CCTCTCCTCT CCTCTCCTTT CCATTCTATT CTTTTTGCTA
103951 GAGCATTTAG ATGGTTATGT AGAACAATTC ACAAAACACA ATCAGACAAA
104001 TCACTCACAT TTTCTGTTTC TTATCACCAA GACTGAGTGT CACCAAATGC
104051 TATCAGTTGT ACATGCTTAT ATAGAACATC TCTCCCATGG AGCTTTTAGA
104101 CTCTAATGTA TTTTGTTTGC AAATGTCTGA ACACTGTGTG TTTTCCTACG
104151 TGATCTGTAC TTTATAAATA GTTGTCTTTC TAGTAAAATA AGCTAACATT
                                            X gene exon 3
104201 TATACCCTTT TTCCTCCTCT TCAACAACCC AGTGTGGCAA ATCCGTGAAC
104251 ATCCACCTAC TCTTTAAAGA ACTCCTCTCT GATATTACTG CATCAAAAGC
104301 CAATTATTCA CTCCGCATTG CCAACAGACT CTATGCAGAA AAGTCACGTC
104351 CTATCCTACC GGTGAGTTGT ACAACAGAGT GATTTTTTGC TAGATCCTGT
104401 ATAAACCCAT AATCCAGGAG TACTGCCCAG AGTATCTGTT AATCCAACTC
104451 ACCTCAGCGG TGTGGACTTC CACAGCTTTT CATTTGACAT TCTCAAAATA
104501 AAACACACAA ATATTCTAAA TCAAATACAT TTTATCTTTA AAAATAGAGA
104551 AAAATGCTTC AAAAATAAGG ATTTTATTAT AACAAAACAG TTGCTAATGG
104601 ATGCTAATGG ACCTGAAGCT GTTTTTGGAT TGGTATTTCT TCAAGAAAAT
104651 ATTTCAGCAT TTCTACTACG TAATCTTATC TGGTAAAGTA ATAAAAATCT
104701 TAAAGATCTT AACATATCAT GCATCGAAAT AATTTTGCTG GCCCAGTTTT
104751 AACCATTTCG TCCAGGAAAT AAGCCATGAA AACAGTCTAA TAGCATAATT
```

Fig. 1-40

```
104801 ATAAAAATCA TGGAACATTT TAACTGCATT TTATTTCACC TTCACAGTCT
104851 TTTTAAAAAC TGACTTGGTA GCTACAACTG TTGTCTTTAC AGATTTACCT
                      X gene exon 4
104901 AAAGTGTGTG AAGAAACTGT ACAGAGCAGG TCTGGAAACA GTGAACTTCA
104951 AAACAGCATC AGACCAAGCC AGGCAGCTTA TTAACTCCTG GGTGGAAAAG
105001 CAGACAGAAG GTAAGCTCAG AGGAGAGTTT ATAATATACT TCCTTGTTAC
105051 TACTTTACCC AAACAACTTC TGGAAAGACT ATTCCTTCCA TCTCCATTAA
105101 TGGATATTTC CTGTGGAAAC TGATGACTCT TGCACACTTT TTTGTGTGCG
105151 GTGACAGTGA ATTTAAATAT ATATGACAAA GGCAGGGATG CCACTGTGTG
105201 CTTTCTGTGT AAGGAGAGCA TAACTCATGC AAGATTGGTC CCAGCTTCCC
105251 TACAATATTG GCATCATTTT ACAAGCATAT GCTGGATGGA TAAGAAATGG
105301 GCTTCCGTGG AAGAAAATAA TGTGGCCACT AAGTTGGTGT AAGAAAAGGA
105351 ATGATTAAGA GTGTATGTAC ATTTATCAGG AAAAAGGTGG GAAGAAAACA
105401 AGAATCAAGT ATTAGAAGGA AGCACAGTGA GAGGCAGAAG ATCGGTATCC
105451 CTGCTTTGCT TTTCACTTCC TTCTGTTCCA TGCAAGTCTT TTTCCAAGGA
105501 CGTTTGAGAT ATTCCTGGGG ATGTGTGTGA ACATTCAAGC CTACATGCCT
105551 CCTTACAGAA ATGCCTGGTT AAGGGTTAGT TGTTCTGTAT GAAATCACTC
105601 GTGAACTTGA ATTCCACATG CCATCATTTA AAGAACAGGA AGTCAACTCA
105651 AGCTTGCTGG TTGACATCTA AAACAAAACA CTCCTGCAAT GAAAACAAAA
105701 CCCCACAAAG CAGCACCCTC CAATCCCTTT GCCTCATACA TGCAAACCAG
105751 ACAGACTGTG TCTTAGCACT CACTGCTTTG CTTCCTTCTT ACAGGACAGA
                      X gene exon 5
105801 TCAAAGATTT GCTTGTATCA AGCTCCACTG ATCTTGATAC AACGCTGGTC
105851 CTCGTTAATG CCATCTACTT CAAAGGGATG TGGAAGACAG CATTTAATGC
105901 AGAAGACACT CGAGAAATGC CCTTCCATGT AACAAAGGTA GGGGACGTGG
105951 TCACCGCTTC TGGGCAGGAC AGAAAGCCAT CAAGGGTGCG ACATACACCA
106001 TCCTACAGTC ATTGGTCCAT GGTTCTTCTG GGCCCCTCGC TGACAGGGCA
106051 TGGGGCTGAG CCCAAGACAG GCTGGCAAAA ATTGTGTCTG ACCAGGCATC
106101 CAAAGCACAC CTGTAGACAA GAGAGGAAAA TGGAGACACA GCTTGAGGAT
106151 CCAGCCCAGT TCCTCTGAAG GACTTGCACA TCTGCCTGCT TCAAGAGAAA
106201 CTGCCCCCTT CTCACATTGT CTCATGCTTC TGTTTTGCAG GAAGAAAGCA
                      X gene exon 6
106251 AACCTGTGCA AATGATGTGT ATGAACAATA GCTTTAATGT GGCCACACTG
106301 CCTGCAGAGA AAATGAAGAT CCTGGAGCTC CCATTTGCCA GCGGAGACCT
106351 GAGCATGTTG GTGCTGTTGC CTGATGAGGT TTCTGACCTG GAGCGGGTAC
106401 GGCCCTGGCA GGGGAAGCCA ACTAGTTCGG AGTTCAGTGG GAGCTGGCTG
106451 CTGTTAGACC TTTGGCTCTG CTCTCGCTCC TTGGCTGTGC TGTGCTGGCC
106501 AGGCAGGGGA GCACAACAGT GGCCCAGGTG CTTCCAGGCG CTCAGGCAGA
106551 GGTTGGCCTC TAAGGAGAGC CCTAGCCTCA ATGTTATTAA ACAAAGAGTA
106601 CAGCAAAGAA TACAAAGGTA AAGGAGCGTA GGGCTGCTGT AATGTTATAG
106651 AAGGGCACGT ATGGGCAATT CTTTTCATTG AGAGGCAGTT TCATCTGGCC
106701 TCTTATATAA ACTCTTCAGC AAATGTTACT AGAATTGATG AGGTTCAATA
106751 ATCCCTAATA TTTTTGACAA TATTCTCATC AAATATTTTA AATAAGCTGT
106801 TCTCAGAATA CCAAAGTAGA TGCAGAAATA TTTGTGTTTG TTTGGTACTA
106851 TCCACTGTAT ATAAATTGTC ATGGCATTTT TTTTTTTGCA ATCTCTTTCA
106901 CCAGCTGACC AATCTGCTAT GTAGTGAAAT TGCTTTATTG TTCTGTATGA
106951 GACACGAAAA TATTTGTACA GAAGGGGATG TGTCAGGTGG AACCAAATAA
107001 AGGAGCACTG AAGAGGAAAT ACTAGAGAAA CAAATGTTAA AATAGGAAGA
107051 TGTTGATAGG ATGCACCTTG GGAAACTTTC TATTTTTTTG TAAAATAATA
107101 GTCTTGATTA AAATGAACGA TGGAAAGAAG TTGCATTCTC ATCACAGGCA
107151 TTTTATTCTC TCCCTCTCTT TTCAGATTGA GAAGACAATT AACTTTGAAA
                      X gene exon 7
107201 AACTCACAGA GTGGACCAAT CCCAATACCA TGGAGAAGAG GAGAGTGAAA
107251 GTGTACCTGC CCCAAATGAA GATTGAGGAA AAATATAACC TCACATCTGT
```

*Fig. 1-41*

```
107301 CTTAATGGCA TTGGGAATGA CTGACCTGTT CATCCCTTCA GCCAATCTGA
107351 CTGGCATTTC TTCAGCAGAG AGCTTGAAGA TATCCCAGGC TGTGCACGGG
107401 GCCTTCATGG AACTCAGTGA AGATGGCATT GAGATGGCAG GCTCCACAGG
107451 GGTGATAGAA GACATCAAGC ATTTCCCTGA GTTAGAACAG TTTAGGGCTG
107501 ACCACCCATT CCTCTTCCTG ATCAAACACA ACCCAACCAA CACCATTGTC
107551 TACTTTGGCA GATATTGGTC CCCTTAAAGA GAGAAAGAGC TGGCAATAAC
107601 ACATACCTTC CCCTCAGAAA CAAAATCCCC TTACCGTAGT ATTATAGCAT
107651 AATCTTATCT CTTTCATAGA AAAGACATAC CCGCAGGAGA GGAGACAGCA
107701 CGAAGCACAC TTACTCCTTC CCTTCTTGTA TTAATTTCAG AATGGCTTGA
107751 TATGAGCAAA GACTGAGCCA ATGAGATGGT GAGAATGAAG ACACCTATCA
107801 GCCATTAAGG TGATAAGTGA TTTTCACCCA AGGAATAAAT AGTAAGAATG
107851 ACCCTAAGTC CTTGGGAGCC CGTTACATAG AAAGCAATAA GCTTTGCTCA
107901 TCCCATTCCC TGGTAACATA CTGCTGACAA ACCCACGTTA CCATTCCTGA
107951 AACATGGGCT TTGAGATCTC CAGTCTAGAG GGGATGTTTG TGGAAGAGTT
108001 TCTGGTGTGC AGATTATTGA TTTGTGATTA TGTCAATTTT ATTTTTCTTT
108051 ATTTGGTAAT TGGGCAATGG TATACATGTT CACTATCAGT GGAGTTGTCC
108101 TCTCACCATA AGTCCTCTCA CCTAGTTCTG AATTTCTTGC AGAGGTTTTT
108151 CAAAGTCCTG AAGAGTCTCC CTTCCATTCC AGAGAAGGGA AATAGATCCA
108201 GTTTTGCATA GGTGCAGTTA TGCCTTTTCT CAGAGTGCAG ATTCAAAGCC
108251 TGAACCATAG AGATCCAGAT GATTCTTATG ACCCAGAACT CAGTGAGATC
108301 CACTGGGCGA AAGAACTGTC TAAATTTTTG TTTAAAACTT TGGAAGACAC
108351 TTCAAATTTG AGAACACCTT TTTGGTGAAA AATCCTGAAA GTGTTGTAAA
108401 ATACTTCTTC TAAGAAACAA ATTAGAATCC TATTTTTTTT CTGTCTTCTC
108451 TTCCTACGTA TAGATTGTCA ACTGCAGATG TGGATCCTCT GGCTCAATAT
108501 TATATTCTGT TTTCATTCTA ATCACCCATT ATTGATTTAG ATACATACAG
108551 TTGATTTTGT TTTGGTTAAC ATAATAAAAG AAAACCACAA ACAGTTTTCA
108601 TGTAAATTAT ATTAGCTTTC TGAACCACAC ACTCTTAAAA ATATCTTTAC
108651 ATTTTAACAA CTGTGAGTAA AACGTGATTT AGCAGAAAAA TGTATTCTTA
108701 GAATGAATAA AGCATGCAGA TATGAAGTTT TTCAGGCATT TATGACATTT
108751 TTAGGAGTAC CTGTTTTCAA GAAGAACTTC ACCAAAGACC TACAACCAGA
108801 GTTTGATTCT TCTCTGTATT TCAGATGACA AGAAGTACCG CAATAGAATA
108851 CAAAGTTATT CCTATCTATT TTTCTGTGCC ATTCCAACAG GCATTAAAGA
108901 TGACCTGGCA ATTTTTTCTG GTAAATATTT CAAGGAACAA CTATTCTAAC
108951 AGTTTTACCC TTTTATACAG AATCACAGAT TCATAGGAGC TGGAAGAGAC
109001 CTCACGGGAT CATCTAGTCC AACCCCATAT GATTTCATCA TTTTATATGA
109051 TGAAATAATC TGGAATTCAT ATAACTTGAA AGGCATAAGA AAGGTTAAAT
109101 AGATCAACAG CTACTAGGCA AAGCATTTCC CTATGCAGAG TCTTGAGAGG
109151 AGGAACTCTG ATGTTAACAT CGCCTATTTC CACATTAGTG TTACCACTGC
109201 AGTGTCAATG ATAAAAGGTG ATCTGTAGAG TAAAAACAGC TGGTGCTACA
109251 GGTATGACAC CCACATTTTT TGTAGATTAT CAGGATACTC ACAATACAGA
109301 CACAGCTGTT TTTCAATGGT AAAACCAAAC ATTTTACCAA GTATACTTTA
109351 TTTTTTGCCT TTAGAAATGG AAGTAGTGAG AAGAACAGTT CCAAGGTAAG
109401 AGAAATATCA GCATCTCAAG GTTTACCATC AGTAGTTTAT TCATCTTTCA
                                         CR1L
109451 CATCTCTTAT GTCCATAGAA TCATAGAATC ATAGAGGTTG GAAAAGACCT
109501 TAAAGATCAT CAAGTCCAAC CATATCCTAA CCATACTACC CCAACTTTAA
109551 CAACCCTCTG CTAAATCAGA AGCAGTTGAT CCACTCTGCT AAATTTAAAA
109601 GCCAGTTCAC TTAAACAATA AGAAAACTAG AGGAAGATTA CATTTGCAAG
109651 CTACTCTTCT ACGATTAATA GACTGGAAAG TGCATAAAGT ACAAAGATAT
109701 GCCTCAATGA TCTGAAAAAC AGCTGAGGTC AAAATGGAGA AATGGGGAAA
109751 AAAATTGAAG GTTTCTTGCT TGCAAGCAAA TATAAAGCTT CCCCTTTCTC
109801 AAAAAGAAAA ACAAGAGACA GGAAAGAGTG GAAATTCAGC AATACTGAAC
109851 AAAAATTGCA ACAAAATACT GATGGCCAAG CCCTGGCCAC CACTGACCAG
109901 GCAGGGGGCA GAACATACAA AGGGCAGGAT AAAAGTGTTC TCCATGAAGG
```

*Fig. 1-42*

```
109951 GGGTGGCAGG CCTGGTGGGT GGGATGATGA ACAAAATAAA TACACTTTTA
110001 AAACCTTCCT GTGGCTCCAG GCATTTTTGC CCCAGCCTAC CAAAGGCTAT
110051 TAGCATTTTT ATTTTCTGGA GTATTAAGAC CCTGTTTCTT TGACAGACTA
110101 CTGTGCAGCA ACTGACAGAA GGTTTAGTGG GTAAGTCACA GGGGATAAAA
110151 TGTTCAGCAT AGACCAAAGC AAAAACATAA TGTCATGATG GGTGATCAAC
110201 TGGCTAACAG GTTGGGCTCA AAGGATTACA GTTACTGGGG TTACATCAGG
                            CR1 GG
110251 CTGGTAGGCA GTCACTAATG GGGTTCTGCA GGGCTCAATT TTAGGGCTAG
110301 TTCTCTTCAG TGTTTTCATC AATGACTTGG ATAAAGGACT TGAAGTCATA
110351 CTAAGCAAGT TCATGGATGA CACAAATTGG GAAGTGCCAT TGACTCCCTT
110401 GAGGGTAAAG AGGCCTTACA GAGAGATTCT GACCAATCAG AGAGCTTGGC
110451 AATCATCAAC TACATAAAGT TTAACAAGAG CAGGTGTCAT ATTCTGCACC
110501 TGGGATGGGG CAGCCTTGGC TGTGTGTACA GACTGGAGGA CAAGAGGCTG
110551 AGAGCAGTCC TGCCCAAAGG GACCTGGGGG TTCTGGCTTA CAGCAAGCTG
110601 TATCTGAGCC AGCAGTGTGC CCTGGCAGCT CCAAGGGCCA ACCGTACCCT
110651 GGGGTGCACC AGGCCCAGCA CTGCCACTGG GTGAGAGGAG GGGCTGTCCC
110701 ACTGTGCTCT GTGCTATGCA GCTGCACCTC CAGCACTGCA TACAGGGTTG
110751 GCTGCCACAA CGTAAGAAGA ACACAAAACT ATTAGAGAGC ATCCAAAGAA
110801 GGGCTATGAA GATGGTGAAG GGTGTGGAGG GCAAGATGTG TGAGGATCAG
110851 TTGAGGTCCC TGGGTTTGCT CAGCCCAGAG CAGAGGAGCT GAGGGGAGGC
110901 CTCATGACGG CTGCAGCTCC TCACAAGGGG AGTGGAGGGA CAGTGCTGAG
110951 CTCTGCTCTC TGTGACAGCA TGGGGCTGTG TCAGGGGAGG GTCAGGTTAG
111001 GGGTTAGGAA GAGGGTGATG AGGCCCTGGA ACAGGCTCCC CAGGGCAGTG
111051 GGCATGGCCC CAAGCTGCCC GAGTTCAAGG AACATTTGGA AAATGCTCTC
111101 AGATGTAGGG CTTGGATTTT GGGTGGTGCT GTGTGGAGCC AGGACTTGGA
111151 CTTGATGATC CTTATGGGTC CCTTCCAACT CAGGATATTC TGTGATTCTA
111201 TGACAAGATG CACTACTGTT CTATGTGTGA GATACTACTG TTCTGTGTGA
111251 GATACTAGTA GCCAAGGCCT TCACAGGGCC TTTCTGAATG TGCCTCCAGT
111301 GAATGGTCAC CGGAGTAATC CCCTCTGTCA ACACTGAGAT ACACATCTCT
                       Y:OV 1 HOMOLOGY
111351 GTCACCATCT GTGACAGGCT AAGGCAGCAG TGCAGGCAAC AATGTCAATC
111401 TCTTCAGAAT GGCACAGCAC TGCTGCAGAA AGGGGTCTGG TACGCTGTGA
111451 GCTTCTGTCT GAAAAACCTT GACCAAACAC TGGTATTCTT TGGACTAAGG
111501 AAGCAACATA ATTCCATAGA ACAACTGAGT GGGAAATCAC CACTGATAGC
111551 TATTGCATCA AGTTCTGCAA CAGCAACTAA GAAATCACTG GCAATCACTG
111601 TGGGCAAGAC AAACACTAAA TGGTCAATAA GCTCCCTGCT ACTAGAAAAA
111651 CAGTGGAAAC ATAAATGAGA ACAAAATCTC TAGTTGTGCA AAGGTTTTTG
111701 TGGTAGAAGG AGAGACTTTG TTCTATGAGT TGACCTGGAC TTCATATTCT
111751 TTTGGAAAGG ATCAGATGTC AAAGAGTCTG TTAGTTTAGG GACAGGCCCA
111801 CAGTGAAATA CCTGGTAAAG CAAATAGCAG CTAAGTCTTA GCTGACCTCT
111851 TTCATGGGAT AAGCATTGTC AAAAAAAGGA CATGTCACAA CAACACATCC
111901 TTTTGTGTTT GTGCAGCATT ACACAGCTGC GCTGGACAGC GTAATCCATC
111951 AGCTATCCCA GAAAGCATTT CACATACAGG AAGGTTTGCT TAATTTTGCT
112001 AGACTTCACA ACAGATCTAA ACTTGATAAG TAGACTACAC AAGAAGTCCA
112051 ATATTCTGAT GATTCTGCAC TGATGACTGA CCACGATCCA ATTTTTCACT
112101 TACTGTGGAC TGATTTTTAA ATTCTGCAAC TCGCTTTAGA TTAACCATTC
112151 ATTTGACAAA AAGAAAAAAT CCAACAGCAA CAGTTGGCTG GGATGTATAT
112201 TAACTTTTTC TGGAGGAATC TGCTGCGCCT TCTCTATCAC AAAACAAAAA
112251 TATTCCTCTC AGCACTGAGT ATATTTAACG CAGAGATATT TTGAAAGCCA
112301 TATAATTACT AACAACATTA GTGCTCTGAA TTAGCTATTA TGACACAACT
112351 GTAGTATCTT TGTAGATCCT GAGTTGTAGG CTGTCTATGA TGGCCCAAAC
112401 ATATGATTCA GGCAGATGGT ACACAAATGC CCAGGGAGCT CTCCTATAGC
112451 AAGCTGTAGC ATGTTGCTAG ACAGTTTGAT AGTAAAAGGA TTTAAGACAT
112501 AATCAAAAGG TAGAGGAGAC ACAGTACAAC TTGTTGGATA ATCCTTTGAC
```

*Fig. 1-43*

112551 TTTTGAGCTG TCAAGTATAC AACCACGGAC CATTGCAGTG AGTATTAAAG
112601 CCTGTTTGAA CAGAAAACAT GCTGATTGCT AGCCTTAAGC AAGAAAGGGA
112651 GAAGGGGCAG CAGCCACAGA AACATCTTGC AGTGTGAGGA GTGCTCTAAA
112701 TTGTGTGATT AAAGATATTC ACCATGAACA GACACATTCA GTCACTTGAT
112751 ATGTCTTCCA CCAGCACAGA TACCAAAATG GAACTCACGA CAGTGGTGAG
112801 TAATTTACAT ATTGTTGAAG CAAGAGAATA GCTCACTCCC TTTATAATAG
112851 GTTTGATGTG ATGGGCTACC AATAAGAGTT AAGGCCTAAT GATCTTTACT
112901 CAAAAGTATT GCTGCTGCAT AGCAATGTCT GCACCAGACT GGACTGGGCT
112951 ATAGATGGTA TCATGTAACA TACTAGTTGT AATTAAGTGT ATCAGACAGA
113001 CTGAGGTCTT CATTATTAGT ATTGCTCTAG CATCTTCAGC TGAACAAGAC
113051 TAATGAGGAC TCTATTAGGC AGAAAGGTAT GGACTATTCA GAGGCTGTTC
113101 ACTTTCACAG ACAACTAAAA GGGTTAAGGA GTCCACCTCT TTTCTCCAGA
113151 AAACATAATT TGTTCTAGAC AATTTCAGAG GCATTTTGTA TATTGACTTT
113201 GGAGTTCTGT TTTAAAATCA GAGCATACTC AGAGGTCAAA GTAGTTTGTT
113251 TGTTGCCCAT TCTTTTATTT CAAAGGATTT ATGAGATTGC TTTATGCTTG
113301 CTATTGTATA TTATGACTGT CCTGCAGACC ATGAATGTTT CACCTGATGT
113351 GGCATGAAGT TACTTGTGAA CGATCTGTAA GAATGTTCTT TGAATGTGCA
113401 AAAGACACAT TTTGAACCTC ACATCTGGTG CTGTGACCTG TTTGAAAAGA
113451 ACAACTCAAA TCAACATTCA AAACTAGCAG TGAGTTCGAA TACTTCTCTT
113501 GTAGCTTCTG ACTGGAGTCT GAATATCCTA ATATCTGAAT TTAAAAAGCA
113551 ACAGAAGTCT CTTCTCTGCT CAACCTCTTC TGCGACAGTA CATCTTTCTT
113601 CAGTTCTGTA TTTTTTTTTT CTTTTAATAC AGATGCTCTG AATATTGCTT
113651 TCAAAATTAA TTTGGATTCA TACAGTATGC TTGTTGATAC TTTCCTACTG
113701 ACAATCTGCA CAGACCATGT TGGCACACAA GGTCCCTGAG TTAGACTGCT
113751 CCAGCAATGC TAGACTGCTC TGCAAAATGC TTTATTTTTT GCAATTCAGG
113801 CTGTAAGTGG CATCAGGCAC AAGAACTAGA CAATTACATA CAAGTTTTCA
113851 CTGTAGGTAT CCCTATTATT TGCAGAGGAT TTGGACTAGA TGGTCTTCAA
113901 GGGTCCCTTC CAAATCAAAT GATGCTTTGA TTCTGTGATT TTATGAAAAG
113951 TTGCAGTAAG TACAGGGTGG GCATAACACA GCAAGGAGTC CTGAATGTAC
114001 TGCATTTTTT ATGTTCTCAG AATGGTGACT GCTAGAGGAA TCTGGACTGT
114051 CAGTACTCAT AGAGGAAAAA AAAAAAAAAA AGGAAATTGA CTTAAATTCC
114101 TTAGAGACAT TGTGTACAAC TAAATATCAC ACTTTTTTTT TTTTGCTTTG
114151 TTTTCACTAT CTGTGCCACA GTATTTGGTT CTGTGCTTGA ATTATACTTA
114201 GTGTTCAAGT TTCAGTGAAT AGCTTTTATC ATTTTTGTTT CAATCTTATC
114251 AGTATACTCC ATCCTTTTCT CCAAGGTGCC ATATGATATC CTTCCTTCTG
114301 GAACTTTTAT TTAGAGACTT CTTTCTTTCT TTCCCTCTTC CATTCTCTCT
114351 TTCTTTAACT TTTTCCTTTC TCCTTTCTTT TTTGTTTTCT TTTTTTTCCC
114401 TTTTATCTTT CTTTCCTTCT TTTTTCCTTA TTTCTTTTTC CTTCTTTCTT
114451 CCTTTTTTCC TTCAATTTCT TTTTTCCTTC CATTTCTTTC TTTTTTCCTT
114501 CCATTTCTTT TCTTCCTTCC TTCCTTCCTT CCTTTCTTTC TTTCTCTCTT
114551 TCTTTCTTCC TTTCTCTCTC TCTTTCTGTC TTTCTTTCTT TCCCTCTTTT
114601 TTTTTTTTAA TTTTAATTTT TATTTTTTTT TTGTAAATAA AGGACTTCAA
114651 CCAAGTAAAA GTGTGTTTCT GACACTGAGT TCCATCCATC ATTCAGTTTG
114701 GCAAACACAG AATAGGCAGC ATGGGGTGTG TCATGACATT ATACAGGATA

Y EXON 1

114751 TATTTCAAGG AGTTCTGCAA GGCTGTACCA CGTACAGCTG AGAAGCTGTA
114801 CTCTTATCAT CACAGGTGAA GCTGATAAGG TAAGCATTTC TTTTGGTTAT
114851 GATTCATGTT CTAACCCATT TTTTAAAATG ATCATAAGAC TTACAAGAAT
114901 ACTGATGGAA CTTTGTGGTT TGTCATCAAG AACAGTCAAG AAACAAATGA
114951 TTAAAGGATG ACTTCTTTAA AAATCTATTC TTACCTTCAC ATTTCTGTTC
115001 TGCATTACTG TACTGTTTCA CAGCCTGCCA CATATGAAGT CAAAGTGTTA
115051 GTACAAAGTA AAGCTATGTT TACTAATTCT GTAACACTGA GAAGCTGGCA
115101 CTGTACTGAG ACACCCTTTC TTCTTTTTCA TTGATGCCCT TTGTTTCTGA
115151 TTTAGAAATT AAATGCAGCA CTGAATTTGT TTAAATTCAA GACTTAAGCT

*Fig. 1-44*

115201 GAGTTGCATG GTCTACCTAA CATACTTTCT GAATGAAGTT ACTGAATGCA
115251 GCATGGTCAG GTATCAACAA CATACTGCAA ATTAATTTCT GTGTATTCTA
115301 AAACAAGCAA ACGAACAAAC AAAAAACACA CACACACATG CACAAAGCAT
115351 TTGCTTCAAC AGTATGTTTT TTCAACAAGA TCATACATGG AGCTTAAAGC
115401 TTAAAATATA ATACTCTGTG GGAGTAGTAA ATAATCCAGA AGTTTGCCCT
115451 CTATCACCTG CACATGTGAT TCAATTAAGA GAGAGATGGA ACACATGAAT
115501 GTGTTGATTC CACACAATGA AACATTTGGC AGAATATCTT GGATTTCCCC
115551 TGTACTTGGG AAATTCTACC CTAGGAAGAT TCTCTCTGCT TGTGACAAAA
115601 TGGGAAGATA TAAGGACCTT AATACTGCAC TTTACAGCAC TGTTGTCTAT
115651 TCTATGTTGT CTTCTTTACT AAAGAGTTTT TTTTTTCCTT TACTGTTAGA
115701 TAAAATGATA TGTGTTGAAA CTACAGGGAA AATTTCATTA GAATGTCAGA
115751 AAAAAAAGAC AGAAAAAATG TTTAAATACT GACGATGTGA AGTATCTGCA
115801 AATGAAACAA GCCTAAACAA TCACTGCCTT ATTAAAAGGT GGATTTTATG
115851 AAAAAGGTGC CAATAAAATT AAAGAACAAT TTTGAAAAGT GAGGTATAAT
115901 TAAGTCAACC AAGAATGGAA CATGTAATAT TTAACAGACA TTTGTCATAA
115951 AGCAGATGAG TTTGGTAAAT CATTATCTCT TTCTATCACT GTGCTTCCAT
116001 TTCCCTAATC TATTTTTAAG AAGGTAATGA TGAGGTTTGA GACCTCTGAT
116051 AAAGTGGTTG GTATAAGAAT CCAGCTTCCA TTTACATGAA GGTGGAGTAA
116101 ATCCAGAAAA AAACTTGCGG TGTTTTTCCA GACCTACCCA CTTTATATTG
116151 TCAATAACTG TAGTTTGGAT CACAGAGGGC TGATCTGTTA ACTGGTCTTA
116201 AAAGTGATGT TAAAAACTAT AGTGAAAAAC CTGGTCTGGA GTCTCAGGTG
116251 AATGAAGACT GAGAACAAAC CTATGTGTGT TTTCTTTCCT GCACAAGATG
116301 GGAAACGATT GTCAATGAGC TTCTTTCAAG GCAAGTCTTT GCAATATTTT
116351 CAACACAGTA CACATGTACA GAGGATAACT CAAGTTTCAA ATAAAACAGT
116401 TGCCAGCCTA CACATAACTG GTACCTATAC AAGATTTTGA TTGCTCACAA
116451 ATCCAAGCAC ACACCTGCCT TTTAAATCCA CACTACTGAA TTCTACTTAC
116501 TGAAAATAAG CTGTGCACTG TGTACAGAGG TTCAAGTGCA CTGACTTCCT
116551 TGGAATACAA CTAATACATT TTAATCTTTT CTTTAGACAA CGATTTCAGA

Y EXON 2

116601 ATGGATTCCA TCAGTGTAAC AAATGCAAAA TTTTGTTTTG ATGTTTTCAA
116651 TGAGATGAAA GTCCATCATG TCAATGAGAA CATCTTGTAT TGCCCTCTGA
116701 GCATCCTTAC AGCCCTGGCC ATGGTCTATC TGGGGGCAAG AGGTAACACT
116751 GAATCTCAGA TGAAGAAGGT AAGTTGCTTA CATTGGTGTA AAGTGGACAG
116801 TGGACTCTAC TTCTGCTTGT CATTCCTTCT AAGTAATAAC ATATTATCTA
116851 CTCATGAGGC TCTCACATAT TTTAATTCAC CAGATGGATC ATGAATCAGG
116901 GAATTGTATT ATTTTTTTCT AAATTCTGAC ATCTTCCACA TAATGTGATC
116951 ATTTTTTTTC CATATTTTTT ATTTTTGTAT TAAAAAGATA AAACCCTGGA
117001 GGAAAGGAAG AGGGAGAACA TTATTCGCAG TGCATAATAC ACAACTAAGT
117051 TAACATCCAG ATGCTCACTG AAAAAAATAT AATCTAAGCA AATAGTGCTA
117101 TTTCCAATTT CTCAGAAGGT GACATGAAGT ATGAACCAGC TGCAAGCTTA
117151 CTTGCAGCCT TTTAGTTCAT CTAATCTAGC ATTTGTTGTG GGTTTTTTTT
117201 TTGTTTCTGT TTTTGAGCCA ACAGCTCTAC CCCGAACATC ACGTGTAAAT
117251 TTTAAATGCA TACCATTTTT GGTCACGCTT GTGTTTTTTT CTCACTGGCA

Y EXON 3

117301 TTTTCTCTTG CAGGTTCTTC ATTTTGATAG CATTACAGGA GCTGGAAGCA
117351 CCACTGACTC TCAGGTAAAG ATGTAACTTC TCTCCTTTTG TTCCTATTTT
117401 CTCCTCAGGA CAAAACTAGA ACTACTCTGC CTCTGCTCCA AGCAGTTTCA
117451 GACTGTCAAA AGTGGTGGCA ATGCTCTCAA ACCAAACAGA TCTGTGGAGG
117501 GAGGAAAAGA GTGTGTAACT CACTCTTGTT TAAAGCCAGG GAAACTGACT
117551 TGGAGATAGG TTTATTTGTC TGTTTAATGC ACCATCATCA GACTAGGTCT
117601 GTGGGTGAAT TCCACCATGG CCTGACTGTT AGTGATGGGG ACAGTCCTTT
117651 GGGGTCTGAT TTTCTAGATA AGGAGAAACT AATGTGACAT ATCATCTTGT

Y EXON 4

117701 TTTCCTGTCA TCACCTCAGT GTGGCTCTTC TGAATACGTC CACAATTTGT

*Fig. 1-45*

```
117751 TCAAGGAGTT ACTCTCAGAA ATCACCAGGC CAAATGCTAC ATACTCACTC
117801 GAGATTGCTG ACAAACTCTA TGTTGACAAA ACATTCTCAG TTCTTCCGGT
                          CR1 GG
117851 GAGTTGAAGT GTGACTTAAC CTCAGTGAGA TTGCCCACTG GGCTCACCTG
117901 GGACTCGGCT CTACTGTGAG CCACAATGGG AATTGGTTTG AGCCACAGGA
117951 TGAGTTCAAA CCTTTCTGTG GCTTTTAGGA GGAGGCTAGG CTCACACAAG
118001 GTATAAGGGC TCTGGAGATA TTCAAGACCC ATTTGGACAC TTTCCTGTGC
118051 AATCTATAAT GAACCCCTGC AGGGGGTTCA AATTGATGAT CTCCAGAGAT
118101 CCCTTCCAGC CCCTGCGATT TTGTGACTCT GTAATATATG CCCATGCAGC
118151 AACTGCTACA GGGAGCAATC AAAATTGCTG CTCATTCACT AAAAAATGTC
118201 TCTTAATGAA AAAGGTGATT TGTAAGGGAG GAAAATGACT TGAAAGCGTG
118251 ACGACTGAAA TTGACAAAAA TATTTTGTTC ATCTTTTCTA AAACTAGACA
118301 TAAAATAACT CACTTAAAGA AAGTTTTGGT TTTGAAATAA AAAACAGGAA
118351 TGTAAGAATA CACAGTTCAA AAGAAAAGGT AGGCACGAAG ATGAGGAAAT
118401 GAGTATTGTC TGTCCTTAAT AATGTTTGCA GAACAGAAGG TTTTATGGTA
118451 AAATGAAGAA AATATTTCAA AATTTTAACT TAGAATCCAA TCTGAAGACA
118501 AAAGTGACAA ATCTAAATAT GTGAAGTAGC CTTGTCCAGC TTTAAGATTC
118551 AGTTACAGCA AGAGAGCTGT TTGACTTGTT CAAGTGTAGG GATAGAAGTT
118601 TCTTTTAACC ATCACTTTCC ATTTCATTAA TTTTGCATTT CATATTCTTC
118651 TATTTTAAAG TTCTCAACAG TCAAACACAA TTCTTCTGCT TATAGGAATA
                         Y EXON 5
118701 CTTAAGTTGT GCAAGGAAGT TCTATACAGG AGGAGTGGAA GAAGTTAACT
118751 TCAAAACAGC TGCAGAAGAA GCAAGGCAGC TCATAAACTC CTGGGTGGAA
118801 AAAGAGACAA ATGGTAAGAA GTAAAAAAAT AGCTGATATT TTCTCCTACC
118851 TACTGTAATC TACGCTCTTG TCTTCTTCTC CTCAAAATGT GAAGAAAGGC
118901 ATATCAAGGA ACAGCACTTG ATTATTGCTA TGAAAGCAAA CTCCCATAAA
118951 ACTCACCATG CCCTTCATTG CAGGCATTCA TGCAAACCAG ACAGGCTGTG
                                                Y EXON 6
119001 TCTTAACACT CACTGCTTTG CTTCCTTTTC ACAGGACAGA TCAAAGATTT
119051 GCTTGTATCA AGCTCCATTG ATTTTGGTAC AACAATGGTC TTTATTAACA
119101 CCATTTACTT CAAAGGGATA TGGAAAATTG CATTTAATAC AGAAGACACT
119151 CGGGAAATGC CCTTCAGCAT GACAAAGGTA GGGACATGGG CACTACTACT
119201 GGAAAAATTC AAGATAAAGT GATCCCTACT CACATTGTCT CATGCTTCTG
                              Y EXON 7
119251 TTTTGCAGGA AGAAAGCAAA CCTGTGCAAA TGATGTGTAT GAACAATAGC
119301 TTTAATGTGG CCACACTGCC TGCAGAGAAA ATGAAGATCC TGGAGCTCCC
119351 ATATGCCAGC GGAGATCTGA GCATGTTGGT GCTGTTGCCT GATGAGGTTT
119401 CTGGCCTGGA GCGGGTACGG CCCTGGCAGG GGAAGCCAAC TAGTTCGGAG
119451 TTCAGTGGGA ACTTCTGACT GCTTTCAGAC CTTTGGCTGT CCTCTCACCC
119501 CCTGGCTGTG CTGTGCTGGC CAGGCAGGGG AGCACAACAG TGGCCCAGGT
119551 GCTTCTAGGT GCTCAGGCAG AGGTTGGCCT CTAAGGAGAG CCCTAGCCTC
119601 AATGTTATTA AACAAAGAGT GTAGCTAACA AAACAAAGGT AAAGGAGCCT
119651 AGGGCTGCTG TAGTCCTGCA GCAGGGGATG TTGGTATATG CAAGTTATCT
119701 CCATCAAGTA CTAGAGACAG ATATGCTAGC AGGATTTCTT TTTTTACTTT
119751 GAAGAAATTT CAATTCCCAG AGATCAAGTA GAGTTCAAAC ACTGTTACCA
119801 AGTCATAGGG ACCAATTCTG TTGATGACCG TTAATAGATT TTTTTCATGA
                                   AT-RICH
119851 GTCACCCCTC CAAATAATTA AATATAATTT TTTTTTTGTA AATATGAGGG
119901 ATATTTTAAA TGATCATTTC TCATTGAATG TAGAAAAAAA TAGGAAAAAT
119951 ATAACAAGAA AACAAACAGC ATTTCTGAGA GGTTAGCTGC AAACATCTGC
120001 AAATGAGCAA AAATTTGATT TGACATAATC AAAAACTGAT TTTTCAGAAA
120051 AGCATTTGAT CTGTTGGAAG AATTTTCAGA TGACAAAGTT TTGGAGAGCT
120101 TCATCAAGAC AGATGATATG TAGGCTATAG TCAGGAAGAA GCACAAGGGA
120151 TAAACAAATA GATTTAAGCT TAAGCGTCAC TTCTGTTTTG CACACAAATA
```

Fig. 1-46

```
120201 AATGAAATAA ATAGCAACAA GTGGTATTAA TACAGTTGGT ATGGCCACCA
120251 TACTCCTGCT TTATGCATTT CATTGTCTCT TCTCTTTGCA GATTGAGAAG
                                 Y EXON 8
120301 ACAATTAACT TTGACAAACT CAGAGAGTGG ACTAGTACCA ATGCAATGGC
120351 AAAGAAGAGC ATGAAAGTGT ACCTGCCCCG CATGAAGATC GAGGAAAAAT
120401 ATAACCTCAC ATCTATATTA ATGGCCTTGG GAATGACTGA CCTGTTCAGC
120451 CGTTCAGCCA ATCTGACTGG CATCTCTTCA GTAGATAACC TGATGATATC
120501 TGATGCTGTC CATGGGGTGT TCATGGAAGT CAATGAAGAG GGCACTGAGG
120551 CGACAGGTTC AACAGGGGCA ATTGGAAACA TCAAGCATTC CCTTGAGTTA
120601 GAAGAGTTTA GGGCTGACCA TCCATTCCTC TTCTTCATCA GATACAACCC
120651 AACCAATGCT ATTCTATTCT TTGGTAGATA TTGGTCGCCC TAAAGAGAGA
120701 AAGAGCTGGA AATAATGCTT ACCTTCCCCT CAGAAATCAA ACCTCTTTAC
120751 TGTAGTATTG TAGCATAATC TCAATGCAAT ATTTTATCCA AGTGGAAAGC
120801 CTTCAATATC TAGGGAGACA TTCTTGAAGA AGCATGTGAA ATTTCAGATC
120851 TTTATATGCA GGAATTTATT CTCAGCTTAG ATTCAGGATT CATATCCAAG
120901 GTGTACATAT TCCCAATGTG CTTGAATAAC TTGGGAAACA GGGCCAGTGC
120951 TTTGGGGTTT TTTTTGTTTG TTTGTTTTTT GTTTTTTTGG TTTGGTTTGT
121001 TTTTTTCTGG TTGGTTGTTT TTTTTTTTTG TGTGTGTGTG TGAGATTCTG
121051 CCATTGTTAT TGAGAATCTG GTTTCTCTAT AGGAGTTCTC TGAAATAAAC
121101 ACAGCTTTCA GGAAAATCCT GGTCCTTTCC ATTGAATTAG CTGGGCAGTC
121151 ATCCTAGAAC TGATGCCTGG ACAACTTGCA GATGAAATTT TTAACTTCAG
121201 CAGACCATTT GTCTTCCAGT AATCCATTTG GACTTATTCG TGCTGCGTAA
121251 CATTTTTTCT GAGGGAGCAT ACAGAAAGTC TACCATTTCT TCTTAAATCA
121301 TCTCCAAACA AAACATCTTC CTGATTGATA TTATTTCCCA TTTTCATCCC
121351 AGTGACATGT CACTGATTTT GTGAATGTTA ATTAATGGTC TTTCTATTTA
121401 TTCTAATAAA AGCTTCGCAA ACAAAACATG TCATTACCTA TTCTGGGTTA
121451 CTGTACTACA CAACCTGAAA AATACGATAT AGCGGGTAAT AATTATTGAC
121501 AGAGGTGACT AAGCTGGTAT GTGGATCCTA TTTTCAAAAT CAGAATGTAC
121551 CCATATATGA GGTCACTAAA TATTTTAAGA TTAAAAAAAA AAAAAACAAC
121601 TGGGTTTAAT CAAGGTAAAC CCTATAGCTC CTACTCTTCA ATTGAGCTTC
121651 TCCCAATACA GCATACCAAA TAACAAAATT TTTTGAATTT ACTGAATTTC
121701 CAGAGAACTT TTACAGAAAT CCTCTAAGGG TCCTCAGTAA ATACATGAAG
121751 GTGATGTGTA CAAGATAGAA TTTTAAAATA TGAGAAAGGT ATTAAAAGGT
121801 AGACTGCTTC AGCTTTCTCA TGCTGACAAG AATCACATGA AGAAATCTTT
121851 CTATTGCCTC ATGTGATATT CCTCTCGAGA TGTTGTATGC TATTTCACGG
121901 TCTTTAGAGG AAAGGGTCTT TAGGTTATAT ATTATCCAAT TATAATGGTT
121951 ACTAGTGTTA ATGACAGTTT TCTGCTAGGA TACACATGCA GAATTGCAAA
122001 TTACAGTATT GGTACTGAAA ATGTAGCGAT ACTTCAGTAA TTCAGAGCTG
122051 CCTCAAACAC ATGCCATGTC AGCATTAACT ATAACTTGAA ATGATGACAT
122101 TAGCAGCAGT GAAACACGTT TCATACCCAC TAAAAATGGG AGAAATGCGA
122151 TTACTGGTCT TCCCAAGAGG GTCAGAAGGA TTAGGTACAG TTTGCACAAG
122201 GATTCAAGTA AAAAAAAGTA TTTCAAGAGC TATGAAATTT CAAGTTTTAC
122251 TGTGTACATC ATGTTATTTC CCTCTTACAG CTGAAATCAG TCAATACAGT
122301 TTTGCTACAA CTAAAACCAA CCAACCAAAC AAACGGCAAA GGAAAAAAGG
122351 CAGGACTGGT AAAATATTGT CCTGAGCAGC AGAGTGTGTA AGGTTACTAA
122401 GCAGTTATAA TACTGTGTTG GAACTGAAAT ATGCAGCTAT GTCACTCTGC
122451 ACTTTCTAGG TACAATAACA GTAAAAGTAC CCACATTTAC TATGGAGGTA
122501 TTTAATATAT AGCGTAAACT AAAAAAACAG CTATTCAATT GTTTGATCTT
122551 TTTAAAGCAA AAGATGAAGA AAATCAAGGC AGAAATGATA AATGAATTTC
122601 AAAAACTATA CAAAAGAGGG TATTCAAGGC ACAGAGTCCA CCTAATGTCT
122651 TAACTGTGAA ATGGAAGCAT TTGACTTGTT TTAAAAAGGC CATTAGGTGT
122701 CACTAAGGGT AAAAAGTTAC GTTTATCAGC TTTCAGAAAG AGGATGGCAT
122751 TCCAAAGGTG CCTCTGAGCT CTGAAGCCCA GCAAGGGATA AGAGAAATGA
122801 ATCCCAAGTC CAGCTATTGT CCAAAAGTCC TTTTTGTTCC CTGATACCAT
```

*Fig. 1-47*

```
122851 GACTGAAGTT GTCATGTCAA GACATTGCCT TCTGTCTGTT CACTACACCT
122901 CATGTTCTCT CAGTGCTGTG TTCTTAGAGA GGCAGTACTG CTAGTGGTCC
122951 GCGGAATGAA AACAGCCAGG TGTAATCACA CTCTTTGAA TGCCTCATGA
123001 GAAGTGCTCT CTGGACTAAG TGTAACTTTC CTTCTCACAT CATTTGGAGA
123051 AGGGACCATC ACAGAATCAT TTGGAGACCA CCTGCATCTA TTCTGCACTT
123101 CTCTCCACAT TTGCCTATCG TCTTCTAAGC AAACCGAATC TATGGCTGAA
123151 GTTACAAGAC TCTGCATGTG GTGTCACAGT CACCAGAGGC AGAGGACTCA
123201 AGAGAATATC CTGGTCCAGA GCTACTCTGG GATCTCAAAA GTCACTTGGG
123251 AAAGCACAGC ATGTTGAACT AGACTTTGGT GTATTTTTCC AATCTTTATC
123301 AGTCTACAAA ATATCAACTG GACATGGAGC AGTGGTTCAC TTTGGTGTTT
123351 CCTGTGGCTC ATGATCTAAG ATTCTTCAGT CTGGAAAATA AACTGCAGAG
123401 ATTACTGTTG AGGAGCAGCA AGTGTCAGTC TGCTCAGCAA GGGAAGGAGA
123451 CTGAGGGCAA GGGAAGGAGA CCGTGCCAGT AAGGCTAGAA GGGCCCGATA
123501 AGGGATCAAG TGCTAAATTT TCCAATATTA TAGCCATAGT TTAGTGATTT
123551 CCAGAGAAAT ATGTAGTGAT GTGGTAGGCC AAAGATCAAA CCAGAAGGCC
123601 CCAGAATGGC AACAGGTGAT GATCCCTGTG GCACATTCTC TATCTTGAAG
123651 TAAAACAGCA TGGATCCATA TAAATACATT CTTGCTCAAC AGCAGAAATA
123701 ACAAACAGTA TTGCTTACTT CTACGAATAT CCTAACAAAA CATGTAGATC
123751 ACAATGCCAC TGAACCTTTG TATGGATGGA ATCTGTGCAA TCTGCCATGA
123801 CTAAAGCTCT GTCCAAAACT GCACAACTTA GGGTGCCCAG CTTCTGAAGG
123851 GATGTGAAAT TATCTGTGCT ATCTCCTTTT CCCTTCTTGT GTTAGCTCCA
123901 GTAAACTCTA TTTTAAGAAA TACCTTACAG TTTCTGATTG TCTTCTTTAC
123951 TGGTATCCAA AGGGACTCCT ATGCATTACA GGGTCCTCCA GCACAGTGAG
124001 GTTCTTGGCC TGGTGCAGGC ATGCAAAGTA GCTTAGGCAC GGGTCACAAT
124051 CAAGATACTC AGTTTAATGC TTCTCCCAAG TGATGGGATG CTAAAATCTT
124101 ACATGATTTT AAAAGGAAAG TGTTCAAACT GTGGAAGAGA AATCCACTGA
124151 CAAATAAGAA AGATACAGAA AATAAAGTTA GCTATAGAAG ACATGGAACA
124201 GGAAATAATG TTAGAACTCT GAGGGCAAGA GTAAGCCTTA ACAGTAATGA
124251 CAAGCCTCAC TGGAGGAGCT CTTCCACATA CGTTGTTCTC ATGGGCCCAG
124301 GAGTCTGTAC TGGAAATTGG CACACAGTTT GGGTACCGGG GGCGATCTTT
124351 GTGAGATGAA GCCCTGAACT GCCCTGGGTC AGCTGCAGGT GTCTCTGTAA
124401 TGGATGAAAA CAACTCACTG TGCACCAGAT TTTCAGCTAA TAAGAAAAGC
124451 ACATGGCATC TCTGCTCAAA CAGAATCATA GAATTGCTCA GGTTGGAAAA
124501 GACCTTAAAG GTCATCGAGT CCAACTGCAA CCTAACCAAC TACCCTAACT
124551 CTAACAACCC TCCTCTAAAT CATGTCCCTG AGCACCACAT CCAAACAGTT
124601 TTTAAACACA TCCAGGGATG GTGAATCAAT CACATCCCTG GGGAGCCTAT
124651 TCCAGTGCTT AACAACACTT TCTGTAAAGA AGTTTTTCCT GATATCCAAC
124701 ATAAACTTAC CCTGGCACAA CTTAAGGCCA AATTTAATTA GAAAATGTAG
124751 CAGCACTGCA ATGTAGCAAA TGTAATTACG AAAAGGTGGT AGCTGCTAGG
124801 GACAGAGGAC ATGCAAATAG ACCCAAAAGA TAAAGACTAG AAACAGAAAA
124851 AGGGGACATG TGAGAGGTAT GTTTGGAGAA ACATAACAGA GGAGATATTT
124901 GAAAGGAGAT CTTGGGAGCA CAGGCAAAGA CACAATCCTG GGAGGAGGTG
124951 CTCCATGCTA GAGGATGTAC CTCTAAGGCA CCGCAGCCAT GGGCAACCAA
125001 CACAGGTCAG CGTCATCCTG GTGAGACTGT ATCCCACAAG CAGCTAACAC
125051 TGGAGTAGGG ACAGCCCCGA AGAACTGCAG CCCAGGCAGC ACACTAGAGC
125101 AGAGAAATCT AGTTAGCAGC AACCACTGGC AGACAGAAAT GATTATATAG
125151 ATTACATACT GACCCTAGCC TCTTACACTG CCTACTGCAT CACTGAAAGG
125201 ACTGGGAAGA AGAGAGTGCA ATAACGTAGC TGAAACTAGG AGGAAGGCAA
125251 GGAGAACTGA AGCTGACTAG GGAAAAGGGG GATTAAAGGT TTAAGTGTCT
125301 ATTCCATAGT TTGCTGGTTT GTTTTTTGTC AATTCCTGAA TCAGTAATTT
125351 TTATGTTAAT TAGCAAAAAA TTACAAACAC TCCCCAAGTC AGGACTGTTA
125401 CCTACAACAG AAGCTCAGAT CAGCTGAGCC TTAGTCTTTT GGTCCCTCCC
125451 TAGGGAATGC TGTATGTGTC TCTCTCTCCA GGCCTGCTCA AAATTGACCT
125501 CAGACCCAAA CTTTTGCTGA ATCTCCAGTA CCACCTCTTT TGCTCCTAAC
```

*Fig. 1-48*

```
125551 TAGATAACAA AGCCCTGAGC GCTTTGCTTT TAGCAAAGCC TTTAAGTGCC
125601 ATTACCAACT GCACCTGGAG CCTTTACCTA CCCCTATGGA CCCAGGCTCT
125651 ATATTTAAGC TCTGCCCTGA ACCTTCACTT CTTTCCTGTC CTAAGTTAGA
125701 TGTACTAGTA TGGTGTGTAC TATGTCTCCA GTTCAAACAC AGCTGTGCCC
125751 ATACCTGGCC AAGGACTCCT AGTATGACCT GGGCTGTGCC TTGCTGCTAA
125801 GGACCTGCTG GGTGATTGCT GGACCTGATC CTAATCCTGA ATTAAGAAAT
125851 GATTTCTTGG CTTGACTGGA TGTGCCCTGT GGTATGATAC TGCCTTATGA
125901 TTTGGACTCT TGTTTGCAGC TGTGCAAATC CCTAAGGAGC CCAGTCTCTG
125951 GCCACCTGGA ATCTTGTCAC TACCAAACTT CCTGAGGGAC TGGTCTTGCT
126001 CTGGGTTCTG ATCTCTGGAC AGTACTCACC CTTTACTCAG CCCAGGCTCC
126051 CAGTTAAGCC CCTTTCCACC CTGCCAGGCT CTCCGCTCCA TCCCTAGCAG
126101 GGGCTCTCAT GACAGTGTGA CCCCCCCTTA CTCAGGTCAG GGCCACTTGT
126151 GCCACGTTCC TTTCCTGTCT TCTGTCCCTG CCTTGGCTCT AAAGCAGTGT
126201 GCTACCATCC ACAACCACTG CATCTCTCTA AAGTAAGCCT CTCCTGAGCC
126251 CAAGTCTCTG TAACGAGGAA GGATGCACTT TGCTCAGAAG GATGCGAGGC
126301 TGCTTCTGAG CTCTGAGGGC ACTGACCTCC CATGAGGTAC ACCCCATACC
126351 CAGGACCACA ATTCAGCCTG CTGGAACCAT CAACTCCTGC TGGAGTAAGG
126401 CCATAGCAAG ACCAGCATCC ACCTCCCTGC AGCCCTGCCC TGCCCAGATA
126451 TTGGGCCTGC TGATCTCAGG ATGCAGACTT GCTTCTCAGC TTGACCTAAG
126501 CATTGCCCTG TCTTTATGGA CCCACCTGGT TAGCAAGTTC AGTGCAGAAG
126551 GAGGCTGTTG GCATCTAGCT AATTTTCCAC CCACATTACT GTCTGCTGAC
126601 TCATTCTACG TCTCTCCCAT CTTGTTACAA TAATAATTTG GGAGATCATA
126651 TTGAAGGTCT TAATAAAGTC AAGGCATGTG ATATTCTCTG CTTTGCCTTT
126701 GTTTCTAGAA TAAGCCACTT CATCATAGAA GATGAAAATG CTGATCAGCA
126751 GAGATCTGTG CTTGATAAAT CCATGCTGGC TTTTCCTATC ACCTTATATT
126801 CCTTCATATG CCTTGAGACA CCCAAGGAGG CCTTGGATCA GAGCTGTCTG
126851 TAGCAGTCCT AACTGGTATA CAATTAGTTG TACAACAGGT AGTGATCCGC
126901 ATAATAGTTG GCGTGAGAAA GTGGGCCTGT GCTGTGTCAA GCATAGAGTT
126951 TGGGTTCCAG TCCTGTTCTG CATGGCACAT ATGCCTGAGC AGCTGGGTAA
127001 TCTCTGCATT CCAATTGGAA GGCAGGGGCC TGTAGGCAGT TCCCACTTGG
127051 CATGGGTGAT TGTACCACCT GTGTCCTCAT CTGTGAAGCA TCATGTTTTC
127101 ATTCAAATAT CCTTTTGTTT GACAGTAGAA ATGAACAGAA TTGTTTTTTT
127151 TTCCTAAGCA AATTCTGCAA GAGCTCTGAA GAACAAGGTG TCAGTGAACT
127201 TCTAGCTCCA TAGATAGGAC TTGCATCACA TGTCATGCCT TGATTGGAGG
127251 TCTATCCGAT ACTGAACAAC TTGTGGTTCC CTGAGGGAAT GTAAGATTAC
127301 TGATACTACT CTCTCTTTAT GTTAGCTACA ATAAATGGTA GGTTAAGCAA
127351 TAGATACAGA GTTTGAGTGC CTTTCTTACA AGCATCATAG TGAACAAATC
127401 CACTGGTGAT CTACCTTTTC AATAACTACA GAGAATTGTA ATCTCTTGGA
127451 TTCTCCTCCT TCCCCGTTCT GAAAATGTGT TCTTTTTTTC CAAATCAGAA
127501 ACCTTCCTCA ACCACCCTGA CTATTCTTTG GACATTGTTT TGTTCTTGCT
127551 CCTAAATAGG CTTTATAATT TTTGTAAGTG AAAGGCTTTG CATGCAGGTG
127601 AGGCTACAAC TCATTCAGTA ACAATGAGGA AGACTGTCAG ATTTTGGGGA
127651 AAATTCTCCC ACCCAACCTT TTGCTAGCCA GTAAGATGTA ATCACTGAAT
127701 GTCATGCCAC AAAGACCATA CCAACATCAG ACCACATATC TACAGGAAGC
127751 TTTAAGGAAT CATTGACTGT ACAGTGAAGG GTAAATCAAA TTAAAATGAA
127801 TGTGAGGTCT GATACGAGAT ATCCTCATGG GAATCAAGAG CAAAGACAAA
                       Y:OV-1 HOMOLOGY HS-III SITE
127851 TAGTTTTTCA CAGTCTTGTC ATGATCTGTC ACAGACCAAG GCAGCACAGC
127901 AGGCAACAAT GTTGGTCTCT TCAGAATGGC ACAGCACCGC TGCAGAAAAA
127951 TGCCAGGTGG ACTATGAACT CACATCCAAA GGAGCTTGAC CTGATACCTG
128001 ATTTCTTCA AACAGGGGAA ACAACACAAT CCCACAAAAC AGCTCAGAGA
128051 GAAACCATCA CTGATGGCTA CAGCACCAAG GTATGCAATG GCAATCCATT
128101 CGACATTCAT CTGTGACCTG AGCAAAATGA TTTATCTCTC CATGAATGGT
128151 TGCTTCTTTC CCTCATGAAA AGGCAATTTC CACACTCACA ATATGCAACA
```

*Fig. 1-49*

```
128201 AAGACAAACA GAGAACAATT AATGTGCTCC TTCCTAATGT TAAAATTGTA
128251 GTGGCAAAGA GGAGAACAAA ATCTCAAGTT CTGAGTAGGT TTTAGTGATT
128301 GGATAAGAGG CTTTGACCTG TGAGCTCACC TGGACTTCAT ATCCTTTTGG
128351 ATAAAAAGTG CTTTTATAAC TTTCAGGTCT CCGAGTCTTT ATTCATGAGA
128401 CTGTTGGTTT AGGGACAGAC CCACAATGAA ATGCCTGGCA TAGGAAAGGG
128451 CAGCAGAGCC TTAGCTGACC TTTTCTTGGG ACAAGCATTG TCAAACAATG
128501 TGTGACAAAA CTATTTGTAC TGCTTTGCAC AGCTGTGCTG GGCAGGGCAA
128551 TCCATTGCCA CCTATCCCAG GTAACCTTCC AACTGCAAGA AGATTGTTGC
128601 TTACTCTCTC TAGACCCCCA AGTCAAACCA ACTATGCAGG TATGCTGACA
128651 ACACTATGAT GACAGCCTGT TCTGATCAAG ATCTCATTTG TTCATGGACA
128701 ATTTTTGTTG CTTGCAGCTG GTCTTCCATT GGGAAAGAGT GTAGTATATC
128751 CTTCTCATCT GACAGAAAAG CAGAAATTCT CATGCTCCAC ACTTAATCTA
128801 CATTGTTTTA AACCACCGGC TACTTCTTGG AGAGGAAAAA TGGCTTTTAT
128851 AAGACTCACA AAACAAAGCT CTGCAAGTCA AATGCATACA AAACTGTTCT
128901 GTAGGTCTGG AATCAGGACA CTATGTGGAA GTCAAATAGA GCAGCTTTAA
128951 AAAGCCTTTG GGATCATTCT CATCTTATAT TTGCAGCACG ATACTATGAC
129001 AGTGATAACT GACATAACTG CATCAATTTC CTTGATATTT TATTTGTCTT
129051 AAAGTACAAG ACATAGAGAT GGACGTAAAG ATGGACATAT GACTCAGGTC
129101 TGGACAGGTC CGTGGTCCAT GTATGATAAA AGAGATGAAG GGAAGGAGAA
129151 TTGAGACTGT CTAAGAAGGG CTTCAGGGAC GTTCTGAAGG CAGATTTGAC
129201 TGAATCAGAT GTACTGTCCA AGTCTCATAT GTAGCAATGG AAGGCTGATA
129251 TTGGAGAAAT ATAAAGAAAT GGCTGTGAAC TCAAAGTGAC CCTGAACAGA
129301 AAAGGGATAT GGAGTTAAAA TAATGTCACA GAACTGAGGT TTATATGATA
129351 TACCATGGGC TGCAGAGGGT CAGAGTGCTC CACCATGGGC CTCTCTTGGG
129401 CTGCAGGGAA CTTCTGTTCT ACACCTGGAA CACCTCCTGC CCTCCTCCGC
129451 ACTGACCTCA GTGTCATCAG GGCTGTTTCT CTCACATTTT CTCACTCACC
129501 TCTCCCAACT ACCATTGTAC AGCAGTTGTT CTTACATATT GCTCCTCCTG
129551 AGGTACATCT AGCATCGATC ACTGGCTCAG CTCTGGCCAG TGGCAGCTCC
129601 CTTTTGAGGA CACGGGACAG CTGCTGGGCT CTGTTCACAG AGGCCACTCC
129651 GGCAGACCTC CACTACCACA ACTTGTAGTG TAAATCCACT ACAACTTTCT
129701 GAGCTACAGA AATGAAATGG AGACCCTCTC TGCTATGGGA TACAAAAGAG
129751 GAAACGTGGC GTTTAGCTCT GGCTCACTGG TACACCCAAC CACAGGGTGA
129801 GAAGCAGCCT GTTGTTATTC ACTACTCTTA GGACAGATTA TGGTGAATTG
129851 TTAATAAAAG CATTTCTTCA TAACATCCAA AGGAGGAAAT ACACTAAATT
129901 ATATTTTTTA TTAATTAATT ACACATGCTT AATTATATAT GGCATGGTTG
129951 CTTTGGAAGA ATCTTGTCCT TACTGACCAG ATCTGCTGTT TGCTGAGACA
130001 AAATGGCTGA CAATTTTGGC CATGGTGGAT ACCTTCCCCC TTTTCTGTAG
130051 CATTAGGACA GAAGTTATTC TGGAGCCTGT CTGACAAGTT AGACTTGATA
130101 CCTTTAAGTA TTTGGAAGTG TGCTTTTCAT GCTGGATGTC ATCTCCAGAA
130151 CCTCCCTGTC TGGTAAGCAG TTCCCTGCCT TAGTAAGAGC CGAAACGGTC
130201 TCTCTTTTCC TTGTTATCTC ACCAGGATAT TACAATGTGA CAGGACTATC
130251 TGAACTATGC CAACCTGCAA ATTCCAAATA TATATATATA TATAAGATAT
130301 CTATACACAA ATTATTAGTG TTTGATTGAC ACCAGATGAC AGAGAAGTGC
130351 ATCTGAGAAA ACCTATTCCC AATCTCCTTT CTCTTTCTGC AGACTGACAT
130401 GCATTTCATA GGTAGAGATA ACATTTACTG GGAAGCACAT CTATCATCAC
130451 AAAAAGCAGG CAAGATTTTC AGACTTTCTT AGTGGCTGAA ATAGAAGCAA
130501 AAGACGTGAT TAAAAACAAA ATGAAACAAA AAAAATCAGT TGATACCTGT
130551 GGTGTAGACA TCCAGCAAAA AAATATTATT TGCACTACCA TCTTGTCTTA
130601 AGTCCTCAGA CTTGGCAAGG AGAATGTAGA TTTCCACAGT ATATATGTTT
130651 TCACAAAAGG AAGGAGAGAA ACAAAAGAAA ATGGCACTGA CTAAACTTCA
130701 GCTAGTGGTA TAGGAAAGTA ATTCTGCTTA ACAGAGATTG CAGTGATCTC
130751 TATGTATGTC CTGAAGAATT ATGTTGTACT TTTTTCCCCC ATTTTTAAAT
130801 CAAACAGTGC TTTACAGAGG TCAGAATGGT TTCTTTACTG TTTGTCAATT
130851 CTATTATTTC AATACAGAAC AATAGCTTCT ATAACTGAAA TATATTTGCT
```

*Fig. 1-50*

```
130901 ATTGTATATT ATGATTGTCC CTCGAACCAT GAACACTCCT CCAGCTGAAT
130951 TTCACAATTC CTCTGTCATC TGCCAGGCCA TTAAGTTATT CATGGAAGAT
131001 CTTTGAGGAA CACTGCAAGT TCATATCATA AACACATTTG AAATTGAGTA
131051 TTGTTTTGCA TTGTATGGAG CTATGTTTTG CTGTATCCTC AGAATAAAAG
131101 TTTGTTATAA AGCATTCACA CCCATAAAAA GATAGATTTA AATATTCCAA
131151 CTATAGGAAA GAAAGTGTGT CTGCTCTTCA CTCTAGTCTC AGTTGGCTCC
131201 TTCACATGCA CGCTTCTTTA TTTCTCCTAT TTTGTCAAGA AAATAATAGG
131251 TCAAGTCTTG TTCTCATTTA TGTCCTGTCT AGCGTGGCTC AGATGCACAT
131301 TGTACATACA AGAAGGATCA AATGAAACAG ACTTCTGGTC TGTTACTACA
131351 ACCATAGTAA TAAGCACACT AACTAATAAT TGCTAATTAT GTTTTCCATC
                                NRE: A,B,C regions
131401 TCCAAGGTTC CCACATTTTT CTGTTTTCTT AAAGATCCCA TTATCTGGTT
              silencer (common site)
131451 GTAACTGAAG CTCAATGGAA CATGAGCAAT ATTTCCCAGT CTTCTCTCCC
131501 ATCCAACAGT CCTGATGGAT TAGCAGAACA GGCAGAAAAC ACATTGTTAC
131551 CCAGAATTAA AAACTAATAT TTGCTCTCCA TTCAATCCAA AATGGACCTA
131601 TTGAAACTAA AATCTAACCC AATCCCATTA AATGATTTCT ATGGTGTCAA
131651 AGGTCAAACT TCTGAAGGGA ACCTGTGGGT GGGTCACAAT TCAGACTATA
                                     Ovalbumin exon L
131701 TATTCCCCAG GGCTCAGCCA GTGTCTGTAC ATACAGCTAG AAAGCTGTAT
131751 TGCCTTTAGC AGTCAAGCTC GAAAGGTAAG CAACTCTCTG GAATTACCTT
131801 CTCTCTATAT TAGCTCTTAC TTGCACCTAA ACTTTAAAAA ATTAACAATT
131851 ATTGTGCTAT GTGTTGTATC TTTAAGGGTG AAGTACCTGC GTGATACCCC
131901 CTATAAAAAC TTCTCACCTG TGTATGCATT CTGCACTATT TTATTATGTG
131951 TAAAAGCTTT GTGTTTGTTT TCAGGAGGCT TATTCTTTGT GCTTAAAATA
132001 TGTTTTTAAT TTCAGAACAT CTTATCCTGT CGTTCACTAT CTGATATGCT
132051 TTGCAGTTTG CTTGATTAAC TTCTAGCCCT ACAGAGTGCA CAGAGAGCAA
132101 AATCATGGTG TTCAGTGAAT TCTGGGGAGT TATTTTAATG TGAAAATTCT
132151 CTAGAAGTTT AATTCCTGCA AAGTGCAGCT GCTGATCACT ACACAAGATA
132201 AAAATGTGGG GGGTGCATAA ACGTATATTC TTACAATAAT AGATACATGT
132251 GAACTTATAT ACAGAAAAGA AAATGAGAAA AATGTGTGTG TGTATACTCA
132301 CACACGTGGT CAGTAAAAAC TTTTGAGGGG TTTAATACAG AAAATCCAAT
132351 CCTGAGGCCC CAGCACTCAG TACGCATATA AAGGGCTGGG CTCTGAAGGA
132401 CTTCTGACTT TCACAGATTA TATAAATCTC AGGAAAGCAA CTAGATTCAT
132451 GCTGGCTCCA AAAGCTGTGC TTTATATAAG CACACTGGCT ATACAATAGT
132501 TGTACAGTTC AGCTCTTTAT AATAGAAACA GACAGAACAA GTATAAATCT
132551 TCTATTGGTC TATGTCATGA ACAAGAATTC ATTCAGTGGC TCTGTTTTAT
132601 AGTAAACATT GCTATTTTAT CATGTCTGCA TTTCTCTTCT GTCTGAATGT
132651 CACCACTAAA ATTTAACTCC ACAGAAAGTT TATACTACAG TACACATGCA
132701 TATCTTTGAG CAAAGCAAAC CATACCTGAA AGTGCAATAG AGCAGAATAT
132751 GAATTACATG CGTGTCTTTC TCCTAGACTA CATGACCCCA TATAAATTAC
132801 ATTCCTTATC TATTCTGCCA TCACCAAAAC AAAGGTAAAA ATACTTTTGA
132851 AGATCTACTC ATAGCAAGTA GTGTGCAACA AACAGATATT TCTCTACATT
132901 TATTTTTAGG GAATAAAAAT AAGAAATAAA ATAGTCAGCA AGCCTCTGCT
132951 TTCTCATATA TCTGTCCAAA CCTAAAGTTT ACTGAAATTT GCTCTTTGAA
133001 TTTCCAGTTT TGCAAGCCTA TCAGATTGTG TTTTAATCAG AGGTACTGAA
133051 AAGTATCAAT GAATTCTAGC TTTCACTGAA CAAAAATATG TAGAGGCAAC
133101 TGGCTTCTGG GACAGTTTGC TACCCAAAAG ACAACTGAAT GCAAATACAT
133151 AAATAGATTT ATGAATATGG TTTTGAACAT GCACATGAGA GGTGGATATA
133201 GCAACAGACA CATTACCACA GAATTACTTT AAAACTACTT GTTAACATTT
133251 AATTGCCTAA AAACTGCTCG TAATTTACTG TTGTAGCCTA CCATAGAGTA
133301 CCCTGCATGG TACTATGTAC AGCATTCCAT CCTTACATTT TCACTGTTCT
                                Ovalbumin exon 1
133351 GCTGTTTGCT CTAGACAACT CAGAGTTCAC CATGGGCTCC ATCGGTGCAG
```

*Fig. 1-51*

133401 CAAGCATGGA ATTTTGTTTT GATGTATTCA AGGAGCTCAA AGTCCACCAT
133451 GCCAATGAGA ACATCTTCTA CTGCCCCATT GCCATCATGT CAGCTCTAGC
133501 CATGGTATAC CTGGGTGCAA AAGACAGCAC CAGGACACAA ATAAATAAGG
133551 TGAGCCTACA GTTAAAGATT AAAACCTTTG CCCTGCTCAA TGGAGCCACA
133601 GCACTTAATT GTATGATAAT GTCCCTTGGA AACTGCATAG CTCAGAGGCT
133651 GAAAATCTGA AACCAGAGTT ATCTAAAAGT GTGGCCACCT CCAACTCCCA
133701 GAGTGTTACC CAAATGCACT AGCTAGAAAT CTTGAAACTG GATTGCATAA
133751 CTTCTTTTTG TCATAACCAT TATTTCAGCT ACTATTATTT TCAATTACAG

Ovalbumin exon 2

133801 GTTGTTCACT TTGATAAACT TCCAGGATTC GGAGACAGTA TTGAAGCTCA
133851 GGTACAGAAA TAATTTCACC TCCTTCTCTA TGTCCCTTTC CTCTGAGAAG
133901 CAAAATACAG CAGATGAAGC AATCTCTTAA CTGTTCCAAG CCCTCTCTGA
133951 TGAGCAGCTA GTGCTCTGCA TCCAGCAGTT GGGAGAACAC TGTTCATAAG
134001 AACAGAGAAA AAGAAGGAAG TAACAGGGGA TTCAGAACAA ACAGAAGATA
134051 AAACTCAGGA CAAAAATACC GTGTGAATGA GGAAACTTGT GGATATTTGT
134101 ACGCTTAAGC AAGACAGCTA GATGATTCTG GATAAATGGG TCTGGTTGGA
134151 AAAGAAGGAA AGCCTGGCTG ATCTGCTGGA GCTAGATTAT TGCAGCAGGT
134201 AGGCAGGAGT TCCCTAGAGA AAAGTATGAG GGAATTACAG AAGAAAAACA
134251 GCACAAAATT GTAAATATTG GAAAAGGACC ACATCAGTGT AGTTACTAGC
134301 AGTAAGACAG ACAGGATGAA AAATAGTTTT GTAAACAGAA GTATCTAACT
134351 ACTTTACTCT GTTCATACAC TACGTAAAAC CTACTAAGTA ATAAAACTAG

Ovalbumin exon 3

134401 AATAACAACA TCTTTCTTTC TCTTTGTATT CAGTGTGGCA CATCTGTAAA
134451 CGTTCACTCT TCACTTAGAG ACATCCTCAA CCAAATCACC AAACCAAATG
134501 ATGTTTATTC GTTCAGCCTT GCCAGTAGAC TTTATGCTGA AGAGAGATAC
134551 CCAATCCTGC CAGTAAGTTG CTCTAAAATC TGATCTGAGT GTATTTCCAT
134601 GCCAAAGCTC TACCATTCTG TAATGCAAAA ACAGTCAGAG TTCCACATGT
134651 TTCACTAAGA AAATTTCTTT TTCTCTTGTT TTTACAAATG AAAGAGAGGA
134701 CAAATAACAT TTCTCTATCA CCGACCTGAA ACTCTACAGT CTTCAGAGAA
134751 TGAATGGCTT GCTAAAAGAA TGTCAAATCT TACTATACAG CTATTTCATA
134801 TTACACTACT AAATACACTA TAAGGCATAG CATGTAGTAA TACAGTGTAA
134851 AATAGCTTTT TACACTACTA TATTATTAAT ATCTGTTAAT TCCAGTCTTG
134901 CATTTCACAT TTGCAAAACG TTTTGAAATT CGTATCTGAA AGCTGAATAC

Ovalbumin exon 4

134951 TCTTGCTTTA CAGGAATACT TGCAGTGTGT GAAGGAACTG TATAGAGGAG
135001 GCTTGGAACC TATCAACTTT CAAACAGCTG CAGATCAAGC CAGAGAGCTC
135051 ATCAATTCCT GGGTAGAAAG TCAGACAAAT GGTAAGGTAG AACATGCTTT
135101 GTACATAGTG AGAGTTGGTT CACCCTAATA CTGAGAACCT GGATATAGCT
135151 CAGCCAGCGT GCTTTGCGTT CAAGCTTACC AGAGCTGTTG TATGCCTGTT
135201 AAGCAGGGCA TACAGTCATG AGGCTCTTGA AAAATCTTAA CAGACAAAGG
135251 GCAATGGAAA ATCGGAGTTA AGGGATGGTA GGGATAAAAT GCATAGAAAG
135301 AGGTACCACA ATTTTGATTT TTGCCCTAAT GCCTCTCTGC GTGGTTCCTC
135351 AATTTTTCTA CTTCATTCCT CATCTCCTCA GAGCATTCCT TTCCCTCATG
135401 CTTGAAACAC AGATGAAAGA CTGTGAATTC TAACTGAGAT GAAAACATCC
135451 ACAACCACAC AACCTCTGGT GTGGAGTCAC ATTCTGTGAA GGCAAAAACT
135501 AGGCCACGTA ATCTATGTGT GCAAGCTACG TGTAAGCTAT GTGTGTGACA
135551 GGACAATGTG AGGAACATAC TATGTGCACA AGGACTGCAG AATAAACAGG
135601 AGCAAAGTTT TTGAAGAAAA CAGAGTAAAA TCCTGTTTTC CTCTTTTGTT
135651 ACATTCTTTA CATATATCTC AAATTTCCTC TTTGGTTAGA AGCAAGTAAT
135701 ATTTATGTTT CTTGGTACTG TTTGGGTTGA AGACCATTCT GGGATAAGAG
135751 AAATTCCAGT GGTTCTTCCC CTAATCATAA AATGTACAGG TTTAGTTTTT
135801 TTGTAACACA GAAATCTCTT CATCTTTTAT CTTTTGTTGT GATTCTTTAT
135851 AGAGAGAGAA ACAAGACTTA CTGACAATAG CAGCAAGAAA ATCAATCTTG
135901 GAAGAACAAG ATTGCAGTTG CAAAAACAAA CCAATGTCCT TGCCCCTACA

*Fig. 1-52*

```
135951 TCCTCTTCCC CATAAATTCT ACATTCTCTA TCTACCTTGT GCTTGCCAAC
136001 ATGATATACG TAAACTCTCT TTTCGTATTC ATTCTTAAAG GAATTATCAG
                          Ovalbumin exon 5
136051 AAATGTCCTT CAGCCAAGCT CCGTGGATTC TCAAACTGCA ATGGTTCTGG
136101 TTAATGCCAT TGTCTTCAAA GGACTGTGGG AGAAAGCATT TAAGGATGAA
136151 GACACACAAG CAATGCCTTT CAGAGTGACT GAGGTATATG GGCATACCTT
136201 AGAGATGTAA TCTAGAATTT ATGAAGAGAG TAGACATGTT GTTATATGAA
136251 CACTGCATTA GCGTATCTGC TCATTTGTCT GCATCTCTTT CAGACACTGT
136301 GTTAAAAGCA GGGAATTTTC CTTATGTCTC TCTCATCACA ATATTCCTGA
136351 CATTGCAAAG CTCCTGAGAA ATAACTTCAG ATTCCCACTT TTCCTAGGAA
136401 GGTCTTCCTG GATGAGAACA ATCAATCATC TTAACTGTAA CTAGATATTT
136451 CTGCATCTAA GAATAATCTT TGTTAAAACT ATATTCTCTC TCTCTTTTTT
                                          Ovalbumin exon 6
136501 TTTTTTTTTT GGTTCTCCAG CAAGAAAGCA AACCTGTGCA GATGATGTAC
136551 CAGATTGGTT TATTTAGAGT GGCATCAATG GCTTCTGAGA AAATGAAGAT
136601 CCTGGAGCTT CCATTTGCCA GTGGGACAAT GAGCATGTTG GTGCTGTTGC
136651 CTGATGAAGT CTCAGGCCTT GAGCAGGTAT GGCCCTAGAA GTTGGCTTCA
136701 GAATATTAAA AACACATGGA AATTTAGCTG TTGTAAAGCT CTTTTCAACA
136751 CAGTTATCCT AAAACATTTA ACCAGCACAA ATTTCATCAT GATTCAATAT
136801 GTGATTGTTG CATAGAAGTG TAGATTTGTC CCACTGGGTC CTGCAATAGC
136851 CCATGCTGAG CATGGCTTGC TGAAAGAACT GCTTTAGAGG GTGAAAAGTT
136901 TGACACAGCA GACAAGATGA TTCTCACCTA AGCAGCTGTT ACTGTAGTGG
136951 CTTGAACTCT AAAGGTCTTG TATCTCCATT CCTGTGCACT GAGGAGCTTC
137001 TTGGAAAGTT CATATAAGGT TTACTAGTTC TAACTATTAT CTCATTTGGT
137051 GGCACTCAAT GTGCTTTGTT CACGTCTTCA TAAATTAATC TATCTAAAAA
137101 TTGGATGTGG TTAAAGCAAT TTCAGAAATA ACATGTACAT AATGTACAAT
137151 TATTGATATG AACAGAACAC AGGCATAGCA TATTGTAATT AGGAGGACTG
137201 TAGTTATTTT GAATAGGAAA CACAATGTAA TAAATGAGAA TTCATTGAAA
137251 TGTTAGTATG CTAACTCAAT CTAAATTATA AAGATAAAGA GGCATTTAAT
137301 CACAGCTAGA TTTCCATCAC TTGTGACAGA CAGGCATATG AATGATTATG
137351 TACAGCTCTA GGAAAAAAAG TATGTAGGAA AACTAGTACA TTTTGATTAG
137401 AAAGTCTGAA AATGAGGTGC CTTGATCAAA GAGAATACGT GTGTTTGAGA
137451 AAAAAAAAGT TTGGATAGAG GTGGTAAGAG AGAATATATT GAAATGGTGT
137501 TTCTACAAAC TGCCATGGCC AGATTTGTGT AAGAGACATT CAGTAAGTAG
137551 GCAAGGAAAG AAATATTACT AGGTACAAAG CAACATTAGT AATACCAAAA
137601 GAAACCAATT ATTCCAGATG CCAATCTCGT AATAGGGTTA AGAGATTTCC
137651 ACCCCTCTAG TAGTCACCAG TGCAACCAGT AACTTTGCTA ATTTACATTT
137701 TCTTTTTTTA AATGGCAGAT ATAGCTTTGA ACTGAGTGAT CATGAACTGG
137751 TACTGTGTAA ATAAGATGGA AGCATACTTG GGAGCTAAAC TTCTAGTTTT
137801 TAAAAACTCA AATTCTCTTG AAAGATCAGT TCCCAGTCTA GTAACAGCTG
137851 ATAGTTTAAG TATCAGTAAT TGGCTACCAT TAACAACTGG CTCCTGAGAG
137901 GTCTTAAATG TAGAGACAGC TTTAAACTCA AAAGCACAGA GTGATTTTTA
137951 GAATAGATTT CCCAAGCAAA GAAAATAAAC AGGGAGGAGC TTTAAGGGAG
138001 TAGCCATCTC ATTATTATTA TTATTTAAAG AAATGGCAGC AAGGCTATAA
138051 AAGAAAAATA AGACAGAGCA GAGAAGAAAG AGTCATGGTA TGCTTTTCTA
138101 TCTTAGCAAA ATTAATCTCT ACATGCCTAG GAAAAAGCCA TGACAAGAGC
138151 AATCAGTTCA AAAGGTGTAT GCAAAAAAAC ACATAATAGT AACTAGTACT
138201 GCATTGCCAG GAAGGAAGTT ATGTCGCCAT TCCATGGATC TCATTCTCAT
                                    Ovalbumin exon 7
138251 TTCCTTGCAG CTTGAGAGTA TAATCAACTT TGAAAAACTG ACTGAATGGA
138301 CCAGTTCTAA TGTTATGGAA GAGAGGAAGA TCAAAGTGTA CTTACCTCGC
138351 ATGAAGATGG AGGAAAAATA CAACCTCACA TCTGTCTTAA TGGCTATGGG
138401 CATTACTGAC GTGTTTAGCT CTTCAGCCAA TCTGTCTGGC ATCTCCTCAG
138451 CAGAGAGCCT GAAGATATCT CAAGCTGTCC ATGCAGCACA TGCAGAAATC
```

*Fig. 1-53*

138501 AATGAAGCAG GCAGAGAGGT GGTAGGGTCA GCAGAGGCTG GAGTGGATGC
138551 TGCAAGCGTC TCTGAAGAAT TTAGGGCTGA CCATCCATTC CTCTTCTGTA
138601 TCAAGCACAT CGCAACCAAC GCCGTTCTCT TCTTTGGCAG ATGTGTTTCC
138651 CCTTAAAAAG AAGAAAGCTG AAAAACTCTG TCCCTTCCAA CAAGACCCAG
138701 AGCACTGTAG TATCAGGGGT AAAATGAAAA GTATGTTATC TGCTGCATCC
138751 AGACTTCATA AAAGCTGGAG CTTAATCTAG AAAAAAAATC AGAAAGAAAT
138801 TACACTGTGA GAACAGGTGC AATTCACTTT TCCTTTACAC AGAGTAATAC
138851 TGGTAACTCA TGGATGAAGG CTTAAGGGAA TGAAATTGGA CTCACAGTAC
138901 TGAGTCATCA CACTGAAAAA TGCAACCTGA TACATCAGCA GAAGGTTTAT
138951 GGGGGAAAAA TGCAGCCTTC CAATTAAGCC AGATATCTGT ATGACCAAGC
139001 TGCTCCAGAA TTAGTCACTC AAAATCTCTC AGATTAAATT ATCAACTGTC
139051 ACCAACCATT CCTATGCTGA CAAGGCAATT GCTTGTTCTC TGTGTTCCTG
139101 ATACTACAAG GCTCTTCCTG ACTTCCTAAA GATGCATTAT AAAAATCTTA
139151 TAATTCACAT TTCTCCCTAA ACTTTGACTC AATCATGGTA TGTTGGCAAA
139201 TATGGTATAT TACTATTCAA ATTGTTTTCC TTGTACCCAT ATGTAATGGG
139251 TCTTGTGAAT GTGCTCTTTT GTTCCTTTAA TCATAATAAA AACATGTTTA
139301 AGCAAACACT TTTCACTTGT AGTATTTGAA GTACAGCAAG GTTGTGTAGC
139351 AGGGAAAGAA TGACATGCAG AGGAATAAGT ATGGACACAC AGGCTAGCAG
139401 CGACTGTAGA ACAAGTACTA ATGGGTGAGA AGTTGAACAA GAGTCCCCTA
139451 CAGCAACTTA ATCTAATAAG CTAGTGGTCT ACATCAGCTA AAAGAGCATA
139501 GTGAGGGATG AAATTGGTTC TCCTTTCTAA GCATCACCTG GGACAACTCA
139551 TCTGGAGCAG TGTGTCCAAT CTGCCGCTGC CCTGATCCTG GCTGGGGTGA
139601 TGGGACAGAC CTTGGCTGCC ACTGAGACAT CTGAGACACT GAGATCTGTC
139651 TCAACTCAGA TTTACCCAAG AACAGATCAT TGCCAACAGA ACAAAATCTC
139701 AAACTTATGG CTAGTGATGA CAGCAGTCAG TTGTCCCATC TGTGACCCAC
139751 CAAGGCTGGC ATGCTGGAAT GAGCAGGCTT TGGTGGCTTG TAGTTACTGG
139801 ACAGCACCAC TGACATGGGC AGGGGAAAAA CTGAGCATGG TGTAAATCAC
139851 TGCCTCAAAG CCACTTCTCT GTGCCTGCAC CATGCTTGAA AGCTCTTCTA
139901 CAGGAGCTGG GTTTGTTCAA GAAAGCTTCT GTTTCTCCCA TCTGCTTCTT
139951 GTACCTTCAC AGGGACAGAG TTAGAAGGGT ACAGCCATGG CTGGAAGGGG
140001 CTGACTTTCA AATGTGCCTA ATTTTCCTTT GGTTGCTGCT GCAGCTGCAG
140051 AAGAAGGGGT TCAGAAGCCA AGAGCTTTGA GATAAGGATG CCTAACCTAT
140101 GTTGAAGACA TTTGTGCTGA CACCTCAGGC CCCAGGATAG GACAACTGCT
140151 GGATTGTGGC TAACCCACTA GCTACAGAAC CTAATTTATA TTACCAGATT
140201 AGGAAGAGCA AAAGAACATG TATTTATAAC AGGAGGTCTT CTGTGCTTCT
140251 CTACTAAAAG GTGCTGTGAA GGAGCCCACA GTGCAGCAGT GTATGAGGCC
140301 TGAAAGAGGC CGCAGCACAC GAAGAGCCCT GGTAGGAGCA GCACACAGAG
140351 GGGCAGGAGG GCTGGGGGAA CTGCCACCCA TGGGGACCTG TGTGAAGCAG
140401 TGCACTCCTG AGGGGTGGAC TGCGTGGGAA AGGAAAAGAA AGCAAACAGA
140451 CCTGTGATGA ACTGTCACAC AGACTGCAGA GTGACAGAGG AGGGCTTGAG
140501 GCAGTGCGCT TACTGCAGGG AGTGGCGCTC CTTCCTCACA GCAGCGCTAA
140551 CAGCTTGGCA CCAATATTCA GTAGTCTGTG GTGATGCTTT TTCCAGTTTC
140601 ACCACACAGC ATTTCGCTTG TTCTACTTGT TTTAGCTTTC CCCCTCCACA
140651 AGATAACACA TACTTTGCCA GTCAGTCCCT AAGACCTTAG CCTAACAGTT
140701 AGCAAACAGG ATCTTGCAAA AGAAGGAAGA TAACATGACA CCACCTTCAC
140751 TGGTGTATAA ATAGTTCAAA TACTTTCCTT CACTTTCCCG TAAATTAGTT
140801 GATTGCAGGT CAGGAGATAA CAGGGGAACT TACTGCAAGA GAGAAAATGA
140851 TGTTTAATAT TGTCTTGGAC TTTCTGGTGG TCTGGGCATG AAAATGGAGT
140901 ACTCAAAATC CTCAGGACGT TTATTTTTCA CCTGATTTAT TCCCAAACTG
140951 CACTATTTCT AGGCCATTGG AGTTCTTATC AATTAAATTA TACTTTGGCT
141001 CTCTGCTATC TCACTCCCTT TCATCTTCAG CATCACTTTC AGCACAATTA
141051 CAGGAGAAGA CTTAGACTCA GAGCTTTAGG ACTCATCATA AGAGGCTTTC
141101 ATTGCTCTGT CACCACACCC CATATAGATC TGTAGTATAC CACACATGTG
141151 AAGAAGCACA GTACATTAGT GCATTACAGA GAGACAAAAC CACACCTATT

*Fig. 1-54*

```
141201 TGTGTGCCTG CAGTCTTACA CCAGCAGGAA GATAATTAAC GTAATGAATT
141251 TCTATAAAAA TGAGAGAATA TGGCCCCTGG GTCCTACTGC TTGTTCTAGT
141301 CCTGATTCTT CAAACGTAAG AATGCAAGTA AAATTACTCA CTTGAACAAA
141351 GTCAGCAATT TGCAAGAACT GATATTCTGA AGTTCAAGTA ATTAGAGTGA
141401 TTTCCAGTAC TTCTGGCTGG AACGGGCAGC TGAAAATCAC CTGGTCCAGC
141451 ACCTTGCTCA AAGCAGGACT ATCTTCAAAG CCATATCAGA TAGCTCCAGA
141501 CCTTCCCTAG TCAAGTGTTG CCTATCTGCA TGGTTGGAGA ACCCACAGCC
141551 TTCTGATTAA TTTGATTTTA AACATAAATT CAAATGTCAC TAGCGTAGCA
141601 GTAGTGAAAG CCATTCAACT GGCTTTACTT TCTCTTACCA AATGAGAGTT
141651 AGCTGCAGGT GAAAATAAGC CCTGCCAGTT CTCATTTTTT CTCCCACAGC
141701 CCACAAAGCT CTCACTGTCT GTCCTCACTT GTAATACTTT TGAACCAACA
141751 TCTACAGATT ATCTCTGTAA ATCCCAAGCA GTACCTAGTC ACCACGTGAA
141801 CAACAAATTC CTACATTTAA CAATATTTAA GAGCAAAGGC CAGACCATAT
141851 GTAGCTGCAC ACTACACATT TTTAGACCCA ATAGTATAAT TTATACTTTG
141901 ACTCCATGTT GCTGCCATGT GGATAACAAT GCGCAATCAT TTGTACCTGG
141951 CTTCCTTTTC TAACTAGTAT ACTCTTAAAC GTCACAAGAT AAAGACTCTA
142001 GTTCTGTATA GTCTAGCTGA CTTGTGACAA GAGCAAACAC TCACAATTTC
142051 ATGGTACTCC TGAGGAAAAA AAGGATCCCA AACTAATTTT GAGCTTTTAC
142101 ATATTTTTTT TTAACCTACA GAGCACCTTG CTACTTCTGC TGAATGTTAG
142151 CAATAGCAAC CCACAGTCTG AAATCAATGC AATGAACTTC TACTATGGGT
142201 ACCATACTGA TGACAGGAAT AGTGCAAGTC CTTACACTGG AAGGCTGACT
142251 CCTTAGTCAC ATAGGTAAAA TTTAGAAATT GCAGCTCTGA TAAGAGATCA
142301 GTATGGGAAA GGGAAAATAA TGGGGTGCCA GATGAGTGCA CCTTCCTGAA
142351 AGGAAGGCAG ATATATGGGA ATTAAAGGTG GACAAGGGAT GCTGTGGAGG
142401 TACCATCAAC TTTCACAGGG CTGTATGTAA AAGCAGCTCT CTTTCCTGTT
142451 GATTCTCCGC TGCCTCATTT CTTCTGGGCA AAGTTTGTTA CTCTCCAGTA
142501 ACGTCCCTTC CTCAAACTGT TACCTAATCC CACCCTCATT GCCTTCTCTG
142551 TTTTGCTCTG TCCTTCAGCA GTCTCTACCT GCTTCTTAAG GTAGTGAAGT
142601 AAGAGGGCAG TTCTGGAGTC AAGCTCTGTT TCTATGAGGG TAAAGGCCAG
142651 GGAGAGAAAG GTTTGGGAGT GTGAGGAGAG CCTTTTTCCT GTGTTGTTCA
142701 AGTACTTAGT CCAAGCTGCT TTCAGCTGCA TCTGCAGAAG ATGGGGAATG
142751 GAGGGTGATC AATGCCATTC CTCCAGCCAC AGAGCAAGGG CTTTGCCTCT
142801 CCTTGCATAC AGTATACTAG CTTTCCTTAG TCAAATGTTT CCTCTGTGCT
142851 GCAGAGTCCA AGGTAAAGAG GCTTTGTCTA CAGCTAGGTC TATGTTCCTA
142901 GAGAAACAAT TAGCAACTGC AAAATCAAGA GGTACTAAGA AAGCCTCTGA
142951 AGCTATACCC AGGGGTCTGG CAAATGAAGG GGGACAGATC AAGAAGAAAG
143001 AAGAGTCTAG AGCAGTTTAA GGGAATAATG CCACTAGTTT TAAGCCACAC
143051 ATCTGGTGGT AAGCTTTTAA CTTTGAAAGA GACAGAAATC TCAAGATACA
143101 CCAGCCCAAA ATATAATGGA GCCATAAAGG TCTGCACGTA GCTGAATCCC
143151 AACTGGAAAG AACAGCTTCA AAGAGCTTGG AAGTGCTGAG GTGAAGAAGA
143201 GCATGTGATC ATTAGATTTC AAAAGAAGGT CCTCAGCACA ATAACCAGAA
143251 AGTTCACCTT TCTGTGGGAC AAAAGATGCG TCCCTCACAA AGGCTGGGGG
143301 AACAAAATCT TTGCATCTCA TTTTGCCTGA GAGGAGAAGG AAATACAAGA
143351 TCATCTTGTT TTACTTGGTG TGTATCACAT CATTAATTTC TATTTGGTCA
143401 CTACTATGCA GAACTTGCTA ACTTGAACCA TGTAAAAAGC ACACTAGGTC
143451 TCAAGAGACT AAAATGCTTC TTGCAACAGG CAGAGTGTGA GAGATGGAAG
143501 GATGGAAAAA TCTTGCAGTG ATGAAGGCAC TGATAAGAGA TGTTGAAATG
143551 ATACTAACAA ATGGCACTCT ATCTTTCCCA AGATCTTTGT CAGCATGAAG
143601 GGAAAATTCT ATTCCAAGCT CTCTTTGAGG GGTTACCATG TTCCAGGATA
143651 AAGACTTGCT GCATACACAA GCGCACTTAG TCAGGTCACT CAGATCAGTC
143701 TCATGCTAAA AAGTGTGAAA ATAGAAATAC AAATAAGGGG CCAAGCAGAT
143751 TACTGAACAG CAAAGATTGC CAGTACGTGT CCACAATGAG TATTTGGACA
143801 TTTCACTGCC GAAACTTCTG AAAATATCAA CTGCCTTATG AAACTCTGGT
143851 TATTCCACCG CACAGGAGTA TTTGTGGTTG AGCTGCATGA AGAAATAGCA
```

Fig. 1-55

143901 AGTGTTTAAA CTGATTTCTT AAAAGAGAGC CTTTCCTCTA CATGCTGCTC
143951 TTGCACATCC ATGCGTGGCT CCTCTTCAGG AGCAGGAATT GGTTTTCTGA
144001 TTCAGCAGTT GTGTAGCTGA CGTAGTTATA CCCTTTGAGA GATTTCTTCA
144051 GAAAAATGAC ATGTTTAGGC TAAAGTGCAT GTAATCCACA CATACACCAT
144101 TACTCACAAT GAAGTACTAT GCAGCATGAA ATTCAGGCTA TTCTTCTTCA
144151 TATTTTTGGT TTTAATTGCT ACCTTGGTTA CTTAAAAAAT GCTCACCATC
144201 TGATTCATGC AAAGGAAAAC TGCACACTGG TAGATGTGAG AACAGCACGC
144251 ATACTCACTT CCAGATAAAC TAATCTCTAC TCAGATATCG AGATCATTGC
144301 TTCTCCAGAA GTGTTGCACT GGTCATCAGA ACTGAGTATC TCAGGAAAAG
144351 CACTGTCTTT TCTAATTACG GCATCTAAGC TAAAGCACAC AGCGGTAATA
144401 GTGCAGTATG ACAAATTATG CCAGTGTTCA ATTCATGTGC CAAATCTCAC
144451 CACGCCTTTG CGTTCTGCAG GTGTGGAGCA AAATGCCTCA GTGATATTTA
144501 GACAGGAACA CCACCACACC TCTTAACAAC TCATAAATTC TAAATGCTAT
144551 TGGAGTATGT CAGCAAAGAT TGCTTGGCAA AGGTTGCAAA TGTACATGTA
144601 ATATGTACGC TTTAGATAGC TATCTACACT GTTTCAAAAT AAAGACGCGT

MAR

144651 GTGTTCTCAC TCAAAGCTTT AAAGGGAAAT AAGATACTCA AAGAAATAAT
144701 CTCTTTTGAA CTTTAAAAGC TATTTGAGAC TTCACGATGA TACAAACTTA
144751 TCCCACATAA AAATCTTAGG ACATAAAATC CATTACAACC ATTCCAGCTG
144801 AGACATATAC ACCATTGTTA CGCTTTAATT TACAAGGTCA GGACAAGCTC
144851 TTGCTGCATT CTGTGACAAA AGGGCTCCTT TGCACACCAA AATCCATGCA
144901 CCCACTCCAA GCACCTGATC ACTGATCACC ATTACCATCA CTTCAGTCTC
144951 CGTGCTCCCA TTCCCCATAC TGTTTTGGCT CTTGCCAATT ACAGGATTGT
145001 TATGAAACTA AATGTTAAGC TGCCCTCCCA CAGGATTCCA ACATTCTCAG
145051 GTTTCAAAAC CATTGTCTTC CCCACCCCTC TTATCTCCTG AAGTCCTTAT
145101 AATGGTTTGG ACATTTAAAG TCCTTTCATG TTTAAAACTT ACTGGCCTGC
145151 TCTGGCTGAG ACAAAAACAC GAGCAGAATG CTCTGTTGGC TGAACCAGAA
145201 ACCATTCCCC CCCAGATAAA TAAACAGCAC TTTTACTGGT AAAAAAAGAT
145251 ATTAGAAGAT GCCAAAGAAA TGGAGTAGCT TTTCTTCAAG CATAATTTTT
145301 TTCTTTTCAA ATACCAAACA CCTTAGGTTT GAATTACATT AGATTTTCAA
145351 GAATTACAAA GGGTTCGTAG TTAAAACAGC ATACGTACAT GAAAACCAGC
145401 CATGGCAAGT TTCACACAAA TACTGTGTGA AAGCAGAAGC TACCAAACCT
145451 TCCTCTCAAA ACCCTCAAGT ACATTTAGAT CACTTTATAA ATGATCTATG
145501 TAGACAGCAA GTATTTAACC TACTCCTGAT CCCAGGTACC AATGAACTGA
145551 GCAACATACT GTGTAGGAAA GTTGCACTGA CTTGTGCTAA GTTGCACGGA
145601 AACTGAAGGA AAACAAAATG TGCTTATATA GCTGAGATCT GGCCAGGGTG
145651 CCTGGTGTGC TGCCAATATT TGTCCTGCCA AAATGGAAAC ATGAATGACC
145701 ACAGTGAATG AACTACAGGC TTACTTCCCA CAGGAAGGAT ACTACCAATA
145751 CAAACATAAG ACTTTGAGCA TGTTGGAGTG TTGACTTAGT AGAGAGTGGG
145801 AGTGAGGGAA CCGCTGCTCC TGAGTCAGCC TCAGCACCGC CCATTGAACT
145851 CTGTACCTCC TAGCCTTGGT AACTTCACAG GATGCTGGAA AATATTATCA
145901 AGTCATCACA TTGATTTATT GAATATCTTC CTTTTAGATT TTAGTTGCTT
145951 TGTATGTATT TTTTTTTCCA CTAATAACCA GCCATGCTAT TCAAAAGGCA
146001 TTTTTAAAAG GCAACGTTAA CACCCTGTAC AAACACCATC CTCTCATTCA
146051 TTCAAATCCC ACATTTCTGC ATATATGGAA CATGTCAGTC ACTTCTTGTA
146101 ACAGAGCAAG TACTATGACT AGTCAGCAAA TTAAATTCAT CCCTGCTTTA
146151 AAAACAGAAA ATCCAAGTAA CTGCTCCAAG GGATGAAGTT TATTTAGTGT
146201 ATCTATCATT TGTTCTACAA CACAGTTAAT TTTGCAAAGA TGACTCAAAT
146251 CATTTAAAGC TTTGGAAATC ATTTAAGGCC AATGTAAACA GATTACAACT
146301 TTCCCAGGCG CAATGGAAGC AATTAATTCT GCAGCACACC TCTCCTACAC
146351 TACTATACTC TGGAAAACGT AACAGATGCA TCTAATTATA ACCCACACTG
146401 AAACATGCTG TCTTTATGTA GCTATGAATT CAAAACAGCT GAGGGGCAGG
146451 AAAGAACCAT CCTCCTAAAG CTATGTGGCT GCTCACCTGT AGGAAAGCAA
146501 CTTCAGCAAA GCTTTGAGTT CCCAGGTTAC ACTGATGCAG AAGCTTCACC

*Fig. 1-56*

146551 ACTGGCAAGG TGCTCCTTGT GTGAGCAACC TATTCTGCTC TATAAAACAT
146601 TTAGCAGATA ATCCCATATC TCAGTCCTCA GTACAAGAGA CTCTGTGCCA
146651 GCCACTTCTG TACGAAATAA GCCCACACGT ACTTTCATAG ACCTCAGGGC
146701 AGAAGAAAAG TTTCAGAAAG CAGTTTGTGC TGAGGAGATA GACCTTGGGG
146751 GTGAGTCTTT CTCCATATTG AGGCGGAATC CCTCAAAGAC AAGCAGCCCT
146801 TATCCAGGTG TTCAAGGTGA TATTTTCAAC AGAGCAGGGA GGTAAAGAAT
146851 GAAATAAAGG GCAGAGTTAC ATAGGATTTT TCAGTCAGAG GTGAGAGCTG
146901 AGATGGACAG GACAATGAGG TAAGGACAGT GTGACTGTGA GGAGAATTAG
146951 CGATGGAAAT GCTTCACTAG CCAAGGCAAG AAGAAAAAGA GTATTCAATA
147001 GAATATCAAT TTCTGGGGAA AGAATTCATC TCTGAAGGGC TACATAGGGC
147051 AAATAGCTGC TTTCAACTTA GAACAGGGAA ACTGAGGCAG CAGCAAAAAA
147101 AAAAAAAAAA GTCTAATCTG AAACCCACAT CAGGTTCTAC TGTTGTTGCA
147151 GTGATAAGAA AAGTGTCTGA TGAGTGTTTC TCAACCTTCG TTATCTCACA
147201 GTGAAAACAT TTTCCTGGTT ATACAGTTTT AGAATCCTCC AATATTACCA
147251 AAAAATCATT TTACTAAAAA TGGAATCCCA CAAGAAATGA CTAATTTTTT
147301 ATCTGTAGGA AACGGACAAT AGAAAAACTC ATAAATATGA TGTCACTGTC
147351 CTTTCGCTGT CTCTTCCTTG GAAATTGTTT CTATTAGAGG AATCATAAGT
147401 AGGTCAGCTA CTGCATTTTT TTACCCTCCA AATTGCAAAA GAAATGTTGT
147451 TTCCAGCAGT GATGGTTCAA GTTGTAACTA GCCTGTTGCC ACAAAAATGT
147501 TTATAGAAAT ATTTCTGCAG TCAGTTTTGT AAGGTTCTTG TATGGTATCA
147551 CTCTCACCGT CACTTCACAT CCTACTCTGA GATGATTCAG TTCTTCCATA
147601 GGGATGTGGC CTTCAGGGCA AAATAAATTG CAGAGTCATG AGTCATAAGA
147651 ACCTTTGAAG AACAGGCCAG GCAGACTATA AATTCAGCCT ACCCATCATC

W gene exon L

147701 TGAACTGCAT AAACCTTGGA CAGACCCAGA GCAGCAGTCT TCCTCCCTGC
147751 ACAAAACAAG GTACTGTAAT TATTTCTAGA GATTATTTAT TTCACCTACT
147801 CTTGGATGAT GTCGATCTGT TGACAAATGC ATAGAAAAAA AAGGCAGAAG
147851 GAATCTGAAT AGAAAACAAT AAATACTTGA GGAAGAAATT TACTAAGATG
147901 GCACAGGCAA GGTCTAGAAG GGGTAAGTCT CAGAAATATG CAGGAAGAGT
147951 GGTTTATTCT ATGTAGTTCT CACTGGCAAA CATGTATATC ATAGCAGAGT
148001 AAGAACCATT GTGTTTGCTT AAGTTAGATC ATTTGTTCAT GTGCTCTTCA
148051 ATTCTTGTGT ACGTCAAGAC ACAGTCAGTA CATCTTTATT TTATGGCTAT
148101 TCTGTATCAA CCAGAATAGC TCCCACTACA TACCTAGGGC TCTCAGCTTC
148151 AACTGCAATG CAAATAACAA AGAGCAGCAC CTGTGTTCTA CCAATAAGGA
148201 AATTTGTCTT GCAGAACTGG GAAGCTATGA TTCGGACTAG CACCATAAGA
148251 CAGAGTTTCC AGAAATTTTT GAAAGTTAAA AATGGAATTC AGGATACTTA
148301 GCACACAGTA GTTAGAGAGC TGCTTGTCTA GTGCTTCAAT ATTTTCTTGT
148351 ATCCTAAAGG AATGGAATAT TTGTTCACTA CAGTTACGAG CTCCAAAAGG
148401 CTCTTGCACC AGTAGTCATA AGAAACAATC TCTCAGCATC TTCTAGCCCT
148451 CGCACCAGTG AGTAGCATTA TCATATGTCA CTCCAAGATG CTGTAAAGGA
148501 CAGTGCAATA AACGTCCTGA TGAACAAATA CAAAATGAAA TATGAGGCTG
148551 CTTTTTCTAT ATCACTTGAG TATGGTTAGT GTTGTTGGTG AAACGGGATG
148601 CACTATACTT AATATAACTT TTTAGTAGCT AATCTTCCTC ATTTTCCATA
148651 AAGATATCTC TCTTCTTTCC ATCTGTAAGT TCCTTACCAT ATCATTATAT
148701 TGCTTACATA GAATTCACCA TATAGTTATA AATTGCATGC TTTTTCTTTT
148751 TAGTATAACA CTGTAACCAT CCTGTTTCGA TGAATTTTCT TTTGTTTCTC
148801 CTGGCTGTCC CTTGCATGGA TATCTGTCTT TCTAAGTGAA CTTCTGCTGA
148851 ACCAAGGAGA GTTCATTCAT GCACTACAAA CAGACGTAGT TGGCAGAAAT
148901 GAATATTGTA CCAGTACTGA CAGGTCAGAA TGCTTTCATT CAGTTTCCTG
148951 AGGTCAGAGG AGAGCTGAAG AAAATACCTG GCACAGTCTA GATTTTGCCT
149001 TTGAACATAC ACTGCCAGTG AGCCTCAGTC ATACAAAGGA TCACTGTGCT
149051 GCACTGGCAT TCTTCCACAG TCAATAAGTG TTAAAAATAC TTTTAGAAAG
149101 CCTACAAATC ATAAAATAAA CTTCAAATAC TGAAAGGGAG CCTGCAGACA
149151 TATAGCAAAC ACAATTAATT CTTAGCTAAT AACATCTTTT GTCCCTTTCT

*Fig. 1-57*

W gene exon 1

```
149201 GCGCAGGTTC AGAACAATGG AAGCTTTAAA TAAAGCAAAC ACAAGCTTTG
149251 CTCTTGACTT TTTCAAACAT GAGTGTCAGG AAGATGACAA CAAGAACATT
149301 TTGTTCTCCC CTCTCAGTAT TTCATCTGCC CTGGCTACTG TGTATCTGGG
149351 AGCCAAAGGC AACACTGCAG ATCAGATGGC AAAGGTGAGT CTGAGAAGAG
149401 TTGATCTACT GGAGTAACAT TCTCTATGAT AGAAATTTAG CATGATGCAT
149451 CAAAGGAAAA CCTTATGCAG GTCAAAAGAT ACAGTCTACA GTAGCTTCTG
149501 TAAGCAGGCC CACACCAAAT GGGAGCAGTG GCATTAGTGA CATTGTCTCC
149551 TTTTAAATGT CATTGGAAGA AAGAAGAGCT CTTAATCCCA AAGCTCAATA
149601 ACTTGAGCAC TCACCAGTGA GAGGGAGACT CGGATTCTCC ACCTGCCTTG
149651 CTCCAGAAAA TTCTCATTTT CTGTCTCATC TCTCTGGAAA TGGCCCTATG
149701 CAGAAAGACC CTCCACTGTA TCTCTAGTAA GTTTTGTGCT TTGCTAACAT
149751 AAATCTACAA ACCCACAAGG TCAGAGAAGA AACACAGTCA GGGTGATAAT
149801 ACAACCCCTT CTTTTGAGTA CGTACTTTAC AAGAAAAATC ACCTACTGAA
149851 GTTCCTAAAC TCTGTGCAAA GTTCATAGCT TCAAAAGGCA GCAATGAGAA
149901 CAGCCCCAGT GCAAACATGG TTACCTAGCA TGTACTGCGG GAGGGGCTGA
149951 TGAACTGGCA TCTGCTAAGG CAGAAGAAGC TGCTCCACCT GCTAAGGCAG
150001 CAATCCAACT ACTGAGCTAC AGGACAAATG AGGACCAGCA GGGTCACAAA
150051 GAAAGGAGAG ATCTTCTGTC AGGAAGAAGG GAAAACAAAA CAAAACAGAA
150101 GGCTTTTGAA AAATGTTCCA AGGTTAGATG TACACCTCTG TAGCCTGGGT
150151 AAGGTGCACA TGCCCAGAGG AAGGCATTTA GGGTATCAAT TTGCTCCCAG
150201 TGTTTACCTG CTTTCTGACA TGTACCAGGC TCTCCATTTT ACACCCATGC
150251 TTTGGCAGTT TCCACCTGCA GATAACTGGC CCGTCCCAGG TATTACCCTA
150301 TGAGTACAAG AGCCGATTTG AAGCAGGCAA GTTCCTCTAG AAATACCAGA
150351 TATATGAGAA TTCTGCTTGC AGCCCTCATC TTAGTGTGCT CAAGACATCC
150401 TGTACACATG GGCTCAAAAG TAAAATCTGT CTTTGTCTCT CTTCATCACC
150451 AGTCCCATGA CATTACTGAA AGTTTTTACT GAAACAGCAA ATTTTCTATC
150501 ATTGCATTTA TTACTGCAAT TTCCACTGCA GGTACTCTAC TTCAACGAAG
150551 CTGAAGGAGC CAGAAACGTC ACCACAACCA TAAGAATGCA AGTCTATTCC
150601 AGAACAGATG AGCGCCTATC AAATCACCGT GCCTGTTTCC AGAAGGTATA
```

CR1-d

```
150651 TAACCAAGTC TAATGATCAT AGAATCATAG AATGGCCTGG GTTGAAAAGG
150701 ACCACAATGA TCATCTAGTT TCAATCCCCC TGCTATGTGC AGGGTCACCA
150751 ACCACTAGAC CAGGCTGTCC AGAGCCACAT CCAGCCTGGC CTTGAATGCC
```

MAR (0.852)

```
150801 TCCAGGGATG GGGCATCCAC AACCTCTTTG GGCAACCTGT TCCAGTGCCT
150851 CATGATCAAG CTACAGTCAT GCTAACACCT TCCCTTGCTT TTATTTTCTC
150901 TCTCTGTTTG CCTTCCTCAA ATGCAGGGTA CACAACTGAT TAGTACAGCA
150951 TCCTGTGATA CCTTCACCTT ATGCAATACT TAAGACATGC TTCCCATTTG
151001 TAGGTAGAAT TGCAAAATTT AACCTCAAAT TTGCAAAATT TGAAATTTAA
151051 TGATGGGACT ATTCTCTATC AGTGGACCTC TTGATCTTCT CCCTTCAGCT
151101 TTGAGATTTC TCTCTTTTTT TTTTCTCTTT CTTTTTTTCC CCTTTCCTCT
151151 TCTTTCTTTC TTCTTTTTCT TTTTCTTTCT TTCTCTCTTT CAATCTTTCA
151201 TTCCTTCATT CTTTTCTTTT TAACTACTAC TGTTCAATTA GTTATTGCTA
151251 GTTATTCAGG AACATGTTCT TTGAACAGGC ACAGTCCCTA TCTCAGAACA
151301 AATCAGAACA ACAAAACTAC TCTCCCACAC ATTGGATTGC AGCATCAACA
151351 CAACAACAAC AACAACAGAA AAAAACAGCC AGAGAAGTAA CTTTTACAGA
151401 CTATCCATGC TTGATACATT TCAGAAATTA GTTTCTATTT CATTTGAAAG
151451 TTTAGTGGAA TAAATTGGCA TGTTGGAATT TCCTAAGGTA GACCTTGCAA
151501 TAAATCTTAA AGAAATGGGA ATTATTGTAT TCCCGAGATA TTTCTTTGAC
151551 AGACTGGCAG GCATCTTTTG TTAAAATAGA CATAATTTAA GAGAGCAGAA
151601 AATTTGGAAG TCAAACTCTG AGTGAGTAAG GTAGTTTTTC CTCACTGACA
151651 ATGCAGCCAC TGTGGTAAAA AGTTCCTCTC CCTACTCTTT CCCATCATTC
151701 TTTTTTCTTT TTGTGAGTAA ATCATTTCCC TGAAGTCTGT CCACAAAACC
```

Fig. 1-58

151751 CCTGTGGCAG CAAGTTTTGA TAAATGGGAA CTTGGGTCTA CATTCCACAG
151801 CTACGGTGGG AAGACTAATT TTGGGGACTA CGCCAACAAA CCATTTATGT
151851 TGCACGAACA GGAGATGGAT TGTTTCTCAT GAGTAATGCT TGTCTGAACT
151901 GTAAGAATTA TGGAGCGCTC TAGGCAGGGA AAAGAAACTG TTCTAATAGC
151951 TTAGAAATTT AGATAGCTGT TCATGCTTCT GATTTTCTTG CAGTAACAAG
152001 ATGAATACAA CACAGGTCCA GTTTCTTAGT CCACTAATTC ACAGCTTCAT
152051 TTCCTTAAGC TGGTTTGACA GTTTGAGTCC ACATTCATAT AATTCTGTTA
152101 CATAAATATA AAGAATTTAC TGCAATTACT ACAACAAAAA GCATTTGCAA
152151 AATATTATTA TTTAGAGGTA GGTTAAAAAA GTTAGAGGCA AACTTACCAT
152201 GTAATTAACT TTCATAAATC TTATCAGGAG TCACACAGCC AGGTCTTCAT
152251 GTATAGTTTA GCAATTACAT TCTGTCTCTC TCTCTGTATG TACTTCATTT
152301 TGCAACCTCC ATTTAAAAGT CCTTAAACAT TCTAAACAGT TCAAGCTTTT
152351 ACTACTTGCA TCCCAGGGCT CTTACAGTGT CTATAGCATA TCTGAAACTT
152401 TTAGTAATTT CACATCATTC TTTTAATATC TGTCTGAGTT AGTACACATC
152451 TTGCATTGCA GTAAAGGCAA CACCACCTGA ATAGCAGTAG TTTACATAGA
152501 GCTGCATGAG GAAAGAATTT AGAAATTTTG AACTGTTTTA CAGAAAAAAA

W gene exon 2

152551 AAAAATGTAT AACCCTTATT TCCTTGTCTC CAAGACAGAA ATAGGCAAAT
152601 CAGGTAATAT CCATGCTGGG TTTAAAGCAC TCAACTTGGA AATCAACCAA
152651 CCCACTAAAA GTTACTTGCT TAGAAGCGTC AACCAGTTAT ATGGAGAAAA
152701 GTCACTGCCT TTCAGTAAGG TAGGTAGGCC ATTTATTCAT GTTATCCTGT
152751 GTGTGTCAGA CTTTATGATC TATCTATGAC AACAAACCAT AAATTATATG
152801 CTTTCAAATA TTTTCATTAC ATCTGCAAAT TGTGTAATTA TCTTTAACAT
152851 ACTTCCTGTG AGGTTCTTCT TGAGAATTTA GATATCATGA CTTTTATAGG
152901 ATGTATATTT AATTTGTGTG ATTCACAGTT GTGGCTACGC AAAAACATTT
152951 AAATTATGTA TTTCCAAATA AAATCAATAC TATGTTCTTT TGACAATGCT
153001 GTGCTTGTAG CCTACACAAT TTTTATGCAT TCTCTCCAAT CGGCTATAGT
153051 TATTTATTGG CATTCACACT GGCAGGCAAC AAACATAAGA CAGATGTCTA

W gene exon 3

153101 TCTTGCACTG CAGGAATACT TACAGTTAAC CAAGAAATAC TACAGTGCAG
153151 AACCACAATC AGTTGACTTT GTGGGAGCAG CAAATGCAAT CAGAAGAGAG
153201 ATCAATTCCA CGGTTGAACA CCAGACTGAA GGTAAGCTCT AGCATCTCCT
153251 CTCCCAGTTC TGAAGGAAGC AGTTTTAGTC TTGAACAATT TCTCTGTGCC
153301 CAAAGGCAGG TAAACAATTT AACTCAGAAA GGAAAATCAG AACAGTTTTG
153351 CTGAAGTAAT CATCTGCTGG CAAGCCCTTT CTAGAATTAT CTTTCACCAT
153401 TTGAAAGGGA GAGGAATGTG GTTTCCTCTA TAAATCAAGG TTGTCATGTA
153451 TTTATGAATA ATCTCAAGCT AGAAGTATGC CAAATCAGCA CTCTAAATTT
153501 CCTTGTCTTA TGACTTCAGA AACTACGCCA GCATTTACTC TGAAACAGTA
153551 AAGCTGCACA AATATGTAAA CGTTCTTTGT TTTTCTCTAG GTAAAATAAA

W gene exon 4

153601 AAGTCTGCTG CCTCCTGGAT CCATAGATTC ACTCACCAGG CTAGTCCTGG
153651 TAAATGCGCT CTATTTCAAA GGAAACTGGG CAACAAAGTT TGATGCTGAA
153701 GATACCAGGC AAAGGCCTTT CAGAATAAAT ACGGTATGGT AACATACTGC
153751 CTTATATACC AGACTGCAGG TTGAAAAAGC AGTGAAAAAG ATGGAGGAGA
153801 TAAATTCCTG TCATTCTTTA AAGCCACATA GCACTAAAAT TAGTATATTT
153851 AAAACATACG TTATATCCTT CTTAGCACAT CTTCAGTACA AAGACCGCAT
153901 ACATATGCTA GCACCCAAGG CACAAATAAA ATTATCAGAA GCCAGCTTGA
153951 AACAAACTTC CATACACCTC TTAAAGCAGG AAAAACATAG ATGTGAATAG
154001 AACTGTATGA ACTAGTTCTA TATATTTTCA TTTTTAACCA TACAATGAAT
154051 TGGAGTGGAA CAGAGCTTCC AGTAAATACG TGTCATCCTA GCTGGCTAAG
154101 ATAACCTTCC CAGCCTCCCA GTGCATTCCC AGAAGAGAGG GGCCCTCTGT
154151 AGATCCTACA GCTTCTCTTA GAGCCACAGG GATGTACCTC CATGCTACTT
154201 CAATGTAGTC TTTACTGTTC TGAGTATAAA TAGCAAGCTT TTCATTTGAT

*Fig. 1-59*

```
                                   W gene exon 5
154251 TTGTTGCAGC ATACAACTAA ACCAGTGCCA ATAATGCACC TGAGTGATAA
154301 ATTTAATTGG ACCTACATAG AATCAGCCCA GATTGATGTT CTTGAGCTTC
154351 CATATGTCAA TAATGAACTC AGTATGTTCA TCCTGCTACC ACGGGATATC
154401 ACTGGCCTAC AAAAGGTAAA GGGTAACTTT AAACTCAAAT TGCGTGAGAA
154451 ACAACGTTTT CATGCATATC CATGGCAAAG CAATCCTGTT TCTAGGAAGG
154501 AAGGTATCGA TAAGGCTAAA GGAAAAACAA ACCCCAAACT TGCCCAAATG
154551 TTATGAAGCT GAACCTTTTC AATGTTTTGT TTGGTTTTCT TTTTAACTCC
154601 TGGCACGTGG CACCTCGTGC TTCCTCATGT TGATCAGTGC TGGAAATAAG
154651 TAGCCCGAAT CCAACAAGAT AGATCTAATT CCAGCTGAAG AACAACGAGG
154701 ACAGAAAGAT AGTTCTGCTG ACTGTCTGTA CTGATTCGGA CAGATATTAT
154751 TACATTAAAA AGAAAAGCAC AAACTGGACA CCCTCCACTA CTTTCTGTGA
154801 TGTTTAGAGC TAATATACAT GTACACTGCC ACCTTCTGTA AACACACTGA
154851 ACCTGACTTC AGATAGTGAA CTACTGTGAA ATTCTCATTT ACATTAGTGG
154901 GTGTTTTGTA GAAAAAAAAA AAAAAAGTTA TTTTCACTAA ATTCTAAGAC
154951 ACACAGAAAA CAGAAATGTG AGCAGCAAGT CAAATAGACT ATTGTTACTT
155001 GACAGTGACG TTGTTTTACA AATATTTAAT CCCTCTATAT TCCCTGATGA
155051 TTACTAAGAA CAGTTCAAAT ACTGCACTAA CATGCTGTAG AGCAAAACAC
155101 TCCTTCCTAG TAGAAAATAT TTCAGAGTTG GCATTTCACT AATGGTTTCT
155151 GTACTTGAAA AGTACAATTT TTTTGCTAC AAAAAAAAGC TACAGAATTT
155201 TTGTAGTTTG AAAAGTTCTT AAATAAGAAT ATAAAAGAAA TAACCCCTAG
155251 GGAACAGTTT TTTGAACACT CTGTAATTTT CTGGTTCTCT TTTCAATTAA
                             W gene exon 6
155301 CTGCAGCTAA TAAATGAATT GACTTTCGAA AAATTGTCTG CATGGACCAG
155351 TCCAGAATTA ATGGAGAAAA TGAAAATGGA AGTGTATCTG CCCAGGTTCA
155401 CAGTAGAAGA GAAATACGAC CTGAAATCTA CTTTGAGCAA GATGGGAATA
155451 GAAGACGCTT TCACTGAAGG TCAAGCTGAT TTCAGGGGAA TGTCAGAGAA
155501 CGCTGACCTG TTTTTGTCAC AGGTTTTTCA CAAGTGTTAT GTGGAAGTCA
155551 ATGAAGAAGG CACAGAGGCA GCGGCTGCCA GTTCAGCATC TCTAGCGTCA
155601 CGAACCCTTG GTGCTACAGT TATTTTTGTA GCAGATCACC CTTTTCTCTT
155651 CATTATCAGA CACAACAAGA CCAAGTGCAT CCTTTTCTTG GGAAGGTTCT
155701 GCTCCCCCTA GAAAATCAGC TATTAATAAA CAAGCCCTTA CAACAACGAT
155751 GAACACAATG TATGCCATGA AGAACACCTT GACAGACTTT GCACTTTACC
155801 ATTTTCCTGT ACTATTGACA ATCTCTTTTA GAAGAGAGCT CAAATTAAAA
155851 ACATGAATTC AAACCTCTGA TTCCTTTTCC TCTGCAAAGA ATCCTAGCAT
155901 CGTATACTGC ACTGTAGAAC ACTGAACTGC ACGCTGAACA ACATGGATGT
155951 GTCTTTTCAG TGCTGTCCAA ACCAGAACTG CTACAATGCA GAACAGACTA
156001 GGCTGATCTA AACAGTACCT TCTGACCCAG TTCCTTTCAC ACGTAAGAAG
156051 AAAAGAAACA GGAGAAACTC ATTCCTGCAT ACAGCTGTTT CATCTCTTCA
156101 AAGCCAGCTG TCCCAGGCCA GCTCAATCAC AGCCTTGTCA GTTTTAAATC
156151 AGCTTCACAA CATAGCATGG CTGGTAATGA AACAAAAGTG CAAAATCCTC
156201 TGTGTTGCTG ATACTGGTGG TTTGCTCTTG CACACAAAGG AGCTAACACA
156251 TGTACTTTCT AATCTCTGTC CCTCATAAAC TAGCAAATAC CAAACAATAC
156301 AGAACCAGAG TAAAGTAAAA TACATACCTT GAAATGCTTT CTTTTGTCAT
156351 AACCTTTAAT TCATTCAACG CTGTTGCAGC CCAGCACTGC ACTGCTTTAC
156401 TTGCCTTTTA CTTTGCCACA TATTTTGCTG CTTGGAGCAA GTGGGAGAAT
156451 AAAGTCTGTT ATGTTAACTC CCTAAGTGCT GTCTAAAAGA TTACATGCAA
156501 ATTCTCCTCT ACATATTCAC TGCTTTCACA GCTTTTACTC CTAAAGGGGA
156551 GGAATTCCTA ATCAGTCATG CACATCTAAG AACACAGGTG ATGCTCCTGT
156601 TTCTCTGAAT TCAGAACAGG GAGGAAAGGA CTGGGTCTCT TAACAGCACT
                                             MAR-like element
156651 TGCACACACA CTGACAGCAT CTCACTAGAA ACATCCCTTC CCAGAAAGGT
156701 AGGATACCTT TTTCCTGGCA GAGGGAAGAG CGCTGACTGA TAGTGAGTCC
156751 TTTCTGTATT ATTCCACGTG ACCAACTGTG GCCAGGCTCC CTTTTGGCTC
```

*Fig. 1-60*

156801 TGCTTCCCAA ATGGGAAGGA ACGTAGGGAA GGGCCAATGG CAACCAAATT
156851 AGAGGGTGAG TCTTGCATTG AGGAACACCA TTTTCCCACC GTAAGTAGCA
156901 CAGCACTGGG GCAGACTGCC CAGAAAAAAA TTGAGGATTT CCCATTCTTC
156951 AAAGGGCTGT AGCTGACCTA ATTTACCAGT GGGTCTGCTC CAGGCATGAG
157001 CTGGACTATG GAAATACCCA TAAACCAGCT TGTGTCTTGT TTCTATCAAC
157051 ATCCATTCTA CCTTACCACC TCAATTTCTC ATCCTCTCTG GCACCCTTAC

MAR-like element

157101 AGCTTGACAA GCAGGGGCAG TTAGCTTGCT TGCTTGCTCT CAAGCATATT
157151 TCTTTGAGAC TTGGAATCTC CCTAGCTTGT ACTTTCCCAT CAATCAATCA
157201 CTCAGTGGAC CTTTCTTCTA CCCTGATTTT TTGACAACTC CTCTCATTGT
157251 ACTAAAGTCA CCACTTGTTT AGTTTCTGGC ATTTCTTCAT TGCCTTGCAT
157301 AATACTGATT TCTATAACTT TTCAGAAGAC TTGACCCGCT CTGTTCTTGT
157351 AATCAAGCTT ACAGCAAAAT GCTTGGCACA CCATACAGTT TCCTTCCCTT
157401 CCTCCTCCTT CCTTCCCTGT CCCCTAGACT CTTACAGATA TTGCCACTAC
157451 CTTCCCCTTC TCTTACCACC AAAGAGCTGC TCTGCTGTCT TCTGGGACAG
157501 CAGAGTGACA ACTATTGTGA CATATTTATC CCTGTTGTAT TGTTTTCACT
157551 CCCTCCTTGC TCAAGCTCTG CCAGTGGGGC CGTTTCAGTT CTTGCCCACC
157601 TCCATGGCAT GCAAGTACTG CACACTAACT CAGTACTCTG CAGTGCTTCT
157651 CTGAAGCGTT TCCCAGCCAT GGATGCAATG AGATTCTTTC ACCAACACAA
157701 GAAGCAAGGT ATTCAACCTT ACACCTTCAA TGGCTTTGCC TCTGCCTATG
157751 CTCCTAATGA TCTTCACTCT GAAGCTTGAC TCTCAGAGTC TCATTCAGTC
157801 AGTAAGCTCC TGACATTTTA TGCTGATGCA TCTTACTCAT AGAATCATAG
157851 AATGGCTTGG GTTAGAAGAT CATCTAGTCC CAAGCCTCCT GCCAACCACT
157901 AAATCAGGCA CTACATCAGG CTGCCCAGGG CCCCATCCAG CCTGGCCTCG
157951 AACATCTCCA GATCTCCAGG GATGGGGCAT CCACAGCTTC TCTGGGGAGA
158001 GGTTCCAGCA CTTCACCACC TTCTCAGTGA AAACTTTCCT CAACATCTAA
158051 TCTAACTCTA CCTTATTTTA GTTTTAAAAC ATTCCCCCTT AACCTATCAC
158101 TACCTTCCCA TGTGAAAAGT TGATTTCCCT CCTTACTTAC AAGCTTCTTC
158151 TAGGTACTTG AAGGCTGCTA TCAGGTCTCC CCTGATCCTT CACTTCTTCA
158201 GACTGAGCAA GCCAAGCTTC CTCAGCCGAT CTTCAGAGAA GAGGTCTTCC
158251 AGTTCTCTAA CCATCTTCAT GGCCCTGCTC TGGACTTGTT CCAAAGGTCC
158301 ACATCTTTCC TGTGCTGGGT GCCTCAGACC TGGACACAGT ACTCCAGATG
158351 GGGCCTCATT TGGGCAGAAC AGAGGGGGGA CAATCACCTC CCTCTCCCTG
158401 CTGGTCACCC TTCTTTTGAT GCAGCCCGGG ATATTGTTGG CCTTTCAGGC
158451 TTCAAGAGCA CGCTGCTGGC TCATGTTAAG TTCTTCATCT GCCAGGATCC
158501 CTAAGTCCTT CTCAGTAGGG CTACTCTCGA TGAATTCTTA TCCTAGTATG
158551 GATACATATC TGGGATTGTC TCAACACAAG TGCAACACCT AGCACTTGGC
158601 CTTGTTGAAC CTCATTATGT TCACATGGAC CCAATCCTCA AGCCTGCCCA
158651 GGTCGCTATT AAAAAAAACA AGTGTCATGG CTTCACAAGG CTGGAAAGTT
158701 GGATCAGGCC TACAATACCT GCTAACATCC AGAAACCAAA ACCATGCATT
158751 CTGGCTCTGT AATCATTTTA CTAGATTTAT TTAGTTTAAA CAACAGGCCA
158801 GTTGTCTTCA CAACAACAGA AGATCACTGA AATGAGTGAG TGACTTGTTT
158851 TACTGTCCTC TCAGTAGACA ATTGTGGTGT AACAGTTAAA ATGAGATTAT
158901 GATCCACATT GTTCCTTTGA AACGCCTAAA ACTAAAACAT AACATGATGA
158951 ACAAGGAAGA CAAAACTGTA TGAGATCTTT TTGTGATTCA TTAGAAGCTT
159001 TGAGTAGGCG GGAACAGTGT TGACATAGGA GAGAAGGAAA AGGAAGTGCA
159051 AACTGTACTA TATTTCTAAA TTTATTCACT GCATAACACA CAGGCACAGA

MENT exon L

159101 ACCTGACTGA GGACAAGACT CAGGTCTTCT CTCTCACGGG ACCACAGGTA
159151 AACATTTAAA CCAATTTAAA TAACTTTTTT GATGTTTTTA AATGGTTATC
159201 TATAGCTTGT ATGACAATGT AAGTATATTA AAACACACCA GAGTTATTCT
159251 GTAGTCGGGA GCATAATTGA TCACAAGAAG GAAAATCTTG TCAGGACAGT
159301 AGCTGTCTTA CTAATTAAAA TGTTCAGTTT GATAAAGGAG TCTCATACTT
159351 CAGGTAAAGC AAAGGCCATT TTCATTCTGC CTTGTATGAG GTCAGGCCAG

Fig. 1-61

159401 GGACTCAGAG GAGCAGAGTA AAACAGACAG ATTTCTATCC TGATGCTCAT
159451 TTGGTCAGGT TCTCCAAGGA GAGGAAGTCA CTCTGTTGGT ACAGATTTGG
159501 TGTAGACTGG ATAACGACTG CCAGAAAAAC TGAAGTGGTT TGGTAACCAA
159551 AATCTTGATA AATATCTGTG GACTTCAGAG ATTGTCCTGC AATTTCTGCA
159601 GTGCCATTCA ATAAATATAA ATCTTTCTTT ACATAATAAT AACTACTACA
159651 ACAACAACAT TTTCCAGTCC CTCTATCAGA AAACAACATC AAGAAGGCAC
159701 TACTGAACAG GTAAGTTAAA GTTTGGAATG CTCATAGCTT ATATGCATAG
159751 GTATTTGCCA GTTTCTGGGG AAAATAAAAT TGCAAGAATA TAAAGAAGAG
159801 ATTGTAGTTA GACTTCGTGA ATAAAATGGT AACACTCTAA AAGCAAATAA
159851 CAACTTTGCC ATACATTATA TTATCTGAAA TGGGTGACTA GCCAGAAAAA
159901 TTCCATAAGC CTAAGAGTTA CACCTAAATA CATTCTCAGT ATCAGCTCCT
159951 AATTCTATCT AGATCCAAAA TGAGGTAGTG AAAAGTTCAA ATGTCCCATG
160001 TACAAAAAAC TACTTAAACT TCCCTAGGAA CATTACTTTG ATAATGAGTT
160051 AAGAATGAAA ATGAACAAAA TATGCAGCTT ACAAATCCAC ACACTTTTGA
160101 AAACCAAAGG CAGAAAGAAA CACAAATAAA AGGGCAGATC TATAAAAGAG
160151 GACATATCTA TAATCATAGA GAAATATGAG ATGGATAACA AAAACCTAAA
160201 AGAAACTGCT GCTCCCAGCA GGTGGCACAT GGTATGTGTA GAACATATAA
160251 CGTACAACTA GGCTATTAGT TTCAAAAGGT ACCTACGTGC TCCGTTGCAA
160301 ATGTAACATG TAAATGTAAA ATGTAAATGC AAATGTAACT AATATGCACT
160351 ACATACATCA TTTTAGACAC TCAAATACTA CAATTCTGTC TGTTGCCTCT

MENT exon 1

160401 TTCCAGGCTG TAGCAATGGA ACAGGTCTCG GCATCAATTG GCAACTTTAC
160451 AGTTGATCTT TTCAACAAGC TGAATGAGAC CAACAGGGAC AAAAACATTT
160501 TCTTTTCCCC TTGGAGCATA TCATCTGCTC TCGCCCTGAC ATATCTGGCT
160551 GCAAAAGGCA GTACAGCAAG AGAGATGGCA GAGGTAAGTA GCTCTGTGAA
160601 GCTATGATGC TCAACACTGC CCAGCACTGC TGTTGAGATG CCCTGCTCCG
160651 TTGTCATAGG GAAAAACTAC ATTTGAGTTT GCACAAATGC ATTGCTATTG
160701 CTGAGTGCAA TGGCTGTGGA AGGGATTTCA GCCTTGTAGT GCACAGACAG
160751 AAGCACTGTG ATGATGCTCA CAGGCAGGAG CAATACTATT CCTTGTTACT
160801 GTAGGGGATT TACATATACT AGAGCTCCAG TGTCCCTCTG ATTAGATCAG
160851 AAGATAGCAC AGTGTGTTAT CATAAGGATC CAAACAAGAC AACCATTTTA
160901 TCTCTTTTAG GTTTTAGGTC ATGCAAACTC TTTCATGTCA GTTTCTTACC

MENT exon 2

160951 TTTGGAAACC CTGTTTGCAG GTTCTTCATT TCACTGAAGC TGTGCGAGCT
161001 GAAAGCTCTT CTGTGGCCAG ACCTTCTCGG GGGAGACCAA AAAGAAGAAG
161051 AATGGTATCT ATTAAACATG AAATCCCAAG ATAAGAGTTC AAATGTCTGG
161101 ATATAGTTTT TAAGAGTCCA CCATTTCTTG TTTGCAGCTC TCTTTATGTT
161151 TAAAGTATAA AACCCAATAT ACTTCGCATC ACATCCAATT TCAGTTCCCT
161201 TCACTCATTC AGACTCAAAA GTATAGAAGC ACAAGTCACT GGTATAATCT
161251 GAAAGGATTG CAATATGGTA AATCAGTTAA TCAAATCATA AAAGGAGCCC
161301 TGCAAACTGC AGTGGTGGTG AATTTGGAAA GATAAAAAGT AAGAGAGAGG
161351 AACAGAAATT CTTCCCCCAC ATCTACCCCT TAGCGTTTCA AAAACTTCAT
161401 GCCAAAAATG CAACTGGTAA ATGTACAGTT TCTCTTTCCA AGGACCCTGA

MENT exon 3

161451 GCATGAGCAA GCTGAAAACA TCCACTCTGG ATTCAAAGAG CTCCTGACAG
161501 CCTTCAACAA ACCCAGAAAC AACTACTCGC TGAGAAGTGC CAACCGTATC
161551 TATGTGGAAA AAACCTACGC ATTGCTGCCT GTAAGTTGAA TGGTTTTATG
161601 TCAAAGAAGA AAAAGAAAAA AAAAGAAAAG AAAAGAAAAG AAAAAAAGAA
161651 AAAAAAGTTT TGCATTGTAT TCACTTACCA TTAATAGAAC AGATCTGAAG
161701 CTGTCCATAA ATGCTGCAAA TGATGAGTCT TGGCTTCCAG TGATAAACTT
161751 CATTGGAAAA TACAATTTGG TCTTCTCCCA GTATATAAGA ATGCACTTGG
161801 CTGTAATGCA GGACTCCTTT TCATGTAATA CAGCTTTATC ACTAGGAACC
161851 TCAGTACATA CAATTGAAAA TGAGATATTA AAATACACAT ATCCAGGGGA
161901 TTTGCACAGT CTTCCTTCCT TCTCCAAATA AAAATGGGAA CGAGAGAATA

*Fig. 1-62*

```
161951 AGAGTATTTC CTTTGGTTAT TTCCTAACCA TTAACTCACT GCTCAATAGA
162001 GAGCAAAATG CTAGATCCTG CAATTGCCTG TGTGCAAAAA GTTAACAAGA
162051 AGTCCAGTAG CTAACAAATT ACTTTTTGGA CTATAAAAAT ACTGTACAAT
162101 ACAGAATGTT TCCTTCTTTC GTTCTTTTTG TATGCCATTT TCCAGACATA
                     MENT exon 4
162151 TCTACAGCTC AGTAAGAAAT ACTATAAGGC AGAGCCACAG AAGGTTAACT
162201 TTAAGACAGC ACCGGAACAA TCCAGAAAGG AAATCAACAC CTGGGTGGAA
162251 AAACAAACCG AGAGTAAGTT GAGCTCAACT CCAACATCCT TCCTCTTCCC
162301 ACTGTTCCCT TCGGGACCCT GTTCCCACTC CTGTGACTGT GGCATCCAGG
162351 TCATGCCCTC TGGTGTGGGC AGTAGATGGC TGTCTGCTTC CAGCTGCTTG
162401 CCTTGAGACT GTGGCGTTTT TTCAGGCAGG AGCCAATTGC TGTCAGCTAG
162451 CCAGGAGAAC TGGGCAACAA ACAGCAAACA GACTAACTGG TTTATGTCAG
162501 GGAAGTAATC CAGGGAGTAG GGCACTGAGG CTTGCACTTT TTCACTAAGG
162551 AGTTGAACTG AGTGGATAAA GAATCAACAC ATTCCCTCAC TGTGTTACAC
                                          MENT exon 5
162601 TGGAGTAAAG CCTGACTTTT CTGATTTCAA AAGGTAAAAT AAAGAATTTG
162651 CTGAGTTCGG ATGATGTGAA AGCCACCACT AGGTTGATCT TGGTCAATGC
162701 CATTTACTTC AAGGCAGAAT GGGAAGTGAA ATTTCAGGCA GAAAAAACAT
162751 CTATACAACC CTTCCGACTG AGCAAGGTAA GCTCCTCTGG TGTCCTCCTT
162801 AAAACAAGCA GACTGGAGAC TGCACCCACT ACCATCTTTT ATTTCATCCA
162851 TCCTTTAGGC ATTCCTTGGT AAACAGACTC TCTGAAAAGT TGTTTACAGC
162901 AAAACATGTC AGTTGTCAGC TCACCAACAT TTATGGAACA TTAAGATGCT
162951 GCTCAGGCAA AGGATAACTA GATCCAGATG GAACACAGTT TCCAAAAATG
163001 CTAGGGTCAA TTAAAGCCTT TTTGCAAGAC TGAGGTATAA GAGCTACATT
163051 GTAAAAATCA GATATTAAGA GTCCATCCTT CCTGCACAGG AACTACATGC
163101 TATGCTATGG ACGAGTGCAG TACCCGCGCC TCTGTGCTGC ACAATCCGGC
163151 TGTGAATACA GCTGCTAAAG TATGGATGCA GCAGCACAGC TCCACTGGAT
163201 GGGTGCATGG CCGAGTGAGA CTAGAAGTAA TGTTGCCAGA GAGGAGATCA
163251 CAAAAAGGCT GCACAACATT TATCCTCTCA CACCATAGCT GTTTCATTGC
163301 TGTAATGTTG GGTGCCTGTA TGCCATGAAT GCTCCATCCC CCTAATTCTT
163351 GAAGATATTT CTGACTCCCT TCCTCTCTCC TCTGTGGGTT GATGTGCATG
163401 TTCTGGGGAA AAGAGAACAT CAGTTAGCTC AGTCCCCAGC AAAATACTCT
163451 GGGAAAAGAG CCAAGATCAG CAATATTGTC CAGTCAAGAA AAGCCTTGGA
163501 AAAAGAATGT CAAATCTCTG TTACAAAAGC TGCTTATGAA AGTTTCCTCT
163551 TTACAAGGAA TTCCTTTTTT CAAGGAATAA TTTTAACCGA TAAATAAATA
                                MENT exon 6
163601 CCTTACAGAA CAAGTCCAAG CCCGTGAAGA TGATGTATAT GAGAGATACA
163651 TTTCCAGTTC TTATCATGGA AAAAATGAAC TTCAAAATGA TTGAGCTTCC
                                   MAR
163701 ATACGTGAAA CGTGAACTCA GTATGTTCAT CCTACTTCCT GACGACATCA
163751 AAGATGGTAC TACGGGTCTT GAGCAGGTAA AAAGTTCTGC TACATCCATT
163801 CTGTATCGCC ACTCAGTCAT CAGAACAAAA AGGACAGGCT GATGACCATA
163851 CGGCCCTTTC TTTCTTTGGC AGTTCATTCG GCAGAAGTAG CGCACAAAAA
163901 CTTGCAGCAT TATGTCTCAC ATTTGCTTTG CAGCCTGTTC TCTGGTCATC
163951 AGTAAAAGCA ATTTATATTT CATATTTTCA GCTGAATGTT AAATACGCCA
164001 TTTAAAAATC TGTTTAAATC ATTAAAAAAA AAAAGACAAT CATAATTAAT
164051 TGGTTTATCC TTGCAATTAT CAAATTCCTC TCATTTCTTA AACAACAGCT
                     MENT exon 7
164101 GGAAAGAGAA CTCACCTACG AGAGGCTGTC AGAATGGGCT GATTCAAAGA
164151 TGATGACAGA AACTCTTGTG GATCTGCACC TGCCTAAGTT CTCACTGGAG
164201 GACAGAATTG ACCTCCGTGA TACTCTGAGA AACATGGGAA TGACAACTGC
164251 CTTCACAACC AATGCTGATT TCAGAGGGAT GACTGATAAG AAGGATTTGG
164301 CTATTTCCAA AGTCATTCAC CAGTCTTTTG TTGCAGTTGA TGAGAAAGGC
164351 ACTGAGGCAG CTGCTGCTAC AGCTGTAATT ATATCATTCA CAACTTCAGT
```

*Fig. 1-63*

```
164401 TATCAATCAT GTTCTGAAAT TTAAGGTTGA TCACCCTTTC CACTTCTTCA
164451 TCAGACATAA CAAATCCAAA ACAATCCTGT TTTTTGGCAG ATTCTGCTGC
164501 CCAGTAGAAT AAATTATTCC TCACTCCTAG AGGGATCCAA AGTTCACTTT
164551 TCAAAGGAAA AAATGTGAAC TGTAGTATTA AAAGCTCAGC CTTCAATCAT
164601 ATAGCCATAA GTACTGGAAG TCTATGTCTT TTTCCTTAAG TAAGGCAGCA
164651 CCCAGACACC ACCACGCGCC TCGAAGACTG TCTCTCTACT GCTCCTTTCC
164701 ATTATGCTCA TGAAATTGCC TTTTATAGAA AGCAAATGCT TGAGGTACAA
164751 TTGCTAGCCT CTGTTCACCT TGCGTTTTGT CCTTATTTCT CTAAACTCTC
164801 AAGACTGAGG TTGATAAGTA TCCCAACCAG CAAAAAAGAC CAAGAAAACT
164851 ACAACAATGT GCCTTATTGC TACCTCTTAC TGAAATGTGA CCTAAACAAT
164901 TCAAATCTGC TTCCCGTTTT CATTAACATA ATTATATGTT TCCTGGCTAA
164951 CATCTGCACG GTCTCCTTGC TACCTGGATC ATTGATAAGT GTATGATTTG
165001 TAACTTACGA GTGCCTTTCA GCTAAGATAG TCCCGGTATT GACAGAAACA
165051 CCAGTAACAT TTTTATGGAT GCTTCACTTC ATTATTTTGC CATGATCTAC
165101 ATTTAAACAA TAAATGAATT TGGAACTGTG TTTATGCTAT GCAAGATTCT
165151 GACTCACGTA GCTCTTTTAC AGCATCCTGT ATAATGGGTG GCTGACACAT
165201 ATTTCCATTC TTGTTATTTC AAACCAACCA TCACATCACC GCTAACGACA
165251 AAGTGCTGAG GCACTCTAAT AAACCAGGGT CTTACTCCCA CTAGATTTCA
165301 TACAACACTG AAAACACTGT CGTTCAACGT GTTATCGTAG ACATATACTA
165351 GACACACCAA TTCAAATCAA AGCCTGTGAT AACAGAGTTA AGGCATTTGC
165401 CCAGTCTTGT TCAACAGCTT CACCAATAGT CTAGATAAAG GGATAGAGTG
165451 AATCCTCAAC AAGTTTGCTG ACAATATGAA GCTGGGAGGA GTGGTTGATA
165501 CACCAGAAGG CTGTGCTGCC ACTCACTGAG ACCCAGACAG GTTGTAGAGT
165551 TGGGTGGATA GAAACCCAAT GAGCTTCTAC AAGAACAAGC ATAGGGTGCT
165601 GCAGCTGGGG AGGAATAACT GCATGCATCA CTACAGATCA GAGGCTAGCC
165651 TGCTGGAAAA AAACCTCTGA AGAGAATAAG CTGGGTGTCT TGGTAGACAA
165701 CAGATTGGCC ATGAGCCAAC AGTGTGCCCA TGTGGCCCAG GTGGCCAATG
165751 GTATCCTGGG GTGAATTAAT AAGAGCGTGG CCAGCAAGTT GAGAGAGGTG
165801 ATTCTCCCCA TCTACTCTGC ACTGGTGAGG CCACATCTGG AGTACTATGT
165851 CCAGTTCTGG GCTCCTCAGT TAAAGGAAGA CAGGGAACTG CTGAGGAGAG
165901 TCCAGTGGAG GACTGCCAAG TTGATTAGGG ACCTGGAGCA TCTCCCATAC
165951 AAAGAAAGGT TGAGAGACCG CAGACTATTC AGCTCAGAGA AGAAAAGACT
166001 GAGGGGTGGA TCTCATCATT GTTTATAAAT ATCTAAAGTA CAGGAGTCAA
166051 ATGAATGGAC CCAGACTGTT TTCAGTGGTG TGCAGCACAA GGGGGCAATG
166101 GCTAAAAACT GCAGTGCAGA ACGTTCTATA CAAACATGAG GAAGTACTTC
166151 TTTATTTTGA GAGTGACAGA GCACTGGAAC AGGCAGCCCA GAGAGGTTGT
166201 GGAGTCTCCT TCTCTAGAGA TATTTAAGAT CTGCCTGGAT GCTTTCCTGT
166251 GCAACCTGCC GTAGGGAACT GCTTTAGCAG GGGTTGGACT GGATGATCTC
166301 CAAGAGGTCC CTTCCAACTT CTATGATTCT GTGATCTGAA CTTGCTTTCA
166351 CTGTAAGCAT TCAGTTTCCC ATTGTTGACC ACTGCTTATT GCACTATCAG
166401 CGCCCCATGG ACCTACTGAG AAAGCTCATT TTCTTCTGCA TTATGATACA
166451 CAAGAAATAA AAGTCTGACC AGAGCAAATA GCCCAGAAGA GTGGCTTCCA
166501 AACATCCAAT GCTGTATCAG CAACATCCAT TTCTTCCATT AGCTTAGGAG
166551 GGCAGTAGCT GTGCTATCTT ATGCCTATAA GGAATTGGAT AAAGTTTTGT
166601 AGCCATTATG ATGCCCACCT ACCACACGTC ACAGGACATT ATTTCAAGCA
166651 ACAAGATCTG AATGCTGGAG GGAAGTACTT TAGAAATATA TACTCCTAGC
166701 AAAATTCCAC CTGTAACTAC AGCTCACTCT ATGCCTCAAC AAAAGGTAGA
166751 CTATTTGGAA ATATATCTCC ACCCAACAAA GTATATATAC GCCGCCTTCT
166801 CTGTACACTG TGCTGCTTCT AAACTCAGTG CCCTCCCTCA CCTGTAACCC
166851 CCAGCTCAGG GTTCAGCTGT CTGTCACTGA GGACCCACTT TGGTTCAGCC
166901 CAGCTGCATG CTACTGACTC AGCTTTGCAA AGAATTGCAC ATTGTAAATT
166951 GTATAAGTGT GGAAAAGCAC ACAAGTGAAA ACTACACAAT ATAAGTAAAG
167001 TAAAAACACA AAGAAGTTAC TGTCAGGATG GAATAGTCAG CATAGCAAGG
167051 ACTCGAGAGG ATTGCACGTA GGGGTGTCAA ACTTCAATTA AAAAAAAGTT
```

*Fig. 1-64*

167101 AAGAATTGGA ATTCTCCAGC TTGTTCAGGT CCTTCTGAAT GGCAGCAAAA
167151 CCCTCTGGTG TATCATCCAC CCCTCCAAAT TTTGTATTGT CTGCAAATTT
167201 GGTGAAGGTG AACTCTATCT CAGCATCCTG GTCATTAATG AATGTGTAAA
167251 TAGTACTGAC ACTGGTGTTA ACCGCTGGAG TACACCACTA GTGACTTCAC
167301 CTTCAGCTGG ACTTCATACC ACTGATCACA GCTCTCTGGG CCTGGCTGGG
167351 CTCACTTATC TAACCCATCG TTTGTCAGCC TGGCCATAAG GATATCACAG
167401 GAAAAAGTGT TAAATGCTGT TTCTAAAGTT AAGGCAAACA ACATTTAGTA
167451 TTCTCCCCTC ATCAAAGAGA CTAGCTGCCT CATGGTAGAA GGCAATCAGG
167501 CTGGCTAAGC ATGACTTCCC CTTCATATAT CAATCCTGAC TACTCTCAAT
167551 CTCCTTCTTA CTCTTCATGA GTTTCACAGT AGTGTCCAAC TCTGTGGTAG
167601 CCTGACCTCG CAGCAAGCAG AAATGGCAGA GAGAGTACAG AATAATAAAG
167651 ACAAGGAATG TTACAGTGCT GGTGTATTTT TAGTACTCAA GGCTTGGATG
167701 CAGAAAAAAA CCAGCAACAA AACAACCTAT TTTAGAACTA AAATGCAAAT
167751 GTACCAATAT TTTTTAAGGT TTTTATTTCA CCATCAGTAA CTGGAACAAG
167801 AAAATCCCTT TTAAAATATT ATTTATACTC CAGTCACTTA CAGGTCTATT
167851 GCAACCACTG TGATACTTAT TCTCCTTTCC TCTCTTGTAG GACAAGGCTG
167901 AATGGGACTT CCCACGGAGT AAAAAACTGT AACTGGACTT AATCTAGCAG
167951 TGATTTTAAA TTGTGCTGCT TGTTAACCAG GCATAAATGC CTAGATGTAC
168001 CAAACTATAG AGTAAACTGA TCACAGGTAT AGGAGTACAA CAGCAGAATA
168051 GAAAGATACA GCCTCACATC CACACTGAGA AAGGTGAGGA TGAAAGATGA
168101 ATTCATGAGA AAGCCCGAGA AAAGTGACTT GCTTTATCAG AAAAATTTTA
168151 TGACCATTTG TCAGAGAGCA ACCTATTTGT GGCCAGCAGG GGTTTTGATG
168201 CTGCAACACA TTGTTTCTAC CATTCTGTTT GCAGTAAGCC ACTCTTTCCT
168251 CTTCTCCACG TGGCACAGCA AAACCAAGAG CACCTTTTCT TTCCCATGTT
168301 TTCTCCCCTT TGAAACTCTA CTCCCTCTTA CTAAACAGGA TCTTGCAGCA
168351 GATACCATAG AGTGTCCACA CAGTTTGGGC ACCCTTTTGT AATTTTCCTG
168401 TATTTTTGCC CAATCTTTGT AGTTTGTAGT ACAGTAATTA TTGCTATTAA
168451 CTGCTTTCTT ACCTCTCCTA AATATTCAGC CCAACAGGTA ACAGCAGTTT
168501 CAGATATGTA GCAGGAACAT TTCTTAACCA CATAACTAAA CATAATAGCA
168551 TTCGATAGAT TTCTGAAGAA AGAAAATGAG ATTGATATTC CAGGTAGGAA
168601 AAATGTGCAC ACTTAGAGAG AGAGCATGTG AAAAAAGATA GGTATACATG
168651 TCACTCCTGA AACCTTGTCC TGTGTATGTA TCAGTCACAT TCAAAGTGAA
168701 TAGCACCATA AAAATTTAGT TCTAGTTCTA GATATGGTTT TGTACTCCTC
168751 ATACAAATGC TTTTGCACAT AGGTTGACTG CATGCTGATA ACTGGTTTAC
168801 TTTCCAGTGT CATAACTGTG AGCAGAGGGC ACTCCTAAGG CAATTCTGAG
168851 TAACCAAACA TGTACTAGAA AATATATACA ATGATTGCAA AGGAAACTGA
168901 TCAATGCATT TCATCCAAGC CACGCAGATA AAAACTGGAA TTGCTAATTA
168951 CATTGGTTAA AATAAAATGC CTGTGTACAG ATAACTGTCT TGCATTATAT
169001 CTTTACTGAT CTGATTCCAT ATAACATGCT ACTTCGACTC TCTACTACAA
169051 AACAACAAGC AGTTTCAGTA AATCAAATAA TTACAAGCAG AACTTCCAAG
169101 CAGCTTGGCA GCTTTTCGTG AGTGGCCCAA ACTCCCTCCC TTCATAGAAG
169151 ATAATAAGCT TGGCACAGTG CAGGGCCTGT AGGTTATCTA AAGCATCTTC
169201 ACCTCCTCTG CTAGGAGGAA ATGCATTCTC TTAAAGCACC ACCCACCAGT
169251 TCGAATAAGT ACCATGCTCA CGTAGACTTC ATCACTTGCT TTAGGTGACT
169301 GTGGGAATAC AGTCTGAGTC TCCTTGAGGA TCTGACTGCT GAGACATAAA
169351 AGGATTAAGG GTAAAATATC ACAACATAAG GGCTTTGTGT GACCTGACAA
169401 CCACAAGTAT TCAAATCTTT CCACTCTGAA ATTTGACAGC AGGATGAATG
169451 ACACTAACAG CCTACTTCTG TACTCCTTTT CAGCTAAATC TTTGAGATTA
169501 GTTTCTCTTA ATTCCCTAGT TCATAGAGTA AAAAGAAAAG GAAACTGTAA
169551 AATTATTTCA ACGTGTCCCT TGTCAATGCA CTGCAACTCT ATTCTTTTCT
169601 GCAATTCCTA CATACTTGCA GACAAAGATT GAGGAGGGCA CCACTGGGAA
169651 AAAGGCATAC CAGGCTTCAT GTTTCAGGAC ACACACCAAC TAACAGTGGT
169701 TTTGAATTGG CCTCTCTACC CTCATCTCTC TAATTCTGAA AGCCAGTGAC
169751 GGAGAGAAGA AATGGGAATA AATGAGGGAA CAGGCATATT AATACAAGAA

*Fig. 1-65*

169801 GAGGATGTTG GGAAGAGAAG GGAGGTGCAA CCATTTCTAC ATTTCCAAAA
169851 GTATTCGTTG CCTCACAGAC CGCCACAGAT CCTGACTGAA GAAACATCTT
169901 AACTCTTCCC TCTCTCACAG GATTTCAGGT AGTGTAAATA TTCTTATCTA
169951 AATAACCAGC TTTATTTGA CAGTCTTAAA AATTCATATA AATTTTCCAG
170001 AATGGAGAGG GTAAATGGTA ACTTAAATGT CATGCAGGGA AATGGAGCAC
170051 TCAAGTCTTC ATACAAACTG CAGCCTTTAG GAAAACACTG CACAAAGGGC
170101 ACAGTGTTCA GGATGCACAT CCAGACTGGG CAAAACCTGT GCAGCACATA
170151 GAGAGCACAA GAGTTTCCTC ACTTGCAGGC AGGGTGCCCT AATCACCAGG
170201 CTACCAGCTG ATTTAGGATC AGAGGACTGA ACACAGAACG CAGATGATAA
170251 TGCACTCCTA CTGATCCTGG AGTTGAACAC ACGTGACTGC ATGACTCCAT
170301 AACACAGTGT TTTAGACAAT CAGCACTGTC CAAGCCACTG CTTTATTCGT
170351 GTTAAATAAC TACTGGATCA GCACCCAGCC TTTTCCTTTC CTGAATGACC
170401 AAAGTGGCTA TTAGACAGGC AGTGCTGATA CAAACACACA TGCTCTCTCA
170451 AGCCCTAGAA ATGCTTGATT GCTGTGTGCA AATTCAGTTT TGACACGCTC
170501 TGGCAATAGT GGAGATACTA GTTTGAAATT CTTTAAGCAA AAACATTCAG
170551 CTGAGCCCAG TTCTCTAGTT ATGCTCTGGG AGTATCTGGC TGATCAGCTC
170601 CTCCAGGCAC AGCAGTAAGA AATACCAGGC TTAAGGTAAA ATGCTTAAGG
170651 TATGAGCTAG GCTGCAGGGC ATTCACCTCT GAAGCACACC TGAGAATGAT
170701 CCAAAGCTGT TTTGGAGCAC TGGGAAGCTT TGATATCCAA ATTTAAGAAT
170751 CCCAAAAGCT CCAGCTATCT CTAAGACTGA ACAGCAGCTG GTTTTGAGGA
170801 CTGCTGCTTT TGATTTCAGC ATGCAAATTG TGAGTGAAGC TGGACTGAAA
170851 ATTCCACTCA TTCTCATTGA CCTAAGGCAA GTCTTTCACT TGATGCAATC
170901 CTGCACCGAC AATGGAAATT TCTGCATTTA TCCTAATATT TGTCAACAGT
170951 ACTAAATTCA TCTAAAATAT GTTAGTTAGA ACCACGAACC TATTCTGGAT
171001 CCAGCTATGA AAAATTACTT TAACCCTGGG GTTTCTATGT TTTTGTTATT
171051 ATCTTTGATT TTGTCCCATA AAGAGGGAAG CAGAAAGAGA ATGGGAAATC
171101 TGCAGGTTCT GATAAACCAG CACGAAAGTA GAACAGAGCT GTTGCTTAAA
171151 ATGGGAACTG TTTGGAGTTG TATGTAAGAC ACAAGAGCTT ACTTGAAAAA
171201 CAGTCATTAA CAAATCCAGC TACAGTTGAC AAATGCAGGC CTACGCTCAC
171251 AAAGATCAAA TAACAATCTA CAGATCTCCA TCAGCCTTCT AAAGCATGTG
171301 GCAAATGGCA TGAATTCGCA ATAGTTCTTT CAGCAGAAAA TAATGCAGTT
171351 TAAGGAAGTA GGAATAAAAG CTCAGCGCAG CACAGTGGGA AATATTTCTA
171401 TTTCGCTCCC TCAGAATGGA AGGATAATTC TAAGAAACTT AAGTAAATGC
171451 TTTTTAAGAA CAAGTTTGGT TTGGGAAAAC GTTCCTAAAA TAGTGTTTGT
171501 CTGATGATGA ATAAGCGAAA CGGCTGAAAC AAGAATATAA GCATTTAACA
171551 GTGATGGGAA AGGGAGAAAT AGCGTAGGTC TTAAAAAGGG ACTTGCTATC

Z1 exon 1

171601 TGACTGTACG TGGCGTTTTG GCCATTACAG AGCCATCCCA TCAGCGTGTG
171651 TACAAGGGTG CAGGCAATCT CCTACCAGCA ACTTCCCATT TTGTTAGATG
171701 TTGTGAAGAT GCAGTCATCA CCTCCCTCTG CTAATCATTC GTCTCAGGCT
171751 GTATTGATGG AGTGTCTTTC AGCATCAACC AACAGCTTCA CCCTGGACCT
171801 TTACAAAAAG CTGGATGTAA CTTCCAAAGG ACAAAACATT TTCTTTGCTC
171851 CTTGGAGTAT TGCAACTGCT CTCGCTATGG TCTATCTGGG TGCAAAAGGT
171901 GACACAGCAA CCCAGATGGC TAAGGTAAGT TCTGAACTTA GCAGTGTATC
171951 ACTTAAAGCT GGCTCCCACG TGACTTGCAT TATTCACCTG CCTACGTGGA
172001 ACAAAAAGGA GCAACATGAG AGAACAGTGA TCCGCCATCA TGTTGGGTGC
172051 AAGAAAAAAC ACTGCATGCA GTCCTGCAGG ACACTGTTGT TCCAACTTAT
172101 TTCCAAGAGC CCCCTTCTCT GCTACCACCT CTACCTTTAG CTTAAAATTG
172151 TTCTGGCAGA GTGAAGCTAT GGACATTAGA GACTGTCTTC TCATTCTCCA
172201 CACCCAGTTA GTAAGTCCTC TGAACCCAAG CTTGGCTGCA CAGCAGCAGC
172251 AGCAACATCT TTGCTTGTGA CATGGTTAGT CCATAAATAA GGTAATACAC
172301 CCATGAAGAA GGGAAGGTTT AGATTGGATG TCAGGCGGAA GTTTTTCACA
172351 GAGAATGGTG AGGTGCTGGA ACAGGCTGCC CACAGAGGCT GTGGATGCCC
172401 CTTCCCTGGA GGTGTTCAAG GCCAGGTTGG ATGTGGCCCT GGGCAGCCCG

Fig. 1-66

```
172451 GTCTAGTATT AAATGTGGAG GTTGGTGGCC CTGCCTATGG AAAGGGATTG
172501 GAGCTTCATG ATCCTTGGGG TCCCTTCCAA CCCAAGCCAC TCTACGATTC
172551 TATGAATAAT GGGGATATAC TAGAAATGAA AATATGATAT CATTTATAAC
172601 CACTTTTGCA AAACTTTCGG TGATGTACTC CTAGATTATA TGCATTTACA
172651 TAAATGCATT TATCTGTGTA ATGTACTGTA GAGTTGTACA TTGGTGCCTC
172701 AATAGTAAGA CTACAAACCA TCCTATGTTG TTTGTTCTGC CTGATAACAA
172751 TCTGAAAATA AATTCCACAT TGCTAAGCAT GAATTGACCA TTTCTCCAAA
172801 TCAATCCATG TCTGAGCAAT CACATTGATC TGTTATTAAG TAGTAAATGA
172851 CTAAAATTAA TATAACTATG ATACGGTTAT AGAATCTAAA TCTAGACCGA
172901 GGTCTTGTTC TCTATAACTT TAATAGACTA ACATTTGTAC GATGGCTAAA
172951 TTATCCTAAG TAGAAAACTA ACATCATTAC GTAACACTAG AGCACTTCTA
173001 TCTTCACAAA ACAAACTGTC CTTAAGAAAA TTTATCACTG CCACAGGTTC
173051 TTCATTTTAA CCAGACTGCA AGAGAAGAAA GTCCTTCTGA GATGACAGCA
173101 CCTTCTCTGC GGAGCCCAAA GAGAAGAGAC ATGGTATTTA TTTTGACAAG
173151 GCTCACAGAA ACAAATCTCG GAGAATGGGA CAGCACAACT GCCTTAACCC
173201 TCTGAAATTT GTCTGTCTAT ACCTACTGTC CTATTGCAGT AAGAACTATA
173251 CATAAAAAAT GTGAACAAGC AGGTAATATT ACTGTAAAAC TCACGAACTC
173301 AGAACTTCAA AGCAGAACAG AGACACCAGA AGCATTCTGA TTGTCTTTTA
173351 CACTTTGTTA CTTGCTTTTA GCTGCTCTAT GGCAATAGGA ATACCTAATA
173401 TTTTACTAAC TTCAGGATTT TTTTTTTTTT CTGGGCTGTA AAACAGCCAT
173451 TGCCTTCACA TCTGACTCCA GTCCTGCTCT CTTAAACTCT GTTCCACCTT
173501 TGCTATGCAT GCACACATCA GGCAAACAAA ATTCCCCTGT AAGCTAACAC
173551 ACACTGATTC ACCCTTGCTC ATCAGCTCCC CAGAGACTTG ACAGCAGGAG
173601 GAACTGCACA GAACTCCTTA CGCCTCAAAG GTCTGTCAAC TCAAACAAGC
173651 TGCAATTCTT TAGCACAGAA ACTAAGAAAG CTCAAAGAAA CCAAGTTAGA
173701 AAAACTGGAA ATAAAAAGGA GCAGTTACAT CATTCTCCAT CTAGATGGCC
173751 GTGGATTAAT ATTTAAGATA AATCATTATG TCCACATTGA TTTTAGCTAT
173801 TCACTGCCTT TCTAAGTTGC ACAGCAAGGT CTGCCTGATG TAGCCTTCCA
173851 GACATTTCTC TCCATTACCT CTTCACTATG TACCCATTGC CTTGCAAAAC
173901 CTATCTACTA TCCTGTTCTC TACCAAGTTC TTCCCCACAT GTCCTTTCTG
173951 AAAGCCTGTA CCTCTGCCTG TGTGAAAAAA TACCAGAGGA AGGAATGCCT
174001 CCTCACCAAT CTTATGACAA GCCCCCATGC ATCAGCAGCA AAGAATCTCG
174051 GTGTCTCACA TGTAGCGCAT GGTACATGCC ATGGAGCAGG AAATTATACT
174101 GAAGCAGCTT ATCCCTACAC TACGAAAGCA ACAGCTGACA AGCAAGCTCC
174151 TGCTCCCTAA AACCATCACC AAGGACATTC TGGACAGGTT CCTTCCAACA
174201 TCCAAGCAGT AACAGCAAAA TTCACATCAA ATAGAAAATT CGAATCAACT
174251 CAATTACATG ACATCAGTAT CTGTCTGAAC AGAGTAGCTC CTCAAAAGCT
174301 GCAATGTTGC CTTAATGATT TTTGTGATAA TCAAAATTAG GCTTGACTGT
174351 GACTGGAATG AGATGACCCA ATATCCTGGG TGCACCATCT GAGGACAGCT
174401 GATGTCCTCA AAGGTGTAAG CAGCTCCGCA GAATCAAATC ATAACCCCAC
174451 AGACATAAAA CAATGTATCC AGTTACACAC AGTGCTGCAA AAGTACCAGA
174501 TACCCGAAGA AGAGCTCCAT CCCTGCACAC ACTTTTTAAA TTAAAATGAC
174551 CTGGGGATTT TAAATAACCA TAGAAAGTGT AATGCTTCAG CCAAAAATAT
                                          Z1 gene exon 2
174601 TTCAATACTA ATTGGTGCCT CTTTCCAAGG GTCTTGAGTA TGAGGAAACT
174651 GAAAACATCC ACTCCGGCTT CAAAGAACTC CTGTCTGCCA TCAGCAAACC
174701 TAGAAACACT TACTTGCTGA AAAGTGCTAA CCAACTGTTT GAGGACAAAA
174751 CCTACCCATT ACTGCCTGTG AGTTGAACGT TTCTGCTTAA GAATGTTTTG
174801 ACAAAGAGTA TTTGACGTAC ATATTTGACA ATCATAATTT TCCAAATGTT
174851 CTGCCTTTTA AATCTACTGC AGCCTTTAAA ACTGTAAGAG TTCTACAGTT
174901 GAACTACAGA AAGCTCCTGT CTCTTTTGAG CCTATTTCTT GTTAGCATCA
174951 CTGTTGGTTC ACTTCTCCTC TAAAGGAAGC TTCTCCATAT CAGTGGTCAT
175001 CTTCCTCCCC CTTCTCACTA TCTATTACAT TCTAGCATTT CTGAGATTGG
175051 AGGCCAGAGC TATATAGAAA AGTCACACCA TACCTTTACA GAGCGGCATA
```

Fig. 1-67

```
175101 TTAACGTTCT CCCTTTTATT ACACTGTCAT TTCCTTCAAC TTTTCACATC
175151 ATATTTGCTT GTTTGACTAT TACTGGGCAG ATTATTTTTT TTTTTCATGC
175201 AACTGTCCAT TAGAACTTCA ATACCTCTTT TCTAAAGCAA TAATCATCCT
175251 TATTAGTATG CTTTGCTGGA TCATTTTCAG ATGTTTCAAT ATTGATACTG
175301 TAATCTATTT CCTTCTTCTC TTAGTTTCTA GCCTTTTAAA CAAGATCTTT
175351 CTCTGTAGTC CCACGGATAC TCAGCTTCTT CAAAAGCCTT TGGTGAGAAG
175401 TCTTCCAAAA TGCCTTTTGG CAATCCTAAT TGGCTGTAGT GGTTTGACCT
175451 TCTCATTTGC AAGCTTCTTT ACACCTTCAA AAACCTCCAA AAGATTCATG
175501 ATGTAGGACT TATTGTTACA AAATGCTGTT CCAACACATC ATGCTTACCT
175551 ACGTGCCCAG TAGGCCTGCT TATCCATTTG CCCTGTACAG ACTCATGAGC
175601 TTGTAATTCT GTGTATCTTT GAAATCTTTT TAAGAAATGG CACTGTATTA
175651 ATCATCCTCC AGTTTCTTGG AAGGTGCTGT TAAATGAGGT TAGCGTTCTT
175701 TCATCTTGGA GTTAAGTTTC AGTCTCCTGA GTAATTTCTC AGTCATTAAA
175751 TTCAATCAGC CTTACTGAAT GCTTGTTGCT CATGTTCTGC ATAATTTTGT
175801 GTAACCGTGG TTTAAGACTA ATCAGGGAAT TTCCTGCCGG GAATCTCCAT
175851 GAACAGTTTC ATAGAAGACA GTAATGTAAA AGTCAGTTCT AGTTTATTCT
175901 ACCATAACAT TCCCTTCATA TCTGACCCTC TACTGACCTC ACAAACTCTT
175951 GGCAGCTTGA CTCTGAAGCA AATCTTAAAA CATTGTTTCA ACTGTCCTTG
176001 AAGCTATTCT TTCTTCTTGT ACTGAACTCT GTCATAAAAC ATAAAAATGT
176051 ACTTCAAGTC AGTCTGAGAA ATCAAAAATA ATTTAAAAAA ATGTGTAGAA
176101 TGTTTATCTC ATAGGATTTC AAAATTACAA ATTTGCATGT TGGATTTAAA
176151 ACACAAAACT TTCAAGCATC ATTTTTTGTG AAACACAAAT ACTGAATTTT
176201 TGATCAGTCC TTGCTTATTA TTTAACACAG AATCATAATC ACAGAATCAT
176251 AGAATGGCCT GGGTTGAAAA GGACCACAAT GATCATCGAG TTTCAACCCC
176301 TCTGCTATAT GCAGGGTCAA CAACCAGCAG ACCAGGCTGC CCAGAGCCAC
176351 ATCCAGCCTG GCCTGGAATG CCTCCAGGGA TGGGCATCCA CAACCTCCTT
176401 GGGCAACCTG TTCCAGTGTG TCACCACCCT CTGTGTGAAA AACTTCCTCC
176451 TAATATCTAA CCTAAACCTC CCCTGTCTCA GTTTAAAAAC CATTCCCCCT
176501 TGTCCTATCA CTGTCCACCC TCATAAACAG TCATTCCCCC TCCAGTTTAT
176551 ACACTCCTTT CAAATATTGG AAGGCCACAA TGAGGTCTCC CTGGAGCTTT
176601 CTCTTCTCCA AGCTAAACAA GTCCAGTCCC CTCAACCCTT CTTCATAGGA
176651 GAGGTGCTCC AGCCCTCTGA TCATCTTAGC AGCCATCATC ACAGAATGTA
176701 TCAGAATTTG TTTTACGGGT TATCTAGTTT CAAATGAATT ACATTTTCTT
176751 CCAGTATGTA TTAGTATGTA TTGCATGATC TGTTGAGATG ATCTTTTTCT
176801 ACTATTTTTG TGCTTAAATT TAACTATATA AGCATACATT TTCCAATTCT
                                Z1 gene exon 3
176851 ATCCTTCAGA AATTTTTACA ACTGATCACA AGGTACTACC AAGCAAAGCC
176901 ACAAGCTGTA AACTTTAAGA CAGATGCGGA ACAAGCCAGA GCACAGATCA
176951 ATTCCTGGGT TGAAAACGAA ACTGAGAGTA AGTATCGCTC TGATGGCTTT
177001 TTCTTTTCTC ACTTCAAAAT CATTTGCATT TCCACTTGAA TTGCTCTTGC
177051 AGTAAGGGAT CCATAAAGGA TGGAAACTGT GGGGAAATGA TGAACAAATT
177101 GCAGTTAAAT GTCTTGAAGA AAGCCAACCA CCAAAACTAA CTGCTGCCCC
177151 TTGCAAAGTT TTTCCCTTGA TTTTTCATGT CATAGTCTCT TCTGAAGTAT
177201 TTCTGTTCAT AAGGAAGCAG AGTGGATACT ACATGGCTCC ACTCTGATCA
177251 GTGAAGGTTT TACTTCTGCA AGCTTCAACT GGTTGCAGCC AACTCCAGAG
177301 AACTTCCACG CTTTACACAC TTCTTAACAT CTTTTACTAC TAAAACTGAA
177351 ATAAATATGG TTTAAAAAAC AGTGATGCTT CAAAAGCCAT TTATGTATGT
177401 ACGCTGTGAA AAATGCACAG GGAAAAAAAA TCTCTGAGTG TAAACACTTT
177451 TGTTAGATAG CTAGGCATAG AGAAAGCACA TCTGAAATTG GTGAGTTGTG
177501 CATTCGCAGC GAATTAACAG TCCTATCTAT TTGATTTTTA AGGGAAGATC
                                Z1 gene exon 4
177551 CAGAATCTGC TACCTGCAGG ATCTCTTGAT TCTGACACTG TATTGGTCTT
177601 AGTAAATGCT ATTTACTTCA AAGGAAACTG GGAAAAGAGG TTTCTGGAAA
177651 AAGACACATC CGAGATGCCC TTCAGATTAA GCAAGGTAAA TTCCTTCAAA
```

*Fig. 1-68*

177701 ATGTCTATTA TGGCAGAGCA AGAATCCTCT AAATATTTCA CCTGCATTTC
177751 ACATCCCAGT ACAACACTAC TTACAGCAGT AGCAGATGGT ATAAACTCTG
177801 AGAACAGCAA CAGTGAAAAT AAATCAGCAG TCTCATTTAT ACAGATGCAT
177851 GAGATTAGGA TTTTCAGTTA AGTTAGTAGC TTCTTGGCAC CAAAACAGTT
177901 GAAAACACCA TGGTTAAGCA GCTTAAGGAC AAGAGAAAGT TTCTCTAAGT
177951 ACTGAGATAT CATTTTCAGA AGGAATTGAG CTAATTCTGA GAGCAGTACT
178001 TCGACACCTA GGTCTCTTTT CATGCTTTTC AGACAGAGGC TGTATAATGT
178051 GAGCTCAAGT AGCCTAAGTG TTCTTTCCTA ATGCCCTGGC CATTGCGTAA
178101 AACCTCACGT GGAATTCTCA AGAGGGTTTG TCATTTTAGC CAGATGCGTA
178151 TGGATGATGT GTTCAGCATG CATTGTGGGC ACGACTGAGC TTACAGTATC
178201 TCAGTGATTG TGCATGGACA ATTTACAGTA GCTGACAGCA TGCATACTTT
178251 CGGCTTGTGT CAAAGGTGAG CAAAAAGAAT TTTCATTCAG AACACGTTGT
178301 TTGACATGAG ATTACGAGTG CAAACACCTT TTGTATGTCT GGTGATGTGA
178351 AGCAATTGTG TCGATACTGT GGCTGTGTTA TCTGAAACCT ACTACATTGC
178401 ATGCGCAGTT TTAGGACCTG TAATAGTACA CGGTGCACAG AAAGGGTTTC
178451 ATTCACAGAG TGGCTGATAG CAAAGCCTGC AAACAGATAA GCTTTTGCAC
178501 TTGTGTAACA ATGGAAAAGA GAGAGTGGAT ATATCAGTGA AGGTCTCTGA
178551 GCATAATACA GCGTAAGAGT TCAGATGATT ACTGTCTAAC GCGATTTCAG
178601 TTGGTAATCC AAACCTCTAC AGTTTGGGAA AGAGAAAAAA CAAGCAGAGG
178651 TCACAGCAAA TATGGTCCAT AGGTAAATTC AATCAATCAG TGCTGTCCGG
178701 AAGCATACAA AAGAGTTGAT GACATCCAGA GAATGAAAGT CAGCATTTTT
178751 TTCCCCTCCC AATCAACACA TTCACTCAAG AAATGTAAAG TTTTGGGGAA
178801 AACTTGAAAC ATACAAAGTA GTTTCTTGTT TACCAAAGCT AACTCTTTCA
178851 AAAGAGTGAG AAATACATTG CATGTAATTA TGTTATCAGG TGGTGTCTGT
178901 GCTTTTTTTT TCTTTTTTTT CTTTTCTTCT GAAGATCCCT TTGACTTTGA
178951 AACAGGAGAA ATGGCACTGG GAAAGAATAA TGCCAAGTCT TATACTTGTT
179001 TACAATTTTT TTTTGCCTTC AGTTCAACAA AGCAAGTAAT CTTTACCATT
179051 CACCTTAAGG AATAAGTACA ACTAATCTTT TTCTTTTCTG TTCTTTTTTA

Z1 gene exon 5

179101 ACATCTGAAT CATTTCACAG ACCAAGACTA AAGCAGTACA GATGATGTTT
179151 CTCAGAGATA CATTTTTGAT GCTCCATGAA CAAACAATGA AATTCAAAAT
179201 TATTGAGCTG CCGTACGCGG AAAATGAACT CAGCATGTTC GTACTCCTAC
179251 CAGATGACAT CAGTGATAAC ACTACTGGTC TGGAGCTGGT AAAACTGACA
179301 TACTGCATCA CACGCACTAC AAAGCACTAA CAGAAATAGA TGAAAACAGT
179351 GAGGAAGAAT GAACTTCAAA TGACACAATG ACTGCTCAGC CTAGGTTTCA
179401 GGGCATCTAT TAATGATGCA AAAATACAAA TCTACCTGAG GATACACCTA
179451 AAAAAGTATG CCCACTCTAC TCTCTTAGCC TATTCGGTGC CTCCTTTTCT
179501 ACCTCCAGAA TAGCAGAATA ACGAAAGCAA GAATCAAATC TAAACCACTG
179551 TGCCCCAGAA TTAATCTTCT GAGGGCAACA CTAACCAGTT TTATGTCATC
179601 CGCAGTCCAG ATTTCCACCT GATACTTTGT AACGAGGCTT TTCAAACTCG
179651 GGGCTGACTT ACCTTGACCC ATGAGGTATC AGCAGCCACT CATGACCGTG
179701 CCAGGATTAG TTCCTGAATC TAAATACATC AGAGCTTCAG AATCTAAATA
179751 CATCAGGGCA AATATCTTTT TATTTGCTCT TGAGGTCCCA TGCATTCCAC
179801 TTACTTACCA CTACTAAGAG AAATGCCTTA CAAATTCACA CATACCAAGC
179851 ACTTATTAAT GTGGTTAAGT TGGACACTGC ATAAAAGCAA CACTTCTCAT
179901 ATCCACCTCC AAAATAATGA ATTATTCTGA AGGTTCACTC TACACCTCAC
179951 TGCATTTAAG GAAACAGATA GAAGTACAGG TCACTCAGCA CTATGCAGGA
180001 TCACATCCTA AGAATATGCA GCACATTTCA GCTGTACTCA CAGCTGGTAG
180051 TTGGACCTTT TAAATCTAGA GCATTAGACA CCAATGTATG CATGCCTTCT
180101 TTTTCTGTTT GCATTATGAC TATATTCTTA TAAAATTCAT TGCAGGTAGA

Z1 gene exon 6

180151 AAGAGAGCTG ACCCACGAAA AATTAGCTGA ATGGTCCAAC TCAGCCCGTA
180201 TGATGAAAGT CGAAGTGGAA CTGTACCTGC CCAAGTTGAA GATTGAAGAA
180251 AATTATGATC TTACATCCAC TTTGAGCAAC ATGGGGATAC AAAATGCTTT

*Fig. 1-69*

```
180301 TGACCCTGTT CAGGCTGATT TCACAAGGAT GTCAGCAAAG AAGGACTTCT
180351 TCCTATCAAA AGTTATTCAC AAAGCTTTTG TGGAGGTCAA TGAAGAAGGT
180401 ACCGAGGCAG CAGCTGCCAC AGGTGTCCTG GTGTTGAGGT CAAGAACACC
180451 TAGAGTAACT TTCAAAGCCG ACCACCCTTT TCTCTTCTTC ATCAGACACA
180501 ACAAATCCAA AACCATCCTC TTCTTTGGCA GACTATGCTC ACCTTAGTCA
180551 GAGTCACTCC CTGCTCTACA GAGCAGGAGA TGCTGGCTTG CCAGCTCAAG
180601 GGCAGAGCTT GATACTCCTG CTGCAGCTGA GGGACTAAGA CCTGCACTCT
180651 TTCAGACTAC ACATTCCACA GCCCAAGGCA AAGCTTCAAC TACTCCAGAT
180701 AGCCATAGCA GTGCCTGTAG ATGCATTTGA TTCCTTCCTC TTGCAGCAGT
180751 AGATACAAAC ACATGGCACT ATCTTCGTTC TCACAAGTAG AGCACCTGAT
180801 TCAGGTGTGC ATCTTCACCC TTCCACCCTG CCATAATTAG CCCCTGCTCC
180851 TCTGTAGCTC TTGACTAGTT CTTTTTGTTA CAGAGGCACA CACAGCCCAA
180901 GCTTAAGTCT TTACCAGTTC ACTTCCATTC TACTGATTGC CTGAAAGACA
180951 TAACAAGCAC ACACTCCCAC GTGGGCTATT TCCTCGCACG GAGTTACAGG
181001 TGTGACAGAA GAGCCTGACC CATGCTGCTG ACTTTATACA AAGCAGCACC
181051 TGCTTCAAAA ATAGCAGTAC TGATAATAAA CAACCCCTCG TAGCTTGATG
181101 GTGCTTTCTG TCAGCTCTAC CAGGAGGGGA AGGCAGAAGG GGAAATCAAG
181151 CAGCGACAAG AGGCTCGCGG AGGTAGCGAC CTCCGAGCTA AAATGGCCGC
181201 CTCCCACTGC TGCAGCGAGT GCTCAGGGCC GCTTTCCGCA GCTGAGCTCC
181251 AGCCCTCTCC CCCACGATGG GCGGCCCGTG GCTAGGCAAA AACTTCCGGG
181301 AGGAGGGCGG GGCAGAGGCC AGGGGAAAGC TGGTGCTCGG CTGGGTGAGT
181351 GTGGAGGGTC TGTGTTGTTG TTTTCTGCGG GAAACACGCA TTGGTTTTTT
181401 GAGGGGAGAC GGTAGCGTTT CCCTCGCGGC GGCGCTCTGA GCGGTTTCGG
181451 CGGGCGCGGC CGCCGGGCGT TGACCGGGTG CTGGAGGCGG GAGGGGCCCC
181501 GCAGAGTTCC GCACCGCTGG AATCCATCCC TGTCATCCAG CCCTGCCTCT
181551 GTGGGTTTTG TGGCAAACAG GCGGAAATCG ATGGAGAGGT GCGAGCTTCA
181601 GCCTGTTCTG AGTCACAGGG AGAGAGCTTG GCCAATTGTC CTGCGCCCAG
181651 CCTTATTGGA GCTGTAAGGT GCACGGGATT AAATCGCTCC TGCTTCAGGC
181701 AGAATGGAAG GACTGTTTCA GTCCAAGTTT TCTTTTCATC AGTGTTTTTA
181751 TGGCTATGGG CAGAAGGAAA CATGAGTACA GCTGCAGCTG TTGAACGTAG
181801 CCAAGCTCCT ACCAAGAATT TGTCTTAGAG GAAACATGCC TGAGGAAACT
181851 TGCTGCTACC GCTTGTTTGA GATGATGAAT CATTAATACA AAGTAGGCGT
181901 TGGCTCTGTA TTTTCTAGCA ACGTACCAAC ACCAGGCACT GCCTTAGGGG
181951 AAAAAAAACA AACCACCTTT ACTACTAGTT GATATCCTGC GATGTCTGCT
182001 GGCACTTATC TGTAACTTAC TCCACGTTCT GGCACTCGTT GCTCCTTCCT
182051 GTAGGTATGT AGTATAACTT CGGATTAGTT AGCTACCTGC TCGGCTGACG
182101 TATGTGAAGT CTGACAAGCA CTGAGCTACG TATGTGCCAT GAAGTTCCCA
182151 ATAAACCGTT TACTTTATTG CGTCTGTTTC CATCGTGTAG ACAATAAAAG
182201 GCAAACTGCA GTGGACTTTG ATTTTGTACC ACAGCAGGAA ACCCCAGTAA
182251 TCTGTAATGC TGACCAGATA AATTTCGTTT GAATATTGTA GATCGAGTCA
182301 TTCAGTTGGA TTCTGGCAGA CTGACTGCTA GGTCTAGAAC ACAAGTGAAG
182351 TAATCTTGAA GGGAATACTG AAGACACACA GACTTTGAGA AGGTGAGTTT
182401 ATAATTCTGC CATTCTGATA CCTTTCTGCT TTGGTTTTCC TGTAAAGCAA
182451 ATAACTGTCT CTGTGGAGCC AAAGGAGACT TATTCTACCA AGTCCTAGTA
182501 TGCTCATCTC AAAAAATATA GTATTATTTA CTCCATGAAG AAGACCAATG
182551 ACTTTTCCTC ACTACAAGAA AGACATTGAG GTCTTGGAGT GTTTCCAGAG
182601 AAGGGCAAGA AAGCCGTGAA GGGTCTGGAG CACAAGTCTT ACTATTGAGT
182651 GGCTGAGGGG GCTGGGATTG TACAGCCTGA AGAAGAGGAG GCTCAGAGGA
182701 GACTTTATCA CTCTGTACAG TGACCTGAAA GGAGGTTGTA GTTGGCCTCT
182751 TTTCCTGGGT AACAGCAATA GGATGAGAGG GGATGGTCTC AAGTTGTGTC
182801 AAAGGAGGTT CAGATGGGAT ATTATGAACA ATTTATTTTC CGAGTGGTGA
182851 GGCACTGGCA CAGACTGCCC AGGAAGGTGG TGGAGTCACG TCTCTGGAGG
182901 CATTTAAGAA ACATGTAAAT ATGGCACTGA GGGATGTGGG TTAGTGGACA
182951 TGGTGGGAAT GGGTTGACAG TTGTACTAGA TGATCTTATA TTTGCTTTAT
```

*Fig. 1-70*

```
183001 GGTTTATATT GAGAAATGTA AAAGACAGAA ATAGGTTGTC AGTTTGTGAT
183051 CAAATAAATT TAAGCCAATC TTCATTTTTT TTTTTCTCCT AGGCTTTGAA
183101 CCATGGATAG CCTCAGTGCA GCAAATTCCA CTTTTGCTCT TGACCTTTTA
183151 AATGAGCTGC GTGAGAAAAG CAGCACAAAG AATCTATTCT TTTCTCCTTT
                                 Z2 gene exon 1
183201 TAGTATTTCT TCTGCTTTGT CTATGATTTT ACTGGGTTCA AAAGGGGACA
183251 CTGAAGCCCA GATAGCAAAG GTATGTATCC AAACGTAATG TATTGGATTT
183301 GATGCATATA TCATCTACTT AATGATATAT GAACTACAGA TCTGAGATCT
183351 GTATTACAGT CTGTGACCTC TAATTGCTGA ATTGTTACAG TCATTCTGGC
183401 CTCAGAGGTC AGAAGTCTTC CTTAGGTATG TACATAAGCA GAACCTATTT
183451 CTATTGAGTT TATGTATAGG ACTTACTGCA GTGTGAAATT AAGAGATTCC
183501 TGTTTTTTGG GGTGTGTGTG GGTTTTTGTT TGTGATACGG AGATCTTCCT
183551 TTTATATGTC ATTAACAGGC ACCTGGAATT TCTTTTTTTT TTTACTTACA
183601 TATTTGTATA TTTAGAGCTA TAGATGAATC TCCAGTTACA TAAAATAATT
183651 TACTCTGTAA TCTTTTTGGG CTTAATATCA GACTTTGCAT ACTTCAAAAA
183701 TGTAGCCAGA TAATCAAGGG AAAAAAAATC CAACATACAA GCATGTCATG
183751 TTAAACAGTC CCAGATTTTA GGAAACAAAC AAAAAAATGA TCAGTTGCTT
183801 GTTCAGTGTA ATAGCTTTTG TTTTCACAAC CTGTAATCTC AATCCTGGAA
183851 CATCCAGAAG AAAGAAGTGA TACAGGGCTA AGAACATAGC TCTGAAGTTC
183901 CAGAGAATAC CCCAGCAAAG ATTCAATGGG GCAAAGCTGC GTGGCCAGTG
183951 AAGAGTAAAA TTCATAATGT AAACTTGCAA TTAAATTACC AGGAGAGCAG
184001 TTAAGGAGTG CAGTGGTGGG CCTGTTGTGT GACAGTAGGG TCAAATCTAT
184051 CATTAACTGC AGTGCAGTTT ATTCTACGTT CACTAAGGTG CGTGCCTGCC
184101 TCTCTCTTTC TGGTATTGTA ATTTGGAGTA GATCATCAAT ACTTTTTCAT
184151 TTGTAGCTAT GGTAGTAGTG ATGAGGCTGA ATGAGGATGA AGCTGATGTG
184201 TTGTTTTAAT GGGAATTTAA ATATTTGCTT GTGTTGACAT CGGCTCCAGC
184251 AGCCTATTTC CTGTTATCGC TTGAAGGATC GGGTTTGCAT CTAAGGTATT
184301 AAATAAGATG CTTTGGTGCT ATTATAATCA GTGTGAAAAA TTATGGAAAG
184351 TTGTTTTTTT TTATTTAATC TTCAGGCTCC TTTGTTTCTG GATTTTAACA
184401 GTTTTGCTAG GTTTTATAGG GTGGAGATTA TAAATCCTCA GTTCTCTAAG
184451 AAGTACTGTG TACAGCATTA AGAAAAGGGC AGAATGTGTC TGCACTCAGA
184501 CTTCTTTGGA GGCTGGATGG GTTCCTTAGA AAGCAGGGAG ATAAACCAGG
184551 TAACCTCCAT AGCTTCCTTC CAACCTCAAC CATTGTGTGA TCCTCTAATG
184601 CTTGGACAAA ATGAAGATAA ATACCACTCA CTTTTCAGCA ACGTAATTTC
184651 TTGCTTATAC AACATCTGTG TGGATACATT GTACGTGACT TGTGTAATGA
184701 AAAATCTGCT GGCTTCAAGT CTCAAAACTC ATTTAAAAAC AGAACAATTG
184751 TGCTGATGCA AGTGTGTCAG AGATTACGTG GACTCCACAG AAGGTATTTG
                                            Z2 gene exon 2
184801 TCTCTCTGCA GGTGCTTTCT TTGAACAAAG CTGAGGATGC TCACAATGGG
184851 TATCAGTCGC TTCTCTCTGA AATTAACAAC CCTGACACCA AATACATCCT
184901 CAGAACTGCT AACCGACTTT ATGGAGAAAA GACATTTGAG TTTCTCTCAG
184951 TAAGTAAACA TTAAATTTGG GTGTTGTGAA GTATAATGTA CTTGCTAGCT
185001 ATTCCCCTTG AAGGTTAGAT AAAGGCTTTG GGTTTTACTC TCCAAATTTT
185051 TCTAGGCTGA GACTTACAAC CTGAGAGTCT ATGCAAAAAG CAGGATGTGA
185101 ACAGAATGGA GAAGCTACTT TTAGATTATA TGAATGCACA ACTGGTGCAA
185151 GACCATGAAA AAAAACTAAA TCTTCTAGGT TTCTTGGTCC ACTTTTGGTG
185201 GGTTCTAGGA TCAAATGAAT GACAAATCTC CTTGCCTTTG ATAACCTGTA
185251 GCTATGATGA AAACAACTGT TACTGCTGTC CAGCATGGGC AGAACTTTTC
185301 TTTTTTCTTA ATTAAACAAT CCAGAGAACA TGCTGAGAGG AGTATGTGAC
185351 TCTTAATATT TTCCTTATAA GTATATATAC ACAAGAGGGC ACAGGTACGT
185401 TGCATATACA TTACATATAC ATTATAACAT TGTATGTTCT CTCACTCAAG
185451 CAAAAAGAAC AAACGGAAGA AACAAAAAGA AACAACCCAG ACAATCATTT
185501 CTCAGTTGAG TACTGTAGAA TGTTCTGGTG TATTAAAGAA GACATTTGAC
185551 TTCTTAATAA CAAAGAGGAA GATAATTCCT AGCTCAGATG GCTAATAAAA
```

*Fig. 1-71*

```
185601 CAACTGATAA GAACATGTCA GACAAAACCT GAATGGCTTT ATATCAAGCT
185651 GGGGGAAGAG AGGATATAGA TTTTTCTCAG TGTACTTAAA AACATCTGTG
185701 GCTGAATGTC AGTAAAATGC ATTGCTAAAA AGCTGTTTTA AATGTTCATG
                       Z2 gene exon 3
185751 GCAGTCATTT ATAGAATCGA GTCAGAAATT CTACCATGCT GGGCTAGAAC
185801 AGACTGACTT CAAAAATGCT TCAGAGGATT CCAGAAAGCA AATAAATGGC
185851 TGGGTGGAAG AGAAGACTGA AGGTGAGTGT TCTGCAGAAC TCCCTGCTGT
185901 ATGTAATGTC AGCCAGGACT TGCATAAACA GCTCTGTCAA GGTGTAATAC
185951 TGTCATTTTT AAAGCAAACA CAAACCTCAG CCATTGTGCT CTGTCTCTGG
186001 TTGGGGCATA ATTCCCATAT CTGATCTATC GTTAATACAT ATTAGATACT
186051 CTGTATTGCA ACAGTTGCTT ACGTACCACT GTTCAATTTG TGTTTTCTAA
                       Z2 gene exon 4
186101 AGGTAAAATT CAAAAATTGT TGGCAGAGGG AATTATTAAC TCAATGACCA
186151 AACTTGTGTT GGTGAATGCC ATCTACTTCA AAGGCAACTG GGAAGAGAAG
                      MAR-like element
186201 TTTGACAAAG AGCGCACAAA AGAAATGCCA TTTAAAATTA ACAAGGTACG
186251 CTACGTTAAT ATGCTGACAA TACAAAGGTC TTTGTAATAC AGAAGACAAA
186301 AATTGTTCAA GCAGATTTAC CTAAGGTAGT CTGCATGGAG CTCCCTATGC
186351 CCTGTCCCCT TAGTATGAAC ACTCTCTTTG TTTAGTTTCT GTTAAGTTTC
186401 ACATAATTAC TAAAAACTTT AATATCACAT ATTTATTTTA TACTCTCTCT
186451 TTTTTTTCCT TTACTCTTTT TGTTTGTGTT TCAGTTGGTG AACTTGACTA
186501 TGTCAGTGTA AAATCTGCAT GGGCAAAAAA CATTCATAGG TTCCAGGCAG
186551 AAAAGAACTT CCGTGTGTGC AGAAATGTCT GAATATAGCA GTCATCTTCA
186601 GTCAGAATGC TTTTCTTTCT GCTGTGTTTC TACCACTAAA TTGATAGAAA
186651 TGAAATGAGG TGAAGAAAAA AAAAACCACT CTCCTTTGAA GGCCTCCATG
186701 CTTGACTTTC TTTTGCTTCT AAAAGTGCAG CAGGGCAATC GAGGAGGACT
186751 TTATGTACTA TCATTAATAG GCTACGGCTG CCCCTTAGAG GTCAATTTCA
186801 AACTCTGGAT GTCCACCCAG GTGTCGTGAG AGTGAACTGC TAATGTGAAT
186851 TGCTTAAGAA CTCACCTGCT TAAAATAACC ACAATGCAAA ATTGAAGCTC
186901 TAGTGCCTAA TTTCAAACTT CAGTGTTGAA ATATATACAG GAATGCTTGA
186951 AACTGCTAAT ACCACTTTTC AAACAGGGAA TAATAATATT GCTCTTGCCA
187001 TACTGTATGC TATAGCACTT AGAAACCACT GCACTGACTT GGTTCCTGTT
187051 AGGAAGGGAG GTTTTTTATC AGTTTCCCAC AGAGATGTCA CACAAAACCC
187101 AAGCTTACAT TCTGCTTAGA GTTTTTTCCT CTCCCTCCTC AGGAGGCAAA
187151 TCCAGTGCTG TTTCTCTGGG TACGAGGCTC AGCCTAGTTC TGAGATTACC
187201 CTTTCCTTTG CAGACACACA TTTATTTTTG AAGACTGCAG TTTTTGGGAT
187251 GCAGATGGCT ATTGGAACAA GTTGTAAGAT GTGAGACTGG GGAATGCTGC
187301 CTTGGCTCAT CAAGTAACAC GCTGTTAGAT GTGCAACCAC AAACCTCTTC
187351 CCTTACAAAA CTAAGTGGCT TAAATTTCTA TTTTCATCCT ATTGATGACT
187401 AGTCACTGAT GAGCTACAGA AGTCAATGAG TAGGCTCAAA TAAGCAATGA
187451 AAAATCCAAA GGGCAAAGCT GAAGTTTTAA GCTAGTTATT TTACAGTCTG
187501 TCCAGGAGTA GTTACTTAAA CATACCAGTA GTCTTCTGAG CATTCTGTGA
187551 CATCTATTTT ATCTGTGACT TTTGCACTTT GTTGTGACTC ACTGGATGAT
187601 TCTAGCATGC AGTGTGGGCT TTTCTTTGCT TATCCATCAT TTTCATGTGT
187651 CACTGATTGC TGTTGCAAAA TCATTTCCGA CATATTCTGT TCTCAGAGTT
187701 CATGGCAGTC ATTTATAGAA TTGAGTCAGA AATTCACTGT CTCAATGGTC
187751 TTTCCTTTAA AAAGAAAAAA CGGTGAAGGT AAGGGGAAGA AGGGATTTAG
187801 ACTCCACAGA AAAGGAGGAA AATAATGTAG ACAAAAGTAA CTGATGCTCC
187851 ATGCAAAAAT GGAGAGAGAT GGGGGAGAAA CTGGTAGTAA GAAGACAAAA
187901 GATTAACCTC TCCATGTGCC TTTTAACAAT TCAAAGTGAT GCTAATACTT
187951 TCCTAGCATT TTTAGTGGCT TAGTAAAATA TTTTTGTTGC CCTACGTCAG
188001 AGTAATTAGA GACACATGGA GTGAAATGAA AATATCGAAG TTGAAGTTAT
188051 TTTGTATTTA TTTAAAGCAA GGAATACAGG CTCTGCTTAT TACCAACTTT
188101 GTTTAGAGCT TGTCACTACT TCTAAAGTGA GCAAATATGT ATTCTTGCTC
```

Fig. 1-72

188151 CTTTACCCTA AAGCAAATTT CACAGATATC TCCAATTAAC AATTAAATCT
188201 CAGGGATCCT TACTTCTCAT CTCTTGCTTT ACGAAAGAGT GACTGTGCTA
188251 TACTATGTTA TGCAGTGTAC TTAGTTCTCT GTGCAGTCAA ATAGTAAAAA
188301 GCCCTAAGTA ACTAGATGCC TGCTTCATGT ATTAGGACTG TCATGCCAGC

Z2 gene exon 5

188351 CCAGTAGTAA CTCTTAGTGT CTCTTTCATT TTAGAATGAA ACCAAACCTG
188401 TGCAGATGAT GTTCAGAAAA GGTAAATACA ACATGACCTA TATTGGAGAC
188451 TTGGAGACCA AAATCCTTGA GATCCCTTAC ATTGGTAATG AACTCAGTAT
188501 GATCGTTCTA CTCCCTGATG CAATCCAGGA TGAATCTACT GGCTTGGAAA
188551 AGGTAAGTTA TTGAGCTCAG TGCAAAGACA GTTTGTGTCC TGCCTTGGAA
188601 GAGAGTTTGG TGCTGCACAT GGATTCACAG TTCAGTTTCA GAGCTATTAT
188651 ATCATTGATG CTCAAGACTG ACTGAAATGC TCCTTGTGTT TCTGCCCCTA
188701 AAGTGGCATG CCATCTATTA CTACTGGCCA AGCTATGTGC TGCTGTGCTA
188751 AGAGGCTCTG AAAGAGGCCT CATCAGAAGC TGTAGTTATG GTGAAGCCAT
188801 AGTATGATGA GCACCAAATG AGAGGGAATT TGGGGCAGCT CTTAGGAAGT
188851 CCTTACCAGA ATTTCTACAG TTTGTCCCAT AGGTCATCTT AGTGAAGACC
188901 TGGCAGATTG TCACTGCCCC TCTACTTGGA AACACGCTCA CAGAATAGTC
188951 CAGGTTCCCT TCCGTTGTGA TGATAGAATA CAAGTCATGC TCTGGCCTCT
189001 TGTTTTTTTT TCTAATGCTG ATTTTAATTT AAAAAGTGTT GTAAGCAGGT
189051 TTTGTCACCA GCCCGTGAGC TGAAAGATCC TGAAAGGCTG AAGAACTGGG
189101 TTCAGTTTGT TTGGGGCCTT GTCAGCAGTT CTCCCGTGCC TTTACTCCCT
189151 ATATATAAAA TAAGGTTTTT ACAATCTGAT AATGTTTTAT AAACTGAACT
189201 TTACTGTATC TACCACGAAA AAGAAAACAC CAAACAAGAA TTGACCTCAG
189251 CTGAAGCTGT AGTCTCTAGT AAGTAGAAAC CTGTAGTGAC TTGTGCTTTT
189301 GACTTGGGAT CCTGTAAGCT CCTGAAAAAG ATGCATATTG CATGTATGTG
189351 TTTACATAAC ACACATACAC AGACAAAAGT AGAGATTAGT GCAAAACTGT
189401 CACTATTCTT ATTTTAATTA CCTAATGTTG GGTTATGTTT CGTTGCTTTT

Z2 gene exon 6

189451 TTTGTTTTAA GCTGGAAAGA GAACTTACAT ACGAGAAGCT GATGGATTGG
189501 ATCAATCCTG AAATGATGGA CAGTACAGAA GTGAGGCTGT CTTTACCCAG
189551 ATTTAAACTG GAAGAAAATT ATGATCTGAA ACCCATCCTG AGCAACATGG
189601 GAATGCGTGA TGCGTTTGAC TTACGGATGG CGAACTTCTC AGGAATCTCC
189651 TCTGGTAACG AGCTTGTGCT CTCTGAAGTG GTTCACAAGT CCTTCGTGGA
189701 GGTCAACGAA GAAGGCACTG AAGCAGCAGC TGCCACAGCA GGAGTGATGG
189751 TGCTCCGTTG TGCTATGATC GTTCCCGACT TCACTGCCGA TCATCCCTTC
189801 CTCTTCTTCA TCCGGCACAA CAAAACTTCC AGTATTTTGT TCTGTGGCAG
189851 ATATTGCTCT CCCTAAGAAG AGAGACAGAA GAGCTACCAT TAACGCAGTA
189901 ATGTGATTTC TTTTAGGATA GAACTGCTCT TTTGCACTAA CTGCTTATTT
189951 CCACTGTGCC TGAATCCCCT TATCTGGTTG TCATTTTGGG CTTGCGTAGA
190001 GTAACAAAGC CACTTACACA TACACAGCAG CTACCACTTG AAACAGCTGC
190051 CTTACACTTT GCACCTAAGT GGAGTTGTTT TCTTGCTGGC CCAAGAAAGA
190101 *TGAACATCCC ACTTGCTCAG TGAACTTCCA CCTGTCTTAT ATTTTCTATT*

MAR (0.658)

190151 *GCACTTTGCT TTTGTGTGGC CACCAGGTAG CAAGGTGACA AAGAGAAAAG*
190201 *AAGTGGATTT TGTTTCTGAC TATAGTGGAA GATATCTTAT GCTCTGCTCC*
190251 *CCATTTTTCT TCCTCTCCCC ACTTATTTTT AACTTTTTCT TTAATGTTTT*
190301 *GATAATAGAG GGAGATGAAA GGAGGCTTTG GCGACCTATT TGTAAGAGTT*
190351 *ACTAAGCATC TGCACTAGAC AGAGGTTTTA TTATAACTGG ATAGCACTTA*
190401 *CACAAGGATG GGAATAAAAG TATGTCTGTA ACAAATGACC TTAGAGGTTT*
190451 *TCATGGAGTA CGGATTCTTA TCTTAACACC ACATGTGCCA CCTGGGAATA*
190501 *TTAGCTATCA CTCACCTACT TCATTAGTCT TTTAAAAAAA GAATGTTTTT*
190551 *AAAAACAAAC AAACAAAAAA AAACCCATAG ATGCCTATGT AGTATTTAAG*
190601 *TGACAGAGCT TTATTTTTGT TTTTCAGTCT TTATATGTTT TTTTCCTATT*
190651 *CTGGGTTTGT AAAGCATCTT TGTTAATCTG AATGCCAAAG GTTTCTTAAC*

Fig. 1-73

190701 *GCAGTGATTT ACGTGTTTTG CTGTTCTTGA AAGAATAAAC AAATTTGTTG*
190751 *TGAGTGCTGT GGGCATTGCC CATAAATTTT GTGGGGTTTT TTTTTTTCAT*
190801 GGCTACTGTA AAGAAAACAA GCAATCAACT TTCGTGTAGC TTATGCAGAA
190851 TTCATTGCTT AACAGAGGCT TTTCTGAATG CTGCAAGACC AAGATGCTTA
190901 CCTGGATTAC GATGGAGTTT AGGTTTTTAC CTTCGAAGGA TTCATAGCAA
190951 GGAGTCTTTG AGGCAAAGGC TCAAGGGATT TTAAAGACTA TCTGGTTCCA
191001 ACTCCCTGCT GTGGGCATGG CTGCCCAGGG CTCCCTCCTC CCTGGCCTTC
191051 GACACCTCCA AGGATGGGGC ACCCACAGCT TCCCTGGGCA GCTGTGCCAG
191101 TGCCTCACCA ACCTCCAAGT GAAAAAGATC CCCCTGACAT CTAATTGAAA
191151 GTTCCTTTCA TTTATTTTAA AGCCATTCCC TCTTATTCCA TCACTATCAG
191201 ACCAAGGCTC CCTTTATGTA TTGGAAGGCC ACAACAAGGT CCCCTTGGAG
191251 TCTTCTCGAG GCTGAACAAG CTAAGTGCTT GTTTCCAGAT GGGGTACTGC
191301 TGCTGTGGGT GCAACTCCTT GGCCCCAGGC CAAGGAGTGT GCCATGCCTC
191351 AGATGCAGCG ATTAGTCACC ATTTGGGGTG AGGAAGCTGC CAAAGTGCTG
191401 CCTGTCAGAC CGATGCTCAG TCAGGGCTGA GAGCAGCAGT GGGTAGAAGG
191451 GAAGTGGGCA GCCTCTGCTC CCAGTGCATT GTCTGGGAAG GGGGTGGTAG
191501 CAAGATGAAA AGTAGAAATT TTTCTGACCC TTCCTACGTG TCCAGGCTGC
191551 TGCTGGAGTG TATTCATGGT GCTATGCTTA AAGTGAAAGC AAAAGCGTGC
191601 TTGTCTAATT TGCTTCTTTT CTAAATTGAA AAGGAAAGTA ATCACATTAA
191651 CGTCTACCAT AAAGCAGAGA GAAGCTGCCA GAAAGCTTGA GAGAAGCTAG
191701 AAGCAGCCAT ATCTACAAAT CCCAGTGCAA ACAAGAAGGA GGGATCCCAG
191751 CTGCACAAGC AGGAAGGCAG GAAGGTTTTA CAGCACTGTC TGCCGCCAGC
191801 CTTTGCGTAA CCATCTGCCC GCCCCAGCAT TGCACCTTTC AACCCACTCC
191851 CAGAGACCTC ACAGCTCCCA GTGGTCCTAG CTCCAGCTTA CTGCTGGCTG
191901 CTCTCCTCCT GGTTTGATCC TCCCTAGCAG CTGCCAAGCA TCACAGGAGG
191951 TAAGTGTGTG CTTGCTGTGC CTCTGCATTT TGCAGCCTGA AATGAATCCA
192001 GCCCTTGGAA CTCGCACTAG GGCATCGAGG AGTGCTTTCT GAAGCCTTCA

Z3 gene exon 1

192051 CTGAAACTTT TATTTTTCAG CTGCAGCCAT GGAGAGCCTG AGCAATGCCA
192101 ACAGCAGGTT TGCACTTGAT CTCTTCCGAA AGGTTAATGA GACGAACCCA
192151 TCAGGAAACA TTTTCTTCTC CCCTCTCAGT ATTTCTACTG CTCTGGCCAT
192201 GGTCCTCCTC GGGTCCAGAG GTAATACAGA GACACAGGTG CTGAAGGTCA
192251 GCAGCATTTT CGCTTGTTTT ATTAAAATTA AATGTTGTTC AGTTTTAGAG
192301 ACAAGGCAAG GGGAGGAGGG CGTTATTTGC GTGAGCTTGG GGCAAGGTTC
192351 CTGTCACTCC TGCTGACTCT TCCCCCCTGC TGCCACCTGC CTGCTGCACT
192401 CCAGAGCCCT CCTCTTGTGC TCACTGATAG CCCTTCTTTC TCACTTCATT
192451 TGGGTTAATT GATGAATCTG GAAACTAATT TCACTGATTT ATCAGTCTTA
192501 ATTTAAAATC GATTAGCATC TCCAGCAGCA AGTCTTTACT AGAGCTTGTG
192551 ATAGGACATG GGGGAACAGC ATTAAACAAA AAGGGAAGAT TTAGGCAAGA
192601 TATTTGTTAG AGGAAGTTTT TCCACTGAGA AAGTGGTGAG GTGGTGGCAC
192651 AGCTGCCCAG GGAAGCTGAG GGTGCCCCAT CCCTGGAGGT GTTCAAGACC
192701 AGGTTGGATG GGGCCCTGGG CAGCCTGAGC TGGTGGGTGG CTGCCCTGCC
192751 CACAGCAAGG CAGTGGAACT GGGTGGGCTT TAAGTTGAAT TCCAGCCCAA
192801 CCCCATTCTA TGATTCTATG AGCCTTTTCC ACAGAGAACT ATTGTTTTGC
192851 AATGTATACA TACATAATGG TATACATAGT AATGCTAAGT GTATCTTATA
192901 AATAAAAAAT AAAATATAGA GCTGTATTAT TCTAAGGCTG ACAACTGTTA
192951 CAATACATGG TGATGTTACC CAAGACCCAG TGTTATAGCA GCCAAGCACC
193001 CAGTATTTCT GAGGAGCAGA ACTCACGTGT CCATTCTCAT GGTATCCTTA
193051 GGTTGAGCAG CAGAGGTTAA ATGAAAATGG TGTGGCTCCT TTACTGGGGG
193101 CTTTGTTGTG GACCCAGCTC ATCAATCCTT TCCCACTCTC CACAACAGCA
193151 GTTGCAAACT GCAAATTCTC ATGTAGGTAG CAGTGCCAAT TCCCTCTCAG
193201 ACTCATGTTC AAAAGGGACC CTGCCTCTTT TTTAATTTGC AAGGCAAACA
193251 CCTGCTAGTG CAAGGGGAAG TATGAAAGAA TTGTCGCTGT AGTTCCTATT
193301 AACTTATTTG CCCTATGATT AAGTTCACCT TTGTATTCCG AACTTTAGGA

Fig. 1-74

```
193351 AGAACTTGTT TAGACCATTA ACTGCTGCCA TTCTTTGTGA AAAGACTATA
193401 AAACTGAATC ACTGCTTGTA GAAACAGACT TTGAACATAC ATTCCTTATA
193451 ACTCAACTGT CAGCCCCACC CAGGAAGAAT CTACTGAGAG CAGAAATAAT
193501 GCAAGAGAAG CATAGGGAAG TTGGAGATAG AAGGTTGGGA TGAATGGTTG
193551 GACTGGGTGA TCCTGTGTGT CTTTTCCAAC TTCAGTGATT CTATGATTCT
193601 AAGGTGTTTC AGCACAGTAA CCTTCTGTAA TGCACATTCC CATGGTATAA
193651 TGTTTAATTG ATGAGAACAT CAGTTAATTA AGGAGATGAT GACTGATGAG
193701 TGTGAAGGGT GTTTATAAGC ATGCAGAAAT CCATTTCTGG GATCATAATC
193751 CTACCTTAAG TTGGAATCAT AGAGTACACC ACGGTGGAGG GGATCCATGA
193801 GGATCCAGCT CCACACAGCA CCACCCACTA TGGTAGATCC TGCTGCCCAA
193851 CCTGCACACC TTGGCTAGTC AGCTTCCCTT CAGGTATCTG TATGCACGCT
193901 TTCATATTAT AACAGCTTTT AATTTTAAGG TGATAGTTGT CTGTAGAAGC
193951 ACTTATATTT TCATAAAACC AAAGGTTATA GCTCTCACAT TTTCCTAACA
194001 CCTCACCTTC CCTGAGTGCT CAGACAAGCT CAGTAGTCCA CGGAGGAAAA
194051 ACATGCAGAC AGCACCCTAT TAGGACTCTG GATCACAATT AACAGCTTCA
194101 GCTGTGGCTA ACTGTATTCA GCTACTGCTT TACAAGTGAC ATGGCTGGCA
194151 CAGCACTAAG GGACAGTTTC ACTTGTTCTT TGATGGTTAC AGCTTTCAGC
194201 TTCTTTCTGC TTTTGTTTTT CAACTTAACT ACCAAACAAA TACCATACAG
194251 ATATGCTGCA TGTTCTCTAT AAATACAGCA TTAGCAGTAG TTAGCTCATC
                                     Z3 gene exon 2
194301 TCTTTCATTT CAGACGTTTC ATTTTGATGA AGTTGAAAAT ATACACTCAA
194351 GATTCCGGGC TCTGACTGCA GACATCAACA GAAGGGATTC TTCCTGTCTC
194401 CTACGGATTG CCAACCGGCT TTATGGAGAG AAGTCCTACA GCTTTCTGCC
194451 GGTATGGGTA CACAGACCAT AGCTGTGTGG TGGAACCTGG GGGGAGGCTT
194501 TGTAACTTCA TCATCTGTTG CTCTCCTGCC TCCAGAACGC GCCCCATAGC
194551 AAAAATATCA CACCAGCAAG TCCAGATGTC AAAACTATCT TTCTGCATCA
194601 ATAAGCAGCA TAGCTCAGGT GTTGCTGTCT TTATAGGAAT GCAGCCATTT
194651 GAGTATTTGA GGTAAAAACA TGACTAGACA TCTAAAAGTT ACCAGGCAGT
194701 CAGTACGAGT GTTGTACACA TGCCTATAGA TGCAGAAATG CATATGCATC
194751 TGGACATCCT AAAGGATACG CCTAGAGGAT ATTACATAAC AAATCCCTTT
194801 CTTTGATAGT TCAGTTCTGC TGCTTTGGGG CTCAAGAGAA ATTGCAAGCC
194851 ATGTAGGTTC TTAGCTTAGA GTACAGATTA GCAATGCCCC ATTCCTCTGT
194901 CTGTTGTTTT TTAGGCTTTT CATTGCTCTA GTACTATATT ACTTAAAACA
194951 TTTTTGAAAA CATTTCTCTG GGGGGAGATT GCCATCATGT CTCAACAGCA
195001 TGCCTCTTTA CAAGGGAACT GTACCTCTGC ATCTATTTAG GTACTGCTAT
195051 TTTTATCCCT CTCCAGCTCT TTCTGGAGT TTTTGTTTTC TTAGTCAAGC
195101 TT
```

*Fig. 1-75*

SEQ ID NO: 2

```
AAAGTCTAGAGTCGGGGCGGCCGGCCGCTTCGAGCAGACATGATAAGATACATTGATGAG   60
TTTGGACAAACCACAACTAGAATGCAGTGAAAAAAATGCTTTATTTGTGAAATTTGTGAT  120
GCTATTGCTTTATTTGTAACCATTATAAGCTGCAATAAACAAGTTAACAACAACAATTGC  180
ATTCATTTTATGTTTCAGGTTCAGGGGGAGGTGTGGGAGGTTTTTTAAAGCAAGTAAAAC  240
CTCTACAAATGTGGTAAAATCGATAAGGATCCGTCGAGCGGCCGC  285
```

*FIG. 4*

SEQ ID NO: 3

```
TGCGATCTGCCTCAGACCCACAGCCTGGGCAGCAGGAGGACCCTGATGCTGCTGGCTCAG   60
ATGAGGAGAATCAGCCTGTTTAGCTGCCTGAAGGATAGGCACGATTTTGGCTTTCCTCAA  120
GAGGAGTTTGGCAACCAGTTTCAGAAGGCTGAGACCATCCCTGTGCTGCACGAGATGATC  180
CAGCAGATCTTTAACCTGTTTAGCACCAAGGATAGCAGCGCTGCTTGGGATGAGACCCTG  240
CTGGATAAGTTTTACACCGAGCTGTACCAGCAGCTGAACGATCTGGAGGCTTGCGTGATC  300
CAGGGCGTGGGCGTGACCGAGACCCCTCTGATGAAGGAGGATAGCATCCTGGCTGTGAGG  360
AAGTACTTTCAGAGGATCACCCTGTACCTGAAGGAGAAGAAGTACAGCCCCTGCGCTTGG  420
GAAGTCGTGAGGGCTGAGATCATGAGGAGCTTTAGCCTGAGCACCAACCTGCAAGAGAGC  480
TTGAGGTCTAAGGAGTAA  498
```

*Fig. 5*

CHICKEN OVALBUMIN NUCLEOTIDE SEQUENCE

The present application claims priority from U.S. provisional patent applications, Ser. Ser. Nos. 60/462,953, filed Apr. 15, 2003; 60/465,215, filed Apr. 24, 2003; and 60/469,488 filed May 9, 2003, all of which are hereby incorporated by reference herein in their entireties.

FIELD OF THE INVENTION

The present invention relates generally to an isolated nucleic acid molecule comprising an avian ovalbumin transcriptional regulatory control region and linked matrix attachment regions. The invention further relates to recombinant nucleic acids and expression vectors, genetically transformed cells and transgenic avians that comprise an avian ovalbumin transcriptional regulatory region operably linked to a heterologous polypeptide-encoding nucleic acid insert. The present invention also relates to the expression and production of the polypeptide-encoding nucleic acid molecule under the control of the isolated avian ovalbumin transcriptional regulatory region.

BACKGROUND

Transgenic technology to convert animals into "bioreactor" for the production of specific proteins or other substances of pharmaceutical interest (Gordon et al., 1987, *Biotechnology* 5: 1183-1187; Wilmut et al., 1990, *Theriogenology* 33: 113-123) offers significant advantages over more conventional methods of protein production by gene expression.

Recombinant nucleic acid molecules have been engineered so that an expressed heterologous protein may be joined to a protein or peptide that allows secretion of the transgenic expression product into milk or urine, from which the protein may then be recovered. These procedures may require lactating animals, with the attendant costs of maintaining individual animals or herds of large species, such as cows, sheep, or goats.

Historically, transgenic animals have been produced almost exclusively by microinjection of the fertilized egg. The pronuclei of fertilized eggs are microinjected in vitro with foreign, i.e., xenogeneic or allogeneic, heterologous DNA or hybrid DNA molecules. The microinjected fertilized eggs are then transferred to the genital tract of a pseudopregnant female (e.g., Krimpenfort et al., U.S. Pat. No. 5,175,384).

One system that holds potential is the avian reproductive system. The production of an avian egg begins with formation of a large yolk in the ovary of the hen. The unfertilized oocyte or ovum is positioned on top of the yolk sac. After ovulation, the ovum passes into the infundibulum of the oviduct where it is fertilized if sperm are present, and then moves into the magnum of the oviduct, which is lined with tubular gland cells. These cells secrete the egg-white proteins, including ovalbumin, lysozyme, ovomucoid, conalbumin and ovomucin, into the lumen of the magnum where they are deposited onto the avian embryo and yolk.

The hen oviduct offers outstanding potential as a protein bioreactor because of the high levels of protein production, the promise of proper folding and post-translation modification of the target protein, the ease of product recovery, and the shorter developmental period of chickens compared to other potential animal species. The chicken ovalbumin gene is highly expressed in the tubular glands of the mature hen oviduct and is therefore a suitable candidate for an efficient promoter for heterologous protein production in transgenic birds. Efforts have been made to create transgenic chickens expressing heterologous proteins in the oviduct by means of microinjection of DNA (PCT Publication WO 97/47739).

Gene expression must be considered not only from the perspective of cis-regulatory elements associated with a gene, and their interactions with trans-acting elements, but also with regard to the genetic environment in which they are located. Chromosomal positioning effects result in variations in levels of transgene expression associated with different locations of the transgene within the recipient genome. An important factor governing the level of transgene expression is the chromatin structure around a transgene, and how it cooperates with the cis-regulatory elements. While the deletion of a cis-regulatory element from a transgenic lysozyme locus can be sufficient to reduce or eliminate positional independence of the level of gene expression, there is also evidence that positional independence conferred on a transgene requires the cotransfer of many kilobases of DNA other than just the protein encoding region and the immediate cis-transcriptional regulatory elements. Scattered throughout the chicken genome, including the chicken ovalbumin locus, are short sequences that resemble features of Long Terminal Repeats (LTRs) of retrovirus. The function of these elements is unclear but most likely may help define the DNAse hypersensitive (DHS) regions of a gene locus (Stein et al., 1983, *Proc. Natl. Acad. Sci. U.S.A.* 80: 6485-6489). Thus, flanking various avian genes are matrix attachment regions (5' and 3' MARs), alternatively referred to as "scaffold attachment regions" or SARs. The outer boundaries of the chicken lysozyme locus, for example, have been defined by the MARs (Phi-Van et al., 1988, *E.M.B.O.J.* 7: 655-664; Phi-Van & Stratling., 1996, *Biochem.* 35: 10735-10742). Deletion of a 1.32 kb or a 1.45 kb region, each comprising half of a 5' MAR, reduces positional variation in the level of transgene expression (Phi-Van & Stratling, supra).

The 5' matrix attachment region (5' MAR), located about −11.7 kb upstream of the chicken lysozyme transcription start site, can increase the level of gene expression by limiting the chromosomal positional effects exerted against a transgene (Phi-Van et al., 1988, supra). At least one other MAR is located 3' downstream of the protein encoding region. Although MAR nucleic acid sequences are conserved, little cross-hybridization is seen, indicating significant overall sequence variation. However, MARs of different species can interact with the nucleomatrices of heterologous species, to the extent, for example, that the chicken lysozyme MAR can associate with the plant tobacco nucleomatrix as well as that of the chicken oviduct cells (Mlynarona et al., 1994, *Cell* 6: 417-426; von Kries et al., 1990, *Nucleic Acids Res.* 18: 3881-3885). The lysozyme promoter region of chicken is also active when transfected into mouse fibroblast cells and linked to a reporter gene such as the bacterial chloramphenicol acetyltransferase gene. In each case, the presence of a 5' MAR element increased positional independency of the level of transcription (Stief et al., 1989, *Nature* 341: 343-345; Sippel et al., pgs. 257-265 in Houdeline L. M. (ed), "Transgenic Animals: Generation and Use").

The ability to direct the insertion of a transgene into a site in the genome of an animal where the positional effect is limited offers predictability of results during the development of a desired transgenic animal, and increased yields of the expressed product. Sippel and Steif disclose, in U.S. Pat. No. 5,731,178, methods to increase the expression of genes introduced into eukaryotic cells by flanking a transcription unit with scaffold attachment elements, in particular the 5' MAR isolated from the chicken lysozyme gene. The transcription unit disclosed by Sippel and Steif was an artificial construct that combined only the −6.1 kb enhancer element and the proximal promoter element (base position −579 to +15) from the lysozyme gene. Other promoter associated elements were not included.

Although individual cis-transcriptional regulatory elements associated with the chicken ovalbumin gene have been isolated and sequenced, together with short regions of flanking DNA, the entire nucleic acid sequence comprising the 5' upstream region of the ovalbumin gene has not been determined and has not been employed as a functional promoter to allow expression of a heterologous transgene.

What are still needed, however, are efficient transcription promoters that allow expression of transgenes in avian cells but with reduced positional variation.

What is also still needed is a gene expression promoter cassette that will allow expression of a transgene in the oviduct cells of an avian and efficient gene expression regardless of the chromosomal location of the expression system.

SUMMARY OF THE INVENTION

Briefly described, the present invention relates to novel isolated and recombinant nucleic acid molecules that comprise an avian ovalbumin transcriptional regulatory region and at least one matrix attachment region element.

The isolated and recombinant nucleic acid molecules of the present invention, because of the presence of at least one matrix attachment region, are useful for reducing chromosomal positional effects on a transgene operably linked to the ovalbumin transcriptional regulatory region and transfected into a recipient cell. Isolating an approximately 195 kb region of the chicken genome that includes regions upstream of the ovalbumin locus ensures that cis-elements are also included that will allow gene expression in a tissue-specific manner. The ovalbumin promoter region of the present invention, therefore, will allow expression of an operably linked heterologous nucleic acid insert by a transfected avian cell such as, for example, a somatic cell.

The present invention provides a novel isolated nucleic acid molecule of approximately 195 kb of the chicken genome, and truncated variants thereof, comprising a region of about 135 kb that is 5' upstream, and an approximately 45 kb region that is 3' downstream, of the ovalbumin-encoding region of the gene locus. The novel isolated chicken nucleic acid sequence includes matrix attachment regions both 5' and 3' of the ovalbumin gene and an ovalbumin transcriptional regulatory region that includes CR1 repeat elements, a proximal ovalbumin promoter. Interspersed among the elements are stretches of nucleic acid that serve at least to organize the elements in an ordered array. The novel isolated chicken genomic region also includes the ovalbumin-encoding region with a plurality of introns dispersed therein.

The present invention further provides recombinant nucleic acid molecules for operably linking an avian ovalbumin transcriptional regulatory region to a heterologous nucleic acid molecule insert encoding a polypeptide to be expressed by a transfected or transgenic cell. The heterologous nucleic acid molecule may be placed in frame with a signal peptide sequence. Translation initiation may start with the signal peptide and continue through the nucleic acid molecule to produce an expressed polypeptide having the desired amino acid sequence.

The sequence of the expressed heterologous nucleic acid insert may be optimized for codon usage by a host cell using approaches well known in the art. For example, codon usage may be optimized for an avian such as a chicken. This could be determined from the codon usage of at least one, and preferably more than one, protein expressed in a chicken cell. For example, the codon usage may be determined from the nucleic acid sequences encoding the proteins ovalbumin, lysozyme, ovomucin and ovotransferrin of chicken.

The recombinant nucleic acid molecules of the present invention may further comprise a polyadenylation signal sequence that allows transcription directed by an ovalbumin transcriptional regulatory region to extend beyond the heterologous nucleic acid encoding a desired heterologous polypeptide and to comprise a 3' untranslated region and a polyadenylated tail. Any suitable functional polyadenylation signal sequence may be linked to the 3' end of the heterologous nucleic acid insert, including the SV40 polyadenylation signal sequence, bovine growth hormone adenylation sequence or the like.

The recombinant nucleic acid molecules of the present invention may also comprise a chicken ovalbumin 3' domain. The 3' domain can include a 3' untranslated region of the ovalbumin gene, a polyadenylation signal and at least one MAR that, in combined action with an MAR upstream of the ovalbumin transcriptional regulatory region, may reduce positional variation in gene expression in transgenic avians.

Yet another aspect of the present invention is expression vectors suitable for delivery to a recipient cell, preferably an avian cell. The expression vectors provided by the present invention may comprise an avian ovalbumin transcriptional regulatory region that can be operably linked to a nucleic acid insert encoding a polypeptide, and optionally a polyadenylation signal sequence. The expression vectors of the present invention further comprise at least one MAR element, and preferably two MARs that flank the ovalbumin transcriptional regulatory region and which can non-randomly direct the insertion of the expression vector into the genome of a recipient eukaryotic cell. The expression vector may further comprise a bacterial plasmid sequence, a viral nucleic acid sequence, or fragments or variants thereof that may allow for replication of the vector in a suitable host.

Another aspect of the present invention is methods of expressing a heterologous polypeptide in a eukaryotic cell by transfecting the cell with a recombinant nucleic molecule comprising an avian ovalbumin transcriptional regulatory region operably linked to a nucleic acid insert encoding a polypeptide desired to be expressed and, optionally, a polyadenylation signal sequence, and culturing the transfected cell under conditions suitable for expression of the heterologous polypeptide under the control of the avian ovalbumin transcriptional regulatory region.

Also within the scope of the present invention are recombinant cells, tissues and animals containing non-naturally occurring recombinant nucleic acid molecules according to the present invention as described above. In one embodiment of the present invention, the transformed cell is a chicken oviduct cell and the nucleic acid insert comprises the chicken ovalbumin transcriptional regulatory region, a nucleic acid insert encoding a human interferon α2b that is codon optimized for expression in an avian cell, and an SV40 polyadenylation sequence. In another embodiment of the present invention, the nucleic acid insert encodes the heavy and light chains of an antibody.

Additional objects and aspects of the present invention will become more apparent upon review of the detailed description set forth below when taken in conjunction with the accompanying figures, which are briefly described as follows.

BRIEF DESCRIPTION OF THE FIGURES

FIGS. 1-1 to 1-75 illustrates the nucleic acid sequence SEQ ID NO: 1 of a region of the chicken genome that includes a chicken ovalbumin transcriptional regulatory region and the chicken ovalbumin gene, and matrix attachment regions 5' upstream and 3' downstream thereof.

FIG. 4 illustrates an SV40 polyadenylation signal sequence SEQ ID NO: 2.

FIG. 5 illustrates the nucleotide sequence SEQ ID NO: 3 of a human interferon α2b interferon optimized for expression in an avian cell.

DETAILED DESCRIPTION OF THE PREFERRED EMBODIMENTS

Figure 2:
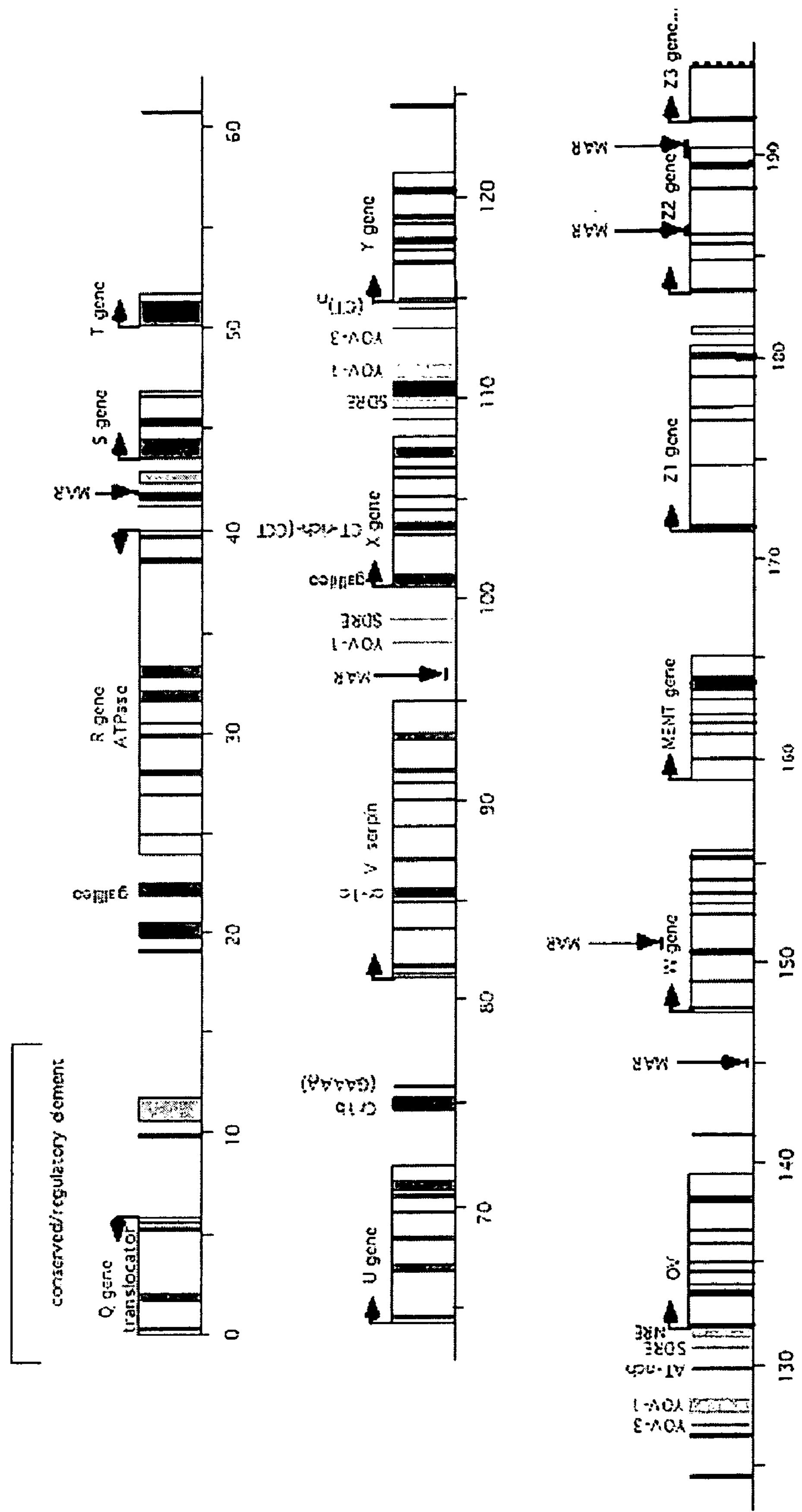
FIG. 2 schematically illustrates the chicken genomic region having nucleic acid sequence SEQ ID NO: 1, indicating the relative positions and orientations of regions having identity with known domains.

This description uses gene nomenclature accepted by the Cucurbit Genetics Cooperative as it appears in the *Cucurbit Genetics Cooperative Report* 18:85 (1995), which are incorporated herein by reference in its entirety. Using this gene nomenclature, genes are symbolized by italicized Roman letters. If a mutant gene is recessive to the normal type, then the symbol and name of the mutant gene appear in italicized lower case letters.

For convenience, definitions of certain terms employed in the specification, examples, and appended claims are collected here.

Definitions

The term "avian" as used herein refers to any species, subspecies or race of organism of the taxonomic class ava, such as, but not limited to chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred in commercial quantities. It also includes an individual avian organism in all stages of development, including embryonic and fetal stages. The term "avian" also may denote "pertaining to a bird", such as "an avian (bird) cell."

The term "nucleic acid" as used herein refers to any natural or synthetic linear and sequential array of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." The term "nucleic acid" further includes modified or derivatized nucleotides and nucleosides such as, but not limited to, halogenated nucleotides such as, but not only, 5-bromouracil, and derivatised nucleotides such as biotin-labeled nucleotides.

The term "isolated nucleic acid molecule" as used herein refers to a nucleic acid molecule with a structure not identical to a naturally occurring nucleic acid molecule and includes DNA, RNA, or derivatives or variants thereof. The term covers, but is not limited to, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions such that the resulting nucleic acid molecule still essentially encodes an ovalbumin transcriptional regulatory region or a variant thereof of the present invention.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin are suggested by the terms described above.

As used herein the terms "peptide," "polypeptide" and "protein" refer to a polymer of amino acids in a serial array, linked through peptide bonds. A "peptide" typically is a polymer of at least two to about 30 amino acids linked in a serial array by peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or noncovalently linked to labeling moieties.

The term "fragment" as used herein refers to any isolated portion of the subject nucleic acid molecule constructed artificially (e.g., by chemical synthesis) or by cleaving a natural product into multiple pieces, using restriction endonucleases or mechanical shearing, or a portion of a nucleic acid synthesized by DNA polymerase, including by PCR, or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical or recombinant methods well known to one of skill in the art.

The terms "recombinant nucleic acid" and "recombinant DNA" as used herein refer to combinations of at least two nucleic acid sequences that are not naturally found in a eukaryotic or prokaryotic cell. The nucleic acid sequences may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques. A recombinant polypeptide may be distinct from a naturally occurring polypeptide either in its location, purity or structure. Generally, a recombinant polypeptide will be present in a cell in an amount different from that normally observed in nature.

The term "gene" or "genes" as used herein refers to nucleic acid sequences that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to an RNA or protein that is encoded by the gene. "Endogenous gene products" are RNAs or proteins encoded by endogenous genes. "Heterologous gene products" are RNAs or proteins encoded by "foreign, heterologous or exogenous genes" and are, therefore, not naturally expressed in the cell.

The term "expressed" or "expression" as used herein refers to the transcription from a gene to give an RNA nucleic acid molecule at least complementary in part to a region of one of the two nucleic acid strands of the gene. The term "expressed" or "expression" as used herein may also refer to the translation from an RNA molecule to give a protein, a polypeptide or a portion thereof.

As used herein, the term "locus" refers to the site of a gene on a chromosome. In diploid organisms, pairs of genes control hereditary traits, each in the same position on a pair of chromosomes. These gene pairs, or alleles, may both be dominant or both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair.

The term "operably linked" refers to an arrangement of elements wherein the components so described are configured so as to perform their usual function. Control sequences operably linked to a coding sequence are capable of effecting the expression of the coding sequence. The control sequences need not be contiguous with the coding sequence, so long as they function to direct the expression thereof. For example, intervening untranslated yet transcribed sequences can be present between a promoter sequence and the coding sequence and the promoter sequence can still be considered "operably linked" to the coding sequence.

The term "transcription regulatory sequences" as used herein refers to nucleotide sequences that are associated with a gene nucleic acid sequence and which regulate the transcriptional expression of the gene. Exemplary transcription regulatory sequences include enhancer elements, hormone response elements, steroid response elements, negative regulatory elements, and the like.

The term "promoter" as used herein refers to the DNA sequence that determines the site of transcription initiation by an RNA polymerase. A "promoter-proximal element" is a regulatory sequence generally within about 200 base pairs of the transcription start site.

The term "matrix attachment region" as used herein refers to a region of a eukaryotic genomic DNA that can be bound to chromosomal scaffold proteins. Matrix (scaffold) attachment regions (MARs) are generally located between transcription units such that the transcription units are within chromosomal loops.

The bases of the loops are connected to the scaffold proteins through the MAR at each base. MARs and MAR-like homologs are identified as several recognizable nucleic acid sequences including, but not limited to, TG-rich spans, AT-rich regions and consensus sequences as described by Wang et al, *J. Biol. Chem.* 270:23239-23242 (1995). MARs may be identified by using suitable software such as, for example, MAR-WIZ™ (Futuresoft, Michigan, USA)

The term "internal ribosome entry sites (IRES)" as used herein refers to a region of a nucleic acid, most typically an RNA molecule, wherein eukaryotic initiation of protein synthesis occurs far downstream of the 5' end of the RNA molecule. A 43S pre-initiation complex comprising the elf2 protein bound to GTP and Met-tRNA$_i^{Met}$, the 40S ribosomal subunit, and faction elf3 and 3lf1A may bind to an "IRES" before locating an AUG start codon. An "IRES" may be used to initiate translation of a second coding region downstream of a first coding region, wherein each coding region is expressed individually, but under the initial control of a single upstream promoter. An "IRES" may be located in a eukaryotic cellular mRNA.

The term "coding region" as used herein refers to a continuous linear arrangement of nucleotides which may be translated into a polypeptide. A full length coding region is translated into a full length protein; that is, a complete protein as would be translated in its natural state absent any post-translational modifications. A full length coding region may also include any leader protein sequence or any other region of the protein that may be excised naturally from the translated protein.

The terms "complementary", "complementarity" or "complement" as used herein refers to two nucleic acid molecules that can form specific interactions with one another to form a base-paired double helix.

The term "probe" as used herein, when referring to a nucleic acid, refers to a nucleotide sequence that can be used to anneal or hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, and the like that are well known in the art.

The term "hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence complementarity with the nucleic acid molecule being used as a probe in the hybridization reaction, e.g., high temperature and/or low salt content that tend to disfavor hybridization of dissimilar nucleotide sequences. Alternatively, hybridization of the first and second nucleic acid may be conducted under reduced stringency conditions, e.g., low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° Celsius. Formulae to calculate appropriate hybridization and wash conditions to achieve hybridization permitting 30% or less mismatch between two nucleic acid molecules are disclosed, for example, in Meinkoth et al., 1984, *Anal. Biochem.* 138: 267-284; the content of which is incorporated herein by reference in its entirety. Protocols for hybridization techniques are well known to those of skill in the art and standard molecular biology manuals may be consulted to select a suitable hybridization protocol without undue experimentation. See, for example, Sambrook et al. 1989, "Molecular Cloning: A Laboratory Manual", 2nd ed., Cold Spring Harbor Press, the contents of which are herein incorporated by reference in its entirety.

Typically, stringent conditions will be those in which the salt concentration is less than about 1.5 M Na ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° Celcius for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1× to 2×SSC at 50 to 55° Celsius. Exemplary moderate stringency conditions include hybridization in 40 to 45% formamide, 1 M NaCl, 1% SDS at 37° Celsius, and a wash in 0.5× to 1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

The terms "percent sequence identity" as used herein refers to the degree of sequence identity between two nucleic acid sequences or two amino acid sequences as determined using the algorithm of Karlin & Attschul, 1990, *Proc. Natl. Acad. Sci.* 87: 2264-2268, modified as in Karlin & Attschul, 1993, *Proc. Natl. Acad. Sci.* 90: 5873-5877. Such an algorithm is incorporated into the NBLAST and XBLAST programs of Attschul et al., 1990, *J. Mol. Biol. Q*15: 403-410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Attschul et al., 1997, *Nucl. Acids Res.* 25: 3389-3402. When utilizing BLAST and Gapped BLAST programs, the default parameters of the respective programs (e.g. XBLAST and NBLAST) are used. Other algorithms, programs and default settings may also be suitable such as, but not only, the GCG-Sequence Analysis Package of the U.K. Human Genome Mapping Project Resource Centre that includes programs for nucleotide or amino acid sequence comparisons.

The terms "vector" or "nucleic acid vector" as used herein refer to a natural or synthetic single or double stranded plasmid or viral nucleic acid molecule (RNA or DNA) that can be transfected or transformed into cells and replicate independently of, or within, the host cell genome. The term "expression vector" as used herein refers to a nucleic acid vector that comprises a transcription regulatory region operably linked to a site wherein is, or can be, inserted, a nucleotide sequence to be transcribed and, optionally, to be expressed, for instance, but not limited to, a sequence coding at least one polypeptide.

The term "transfection" as used herein refers to the process of inserting a nucleic acid into a host cell. Many techniques are well known to those skilled in the art to facilitate transfection of a nucleic acid into an eukaryotic cell. These methods include, for instance, treating the cells with high concentrations of salt such as a calcium or magnesium salt, an electric field, detergent, or liposome mediated transfection, to render the host cell competent for the uptake of the nucleic acid molecules, and by such methods as micro-injection into a pro-nucleus, sperm-mediated and restriction-mediated integration.

The terms "recombinant cell" and "genetically transformed cell" refer to a cell comprising a combination of nucleic acid segments not found in a single cell with each other in nature. A new combination of nucleic acid segments can be introduced into an organism using a wide array of nucleic acid manipulation techniques available to those skilled in the art. A recombinant cell can be a prokaryotic cell, or a eukaryotic cell, such as, but not limited to, an avian cell. The recombinant cell may harbor a vector that is extragenomic, i.e. that does not covalently insert into the cellular genome, including a non-nuclear (e.g. mitochondrial) genome(s). A recombinant cell may further harbor a vector or a portion thereof that is intragenomic, i.e. covalently incorporated within the genome (including non-nuclear genome (s)) of the recombinant cell.

As used herein, a "transgenic avian" is any avian, as defined above, including the chicken, in which one or more of the cells of the avian contain heterologous nucleic acid introduced by manipulation, such as by transgenic techniques. The nucleic acid may be introduced into a cell, directly or indirectly, by introduction into a precursor of the cell by way of deliberate genetic manipulation, such as by microinjection or by infection with a recombinant virus. Genetic manipulation also includes classical cross-breeding, or in vitro fertilization. A recombinant DNA molecule may be integrated within a chromosome, or it may be extrachromosomally replicating DNA.

The terms "chimeric animal" or "mosaic animal" are used herein to refer to animals in which the recombinant gene is found, or in which the recombinant is expressed, in some but not all cells of the animal. The term "tissue-specific chimeric animal" indicates that the recombinant gene is present and/or expressed in some tissues but not others.

As used herein, the term "transgene" means a nucleic acid sequence that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout).

The term "chromosomal positional effect" as used herein refers to the variation in the degree of gene transcription as a function of the location of the transcribed locus within the cell genome. Random transgenesis may result in a transgene being inserted at different locations in the genome so that individual cells of a population of transgenic cells may each have at least one transgene, each at a different location and therefore each in a different genetic environment. Each cell, therefore, may express the transgene at a level specific for that particular cell and dependent upon the immediate genetic environment of the transgene. In a transgenic animal, as a consequence, different tissues may exhibit different levels of transgene expression. The term "reduced chromosomal positioning effect" as used herein refers to a decreased intercellular variation in the level of gene transcription because of a reduction in the number of sites of insertion of a heterologous nucleic acid molecule into the genome of a recipient cell. Consequently, a reduced chromosomal positioning effect provides a more uniform population of genetically transformed cells with respect to transgene insertion sites in the cellular genomes. In transgenic animals, different tissues may exhibit reduced variability in the levels of transgene expression.

The term "cytokine" as used herein refers to any secreted polypeptide that affects a function of cells and modulates an interaction between cells in the immune, inflammatory or hematopoietic response. A cytokine includes, but is not limited to, monokines and lymphokines. Examples of cytokines include, but are not limited to, interferon $\alpha$2b, Interleukin-1 (IL-1), Interleukin-6 (IL-6), Interleukin-8 (IL-8), Tumor Necrosis Factor-$\alpha$ (TNF-$\alpha$.) and Tumor Necrosis Factor $\beta$ (TNF-$\beta$.).

The term "antibody" as used herein refers to polyclonal and monoclonal antibodies and fragments thereof, and immunologic binding equivalents thereof. Antibodies may include, but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The term "immunoglobulin polypeptide" as used herein refers to a constituent polypeptide of an antibody or a polypeptide derived therefrom. An "immunological polypeptide" may be, but is not limited to, an immunological heavy or light chain and may include a variable region, a diversity region, joining region and a constant region or any combination, variant or truncated form thereof. The term "immunological polypeptides" further includes single-chain antibodies comprised of, but not limited to, an immunoglobulin heavy chain variable region, an immunoglobulin light chain variable region and optionally a peptide linker.

Techniques useful for isolating and characterizing the nucleic acids and proteins of the present invention are well known to those of skill in the art and standard molecular biology and biochemical manuals may be consulted to select suitable protocols without undue experimentation. See, for example, Sambrook et al, 1989, "Molecular Cloning: A Laboratory Manual", 2nd ed., Cold Spring Harbor, the content of which is herein incorporated by reference in its entirety.

Abbreviations

Abbreviations used in the present specification include the following: aa, amino acid(s); bp, base pair(s); kb, kilobase; cDNA, DNA complementary to RNA; SSC, sodium chloride-sodium citrate; DMSO, dimethyl sulfoxide; MAR, matrix attachment region; CPE, chromosomal positioning effect; BAC, bacterial artificial chromosome; YAC, yeast artificial chromosome.

The present invention provides novel isolated and recombinant nucleic acid molecules comprising an avian ovalbumin transcriptional regulatory region and at least one MAR element, which are useful as vectors for inserting a heterologous nucleic acid molecule into the genome of a recipient avian cell. The novel isolated nucleic acid molecules of the present invention are particularly useful for directing the incorporation of a heterologous nucleic acid that is under transcriptional regulation of an avian ovalbumin gene promoter, into the genome of a recipient avian cell while reducing or avoiding chromosomal positioning effects that would otherwise result from randomly distributed insertions of the heterologous nucleic acid molecule into the recipient avian genome. The present invention further provides methods of delivering a heterologous nucleic acid under the transcriptional regulation of an avian ovalbumin transcriptional regulatory region, to an avian cell, whereby the heterologous nucleic acid desired to be expressed under the associated avian ovalbumin gene transcriptional regulatory element can be integrated into an avian cell genome. As well as providing recombinant nucleic acids, vectors and derivatives thereof, the present invention provides transfected and transgenic avian cells and birds derived therefrom that are capable of producing a heterologous polypeptide in the serum or the white of a laid egg.

Nucleic Acids Comprising the Chicken Ovalbumin Gene and 5' and 3' MAR Elements

The novel isolated and recombinant nucleic acid molecules of the present invention comprise the chicken ovalbumin gene comprising transcriptional regulatory elements positioned 5' upstream of the ovalbumin-encoding region of the native chicken ovalbumin locus and which are necessary for the regulated expression of a downstream polypeptide-encoding nucleic acid, and at least one MAR element.

The inclusion of a MAR element, and preferably at least two MARs, in the same nucleic acid and flanking the ovalbumin gene region, may confer positional independence to a transfected gene operably linked to the ovalbumin transcriptional regulatory region. While not wishing to be bound by any one theory, it is believed that the 5' and 3' MARs of a transfected nucleic acid molecule of the present invention restrict the number of possible transgene insertion sites within the genome of the recipient avian cell, thereby reducing chromosomal positioning effects upon transcription levels. Thus the isolated novel nucleic acid molecules of the present invention are useful for reducing the chromosomal positional effects exerted on heterologous transgene expression. The heterologous transgene will be operably linked to the ovalbumin transcriptional regulatory region within a novel recombinant nucleic acid molecule transfected into a recipient avian cell. Included in the nucleic acid molecules of the present invention are a region of the avian genome encompassing a MAR upstream of the ovalbumin locus and cis-regulatory elements that may allow gene expression in a tissue-specific manner. The ovalbumin promoter region of the novel nucleic acid molecules is especially useful for directing expression of an operably linked heterologous nucleic acid in a transfected avian cell such as an avian oviduct cell.

Also within the scope of the present invention that nucleic acid molecules further comprising a region of the chicken ovalbumin locus that is 3' of the ovalbumin-encoding region, or of a nucleic acid insert encoding a heterologous present invention includes at least one nucleic acid sequence encoding a 3' MAR element which may cooperate with a 5' MAR to limit the number of sites of insertion into the genome of an avian cell of a transfected nucleic acid molecule. In either event, the directed insertion induced by one or more MARs can reduce or eliminate chromosomal positioning effects, resulting in a more uniform level of gene expression of the heterologous nucleic acid insert in a population of genetically transformed cells.

(a) Isolated Nucleic Acid Encompassing the Chicken Ovalbumin Gene

One aspect of the present invention, therefore, is a nucleic acid molecule isolated from the genome of a chicken and comprising a proximal ovalbumin promoter suitable for directing transcription of regulation of a transcript encoding ovalbumin, and 5' and 3' MAR elements flanking the ovalbumin gene region.

BACs 120 and 77 containing overlapping regions of the chicken genome, were sequenced and compiled as the contiguous sequence SEQ ID NO: 1. BAC 120 includes the sequence from nucleotide position 1 to position 157354 of SEQ ID NO: 1. The sequence of BAC 77 begins at nucleotide position 157355 of SEQ ID NO: 1 to position 195102. The nucleic sequence of the 195,102 bp chicken genomic region SEQ ID NO: 1 is shown in FIG. 1. A schematic showing identifiable domains within SEQ ID NO: 1 that have sequence identity or homology to known domain families or previously identified genes mainly identified using BLAST, GenScan and MARWIZ software is shown in FIG. 2. BAC 26, constructed as described in Example 1 below and containing the entire nucleic acid insert SEQ ID NO: 1 less about 11.5 kb at the extreme 5' end, was deposited with American Type Culture Collection (ATCC), 10801 University Blvd., Manassas, Va. 20110, as ATCC No. PTA-5548 on Sep. 24, 2003, under the conditions set forth in the Budapest Treaty.

The nucleic acid molecule SEQ ID NO: 1 of the present invention has at least four MAR elements. One MAR element is 5' upstream of the ovalbumin gene, between about nucleotide positions 41701 and 41900. MAR-like elements are also between nucleotide positions 56001-56201, 56501-56901, 58401-58701, 76251-between nucleotide positions 56001-56201, 56501-56901, 58401-58701, 76251-76451 and 80151-80451. Another MAR element is between about 96401-96800. MAR elements located 3' downstream of the ovalbumin gene are at nucleotide positions about 144651-144850, about 150601-151600, about 156681-157181, about 157081-15781, about 163701-164100, about 186201-186590 and about 190101-190800 of SEQ ID NO: 1. The chicken ovalbumin gene ATG start codon is at nucleotide position 133372.

Also dispersed along the nucleic acid molecule represented by SEQ ID NO: 1 are other identifiable domains listed, for example, in Table 2 below, including several serpin- or serpin-like encoding genes, cis transcription regulatory elements of both the serpin-like and ovalbumin genes, and at least two other, putatively functional genes, X and Z. Between the various domains, genes or other elements are stretches of nucleotides, the functions of which may serve to maintain the position and configuration of the elements relative to each other.

The isolated nucleic acids of the present invention and derivatives and truncated variants thereof may be incorporated into a vector, such as a bacterial or yeast artificial chromosome. The BAC cloning system (Shizuva et al, *Proc. Natl. Acad. Sci* (*U.S.A.*), 89:8794:8797, (1992) has been developed to stably maintain large fragments of genomic DNA (100-300 kb) in *E. coli*. An exemplary BAC vector consists of the pBeloBAC11 vector that has been described by Kim et al, *Genomics,* 34:213:218 (1996). Genomic DNA can be partially digested, for example, using enzymes that permit ligation into either the BamH I or Hind III sites in the vector. It is contemplated that any suitable restriction sites may be used that are useful for incorporating genomic DNA into a selected BAC vector. Flanking these cloning sites are T7 and SP6 RNA polymerase transcription initiation sites that can be used to generate end probes by either RNA transcription or PCR methods. BAC DNA is purified from the host cell as a supercoiled circle. Converting these circular molecules into a linear form precedes both size determination and introduction of the BACs into recipient avian cells. A suitable cloning site may be flanked, for example, by two Not I restriction sites, permitting cloned segments to be excised from the vector by Not I digestion. Alternatively, the BAC vector may be linearized by treatment with the commercially available enzyme lambda terminase that leads to the cleavage at a cosN site. However, this cleavage method results in a full length BAC clone containing both the insert DNA and the BAC vector sequences.

One embodiment of the novel isolated nucleic acid molecules of the present invention, therefore, is an isolated chicken nucleic acid molecule encoding an ovalbumin transcriptional regulatory region and a 5' MAR. In one embodiment of the present invention, the novel isolated nucleic acid molecule further comprises a 3' MAR downstream of the ovalbumin gene. The isolated nucleic acid molecules of the present invention may also include nucleic acid elements such as, but not limited to, a transcription enhancer element, a negative regulator element, a hormone responsive element, an avian CR1 repeat element that together may constitute, in whole or in part, the ovalbumin transcriptional regulatory region, a proximal ovalbumin promoter and a signal peptide-encoding region. There are also stretches of nucleic acid between these constituent elements that organize the various elements into an ordered linear array. While the constituent elements of the ovalbumin transcriptional control region are preferably ordered as in sequence SEQ ID NO: 1, it is within the scope of the present invention for the cis-elements of the ovalbumin transcriptional regulatory region to be in any linear arrangement that will allow the formation of a transcript comprising the nucleotide sequence, or its complement, of a nucleic acid insert operably linked to the ovalbumin transcriptional regulatory region.

The novel isolated nucleic acid molecules of the present invention allow one skilled in the art to, for example, (a) make copies of those nucleic acid molecules by procedures such as, but not limited to, insertion into a cell for replication by the cell, by chemical synthesis or by procedures such as PCR or LCR, (b) obtain nucleic acid molecules which include at least a portion of such nucleic acid molecules, including full-length genes, full-length coding regions, transcriptional regulatory sequences, truncated coding regions and the like, (c) identify and obtain ovalbumin transcriptional regulatory region homologs found in other avian species such as, but not limited to, turkey, duck, goose, quail, pheasant, parrot, finch, ratites including ostrich, emu and cassowary and, (d) to obtain isolated nucleic acids capable of hybridizing to an avian ovalbumin transcriptional regulatory region nucleic acid and of being used as a probe to detect the presence of nucleic acid-related sequences by complementation between the probe and the target nucleic acid.

Such nucleic acid homologs can be obtained in a variety of ways including using traditional cloning techniques to screen appropriate libraries, amplifying appropriate libraries or DNA using oligonucleotide primers derived from the novel nucleic acid molecules of the present invention in a polymerase chain reaction or other amplification method, and screening public and/or private databases containing genetic sequences using nucleic acid sequences of the present invention to identify targets. Examples of preferred libraries to screen, or from which to amplify nucleic acid molecules, include but are not limited to avian BAC libraries, genomic DNA libraries, and cDNA libraries. Similarly, preferred sequence databases useful for screening to identify sequences in other species homologous to chicken ovalbumin transcriptional regulatory region include, but are not limited to, GenBank and the mammalian Gene Index database of The Institute of Genomics Research (TIGR).

Nucleotides used to construct the nucleic acids of the present invention can be labeled to provide a signal as a means of detection, using conventional labeling technologies such as radioactive labels, fluorescent compounds, enzymes and chemiluminescent moieties. Methods useful in selecting appropriate labels and binding protocols for binding the labels to the synthetic nucleotides are well known to those of skill in the art.

In one embodiment of the isolated nucleic acid molecule according to the present invention, the nucleic acid is isolated from a chicken.

In other embodiments of the isolated nucleic acid molecule according to the present invention, the nucleic acid molecule comprises a nucleotide sequence having at least 80% identity, at least 95% identity or at least 99% identity to the nucleotide sequence according to SEQ ID NO: 1, or the complement thereof.

In other embodiments, the isolated nucleic acid molecule of the invention comprises the nucleotide sequence according to SEQ ID NO: 1 or has the nucleotide sequence according to SEQ ID NO: 1. In another embodiment, the isolated nucleic acid molecule can be an allelic variant of SEQ ID NO: 1.

(b) Fragments and Variants of SEQ ID NO: 1

Fragments of the isolated nucleic acid molecules of the present invention also are within the scope of the present invention. As used herein, a fragment of a nucleic acid molecule refers to a nucleotide sequence having fewer nucleotides than the nucleotide sequence SEQ ID NO: 1 but which includes a nucleic acid sequence of the ovalbumin transcriptional regulatory region able to direct and regulate transcription of a nucleic acid, and at least one MAR element.

The isolated nucleic acid molecule having the sequence SEQ ID NO: 1 may be reduced in size by truncating regions that do not affect the expression of a heterologous nucleic acid placed under the transcriptional control of the ovalbumin transcription regulatory region. A truncated variant of the nucleic acid molecule of the present invention is understood to be any variant of SEQ ID NO: 1 less nucleotides at either the 5' and/or the 3' end of SEQ ID NO: 1. For example, it is contemplated that any of the nucleotides from positions 1-about 40500 may be individually, in part, or in total, deleted from the variant nucleic acid molecule. Similarly, nucleotides from positions about 151700, 164200, 186690 or 190900 to 195101 of the nucleic acid molecule having sequence SEQ ID NO: 1 may be removed, retaining 1, 2, 3, 4 or more of the MAR or MAR-like elements respectively located 3' at the chicken ovalbumin gene. Useful truncated variants of SEQ ID NO: 1, therefore, include, but are not limited to, from base position about 41000 to about 191500, to about 187000, to about 164500, to about 152000, or to about 145500 and from base position about 96000 to about 191500, to about 187000, to about 164500, to about 152000 or to about 145500. Other useful truncated variants of SEQ ID NO: 1 include regions from nucleotide positions about 56000, about 58350, about 76200 and about 80000 to about 191500, to about 187000, to about 164500, to about 152000 or to about 145500.

Therefore, the invention encompasses nucleic acid molecules which do not include regions that do not contribute to the desired functionality of inserting a heterologous nucleic acid into an avian genome with reduced or no chromosomal positioning effect. The region 5' upstream of the MAR located at nucleotide positions 41701-41900 of SEQ ID NO: 1, may be deleted to give a truncated variant of SEQ ID NO: 1. For example, the approximately 11.5 kb region extending from nucleotide position 1 of SEQ ID NO: 1 not present in BAC 26 may be deleted. Likewise, it is contemplated that other regions of SEQ ID NO: 1 as listed in Table 2, such as encoding the serpin-like proteins, may be selectively deleted.

Recombinant Nucleic Acids

Another aspect of the present invention is recombinant nucleic acid molecules comprising at least one, and preferably at least two, avian MARs and an avian ovalbumin transcription regulatory region, including the proximal promoter thereof. The recombinant nucleic acid molecules of the present invention are particularly useful for delivering a desired heterologous nucleic acid to a recipient avian cell while reducing chromosomal positional effects upon transcription from the integrated heterologous nucleic acid. It is contemplated that regions of SEQ ID NO: 1 may be omitted from the recombinant nucleic acid molecules of the present invention without substantially affecting the reduction in the CPE compared to a similar nucleic acid molecule not including MAR elements. For example, one or more of the serpin-encoding regions of SEQ ID NO: 1 listed in Table 2, below, may not be included.

The present invention, therefore, provides recombinant nucleic acid molecules that comprise at least one avian MAR and an avian ovalbumin transcription regulatory region optionally operably linked in a linear array to a selected heterologous or endogenous polypeptide-encoding nucleic acid insert, and which may express the nucleic acid insert when transfected to a suitable host cell, preferably an avian cell.

The nucleic acid insert, such as a heterologous nucleic acid can be operably linked 3' downstream of the ovalbumin proximal promoter and is thereby expressed as an RNA transcript by a transfected recipient cell. The heterologous nucleic acid may be inserted into the recombinant nucleic acid of the present invention 3' downstream of a region encoding a peptide leader region so that a heterologous polypeptide encoded by the inserted nucleic acid may include this leader region. It is within the scope of the present invention for the recombinant nucleic acid to have the nucleic acid insert encoding the desired polypeptide to be operably inserted into the ovalbumin coding region, or operably replacing the ovalbumin coding region in whole or in part. The generation of BACs comprising a heterologous nucleic acid under the transcriptional control of the ovalbumin gene control region according to the present invention are described in Examples 2 and 3, below.

To increase the efficiency of expression of the heterologous nucleic acid insert, a polyadenylation signal region may be included at the 3' end of the inserted nucleic acid to allow the transcript directed by the novel ovalbumin transcriptional regulatory region to proceed beyond the nucleic acid insert encoding a selected polypeptide thereby providing a transcript further comprising a 3' untranslated region and a polyadenylated tail. Any suitable functional polyadenylation signal sequence may be linked to the 3' end of the nucleic acid insert including, for example, the SV40 polyadenylation signal sequence SEQ ID NO: 2 as shown in FIG. 4, bovine growth hormone adenylation sequence or the like. It is further anticipated that the recombinant nucleic acid molecules of the present invention may comprise the chicken ovalbumin 3' domain, or a variant thereof. The ovalbumin 3' domain may comprise the ovalbumin 3' untranslated region, an ovalbumin gene polyadenylation sequence and at least one of the 3' MAR elements identified downstream of the ovalbumin-encoding region of SEQ ID NO: 1. If the heterologous nucleic acid is inserted within the ovalbumin encoding region, and in-phase with the ovalbumin gene, the polyadenylation signal region of the ovalbumin gene may be used.

In one embodiment of the recombinant nucleic acid molecule according to the present invention, the recombinant nucleic acid molecule comprises the nucleotide sequence according to SEQ ID NO: 1, or the complement thereof.

Another aspect of the present invention is a recombinant DNA molecule comprising a MAR element and an avian ovalbumin transcriptional regulatory region. In one embodiment, the ovalbumin transcriptional regulatory region is operably linked in linear array to a nucleic acid insert encoding a polypeptide sought to be expressed, and a polyadenylation signal sequence optionally operably linked thereto. It is contemplated that when the recombinant nucleic acid molecule is to be delivered to a recipient avian cell for expression therein, the sequence of the inserted heterologous nucleic acid sequence may be modified so that the codons thereof are optimized for the codon usage of the recipient species as described below. In a preferred embodiment, a MAR element is located 5' upstream of the ovalbumin transcriptional regulatory region. Suitable MAR elements, for example, are located at about nucleotide positions about 41701-41800 and about 96401-96800 of sequence SEQ ID NO: 1.

In one embodiment of the present invention, the recombinant nucleic acid molecule comprises the nucleotide sequence from nucleotides position about 40750 to 195101 of SEQ ID NO: 1. Various embodiments of the recombinant nucleic acid molecules of the present invention comprise a 5' MAR and/or a 3' MAR, and the ovalbumin transcriptional regulatory region. In one embodiment, the recombinant nucleic acid further comprises a T gene. In others, the recombinant nucleic acid further comprises at least one nucleic acid region selected from the group consisting of the U serpin gene, a V serpin gene, an X gene, a Y gene and a Z serpin derived from SEQ ID NO: 1.

Another embodiment of the recombinant nucleic acid molecules further comprises at least one avian MAR 3' downstream of the nucleic acid insert. Suitable MAR elements for inclusion 3' downstream of the ovalbumin transcriptional regulatory region of the recombinant construct of the present invention are found at nucleotide positions about 144651-144850, about 150800-151600, about 163701-164100, about 186201-186590 and about 190101-190800 of sequence SEQ ID NO: 1. In one embodiment of the recombinant nucleic acid molecules, the ovalbumin transcriptional regulatory region, the avian 5' MAR, and the avian 3' MAR are independently capable of hybridizing under high stringency conditions to the nucleic acid sequence according to SEQ ID NO: 1, or the complement thereof.

In various embodiments of the present invention, the recombinant nucleic acid molecule is inserted into a vector such as, but not limited to, a plasmid or viral vector.

Other embodiments of the recombinant nucleic acid molecules further comprise a plasmid or viral origin of replication. In one embodiment, the recombinant nucleic acid molecule is a bacterial or yeast artificial chromosome.

Yet another embodiment of the recombinant nucleic acid molecule according to the present invention, therefore, is a recombinant nucleic acid molecule comprising an avian ovalbumin transcription regulatory region, an avian 5' MAR, a heterologous nucleic acid encoding a heterologous polypeptide desired to be expressed by a recipient genetically modified cell, a polyadenylation signal sequence, and an avian 3' MAR, wherein the avian ovalbumin transcription regulatory region, 5' MAR, and the 3' MAR each independently hybridizes under high stringency conditions to the nucleic acid sequence SEQ ID NO: 1, or a complement thereof.

Polypeptide Expression Under the Control of an Avian Ovalbumin Promoter

Another aspect of the present invention of the novel isolated ovalbumin transcriptional regulatory region is increasing the amount of a heterologous protein present in a bird (especially the chicken) by gene transfer. Typically, a heterologous polypeptide-encoding nucleic acid insert transferred into the recipient animal host will be operably linked with the ovalbumin transcriptional regulatory region to allow the cell to initiate and continue production of the genetic product protein. A recombinant DNA molecule of the present invention can be transferred into the extra-chromosomal or genomic DNA of the host.

A useful application of the novel isolated and recombinant nucleic acid molecules of the present invention is to increase the amount of a heterologous protein present in a bird, (especially the chicken) by gene transfer. Typically, a heterologous polypeptide-encoding nucleic acid insert transferred into the recipient bird host or an isolated cell or cell-line from the bird will be operably linked with the ovalbumin transcriptional regulatory region to allow the cell to initiate and continue production of the genetic protein product.

The isolated nucleic acid molecule SEQ ID NO: 1 is useful for inserting therein a heterologous nucleic acid that is desired to be expressed as a transcript or, ultimately, as a polypeptide. A heterologous nucleic acid may be operably linked to the proximal promoter region of the ovalbumin gene at any position 3' downstream of the promoter that allows transcription from the heterologous nucleic acid and synthesis of the desired encoded peptide. Some, or all, of the ovalbumin-encoding region of the isolated or recombinant nucleic acids of the present invention may be replaced by a heterologous nucleic acid to be expressed under the transcriptional control of upstream ovalbumin gene control region. The heterologous nucleic acid may be inserted into the isolated or recombinant nucleic acids of the present invention so that the expressed amino acid sequences derived from the ovalbumin may be linked to the expressed heterologous protein either at the N-terminus or C-terminus thereof.

Any of the vectors of the present invention may also optionally include a sequence encoding a signal peptide that directs secretion of the protein expressed by the vector from the transgenic cells, for instance, from tubular gland cells of the oviduct. This aspect of the invention effectively broadens the spectrum of exogenous proteins that may be deposited in avian eggs using the methods of the invention. Where an exogenous protein would not otherwise be secreted, the vector bearing the coding sequence is modified to comprise, for instance, about 60 bp encoding a signal peptide. The DNA sequence encoding the signal peptide is inserted in the vector such that the signal peptide is located at the N-terminus of the protein encoded by the vector.

The expression vectors of the present invention comprise avian ovalbumin transcriptional regulatory regions that can direct expression of either fusion or non-fusion proteins. With fusion vectors, a number of amino acids are usually added to the desired expressed target gene sequence such as, but not limited to, a protein sequence for thioredoxin. A proteolytic cleavage site may further be introduced at a site between the target recombinant protein and the fusion sequence. Additionally, a region of amino acids such as a polymeric histidine region may be introduced to allow binding of the fusion protein to metallic ions such as nickel bonded to a solid support, for purification of the fusion protein. Once the fusion protein has been purified, the cleavage site allows the target recombinant protein to be separated from the fusion sequence. Enzymes suitable for use in cleaving the proteolytic cleavage site include, but are not limited to, Factor Xa and thrombin. Fusion expression vectors that may be useful in the present invention include pGex (Amrad Corp., Melbourne, Australia), pRIT5 (Pharmacia, Piscataway, N.J.) and pMAL (New England Biolabs, Beverly, Mass.), that fuse glutathione S-transferase, protein A, or maltose E binding protein, respectively, to the target recombinant protein.

The present invention further relates to nucleic acid vectors and transgenes derived therefrom that incorporate polypeptide-encoding regions, wherein a first polypeptide-encoding region is operatively linked to an avian ovalbumin promoter and a second polypeptide-encoding region is operatively linked to an Internal Ribosome Entry Sequence (IRES). It is contemplated that the first polypeptide-encoding region, the IRES and the second polypeptide-encoding region of a recombinant DNA of the present invention may be arranged linearly, with the IRES operably positioned immediately 5' of the second polypeptide-encoding region. This nucleic acid construct, when inserted into the genome of a bird and expressed therein, will generate individual polypeptides that may be post-translationally modified and combined in the white of a hard-shell bird egg. Alternatively, the expressed polypeptides may be isolated from an avian egg and combined in vitro.

Expression of a heterologous nucleic acid by a recombinant expression vector according to the present invention can be obtained using eukaryotic host cells, preferably avian cells, more preferably chicken cells, and still more preferably chicken oviduct cells, especially tubular gland cells. The use of eukaryotic host cells permit partial or complete post-translational modification such as, but not only, glycosylation and/or the formation of the relevant inter- or intra-chain disulfide bonds. Examples of vectors useful for expression in the chicken *Gallus gallus* include pYepSec1 as in Baldari et al., E.M.B.O.J., 6, 229-234 (1987) and pYES2 (Invitrogen Corp., San Diego, Calif.), incorporated herein by reference in their entireties.

One aspect of the present invention is methods of delivering a novel nucleic acid molecule of the present invention to the cytoplasm of an avian cell having a nucleus, thereby generating a transfected and genetically transformed avian cell. Such incorporation can be carried out by the various forms of transfection, depending upon the vector/host cell system. It is contemplated that the incorporation of recombinant nucleic acid molecules of the present invention into a recipient cell may be by any suitable method such as, but not limited to, viral transfer, electroporation, gene gun insertion, sperm-mediated transfer to an ovum, microinjection and the like.

In the various embodiments of these methods, the avian cell may be a chicken cell or a quail cell. In some embodiments of the methods of the present invention, the avian cell is within oviductal tissue of a bird, an isolated oviduct cell or primary cell line, or a sustainable oviduct cell line. Preferably, the oviduct cells are tubular gland cells.

Heterologous polypeptide can be produced by transfected cells of the invention in vitro, i.e., in tissue culture outside the body of a living animal. Alternatively, the nucleic acids of the present invention may be delivered to an animal such as a chicken, whereupon the nucleic acid may enter cells and be expressed therein. It is anticipated that the nucleic acids of the present invention may integrate into the genome of the recipient cells and then express the encoded, typically heterologous, polypeptide therein. Preferably, a heterologous nucleic acid is delivered to oviduct cells within a chicken for synthesis of the desired polypeptide and its deposition in the white of an egg.

Another aspect of the present invention is a eukaryotic cell transfected with an expression vector according to the present invention and described above. For example, in one embodiment, the transformed cell can be a chicken oviduct cell or cell line, including a sustainable cell line, and the transfected nucleic acid insert comprises the chicken ovalbumin transcriptional regulatory region, a 5' MAR and/or a 3' MAR, a nucleic acid insert encoding a human interferon $\alpha 2b$ and codon optimized for expression in an avian cell, and an SV40 polyadenylation sequence. In another example, the nucleic acid insert encodes an immunoglobulin heavy chain and a second chain under the transcriptional control of an IRES.

The transfected cell according to the present invention may be transiently transfected, whereby the transfected recombinant nucleic cid, such as DNA, or expression vector may not be integrated into the genomic nucleic acid. However, the transfected recombinant DNA or expression vector may be stably integrated into the genomic DNA of the recipient cell, thereby replicating with the cell so that each daughter cell receives a copy of the transfected nucleic acid. When the recombinant DNA or expression vector of the present invention is integrated into the genomic DNA of the recipient cell so that the cell is genetically transformed, it is anticipated that the MAR element(s) of the integrated nucleic acid will direct integration a limited number of integration site within the target genome, thereby producing a population of cells more uniform with regard to the level of expression of the heterologous nucleic acid.

The the present invention also includes a transgenic bird producing a heterologous protein expressed from a transfected nucleic acid according to the present invention. The transgenic bird is selected from a turkey, duck, goose, quail, pheasant, ratite, an ornamental bird or a feral bird. In a preferred embodiment, the avian is a chicken and the heterologous protein produced under the transcriptional control of the avian ovalbumin transcriptional regulatory region according to the present invention is produced in the white of an egg.

Viral Host Cell Transformation

Nucleic acid sequences or derivative or truncated variants thereof, may be introduced into viruses such as an adenovirus or vaccinia virus. Methods for making a viral recombinant vector useful for expressing a protein under the control of the ovalbumin promoter are analogous to the methods disclosed in U.S. Pat. Nos. 4,603,112; 4,769,330; 5,174,993; 5,505,941; 5,338,683; 5,494,807; 4,722,848; Paoletti E., 1996, *Proc. Natl. Acad. Sci.* 93: 11349-11353; Moss, 1996, *Proc. Natl. Acad. Sci.* 93: 11341-11348; Roizman, 1996, *Proc. Natl. Acad. Sci.* 93: 11307-11302; Frolov et al., 1996, *Proc. Natl. Acad. Sci.* 93: 11371-11377; Grunhaus et al., 1993, *Seminars in Virology* 3: 237-252 and U.S. Pat. Nos. 5,591,639; 5,589,466; and 5,580,859 relating to DNA expression vectors, inter alia, the contents of which are incorporated herein by reference in their entireties.

Retrovirus vectors and adeno-associated virus vectors provide efficient systems of delivery of genes into cells, and the transferred nucleic acids may be stably integrated into the chromosomal DNA of the host. Protocols for producing recombinant retroviruses and for infecting cells in vitro or in vivo with such viruses can be found in Ausubel et al., 1989, *Current Protocols in Molecular Biology* §§9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include psiCrip, psiCre, psi2 and psiAm.

Furthermore, it is possible to limit the infection spectrum of retroviruses and consequently of retroviral-based vectors, by modifying the viral packaging proteins on the surface of the viral particle (see, for example PCT publications WO 93/25234, WO 94/06920, and WO 94/11524). Roux et al., 1898, *Proc. Natl. Acad. Sci.* 86:9079-9083; Julan et al., 1992, *J. Gen. Virol.* 73:3251-3255; and Goud et al., 1983, *Virology* 163:251-254); Neda et al., 1991, *J. Biol. Chem.* 266:14143-14146), which are incorporated herein by reference in their entireties.

One retrovirus for randomly introducing a transgene into the avian genome is a replication-deficient ALV retrovirus. To produce an appropriate ALV retroviral vector, a pNLB vector may be modified by inserting a region comprising at least part of the ovalbumin transcriptional regulatory region, a MAR element and one or more exogenous genes between the 5' and 3' long terminal repeats (LTRs) of the retrovirus genome. Any coding sequence placed in-frame and downstream of the ovalbumin promoter will be expressed at high levels and especially in the tubular gland cells of the oviduct magnum because the ovalbumin promoter drives the high level of expression of the ovalbumin protein and is only active in the oviduct tubular gland cells.

Another viral gene delivery system useful in the present invention utilizes adenovirus-derived vectors (see, for example, Berkner et al., 1988, *BioTechniques* 6:616-629; Rosenfeld et al., 1991, *Science* 252:431-434; and Rosenfeld et al., 1992, *Cell* 68:143-155), incorporated herein by reference in their entireties. Suitable adenoviral vectors derived from the adenovirus strain Ad type 5 d1324 or other strains of adenovirus (e.g., Ad2, Ad3, Ad7 etc.) are well known to those skilled in the art. Introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA).

Yet another viral vector system is the adeno-associated virus (AAV). Vectors containing as little as 300 base pairs of AAV can be packaged and can integrate. In the present invention, at least part of the heterologous nucleic acid will include an operable region of the avian ovalbumin transcriptional regulatory region and a MAR element. An AAV vector such as that described in Tratschin et al., 1985, *Mol. Cell. Biol.* 5:3251-3260, can be used to introduce DNA into cells.

Other viral vector systems that may have application in the methods according to the present invention have been derived from, but are not limited to, herpes viruses, vaccinia viruses, avian leucosis viruses and several RNA viruses.

Non-viral Expression Vectors

Most non-viral methods of gene transfer rely on normal mechanisms used by eukaryotic cells for the uptake and intracellular transport of macromolecules. In preferred embodiments, non-viral gene delivery systems of the present invention rely on endocytic pathways for the uptake of the subject ovalbumin transcriptional regulatory region and operably linked polypeptide-encoding nucleic acid by the targeted cell. Exemplary gene delivery systems of this type include liposomal derived systems, poly-lysine conjugates, and artificial viral envelopes.

In a representative embodiment, a nucleic acid comprising the novel recombinant nucleic acids of the present invention can be entrapped in liposomes bearing positive charges on their surface (e.g., lipofectins) and (optionally) which are tagged with antibodies against cell surface antigens of the target tissue (Mizuno et al., 1992, *NO Shinkei Geka* 20: 547-551; PCT publication WO91/06309; Japanese patent application 1047381; and European patent publication EP-A-43075, all of which are incorporated herein by reference in their entireties).

In similar fashion, the gene delivery system comprises an antibody or cell surface ligand that is cross-linked with a gene binding agent such as polylysine (see, for example, PCT publications WO93/04701, WO92/22635, WO92/20316, WO92/19749, and WO92/06180, all of which are incorporated herein by reference in their entireties). It will also be appreciated that effective delivery of the subject nucleic acid constructs via receptor-mediated endocytosis can be improved using agents which enhance escape of genes from the endosomal structures. For instance, whole adenovirus or fusogenic peptides of the influenza HA gene product can be used as part of the delivery system to induce efficient disruption of DNA-containing endosomes (Mulligan et al., 1993, *Science* 260-926; Wagner et al., 1992, *Proc. Natl. Acad. Sci.* 89:7934-7938; and Christiano et al., 1993, *Proc. Natl. Acad. Sci.* 90:2122-2126, all of which are incorporated herein by reference in their entireties). It is further contemplated that a recombinant DNA molecule of the present invention may be delivered to a recipient host cell by other non-viral methods including by gene gun, microinjection, sperm-mediated transfer, or the like.

Another aspect of the present invention is a method of expressing a heterologous polypeptide in a eukaryotic cell by transfecting a cell with a recombinant nucleic acid molecule of the invention, as described above, and culturing the transfected cell under conditions suitable for expression of the heterologous polypeptide under the control of the avian ovalbumin transcriptional regulatory region.

In one embodiment of this aspect, the nucleic acid molecule is integrated into the genome of the recipient avian cell. In some embodiments the recipient avian oviduct cell is a chicken cell, preferably a chicken oviduct cell, more preferably an oviduct tubular gland cell.

The protein of the present invention may be produced in purified form by any known conventional techniques. For example, chicken cells, an egg or an egg white may be homogenized and centrifuged. The supernatant may then be subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC or other methods well known in the art of protein purification.

Expression of Heterologous Multimeric Proteins by Transfected Avian Cells

The present invention provides methods for the production of a multimeric protein by an avian cell, comprising the step of culturing an avian cell transfected with a first expression vector and, optionally, a second expression vector; the expression vectors may each have a transcription unit comprising a nucleotide sequence encoding a first heterologous polypeptide, a transcription promoter, and a transcriptional terminator operatively linked to the nucleotide sequence encoding a second heterologous polypeptide, such that the cultured avian cell produces a multimeric protein comprising the first and second heterologous polypeptides.

The isolated nucleic acids and recombinant nucleic acid constructs derived therefrom of the present invention are useful to express nucleic acid sequences of polypeptides that are optimized for expression in avian cells, and derivatives and fragments thereof. Such derivatives include, for instance, polypeptides with conservative amino acid replacements, that is, those within a family of amino acids that are related in their side chains (commonly known as acidic, basic, nonpolar, and uncharged polar amino acids). Phenylalanine, tryptophan, and tyrosine are sometimes classified jointly as aromatic amino acids and other groupings are known in the art (see, for example, "Biochemistry", 2nd ed, L. Stryer, ed., WH Freeman and Co., 1981). Peptides in which more than one replacement has taken place can readily be tested for activity in the same manner as derivatives with a single replacement, using conventional polypeptide activity assays (e.g. for enzymatic or ligand binding activities).

Regarding codon optimization, for example, if the recombinant DNA is transfected into a recipient chicken cell, the sequence of the nucleic acid insert to be expressed is optimized for chicken codon usage. This may be determined from the codon usage of at least one, and preferably more than one, protein expressed in a chicken cell according to well known principles. For example, in the chicken the codon usage may be determined from the nucleic acid sequences encoding the proteins lysozyme, ovalbumin, ovomucin and ovotransferrin of chicken. Optimization of the sequence for codon usage elevates the level of translation in avian eggs.

One embodiment of the recombinant nucleic acid of the present invention, comprises an insert encodes the human interferon α2b polypeptide. The exemplary nucleic acid sequence SEQ ID NO: 3 (FIG. 5) encodes the polypeptide human interferon α2b in accordance with avian cell codon usage, as determined from the nucleotide sequences encoding chicken ovomucin, ovalbumin, ovotransferrin and lysozyme.

The invention methods for producing multimeric proteins include immunoglobulins, such as antibodies, and antigen binding fragments thereof. Thus, in one embodiment of the present invention, the multimerie protein is an immunoglobulin, wherein the first and second heterologous polypeptides are an immunoglobulin heavy and light chains respectively. Illustrative examples of this and other aspects of the present invention for the production of heterologous multimeric polypeptides in avian cells are fully disclosed in U.S. Patent Application Ser. No. 09/877,374, filed Jun. 8, 2001, by Rapp, published as US-2002-0108132-A1 on Aug. 8, 2002, and U.S. patent application Ser. No. 10/251,364, filed Sep. 18, 2002, now U.S. Pat. No. 7,312,374, issued Dec. 25, 2007. by Rapp, both of which are incorporated herein by reference in their entirety.

Accordingly, the invention further provides immunoglobulin and other multimeric proteins that have been produced by transgenic avians of the invention.

In various embodiments, an immunoglobulin polypeptide encoded by the transcriptional unit of at least one expression vector may be an immunoglobulin heavy chain polypeptide comprising a variable region or a variant thereof, and may further comprise a D region, a J region, a C region, or a combination thereof. An immunoglobulin polypeptide encoded by an expression vector may also be an immunoglobulin light chain polypeptide comprising a variable region or a variant thereof, and may further comprise a J region and a C region. The present invention also contemplates multiple immunoglobulin regions that are derived from the same animal species, or a mixture of species including, but not only, human, mouse, rat, rabbit and chicken. In preferred embodiments, the antibodies are human or humanized.

In other embodiments, the immunoglobulin polypeptide encoded by at least one expression vector comprises an immunoglobulin heavy chain variable region, an immunoglobulin light chain variable region, and a linker peptide thereby forming a single-chain antibody capable of selectively binding an antigen.

Another aspect of the present invention provides a method for the production in an avian of an heterologous protein capable of forming an antibody suitable for selectively binding an antigen. This method comprises a step of producing a transgenic avian incorporating at least one transgene, wherein the transgene encodes at least one heterologous polypeptide selected from an immunoglobulin heavy chain variable region, an immunoglobulin heavy chain comprising a variable region and a constant region, an immunoglobulin light chain variable region, an immunoglobulin light chain comprising a variable region and a constant region, and a single-chain antibody comprising two peptide-linked immunoglobulin variable regions.

In one embodiment of this method, the isolated heterologous protein is an antibody capable of selectively binding to an antigen which may be generated by combining at least one immunoglobulin heavy chain variable region and at least one immunoglobulin light chain variable region, preferably cross-linked by at least one disulfide bridge. The combination of the two variable regions generates a binding site that binds an antigen using methods for antibody reconstitution that are well known in the art.

The present invention also encompasses immunoglobulin heavy and light chains, or variants or derivatives thereof, to be expressed in separate transgenic avians, and thereafter isolated from separate media including serum or eggs, each isolate comprising one or more distinct species of immunoglobulin polypeptide. The method may further comprise the step of combining a plurality of isolated heterologous immunoglobulin polypeptides, thereby producing an antibody capable of selectively binding to an antigen. In this embodiment, for instance, two or more individual transgenic avians may be generated wherein one transgenic produces serum or eggs having an immunoglobulin heavy chain variable region, or a polypeptide comprising such, expressed therein. A second transgenic animal, having a second transgene, produces serum or eggs having an immunoglobulin light chain variable region, or a polypeptide comprising such, expressed therein. The polypeptides from two or more transgenic animals may be isolated from their respective sera and eggs and combined in vitro to generate a binding site capable of binding an antigen.

Examples of therapeutic antibodies that can be used in methods of the invention include but are not limited to HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-1A cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD2O IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (CS) antibody (Alexion Pharm); D2E7 is a humanized anti-TNF-α antibody (CATI-BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-$\beta_2$ antibody (Cambridge Ab Tech).

Production of Exogenous Protein by Transgenic Avians

Methods for the production of heterologous protein by the avian oviduct and the production of eggs which contain heterologous protein involve providing a suitable vector and introducing the vector into embryonic blastodermal cells so that the vector can integrate into the avian genome. A subsequent step involves deriving a mature transgenic avian from the transgenic blastodermal cells produced in the previous steps. Deriving a mature transgenic avian from the blastodermal cells optionally involves transferring the transgenic blastodermal cells to an embryo and allowing that embryo to develop fully, so that the cells become incorporated into the bird as the embryo is allowed to develop. Another alternative is to transfer the transfected nucleus to an enucleated recipient cell which may then develop into a zygote and ultimately an adult bird. The resulting chick is then grown to maturity.

In an alternative embodiment, the cells of a blastodermal embryo are transfected or transduced with the vector directly within the embryo. It is contemplated, for example, that the recombinant nucleic acid molecules of the present invention may also be introduced into a blastodermal embryo by direct microinjection of the DNA into a Stage X or earlier embryo that had been removed from the oviduct. The egg is then returned to the bird for shell development and laying. The resulting embryo is allowed to develop and the chick allowed to mature.

In either case, the transgenic bird so produced from the transgenic blastodermal cells is known as a "founder" Some founders can be chimeric or mosaic birds if, for example, microinjection does not deliver nucleic acid molecules to all of the blastodermal cells of an embryo. Some founders will carry the transgene in the tubular gland cells in the magnum of their oviducts and will express the exogenous protein encoded by the transgene in their oviducts. If the exogenous protein contains the appropriate signal sequences, it will be secreted into the lumen of the oviduct and onto the yolk of an egg.

Some founders are germ-line founders. A germ-line founder is a founder that carries the transgene in genetic material of its germ-line tissue, and may also carry the transgene in oviduct magnum tubular gland cells that express the exogenous protein. Therefore, in accordance with the invention, the transgenic bird will have tubular gland cells expressing the exogenous protein and the offspring of the transgenic bird will also have oviduct magnum tubular gland cells that express the exogenous protein. (Alternatively, the offspring express a phenotype determined by expression of the exogenous gene in a specific tissue of the avian.)

The invention can be used to express, in large yields and at low cost, a wide range of desired proteins including those used as human and animal pharmaceuticals, diagnostics, and livestock feed additives. Proteins such as growth hormones, cytokines, structural proteins and enzymes including human growth hormone, interferon, lysozyme, and β-casein are examples of proteins which are desirably expressed in the oviduct and deposited in eggs according to the invention. Other possible proteins to be produced include, but are not limited to, albumin, α-1 antitrypsin, antithrombin III, collagen, factors VIII, IX, X (and the like), fibrinogen, hyaluronic acid, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), feed additive enzymes, somatotropin, and chymotrypsin. Immunoglobulins and genetically engineered antibodies, including immunotoxins which bind to surface antigens on human tumor cells and destroy them, can also be expressed for use as pharmaceuticals or diagnostics.

One aspect of the present invention, therefore, concerns transgenic birds, such as chickens, comprising a recombinant nucleic acid molecule of the present invention and which preferably (though optionally) express a heterologous gene in one or more cells in the animal. Suitable methods for the generation of transgenic avians having heterologous DNA incorporated therein are described, for example, in WO 99/19472 to Ivarie et al.; WO 00/11151 to Ivarie et al.; and WO 00/56932 to Harvey et al., all of which are incorporated herein by reference in their entirety.

In various embodiments of the transgenic bird of the present invention, the expression of the transgene may be restricted to specific subsets of cells, tissues or developmental stages utilizing, for example, trans-acting factors acting on the ovalbumin transcriptional regulatory region of the present invention and which control gene expression in the desired pattern. Tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences. The inclusion of a 5' MAR, and optionally a 3' MAR region, in the novel nucleic acid molecules of the present invention will allow the heterologous expression unit to escape all, or in part, the chromosomal positional effect and therefore be expressed at a more uniform level in transgenic tissues that received the transgene by a route other than through germ line cells.

In various embodiments of the present invention the transgenic avians comprise a recombinant nucleic acid comprising SEQ ID NO: 1, a truncated variant of SEQ ID NO: 1, or the complement thereof.

In one embodiment of the present invention, the transgenic avian is selected from the group consisting of a chicken, a turkey, a duck, a goose, a quail, a pheasant, a ratite, an ornamental bird or a feral bird. In a preferred embodiment, the avian is a chicken.

In various embodiments, the transgenic avian produces the heterologous polypeptide in the serum or an egg white, or both.

The present invention is further illustrated by the following examples, which are provided by way of illustration and should not be construed as limiting. The contents of all references, published patents and patents cited throughout the present application are hereby incorporated by reference in their entireties.

It will be apparent to those skilled in the art that various modifications, combinations, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

EXAMPLE 1

Construction of a Complete Ovalbumin Locus from Two Overlapping BACs

Figure 6:
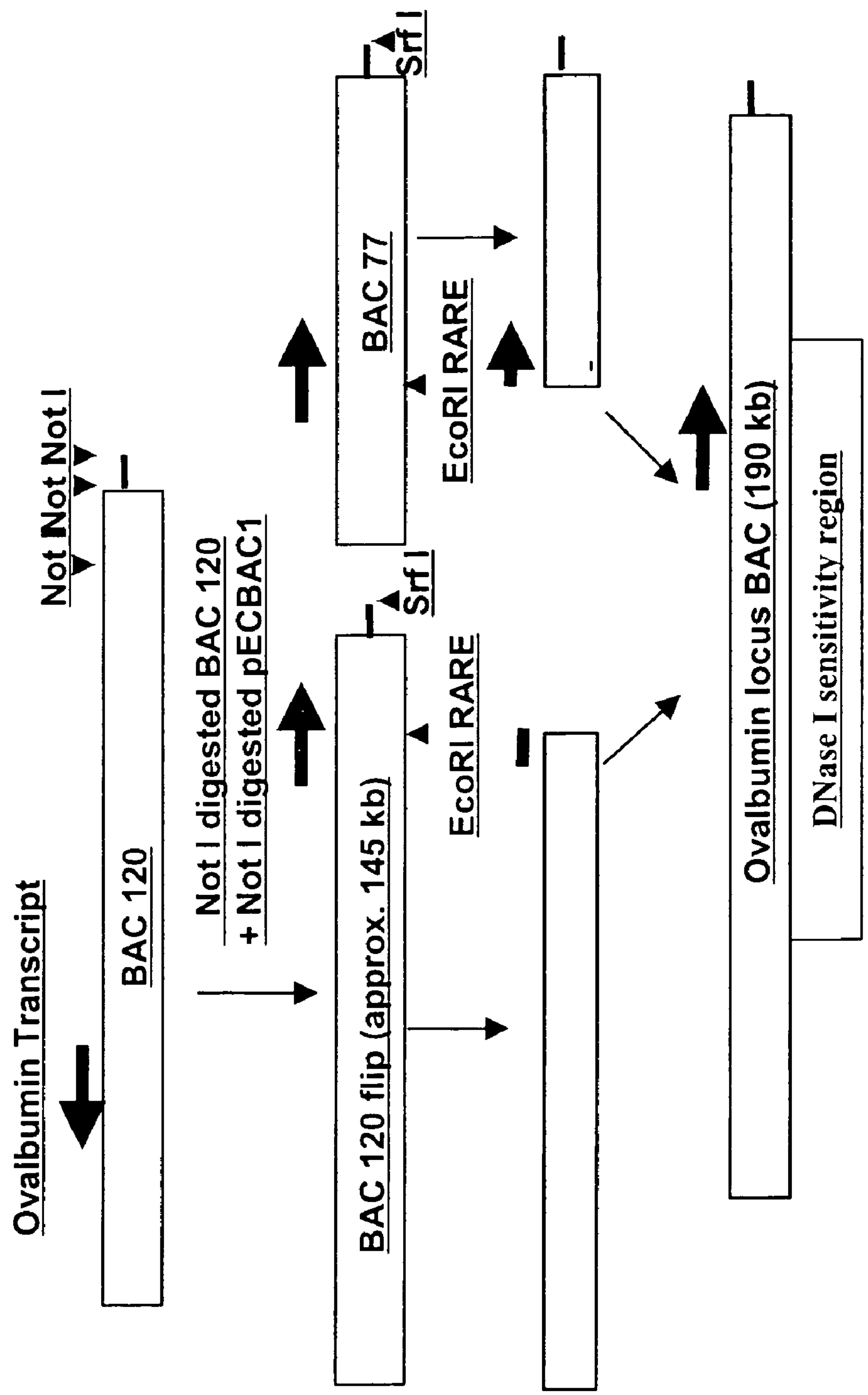
FIG. 6 illustrates the reconstruction of the chicken genomic region containing the ovalbumin locus.

A complete ovalbumin locus BAC was created from two overlapping BACs that together contained the complete ovalbumin locus, as shown in FIG. 6. The nucleotide sequences of BAC 120 and BAC 77 are in opposite directions with respect to the vector backbone pECBAC1.

BAC 120 was digested with Not I and a 145 kb fragment was re-cloned, but in the reversed orientation (flipped), into Not I digested vector backbone pECBAC1. This resulted in a deletion of a region of approximately 11.5 kb from the 5' end of the insert sequence of BAC 120 and which was upstream of the DNase I sensitivity region. The reversed BAC 120 'flip' and BAC 77 clones were digested with Srf I and RARE digested using an oligonucleotide targeted to an EcoRI site within ovalbumin. 5' and 3' fragments were isolated by CHEF gel electrophoresis, and ligated together to yield the complete contiguous ovalbumin genomic locus BAC.

EXAMPLE 2

Figure 3:
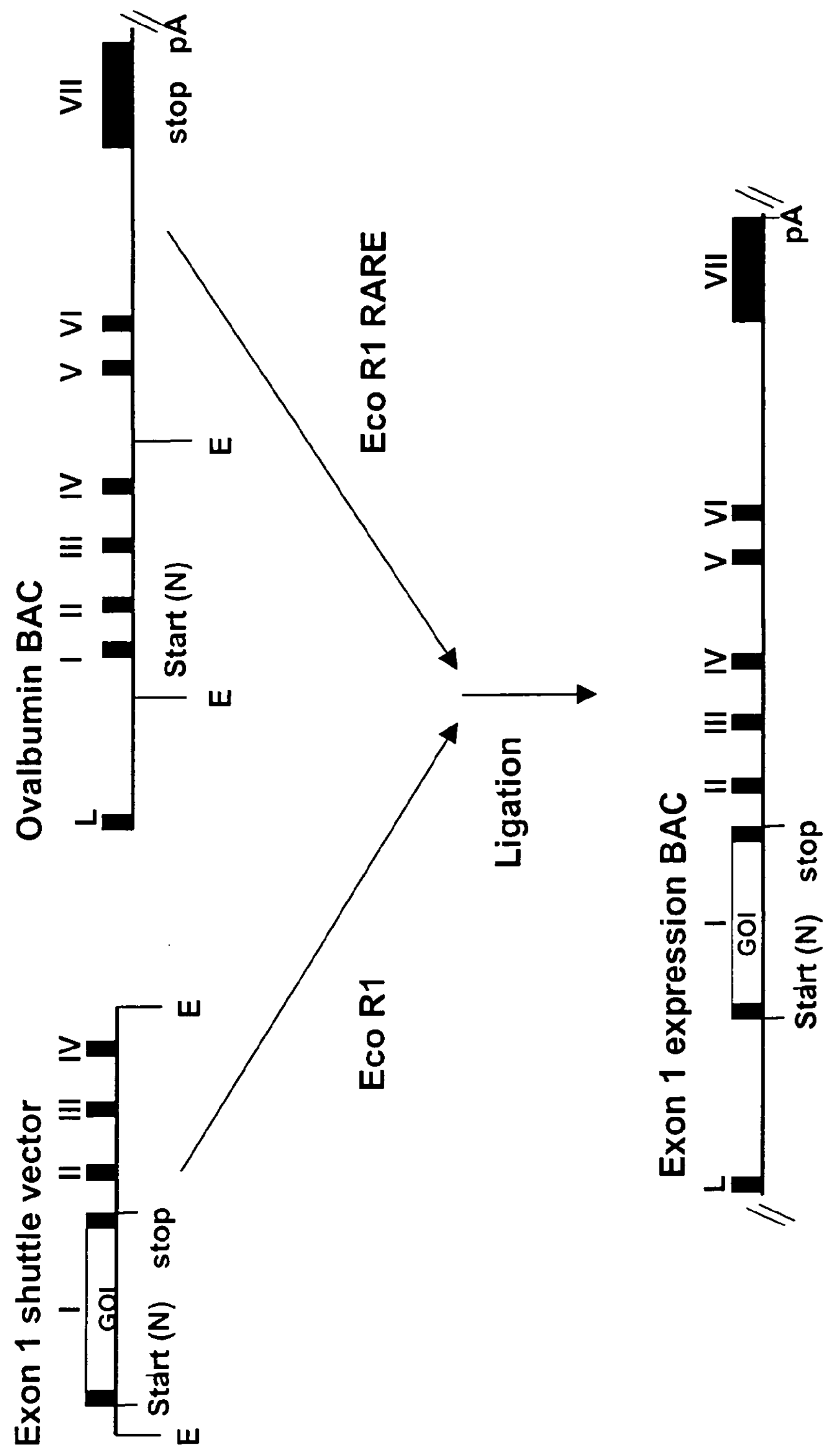
FIG. 3 illustrates schematically the construction of an expression bacterial artificial chromosome where the insert gene of interest is under the expression control of the chicken ovalbumin promoter. Genes of interest may be inserted into the native translation start site of the ovalbumin gene. L and roman numerals, ovalbumin exons; GOI, gene of interest; start, translation start site; stop, translation stop site; pA, polyadenylation signal; E, EcoR1 site.

Expression of a Heterologous Gene by a Chicken Ovalbumin Locus BAC cDNA constructs encoding immunoglobulin light-chain and heavy-chains of a human $IgG_1$ kappa monoclonal antibody were inserted in-frame with the ovalbumin translation start site of separate ovalbumin locus-containing BACs, as shown in FIG. 3. The immunoglobulin chain-encoding cDNAs were first inserted into a plasmid that contained a 2.7 kb EcoR1 fragment from the ovalbumin gene and which included the ovalbumin start site. The resulting vector was then digested with restriction endonuclease EcoR1 and cloned into an approximately 195 kb ovalbumin BAC which had been subjected to EcoR1 recA-assisted restriction endonuclease (RARE) digestion as described by Boren et al., 1996*, Prot. Sci.* 5,: 2479-2484 and incorporated herein by reference in its entirety.

Transgenic birds were created by cytoplasmic co-microinjection of human light-chain and heavy chain BACs (figure b) followed by ovum transfer as described in U.S patent application Ser. No. 10/251,364, now U.S. Pat. No. 7,312,374, issued Dec. 25, 2007, incorporated herein by reference in its entirety.

A hen carrying these constructs was grown to sexual maturity. Eggs were collected and the egg white material was assayed for the expressed human monoclonal antibody using sandwich ELISA as described by Harlow et al., *Antibodies: a Laboratory Manual*. 1988, Cold Spring Harbor, N.Y.: Cold Spring Harbor Laboratory. Xiii incorporated herein by reference in its entirety. The human monoclonal antibody was captured by a goat anti-human kappa chain specific monoclonal antibody and quantified with an alkaline phosphatase conjugated goat anti-human gamma detection antibody. Hen # AA698 expressed up to 1025 pg of human monoclonal antibody per ml of egg white.

EXAMPLE 3

Expression of a Heterologous Gene by a Chicken Ovalbumin Locus BAC

The open reading frame of the firefly luciferase gene was inserted into the ovalbumin translation start site of an ovalbumin locus BAC as shown in FIG. 3. The luciferase gene was inserted into a plasmid that contained a 2.7 kb EcoR1 fragment from the ovalbumin gene and which includes the ovalbumin start site. The resulting vector was then digested with EcoRI and cloned into an approximately 195 kb ovalbumin BAC which had been subjected to EcoR1 recA-assisted restriction endonuclease (RARE) digestion as described by Boren et al., 1996*, Prot. Sci.* 5,: 2479-2484 and incorporated herein by reference in its entirety.

Primary tubular gland cells isolated from the oviduct of laying quail (Sanders and McKnight, Endocrinology 116, 398-405(1985)), were transfected using the ovalbumin-luciferase construct or with a negative control CMV-IFN construct. Luciferase activity in cell extracts was analyzed two days post transfection (Table 1).

TABLE 1

| DNA | RLU |
|---|---|
| CMV-IFN | 60 |
| Ovalbumin Luciferase | 274 |

EXAMPLE 4

Basic Local Alignment Search Tool (BLAST) Analysis of the Complete Ovalbumin Promoter Sequence (SEQ ID NO: 1)

The complete approximately 195 kb ovalbumin promoter sequence (SEQ ID NO: 1) was submitted to the National Center for Biotechnology Information for BLAST alignments with database sequences. Further analysis was by using the GenScan and MARWIZ software. Percent identities between the ovalbumin gene region sequence (SEQ ID NO: 1) and corresponding known ovalbumin promoter features are listed in Table 2 below.

TABLE 2

Nucleotide positions of identifiable elements in the region of the chicken genomic within BACs 120, 77 and 26

| Nucleotide Positions[a] | Domain Identity |
|---|---|
| 5963-1 | **Q**[b] |
| 9730-9922 | CR1 |

TABLE 2-continued

Nucleotide positions of identifiable elements in the region of the chicken genomic within BACs 120, 77 and 26

| Nucleotide Positions[a] | Domain Identity |
|---|---|
| 10772-11935 | CpG Island |
| 18914-19088 | CR1-GG |
| 20106-20921 | CR1-GG |
| 39975-24820 | **R ATPase** |
| 41119-41177 | CR1-GG |
| 41586-41700 | CR1-GG |
| 41701-41800 | MAR element |
| 42221-42742 | CpG Island |
| 43505-46990 | **S Gene** |
| 50017-51427 | **T Gene** |
| 56001-56201 | MAR-like element |
| 56501-56901 | MAR-like element |
| 64599-71919 | **U Serpin Gene** |
| 58401-58701 | MAR-like element |
| 74883-75634 | CR1-GG |
| 75420-75634 | CR1b |
| 76251-76451 | MAR-like element |
| 80151-80451 | MAR-like element |
| 81125-94938 | **V Serpin Gene** |
| 81832-82120 | CR1 |
| 85473-85922 | CR1-GG |
| 88654-88797 | CR1-GG |
| 90120-90167 | CR1-GG |
| 96401-96800 | MAR element |
| 97884-97965 | Y:OV-1 element |
| 99080-99107 | SDRE element |
| 100602-107839 | **X Gene** |
| 110247-111200 | CR1-GG |
| 114779-121099 | **Y Gene** |
| 117849-118132 | CR1-GG |
| 131729-139290 | **Ovalbumin** |
| 144651-144850 | MAR element |
| 147721-155849- | **W Gene** |
| 150801-151600 | MAR element |
| 156581-157181 | MAR-like element |
| 157081-157581 | MAR-like element |
| 157132-157331 | MAR-like element |
| 159095-165114 | **MENT** |
| 163701-164100 | MAR element |
| 171633-180432 | **Z1** |
| 183204-190418 | **Z2** |
| 186201-186590 | MAR element |
| 190101-190800 | MAR element |
| 192078-195101 | **Z3** |

[a]Nucleotide positions of protein encoding regions are from the beginning of the first exon to the end of the poyadenylation signal-exons are shown in FIG. 1
[b]protein coding regions are given in bold Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. An isolated nucleic acid molecule comprising a nucleotide sequence having at least about 95% identity to the nucleotide sequence of SEQ ID NO: 1, or the complement thereof.

2. The nucleic acid molecule of claim 1 wherein the nucleotide sequence is at least about 99% identical to the nucleotide sequence of SEQ ID NO: 1, or the complement thereof.

3. The nucleic acid molecule of claim 1 wherein the nucleotide sequence is identical to the nucleotide sequence of SEQ ID NO: 1, or the complement thereof.

4. The nucleic acid molecule of claim 1 wherein the nucleic acid molecule consists of the nucleotide sequence of SEQ ID NO: 1, or the complement thereof.

5. A liposome composition comprising the nucleic acid molecule of claim 1.

6. The nucleic acid molecule of claim 1 further comprising a polypeptide encoding region.

7. The nucleic acid molecule of claim 1 further comprising an Internal Ribosome Entry Site.

8. The nucleic acid molecule of claim 7 further comprising a polypeptide encoding region operably linked to the Internal Ribosome Entry Site.

9. The nucleic acid of claim 1 comprising a vector selected from the group consisting of a bacterial artificial chromosome, a yeast artificial chromosome, a plasmid vector and a viral vector.

10. The recombinant nucleic acid molecule of claim 1 further comprising a polyadenylation signal sequence.

11. The nucleic acid molecule of claim 1 wherein the nucleic acid molecule comprises a bacterial artificial chromosome.

12. The nucleic acid molecule of claim 1 comprising a heterologous coding sequence encoding a pharmaceutical protein.

13. A vector comprising a nucleotide sequence having at least about 95% identity to the nucleotide sequence of SEQ ID NO: 1.

14. The vector of claim 13 selected from the group consisting of an artificial chromosome, a plasmid vector and a viral vector.

15. The vector of claim 13 further comprising an origin of replication selected from the group consisting of a bacterial origin of replication and a viral origin of replication.

16. The vector of claim 13 comprising a heterologous coding sequence encoding a pharmaceutical protein.

17. The vector of claim 13 comprising a nucleotide sequence having at least about 99% identity to the nucleotide sequence of SEQ ID NO: 1.

18. The vector of claim 13 comprising the nucleotide sequence of SEQ ID NO: 1.

* * * * *

SEQUENCE LISTING

```
<160> NUMBER OF SEQ ID NOS: 3

<210> SEQ ID NO 1
<211> LENGTH: 195102
<212> TYPE: DNA
<213> ORGANISM: Gallus gallus

<400> SEQUENCE: 1

tgcaagcttg caagttttac tgtctcatat ggttcacata ccattcattt agcgtggcct      60

cacaaccaac ttgggaacca ctgccctaag taacaatacc tcacatatcc ataggatctt     120

caacaccatt ctgcttaaaa ttcaaatccc tttcattaaa atagaagata tttagataca     180

agataaatag agcatatgtt tgtatgtggt catcttcagt tctagaaaca gtttcttctc     240

tcttatgcaa ctgaaagtag cttagtttcc acagccccgt gcagagcaat acggttgtac     300

tgctctcaaa gaagtaccaa cacaacatgc atcagcagag ttgcacaaga ctactgaaat     360

aaaatttgct tagctgctag tgaaaacata agtatccttg cttgtaaaca aaagcataag     420

tcatttcaca cacctccatt tgcagggctt cagctaatcc tcgaagagca aacttggtcg     480

gagaataggc tgtataacca aaaaggccta attgcccagc ctgagatgat acaaacacaa     540

tccttcccat ccgtcgttcc ttcatggtag agatgactgc acgactcggg taaacactac     600

ctagataatt gactgccatt aatctctgtg ggaaaaaaaa aagatattaa aatggtattt     660

cagtcactga ttcagaattc ttcagatgtt tagttttatt tctccaaaat ccctactgag     720

gcttgcttta acatcaaact ccactacatt tctatcagcg agcaaagtaa acaattgttt     780
```

-continued

```
tctactgtat ttgtttcata aacgttccat agcaaagaat ctcaccgtaa gacaaaaaga    840
aatgcactgt atatacaagt gttaatggca ttgaggatac taatgatgtg agctattatg    900
gctttcacaa agaaaaaagg gcaaattaca aaaaaaactg acttgaacag tgtctaggaa    960
gcaatccatt tatacaagaa gtacaaaaac attgaagtga aagtttaaag ggcttcctaa   1020
aaaaaagaaa gaggaaaaat tctatgtata tatgcacaag ctctcatctt ggcaggtaag   1080
attaattcct gtttcaatct cctgaagacc taaaacacaa ctggtggcct acacaagcaa   1140
taaaacagat tatttaccct tactgttaca cttactataa cattatgcct attcagtatc   1200
acgtgcattt tcagatggct ctgtgatgaa gtgagaatca aagtaaccag aaagtagaga   1260
ggctgtttgg tttttttaa tgtattttgg tttgggtttt actgttgttc ctttctttcc    1320
accaagctgc accaagttac caacagttta cataccgcag agttgaatgc tgacaagatg   1380
gattcttctt taacagattc aaaatatggg aaaaagaccc acacatcttc accaggaaaa   1440
aagagcccaa ttcagtgtct ttcacagcgt gttaaataaa agcacacatc aaccttcctt   1500
tccatcttga ggtccttccc tatcccaggt ggggaattca ctgttctgaa ttgtccatgg   1560
accaataatc aggtaaaaaa ataagttgca atccttgcaa atctaaaaat gcatacaaag   1620
accaccacta acgaaatata ttgctactca cacagtccgg aaagacacag taaaataatc   1680
tattccttag aacagcggaa tgacaaatta cttgcaatga aataaagcat gatcactcac   1740
ttcaaaagaa tttacttcaa tatcctcaaa ttttcctgta actgatgttc ctgcacagtt   1800
gacaagcagg tcaactggtc ccagcttctc ctgagcctgc aagaggacag aaattaagct   1860
ctccagcagg aaaaaaagca ttcatatagc atagtgtcat cattaaatat actgccactt   1920
gaaacacatc gtacagagat gaccttaata catacgctgg tggaacagtt gcttctcacc   1980
tgttttagaa cgttctccac ctgttcatag tctttagata catcaacaga aatacacagc   2040
acaacctaaa aatggaaaat gaaagaacat attataacct cagtccaaga atggttggcc   2100
ccaagtctta caaaagaaac tgcacactgc ttcatgaggt catattaggg acaaaattag   2160
aaaaaaacaa gactaaaaaa aactgattag tggcacagag ctaaatatgc ctaaaaagtg   2220
atttaacgtt tactctttgt ctgggaacaa gaggttatgg atcttagttt gaacgataca   2280
ggaaaatgaa aatagacact ggcccagggg agaataaata aataaatagt aaaaaaaaga   2340
gagacagcaa tgtcttaatt tttgttgcag ctggaacgta ggtattgatt ttctttaaaa   2400
ctgctgatta catttagcaa cttgatctca gaatctaagt tttgaagcac cttccagtca   2460
acttccagcc aaaggaagca ctgactttgg ggtatcacca actgtaagat cactgccaac   2520
tccagcttgg ccggggattt acaaagagat tatcccctct gctaaacaac tatcaaggtt   2580
ctgaggcaac tcagtatctt gaaaggagaa gcaatcacat accacaatag aagtagagac   2640
tcctgtattc tcattctgat ttctacgtct tactttgtcc aattccctta aagctggttt   2700
gaggtgaaat aaagtcatca ccggattcta acaagcgtca tcagggtcac ttgtcatgaa   2760
gcacgccaac aaaaatgaag aaaagcttac caaagtgtaa ctaactgctt tggcagctag   2820
tcatttgtca gttttgcctc tggtcagact gcaacacttc ccagctacat aaacagaatc   2880
tgcttgccat tcctgtgcag caggttggct attcctgcct tccagcactg tgcatagctg   2940
gacatcggag taaacttgtg gtgcaagtta atggttggcc agcaagcatc tcccccttagg  3000
gcatttttag attttagaaa tatttatctt ttacataagt ttgagaacaa aaataacagc   3060
tgagctaaga taacactgat ttactatctg gatgtcttta caagatcagc aaggttaaaa   3120
```

-continued

```
atcacagttc catacgaaaa ttggacatcg gaccacagat cagttaatca tactgagaac   3180
aatatactca ggaactacta aagcttgtat tggctaccag cacattatac aattcatctt   3240
tttgcttcta ttattgtatt tcctttctgc tacattaagt tgattacctc cagtccagag   3300
catgcactgt gaatgtggtc ctaataaaca gactatgctg ccaggaagtc taatatcctc   3360
attccagttt ctcgtctttt gttctaatag cgcattatct gaccattcct aaagcattcg   3420
tttctcaata aaagctcaac tccactccca gtgaagtaac taggaatatt ccatactgag   3480
aaagtgattt taaccatttt ccaaaaaaat tatgggcaag catttcattt cactgcatcc   3540
ctttatttgt aaaggctgca ctgtcagcat tctaaataaa tcacatacaa atgtatttca   3600
gagaacacgt gccaaatcca acacctaaag gtacgttgac accagaatcc tggttctcaa   3660
tgcaacttag tttgacatat atatacatga gcagaatgca cagcatataa tcatgtaaaa   3720
actggtattt cctctggatt tttgctccct agcttggcat cttgcaaatg taacagcctc   3780
tgtggtctgg caacccatcc cagacaactc tatactttca gcaatcttct tgtacagcct   3840
ctgtctcttt cgctgccctc atttgtcagc ttcttatctg ccgttcttct tctatttgtg   3900
ttctttgaat ttagaacagg cagacttccc tgtgacaatg actacaactc aacagtaggt   3960
acacgagggc actcccacta cagccagatg aagtatggac aagtctaaat ttgctactgc   4020
taaaacaatc ctgtttagct cacactgaag cttgttcagt cttgaactta ctgaaatttt   4080
aactgaaact cttgcagaca catacctagt actcttctta agaaaacaga aatgtaagtc   4140
cacatctgtc aagcttggac agatttttaa caagagcatt gtgacagtgt ttgacaaagg   4200
atcaaagtca ttgtcaaccc tgggaagaga ctagagcaac taaagggaaa cccttactgg   4260
ggtttatttg tttttaaaag gggacaaaac gttgctcctc ctcacctcac atgacttcat   4320
atttcaagat aaatttgatc tgagtaaggc aacatgcaca gaaagaaaga tcaccttgaa   4380
ccatttgaca ggaatgagca aagacagaat cttgctgagt gttcttgata tcttcattta   4440
catcggctag tactaacatt gcttccaaat atccatcttt ctccactgct tcttttcagg   4500
agaatatcca acttatccat tcaccagatt attatacacc caatagacac caaatccctt   4560
atcacaaaca aattgcttgc acttgtaata aagaaaataa gaaccaacta ctggagcaca   4620
agagagagga aatcaaagat gcgatggtct caatgctgtt tcccgtctct tttggattat   4680
gagtattaag aaaaaaaagt tgtagtattt catcttgaag ctgtgttttt ttgaacacag   4740
aaagctgccc tattttaaaa catagcaccc cagcaagcat taatgcactc aaacagtgca   4800
ttaagcgtga atacattatt tatttaccaa agtacctcca gtgtttagaa acctcagtgc   4860
tttgccagga aaacagcaat acacagcaca acatagggaa tgaaatctga aaataagtac   4920
ctaaaattta ttccccatta caattgctgc atttacgatc tctcgaagag aaacttgaaa   4980
aaagtaggtt attctcctca atcttgaaca atacaaacac ttatcaagtg acagcaaatt   5040
gcagctatca aaaaaaactc taatacacct acaggtgaag ataccaatct ttttctctgg   5100
gaaaaaaagt tagcatacta accaggcaac atcaaatgta gctgagtttg gaacatcaca   5160
cgtagacaga ttggaatttt ttgaattcaa gtgaggcctc acctattttt aatcaaacag   5220
tttggtttta aaaaccagac tactgaagct atgttgaagc gactaccttg aaacacaaca   5280
gttataggta gcagcgatct tacctgcttg tcattaacag agtacttttc tatttccttc   5340
tttgtctgta acagcttgtt ctgaaacgga taataagaac agctaaagca ccgcagttat   5400
gagaacacat ttgtcttcag tatttcgaga agccctagaa acactctcta aaaacaagaa   5460
cattatcatc agctagcgat aacgctttac tatgttcatc ttagaggttt atgaacgtac   5520
```

-continued

```
aaaacatcaa ctccatgcca tagcaatgga agagttttaa ggcaagctca tcacaaactg   5580
catgttagat tacactactt acaaaggcag ccatctctac tctgcaaata catcacattt   5640
aaattattag gatcacctta aagcatacag tggaaaaaaa accaatgagt aattatcaat   5700
tcccaaatta ctcctcaacc ataccaattt cattaatata aggtagccag caaaaataca   5760
aatacgctta cctcatctct tgcaatcagt gttatgaaag ctccttgctt ataacattca   5820
atagcaatac attttccaat tccactggag cctccagtaa cctggaagtt atttgaaaag   5880
tcagttagtc cgttattctc atccctaccc ctgtatcata acaagtcaaa tcaaaactct   5940
aaaagtgtac tgagattcaa atatcaccca gtgaagtatg aacacatgag atatacaaaa   6000
gtttctttac ttactgagta cgaatggaaa aatgaaatct aactaccttg tcaggcaact   6060
ctctctgtcc caaaaaccag ctttacctta atggtatttt ttccatattt cttatgtcag   6120
gctcacttag acccactctc acgtgccttt gattaactta tttttgaagt acggtaatag   6180
ttataagttt gcaatcacta ttaacattaa gaacgcaatt acatcctgtc cctccatgcc   6240
aggctacaat aaaatgcata aaaagagcaa tcatagcttg tctgccaaaa acaccgtgta   6300
aacaaacaca atttaaaaag ttatcttctt tcttattaaa taaacatcct taatttgaca   6360
gctggccccc tgcagagcac gtctcacagt tcacatctgg atgctgaact gcctcaatgc   6420
ccttctgtgg ggatcccagt tctaagcctc cataagcctt tccttcttcc tctaaaccat   6480
aactctcagt ggtctcccat gcaaacggga aataaacagt ttgcctgcag acaaatgcaa   6540
ggcgatggct acaacccccc actaataaac aggttaaagt cacctgaaca ccccccctctc  6600
taccctccag aaaaatctat ttgtgaactc catttaaaac aaaacataga tggtgaccca   6660
actgctcttc ttcttatcgc aaataaaact gtcatcctga tactgacttt tggtgatttg   6720
ttcatttaaa cccagcctca gtttgtacgt gccttcagtc cttaaacaca cagagttgta   6780
ttttccttgt atggccaaat gtgttgaatt ttctcctaag agcgtatcac tgagaaaaga   6840
ttggaatgtt tcattgatga agggagttct gaaatacagg cttaaatatt tgagaaagag   6900
attcatattc ctctggaagt tgtcatttct gttctttatc aagacttcag agaaagtaag   6960
gtatcacctc tatttcaact atgagaaatg gaatgcactg agccaatcag tggaagagca   7020
aaggcttcca gtctcatctg cacgtgcctt tgttttgttt tcaggctcac taccctcaaa   7080
attctttcat attcctgggg gcagtaaagt caaaagagtt agaagtacgc tcccatgagt   7140
caccaagctc ttctttctta cgagtgtttc atcacaaacc ttcaaagaaa acagctcagt   7200
acacaaaggg tgatcatgta acctcagcaa acttattttc aacagattcc acagtttttg   7260
tctaatttgt ctgctgtcac cagtgggtca agaacttaga aagactaact tcaacttaaa   7320
cagagtttca tagacttccc ctattagaga aagtcgcttc aaagcagctt ctaatcgact   7380
ctttactacg ctaacctttg tgaatgactt taagatgcac gttctgttcc ggagatgttt   7440
aatgctgttg cattctgaat aaaggatggc tgcttcctaa gcaaattaag tctgtaagaa   7500
cgagtgttaa cgtttgggaa ccctagcatc atttaattct tcacaacaga aagaagttaa   7560
atttttagtt cattcccaaa gcacttttga agattccaat acatctctag aaggattagg   7620
agattcagtt tgatgtattc aggcaaacct cagttccaga gcactcatga gctgccttta   7680
cagattttca gcagcagctg gtacatcagc acaggaacta atgaatgcat gtggaagact   7740
gctccaattc ccatttttgg cacagcactg aggcacagct gattgctacc tgtacaaatt   7800
gctaagtgtc atgaacaggt caactacagc agtgtttgaa ggtgaaggtg gcataatgcc   7860
```

-continued

```
tatggcttgt tagacaacgt taacgttcac ttcggaaaga caaggtctga agtcaagcaa   7920
gaaagggaag tttttatttg cagtcatacc caagaacgct agatagggct catgtcagat   7980
tggtcagtga caaaaagcag aatcagttag ctaggaactt cagcatttag gtggaaggct   8040
gttactaata cgttggaggt tgttactaac atgcaccacg agatgcaatg taacagtaaa   8100
gaaacagaac aactcatcga tcaatgagta agcacaattc caaatcatca caactatcat   8160
cagaagcgat caaaatgaag acttgatatg ctctttccaa cagggcttgc tagctttcac   8220
tgagcagcag cacaggatgc aagctggctt cttgctttta gacagtactc taacagtagg   8280
cattcagttc cactgaaaca gaacatcccc gtaacttgct ccaattggct ggtgtgcctg   8340
actggactcc aaatgacctc ttcctgaacc acccatgtgc atttaagcca caggtcacgc   8400
tgctcccaat gcaagagcta caaagctgag acacggagat gggtcaactc caggaacacc   8460
caaagcctgc tgtccttatc tgatgggctc tgcagggaaa tgctgaaact actcctagtc   8520
ctgagatggc ccttacacct gtggcttggg catactgaag cttaactatg tccaagttaa   8580
aggccctgct caaactgaaa ggaagacaat cacaggcagc aaatatcctt acattcctgg   8640
catagttagc ctatgaaagc aaaaatacat ttaaaagcat tttgttttac taaataagca   8700
aaaactgatg cttgagtcaa cctgatagct gtgaagtcct tcctatttaa cagtgcccac   8760
tgagattacc aaaacacaca gcagatatgg aacaggaaaa cacccccaca agattagatc   8820
agtaatttgg agttctgtgg agctccattc ctctctaagc agaagagaca cctgtggtct   8880
cggtcccact ctaaagcata cctcatgtca cacagcaagt gactccagga gaggacagga   8940
gggaaaaaaa ccccaacaaa aaaacaacca cacattttct gcctcagatt tctgtccttg   9000
tacctcaaac acctagctct attaaccatt acaactgtta ggagcagaga gaaatagatt   9060
ctacaaatga ttaagtaggg tgtgaaaaaa tgctgattta aattgagaat tcaacaagta   9120
actgctagga aacaatatac acagtagcgt ccaaacacat tcaatgaccc tctttaagaa   9180
atactacagg tattctcctg cacatatgaa gggggaatta tacatacaga tcacacaaac   9240
agattttgac tttttctgtg aaaacacttc aaggaagttc ttaacagtgc tacggtcctg   9300
aatattttca tgacaccttc tgataatttc agtagcagag aacactcact cccattatac   9360
gatgcaagaa ttcaccttgc acatgtgatg tgtacagcct tcacaagtac agtttctaat   9420
ttacaaaact atcatccaat gtttttcctt acacaattca cccaaacatt tgaaacccaa   9480
acatgcaagt ctaacagcat cagggttatt agcagcacct acatatcaaa aaaactaaaa   9540
ctctgaaaca actgctccat gtttcatgtg tttgcacaaa tgctttcaga gcataactga   9600
agccatagtc aaacaagtgc ttctgccaga agcaatgcca ctgaagctga tcacccacag   9660
atttgtaccc tgatgccaat aaatacctac agcctttcct tctattggga tatgaacaca   9720
gttaatcctc cagaaggtgg tgacgcactg gaacaggttg cccaaggaag ttgtagatgc   9780
cccatccctg gaggcattca aggccaggct ggatgtggct ctgggcagac tggcctactg   9840
gttggcgacc ctgcacacag caggggggtt gaaactagat gctcattgtg gtccatttca   9900
acccaggcca ttctataatc ctacgaatag tcattttgag accatcactt atgtcaaatt   9960
caggttacgt ggctaataca attagcagta gtggctgtga gggaagattt ctccaacaag  10020
attattcttt gtcattttca ttgtgagcca actgaagtgg ctctttgaaa aaagaagaac  10080
cagcagagta gctttggaaa aagcgtaacg acacaaagaa aagacaacac tcgggataat  10140
cagattaaaa acaaacaggt ggacaatact ctgggataga atacactgaa cattttgttg  10200
cttactattc tgtttccacg caagcactgc agtaccctta ccctgcttca cctttgcttt  10260
```

-continued

```
tacacagtac agaaggattc ctgcttagca agagttaccg ctgtgggaag aacctcagag  10320
agccttcact cacgctctac tatctccagc aggacatgat gctgtaaagc cagttacaat  10380
acccagcaat acctattgca tcaagtaatt tgggaacact gttgcaactt ggacagctcc  10440
aagccgggac agctctatcc gcaaagagca gccctaaaac aaataggcag ataaaaatga  10500
acacaaacaa acaaggcacc acacagagct caaaaaaatc ccaaatgcca agcagctgtc  10560
aattccctcg cacctcagag gtctaacttc tgcattacac ccaagtcctg tagtaaccaa  10620
gtcctgtagg cagcctgcat gccctactca ccccccaaaa gcagattcag caagcaaaca  10680
gcacagctcc tctacacgga gcacaccacg ggtaactaca gctaagtccc cagagctgac  10740
tgaaggacca cagccgcccc gacccgctct cacgcaccca catgctccac acacacctgc  10800
aggcccctgg ctgctgctcc ccatcacgca cccgcccagc tttcagcggt acgctcctgg  10860
ggaaccgttc aaaagctata ttttcccgaa taaaccctcc caaaggctcg ctcctacaca  10920
gctgattaca gacaagccaa acgtcgctcg tggacacgga tacccgcgct gagtgccgcc  10980
tgaccgcttc ccttcgcgtc agcccgcccg tttcctcagc acgggtcgcc tttcagcccg  11040
tgccttccac cctcgtgagg agggccgcac tccagcacct cggcagatgc agcggggcct  11100
tccccgggac acggcggccg cggcctcccc gctccctcct cccgcccagc gccggcagcg  11160
gaccgctccc ccgcggtcgg tcagccagca gcggccggga tcggggtggg gagggggagg  11220
cgagaggcct cgttcgactc accacgacgt gtgcgccggg cagcttgagg ggcttggggc  11280
tgatgagcgg cgacaccatg tagaggagaa ggacgatggc cacgatgaag gcggccgcca  11340
ggagcagcat ggctcgggcc gggcttgccg ctggggaggg ggcggcgggc ggtgacaagg  11400
cccctggggc tgcgggaggc gccgagcgcg gcgcggcccg gcgcggcacg gacagcggga  11460
gtagaaccgg tgcccgcctg cgccgcggcg ccacggggcc acaggggagg gggaggagga  11520
agaggaggag ggaggaggag aacacggccg ccactccgcg ccctgattgg ctggtgggcg  11580
gggcgggcgc ggcctcgcga gcggggattg gccagtgagc gacgggaagg agctggcgga  11640
ttggccgaga ggcgggacgg cgctcggaga ttggagccgc aggctgtttg cagggtcacc  11700
gttggaggca aagggcggcg gagaagagag agttcctccg gagaagacgg ggtgcgggac  11760
ggcgcccccct acggtccccg cctagggcgg gtgaggcgag gagtgaggta ggccccgccc  11820
cttctcgtca cgtggggctt cccgccgaaa ggagggggcg tggctccgtg aggtgagaga  11880
cgggaggctg cgggcggcgt tcacgctctg gaacgcgagg gcagctgttt gtggggaaaa  11940
aaatgtgtag aagcgtggtt tcaaagcata ataataaaag attaactaaa acgaaaacgt  12000
cttgcagctc aaataaaatg attccgtgcc tacgttcaat atttccttcg ctgtttatga  12060
ctgaaaggaa ctccctgaaa tgatttatgt tgtaaacgct gtgcagcctc tgacttgtag  12120
aagggagttt gcagcgtacg cggctttacg gcctcggaga gattacgatt acgggcgaga  12180
gggcgtgcgg aagggtgtga agataatgca ggagatgaga ttggagcggg gagtaggcgg  12240
aaatgggagc agggctgcgg gcagggatta ggcagtcgtc aaggggagag caaagaatct  12300
ggaacaaaag aatccaggaa ttagttctgg aatgggattg agccgggatc gggcttcggt  12360
gacgctttga gagtggtgct gtggggtgga ggtgtgagga aatgagagga agaaagagcg  12420
cgtgctgagg taacagctgc cacggcaagg gtggggagag agctgacaaa gtggtgtgtc  12480
caaggaaagg cggtgtggaa tcgtaggcat ccttaaggct ggaaagggtc accaagtcca  12540
agcaccaagt ccaactagca gaagttggtg taggatatgg actaggaacg ctgcaagcac  12600
```

-continued

```
agataccgac ttcattcttt gcatacaggg cagtgtatgt gttatctttt gtagaatatt  12660
aattaaacac aaaggaggag attgataatg taatagagcc tatttatagt tatctagtgc  12720
agaatatggc gagacttgaa aagcccaaat gtcagcagca tggagataaa gcagacggag  12780
ataaatccat ctttcacaat gcgatatcgc tttcagaatc aacatgaggc aagggcatgg  12840
ataaaaacaa tcatctgcag ttaatttcta gtaaaatgaa ggttaaacat gttggtaggg  12900
ggcctctaaa aacctcaaat gcatgatatg ctcctgattg gtcacagtta ggatcacata  12960
ttactaaata tttgagaagc ccttgtagat taacgaggaa tcccctcggt gaattttatg  13020
cagaaatcca tactgtcttt tccttttagc taagtggcca ctttacaacc gtgtgattga  13080
caatccaggt agcgtccact cacattttgt tcctggggca gtgaagtgtc atgaatttat  13140
ctccaagaaa aacattcaaa agtgaagacc ttgtgaactg cttataactc accaatgtat  13200
cgccacagca gtaggttttt gactcttttt aggtatgcca gcaggcactg aagtttgccc  13260
tcctgagctg tctgctgtct ggtttgtatt tgtctcatgt gacctcattc actgaggaag  13320
tgcgttcctg acacacggga atggtttgct acgaaactct tttctcagtg actgtggaac  13380
tggaaattga accctaaaaa aaaaaagtgt tgaagccctc cagtccaaac tttggttgta  13440
cataaagcag tatttaatta atctgacctt gattaacaac atcaaaaagt gtaattttga  13500
agcacaaact gaccaaggta tgtatgtacc ttcgggatgg gtaagaaaat aaaaaggtta  13560
acacatgcta attgctttgc taattaatcc ttagaagcag cttcaacaca acagcgatgt  13620
gtttagagaa gaaaatcaaa tacaggtaga ttaaagcgtc caaactatag gaccagctgt  13680
ggttttctgc ttcctcagtt ctgttcatat aatctttcaa cagacgtttg cagtaacaat  13740
gttgtgggtt gagataaatc agtatgaaca aagcatggca accgaagtaa gaaagtagtc  13800
atttaaacac ggaaacaaat gtatgaattg ataatattac aacacaagtg actgatacta  13860
gaggtgtcct tttgatcttc ttgttcccaa agcatacaag gtacacacag aagagacaca  13920
ggctgtgtta agatgccatt aagagaaggc ataaaggttt gacagagcag gtagtgaggt  13980
tgcagcctgg acagactttc ttattgcact tgagtactca tctgctggat tttctggttg  14040
tgtcatattc acgttaggga gagaggaggg aaaaagagca ggatgcgtag gctactcagt  14100
gattaaacaa aaaaaaaaag ctggaaactt cttcatgtga tttccatcca gtcagtcctt  14160
ctgcttttag agaaagcagc atgaaggaaa aacttcagta gccaaggaga acaacttttt  14220
ccttctgttt tcctgaatta acttactttc ctctccaacc ttctcccttt tgtgtagcaa  14280
gcataggtgt tctatgctca tttcttaaga ggtctgttgc agtaatcatc ataagacatc  14340
aaaggcatgt tggcagttct tggattcctg caaagcttca agatttagaa tgatggcagt  14400
ctaggtgagt tgttcctggt caacaagctg tcttgatccc gtgtcccaaa tgagaagagc  14460
taatagggac ataagaactg aaatcagaaa aggatttaca taacatgctg gcagtagagg  14520
agaattgggc aagaaataat gatctgcaca tggtagtgac taaagcagtg tgactgaaat  14580
acttatcaca cccagctgct tgccttgctg ttcttcccca aacaaacaag caaatccctt  14640
gtagctgaac aatagcttct ttactggtcc atcacgctgg agagatcatc agctacccca  14700
tgcatagcag ggtgaaacag ctcccagagc actgtgcagg tcaaagtact atatgtaccc  14760
tgtctgctgg agtgctatca cggtgatctt ctgggtattc ctagaaggag atttcctgta  14820
ctcccaagct caacgtatca tccagaaagt gctcgcctgc agcagggacg ggttctggcg  14880
atctctgcag cttccagcta tgccgcatgc ccttatcgca atgaactcag gctgggctga  14940
tggcccaggt gctggaggct gccagcacgc aggcaggagg tggttatagc agctcaggct  15000
```

```
caggtcaaac caaggcttct tgctggggca gaggggactg actctgtggt gcaaaagcag  15060
gtagtatata tatatgtata tatatacaaa gcccagctac cagctgagag tcccaaggct  15120
gctgcagtag ttttgcaatg agcacacagg aaacaagaag atcgctgaga acactgctga  15180
aatcagattt ctgtcttcac acaggtcaag ctgatttaac tgtttaatgt aattgctgca  15240
gttgcttgga aaaaaaaaga aatagtaaaa ccatgtccaa aatgaaccat tcataactgg  15300
tggcccatta tgtgtcacag ccgatgttgt gctgaataaa taactgtaca ggtattttat  15360
atattgagca acatatttat tgaaacaaaa ataatttacc tcaaaccagc ggtaaaagga  15420
agtctttact gtctaattta aataggcata agttaaactc gggactgaga tgatcttgaa  15480
tttcatttgg tgcccatggt tctttttatg tggtacacct gcttacactt accatcacac  15540
tggagcagtt tgcttttgcc acccgaatgt cagacactgc tatagattta cagtagcttg  15600
ggggggctgc aggttggaag agggggttga ggcctcatca agtgccatgg caaaacaccc  15660
tcaagtaagc acggctggaa gcaggaagga tgagggaatg agctgccatt tcctttgcgc  15720
tggaaggatc actgctaaaa cttgtaaata tctgttagaa acaaacaggg acgttcactt  15780
tgtcctgtga tgcaagagca cccattctga atttttatct cctgcaaagt tgtatttaag  15840
ctgatgttta ccgtggacgt tcgtgttaca agatagcctt tgatactatc aataacaagt  15900
cctctttgat gaagtaaagc tacagagtca caaagcatgc acttgtctga ccctttgcct  15960
ggctgcctgt ccaaccacgt tgcaccacta cacccagccc cacgagacct gctccagggc  16020
caagggaatt gagcacttaa gggaaagtgc tttgtacaaa acatggcgct tatgagtttg  16080
aaaacgtaga tccaccaaaa cctcctcagg cacgatgagt atatttttc tccactactt  16140
acagcgctgt gaattctagt taagggcgtt ttgattccta aagaattttt ccttctaatc  16200
atagacgtac tccagtcctt attccagaag gcttactcct tgtattttga aggtcttatc  16260
ctgaaattgg gatgcagagc cattctgaaa atgacagtat tttaagactt tgctgcactt  16320
actctggctt cccacatacc ttcctcttgc aaccttccac ctcccagaac tgcagcccag  16380
cctatcctcc tctgccagaa aatcggatcc cacaggccct atctcacacc tcccggttcc  16440
ccatcctcat ggcagctgcc ctctttccca aggcactcta tggagcagca gaactgctga  16500
gtgcacaggg caaagatctg ccgttccgag agagcagaga agcatcgctc gggaatcact  16560
gcactgctgc agcactattg tattctgcct ttattcagag gcagtccttc acctatgaat  16620
atcactacta ccttactgaa tatatatttt caggaatatt ttcacttttt agccagatag  16680
gaagcggatt ttgtaattac ccttccagca acttacagcc aattactgtc tctcctcctg  16740
attcctgtcc agcaatttgg ttgcagttat tgcttctcca gagcgggcag aattttttgc  16800
tttaggaaat gtacacctcg aggtaatctt tgaagagtga caggttctaa agttcacaag  16860
tttgatctgc tttgggatta agctacctgc taaactacca cacgccatcc agtcaagcca  16920
tttctattat gtgcgtatgg ctgattctta tcacaaaaga tcaagttaat gatttgcagt  16980
cttcggcaag cctctggttt ctttgaactt gctttttgta agcgatattc tcgggtactt  17040
tttgtgcttg tgaagctact gcagtgctct ggagattttc tttgtgctcc tggctgtcag  17100
agttatccat ttctaggcct gcttggccat ccccatagca cggggagaac cgtactttcc  17160
cattgccctt gtacctgcac ttgtaaaaac gctagaggaa ctgaaattac ttcaagttcg  17220
tgccctgtcc tctttcaaag ccattctgag aactttcttt gcacaacctt tttacaagag  17280
ttaaatccgt ttctagttcc aggcaacaca cttgtcatac acagcgctgg caagggactg  17340
```

-continued

```
ctgtttattt cttgcttgga tgcaattaca cagccatgtg cccttgtttt cagtccctga  17400
tccattatct ttggcattta ctgcaaagaa gctgctgtta cgcaatggaa atttagatga  17460
tctctttttc ttagcttact tctcctctaa cccaagaaat gagtacagta tagcctgctg  17520
aatgcaagga aacctgcacc tgcaaacttt tctccccact gcgtcactac caaatatgtc  17580
agagttgctt gtacttctta agtctgtttc catcccctaa tggcacgaac cgttgccctc  17640
ctgttgtcag actgcaaaaa ggccagcttg tacagatttg ccctgtaggt ttgaatggaa  17700
gaagggaaaa aaatcagaga aactgccagc ttttgttctg ccgcttgtaa gcttgctttg  17760
gtagaaaagt tgaagaaata ggaacatgct ttgaaatagg attttaaaag gaatcagctt  17820
cttatcttcc ctttgggaaa aaatagtgtg aaggacagaa taaatcagac ggaaaaagaa  17880
agaaattgac gtaagagaac tagtcgggca gaaaggagga ggtggaaaat acccaaaagc  17940
agcaggaaag agggaggcac aggttgccaa ttaacacttc gatcaaagga aaggcccgat  18000
caaaaccttt ttcctcctct aagaagcatc accccttccc actgcttact gcaatgaagc  18060
gagcttttag actaagactc aagagaataa ccccaatacc agtaaagcct gcagaacttg  18120
ttttttttcat agctgacacc acagacaaac aaacaaataa ataaatagta gcgcagagca  18180
tcagcaccgt ggcagtcatt ccagcaatca cttccccacc gtgctctcct ataggagagc  18240
tgcagcacag gtcagcgtct cccaacccgt gcacttcttc acggacagat ttgcatcatg  18300
cagaccctca gattgcccag gaagaacaga actgcaatgc ccagaaagag tgtggaagct  18360
ctgagaattt atctgcctgc tggacagagc ccatctacac ctggaacaag cgggcacctc  18420
tctgtgctac cagtgctggg taaagaaagc tgtgcagcag ctcctccctg aacactggct  18480
acgttgtgac atcagccctg tggttcctgt ggcagctcct gcgcttctgc aactacatga  18540
gtctagctgg caggccacct gcttgtttcc atatcagcag cagccacgtg caccatgtgc  18600
accatgtgca gggggcctcc aggcaggtaa aaaaaacaaa caaacaaaaa catctcttaa  18660
ttacaggggc agagcagggc tggatacgaa caaacaaaac cataccaaaa caagcacacg  18720
tgtaaagagg aaaaaaaaat aaaataaatc acagctttgc agtttgtctg tcttcagagc  18780
aaatcaaggc tgtgattaat tcgttacaca tcagaactcc aagcaggctc aagctgagcc  18840
gttgcaactg gcattatgaa tggcacactt gaaaaacagc caggttgctt tccagattca  18900
tggaatcata tcatagaatc atagaacggc ctgggttgaa aaggaccaca atgatcatcg  18960
agtttcaacc cccctgctac gtgcagggtc gccaaccacc agaccaggct gcccagagcc  19020
acatccagcc tggccttgaa tgcctccagg gatggggcat ccacaacctc cttgggcaac  19080
ctgttccaag atgttagctt ctctaacatc ttaccacaac ataataatga aagaatattt  19140
aaaaaatccg tgatgggtag gaacttcctg gctgcagcct gtgctccagc cctcaggtgg  19200
tggaaggaaa taatcatttc tagttggaat tttcattttc tttttttttt cctcagcttt  19260
caagtaggca aacaattcac ttgtcttcca gagctcaaat cactgctgta agtaacagtt  19320
ttcatttgtc atttttattt cctctgtgag atggtgatat ttatagcaac attctcggtc  19380
ccttgcttgg atgacttgtg attgctacgg ttcttgtaac agcattgcca gaacagtagc  19440
aaaaggcaac tgctccagca ccggtttttg taagccatta cctgtagaca ctcatctgcc  19500
tacagtagta tgagtcagtg gaaattactg tttatagttt acagaccaca tgtgacaccg  19560
agcatgtttg aaagcaaagt ccctgccttg aatagctgag atttaaatta gctgaggcag  19620
cagaggagga gggagggcaa gcaaaagcag gtcttgccaa tccatggcat ggtgcctagt  19680
gataggtcac caagcaggaa agaaaaccca accctggctt cattatcaac atcaggccta  19740
```

-continued

```
tgctcaggtg cccgtgactt atttcctgag aagtctcaaa acacgaccaa cacctgtttg  19800
aactcctata agagagctta gcgcctgcta tgatgcaggt aggatactga tgtttatttt  19860
cattactagt gcgtgacaca tccaaagaaa ttagctgtaa aatgtctagt attcctgcaa  19920
aagaacgtaa cagatcctgc acgtggcagg taccatgcac agatggcacc aacggatgga  19980
tgctggcttc ctcacacgtt gagttgttgt ggagttgctc tgatgaaggg gagcagcatt  20040
tgtgagcatt cattcatgga gctggagtct cctaagcaag gtaacgaatg caaaggtggg  20100
agtgttcaag tggcctaggc aggcttgggc agtgagccca ggtgaacctc atgaagtcca  20160
acagaaccaa atgcaagatc tggcctctgc attgaggcag ctcccactac caatacaagc  20220
tgggaaagga ctgagtgcag ccctgctgag gaagacctgg ggggtattgg tggttgggaa  20280
gctggacatg agccagcaat gtaccctcac agcccagaaa gccgactgta tcctgggctg  20340
catcaaaagt agtgtggcca gcacagcaag ggaggtgctc ctgcccctct actctgtgct  20400
ggtgaggcct cacctggagt actgcatcca gatgcggagt cctcagtaca ggagagacat  20460
ggacctgttg gagcgcatcc agaagaggac cacagaaatg ttctatggaa tgggacacct  20520
ctcttacaag aacaggctga gagagctggg gctgttcagc ctggagaaga gaaggctgtg  20580
agttgacctg atagcaacct ggcagtatct aaagggcagc tacaggaaag aagggaacag  20640
actttttaag cagggtctgg tgtgatagga gaaggggaaa tggtttcaag ctcaaagagg  20700
gaagatttaa gttagatata aggataaaat tttttacagt gaggatggtg aggcactgga  20760
acccagcgtt gtggttgaag ccctgacccc tgagactttc aaggcgaggc tggctcaggc  20820
cctgggcacc ctgatctagc tgtggtgtcc ctacgcactg caggggagtt gaactagatg  20880
gccttcagag gtcccttcca actgcaaaga ttctgtgatt ctagtaaaca gaaagcgtac  20940
agaacagtga cctagtcaaa aattgactat cggaagggcg tgtgggtaga ggtaggcagg  21000
caaaactgta attaggtcaa agaaaaatga caggacaagc ttatctaata tttgggatgt  21060
cagtagccaa atgccagtac agaggatgaa cagcaaccat taagaatttt ttacacaggt  21120
aattctgaca acagagaatt tggggagtaa taattgaaat attattggta aaacggtatt  21180
tttaaagaaa aatcaaggtg agagcacaat agctacaaca tagactaccc gctcaagaat  21240
agaaggagca atgttttgat aataataaag tagctgttgg aaaagcagca aaattggaag  21300
caaacagtcc atcaagtgct tgcaataggt tatgtaagtt gtgtgaatgg ctctaagtca  21360
gccatgatta ctaggatgaa tctggttaag acaaacatgt atggaagcca accatgaaac  21420
cacggtcatc attctggagg aaggaagaat tatgcagcaa aatcaaggca ttcctgcata  21480
tttcaataat tcagagctat taaaaagctc cctgtcacga taatcttcag aaataatgtg  21540
aaaaaaatac atagcggagc aaattttcat taggaagaca actaaataaa cacaaaaagt  21600
agatcaaaca atggctcaac agaatattta aagcagtttc tttgcttcag ctgccaaaga  21660
gcaaactacg atcaggtgca gctgactgat aggagcacaa aagctgattc aagggtatct  21720
gcccagacga cgtgtcgaca tgttctgctc cactcattaa aacaaaagca gtcaactcaa  21780
ctctgaaggc tagtagttga ataataataa taaaatcaaa accaaacaaa ccttaccaat  21840
ctctaagaca gacaaaacca gtacttaaac cagggaaggg acagaactct ggattcagag  21900
attaatcagg tgacgtgggc aaagatacag ccagagaatt taatgagttt ttctaactct  21960
atgaaaatat gtgttgagaa aatccactgt tagtcaatgg gaagaaacat ctgtgaagaa  22020
caaagcaagc aagcacagac acaactgatt taaaaactat tttacccaca gaacataatt  22080
```

-continued

```
tttcatactg cagtcagagg tagcaatagc actagaagtt aggaaaaaaa cgtaggccaa  22140
gtagtcaaag actagtcaca gctggcagca tgaaagatat gcaagtaatt tatccagtgc  22200
ttagaggctg tggttatata aagcaaatat aacctttaat caactataaa ccaggcagca  22260
ttgtttagag tacataggtt gctctgaaag taacgcctcc tatttatttc cacagaaact  22320
acaactgata cgaagagcat aacaacactg atagagcata ttcccagcta caaaacacta  22380
cttttcaact cagtcatcac gattagctct gcatttttgc cagcgatgag tgagagcctg  22440
catgctacgc gcacagaaat ctgcaccagt ggaggtgccc caccgtcact ggtgctgaaa  22500
tgcaccaccc actgcctcac cgcgctcaca tccactgctt ggtctccata aatattcagc  22560
aagcattgat gaatgtcaag aggtgtaatt ttttctgtgt ggaggaattc agtgacacct  22620
ctgcttcatt tgcgcttcca gccaaatgcc attctgtcat gctgcctctc tgctgccatc  22680
tgtcgcacag ccagagcaca taatggaata ctggtaggaa ggttcaacca ctaccgccat  22740
accaccaatg acaccttggg ctgatgatat actaaaataa atactacctt tggggtagca  22800
ctcatagttt aggttaaccc tgaaaactga agtaaatgac acctccccct acctcccgca  22860
gccatttagc tacatcttct gggataactt agctaggaat ctgtgataat atttcaactt  22920
atcctcattg tagaaaaaca gcagaacaaa aggttatcct tagagctgca gttctaaccg  22980
gcagtgttta tttggaatat ttctaaaaac aacttgaaac accaaacatt aatgtttcca  23040
tttccatgag caagtagcga gatgcaagtt taaaacatac agtatatttt tctacgttaa  23100
agataaggga ttacacagtt aggtttaggg aaacccatag gacaaactga cctacgacaa  23160
caacaaagaa acgcatttcc tgagaatttt aagattgcca taaggactgt catataggac  23220
tgttataaag gtcaattaac aagtaattca ggcagtagct tcaatcctcc aggtgagagc  23280
cctgccagtg cgtggctcgc ttctgaagtg ttcaccagag gcaacagagc aaagaatcct  23340
gctgcaacta agatcaagtt tacaaaccac agtaacttgc atctacactt gaatttcccc  23400
cgcttgccca caaaggtcca caaaaagatt tgcagccccc tgaatcacat tcacattttc  23460
cagtgcgaga ccgaagtaaa gctgcaaaac tgaatgactt tggaaagaac atttcattat  23520
gttagcaaac aaaagctcag caccttgcag atcaaagaat ttgtatttaa gtgttttgtt  23580
tagctgtcaa acgtagaaac aaaagtctaa acaaaagtga tagttttgaa agtaacactg  23640
aagaaatact caagaacata actgatgttg tacattttac ttcatttaag tacagcaaat  23700
ttcacccatc ctatgattta tcgagtacgc aaaatatgta catagaggaa accaaaaccc  23760
ataaaaagac aatcatctat gtgcatatgc gcatgtaaca tatgcacatg aaatgtgcaa  23820
ttttctttta atgcaagtta aacaaagcat atgcacaaca gagttgcaca accattacag  23880
aacagagtgt tctgggtatc ctcatgatgt ttcgcatcta cagccagtgc aaacttacaa  23940
ggcacaaact cagtgctgac accgtagtgt tgtaagttca ggcacatttc aatttgtagt  24000
tcttaaagat aataatcaac agaagtgcta cttctgtact aaagtgccag cctcttccca  24060
aagattaagc attaagttga tgtaacctgt acacagtaat gatcagcggc gttcggattt  24120
aacctaacct atcactgcaa ggtctgtggc tatatcgtgc tatgcgctcc acacctctga  24180
gggtatgctg cttcccaaaa tgcctccctc acactcttca aagactaccc atacctcgcc  24240
agccttgacg cgtggactct tacaggttac tactcaatgc tttttcctaa ccttagccaa  24300
acctctgata aaaccagact taaaaaatca gccatcggga aatctttcgc acacttgcat  24360
ttaacaaacc tttgctcaat tgcatagtga catgtgtatc agctaggaaa gaattaaaaa  24420
caaaagcttg ctgcttaagg caaaaatttt taacacagca cagcagaaaa agccaaatac  24480
```

-continued

```
cgggttcatc agtatttaaa caaagcactg gctcatacag tcttctcctc acagtgtttt  24540
cttccttact ttcacagcaa acacacacag tatgctcaat tagcaaattt tgttgcattt  24600
ctctaaacgg agtgattaac acataggctg actgctactg aaaacacctg acaaatcgct  24660
tctcttgcac cctcaaaaaa gggtttcttt ttgagcctac cagaagttga aaacccgctt  24720
gcgcccaggt ctaatataac agctaaaact gatcatttaa aaattacaaa tatttaccat  24780
gagttgccac atcactctgc taaaattgtg ttttccgtat tattttccaa tagaagacat  24840
ttaatagaca tctgaagaaa acaatacaat ataaaagcgt aagggtcttt gcaaacagat  24900
cttctattcc ttctgcaaag taagaaagga gagagtttat tggcatttat ttgcagtgcc  24960
atcgataaag acacgagaat acttaagaaa gcaaaaagtt ctagtgatcc acagacatct  25020
ttggcttagc cttcctgacc aaagtcttct gtaaacttct ttaacttctc caggtcctgc  25080
tcattaactg ttggctttgt gctagctagc gacctgagca tatcggcctg tgagaaagaa  25140
agcaagaaaa catgcattca gaaaacgtac cgctgctaac agtattgctg tgaagaaaag  25200
taagctttga aaagcctttt aaaacaagtt gactgtagga actcttattg aaacaaaact  25260
tcgagtaagc ctgaacattt ctgcacgtgg accacttttt aacctcctga cgatagacaa  25320
ttagtgagtt tttacaggac ttaagccaca atctgaggtt cagctttaaa acaattcatc  25380
cattcaacaa gtgttatcta ccactgctta ctgcaacaaa ctgagcttcc catcttacag  25440
attcgtattc caattcactt ttaaggacat caggttgaag tggaaaacca tcacacgttc  25500
ccacatattc caatgcccac caacacagaa tacttcatca ttgatctcca gcaaagtttt  25560
actgctcatg actgctaact tctgtttctt cagctcagtc agttttgtat atttacattt  25620
ggctactaga aaatggagtt cagaaaaaaa aaccacagag gtatgaactc aaattcagca  25680
gttaagaaac cttattaaaa aaaaacgtat ataaaaagtc ctggccaaag gcaaagcgag  25740
gagctgctca acacctcacg ttactataaa agcacagggt taagttaaag tcagcatcat  25800
gattttctag gctttctcat ctcatcgtac tacagacatc ctacttagaa agaattcaag  25860
tctgatcttt ttaatgacaa gaactgattc tggactctga aataagtccc tgtgcaactg  25920
tagcacatca gagtctacct tccattagaa gcactgaagg aattgtattt aattccagga  25980
aagactgatg aaaaatccac ttagtttaca caggcagaag ttttaaggca ggcctgcact  26040
tgcttgcatc ttttcatgcc tcctccatgt gcaaatatgc agatatttct ctcctcaaac  26100
tagtgatggt tacatgtgca aagcagtgca ctctacttta gagggttttt gatccctatg  26160
caacacacct tcctttcatt cattacagaa acgtttgcac acaggaatgg ccatcagcac  26220
agatctgata tcgagtcctt ccttcagaca atgcaattac attcagaacc ttttgctgct  26280
tgagggtaaa atatacgagt gctcaatgat ttgtaacctt ttaaacaatg tatttaaact  26340
tcaatttctc tcaaatatga tgttttggtc tgtagacaga agcaaatatt ttaacatata  26400
caaaaaattc cagctgaatg ttagcaagag ctggctgcat catctgtgat gaagtataat  26460
ccaaactacc attgcatcca ccagcttttt acattgcatt ggttatgctt gcatttcttt  26520
tgtgggcaaa atttacctac agcatgttat tcccagttta cactgaatat aatttcccac  26580
ttctcgatgt caataataat gctacagagc aacaggaaag taacatatcg tggggcaggg  26640
attctgaagg ttttaaatga ataaaagaaa aattaaagaa gggaggaaga ttcaggtgct  26700
gtctatactg catgccacta gacaataata aatgcttatc agggatggag agctggctcg  26760
ctgataagca tgttgtattg tcatgctgtg tgttgcgatt aaaatgtcat ccagtatgtc  26820
```

-continued

```
caagcatgtc taaaaacaaa gggctcagcc aattgccttg catgctggct ctaaaatgtc  26880
ttgagtattt tcagggttct gcaaagcaag aaacaccacc aaaaaataaa aaaataaaaa  26940
caaataccca ccatggaaac tttaggctcc agtaatttat cccctggaac atccatccat  27000
gtcatttctt cagcttcagg atcacctgga gagcaaggag tgaacaaatc taccatgata  27060
tttggattcg tcactgatgg tccttttacc taataaatga atacataaat aaataaaata  27120
aacaaactga agctgaacat ctttagagca aaagcatact cttaattttc tgtacatgcc  27180
ccacccgttt ggagttgtgt agtgaagtgg aattgtgtaa aggtgctggc atcgttcact  27240
ttgaaaacgc acagcagtag tcagatactt gaactcatac catgtcagaa ccaatgagcc  27300
tttaaggtag gaatgcttgt agaaagctaa tgtgccaggt ctactgtttg gagaagacca  27360
ctctcttctt agtcctcagt cactttggga gtccattcac cactggttaa catttctaaa  27420
aaattctcag tagttattac tgactgaccc tcaagttggg ctgccatggg tgtcctttta  27480
agcttccact cactgcacta aaaagttccg ggcacctttt ctgacacaat ctctaacagc  27540
acttgataga agatggggcc atctagtgga ggaacagaaa ccatcccttc ttccagatac  27600
atagacagaa cctgaaaagc tccatcagct gcctcttatc tttttgcaat gcatatctca  27660
gacctgtagt tctaccatcc ttcctttgtc agtcactgaa gtatcacaca tccccatgaa  27720
cacagaacac atgcaaaggc gaaaaaagaa ctgcttttaa cagcagagaa ctggatttgc  27780
tgtttcaatc tgcttttaaa gcacagcgaa gaaaagcatg gattataata ctggaaactc  27840
aacttggaca aaccgctatc aataggctgg aacaagcaat gggttacagt gagttacaga  27900
aattgagcaa aacgctacaa acaggaggca ggggcagatg gcgattggga caagggggaa  27960
tagtttaaac caacagaggg gagatgtagg tgagatgtta ggaggaaact tcttactcag  28020
agggcagaga ggcgctggca cagctgccca gagaagctgt ggtgccccat ccctggaggc  28080
gcccaaggcc aggttggatg gggccccagg cagcctcagc tggtgggggg cagccctcac  28140
catggcatgg ggttggagct gggtgggctt tgaggtccct tccaaccccc aaccatccca  28200
tgattctatt taactgggac aaactgctac tatggaaata gttaataaag caaaggtttt  28260
tcttataaaa ataagaatct gcatccaatt aaagcacaaa caaaacaagt ggaatagact  28320
tgcatcagaa cactcaaagc acggtaggct ttttttcctt tttggcaaaa gaggtaagaa  28380
ttgcctttgg ctgctctgca aactgtggta actgagatta tttcattgtt ctgtggcagg  28440
ctgaggcacg cctcagatgt ctgcaaattt caatgaaagg ctaaaatgtg acaacccatt  28500
ggccagaaat gccatcattg tataaaaaca acaatggata aatacttcag gcatcactgc  28560
ttaagggaag gaataaccca gaaaatccct gatatatcaa aatagccgct tattttttaa  28620
gcaaatacag tttacaacag ctcaaaatac tgtttcaaaa tgttctttga ttttaaactg  28680
ggaaaagttc atcaaaatac ctaccaaata ttcttcctca ccaccaaaat tacagactgc  28740
tggcgtattt taacaagttg ataaggcttc ctcactgcaa gcactggaac tttaacagat  28800
ctcttacatt ctgaaccata ttgtatttaa gcgttccttt cccttggtgt cttaagctga  28860
atgtgttcct tacaattaca tggagaaaag tgcccacctt cagttcacac tgactctagc  28920
tgttcagctg agggctctgg atgagttact ggtaaaaaac taagaaactg tcatcataac  28980
tcatgagcaa caactgctgc caacacaagt tgcgtgtatg acacgcagag caataaaatg  29040
aaagctctga aagcttccct ttccagagtc aaaagtccct gcagataaca agaatccacc  29100
ttcacctgaa gtttgtgaat ttctgtgaaa acaaagtctg cagtacaaat gtaaacagat  29160
tattttagtt tcgctctcta aaaccaaaac aacagcaaga aaaaactaga caagaaaaat  29220
```

-continued

```
actatcatgt tatttataaa atgtaggcga aactccaaga taagcaaaaa aaaaaaagtc  29280
ttatctatct atagttacac tctttttaga catcaactaa gtgtaaagta gttttcactc  29340
tacagcagca tccataagat gttccttgct gccccagcaa tgacaacgac cttactcagc  29400
cgtcttgcat cttaactact gtgacaagta acattagggg attcaatttt ttactggaat  29460
cttaggataa tcttaatttt acagtttgaa ggacatcctg agcaaacagt tgtgcagttg  29520
taattcctct gttcccacgt agataaggaa tacgtttatt tacacacatg cgctagaaaa  29580
acaattacgt aatttgatat agaagaagag caccactgta agactccgat ttaagttgaa  29640
ctccaaaccg aatgctttta acagcagtta tagacgtgaa gattgattag agcttggatt  29700
acacaacatg aatacctaga gatgaggtgc atcaacttat ggcaggagta ctcctttggt  29760
aggtaatgaa gaacagcata cacacatctg taagcacacg gtattacccc aaaccgaact  29820
tggcttactt acaacaagtt ttcagatcaa gttaattctc agagttgaag caatatgaaa  29880
aacgttttgt ttttacttac ttttttaaag tgagtagctg attgcacttt tctaacaggt  29940
tgcatcagtg catcgcgtac aatgatgctt atatctgcac cagaatagcc atcggttctt  30000
ttcccaagct cccgataatc tgcttctgtt aggagattgg gagtcgaccc gaggtgaagt  30060
ttgaacatgg cagccctggc atggtcttca ggtaaaggaa tataaattcg cttctcaaac  30120
ctggtttcca aaagataaaa gcactggctc acgcaggtgc acgatggaaa gaagtttatg  30180
caaatcagta tatactttgt ttgtaaatga aactgctttt ttcttatgta ttataaatgt  30240
ttaaaaatat atatctcaga tattctgcag cctgttctca taagtaatac catggctatc  30300
ataagctaac atctacaatt taacaacgac ttccttttta tgacagaaag tctcttcaga  30360
ctgtagtttc tccaggttca ctccagagaa gtttgtttta aaagaaaata actgaaggaa  30420
aaggagtctt ttagttttta agtacatctg aacagttttc atagaatctt agaatcgcta  30480
aggttggaaa agacccacag gatcatccag tccaactatt cacccatcgc caacggttct  30540
cactaaacca tgtccctcaa cacaacatcc aaacattcct tgaacacctc caggctcggt  30600
gactccacca cctctctggg cagcccattc cagtgcctga tcactctttc agagaaatag  30660
tagtggtttt tcacactcaa agaaagagct gcccgataac acgttcacac aaccagtttc  30720
taaagtttgt aagtagagaa cgttgtagtt ggaaacgaat ttgaagtctt actctcaata  30780
tagttgttgg taggaatggt tgatacttgc ggtgcttcct ttgaagcatc tgttctcaaa  30840
gagaggacga cctcccatca gggaaatagg accgactcca agttctgtag aacactatta  30900
acttcctata ggtaagtggg cccaagccat gaaaaattaa ttctgttact gccacgctct  30960
acaagctcct ttaagttttt cggacaagaa tgagagatac tcgttcacac tgcaaagaat  31020
gacttgaaat gttaagtacc acattcgcct cttattcctt gtatgaaact acacatgcac  31080
aggatggaag cgacctctgg aggccacatg gtttaaactc cccagtcaaa gcacggtcga  31140
gttgaattaa gtacatcgat aaaatgacac tgtcaccaaa aaggattgtt tctttagcct  31200
acaaaaatta ccattataca ggttgtatca tcatcacaac ataatcacat ttgtcacgta  31260
actgtgtttg tcctttgctg ctctgcaact gaaagatcca gctaatcaga tacagataca  31320
aacgtcatcc cattagagaa aggcagttga aacgtacact gaaagatcac acaaactgtg  31380
tgaccagtac agcaaaaaca atgcttctgc attacttaaa ttctgtgaaa ttactcaagc  31440
tatccaaggg tttgctaaag ttgaaaacga tagctctgct gcctcttacc cttctgactt  31500
gcttatgttg taccttgccc cccatgctca ccaggagacc agtcagcaac gaaacacaag  31560
```

-continued

```
tttttgctt agtcaagtgg aattagctga ctaagagatc agacagacta caagatatac  31620
ataagagaga acaatccacc acttaagtga aggggatatt tgactcagtc cacctcatga  31680
gacatgcctg caagaatcaa gtggatcact cactcaaata gcctcaggat gaaccctcac  31740
aatagttgca aatttcttag cataaacatg aatacatcaa tcataggcca acataccttc  31800
tcctgatagc agaatccaaa acccagggta tgtttgttgc tcctaagacc aatattcctt  31860
cattatcaac accaacccct ataccaagga agaaatcatt tcaccattta gaaaataaac  31920
agagactgcc tgataatgtt ttagaacatt tacaaaacgc aagggggtaa agctgcacat  31980
cttttcacat gtaagcaatg cattttatgc gtagctgaac tcctttgatt ctgaaaacta  32040
ttaaacttac cttgcatctg gactagaaat tccgttttaa tccgtctagc agcctcgctt  32100
tcattttcac ttcttgaccc acatagtgaa tctatctcat caatgaagat aatagagggc  32160
ttgttttctc tggcaagctg gaataggttt ttcactaatc ttaaaaaagg aaacagctgc  32220
agttatctta ttgtacacac aagcaaaaac atgcaacttt ggattatgat acagtgactt  32280
tgttaagaaa aagctaaaag taaaaaataa aatgaatccc acataagata ttaacaaagc  32340
tactcaaaga tacaacatcc cttcagaact actaacacag cattaggctg agatgctgag  32400
tgagatacca cagaataagg taactttagg cttcctagtc ttgttaacac atctcattgt  32460
aacatgcaga gtggatatat caaaggcgct catcacttcc aacccatata tgcccatctt  32520
ttatgtcttc aagattttgt ttgaaaacag aatgtagaaa aaaaaccttc acacagagga  32580
agaaacaaca tgtattatct gcagggctac tgcaacagat gagccagaag gtgacaagaa  32640
tcaaagtacc ccaacacttc agaccacttt gttgtacaat cacagctggg ttcagaaggg  32700
cattgatcac cattgtgctg ctaatacctt tgtccaaact agttttaaaa acagtcttga  32760
gtgctgaagc tgctgtagca caaaatacag tgcattatgg tacttttacc tgacactgca  32820
ctgaagcaaa gaaacatcta aggtttgctt taacaagaca catgaacctt ccttccattt  32880
aatttcttta gagtgtccta tctagctctg aaaaattaat ttcctcttga taatattttc  32940
ctggaactct ggaaactcca acttacttct cactctctcc taaccacttt gagaccaggt  33000
cagaggaaga tactgagaag aatgtggaat tgttcgcttc cgttgcaaca gcttttgcta  33060
gatacgactt tcctgttcct ggaggtccaa atagaagaat ccctctccaa ggtgttctct  33120
tccctgcaag aaagaaatca gctatcatca aaatgctgta tcaagagcaa gtctatcttt  33180
ctgatgaagc ctccctaatg tactaagttt tctgtatgta cctaagaaac acctgtcaga  33240
tcgatcattt acagctcagc tggagcctct gatatagcag cataatgctc ttctcagact  33300
ccgcttacac tactcacttc aacagcagta tttagaatgg gaaataaatg ctgtaatact  33360
gacctgtgaa caagtgtgga aatttaatgg gcaagataac tgcttcttta agagcttctt  33420
tggcaccttc aaggccagca acatcactcc atttcacatt tggtcgctcc ataacaatgg  33480
cacctataag aaaagattgg ataaatcact gatacgtatt tttccactgt ttgcttacca  33540
tatatttgaa aaaagaaatc cacgtgtatg tttacattaa ataaaaacga gccatttcca  33600
cacagatttc agcatcaaac agtgctactc aaatggatat tatttctaca gagatttggc  33660
aatctttttt tctttaacca caataaacca tcaataagca gagagttgtt agaagttctg  33720
cagtgtgcaa actaactctg caactgcgca gaaaacatac caatggcaga tacagaagag  33780
tacacttcct aaaaagagat caacatgacg tacaccctga tgaagcaggc ccactacagt  33840
aggatgcaca ggaaagcatg agcaaacacc ctgctgtgag cactcagtgt aaaaagaaag  33900
cctggagtag agaccaacat caatctgtat tgcatccaaa ccagaagagg caaaaaagtg  33960
```

```
tctcactaag ttgcagaaaa tgtgaacagt tcacacaaga cggattactg tggagagagt  34020
aaatatgtgc actttttatt ttccccaata tgtcaccatt acaaaggaaa atcatggaat  34080
ggtggagggt gatggaggcc cagcctgggg ccccaataca tgcagcaatg gacagtgagg  34140
tcaccgacca agcggttgtg atgtcagcaa tggaaatgac tgtgtcctcg ctagccctca  34200
ctgtacagat ttgggatctg gcagaggcca gcgtgtactt gtacctggac ttctactgag  34260
catagctgcg agactcggag cactgagcga gttggttgag ttgtgctgtg ggctgctgg  34320
cagcagttct tggtgcccac cccacagtac caccaacgtt tcccccagcc ctgcctgtct  34380
caggcagctg gggccacaca gggtgcactt gtagcagcag aggtgagtgg tgcaggacat  34440
ggcctctgcg gcggctggtg gggaagtggg agggtttgct gctgagggac caggacatca  34500
cagctgcctg cccatgggac gagtgaccat ggcctctctc tctctttgca gttcgtaaca  34560
ccttctgcct gctgcagtac ctgtgagggg agcagcttcc cgacctcagc tctcccagcc  34620
caccgcacag cccggggcca tggacgtgcc atctaactgg acctgcccca tctgcgggca  34680
aattcgggag gatgtcacct atgtgacccc ctgcaaacac cagctttgct acggctgtgc  34740
catctggtgg gcaaacaaga agccgagttg tgccgtatgc gggcaccaaa tcaccaccat  34800
ccgatactcg gtgaggtcgg acgacgacta cctcgagtgt gctgtcccgc agcccgcagc  34860
acactctgat gatagcctgc aggatgagca ggggcctgca gagccggtgc tcatcccacc  34920
tgagcacaac ttccctgccg aggtctgggc tgccttcttc aaagaacatc agggagacct  34980
cgagcccctg ctccactggc tgcaggagga gatccaggag gcgtccagca gtgactggtg  35040
ggaggtggaa gtgggacagt ggaccactgt caacttcctc tgcgagcacg gcctggacga  35100
ggaggccttg atgcgggagc tgcagccgat cactaacggc gatgtgctgc cctttgtaag  35160
gcagctcatc agcaccgcta cagccctgta cggcccagcg atccgccgcc agctcgacca  35220
ccaggaaggc cgtgctgcag gacagcggga ggacagcccc gcagccagcc ccagcaccac  35280
cacctcccat caggagcctc ctgcctcggg cctgggccac tccaccagcc ccgcagggcc  35340
cagcaccgag gagctgcccg gcagctctac tgggggaccc gggcacccca gcaccaccac  35400
cgcgccctca gcggaggagt cgcaggagga gccatggcag gcggtggcag cgggcccctc  35460
cgcccagggc agggaccgct cgtgtggggg gccccggcgc cccccgaaga ggaaggcccg  35520
cagcagcccc caggcctcgc ccccacctcc caaaaggcgg ccccggcggc ggcgctaggc  35580
tggcaccgca ctgccgtcag agcacagcgc cagcgggctg ggaggccaac atctacctct  35640
cggcctgctg cttgctggca gaataaacat cagttaaaac aaagaagaaa atgtctctgt  35700
gttattgaca agactcttgc tgttgctgtc cctacccatg ctgctttctc tctcttccgg  35760
tcctagagga gagaaatgca actttatttc caccatcata attcagcatt catgacagta  35820
ctaacaaagc acacataggc tccaaaaagc cgaagatgga cccctcatgt tgctctaatc  35880
ataatccaac caccaggact tggctaaatt cctctcctat tgccaagctc tgggccacag  35940
attacttcgt ttgattttag ctgctgagct gtggtgtccc cctcccttca gacttcccgt  36000
tagtcagtct gaagataaaa actctgttac cagatgactt ttagatggga cagctcacat  36060
ctgagctagt gacccagctg cacattttga aaccctactc aagacaaatc caaaaggcaa  36120
gagaaatctt cccaaatgaa ttaatgccaa ctaccccaat gcttatcttt ctgtactcaa  36180
gcacggtgaa ctgttcagtt gccatttttc tctacaaagg gctttctatt agttcacaac  36240
cagtttctgc tagctatttt cttgtcactt tccccttgtg ccttcagagc tctgtgaatt  36300
```

-continued

```
ggttgatggc cattttctac aatggaaagt gtaccgctac tcgtggctaa caaataaagc  36360
aagtgacatt tgttcacttt ttgtccatct ccttagagat ttttactttt cctgcacgcc  36420
tttctcatca gatagaaagg aatatttttt gcttgcaatc tatatacagg aatccagcca  36480
ctcactttta atgccctcaa tacttttgct aggttgatta caactcagtt tttcctgtaa  36540
ccaggctcca tcactaaatt aattagtagg acaagtagga acatgagatt agttccaagc  36600
tatcagttat gtggacctgg catactgtgg taatttaaat tagcacactg taagacatta  36660
cccataccag gaaacaaatg gaacaggaca tcgatcatgg cttcctcatt ttgtaggtgt  36720
aaaagaacag ctggaagact aagccaacag agcgcaaaag gtctttaaat atcaagctaa  36780
gccacttctt ttctatgtaa aaaactactg ctagctgcta tatattgcat cactggatgt  36840
gtacagcacg ttatttcaaa aacacaaaca attatgttac tcaactgagt aacacccctt  36900
atcactgcaa cacgaggaaa tcccgcctgt tgctatgaac aaacaagaat ccatcttccc  36960
gccttatcaa cttgagttca agccttcctg tgaaaatggt cctgcttata ctacgtactt  37020
ggatgacatc tgttacttgg atgacatcta ttgcctctag gcaataatat gtcaatgcac  37080
ataagagtaa aactagcaca gtctaacaaa atagctatct gggatcttgc aactactccc  37140
tttggaaaat gttttcttga taaatgatcc aatttcaaca tatgcaccac tgaatttcat  37200
ggcatgcaaa cccatactgt cataaagact gtacttctgg atgtaaagag tatatactag  37260
ttgagccacc taaagacaac aagttaactg gcaaaacaaa caaacaaaca aacccccaa  37320
acaactagaa attcacttga ccaaagtcac ctctatttaa ataaatggag gcttcaaagt  37380
taccttgaag ctgattctgt agtttctttt tctcaggatc ctctgactct ccttccccat  37440
cactgtcatt cctgatttgg aaacaagaaa taaaacgttg aaatacactg agaaactgct  37500
gtcctaggtc acaaatcaga aagcaggaag tagaaaaaac atcacttcga ggaatgaaaa  37560
accttatgat tttagatttt ttcagctctc tacaagttta catccttgta gtcttgtttt  37620
tctacactat attctaaccc ccccctctca ctgcaaccat ttcaacttct gtacagaccc  37680
gagcccttcc tcttaacaca cttctacatg tgttgactca gcctctagga aacaaaagca  37740
tcgtggaagc agcaaaatgg cttcactgta gatgctggca cttactcctt gtccagaatt  37800
gcaactggtc ttggtcaatt ccatttagta ctacgaaact ctctagtctt gtcagaataa  37860
aggaaactgg aagttaaaag tagaaaaaag tagacgagct aggggacaaa tggaatggag  37920
acgtgtagcc tcatgtttcc ttctactata aaccagcaga acacagtaca gctcaaaaaa  37980
ataaaaccca tgaaatgagc agacaatgaa agaagctgaa aatcagggga ggtttcaaga  38040
gacaactgag cagttctagc tgttcaagac taccaaaaag ggcaacctca cccagagaca  38100
ccattgtgaa acctttcttc taccctagca aatacaaaag aggctctgct tgttcaggtg  38160
ggctgattca gctctcagat gtgcaaagtg aaaaacagat gtaataaaag gagagcggtg  38220
cataggcagg agcaaggcaa tagagcgatt cagaccatca gaacatcagc ctatgacaga  38280
accttggaac ccctcatcaa atgtgagaca gataaaactc agaccacagt aatcatccaa  38340
accaaaccaa ccaaatctgg acttattttc tagtcattaa gtattttcat gcagaagaat  38400
tgtgttacta ggctcactgt catcgaaaca aaaagtatta gtgtaaaaca gctttcattc  38460
ttcagtgaat gtcctacaga agcattgaaa gatgtagcaa acaagcacaa aaaagcccat  38520
aatattaact cacattattt ttcctttttta agcccactgt ccttcagcat tagtagttac  38580
ctgaagcgaa gcacttcaaa aacactactt aaaatgatct ctgttgagat ctaagttgaa  38640
tcttagaata agcggagttc aggaagtatt ttgctttacc ttctcccaaa acataccctt  38700
```

-continued

```
ttccatcggc aggaccagac tctttaactg gctttggtgc agtttttct ctctttttca  38760
gatattcttt cagtttttct gctctgtcca agtattccgc acatttcact ctaatgctct  38820
gttttgcttt atcaccctgt gtttcatcta agagtgtgaa aagaaacaat gcgttgttaa  38880
caacaaaaca cacgtgcatc attcagaaaa catctttatg tgttatcaag atacctctct  38940
cagggctcac cacgcatcca aatgtttcat ttacttattt tttcccctat gccatggaaa  39000
gaagtgacag gaaagaagtt aacgcctaca aatcaatggt aagtaatcac tttcaaatca  39060
aatacacacc tgaacgttgc tttgccttaa aaacttgcct gaacacgagt aaggacagtg  39120
gcactggaag ctttttctgt cagtctctca aactgctata tagtgtctta actacttttc  39180
taaactaagc cattgagagg ctgacttctt gtttttagag accttttttt aatctaagac  39240
cactttattt ttccccggcc tgctaatttt gaaagttgtg cacatcaaag gaagaaaaaa  39300
gtcacaaaac atctgaaaaa atgaggagtg gtccaacagc cacagttctg ttagtcgcta  39360
ctgcagtatt ccagatcagc aatcaagctt gaaaatatta agttcatgcg ctacgttccc  39420
aaaagtccat cagtatggtt aaaagcatag ggaagtaagt ggcatgagtt aatgagcaca  39480
aaacaacctg tggatactac taagagttct tacaagaagg gagcaggcat gcaatatgca  39540
acttttgtcc ttgctataat ataacacctc agccaaacta cagagagcaa gtgtcaactg  39600
acaacaacag tcagaagtta aacgttgatg tcgacagagg agactactcc gggcaatata  39660
aaacttgact tcatcacccc atgcattaca cttacattta acaacgtgga ttaaatactg  39720
cacagcatgc tggtacaaac ggaaggcttc ttcatagttt cctgctttat cttcttgtgc  39780
tgccttacta gcgaggtcta tcgctttctg taacataggt aaataattca aatgagtgtt  39840
gtgtgagtgc tttgtgcgat caaagaggtt tttaagctgc tgctctgacc gcttcttggt  39900
ggccagcttt tctgctcctt gatgtttacc caaaagagct gctgttattg aagacttgct  39960
gtcagttgtc ttcatcaaat cccatcggca tcagtgttga tactggaagt acacgattac  40020
aaagcaatga aagcagcacc ctttcccttc tgacccagtg ccaggagttg gtttcaaaga  40080
ctcattattt ggtaagcttc tcatgaaggc tttaggtact tgacgtacag aagtgagaaa  40140
ttctaaccat ctcttcagtg tgcatatggg ggggagctca gtggacagga aacataccta  40200
aattatcaca gaagttctat caaggacaat ttagagatgg atttttattt gtttgttgag  40260
ataatttcaa atacatctgg tcgtaatcta agacactaca tcggcctgta gatatattga  40320
tattactgtt attcctttga tcccgagtgc tttttattac atttcagatt acattacaga  40380
tttttattac atccttggaa catccgtact gcttcaggac aattaagaat gacaattcca  40440
atgactaagg cacgtatgct taaaaaagcc agagttgact aacgctacct cgaacttcta  40500
cagccctgtc tgcatatttc caccttctgc cagtttattt cccaaaggca gggacagcgt  40560
gctcgtgatg actgtgctaa catcagggag caaggtgaag atattcaacc tcatcacagg  40620
gttttcacta cacactgctg tgcacatact ctcaacagta accagacgct ctgatgcatc  40680
tcagtcaaaa ccgagcagat aaactgcagc catcagagaa ggaggaacaa catttctcct  40740
tctattgttt tgtcttgcct ttttggaagt agagatcacc tcattggatc catctgaaat  40800
caagagtaat ttatttcaaa acaatcacct gacaagtaag actatggatc ctttgtgaca  40860
agtgttgaaa acagagcaac catctgtttc tttgaaacag aacttggtct ttcctcactg  40920
ctgacctcgt gctgccctct acaaattcat tgtagagggc aaaccattca aattcagcac  40980
aacaaaaata aattccaagc aataatttct gttactttag tgatttaatt accacaggaa  41040
```

-continued

```
cagtccaatg attcctggat gcagaacaac aaaaacaggg ctatgacaaa aatgacaata  41100
tatccaaaca acaaataaga gttggacttg atgatccctg tgtatcactt ccaacccagg  41160
acattctatg atgctatggc tctgtgttct aaatggcaaa gaccgcctct gttcaatggt  41220
aactctctta acagggcatc ttagagccct gctcctctga aatacaaaaa caaaggtcta  41280
catcctgtgc tgactgtttt tggtattttt tcaaataaaa acccagaaaa ccatcacttc  41340
ggttttagac tctcagctct ggtactttat tacattagga aggctcttag cctgctactg  41400
caatgaaaaa caccagtaac aaacaggaaa taatttatga aagttgtatg aaataaggca  41460
tagctgtaac cataaatgag gcacaacctg tatctatggg gctatagttt gagagctgga  41520
tgaacaccac cctcagaacg aacatcggct ttgctcttct gcttactctg ggccctctga  41580
tttcacagaa gggcgcaggt tggaagggac cgtaaagccc attcagttcc aatccccctt  41640
gcatggtcag ggctacaccc caccagctca gtccgcccag ggccccatcc aacctggcct  41700
tgagcacctt caaggatggg gcaccacagc ttctctgggc agctgtgcca gggcctcgca  41760
accctctctg agtaaggagt ttcttcctaa catctaactt taatctcccc tcttttggtt  41820
taaaaccata cccctttgcc ctacctctat cagaccatgt aaaaagtcag actccctcct  41880
gtttataagc tcccatcaag tactggaagg ctgcagcaag atctctccca gcttggtcac  41940
tataagcact acatagcctt aagcttacag gcatggacat ggtttaaata ggtttaaaac  42000
tactttttgc acagattatt cctggatcta ttttgaaccg gcaacacaag cagttcactc  42060
ccacaaccga aggctaaaat aaaataaaat aaaataaata ataattaaaa aaaaaaaaaa  42120
aaggaataga gagcagacaa gcatttccaa gagtcgtact ctcagcagaa acccagtcca  42180
aactacgcct ccagctcaca gcaggccgca gtcttgcctc agaggccaac gggtcttctg  42240
gtcccagccg ggcaggtgac tacccggggt cctccggcgc ctccgagccc ccacccaggc  42300
ctgctcgacg ccccaccgct ggtgtcagcg cttctgcccc caggcccagc ctggcgcccc  42360
accccgccga gcccgccctc ccacccgccg gctgcagcgc accggggttc aacaggaccc  42420
gctctacctg caagttgccc gacatggcgg ggagccggga aggggaagga cacgagacga  42480
cactggctac ggccgaccgg agctgccctt cccgccaccg ccgcccaccg aaccgaaaag  42540
ccggccttcg ctagccgctt ccgcacctca gcgccggccg gcccgcttcc gcttccgggc  42600
agcgccccgt acgcgtcact tgacgtcagc acgccgcgcc tcgccccgcc ctatccgagg  42660
ggctgagcgc atgcgggccg ggcgccggaa gcggaagttc gtgggttggc gcgcagcagt  42720
ggtgctgagg gaatgggggt ggtgttaggt ccagcactga cgtaggggat agggctgaga  42780
tctgatcatg acctactgtg gggagcctgc tgtagcagag gttgggctgg atgctctcca  42840
gatgtccctt ccagtccctg cgattctatg atcatttctg taaaatgtta aatagtcact  42900
tatagggttt tgaataaatc acgttttttc ctcatgcctc acgtttggga cacaaagaca  42960
tttttttctt acatctcttc tttctcgtac catttgcttg ctttcagcgg cactgtcttt  43020
tgcataatct gagtgcagaa tgctttttat tcacagaacc agctcttaat aattcctgac  43080
agtcataagc agtcaggcgt tagtcacctg cagctcagta atgaaactca actaacaggt  43140
ctgcagagta agagcaatga cgtgactcag aaagcacagc acattgtaaa caactcttgt  43200
aaacttgcta tatgggtttc agactaatga acttctgcta agtcggtgca acagttgtgt  43260
taaattactg tcatatcctt ccctatgtta ttgtaatact gttgaggaaa tgcttcctta  43320
gattcacaat cctcgttttt ctacctgcct ccaactaagc ccagtacagt ctgctctggg  43380
atgaaggtaa aaggcacaag cacagtcagc cctatatcta ggaaggttga tgtaatttct  43440
```

-continued

```
tcctaaagtc ctctgcttgg cagcttgttt tgcttaatgt cttcatatgt gcacaccagg  43500
caggatgctg aaggctcgtt gtttggggat gatcagtaac agctgttctt ctattgcaaa  43560
tgtgaaaggg tacaatgtag caaaaattcc tggatgtaat caggctctgg gaaatgagaa  43620
ggcaaaggaa atgttggagg taagagcagc gttcaggaac cagaatgata tgggttggaa  43680
gggatcttaa agatcataga atcatagaat cgctaaggtt ggaaaagacc cacaggatca  43740
tccagtccaa ccattcaccc atcaccaatg gttctcacta aaccatgtcc ctcaacacaa  43800
catccaaatg ttctttgaac acctccaggg tcggtgattc caccacctct ctgggcagcc  43860
cattccagtg cctgaccacc ctttcagaga agtagtattt cctaaagtcc agcctgaacc  43920
ttccctggcg cagcttgaag ccattccctc tagtcctacc actagtcaca cgagagacga  43980
ggccgacccc cagctcacta caacctccct tcaggtagtt atagagagca ataaggtctc  44040
ccctgagcct cctcttctct agactgaaca atcccagctc cttcagccgc tcctcataag  44100
gtctgtgctt cagacccttc tccaactttg ttgccctcct ctggacacgc accaggctct  44160
cgatgtcttt cttacagtga ggggcctaaa actggacaca gtacttgagg tgcagcctca  44220
ccagtgctgc gtagaggggg agtcatcttg ttccaaccct gttttcctgt aggtagtatt  44280
tctggctgtg ccatctgtac ctatggtttt caaatctgta atgctacacc tagcttttag  44340
acctaggtct aaaacagtac acaagtcaca ggcatgttag taatgcctct ccagtcacac  44400
tttgcagtct tccgaaactc cacatataga catgtttcta tgattgtgaa tgagattaaa  44460
aaaaaaataa attaataaat cagaaaaggc acgtgtatat ttacagataa caggctaaat  44520
attatacttc ttaattaagc tttactatac agtattcctg ttatgtgact ttgcagctag  44580
ttttgcctaa ggaaatactg gctgaatgct gagtaataac atcacgacag actcctgagg  44640
agctaatgaa gtattacacc aagagtgtag cttcagtttg agagacgtgt atggtcacat  44700
tttggaatgc ttcccattgc tgagttgctg tgttacaata ttctcaaaat ccgtgtcagt  44760
tattgtgttc aactgagtgt aatgacaata aaatatatta atgacgttaa atgaagatat  44820
catagaatca tagaacatcc caagttggaa gagacccaca gggatcacca tgtccagctc  44880
ctggctccac acagcaccac ccaaaattca aagttgatgt ctgagagcgc tgtccaaatg  44940
ctccttgaac tctggcagct tggggctgcc ctgggcagcc tgttccatac ccaccaccct  45000
cttgttccct cgggctctgt cgcagtcaca cagagcagag ctcagcgctg cccctccgct  45060
ccctgcgagg agctgcagcc gccaccaggc ctcccctcag ctcctctgct ctgggctgaa  45120
cagaccaagg gctctcagct gttcctcata cacgttgccc tccagatcct tccccatctt  45180
tgtggtcctc ccttggacag tctctaatag tcttatgtcc ttatattgtg gcacccaaac  45240
ctgcaccctg tgctggaggt gcaactgcac agcacagagt agagaggaca accctttcct  45300
gcactcgatg gcagtgctgg gcctgatgta ccccagggta tagttggccc tttgggatgc  45360
tagggcacaa cgctcagtca cattcaactg tctgtcaaca agtacctatt ggcctgcatg  45420
aggcctgtct gctaattggg actctattaa atcacatcac tgtgacacta ggtggcacag  45480
gcacacatga tctccatgtt ccttaaggct gagtgaatca tggagaatgc ttcctgctat  45540
cagtttttgg catggaaaga gaggagccaa accaccggtt ggttcaatgc cttgtgccag  45600
gaataggtga atgcatcaat acaataagtc acgtctacag cacagccagg cctcatgtca  45660
gcaatactgc tccactgtga tagctgaaag tgactataaa tgactaacgt tagtgtggga  45720
ctttggtgtt agatgacgtg agagccatgc agtgaaagag aattagtgtg gcagagtatc  45780
```

-continued

```
taacagtgca ggtagataag gcaggaagga taagtgtaag gaaagataag gagaaaggca  45840
ggaaagtaaa acctctgttt ttctctagtt ttctacctgg tgaaatgatg aagaaagatc  45900
agtttgacat aggttaacaa aaactgtcag taagaaaggt aggagttaag atgcatgttg  45960
tccaaatccc actacattac tttgaccctc ttcagcatat gcacaatgag atcacttgcc  46020
caagacagga cctccagtgg gcatgaaatc tgaaaatcaa ttatttgcta tttgtgttgc  46080
ttatcatttc cagatgaaat tctacacgag ataattagag tgatgtcctt gaagatcaac  46140
ctttttgtct aattaaggta tttgctatag cttccagatg tattgcttat ctatgataaa  46200
tatccttcct aactacaagg cttctataat aagagtaacg tcctctatag taaccagtag  46260
aaagtaggtg gaagctgggt gttcttagac aacctgtgcc catacatgga caaagtgagg  46320
aggaggacac ctccctaaat gaccaccaga gaccactgaa gacccacatg caagcacaga  46380
agattcagat gtgttggtgt aaccttgtaa acgcagtaat ctcgtgaata tgtgatagat  46440
aggtgtgcct tatgtattag ataggcgagt attgagaact tttggtttat ggatgtggat  46500
agtgctgtta tccatcttgc accctgagca taaataaagc aatatctctt ctatagtgcc  46560
ttgtcttttc attgtatttc aggagacttt gaaactgaca acaggcatgc agcttgggag  46620
tgctcacagt cagtctggcc acagtgcctt caagcctccc ctgcactggg atgtggtgtg  46680
acaaaaagca caaacactgc ttttgtagaa gacccagacc acaggctgca ctagggaacg  46740
tgtctgcctg gagcacagtg ccctggggag tgctgctggt acagtagtcc tggatgagtg  46800
gcttccttct gtaacctttt aattgcacta gaagtacacc agcatggcag agaagggctg  46860
ggtcctaaga gcccttcttt caaattcact cagaactcca gatgtttagg cagggtgttg  46920
tagctgtaaa gtccaggaag aaaaggttta aagctgtact cggcaccaga aagactggag  46980
ccaaaataaa gccacattgc acccatggca ctataggcaa agggtagcct tggggcaaga  47040
cttgatgtac tagaagttga ggagtcctca gactctgtgt caaggggatg tgccacaact  47100
ctactgtgcc cctacctgaa gcctgaatca gtacaaatgt ctcacgcatg ggttaggcat  47160
ccttctctca aagctcttgg tctttgcaca ctttcttctg cagctgcagc agcagccaaa  47220
ggaaaattag gtcttgcttt gaaagccagc cccttccagc catgactggt cccttctcac  47280
tccacatctg tggatgatgc tcccacagca ggtgggagag acagaggctt tcttgaagaa  47340
acccagcccc tctaggggaa cactgtaaag tcacagggga ggagacgtgg ctttgagaca  47400
gtgatatact ccatgcccct ggcgttcttc ccctgagtgc cactggtgct gctcagtggt  47460
cacatgccac caaagtctgc attcatcttt aaatgctgct gagaattcaa cctttgataa  47520
atcatctgct ttgacaaaat cgacatttaa aaattaatat ttcctcttcc atcccctact  47580
tttacaggct ggctcaagaa aatgggaagc ttaatgtaga cttgggtctt actaaaccat  47640
ttcactggga aagacattca cagtctgtgg cagatggtag cagtatattt tctctcatag  47700
tacaggaatg ggtctggtag tacctctttg gaaaggaaaa tgtaaactca tacgttttga  47760
gccaaattcc atcagatttc ttagttttgt tagttttcac tccactcctg ctggaaactg  47820
aaaatatgga aatgcttgga aatttactgt gatttgggtt caggtgtgtg tatgcaggaa  47880
atgtgttacc ttccagagta agtcagttta ttctagaaat gggatgactc cacttttata  47940
cacttgtaat tcacagtgag attaatccag ccaattggga aaacagcctt tcttaaattg  48000
tgaaaaacat gctccacttc tatgtatttt ttaatatact tcagcattgt gaatttgaag  48060
tttttcttct actgttacat gcattccaac agaatttgtc aggaacaaaa atgaaatctg  48120
aaataatatt tttcttagct ttgcatgtgt tatcctcaag ggtaatcact gtcctaaaca  48180
```

-continued

```
acatacttat ggctgtttct gagcctttct tcttcatgaa ctcatcagaa agggacactc  48240
atattggcag tctgtataga gagccaagga caaatatttc gcctacgtct tctctgcgta  48300
gcattttata tattaggtct tgctagtgaa ttatgactga atggaataca gtcccttcag  48360
tgatgacttc attcatgatt gaataaatgt agcttcaggg ctgtatggtt gacttacatc  48420
atccaatttt gccatctgca acagccaaca cctctaccca tatatgaatt cagcgaggga  48480
ttttgtacta tgtgttgctg ggatgtagca gcatttctct ttgaaatgtc tttacagatg  48540
caatgcctag caggcttaac agccctacct gcttcagaga cactgctgta aaaagaaaaa  48600
gagaagcttc ccagccagta tttcatcaag ttaaaaaaaa tctaaaagtt tatactgtac  48660
catttggatt gctgcatgtt gacatcattt aggattctga aaacctaaag aagctttgga  48720
gcaactccta agtgtatggt agatgctctc attatgtaag agtgacaaat cactaccagt  48780
cttccaaaaa tgcatgctga aatcaaaaaa gaaataatgg atctcacaaa actggatctg  48840
cagatcaggt tctacagcct ctggtatgca agggttaaag tagagtgatt gttgtagctt  48900
gtgtctcaca gtcagacata aatctgtaag caggtccagg ttttgtaaat tgttgcttat  48960
caccacatga gcaataagta atctgaacac ccaatgtaac agatttctag gagttagggc  49020
tgaaagcatc atgaagttta ttcttttcta cagcaaagca ggctctgtgt acctgtctag  49080
ccacattgtc tctgacaaaa tttatcatca attctcatct ccatcaactt ttaagaatta  49140
cagaattgaa gggagggatt gttgaaaggg atctctggag atcatctagt cttaccccat  49200
gatgaagcag gttccttaca ataggtggca taggaaagtg tgagcaaaca ccctgctgtg  49260
agcactcagt gtaaaaagaa agcctggagt agagaccaac atcaatctgt attgcatcca  49320
aaccagaaga ggcaaaaaaa gtgtctcact aagcttcaga aagtgtaaac aattcacaga  49380
agatggatta ttgtggagag agtaaatgtg tgcaattttt attttcccca atatgtcacc  49440
attacaaagg aaaatcatgg aatggtggag ggtgatggag gcctagcctg gggccccaat  49500
acatgtagca gtggacagtg aggtcaccga ccaagcggtt gtgatgtcag caatggaaat  49560
gactgtgacc tcgctagccc tcactgtaca gatttgggat ctggcagagg ccagcgtgca  49620
cttgtgcctg gactcccgtt gagcatagct gcgagacttg gagcagtgag cgagttggtt  49680
gagttgtgct gtggggctgc tggcagcagt tcttggtgcc caccccacag taccaccagc  49740
gtttccccca gccctgcctg cctcaggcag ctggggccac acagggtgca cttgtagcag  49800
cagaggtgag tggtacagtg gggaagtggt ggggaagtgg gagggtttgc tgctgaggga  49860
ccaggacatc tggacagctg cctgcccatg ggacagcgag tgaccatggc ctctctctct  49920
ctttgcagtt cgtaacacct tctgcctgct gcagcacctg tgaggggagc agtttcctga  49980
cctcagctct cccagcccac tgcacagccc ggggccatgg acgtgccgtc caactggacc  50040
tgccccatct gcgggcaaag tcgggaggat gtcacctatg tgaccccctg ccaacaccag  50100
ctttgctatg gctgtgccat ctggtgggca gagaagaagc cgagttgtgc catatgtggg  50160
caccaaatca ccactatccg atactcggtg aggtcggatg acgattacct cgagtgtgct  50220
gtcccgcagc ccgcagcacg ctcagatcac ggcctgcagg acgagcaggg gcctgcagag  50280
ccggtgctca tcccacctga gcacaacttc cccgccgagg tctgggctgc attttttgat  50340
ggacatcccg aagacctcga gcccctgctc cactggctgc aggatgagat ccagcagttg  50400
accagaaatg ggtggtgggc agtgtgtgtt ggacagtgga ctgttgtagg cctcctttgt  50460
attttcggac tggacgagga ggccttggtg caggagctgc agccattctc tgatgctgac  50520
```

-continued

```
ttggtgccct ttgtaaggcg gctcatcagc accgctgcag ccctgtacgg cccagtgatc  50580
cgccgccagc tcgaccagca ggaaggctgt gctgcaggac agcgggagga cagccccgca  50640
gccagcccca gcaccaccac ctcccatcgg gagcctcctg ccttgcgccc aggccgctcc  50700
accagtcccg cagggcccag caccgaggag ctgcccggca gctctactgg gggagctggg  50760
caccccagca ccaccaccgc gccctcagtg gaggagccgc aggaggagcc atggcaggcg  50820
gtggcagcgg gcccctccac ccagggcagg gatcgctcgt gtggggggcc ccggcgcccc  50880
ccgaagagga aggcccacag cagcccccag gcctcacccc cgccccccaa aaggcggccc  50940
cgacggcggc gctaggccgg caccgcactg ccgtcagagc acggctccag tgggctggga  51000
ggccaacatc tacctctcgg cctgctgctt gcagataaaa tgtggggatt caagaaagaa  51060
tatttagagc acaagctgca gaacaagata aacagcatgg gaaaggaatg ctgaggacag  51120
aggatgcctc caagagagaa gaaagtcaag tgagctgcat gatcgctgcc taacaatcct  51180
aattggaaga agagtatgtg gctaggaatg actcataact ctgattggag aagcgcctgc  51240
atgcgtggtt aaggagtaga acaagagcaa gggtgaccct gtgggatgtt ttgttgacat  51300
gtaaaggggg tgggaaagat accagagaaa acttggcagt gtatttaagg gatattagaa  51360
tatgcaataa atgatttgga ttgctcatac atctgagtcc gtgccttgga tgctgcaaga  51420
aaataaacag aaattcaaaa aaaaaaaaaa aaaaggataa gaaaatgtct ctgtgttatt  51480
gacaaggctg tgggcgttgc tgtcctttcc catgctgctt tctccctctt tttctcctgg  51540
aggtgagcac agacatgcag ctttatttcc atgaccataa attggctttc atgacagcac  51600
taaaaaaaca cacgagggct ccaacaaaca gagaaaggaa cttatgttac tctaataata  51660
atccaataat cagggcttca ctaatttcct ctcatactgc cagctccagg ccacagataa  51720
ttaagttttg tttgatttca gtgactgagc tgtgatgtca ccctctctgt agacttccta  51780
ttagtctgat gttaaaaaca ccaaaaatat gtgctgtaat ccaaagagaa attatgggtc  51840
ccattaaatt ggtactttgg gttctacagt ctctgttatg caagagttca agctaaatga  51900
ttgctgtagc ttgtgcacga gttttgaaaa gataccaatc tgtgaacaga cccagatttt  51960
ctttctggaa ttctcctccc ctgtgcaaag gaaagcacat tgttttttgc tctcatcaga  52020
gagtactctg aaatgaacat ttttgagtta gacagtgagg agcagaaaag aaattctatt  52080
cacataggtg cttttaaaag cattaccaga ttcttctaga caaatgacag aggaataact  52140
tttgccattc cattacacaa tagaataact gaactgcaaa acaaagagtc acgctacagg  52200
agtaagtttt gaaactgact tgcttacctc tgatgcttcc agctgacttt ctccattctc  52260
acagtagatt caaagttctt tttttttaa ctgtgtgact gtagagagta gtgttcacaa  52320
cttaactgca tgctgtgcag tctgaattag agctgggggt aggtgataac acacctcctt  52380
caactgtttt gttttcctga actgtggttt gtctcattat tttcttctaa atgctatttt  52440
aagcagtaag agtttaaaca tgccttctgc ctgccttaga actgcagaag accttaaatg  52500
cagaactctt actgttcttg aattcatggg aaggtctgag gaaatggggc catccaagat  52560
gtcctccaaa caatacgttc cctcattcca ttatgtgtaa ggtacagtgg tgttgtacca  52620
gggggtgagc actgcagtgg taagtgctgt tggacctgtc gtgcaagaat agaaagaagt  52680
cccacaacag ccaaagtcca gtggctggac caggagtagc caactatgtg gctgctgtga  52740
tttgatccac accagatttc caggttagca ttttcctctt agacccatcc ttattaatcc  52800
ctaagccttt taattagttc ttgtatggaa agtagcagaa actgtatagg aagtcattta  52860
tctttctctt catcctagcc actcttacca gagtaatttt catcttaagc aggaagctct  52920
```

```
tcaagccagg ctattattcc atcataaact gtctataatt cttctacacg tatgacattt  52980
tgtctacatc ttccaatatc tgtctcacta acaagcctgt ttctgttttt tatccacaac  53040
ccatcgaatt tggtagccat ctttgcagtg ggctttggat cttgacccaa gaaaggaaaa  53100
cggaagggta tttgcactgt cacaagttcc tatagaccta attgcagctt tccaagtcac  53160
ttatgcctgt tatgtaaatg ttaacgctat tgtggagttt attaactcgc tggattatgc  53220
atgaagtatc ctctggagtt tccccatcaa gcttaatggg accattagat ctcagaagaa  53280
tgacgaaagc tatttctcag tagcttacat attacctggg tagatgtaat gggaaagaga  53340
aaaagaagca ttctgttatc aattcctagc actttctttt gttaaatata ggctattttt  53400
tttatcattc acaatttttc ctacttttcc tttttttatg gcctagtatg ttctgtgctt  53460
tgttacacaa atctagggat cctgggttag tggtgatatg agctgaatca gctgctgaat  53520
gtaggaatag ctcacttgct ttcatgggtg ctaatcagtt tacattagct gaggttcagg  53580
gccattgttt gttaagattt acatctggat gtcaagatgg gtttgcaggt ataactttta  53640
taagtgactg gtgagacagc gacactgtag ggtgttttac ttcgagtaat gcagaagaat  53700
gtacactgat tttgttgcct ttagcagatc tgccaaatac caactgaaga agcaagaatt  53760
aacatgtttg ttcctcgtct tagttgcatt cagggacaag aaaagctcca tcctctcctg  53820
aaaatacaca gctggagaaa attcagacca tggaggcaga cccatttcca gtgtctattt  53880
cagcaaatat tgactctaag cttttattgt cctttaatat gcatatattc atgctgtgaa  53940
tctatgctga agaactctgg gaaggtgtgt gccctcaccc acattaatca cccagacact  54000
tcataactac ctggattaca ggagaaagtg actcatctac tgatgacgct ggataaaagc  54060
aagaggggaa agaaatcccc agttctcaca cctccctcct ctgcacatag taaggaggca  54120
ctcaagggca taatgcaaac ccagagctgg aagggaggct gtgtgtcagg gcccaggcct  54180
gctgctgtgg gcagcaaagg ccatgtaatc gctggacatg tcagttccta ctgctccgat  54240
ctgaaaccag ttcagagtta gagggagagg tctgcttggt ctctctgcta ctcatgggaa  54300
aagcacttct gccaatgtga tctactctct cttcaaagtt tccacattgc ttacgtgagc  54360
aatcctatcc ccatgcaggc tttcttttgg taggtgagcc cctgataatt cgaaaatcac  54420
acctacactc agctaggagc taaccagatc tataatcaag cacagtatgg tgtggctatg  54480
tagaggaagc atcttcaata aatgtactgc agtggtaata tgcttttaat aaggcaactc  54540
tgttcacatg aacagtacta gagagaagca caccaggccc tgaaacttca gggcaaacaa  54600
aggtttgaaa gtatccctga attaaaataa ttgaggaaag gtgacaaacc taagcatgtt  54660
tgggtttttt tctgagacaa gcatcgtgta ggttgttttg agccctagtc acagcctggc  54720
aaaaggaacc tggtgcagtc actatgggca ccagagagga aggaagaaca gtgttgtccc  54780
tgtccttgtg agaaggagct ctgaaccaca gtgcacatgt gtgggggttc acaatactgt  54840
cttcctggaa ggactggatg cttcagtggg aagtgattaa tccaaagcac tgtctctctg  54900
catctgattt atctgtgcca taccaaggcc agttatgccc agtgctaaga gttgggagca  54960
atgtctttag ggaaaaggtc agatgccaaa tgatctgatt ccagcacttt catttcatct  55020
ttcatttcct gttctccagg ttaaaggcct tgttctcact gaaagctggc aactgtttgg  55080
ccgcctgtta tttcagagtt gttttatcat tattattatt ttcctgatga gatgtatatc  55140
ccaaacaaga acaggctcaa taaaataaat gaatgaaatt aatttcctgt ctttgattag  55200
aaatattcac tggtgaggca cacttctacg tcagcagaca tgtctgcaga aggctgagtt  55260
```

-continued

```
cttgctggac gtgttgaagc agtgtgttgc tgtgtgacac catccctcat ccatctcagt  55320
gcagatgcct tgggaagaaa gaggaaaaaa gagaggtcag cttgctgctg ctcagcttgt  55380
gtctctctca gtataatcct agaatgacac ttgattattc taagtgctat tgtagttgca  55440
aatcatcgtg tggtttgtaa ctgtcagtct gacctttact agacatatac tggaaaatat  55500
tcttgcctgt gacttctctc tattgctaaa taatgatcta gacagataca cagtgaatac  55560
agaaagttca gttgtataga ccaactgaca gacattgtga ttttaccctt tgtttttttct  55620
aagtgtgccg aggaagcagg ttgttgtatt gaaataaagg catgcaaata acctgctact  55680
ggctccctcc aagatctcag gcttgctgta aaagccgtag ctaggtcaaa aggggttgca  55740
ccttttgtga ctggcagcat aataaacatt ccccagttta ttctgctcat tattccatcc  55800
cacttgtagc caatttcctg tgtggtctcc aaagcatgaa atctgcaatc agacatgtcc  55860
tgagtgtcaa tgcattaggg aaataaaata aggaaaaaaa gacaacagcc gtcagttgga  55920
gtctgtgaag gagctgagct ggttcataga actgtgttga gcagcaggag cgttccttgc  55980
cccaaacgag cctgtccaag gggtgggagg aaggaagctg tttttctttt ccactcagca  56040
gcgtgtagca acaacgccct gaaggagtgg cagggtgagc cgagacctgg ggctgagagc  56100
agacaggatg acaggagtgt taccaggtgg ctgcatccct cctgcacacc gcatggccag  56160
gtggtggcac atggggatgg ctgctgcgtt ctggtgccca gcaaggcctt cgcttgtgtt  56220
tccccttggg ctgttgaaga cctgaaaatg ttggtgacct ggaaaaggaa gatgaaagct  56280
cctctgttgc tttgtcagaa gactgtggct tgtccttgtt atgaaacttt ggactgcaat  56340
aatgacggtg tttcactttg cacatccctt gttcctatgt tgttttgcct ctgtcttttt  56400
tcagagacag catcatgaca ggagatgtcc aactcacagg gagctttaaa acagctttga  56460
ttttattatt attattatta ttattattat ctagtaaaga aaaatcctgc tcttcattct  56520
gctatctttt taacttgatt aaaaaacagg ttgcaataga tgtgtgttga aaattcttgg  56580
aggtcaaacc aagcaagact aattcggtga caggtaaatg caggagatgc acaagctgat  56640
gcagttagtt agatgtcatt cagtcagact gaggaagatg aactgggaag ccaagctcca  56700
gtgcttgtcc cttgcaaacc tcaggtacct aaggctcagc atcttctgct tttcaagtca  56760
gcatcttttg ctttactgct tcttcctggt tgggccataa gtaagatcca ggtaagtgac  56820
aggcactccc ataaatacta atgtgaagat acatataaca tatacataaa atgactttag  56880
gatgttattt gtctctatat gtgacaccta atattatttc aacattatct ccaactgtaa  56940
attaacccca aatatccatt ctctggggaa gcaggactgc cctgtgagcc actcagttac  57000
aggagcccgt gtggactcct ttctttgaag catggcaatt ggttatttct ctcatggcac  57060
tatgatcaga aatcagtcat ttctcagcag cagctgggtc aggcagaaga gttctgtaag  57120
cctacaaaat gccagacctc agctatcaaa gagaagttac agagtggagc gcagtaatgt  57180
tcatgcacct tcagctttgt aatgtagagt tctttcacct ttccctgctc agcttttaga  57240
agtaaccagt gcaccccctt gtatttgtat ttccagccta catggtgatg gagctggtga  57300
tggtgatagg aggtgaaggt ggtgacctgt gctatctctg tcaaggcagt tgagttgtca  57360
gccactcccc accagtgtgc atccagaagc tcctgaacca cttcacagag ggccgtcttt  57420
agtagacttg ggcctgaagg aaagtttgtt cctttggctc tagattacct gcagacatct  57480
gagaagagtc tggcagccaa cattattgca gatttttatc aaaatttctc tcatagtgta  57540
aggcataatt agatatgtga caataattgc ccagatgaca catttttgcc agctgttctc  57600
gatgttcttt gaattgctta aacatatcca caccttaatg tttgttatga attcacttat  57660
```

```
ggtaaagcat actaatttta tgttcactgt ctggtaaata aatgaagttg aaccctactt  57720
catcacagca gaaaggaaaa taagatttcc tttgggtaat aatgagtctt ttggaagcac  57780
atattgctgg gatctgatca ggaagcagtg gtgtgattta cactcaaaac tgtcattcca  57840
gaagtagata actcctcagt tgccactgcc accaaggagg tatcacatca gggaagacac  57900
gtactttggt ttcctagccc tttcatttgc cagcatagca atcttgaaag caagctcaat  57960
aacgtttact ttttttgtag cacatcagta gtctaagggc atatagggct gcctggggtg  58020
ggtgaggtgt ggacagcagc tgtgtttgtg ggtggcagtt tcctcatgaa ggttgacttg  58080
gactccagga agtccttgtt agtgtggtgg gcagctagac ttcgtgatgg gagaagcagt  58140
gtggagcaga gtaggccacc ttttccttgc taaggactac atacattttt caaatcaaat  58200
aagactgtca ggctgcacca ccacctttcc ctctcccttt cttcaacccc ctccgcattg  58260
gattcatcag taatcatgtg gccaatgagg cctgaaccca gtggttccca ttctggagat  58320
gctggaaagg agctgtggct tttccaccc tcccagctga aatcatctgc ttgagagcaa  58380
cacggtgagc agacatttct ctttgagcac gagccccact ctggccttgg gcttttgagg  58440
caaccaagta caccacacaa ccctcacaaa gacaacactg agacactatc ttaacgcaga  58500
cacagatgca aagtactggg ttgccatcac acgttttggt tgccttccct gtgtgtcttt  58560
ttcacaatta caatttttta cgaatcacag caattccaat gtaccttgga gcactggttt  58620
tgctcagaag ctccttcagt tgctccttca ctcctgcacc ctctctttca gagtctttgc  58680
tccctcctgt ctggtgccta ttgtagggca cttgctgcag gcaacgtgcc gaggctgctg  58740
tttcctgctg gagcatgttg ttgtgttcag tagctaggca ggcaaagaca actcaggtgt  58800
gactcatact gctcctccag tttaggagtt gcttgaagaa tgattaaggg aaagaaaaaa  58860
aaaaaaaaag aagaaaaaaa aagcgagagt gtgtgcgtaa ttagggctgg gaaagtggga  58920
gtggtgtcaa tgagcaggca agctaacaga ctcttctgct cagcaaggtt tcgccacagg  58980
tctctagttc ttcgtgttgg acccatttca ttgattcatt taccaggatt atacccttgc  59040
aaagtaagta caacattttt tcttcctctg gtactttgat gcctaactaa cagttataaa  59100
atctctgccg tgaaacgtaa tcgcatagag tgagcaggat aaggaagctt gtacaaaaag  59160
acagcatgtg aaactaaagg tggaaaaaag cctgctcaga ctacaacctt ctggttttgt  59220
cccagcattg ctgtgtttgt ccgtctacat tccttacccc tgaaaagatt cgttgcaaac  59280
ggtgagtggg gtctgtcagg tgagactgcg aagacattag gaattattag aatatttaga  59340
ctacctgttg gctgttccca atggcttttc ctgaatcaga agagcaggct gtatatgatg  59400
ccatgaaaat gctccatatc tctaagtagg tgtagactgt ttgagaagtt tacaaaagaa  59460
tattcttctt gttttccaca tgggttcgta tgctttgctc tgtttgcttt gtctaagcct  59520
tgctagttca aaggacaaga acttaagtct actaattacc tacttgatct tcagtgtgct  59580
catccggttg gaaaaattca ctgactcttg aggcacaata aagggtattg tggagactct  59640
ctaattcctg gtgtgacttt ctcaattgtg ttgctgatgg tgctttttcc acaacctgat  59700
gaacactctg atctcgctaa agcaaagcat cagtctgata ttgtgtgttc ctcagagaaa  59760
catctgttca gaggaaatca tgtcttagtc acggagctgt gtaacctgcc tggtggagag  59820
ctgccatttg tgtagaagta ggaggaagag gctcacaaga gttttgttcc tttatatttt  59880
gtgttatcca agcaagagct ccagtaaggt catgttaaat gagctagttt ggagggggaa  59940
tgccccacat gtgggttctt tcatatcgtt tatctaaact gaagtgactg cagggtgttc  60000
```

-continued

```
actcacagct catgagctgt agccctagtg cacagcccca atagcagccc agcttggatg  60060
gccaccgccc ggtctgcccc gggtgcgcac tcctcagggc tctttaacaa aggcaagaat  60120
aaaataaata cttgctctgc tttatcagat gatgcttacc attcagctga cgtgacttgt  60180
caggtttcca cacagatgtt gccgttctcc tgattaatgt tcagaagata aactacattt  60240
agcttttctc ttagtaagca aatagcaaac aaagctttgt ttctgttggt tgcattcagg  60300
agtgacaaag caaaaatagt gtcctatact actaaacacc tttaagttat ttttttctg   60360
cactgattct agagcctctc agcttcctcc tgtatctgaa cgtgtttctt gaactctgtg  60420
gccccatcac agctttaagc aaagctgggt ggatcacagg ctgcatgtgc ttagaaggtg  60480
ccaccgtgcc gcgggcctct cagaatgctg acttgttgct ctcctgggaa agcagggatt  60540
cagccagaat ccaagcagcc cttcttgaaa tttcatttcc aattttgttg actcctccct  60600
gtgtgagagt ttcctgtgat tactgactca ggagctgtgt ctggtttctg ggactgctcg  60660
tgggcacctc atgggctttc gtcttgagtg ggggcctcag cccttctcac tcagccagaa  60720
cttgctgcag tggggtcact gacacagctt ggggtgctca gggctttaaa gaggttcaag  60780
acttcgtaat atttcatgca gtaaattcct ttcaagcatg tgaacgctgt gagctcctat  60840
gtgttgtatg tcattaatga atgcagcatt aaaaaagaag gctgatcaga tgcagttaaa  60900
aaagatggtg agatagagat tattctttgc tatccagccc ttattgaaac agcagggtga  60960
aactgagggt gttttttcc caacaaaatc ctctgaatgt gcaatatatc agtagcagca  61020
ctaaaagaaa gaaagtgata agccttgcca ctaccaggaa tagattctct tggcataaca  61080
aaggcattga gaagcatcat cagctactga gtgaacagga ggactgtaaa aggttcacca  61140
cgaagtacct ccaggtttcc tcactgaaga ggaacacaga aaccttgcaa aaacgatcca  61200
gcttgaatgg taccagaaaa gaatttctac gtcctggtgc agaattccac tggtgtaagg  61260
aagaagagag tcatttaagt ttgcaaaatt tcacaattta tttccttgct ctgaatattt  61320
tgccacccag gagagtgaag cacaggtagc acatgcacat tttaatatca ctgtaggtca  61380
tttgccaata cgactgaaaa tgctgatgtt agaaaggcag gattgcattt ctggcatgaa  61440
gacagaaagg aacgtgaaat gttttgaagt tattatgatt gcatatattt tcttaggcgg  61500
taaggaagat ttggaagtca aaatagcatc agggcagccc taactgaaga aggatatttt  61560
actccgctag caaatgaaat atttttcagg tagactgcac acatcattct ggcattgtga  61620
gattatgcgt gttgtttatc ttcacgagag tggtagatgt tgaatgacac attcttggtt  61680
ccttgggtaa ttttccacgg tctccccagt gagaaatgcc tgggaagttg gtacttgccc  61740
atttcttcca tttttacttc agacagagaa agtatgcata tggattgtgt gctcgtgggc  61800
cttaaagtgc ccttaaagag aatgagttca aagggaaaaa taaggtaggc atcctgttca  61860
gagcagtttg tgtaaggtgc acagaagtgc gtgtctgtgt tgagcgagtg cagaaaggca  61920
ttttaaagga tgatttcaca tgtgctcctt tgacctgttg ttccaagtga ctccctcagc  61980
agcagtccca ggtcttctta tttgttttca ctgtcttttg ccaccatttt gcccaaagct  62040
ccctcctcct ttgatgtatg cggagtccat cgtttctagc aagcttgact tttctggtta  62100
ttagttgctt ttatatgtga gaagttgtga ccacaggagt gacacaggaa tgatgcttgt  62160
agtgctgact ggcactgagt tctcactttt acacccagaa aaactctgag aacacttccc  62220
aaacctcact ctgacaccag cttgattcct gctgacactg taaaatggga tctcccaggg  62280
taagcttcgt taccaagcat cttgggacac tgccagtgtc aagggagatg gacagaccca  62340
ttctgcttga aaagcatctt acagggatcc tttacatgtt gtaaacatcc ttcttttcat  62400
```

```
ttttatttgg ggataacttt ctctggtgct gtatatttaa tttttttttcc tcctcaagat  62460
gaattgcttt ctttgcgttc ggaggcaatt aggaaatact ttgttgctga taccaacagt  62520
cagagcactg tgtgagggca cactgctggg taagtgtgtt tttcaaattt ggatttaaaa  62580
agtcttgatt ttatgccatt atcctttttt cacttaatta gattgtgcat tatatttcag  62640
taacctttttg tacagcgtct tttagctaaa attaagccag gtgccttact aaatatatag  62700
aacatatacc tatgtaagtt aatgaaaaca aagacgtgaa ggccttttct aatcaaacag  62760
attttacatg gaaatcaaag ttttctcagc tgtgttgcag aaaaaaaata cccccctgtt  62820
ctgttactcc tataaaaacg tgtgaatacc acagattatt ttggaaatct ctactctcaa  62880
ctaccaaaac tgccacagca tctcgataca ttgatgtctg atgttcagcc aagtttggac  62940
agtatgacac atgctcttga atgcagattt ttgtcattca aaacaccatt ccaaacaggg  63000
atgagagtga gcggtcagaa gcaggtgtcc ttgctctgga gacagttccc tgcccacatg  63060
tcccctcttc cctttcctgt cttctcttac ctaactgctg tcatctggtg agatctttac  63120
tcatctgatg caacctagaa tgcaaaaggt atgaactagg taaatgttta agactgcagt  63180
attaagtagg catttgagag aaatctctgt ccttaaggtg cttcttggaa gatcagcaaa  63240
cctctcaccg aggtaatgct tcagataatg ctacagactt tcctgtttgc gtcttctgtg  63300
tcagagcctg aaacgttatt gcaaatagat gtctggataa gaacagaact gttaaaatca  63360
ccttgccatg ccatataagt tccaatattt tgccattttt tttcctgggc agggaacatg  63420
ttgaagaaag tttttgagtt ctgttggaag tctttccctt ttgaagtccc ttgcagtatt  63480
catcttttcc ttttccttct gtctctttca atagacagag ctgctgagca ccaatttatc  63540
agattgtctt tccccttctt tagggacatg tgattctggg gatagaagac agtcaaactc  63600
actgtgccaa aggagttacc gtcttccata tttgtgctgc tcttaagctc gatgcgatat  63660
tgactgaaat tctgtggttt ccctttgttg tctttaatct acaccaatgg agttacaccg  63720
aagtgcagtt ttagatctat gaaagcagtc tggaagatcg aatattccgt gtcattccca  63780
gaacgtggtc cagaacatct gtcgcttggc accacctttt ccattcctga ctgcatagat  63840
cagctaacag ccctacggca attgcagtta ctctgaactg ctaggaaaat atttgcagtc  63900
atcattgtaa gtgatgagtg ggcacatagc agtatttatg taggaggcta agtacttaga  63960
gtttctagga tgatctcaac ctacaggacc ggacagcttt ctggagagtt ctagcaaggg  64020
taaggagaac agggaatcac ctcttagaga gaggacatgc cacagctaaa gctttaatga  64080
acaattagat gtgaagcaag agacaggaaa gatgattgtg agacttttaa aagcctatca  64140
aagcactagg agagcccaaa gcataggcaa agtaccttat aagttggcac atctgaagag  64200
tatcaattaa aaacatatta aatccatatg ttatccgatg tgattcaata tgtgtgggtc  64260
accctgacca acccagattt ctccacgtat gtctggtaat actggctcta cgtagcacgc  64320
agaactgcca gctgtcactt gaaggtaagg gcttctactg agccactcgc attaccttgg  64380
ttgggcatgg atgagagact cctcaaaagc tgctggtggt gtctgagact gggcaggatt  64440
ggtcaggcct ttctcgcctc ccagcgtagg ttcaagctgc ccagtcccca aactggtgtc  64500
cagcctcctt cagcaaggaa atcagtgacc tgccagcctc actgcaacag gagctcactc  64560
tgtgggtcat ctctatcctt ttctgtttca ggatgacgat ggatgctctg caactagcaa  64620
acactgcctt tgctgttgat atgttcaaaa agctatgcga gaaggacaga acagccaata  64680
ttgtgtttgc ccactgtgt acctccacat ctttggctct ggcatataaa gctacaaagg  64740
```

-continued

```
gtgacactgc agaccaaatg aaaaaggtga gctgtcggca tcctgctgtg tagctgcaaa  64800
attgtcagag gtggctttcc tatttattcc tcttaatgct gtataggact gctggttccc  64860
ttgtaagcca ggcagaaaac tgtccatcca aaattccaga atatttcccc actccatggc  64920
tccacacaac caaagaggct gaaaatcact agcataggga aaaaagcttt ctcaagcatt  64980
tacaaggtgg atggggacat ggcagagtcc tcagcagttg tattaaggcc ttgtctcctt  65040
tcagcaggaa tgctgattgt ggctgaaggt gactgctgaa gtcactgcat tttctggata  65100
attgtttagt gattattcag gactgcctaa gcttaacagg actggaaata attttgccat  65160
taccaagtaa ttttagcagt tctgtctgtg ccatttcccc tttctcctgc catacagcta  65220
agaggaagat aatgcagtag gaggcagctc agcttgagta gtagtttgcc ttgcaaatag  65280
ctctagatgc tcaagggttt tacagcacca cgaagcagca tcatggtgat ggtgcaatga  65340
gtttatcaag gttgctctgt ggcggtgaga ggctgcacga ctgcctctgt gagagccagg  65400
atttacacag cctcttttta ttccagtgcc cacagtctca gcagttacct agaggtgaat  65460
gagaagcaaa ttcagcatgc atttatatgc tgattatcac ctggctctca ggggcattcc  65520
atgtatttga atacattttt cttcgtttag cagttcctcc ttgtaccttt ggtttccctg  65580
acggcacatt gctggagcac agcctctggc gcctctgctc atcctacaga ttgcaatgag  65640
tctatttgca cagaaacaaa gtggtatatc cacaaaggcc tgctgggtgt tttcccaaat  65700
aggattattt taaaaaaata aaaataaaaa tgatttttag atcttatttc tagtttaaat  65760
gacaccccaa agcttccttg tcatttcaaa gttcaagcac tgtctttgca atggaagagc  65820
ttaaaacatt aacctgtgct taatttcact ttcacttgtg cctgcaattt gcattgaacc  65880
gtcccacaat aagtgaacat ccacatccac aaatagggtt ctgttacaca agtgcactta  65940
tgtttcacat ttctcaaggt aatttactgt gcctgtaaag acatggtgtg ttcagggaga  66000
aagagcagga gtgaggctga aagggaaaag gaggtcactg atgctggttg ggaaagatga  66060
gaagggttgg gcaggctgtt tttaatggaa catgcactct cagagacctt gcaacaggca  66120
ggcacctaaa agcagagagg tttaggtcat gctagaatat cctggaactg ggcatgtgat  66180
ttcccggagc tgggaggtgg gtcagcagcc ttacctctaa cttacgttct gtctgccaaa  66240
gctcacctgc ttatctgact gatttctact gaaataccac atgacatcat gtgtcaataa  66300
tcagaaaacc ttgccatatg gtaagcagtt tttaaagaag taacccactt ccagaaagga  66360
aactaactgg aacatttatt tatctggcct ctaaactcca gatttttgga caagaatgtg  66420
agtttgataa aagcatgact ccacgctgca gatatgtagt tcactaaatc actttgctag  66480
tatgaacagc tctatggaat tctttggact gctcacagga aggaaacaca tttggttaaa  66540
gttttgatag gatcaagttt ttagatttat gtggggatgt caaataaatt aattttttttt  66600
ttagtaataa ataagagtga gaagtcgtgt tgttagcttg aacacaaaaa agtcaaagct  66660
ctggtcacaa acaagcatta tttattgcca agctgtcagg cctggagcat gtccagagaa  66720
ggacaacaaa gctgtgaagg gtctggaaca cagatcttac aggagagcag ctgaggaaac  66780
tgggattgtt cagtttggag aaggagaggc tcaggggaga ccttatccct ctctacaact  66840
gcatgagagg aggctgtggt gagcttgggg ctgacctctt ctcccaggta gcattaatag  66900
aatgagaggc cgtgtcctca agttgcacca gaggaggttc aggttggata tgaggaaatt  66960
tttctttttc tgaaagagca gtgagatatt ggaacaggct acccagggag ctgttcaaga  67020
actgtgtaca tgtggcactg tgggatatgg tttagcgggc acagtggtgg tgggttgaca  67080
gttggactag atcatcccag aggtcatttc caaccttaat gatactatga tgctatgagt  67140
```

-continued

```
ttttagataa taaaaagaaa ggtgctcagt attttatctt gttcattatc aggtgctcca  67200
tttacaagac gtcaaagatg tttcttttgg gtttcaaacg gtaactgcag atgtttccaa  67260
actcacctct ttctttgcac tgaaaatggt caagcggctc tttgtagaca agtcgctcag  67320
ccctaccaca gtaagtactg cagaaaagtg cttgaattgc tcgaccaacc agacttcaat  67380
gttattcaaa atacgttctc tcactattag cttttacttg actagactca gatgatgaac  67440
agcataataa gagtttgtag gaggatgatt gttctgcttg accccaagca atgcagccac  67500
tgctagagtt gcaattcttt cattaatatg ttttaggtca gtaggcgcag taggttttga  67560
atgcaatatg acttctatgc cacatcaagg gctttgcaat ataagtatga ctgggaagga  67620
ttttaaataa agatggtggt gcaagtgtgt ctagtccaca cacccaagta attactgcat  67680
aaagagtagt tttcttaatc taactgagga ggcacaagcc tggttattca aacaacacaa  67740
gtgaggaaag tgttgtttgg ccatgaaact taaggacctt gcaaacaact gagaaaaatg  67800
ttgtgtttgt tttatcagag ttgcctttga atagggcccc aagcaagggc aacttcagcc  67860
tagaagtgat gtttcagaag actcacagcc tgcttgaatg gtgttataat caggttgcct  67920
gctttttggc cccatccaca gcagtgagca tctcacctga caaggatagg cacactgtga  67980
gcagcctgtg gcctttgtct catccctttc ttttgcccag gtgtagactg aaggctactt  68040
tatcctttca aactcaggca acatgttcac tcctgcagta cgaaaggtac tttagcagcc  68100
agtataactg tattgaagac agtcttggga gcaatctgct gaatgcggct gcgtgtcctg  68160
gctgtcacct gctgttactt attagctgtc ctttgtaata tactctctgc ctacaccgta  68220
atgaagcttg ggatactggt tttgtaggcc gtgtggagag tcatctagtg aagaacatct  68280
aaggaaggtt agctttggta ccttgtgtct ttcaggactt tgttaactcc acaaagaggc  68340
cttttccatc agagctggaa ctagtggagt tcaaggaaaa aactgaggaa acacggcaga  68400
agatcaacaa atctctctca gagctaactg atggtgagta gggcctaacc tcggggatgc  68460
tgattacctc tttgaagaat gatgtctttg tcttcatgac atctcctaac tattgctttt  68520
agaagtaaat atacagtgaa agcaaaggga ctgcacctat tatttggatt catgaggatt  68580
agctgtgtta gcatgtttta aaatcattta ctttactact gtggcatttc tggaggcaga  68640
ccttacatta gcctttggca aagcatctca tttgttttca ttgggaaagt ttggctcctg  68700
gctgcagagc ttcacaaaca tctgacatca atacatcaaa tcctggcccc gttctctaat  68760
ggagagtatg tgctgaactc tgaatttcag gctgttaatt agtagctcat ctcagcagca  68820
cagctgattt tgaccacagg tggacatgtg tttcttactt ggaaacactc ccgtggcaat  68880
agttctgcag cacttttcct gcagtaccac tgagccacta agtcacaaga agtgcctctc  68940
agtgaccatc aaggctccca ggcagaacct gcccagtctg tgcagggtag aggtctggta  69000
cgcagtgccc aaggcagagc tcatgtacat gctgtccata ggtagctcca gggttggttg  69060
ctgcctattg ccctcatgtg gtacacatat gaaaatatgg gtgcctgagt tacatctgct  69120
ccatcccgag gtgacacagg tgcccacagg gaagtacttt gcgctgcctg tgtgatttgt  69180
gcatgaatga agactaacat ccacaacact gtggattcag tgcctcatga cagtgtttga  69240
acagacacaa aataaagcaa gggaaagaat tacgttctct ttttgaaatc catggcacta  69300
tttggttatg aactgtaatt agatggttag cggcatttct tattcgggtt tattcttatg  69360
tatcactcca aaagtgagta gaagctaaac tggaacttcc cttgaagtct cgctctccaa  69420
atgagaaata tttttttcag ttctacctgc tgaatttcgc tgaagtttca gtaccttctt  69480
```

```
taaagtacta aagaaaagca gtagacatat tttttattct gttttatgta aaccgagtaa  69540
aaatgtcact tggaagatct gtcttgatcc caaattccat tttaaacatg gagctgcagc  69600
taaggaacta aatgcttcta tttggggatt tccctttata attaaaactg ctatctgtga  69660
ggtgcagggc agaaatattt taattcagta cagtgtttcc atgttctgtg aaaacagcac  69720
atatgttgat aatttactgt attaatgacc agcttaacca tcttcacagg caaaatggag  69780
aatattctga atgaggacag tgtaagtgac cagactcaga tcctcctagt taatgcagct  69840
tattttgtca caaactggat gaagaagttc ccagaagcag agatcaagga atgtcctttt  69900
aaagtcaaca aggtacgtcc tgaaataaaa tagagtacac cttctactca gatgaatgtt  69960
tgccaatttt gtgctaagga aatttcagtg agagcaagtg aaaaatattt gttactacta  70020
tggcattctt agactctctg tcaaaaccta tgtgctgttg caaaagtacc taagccagtt  70080
ttcttgttac gttgctagtt tgaagctgtt ggtgaaacaa gcactaaagg tcaccgatag  70140
taggtaattc tttcctttaa agcacatccc cagtatattg tattaagtac accttgtcac  70200
atgaaaactg ctccccttaa agtaccaaca gctttcacta gcagtcttac agctgatatc  70260
gttacttaca gaagccaaca aattccatga tggtaatcaa tgtaccactt tcatgcaagc  70320
ttgcaaagtt tcctctctca tcttctctgt gaattaaaag gagtgctaga ttgtctcctc  70380
ttgtgttttg cagactgaaa ctaagccagt gcaaatgatg aatctggaag ctactttttg  70440
cctgggttat gtgaaagagt tgaatgttgc aatccttgaa cttccatgcc ttaacaaaca  70500
tataagcatg ctcattctgc ttcccaaaga cattgaagat gaaacgactg gcctggaaaa  70560
ggtgagagaa aaaaacagta ctgagatgat gctttccatg cacagctgtg tcggttagct  70620
gtgggtagct tgggtaggga ctgtcttcct tgaattcctt cattgggttg ttgagctgat  70680
tacatagcaa acgcttgtga agaaccagta atcagagtat gcacatttag tggagtttct  70740
ctggaagtct actctatagg ttaaataatc attatatcaa tataactgag agtgtaagtt  70800
aactctgaat gctacaagca aaagttgtct tttggacttt gttttttttgg ggtttgatag  70860
gactgatgag ttcagaaatg gtctttttgt tcccactttc tctggactgc acattaattt  70920
cctttgttct ttatgtcctc agctggaaaa ggcactcacc cctgagacat tattacagtg  70980
gaccaatccc agcatgatgg ccaacaccaa agtgaatgtg tttcttccaa agtttagtgt  71040
ggaaggcgat tatgacctga agccactcct ggaaagcctc ggcatgacaa atgtctttaa  71100
tgagagtgca tcagatttct ctgagatgtg tgaaaccaaa ggtgtggttt tgtcaaagat  71160
cattcataaa gtctccttgg aagtaaatga acagggtgga gagtctctag aggtaccagg  71220
atatcggatt ctgcaacaca aagatgaatt taaagctgac catccgttta tctttttgtt  71280
taggcacaac aaaactcgca atgtgattct ttcaggcaga ttctgttccc cataagcaga  71340
gaatattaat tatgaaaaag accataaatt tatggtgatg catgttcctg taaagcttgg  71400
tgtcctgact atcacctttg aaaggaattc taagaggttc atatatcaac agggtaatac  71460
aatgtactct acatatgcag cagaactagt ttatttcctt ttatttaatc cccttaagct  71520
gaaggattcc cactgtgcag aacacatgat atttgactaa gaagtattcc atcctcatcc  71580
acgagaatat tttgttcctc tgtgacatct ttttccaaaa caaaatgaac agagaacctg  71640
tttttgaaag actaggagct ggaagaggct ctgggggaaa gagctgcatt cctgtttcat  71700
atccaaaaca ccttcccttg agactcatac tcactgccta aagggggaaa atgtggacat  71760
gtggtgtgat agccctcctc ttgtacttgg ctgtagtctg gtgatccagg gtgccctgct  71820
ggaccctgct aatgcacggt gaaatagtgc agctgaacaa ctcagagttt gcatctgtga  71880
```

-continued

```
aacagcagct gcaatatgga tgcaagaggc aataataaaa cacccagaag actcttcagt  71940
gtgtgctacc tcagtttgta ggttggggag gttgcactct actgtgtggg attttttcac  72000
tcattctcct tcagacatgg cagaggtgac cagttcactg cagctgagag gaactctgtt  72060
gtatatatcc tgagaaaaag aaggctgtgc agttctagga tagaaatcac ttggattaat  72120
attgaaaatg ccacactctt cagatacaga ttttctgtca cttctggatt cagcattaag  72180
gaggctccac acgtctacct aacctctggg attcaagaaa gaaataaagg ctttgacttg  72240
agtgagatta acactgtaat tagaagtctc caaattccat atgaaattat ggtaattagt  72300
tttcctttct atctaaagac tgcctgctgc atatgttcag tactgattta cctaattact  72360
gttcagaata aagcactaca aaacctgtgt caaatgtctg tagcacatcc agtgtcagtc  72420
tgttctcctt cactcagctt ccaagagggg ataggaacag aaattggtag attcattcag  72480
gacacagtta aaataaatat atgaagaaat taaatctgtg actgaattgc ccttttggac  72540
cacacgataa tagctgacaa ttaaggagta tagtactatt tggtcaatat atagagtgag  72600
ttcaattata tatcttcaaa gaaggggcca ttttaactga gtattcccct tggttcttca  72660
gatctgaaag aacctagaga tttctaaatg ggaacataca acccttaata catattcctt  72720
tcttctcata gcagagaaca gcacagtggc tattatggat ttggagagag ttctgttttg  72780
attcttggcg ttcccaaccc acatgtagcc ttcagtcaca aacgttcagg gtttcaccag  72840
ttgtcttccc tctgtgagtc tctaatgctc tctgacttat cttaatatca gacagttagt  72900
ggatacattg gttcacatct ttgaaggcac tgaggggact aactcaccaa aaccaacaag  72960
agatgagtcc ctgcaggcat ctgggggtct ctgctgctct tcatcaggca ctctgataca  73020
tagatagaag aatgctatgt gtaagactta atttcatact gtctgagagg agacagcctg  73080
caaagacctt tactagctca atagcttcag tgataaatga gtgtctggaa aatgttttaa  73140
tgtgtcccat cattgtctga tctgttttgg aggctgcggt tggagttatt cagagctgtc  73200
atcactgcgg tgtcccctgg ttctcccatt ggtctgggca ttgcacgtgg ggttggcagc  73260
cgatgagcag ctgggcagtc tgtacatagg caaggtggac tggttgccta cagtctgtgc  73320
agtttctctg tgtttcagca ctgactcgtg gtctagtaat tgcaggtatc cagcaagcca  73380
aatcacactt cattgctact gctgtgctgg tctgctagac tgatgaaaat ctctgttaga  73440
ctgcctcatc tctcttttc tgcctggata agacttatta aaggagaaaa gctgatatat  73500
cactctcaga ttttctagat cacgaaaaca ttgcagtgca ggagccattc aatccagctc  73560
atactccatt taaatgctga tcagaacact tagtgcatcc acgtacgttc ccagagagct  73620
ccttgttggt gcctttgcca aggagggcta tcccatgaaa gcacacagga atgctgcctc  73680
cggcagagac ctgtctgtct ccaccttctg attaacacaa aggtacccaa gactatgcaa  73740
ggcaagctga tatttcagat aagaagttgc ctcagtttac agaaggccat gaaaagctct  73800
ggttcatttt ccatatctgc ttcttctctc tgcttttgga aaataattct tatttcctac  73860
tagcaagtcc agactagtgt aatatttagt cttgatttgt taaatcatcg tgaattttag  73920
cttttactaa tggtatctta gatgatctaa tatactaaca cctagtaagt gacttcagat  73980
aaggtgttag gcttatacca cagcccagtt tgaaggagct aagtgcagat ggcaaccaaa  74040
caagcaacaa cacaaatagg cccaaatagc ccatggaggg ccagaaagta cagctgcagg  74100
cagagctgtg atgtaatcca tttttgtgag ccccttgaag ccagcaggcc agcctcgtgc  74160
ttttagtgta atggacatca tacagccaaa aaggaaggtt atgccataat ccttgctcca  74220
```

-continued

```
ttcagcaatt ggactcgagt gtactagccc tgtttcctag acccttccag tcctatggaa  74280
atttagaagt cccaatgtaa aacctattca acttgcagca tgtgagagga agatatcaga  74340
acagctcccg ctaacgtgag aaatgccatt acagggtact gtactgttcc acccattctg  74400
gcctctgggc tgtgggcaag aaactgcatg ggaggacatg ggaaaacctg tgtgggagct  74460
tgcatataga aatgtatttg tactcaaagg cgttggctgt gacggagaaa gtgagcatag  74520
gtgaggactt gctcagatca ccaagcaacc ccacctcacc tttcaacaca gcattactat  74580
ccaatgatgg gtaactggcc tgatggaaaa aagcaagcca tggctggctt ttgcaggcag  74640
ttgcaaactg cagtgttatg cagtctagcc atctcataac ttgcttagct gcatagtcat  74700
tgcccacttc ctgctcccag cattttgtag aagagaactg gtacatctaa atgctttgca  74760
gtagcaggaa ttggttttgg agatgagcag ctggttttga aacttgaaaa atgccacata  74820
caggcaattg gcctggctgg aaaagcagtg cggttttgag ccttaggtat gttacatgtg  74880
caagtgtaga gtcctacacc tggggaggaa tgactgcagg taccagtaca ggttaggggc  74940
tgagctgctg gtgaggagct ctgtggaaaa gaacctcggt gttctggcgg gcaacaggtt  75000
ggccatgagc cagcagtgta cctttgtggc ccagaaggcc aatggtatcc tggggtgcat  75060
taagaagaat gtggtcagca ggttgaggaa ggtgatcctc cctctctgtt ctggtgaagc  75120
cacatctgga gtactgtgtc catttctggg ctcctcagtt caaaaaagtc agggagctac  75180
tggagagaga gtccagcaga gggccacaaa gatgcctggg gtcctgtagc atctcccttg  75240
tgagaaaaga ctgagaaacc ttgggttttc cagactggag aagataaggc tgaaggggga  75300
tcatatcagt gattacaaat acttaaaggg cagaagccaa gtgaataggg ccaggctcct  75360
tttggtatcc tgtgacagga aatgggcgaa aattcaacac caacaagagg aagtacttct  75420
ctactttgag ggtaacagag gactggaaca ggctgcccgg agaggttgtg gagtctcctt  75480
ctctggaaat attcaaaacc tgcctggatg ctttcctgtg caacctactc tagggagctt  75540
ctgtaggagt gagttgaact cagtaatctc cagaggtccc ttccaacctc tacaattcta  75600
tgattccatc ctaacggcct tagaagggtc agaatttgca catacggtat aatgttctga  75660
ggcaaagcag tgaaacagat tgcaaagaag ctctaaggag atatagagag caaatcaaag  75720
aaatgagtgg aggaacgacg tcagtgtaaa agggagggag aaagcacaga gtttggaaga  75780
acgaaagcag tgaaaggtat tcaaaaatgg cactgaaaag tggctaggac tcacaaaagc  75840
agcagaagaa aaaatggaga atggaatggg aaaggcaata ggcagaaaga aagaaaaaga  75900
taaagaggca ggaacaaatg actaagaagt ctgaagaaat atgcagaaag gaaaagcaaa  75960
caacaaagcg aatccaaatg gaacagaaaa aaagtgaaaa gaaggaaaat attactgagg  76020
agatctgata ctgtgtgcag atttgtgctt cccatctctt tctttgcatc tcactgcatg  76080
ttggggacat aaccccatgt gatcagcctc tcttggactc ctattcttag ctccagtgat  76140
ttaaaagaat accccctggg tggggattcc tgttacagat caaggaaata cttcttcctc  76200
tctctaatta aaatccttcc actcacagaa agctggctct gtacctgaat gcgtgcctac  76260
tacctgtagg caacataaag ctcatgcatt tcctattcat ttgctctatt tctgcaagca  76320
agctcagccc caaacaaggg atctctaaat cctagcaaga accctgcaca ccccagtgtt  76380
caagtcctga caccaccaaa ttcaaaagga actacacaca gcaccacagc catggatctc  76440
cagtgttaat gctgttctcc agctaagggc gacttggctt tgcagtcagg agatgttgcc  76500
aggatgcctc ctgtcaaact agttgggcag ctttgagcga aatgctgtta gcacattgct  76560
agatataggt ttcctggtct tctgcaggaa actgaaggat gacatttgca tgaaattaca  76620
```

-continued

```
acgtgcagcc tttatcaaca attggctaga gactgaattt tcccacaaga aagtggaaga  76680
aatttaaaat agagtataca caggaaggtg ctccagagct cagctgttgt gttcttcatt  76740
tgacctcctt gctcaagaag gtaaacatta tttttctctt caaaaataac ttgtcttgtt  76800
gttgttgttg ttttggccaa atcagtctaa aagttggtaa atttcatgtt tatagatggg  76860
gcaaaggggg aagtactttc acaggctgga gagagcaaaa gacactgcta aaatttgggt  76920
ggtcttcacg aagggaggtg gtcttctctg gggtgaggct gggaatttag gaacacatgc  76980
ccaaagctat gaatctaaag atgcctgtct aaattcctca gacttttgac tgaaatttcc  77040
ctcggttctc cctgcctgct tggagagcta taactgccac agactgagtg gtttatacca  77100
catgcagatg ctttgctgcc tacatctcca gaagggtcaa agggctgttt tagaacagcc  77160
caactcactc taaaaaaatg ggctttatga gaagcgatgg tgcagatcat ctggataaac  77220
tcacccataa attaatagaa acaggttaat tttccttctt tactcaggtt tccacagcac  77280
aaggaaaagc cttgaaatgt tcactagaca agagagggca cgcaactctt tggttgcgtg  77340
cttgggtgtt tcctctgtac cctggtctct gctgctagga ttgtttatgt tcttaaacaa  77400
tggctgtata taataggaag ggtggagtat tcttcagatt ttgttttggt aatggggatg  77460
cttcactatc aacatatttg ctcctggctt tggcagcggt gttcaaaaat ttgctgagaa  77520
gtttatgtaa ctacacattg gcataacaaa tagcttgcca ctgtatggcc aatgtacatc  77580
cattcctgtt caagcaggaa taatcagcct agaaagaagc aggaaagata catcctggag  77640
gtaccgatgc aaaataatag aaccagtcag gaaaagccct ttcctgtata aaaacagcat  77700
catgaggggc taagttgctt gggagatgga cttggcaaca cttctcctga aaagatattt  77760
tgtgctgaaa tgtattgggt tttaatttaa agcacattgc tttggaaatg ctttgtgttg  77820
catggggaag actcgaattt ctgcgttaaa ggaaatttca tttttcttat gtgttgtgtc  77880
cctttaaacc caaaaagcca cagaaacact ttgaaagttt ttgtatgaat ggtcatgaaa  77940
aataacttct acaaccatag gcttttcatg tgaggacact gtattatctg ttgtgttctc  78000
cttttctagg atagacacgt atcatttccg ccaattctct cttcctttgc ttatgagaaa  78060
taaatgtata ttaaagcact taaatgagaa gaagagtaag tatgcaattg gaattatcat  78120
gcagcatcag ggaaaacagg tttcttcttg ctttcccttt ctacatatag aactgcctta  78180
caaaccaggc taccactctt tcagaatctg cattttattt actgcctcct cctgttgact  78240
gcataatgta acataccaca tcttttaatt atgatagctt tgagcgcagc ttttcattct  78300
tcagtaagtt ttgccttgat ttcatcttta gcctaaaaca agctctacag agagaacaga  78360
gcgtgaacag ctatagaaaa ggagtatttt tcacttcacg gagccatgga agcaatttgt  78420
tatccttaca agacttctgg tatacagtgg tatctacgga aggaggctct tttcctgggt  78480
agatccctgc tcacatataa caacgccagc aattccacct cccagactgt taacagctac  78540
tgagccatca tgcaaagcat ctcccttcat cagccataaa accacagccc tgcttgctgc  78600
ctctgcacaa ttgctaatgt tctgtgcaaa cagtttgtct ggtgcagaac aacagctgtg  78660
atctttctgg aacacttctt ttgatcttgt attttctctc cttcccactc caagatcttt  78720
taaaagaacc atttccattt gttgcccaac atctaggtgt tctcaaagtt actctgccct  78780
cacggtggct ccaaaactca ccaacaaatg attacagaga tcataagcat ggcttaatga  78840
tgtggaatca tacctacaca tactccctct ccaaatatcc attaagaaag ttcactaaat  78900
cctttggttc tctagtaaga aagttccttc tccagcccac atcccttctc cctccactgt  78960
```

-continued

```
tgcattgctt ttctggggca gccctgtaaa tagctcacat gaagccatgg aattggtggc  79020
agtggttgta cctggacgtc actctgaaga cagtctgctg ctttttctaa aggcatggac  79080
acctctgtac gccagacgct tgcctttaag acctgtttcc agctctcatg ctctccctct  79140
gtgcttggtg gttggttctt tccctgtggg ttggggtgga ggtgcctctc ttctgttgag  79200
gaagttcatt agctcctgtt gtctcctcga cgccttctga ggtctagaca cacctacaac  79260
atgcatcctg acctacattc acagtaaaca acctcttaga tccattttag atcttttacc  79320
agctgtgaaa gtggagcaac acaaacttta acatgaaaga agtgctgagt tttgttttca  79380
gaaggttgtg aataatagct aacgagggtg gaagaaaaga gaaatgatta ctgcaatgtg  79440
tttttcttgt ggtaggatga ctgcccattt atgttaggcc ttcatatgaa gtactactgg  79500
acttcagggt gaaacaagtg tcttagaatg aaacatatat gaacttttta tttcaagtta  79560
ggtaaaagga aataaatgcc tgcacttgcc acatatcagc accttcatat gttcagcaac  79620
ttgactttcc tgtcaatcta tcttaggcta agcctttttt cttgtgggct gagttcattc  79680
ccattgtctg ggacttgctg caagctaagc tgctcgcaca gacaacttgc tgcacctcag  79740
cagagccata gcaacttctt acaccctgtt aactttggtg cctgagcccc cacttgtcat  79800
acaaagatcc tgcctgtctc acacctgaat gagaggcagt gtgtgttccg catccttgca  79860
gtcagtgcag gacgctgagt agttcttgtc ccagagcagg ctgaaagcta gagccaccct  79920
gacctgagtg ctttctctcc acactgtgct atatattttc ccctaaataa aatatctttc  79980
tggaacacag gccacagtta cttatgtctg caagcagcca agagcatatg ctttgctttt  80040
cttacatatt tctggtgtgc tgtccagaac atcctttgtt tgacactaaa attgatgtgt  80100
gctttttatg gtacaatatt ttgagaaaaa cttgagtact ccactgctat ccacacaaca  80160
gctttacagt tatttcccta aaggactgat aagggcttct taaaagcctt tttttttttt  80220
ttcagatggc attcttcatg aaaagaccaa gctgaaactt agtcccaaat tcttcttacc  80280
agagtggatt taatggccca taggaaaggc atcagactgc tgtatttaca gtacaagaga  80340
aaagaatgag acagatcttg tcctgccatt gaacaggaag cttacagact ttctggggct  80400
gctgagctat tgcttcgttg tgaaattgcc attcgttatc cattctgaat cagtggttcc  80460
tatcaaatca atgaggagac atgaagtata ctgcaaacag tgcatgtttc cataggtagt  80520
agcattcata gctgcttacg ttccttcttc atacatgaaa ataattacta gtaattttac  80580
tttcatgaat ctgttgtttg aatccttcac actgcagctc aggttaccag atgtggttag  80640
atgcccgtgt agtttctgtc accccaatct gtctctaatc atgttgttac aagaggaaag  80700
aactgatgcg atgacacaca ttaaactagt ttgtagaagg aaatccacgg ctgactgatt  80760
taaataccac aacctttttgc ttacaaataa gaacaagaca gacagaccac gggaaactct  80820
tttggaaggg atcagataca ttgtgggata agatggaaaa acaattctct ctaaggaatt  80880
ctcatatggt atgagtattg gggccccttt ccagatcctg ctgtattcac atgagtgtga  80940
attaatagat gtgtgcaaaa tcagctattt caaactcaga attcagcaca cttctactat  81000
ttagcaaccg actatgggat gattttaggg cggacagata cttcacagta tgatacagat  81060
aagcaatcag ctgattcaca tttctccttt cccttttttgc tcccagtaag ctgcaggctt  81120
cacaatgggc tccatttcta gaatgattat tgagttttgc cttgatctct acaataaact  81180
caacagaaca gcaaaaggcc aaaacattgt cttctctcca atgagcatct ctacctccct  81240
tggcctgatc cttctagggg cacgaaacaa cactgctgct cagatagaag aagtaagtac  81300
tgctgaaatg ttctgagata cttccacata gcctgctgtt cccccagtgg caatgctggg  81360
```

-continued

```
ctttgcagca caacatgtgt gcttaggaga caaagataaa cacaagctca actgctgcct  81420
tgagagcagt gcttggtgtg ctgtgatccc tgctcactta tcaactgtga cattcaaacg  81480
attcaacatg tctcacctac agagcacacg gagcctgggg gtacagggtg ggcatgcaga  81540
agtctgttcc tctggtcacc atgcctttta ctccctgcag tgcaagctgt atgctctgag  81600
atcttttatt tcttttctta tttgtttctg agagcagtaa gtgaccaata ctcctaaggt  81660
atatgtggca taaggcagta gctggctctg gctgtgtcct ggtggatctt catccattgt  81720
attataatat tgccacaggt cagctgctgc caagggaaac tcattctcct tatgaggttc  81780
tgagtgactc ttgcttagtt taggaaagca atggagatcg agtactctca acaaggggga  81840
atggcgtcta actaaaagag cggaaattta ggtaagatgt taggcatata ttctttacac  81900
agagggcaat gaggcaccag cacaggcttc ccagagaagc tgtggtgcgc catccctgga  81960
ggcgctcaaa gccaggttgg atggggccct gggcaacctg acctggtggt ggcatccctg  82020
cccacagcat ggggttgggg ctgagtgggc tttgaggtcc cttccaaccc aaacctttct  82080
atgacagtta ataaatctac atcacttatc caggacagcc cagtaaatct ttcaaacaag  82140
gaaaatgcct ttatcccagt taaaattgcc attaatttga cctcttcaac tgcaggttct  82200
ccacgtcagc aatgccgcag gaactacaag ccttgaatct gagcttgaag gtgcagtgcc  82260
cgaaaacaag tctgaactaa gccaggaaag agagtcttcc ccctctctgg tatgtctttt  82320
ttagtacaag agtctttcac tccacagtag cctattagtt gtaaagcacc acagcctgcc  82380
acaggaggga gtcaagatcc catgcacaac gtctgcctgg tctactacgc ctgattgaag  82440
gtgttccctt gtaatcagcc aagtcctcca taaagtcaaa tacaaagccc ccaccagaag  82500
gaagatcagg ttacaaaact tagattagct gaatttaaat ataattacag tgggagctag  82560
ccctacactg caatctaatg aggatgcaaa tgaacaacca aagctatact gaggaatact  82620
tgtaattggt gtgtttgaaa tattcctagt gcaacacaga tgggaatctt aaccacgaag  82680
cgttccatgc actgctttta caactacaaa accttggcaa agactatgtt ttaagcctgg  82740
ctaacagcct ctttatccaa caaggatttg aaccgcatca ggtaagataa ctgtaccttg  82800
taacctctgt ggcgctgacc cccagctttc tggcaaccat atgcttcact gttgtccctc  82860
catgtgtatt tttgagcatt ggaggtgctt cttggagcca tatctcttag ggttgttggg  82920
aaagagacag aagtatcagc tttcagtgct tctgtttaaa acaaacaaac aaacaaagtc  82980
aagacaacac tctgtagagc aaaaataaag cagaagacct ttgacttttg gcatatctaa  83040
cttgagccag aagtgcgact acagcaaaaa aatggcctat tcaagctgtc tgcaagctgc  83100
ttctgggcta tctttctatt tgcagctttg cattgctggc tttcctcttt ttcttctttc  83160
tttcttttt ttttttttc cccctgctga atgatttgga tacttgagaa tcacccaaca  83220
catcttgcat cttctctaat tttttttct tttctatttt tttaaatttt tatctggata  83280
cctgcatact tcaggtatgc agttttctgt gggaagacat tgtcatctag aggcaaaaat  83340
gtatataaat aataagaaag acacaataat aatctctttt tcaaagatta tctgaatcag  83400
cttctgatag ttgatgtttc caaagccaaa ttttgtctct ttcagtcaag aagaccctca  83460
gaatttctaa aacgtttctg aattgttgac ttcatgttaa agagaataag ctctgaacag  83520
gtttggctaa ttcacaatct ttattctgct ttacagaaat atctaatgtg cagtaaggaa  83580
ctatacagag cagcccttga aacagtggac ttccaaaggg ctcttgaagc aagcaggcta  83640
aaaattaatg attgggttga aagcgagaca caaggtaaaa cagagcaaaa ctgtagctgt  83700
```

-continued

```
gctatcttct ccctcttcca gtgctccttc aaaaagaatt cagcatatga taagtcttgt  83760
tcatgtttct aggtttctca tgcccgtcaa agatagtttg ttgttcccaa tcattcttta  83820
gagtcatcta ccagctaaac tatttctgag ttaaagatgt gtttgttgtc acatactgtc  83880
atactcctac ccacatgcct agcaagataa ctgcaacagt acctctaagg gttaaataga  83940
ttaattgctc ctgcaaatag ccaacactgc aggtacagta aagcagagga cggaagttat  84000
gagcgtcaca gtgagactgg gaacagcata gcagagagag aagacacctg aggacctggt  84060
gttgacctgc tctggtcgta cacagagcaa tgctaacaaa gatgagtgat gtgcccacca  84120
gagagatttc actgttacaa gtaacaacca accagctttt gccctttaca ggcacataga  84180
ggtcattggc tttttttctg attaagctga acatgaaata tgccactttt attttgtcag  84240
agatgcaaca tcagcagggt gaaaacctta taaatcttcc agctgaactt aagccagaac  84300
ttactgaggg aaattactga tggatgaata gatttgaagg cttctgattt cttaatggtc  84360
atatcctgac caaacctgtc cttgggctga cagagcagcc tgtgactaat gtgggaaaga  84420
gctgcaaacc ccagaccatc attgctctgt gtgcctgtac aaagcctgcg cgcttgggaa  84480
atcctacttc acctctgtac agaaaaaaaa agggtaaagg gaaagatgcc ctcatgtaaa  84540
ctgaaacaga ggattaatgg cgctgcgcct tttactgtgg acaggtgcca cctggaacat  84600
tcattttgcc actgatccca cagtaggcta atttgatgat cggtgcccct tcctctccct  84660
aacaggccag tactaggtaa cagtgctgag aaatttacca tttctttgct tgtatcgtcc  84720
ctgttctgtg aagaaacaaa cagttggatt tctaaggtac tctaaagcta agttcacaga  84780
caagtaattg agtctcaatc cagagcctta ataacaacta ataaacacct gtgttttcca  84840
aaatttcctc caggtaaaat caaggaactt tttgctccag gagtgattga ctcacacacc  84900
attctggtgc tggtgaacgt gatctacttc aaagcatcct gggaacacaa gtttgaggag  84960
aaaaatacag tacagagaga ttttaaactg aatcaggtag atatgcattg tataaatctt  85020
agcatgattt acctgagtta gcatgattta catgagttgc aacgactcag cattttgttt  85080
caatggctga caaaacacaa agcttcagcc ctgatcagcg cttttgaacc taatagtcac  85140
tatgggcagc tgtcatggat agaagccaat tgcaaagatc tcatttcaca caggctctgt  85200
ggggccatcc tggcttttat gcatcccgta caattcagcg tgagccatgc aacagatagg  85260
ttaaaccaaa ccaatcaaaa aaagaggcca gatattaaca agccacatat atgaagatgg  85320
aatttgaaac aggaaaaatc ctcacagagt gttttggttt atttatagta tctgcaatgt  85380
ttaaaaggtt ttttttaaaa tatttttttt attttgattc cttttttcca ccgtacatat  85440
aaaatggaag ttttcattgc tcaactaagg tacagaatca tagaattact caggttggaa  85500
aggacctcaa agatcatcaa gtccaaccgc agcctaacca tagtacccta actctaacaa  85560
ccatctgtta aatcatatct ctgagcacca catccaaacg gctcttaaac acatccaggg  85620
atggtaactc aaccacctcc ctggggagcc tatcccagcg cttaacaacc ctttctgtaa  85680
agaagtgttt cctaacgtcc aacctaaact taccttggca caacttgagg ccatttcccc  85740
tcgtcttgtc acctgttgcc agtgagaaga gacctacccc gctctcactg taagcacctt  85800
tcaggtactg gaagaaaata ataaggtctt ctctcagcct cctcttctcc agactaaaaa  85860
gccccagctc cctcagcttc tcctcgtagg actgattttc caagcccttc actagccttg  85920
tgaagctgca aaaagttctt taacaaccac attaatccaa gctctgtaca gctcaagtct  85980
aacaaatgtc ttcaaaaaag atgatcaaaa ccattttatt tcatttaatt cagttttgtc  86040
ttcattccat atgctgtgcc tatgttacac taaataatga agccgccaaa aaaatgaacc  86100
```

```
cacaaaaaac acagatttag ctctgatctg aagttgaaga gctttgtatg ggaaaaactg  86160
tattctaagt gtttcttatc tatacaaaca aaaggtcaga aagacatctg ttgctagccg  86220
tagtgttgca ctgccattta ttaagacacg taagaaagtg taattttggt cccttaattt  86280
ttttacttga aatatgtctt tgaatttgaa tactgaaaac tgaccttagg taggaacatt  86340
tggaacactg ctgcagtcac agaaactatg agattggggg aatctgcata tacttttctt  86400
catgcactaa ttaataatgt tctctactaa aattcttccg ctgatttaga aggtaagtaa  86460
aaacttagct aatggtgaaa tgaaccttga gcctttacac aggatttgaa caaactcatc  86520
acaaaagaaa atgaggctta gaagacctag aagaacatgc ctgagattgc tcttaatctg  86580
tctattgctt cctgcctaaa acatctacct gataaatgac aacctgattc ctgcagtgct  86640
atttcttctc tatcccattc caaaccagga cttgcaaatc ccatcagcat cagcttgttt  86700
ggctggagag taatggtatt aagccacttc actatctgat cagttgcagg gaaattgctt  86760
tgttttattt tgccccccag agaattatct cctttataca tgaatggcaa aactgatgtt  86820
ttacgtgtcg ttgtatgtgc aacaaaataa agaaaaaatg tttagcttta taacaattac  86880
tgctgcaaac acagactact gatattgcac ctgaagttta aacattaagg tctgtattgc  86940
ttgtgtgatc attccaattt ctttttaaat agaatgagag aaagccagta cagatgatgt  87000
atcagaaagg cacatttaaa ctaggctata ttgaagagct gggaactcag gtgcttgaac  87060
tcccttacgc tcagaagttg cttagcatga tcatcctgca ccaggagaga cagcagatgg  87120
atctcccagt ggggctggaa caggtaaggg tgaggactgc ggctaagccg gactgaaagc  87180
tggttgtctg aattaaagct gggcaaaaat ctaaacttgt taatttcccc atcttctaga  87240
ctgaaagcac aatgacctat gaaaatttaa tgctgtggtt ctcttccgaa catatgtttg  87300
agatggtggt agaggtgtac ctgccccgat tcaagctcga aggcaccttt gacctcaatg  87360
aggtattaaa agcaatggga atgactgaca tcttcagtga atccaaagct gatctttctg  87420
cattgtcatc tgagaaatcc ctggtgttgt caaacattgt ccacaaggct tatgtggaag  87480
tcaatgagga gggtactaca gcagcagctg ctacaggagc taccattgtg aggaggtctc  87540
ttcccctcat agaggtgttc atagctgacc gtcctttctt attctttatt aggcacaatc  87600
ccaccagtac cattcttttc tttggtaaat tctgctcacc ttaaaatcaa ggccatcttc  87660
tagcattgtg agaaaaacct ggatgaatca gaaatactat ttttcccct acaccttctt  87720
attcctatga atgattgtag atcaaagtaa tcactgcagc caacctagcc tagaaccatc  87780
aattgaatgc cctcctgtta tgctccttga atggcaaata ttgatctgaa tctaaaacag  87840
gagtaagttt tcccttaacc tgactggaaa tcaagaatat tttgtttctt caaggcgtac  87900
atacactcct gtatagccaa gtatgtccgg catagccaag taatgtagta cactatttgc  87960
ctggcaaagg tagaatttgt atgctgctac ctgaggagaa ctgtttgtaa caattttcag  88020
taactgccag taaaagtgga gtatttttat tttctctgta gtttttgatt tcctgccagg  88080
tgggacttga ttaacagaga ggggctttgg aaatgcttta tacttataca taatctgtat  88140
ttgtggcaaa tccttcgcac agtggagatc tcactttgat aattcccttt cctgtagcag  88200
cagtcacaag caagcaggaa atacttattt acagcaaatt cacgtgttta ctgacaactg  88260
taccaccttt ccccccatga tgtatgctgg atctatcctt ttgccatata aaacgtttat  88320
gctagaagca gctttggttt catttattta tttagatata agcctgcatc tgaagcacca  88380
actcatcaac tggaagatag atggaatatg acatataccc ctttcacaat cccttggttt  88440
```

-continued

```
tttccacatg agttctgtta gaagcactgt atttttcctt ttttaagata acaacagtag  88500
gaacactcat ggaaaggaca agattacgcc tcatgaacac atctagtaag agagttgatt  88560
ataacagcaa ctgagtatgt gggaaggcaa gattttgacc ctcgttttac aggatttttt  88620
ggcactcttt tttgaaaata aatccaccct taaagaatca cagcatggtt gatgttgcaa  88680
gggacctctg gaggacattt tgtccaactg tcctgttcag gcagggcaac catgtccagg  88740
gggcttttga gaatccccaa gcacagaaac ttcacaacct ctctggacaa cctcttctga  88800
gttcccacaa ttttgaatga caccaaagag aattttgtat gcgcagtgtc tgcaggaatg  88860
ggatgtgaaa acacacattt ctaaagctta attacttaca tagtgaagta attggttttc  88920
ttccttgagt tctgctctct ggtgaagttt aatgatctga gatgcatgta tatagatata  88980
caggtctctc cagccctgag gaatgaagaa aagttttgaa aagggcaatg taagcaatag  89040
aaatcacagt caaatattac ctggaaaact ttttagtctg agagataatt agaaaaatag  89100
aattagcagc tgactgatag agagacataa ctgttaagtt gctggtttaa cacaagtaat  89160
atcttcctca cagagttcta tgtgaggttt aactaactag cgttggcaac ttgtgctttg  89220
tgacctataa aaaggcaagt atacattagc tattagtcat ataattgagt gtaaagctcc  89280
ataaagtaat tcatgattag cacagtttat gtaccaaaag ttacctgcgg ctctttggat  89340
aagaaagtct aggcatgatg ttcgagcaag aacaggcagg agtaggacaa taatattcaa  89400
acaacttacc cttactgact aatctgaaag cacagtacaa tgtaagcagt acttttccag  89460
attgtgtcca tgtttccatt ctggaggctg acagcacaga ttgcctacta agctatgttt  89520
ttattacctc caggtgtcat cacttggttt ttacataccc tggggaagtt ctgagcacca  89580
caacctcaaa catcagtccc acttctgcaa cgacaggaac agagattcct gtgatgaagc  89640
gtcgaataac acagtgtctt gctccagttg ttggaggaga tggttcatga taaatctaga  89700
gtgagattaa gacacagatg aggtcaaatg tcatccagct agtttatgac aaattctaag  89760
cagttaagga atgtgggaaa catggcaaag ttagcaacag taaagggagg aattctagca  89820
aactggctat agagcaggga tactcacccc catggatcta gcagtatccc attggtttgc  89880
aggaggttgc aggtcagtca aagacatatc actgatctgc acagctgcag ttcagtggag  89940
gattgtctct gttctaccac tgaactcttc aggctttatc ctcttcattc tgctctcatg  90000
caccttcagt tactcagggc caatggcatg tgtgcctccc attgggtgat cggctgttga  90060
tcatgcagca atcacacacc tgccacctgg cacgctgttc ggcatgtgta ctgacttaat  90120
ggaagagacc ttttaagctc atctagtcca actcccctcc actgaagagg gacacctaca  90180
gctagatcag gttattcaga gccccgtcca gcctcctcaa tgtctccagg gaaggggctt  90240
ctaccatatc tctaagcagc acattccagt gccccaccat cctcactgta aaagaatttt  90300
tctttatatc caagccaaat ctcccttcct ttagtttgaa actatttccc cttgtcccat  90360
tacaacagat cctactaaag aatctgtctc cttcttctta agagctccct tgagaaggga  90420
gctcttctca ggtcaccttg gagccttctc atatccagac tgagcagtgc tagttctcag  90480
cccgtccttg taggggaagc attccatccc ttggattatt ttcctctgga ctcacttcaa  90540
cgtccatgtc tcctctgtac tgaggactgc acatttggat gtagtactct aggagaggcc  90600
tcaccagcat agagcaaggg acaggatcac ctgccttgcc ctgctggcca tgcttctttt  90660
gctgcaacct aagatacggt tgactttcta ggctgcaagg gcacactact gactcacgtc  90720
cagatgccat ctaccacagt acccctaaat ccttttctgg cagggctatg ctccctcttt  90780
tcgtattcca gcttgtaaat gtagtggggg ttgccataac ccaggtgcaa gaccttacct  90840
```

-continued

```
ttggatttgt tgaccctcat gaagttctct cgggcccact gcttgagcct gtatggatcc  90900
ctctgaatgg catctcatcc ttcaggagca tccactacac catacagctt ggtgtccttt  90960
gcaaacttgc tgagggtgca tcaaaatcct gttgacaatg ttactgatga agacactaaa  91020
gagtactgat cccagtactg atccctaagg aacactactg gtcactgatc tccatccaga  91080
cattgagcca ttgaccacca ctctctgggt ttgatcccgc agccagtttc tagtccacta  91140
gtcagcacac cactgatcat agccacactc gaaggggcag tcatgcaagc accaccctgg  91200
gtatttattt cccagcactc taaagcagag ctcttgctcc agctcatgtt attttctgtg  91260
tggcaaggag tgagattcat cgactctagc aaatggaact aatggctcca tgtgccccag  91320
gtctcagctc agcaccagcc aggccagggc tgagtccccc cacatccaac ccataaggtc  91380
ccagaggact cctacgttta ccagtggtgc acagagatga gtttagccca agtccacccc  91440
tcagcctcaa ctcccttcaa cacctcttca ccaagaggcc caatccatca ctccttacca  91500
gccaaaacat atacttgttt aataccacag ccacaaaagc cacgtggtaa ggtctgaaga  91560
gaccaaaact gtggtttgag taaaacagaa ggaaagcctc tactcagtac cccacttatg  91620
actgagttac taggatagga cctgattcta cagcacccca ataccctgta gatgtattcc  91680
tttaattctt cacaccagat taaggctgct gccaccaccc accacaaata aatccttgct  91740
taggctgatt ataacttaca cctgtggctt ccacagtcaa atgagattcc cagtgcccac  91800
ctgcgtgttc aacttcctta aggcaaagca tcttgcagtt agcagagtgt taagaaatct  91860
tcttgtattt cctttaacac acgtttatct tccccagtga tgctgaattt gcaaatgctt  91920
tagggaaaaa ttggcagcaa gtccttacat aattactgtt tagcctagaa aataacaacc  91980
gaggtagaat acttcagaaa gtttctaatt taaggttttt ttcttgatga gagaaaagtg  92040
ctatcagagc tgtttagtaa ttccagtcat gcatgggtaa ctcattcttc tgtgttaggg  92100
tttactgaga ggtgaagaaa caagtagttt cttttcctta tgaaaaaaaa aaaaagtggt  92160
attagaagaa ccccataaaa gaatgccaaa cattgcagct tatgatgtgc aatgtgtcac  92220
tcagtcttac agatgacaca gcctggaagt aagcttaaaa aaaatgttta attcctaact  92280
tcttttgaca ccatctgtgc tgtggtttat gacatccatt aataatgttt atcactaaac  92340
aacaacagat agagagacca gaaactaagg atgctgctgt catttccttc tgatgcaagg  92400
tagaaacatc aggaaattaa ggcacactga aatattttgt aatattttgg actagaagca  92460
aaaccagaaa ctgagttgca tttgtctcct ggagtacatt ctacaggtat ttaaaaagag  92520
acaaaaacca taaatctact tgaatttaat ttgaagtatc aaatgaaaaa gatgtacctg  92580
attttattat cctccacact ggtcttctga acttgaccaa tcccactggt cagttactgg  92640
tttacgactg ctcaagctgt ttgtagcaac tatgttgtac cacaaaatat ctgagccatt  92700
acaaaacaga agagtcatta ggcattttat ctccaaccca aagcatacat gcatgtttta  92760
aaatctcaaa ttctcctgac tttaattgtg catattatgt tcaccaaacc ttttagaacc  92820
tgccttgttt tttttgttct ggtctgtagc tgggagtcag agaaattcaa ctgtgattgg  92880
aaaaatggtt actggcaagc tatagagttt ctaagccaga aggtgaagaa atactacttt  92940
tttaacactc ttggcctggg actagactta cagacatgat caatattgaa aggcaatttg  93000
gaggtataca ttttaacatg tcctcagtct ggagttagct gtgtgtccag tttcctctca  93060
gtgtgagtca agcaatagca ttagaaagtt atgccccaag tctcatcccc tcctattgaa  93120
acttggcaca gcacattcag gctgtaagcc accaggtcac agccccctta aaggattcgg  93180
```

-continued

```
caacagctgt ggttgctatc acatggtgtt gatcatcgtt gggcccctca ctgtaagaaa  93240
gacattgaga ccctggagcg tgtccagagg agggcaacaa agctgttgag gggtctggag  93300
cacaggcctt atgaggaacg gctgaaggaa ctgggattgt tcagtctaaa gaagaggagg  93360
ctcaggggag accttattgc tctctataac tacctgaagg gaggttgtag tgagctgggg  93420
gtcggcctct tctctcgtgt gactagtgat aggactagag ggaatggctt caagctgcgt  93480
cagggaaggt tcaggctgga tgttaggaaa tactacttct ctgaaagggt ggtcaggcac  93540
tggaaagggc tgcccagaga ggtggtggag tcactgaccc tgaaggtgtt caaagagtgt  93600
ttggatgttg tgttgaggga catggtttag tgagaaccat tggtgaaggg cgaacgaatg  93660
gttggactgg atgatcttct gggtcttttc ctaccttagt gattccatga ttctatgatc  93720
attacactgg atttgatact ctgtgagcaa aggcattgaa gtggtacaaa aaattcaaca  93780
ttctgcatta aattgtagaa tctggcaagt ggaaatcgtt ttctataggc acagccacgc  93840
actcagaatg tgtttgcaat ttgcttgcat ttagtcttct gcaagtaatg actgctttct  93900
gtatgcaaat gattgatcca tgtgaaaaaa tctgcttgtg tatctgtgaa tcaaatgcat  93960
tgctttataa tgtgcatttt ggatcattta tttgtggaag taagtgtaaa aaacagagcc  94020
tgcaattgtg cttctgcagt atacaaggcg ttactcaact ccagctgtac agtcagtcag  94080
gccctgagat aatctagact tatactttcc atagttatta taattttgtc tcttactaaa  94140
tctttgattc tgcttgtttg ataaagtaac actcattttc tatatagtat tacaatcgct  94200
tctagaaggc attacatcac tgaattcata ggctttctga aaaacagatt cagaaatcag  94260
attttctaac tgtatttttc catgtatatg tattggagaa ctagtgaaga acgtgtttaa  94320
tatacagaac tacagataaa tccagaaagg agaagcaaca ctcaaaataa ggatgtggca  94380
atcctaaata ggctgtaagc tggcttgaag catgtccctc caaaaaagcc atctgagaga  94440
aaatttctca tttaccatgc atgtgcaagt ttccaaactc tgcaggtatt ttattttctc  94500
cttttgcaaa ttcccttgca gatggcattt tgctttgctt gctctgaact gcgttgatgt  94560
gagcagtgag gtgcttttct catgctgaaa tacaagaata aagaagattg aagcacaggt  94620
ctgtgcagaa catctagtga atgtattcag ggcatgccaa gcacaagcta ttcaaatatt  94680
gctccctgaa aatgcagtca gagtggactt catgttttta agtggaagtg gtacataact  94740
tctgtagtgg agaaatcgtg tgactcaggg ggtgaagggc ctatcctcag ttaatcccat  94800
attcttgttg caatatgggc ctgcatcttc cagcactgtc agactccagg ttttagcata  94860
agatcagtgg aaaaaaatat acacaaatat accccttgct tctgaagctc tgccctaatt  94920
gggatgattg caaataaatg aaaaaaaaaa aaagggaaat tcaaatactg atgataactc  94980
tgcagttcaa caaccaggac acctagtagg tgagttctgg cttccagtcc ctgctgctag  95040
gactattctt gttttaatgt ttaagagaaa acaagtattc acacatgggt gagtacccta  95100
gcaataatga cagagaacta ttctgctcta tagcattctg atagtatgaa tctcgcctta  95160
attccatagt cttctcttag taccacgtcc cccagctcct gttgtctgaa ttaagcaatc  95220
actgtgtgac acctacgtcg gagcttagct ccattacact caatgaaatc agttgctggt  95280
cttctgtgga aaatatacta ttgcgccctg agcagtgctg agcacagcac ctgtttgcct  95340
aatattaatg cagcactcag accacaacca gcctcaagac actcagcaga aggaatatta  95400
tgaaaacagt aggtgctgct cctgaagcat aacagcctcc agagatggaa gacaagaaga  95460
tgtgctttgg tagtgtgtgg tgctcatttc cttgttcatg aatgatgatg ggaatgactc  95520
tggaagacac accagaggcc tctggtgtat accccatgcc tccagcctgg gcaactcctc  95580
```

```
cttgctgcct ttttgacttg ttttgtgcaa gccatccatc cagaggtgca gagtgaaaac  95640
aaccatggag ctcaagaaga gcctcatcag gtccatacac acttcaaacc cagagcaaaa  95700
cattggagcc tcgggctcac tgcacagttc tgctgaaaac tgtgatgaag agctaggggt  95760
tagaggaaaa atgtgctgta gttatcagtg cagctccatc atctgttccg ggagcatcaa  95820
ggcttcctgg agagaacatt atcagaagga cacaaattat tcagtgagag ggagaagtgc  95880
gcctctgaac gctctgagtc agatgcttat tttgtgaatt tttctgtttc cctcttcctg  95940
ttatgcttcc tgcagatact tggcacatcc ttgaggcgat tcagcaatat atgctcatat  96000
tcagccacat ctacagagtg cctcctccct gagaggagaa aaatatttgt tttagggggt  96060
aaaaccagaa tagctgtgct tggacctcct gctctgctgt gggacaagag aagctaggct  96120
cctggtaacc tcaggaggca gagggaggca cattataatt tggctaagac ttgaaaatgc  96180
aatttgttgg tatatttggt aaatatactg atggcctagt cccataaact accttctaga  96240
tgtggagtaa gtggtttaaa ggcatagcta agaggttgca gaaaagaaag gaccacatcc  96300
aatttggtag caaccaacat ccagcattca cagactcatg agaaatacct tttaattaat  96360
ttatttatat taaataaaaa aaaaaaatcc tttgatgact caccctgctt ttcctgttac  96420
tctcagttgg gaagaaagta accgctgggt acatactact gcaatttcag agctgcagac  96480
ttgaagagct ttcccaagtg ctgagatatg caggaaaaaa aaccctgtaa attacagtac  96540
caggcattta attttgattg ctaaataaag aagactcgtg acagtccatg actacgtctt  96600
ggagggctgc aattacatat gaaatatagt ctgaattagg agagttactg gcagaggcaa  96660
agtttgcatg ccaattaatt ggtaaaagga gagtacgcca aacacaggct gtggactgct  96720
ctgatgaact gagtatgtaa aaaatagcca tgtgtgtttt tcagtgaata ccatggtata  96780
tgtctggttt gagtcaaata tgtattaaaa tgaaaaaaaa aaacaacaag aacagtgaaa  96840
taaacagtgc tagcatatat tagcttgtat aatcagacct atatagtttt caaataaatc  96900
ttcaaggaga acaaaatgta tagtatgtat gataaggata agtactataa aacatcatca  96960
tgaggagtgc cagtctgaca acaggaaaag gaattcagcg tgtgaatgaa ggggaaagtg  97020
tgactgaaac aattgtcact cagcttacta cagcagaagc aatcatttat gatcttagat  97080
tttttttat ttttttttt aacttgcttc agagatatct aagtaatctc aaaaacagga  97140
acaaaatacc aacgcaagga aaaattctat tttcgcttca tataatcttt tcttttttt  97200
tctagttgca ttcttaccta aaaacaacaa caacaaaaca tttaaacaat gtttaaatgt  97260
ttactgctgg tttgattaca tcaaaccgag ttgttgctgg agatgaccag ctatcaaggt  97320
gcataatgga ctggcagatg tgcttggtct taccccaggt tgctgtgcaa acacaataca  97380
cattgacata taagctacta tgagttctga agggcagttt agacattaat tctactccag  97440
gccagacacg ctgactatct gagtggttta tagcaaggga ctggttgact tcaaagtggt  97500
tccaagtcaa ccactgccaa gtgcttaaga ctgtgtatgc acaacagagc tgatcatctc  97560
cagtgcaaca aataacatga gagcaaaaag catctgaaat tctgtaaatg aggctgttct  97620
ggccacacct tggctcatta aaagactttg agagatgcca gaatagcctc tgctaaatgt  97680
gatgcagatg gacaagctat ggaatgaatg ggtccagggc ataaggaaac attaccctca  97740
agcactacac aggagctgct gaacaaccac aggaaaggaa atgtgaaaat gtgaacagat  97800
aaatgttgga aagagccgca tttctgctgc ttactatgtc cttgattatg ccaacattaa  97860
ggaagaatgg caaaccccgt gaattggttt aggaacagct ctacaatgga ctgcctgacg  97920
```

-continued

```
gaggaaaagg gcagcagagt ccttgctgac ctctttctgg tacaaacaca gatctggaac  97980
agagtttaac caattagtct tgcttgcatt catgcctctt gaatttcaag aggtgccttt  98040
gatttcccct ggcctaacac cccatctaaa attacaaaac catattttgt ctgctgagga  98100
ctgtgcacgg atagcccgtt ctggtcaaca tactcaggct gcttctgcaa caagttttgc  98160
actggcattc agtgtagaaa aaatgcaaga cctgtgtagc ggcagacttc tctctggaga  98220
acatgtattg cctcaactat cttacctgtg caaaactgtt gtggtgactg tgctattgca  98280
gaggtagagt gttcaaagaa ggcaaacgta ctgaatgaga gaacacatca aaaacacctt  98340
catgccctct tctaggggag acagcgaaac aaaatgttta ttgagaaaat cttggacatc  98400
agtccaagag atgaaaacac tgtccatatg tgcagggctg gttgtgttct acaggtccat  98460
gctgcataga tgaccacaga ggacaaagac attgaaacca agcatacaaa gggctgtggg  98520
tacccaggaa agttcttcaa ggaagccttg aagggatgtt tgagtaccca cctgacctgt  98580
agctgcaacc ctgatgtaaa catgtgaaaa tgggagcata agagaagaca ctacacactg  98640
caacaaaacc tgtgcccttg gggaggaaaa gtttgacaag ataaagtaga agctattgaa  98700
aaaggaacat taaacaagac aggaggaaag cttcttacta tctgtagatt tccctactcc  98760
cgacatgact actgtcatgt tgacagataa aaaatactca ttttgagtgt ggaaactgaa  98820
agccattcca gttatcatgg tctgcacata cacacatgac tgaatttcag caacacaaaa  98880
cacagtgctt atgataaagg agctcccttt tacctttacc agtgggtacc accaccactg  98940
tgtactgtct gtcttaatgt gcaaaaattt gggatttcta ttattcattc ccctggcctt  99000
aacagaagct ggattttttt ctttagtgct catcaagggc attattcaat aaagagtaat  99060
agctttttac aattgactaa tatttgatat tgtgcattat gattgtctaa cagaccatga  99120
atgttccttc agacagattt ggtagtttat ttacctgtca tagtaaaata ggaggtacag  99180
aagatctatg agaatagcct gtgcatgtac aatgggcctt gttgccatga cctatgaaga  99240
atgaaaatca aaagctgacc accaatcatc ccttgaattc cactggctgt tcagcattca  99300
cttctgaata tctgaatact ctggagtctg ccttcgcaaa gcagcaaata ctttcagact  99360
gttccctaaa tctcttcctc ttacctattc acactgagtt ctctaattca tcccaacacc  99420
tctgctctga atttttttcat aagaagcttc agcaaaatgt gctttctcct ctcaaatgta  99480
tgctgcagag cctttggctt acagtggata tagcccaaat tccagtgaaa aacttcagtc  99540
ttgcctaggt gcagaaatag atggagctgt gcttttaaca agtactaact ataagcttct  99600
tcagttctca aactctttca gcagaccaaa acatttttca gtacagtttt gttctttaaa  99660
aaactcataa agctttgttt ctattcttac atggaaagca atccattaca aaatcctcaa  99720
aatagaatga ccatcctgca gctgactctg cttggaactg cattattttc tctacatcaa  99780
gtggttgcca tccatgagaa gcatccctat gtttctctgc acactgcagt aagagatcac  99840
gtatatatca cacttttccc ttcacccatc ttgggagcag tgctacagta aattgtataa  99900
ttacagtgcc ccagagatga gaagaaactg aacagcagga aaggagacac agtcttaaaa  99960
agaagaatgt tttccaggaa ttgatgcact ttcttgcact ccttggtaat atgggactac 100020
tcttgcctca cctttagcag tgggtgctca ttaaatggtg aatggtggtg ggtcttctgg 100080
ttctccaatc atgtcttatt ttctcataat attttgggat ccttagattc atctgactgt 100140
gagaatcact tgatctgatt ttttttttta atctgatttt gcagctaagt ttatctgaag 100200
tgtattatgc ttatcctctt ttttaagggt tttttttttt tttaaagtgt gtgtattcat 100260
tattcgtttg gctctagtta tcgatatggc tcaatcaaat taatgtttaa attctgaagt 100320
```

-continued agagcatgag acatgctaga cttgaagttg gtacagcttt ataagataca agaaaagcct 100380
gaataattac attctactat taggtttcac ttcacaaaat aaatttggct ttctccaagt 100440
agagtaccag tctaatgttg gcctactcag tgctttcaag cacaatgaat caaaaggcaa 100500
tgacaaaggg tagtaactca aaggatgact cttagaaggc taacaggggg agtgtccgaa 100560
agggtactgt atatatcacc aaggactcag agaatctgtt caggttcaac tggcaagctg 100620
gattattacg agcctctttg atgtttttct gtaagtactt ctccaaataa aatgtaactt 100680
ctaagttgta ttcttgaata tggaaaaaac aaaacaaaac agaaatatat tatgtaagaa 100740
cttagaggaa aaaagggccg ccttctattt tatgatgttg gcccaccaca tcagaggcag 100800
atggtggtgg tatggcagta gaggttgaac cttcccacca acaccccgtt atgtgttgtt 100860
gctgtgtgac agatggcagc agaggggcag tctgacagaa tggcgtctca catggaagtg 100920
tgtatgaagc aaaggtgtgt cactgaattc ctccatatgg aaaaaaatgg cacccactga 100980
cattcatcga tgcttgctga atgtttatgg agacaaaaca gtggatgtga gcacagcgag 101040
gcagtgagtg gtgtgtttca gcagtggcga cagtgacagt tgttcacctc cactggtaca 101100
gaattttgcc agcaggaaat gcagattctt gtacattgtg ggcaaaaatg catagctagc 101160
tgtggtggct atgttgaaaa ataatgttcc gtggctgaga atctgctcaa ggaaataaag 101220
ttattgtaat cattataata atattataca tgtgctttct atctattgta gtttacatga 101280
aaataaatag gaggcattac ttttggtgtg atctgtatac aggacagata tgtaaaaaat 101340
atttctggaa gagaaaattt ttgttttcac agtctcactc cctgcagaac acaggtgagg 101400
tacagtagga taattcacag agccttgtta gcaccaggaa cctctcaggt tatgtagtag 101460
atcacatttg ctacaaacta tggatatgct attattccaa cttaaaactg ttttagaacg 101520
gggagggcac tattcagctt tcttgttctc ggattaaaga aagagaagga ctgtagattt 101580
caataatttc ccctaagtct tgacattaaa ttgcatgtac aagaccttca cctggctgat 101640
ctgatgcagc tttacagtgc attaagtaat ttagccagac tgtgtattta cggtatatag 101700
acgtttgttt gtttttgtca acaacaaaaa aaaggaatca gcagagatta aatgtcaaaa 101760
aatgagaata tagagaagaa gcccactaaa gctatagttt ggcatctaag caactggcta 101820
gatttacaaa gagattcact ctataaatta caggacagca acctccaatt ttatggccag 101880
ttgtacaaag aagcagtttg aaacaagcta agactattgt ggtttgacta catttgattg 101940
aaatatccag agtatggtcc agagtagaca cagaagaaat gaaatgtgtt tacattgtct 102000
caaaaatcat tcagagttct ctggatggct atagggaaac tcatctagtc cacactgtat 102060
tcatcatact gaagcacaga tgaaactatc tatttcctaa agggcaagta caagatagtg 102120
tttttataat gaaccagtac ctttctgaag gaaagtaaac atgcatttgg gaaacaatgg 102180
gtcagtcttt acaatatttc taatgatcac agaattttta ggctttacat tattgtttca 102240
gcatcacaga aacagcaatg aacaagcagc ttctgggcta caggaagtac tttttactac 102300
aagtgccaca cgtcaacacc acacagtaat aatcctgttt cttttagaca acaccgattt 102360
caggatgggc tccatcagtg cagcaaatgc agaattttgt tttgatgtat tcaatgagct 102420
gaaagtccag cacacaaatg agaacatctt gtattccccc ttgagcatca ttgtagcctt 102480
ggccatggtc tatatgggag caagaggcaa cactgagtac cagatggaga aggtaagtta 102540
tgcaagtaaa tacaagctca ttttgatcct ggttaacaga acaagttatc catgaagatc 102600
tttgagactt tctcccctta aggggccagc tgctgtacat ttgccactgg atttgaactt 102660

-continued

```
ggctagcaga aggacattga gccatgaggt ttggatctgg aactaacttt tcacttattg 102720
cttttcacta caaagggtaa caacagtttc tactaaggag gagatctcct gcttcagttt 102780
atattatctc acaaacctga ctccttccag ataaaatgaa caaattttca tgtataaaag 102840
atgaaacact cagaaatcag gagtcacagt tctaagtaca gtatgggtgt agctggtttc 102900
tggatggaaa aataagtgaa ctaattggaa gatcctatca aaaaatgttc agagcagcac 102960
atgcagtaaa aaaacaaaca aacaaacaaa caaaaaaaaa ccacacaaat ttcaacctcg 103020
aatgaaactt ctcagttcag ccattggtta tttcaagccc agaatttgaa cacaaaatcc 103080
agagactctc agtgaacttt gcatacttca tttcttcttc tgctacttcc atttgcaggc 103140
tcttcacttt gacagcattg caggacttgg aggaagcact cagacaaagg tacagaaacc 103200
taaggtacat tatttttctc tcacattcac tttttttttt tttcctgaaa acttaaaact 103260
gttctgactg tgcttccaat aggtccagcc ccttcccaaa ccctagctaa tgctctcaac 103320
acatgatatg caaatgaaaa actaaaattt gttctaaaaa aaaaaaaaat aatgacaaaa 103380
agaaggctca tttcacatgt tgcaccagaa aaagtgatag gatagttgaa ggacattttg 103440
agcaccagga taccttccta cattgataag aacttgcaca cttgtagggc ttgctggagg 103500
accacacatg aaccatgtgt gcttttctcc ttggtcactt gatacatttg gaaagataac 103560
acaagccatg ctcccagggc tgtcctcatc cacttgggtt ctccaagcac aatgtggggc 103620
ttgtaaagga caagaagatt tttccgtttc cttttctttt tcctttcccc ctttcacttt 103680
ttcctttccc cctcactttc tctctccttt tcccacttcc ctctttcctt tacatttccc 103740
actctcctct cctctcctct ccactccact ccactcctct cctctcctct cctctcctct 103800
cctctcctct cctctcctct cctctcctct cctctcctct cctctcctct cctctcctct 103860
cctctcctct cctctcctct cctctcctct cctctcctct cctctcctct cctctcctct 103920
cctctccttt ccattctatt ctttttgcta gagcatttag atggttatgt agaacaattc 103980
acaaaacaca atcagacaaa tcactcacat tttctgtttc ttatcaccaa gactgagtgt 104040
caccaaatgc tatcagttgt acatgcttat atagaacatc tctcccatgg agcttttaga 104100
ctctaatgta ttttgtttgc aaatgtctga acactgtgtg ttttcctacg tgatctgtac 104160
tttataaata gttgtctttc tagtaaaata agctaacatt tataccottt ttcctcctct 104220
tcaacaaccc agtgtggcaa atccgtgaac atccacctac tctttaaaga actcctctct 104280
gatattactg catcaaaagc caattattca ctccgcattg ccaacagact ctatgcagaa 104340
aagtcacgtc ctatcctacc ggtgagttgt acaacagagt gattttttgc tagatcctgt 104400
ataaacccat aatccaggag tactgcccag agtatctgtt aatccaactc acctcagcgg 104460
tgtggacttc cacagctttt catttgacat tctcaaaata aaacacacaa atattctaaa 104520
tcaaatacat tttatcttta aaaatagaga aaaatgcttc aaaaataagg attttattat 104580
aacaaaacag ttgctaatgg atgctaatgg acctgaagct gtttttggat tggtatttct 104640
tcaagaaaat atttcagcat ttctactacg taatcttatc tggtaaagta ataaaaatct 104700
taaagatctt aacatatcat gcatcgaaat aattttgctg gcccagtttt aaccatttcg 104760
tccaggaaat aagccatgaa aacagtctaa tagcataatt ataaaaatca tggaacattt 104820
taactgcatt ttatttcacc ttcacagtct ttttaaaaac tgacttggta gctacaactg 104880
ttgtctttac agatttacct aaagtgtgtg aagaaactgt acagagcagg tctggaaaca 104940
gtgaacttca aaacagcatc agaccaagcc aggcagctta ttaactcctg ggtggaaaag 105000
cagacagaag gtaagctcag aggagagttt ataatatact tccttgttac tactttaccc 105060
```

```
aaacaacttc tggaaagact attccttcca tctccattaa tggatatttc ctgtggaaac 105120
tgatgactct tgcacacttt tttgtgtgcg gtgacagtga atttaaatat atatgacaaa 105180
ggcagggatg ccactgtgtg ctttctgtgt aaggagagca taactcatgc aagattggtc 105240
ccagcttccc tacaatattg gcatcatttt acaagcatat gctggatgga taagaaatgg 105300
gcttccgtgg aagaaaataa tgtggccact aagttggtgt aagaaaagga atgattaaga 105360
gtgtatgtac atttatcagg aaaaaggtgg gaagaaaaca agaatcaagt attagaagga 105420
agcacagtga gaggcagaag atcggtatcc ctgctttgct tttcacttcc ttctgttcca 105480
tgcaagtctt tttccaagga cgtttgagat attcctgggg atgtgtgtga acattcaagc 105540
ctacatgcct ccttacagaa atgcctggtt aagggttagt tgttctgtat gaaatcactc 105600
gtgaacttga attccacatg ccatcattta aagaacagga agtcaactca agcttgctgg 105660
ttgacatcta aaacaaaaca ctcctgcaat gaaaacaaaa ccccacaaag cagcaccctc 105720
caatcccttt gcctcataca tgcaaaccag acagactgtg tcttagcact cactgctttg 105780
cttccttctt acaggacaga tcaaagattt gcttgtatca agctccactg atcttgatac 105840
aacgctggtc ctcgttaatg ccatctactt caaagggatg tggaagacag catttaatgc 105900
agaagacact cgagaaatgc ccttccatgt aacaaaggta ggggacgtgg tcaccgcttc 105960
tgggcaggac agaaagccat caagggtgcg acatacacca tcctacagtc attggtccat 106020
ggttcttctg ggcccctcgc tgacagggca tggggctgag cccaagacag gctggcaaaa 106080
attgtgtctg accaggcatc caaagcacac ctgtagacaa gagaggaaaa tggagacaca 106140
gcttgaggat ccagcccagt tcctctgaag gacttgcaca tctgcctgct tcaagagaaa 106200
ctgccccctt ctcacattgt ctcatgcttc tgttttgcag gaagaaagca aacctgtgca 106260
aatgatgtgt atgaacaata gctttaatgt ggccacactg cctgcagaga aaatgaagat 106320
cctggagctc ccatttgcca gcggagacct gagcatgttg gtgctgttgc ctgatgaggt 106380
ttctgacctg gagcgggtac ggccctggca ggggaagcca actagttcgg agttcagtgg 106440
gagctggctg ctgttagacc tttggctctg ctctcgctcc ttggctgtgc tgtgctggcc 106500
aggcagggga gcacaacagt ggcccaggtg cttccaggcg ctcaggcaga ggttggcctc 106560
taaggagagc cctagcctca atgttattaa acaaagagta cagcaaagaa tacaaaggta 106620
aaggagcgta gggctgctgt aatgttatag aagggcacgt atgggcaatt cttttcattg 106680
agaggcagtt tcatctggcc tcttatataa actcttcagc aaatgttact agaattgatg 106740
aggttcaata atccctaata tttttgacaa tattctcatc aaatatttta aataagctgt 106800
tctcagaata ccaaagtaga tgcagaaata tttgtgtttg tttggtacta tccactgtat 106860
ataaattgtc atggcatttt ttttttgca atctctttca ccagctgacc aatctgctat 106920
gtagtgaaat tgctttattg ttctgtatga gacacgaaaa tatttgtaca gaaggggatg 106980
tgtcaggtgg aaccaaataa aggagcactg aagaggaaat actagagaaa caaatgttaa 107040
aataggaaga tgttgatagg atgcaccttg ggaaactttc tattttttg taaaataata 107100
gtcttgatta aaatgaacga tggaaagaag ttgcattctc atcacaggca ttttattctc 107160
tccctctctt ttcagattga gaagacaatt aactttgaaa aactcacaga gtggaccaat 107220
cccaatacca tggagaagag gagagtgaaa gtgtacctgc cccaaatgaa gattgaggaa 107280
aaatataacc tcacatctgt cttaatggca ttgggaatga ctgacctgtt catcccttca 107340
gccaatctga ctggcatttc ttcagcagag agcttgaaga tatcccaggc tgtgcacggg 107400
```

-continued

```
gccttcatgg aactcagtga agatggcatt gagatggcag gctccacagg ggtgatagaa 107460
gacatcaagc atttccctga gttagaacag tttagggctg accacccatt cctcttcctg 107520
atcaaacaca acccaaccaa caccattgtc tactttggca gatattggtc cccttaaaga 107580
gagaaagagc tggcaataac acataccttc ccctcagaaa caaaatcccc ttaccgtagt 107640
attatagcat aatcttatct ctttcataga aaagacatac ccgcaggaga ggagacagca 107700
cgaagcacac ttactccttc ccttcttgta ttaatttcag aatggcttga tatgagcaaa 107760
gactgagcca atgagatggt gagaatgaag acacctatca gccattaagg tgataagtga 107820
ttttcaccca aggaataaat agtaagaatg accctaagtc cttgggagcc cgttacatag 107880
aaagcaataa gctttgctca tcccattccc tggtaacata ctgctgacaa acccacgtta 107940
ccattcctga aacatgggct ttgagatctc cagtctagag gggatgtttg tggaagagtt 108000
tctggtgtgc agattattga tttgtgatta tgtcaatttt atttttcttt atttggtaat 108060
tgggcaatgg tatacatgtt cactatcagt ggagttgtcc tctcaccata agtcctctca 108120
cctagttctg aatttcttgc agaggttttt caaagtcctg aagagtctcc cttccattcc 108180
agagaaggga aatagatcca gttttgcata ggtgcagtta tgccttttct cagagtgcag 108240
attcaaagcc tgaaccatag agatccagat gattcttatg acccagaact cagtgagatc 108300
cactgggcga aagaactgtc taaatttttg tttaaaactt tggaagacac ttcaaatttg 108360
agaacacctt tttggtgaaa aatcctgaaa gtgttgtaaa atacttcttc taagaaacaa 108420
attagaatcc tatttttttt ctgtcttctc ttcctacgta tagattgtca actgcagatg 108480
tggatcctct ggctcaatat tatattctgt tttcattcta atcacccatt attgatttag 108540
atacatacag ttgattttgt tttggttaac ataataaaag aaaaccacaa acagttttca 108600
tgtaaattat attagctttc tgaaccacac actcttaaaa atatctttac attttaacaa 108660
ctgtgagtaa aacgtgattt agcagaaaaa tgtattctta gaatgaataa agcatgcaga 108720
tatgaagttt ttcaggcatt tatgacattt ttaggagtac ctgttttcaa gaagaacttc 108780
accaaagacc tacaaccaga gtttgattct tctctgtatt tcagatgaca agaagtaccg 108840
caatagaata caaagttatt cctatctatt tttctgtgcc attccaacag gcattaaaga 108900
tgacctggca attttttctg gtaaatattt caaggaacaa ctattctaac agttttaccc 108960
ttttatacag aatcacagat tcataggagc tggaagagac ctcacgggat catctagtcc 109020
aaccccatat gatttcatca ttttatatga tgaaataatc tggaattcat ataacttgaa 109080
aggcataaga aaggttaaat agatcaacag ctactaggca aagcatttcc ctatgcagag 109140
tcttgagagg aggaactctg atgttaacat cgcctatttc cacattagtg ttaccactgc 109200
agtgtcaatg ataaaaggtg atctgtagag taaaaacagc tggtgctaca ggtatgacac 109260
ccacattttt tgtagattat caggatactc acaatacaga cacagctgtt tttcaatggt 109320
aaaaccaaac attttaccaa gtatacttta ttttttgcct ttagaaatgg aagtagtgag 109380
aagaacagtt ccaaggtaag agaaatatca gcatctcaag gtttaccatc agtagtttat 109440
tcatctttca catctcttat gtccatagaa tcatagaatc atagaggttg gaaaagacct 109500
taaagatcat caagtccaac catatcctaa ccatactacc ccaactttaa caaccctctg 109560
ctaaatcaga agcagttgat ccactctgct aaatttaaaa gccagttcac ttaaacaata 109620
agaaaactag aggaagatta catttgcaag ctactcttct acgattaata gactggaaag 109680
tgcataaagt acaaagatat gcctcaatga tctgaaaaac agctgaggtc aaaatggaga 109740
aatggggaaa aaaattgaag gtttcttgct tgcaagcaaa tataaagctt cccctttctc 109800
```

-continued

```
aaaaagaaaa acaagagaca ggaaagagtg gaaattcagc aatactgaac aaaaattgca 109860
acaaaatact gatggccaag ccctggccac cactgaccag gcagggggca gaacatacaa 109920
agggcaggat aaaagtgttc tccatgaagg gggtggcagg cctggtgggt gggatgatga 109980
acaaaataaa tacactttta aaaccttcct gtggctccag gcatttttgc cccagcctac 110040
caaaggctat tagcattttt attttctgga gtattaagac cctgtttctt tgacagacta 110100
ctgtgcagca actgacagaa ggtttagtgg gtaagtcaca ggggataaaa tgttcagcat 110160
agaccaaagc aaaaacataa tgtcatgatg ggtgatcaac tggctaacag gttgggctca 110220
aaggattaca gttactgggg ttacatcagg ctggtaggca gtcactaatg ggttctgca 110280
gggctcaatt ttagggctag ttctcttcag tgttttcatc aatgacttgg ataaaggact 110340
tgaagtcata ctaagcaagt tcatggatga cacaaattgg gaagtgccat tgactcccctt 110400
gagggtaaag aggccttaca gagagattct gaccaatcag agagcttggc aatcatcaac 110460
tacataaagt ttaacaagag caggtgtcat attctgcacc tgggatgggg cagccttggc 110520
tgtgtgtaca gactggagga caagaggctg agagcagtcc tgcccaaagg gacctggggg 110580
ttctggctta cagcaagctg tatctgagcc agcagtgtgc cctggcagct ccaagggcca 110640
accgtaccct ggggtgcacc aggcccagca ctgccactgg gtgagaggag gggctgtccc 110700
actgtgctct gtgctatgca gctgcacctc cagcactgca tacagggttg gctgccacaa 110760
cgtaagaaga acacaaaact attagagagc atccaaagaa gggctatgaa gatggtgaag 110820
ggtgtggagg gcaagatgtg tgaggatcag ttgaggtccc tgggtttgct cagcccagag 110880
cagaggagct gaggggaggc ctcatgacgg ctgcagctcc tcacaagggg agtggaggga 110940
cagtgctgag ctctgctctc tgtgacagca tggggctgtg tcaggggagg gtcaggttag 111000
gggttaggaa gagggtgatg aggccctgga acaggctccc cagggcagtg ggcatggccc 111060
caagctgccc gagttcaagg aacatttgga aaatgctctc agatgtaggg cttggatttt 111120
gggtggtgct gtgtggagcc aggacttgga cttgatgatc cttatgggtc ccttccaact 111180
caggatattc tgtgattcta tgacaagatg cactactgtt ctatgtgtga gatactactg 111240
ttctgtgtga gatactagta gccaaggcct tcacagggcc tttctgaatg tgcctccagt 111300
gaatggtcac cggagtaatc ccctctgtca acactgagat acacatctct gtcaccatct 111360
gtgacaggct aaggcagcag tgcaggcaac aatgtcaatc tcttcagaat ggcacagcac 111420
tgctgcagaa aggggtctgg tacgctgtga gcttctgtct gaaaaacctt gaccaaacac 111480
tggtattctt tggactaagg aagcaacata attccataga acaactgagt gggaaatcac 111540
cactgatagc tattgcatca agttctgcaa cagcaactaa gaaatcactg gcaatcactg 111600
tgggcaagac aaacactaaa tggtcaataa gctccctgct actagaaaaa cagtggaaac 111660
ataaatgaga acaaaatctc tagttgtgca aaggtttttg tggtagaagg agagactttg 111720
ttctatgagt tgacctggac ttcatattct tttggaaagg atcagatgtc aaagagtctg 111780
ttagtttagg gacaggccca cagtgaaata cctggtaaag caaatagcag ctaagtctta 111840
gctgacctct ttcatgggat aagcattgtc aaaaaaagga catgtcacaa caacacatcc 111900
ttttgtgttt gtgcagcatt acacagctgc gctggacagc gtaatccatc agctatccca 111960
gaaagcattt cacatacagg aaggtttgct taattttgct agacttcaca acagatctaa 112020
acttgataag tagactacac aagaagtcca atattctgat gattctgcac tgatgactga 112080
ccacgatcca atttttcact tactgtggac tgatttttaa attctgcaac tcgctttaga 112140
```

-continued

```
ttaaccattc atttgacaaa aagaaaaaat ccaacagcaa cagttggctg ggatgtatat 112200
taactttttc tggaggaatc tgctgcgcct tctctatcac aaaacaaaaa tattcctctc 112260
agcactgagt atatttaacg cagagatatt ttgaaagcca tataattact aacaacatta 112320
gtgctctgaa ttagctatta tgacacaact gtagtatctt tgtagatcct gagttgtagg 112380
ctgtctatga tggcccaaac atatgattca ggcagatggt acacaaatgc ccagggagct 112440
ctcctatagc aagctgtagc atgttgctag acagtttgat agtaaaagga tttaagacat 112500
aatcaaaagg tagaggagac acagtacaac ttgttggata atcctttgac ttttgagctg 112560
tcaagtatac aaccacggac cattgcagtg agtattaaag cctgtttgaa cagaaaacat 112620
gctgattgct agccttaagc aagaaaggga gaaggggcag cagccacaga aacatcttgc 112680
agtgtgagga gtgctctaaa ttgtgtgatt aaagatattc accatgaaca gacacattca 112740
gtcacttgat atgtcttcca ccagcacaga taccaaaatg gaactcacga cagtggtgag 112800
taatttacat attgttgaag caagagaata gctcactccc tttataatag gtttgatgtg 112860
atgggctacc aataagagtt aaggcctaat gatctttact caaaagtatt gctgctgcat 112920
agcaatgtct gcaccagact ggactgggct atagatggta tcatgtaaca tactagttgt 112980
aattaagtgt atcagacaga ctgaggtctt cattattagt attgctctag catcttcagc 113040
tgaacaagac taatgaggac tctattaggc agaaaggtat ggactattca gaggctgttc 113100
actttcacag acaactaaaa gggttaagga gtccacctct tttctccaga aaacataatt 113160
tgttctagac aatttcagag gcattttgta tattgacttt ggagttctgt tttaaaatca 113220
gagcatactc agaggtcaaa gtagtttgtt tgttgcccat tcttttattt caaaggattt 113280
atgagattgc tttatgcttg ctattgtata ttatgactgt cctgcagacc atgaatgttt 113340
cacctgatgt ggcatgaagt tacttgtgaa cgatctgtaa gaatgttctt tgaatgtgca 113400
aaagacacat tttgaacctc acatctggtg ctgtgacctg tttgaaaaga acaactcaaa 113460
tcaacattca aaactagcag tgagttcgaa tacttctctt gtagcttctg actggagtct 113520
gaatatccta atatctgaat ttaaaaagca acagaagtct cttctctgct caacctcttc 113580
tgcgacagta catctttctt cagttctgta tttttttttt cttttaatac agatgctctg 113640
aatattgctt tcaaaattaa tttggattca tacagtatgc ttgttgatac tttcctactg 113700
acaatctgca cagaccatgt tggcacacaa ggtccctgag ttagactgct ccagcaatgc 113760
tagactgctc tgcaaaatgc tttatttttt gcaattcagg ctgtaagtgg catcaggcac 113820
aagaactaga caattacata caagttttca ctgtaggtat ccctattatt tgcagaggat 113880
ttggactaga tggtcttcaa gggtcccttc caaatcaaat gatgctttga ttctgtgatt 113940
ttatgaaaag ttgcagtaag tacagggtgg gcataacaca gcaaggagtc ctgaatgtac 114000
tgcatttttt atgttctcag aatggtgact gctagaggaa tctggactgt cagtactcat 114060
agaggaaaaa aaaaaaaaaa aggaaattga cttaaattcc ttagagacat tgtgtacaac 114120
taaatatcac actttttttt ttttgctttg ttttcactat ctgtgccaca gtatttggtt 114180
ctgtgcttga attatactta gtgttcaagt ttcagtgaat agcttttatc atttttgttt 114240
caatcttatc agtatactcc atccttttct ccaaggtgcc atatgatatc cttccttctg 114300
gaacttttat ttagagactt ctttctttct ttccctcttc cattctctct ttctttaact 114360
ttttcctttc tcctttcttt tttgttttct ttttttcccc ttttatcttt ctttccttct 114420
tttttcctta tttctttttc cttctttctt ccttttttcc ttcaatttct tttttccttc 114480
catttctttc ttttttcctt ccatttcttt tcttccttcc ttccttcctt cctttctttc 114540
```

-continued tttctctctt tctttcttcc tttctctctc tctttctgtc tttctttctt tccctctttt 114600 tttttttaa ttttaatttt tattttttt ttgtaaataa aggacttcaa ccaagtaaaa 114660
gtgtgtttct gacactgagt tccatccatc attcagtttg gcaaacacag aataggcagc 114720
atggggtgtg tcatgacatt atacaggata tatttcaagg agttctgcaa ggctgtacca 114780
cgtacagctg agaagctgta ctcttatcat cacaggtgaa gctgataagg taagcatttc 114840
ttttggttat gattcatgtt ctaacccatt ttttaaaatg atcataagac ttacaagaat 114900
actgatggaa ctttgtggtt tgtcatcaag aacagtcaag aaacaaatga ttaaaggatg 114960
acttctttaa aaatctattc ttaccttcac atttctgttc tgcattactg tactgtttca 115020
cagcctgcca catatgaagt caaagtgtta gtacaaagta aagctatgtt tactaattct 115080
gtaacactga gaagctggca ctgtactgag acaccctttc ttctttttca ttgatgccct 115140
ttgtttctga tttagaaatt aaatgcagca ctgaatttgt ttaaattcaa gacttaagct 115200
gagttgcatg gtctacctaa catactttct gaatgaagtt actgaatgca gcatggtcag 115260
gtatcaacaa catactgcaa attaatttct gtgtattcta aaacaagcaa acgaacaaac 115320
aaaaaacaca cacacacatg cacaaagcat ttgcttcaac agtatgtttt ttcaacaaga 115380
tcatacatgg agcttaaagc ttaaaatata atactctgtg ggagtagtaa ataatccaga 115440
agtttgccct ctatcacctg cacatgtgat tcaattaaga gagagatgga acacatgaat 115500
gtgttgattc cacacaatga aacatttggc agaatatctt ggatttcccc tgtacttggg 115560
aaattctacc ctaggaagat tctctctgct tgtgacaaaa tgggaagata taaggacctt 115620
aatactgcac tttacagcac tgttgtctat tctatgttgt cttctttact aaagagtttt 115680
ttttttcctt tactgttaga taaaatgata tgtgttgaaa ctacagggaa aatttcatta 115740
gaatgtcaga aaaaaaagac agaaaaaatg tttaaatact gacgatgtga agtatctgca 115800
aatgaaacaa gcctaaacaa tcactgcctt attaaaaggt ggattttatg aaaaaggtgc 115860
caataaaatt aaagaacaat tttgaaaagt gaggtataat taagtcaacc aagaatggaa 115920
catgtaatat ttaacagaca tttgtcataa agcagatgag tttggtaaat cattatctct 115980
ttctatcact gtgcttccat ttccctaatc tatttttaag aaggtaatga tgaggtttga 116040
gacctctgat aaagtggttg gtataagaat ccagcttcca tttacatgaa ggtggagtaa 116100
atccagaaaa aaacttgcgg tgtttttcca gacctaccca ctttatattg tcaataactg 116160
tagtttggat cacagagggc tgatctgtta actggtctta aaagtgatgt taaaaactat 116220
agtgaaaaac ctggtctgga gtctcaggtg aatgaagact gagaacaaac ctatgtgtgt 116280
tttctttcct gcacaagatg ggaaacgatt gtcaatgagc ttctttcaag gcaagtcttt 116340
gcaatatttt caacacagta cacatgtaca gaggataact caagtttcaa ataaaacagt 116400
tgccagccta cacataactg gtacctatac aagattttga ttgctcacaa atccaagcac 116460
acacctgcct tttaaatcca cactactgaa ttctacttac tgaaaataag ctgtgcactg 116520
tgtacagagg ttcaagtgca ctgacttcct tggaatacaa ctaatacatt ttaatctttt 116580
ctttagacaa cgatttcaga atggattcca tcagtgtaac aaatgcaaaa ttttgttttg 116640
atgttttcaa tgagatgaaa gtccatcatg tcaatgagaa catcttgtat tgccctctga 116700
gcatccttac agccctggcc atggtctatc tgggggcaag aggtaacact gaatctcaga 116760
tgaagaaggt aagttgctta cattggtgta aagtggacag tggactctac ttctgcttgt 116820
cattccttct aagtaataac atattatcta ctcatgaggc tctcacatat tttaattcac 116880

-continued

```
cagatggatc atgaatcagg gaattgtatt attttttttct aaattctgac atcttccaca 116940
taatgtgatc attttttttc catatttttt atttttgtat taaaaagata aaaccctgga 117000
ggaaaggaag agggagaaca ttattcgcag tgcataatac acaactaagt taacatccag 117060
atgctcactg aaaaaaatat aatctaagca aatagtgcta tttccaattt ctcagaaggt 117120
gacatgaagt atgaaccagc tgcaagctta cttgcagcct tttagttcat ctaatctagc 117180
atttgttgtg ggtttttttt ttgtttctgt ttttgagcca acagctctac cccgaacatc 117240
acgtgtaaat tttaaatgca taccattttt ggtcacgctt gtgttttttt ctcactggca 117300
ttttctcttg caggttcttc attttgatag cattacagga gctggaagca ccactgactc 117360
tcaggtaaag atgtaacttc tctccttttg ttcctatttt ctcctcagga caaaactaga 117420
actactctgc ctctgctcca agcagtttca gactgtcaaa agtggtggca atgctctcaa 117480
accaaacaga tctgtggagg gaggaaaaga gtgtgtaact cactcttgtt taaagccagg 117540
gaaactgact tggagatagg tttatttgtc tgtttaatgc accatcatca gactaggtct 117600
gtgggtgaat tccaccatgg cctgactgtt agtgatgggg acagtccttt ggggtctgat 117660
tttctagata aggagaaact aatgtgacat atcatcttgt tttcctgtca tcacctcagt 117720
gtggctcttc tgaatacgtc cacaatttgt tcaaggagtt actctcagaa atcaccaggc 117780
caaatgctac atactcactc gagattgctg acaaactcta tgttgacaaa acattctcag 117840
ttcttccggt gagttgaagt gtgacttaac ctcagtgaga ttgcccactg ggctcacctg 117900
ggactcggct ctactgtgag ccacaatggg aattggtttg agccacagga tgagttcaaa 117960
cctttctgtg gcttttagga ggaggctagg ctcacacaag gtataagggc tctggagata 118020
ttcaagaccc atttggacac tttcctgtgc aatctataat gaacccctgc agggggttca 118080
aattgatgat ctccagagat cccttccagc ccctgcgatt ttgtgactct gtaatatatg 118140
cccatgcagc aactgctaca gggagcaatc aaaattgctg ctcattcact aaaaaatgtc 118200
tcttaatgaa aaaggtgatt tgtaagggag gaaaatgact tgaaagcgtg acgactgaaa 118260
ttgacaaaaa tattttgttc atcttttcta aaactagaca taaaataact cacttaaaga 118320
aagttttggt tttgaaataa aaaacaggaa tgtaagaata cacagttcaa aagaaaaggt 118380
aggcacgaag atgaggaaat gagtattgtc tgtccttaat aatgtttgca gaacagaagg 118440
ttttatggta aaatgaagaa aatatttcaa aattttaact tagaatccaa tctgaagaca 118500
aaagtgacaa atctaaatat gtgaagtagc cttgtccagc tttaagattc agttacagca 118560
agagagctgt ttgacttgtt caagtgtagg gatagaagtt tcttttaacc atcactttcc 118620
atttcattaa ttttgcattt catattcttc tattttaaag ttctcaacag tcaaacacaa 118680
ttcttctgct tataggaata cttaagttgt gcaaggaagt tctatacagg aggagtggaa 118740
gaagttaact tcaaaacagc tgcagaagaa gcaaggcagc tcataaactc ctgggtggaa 118800
aaagagacaa atggtaagaa gtaaaaaaat agctgatatt ttctcctacc tactgtaatc 118860
tacgctcttg tcttcttctc ctcaaaatgt gaagaaaggc atatcaagga acagcacttg 118920
attattgcta tgaaagcaaa ctcccataaa actcaccatg cccttcattg caggcattca 118980
tgcaaaccag acaggctgtg tcttaacact cactgctttg cttccttttc acaggacaga 119040
tcaaagattt gcttgtatca agctccattg attttggtac aacaatggtc tttattaaca 119100
ccatttactt caaagggata tggaaaattg catttaatac agaagacact cgggaaatgc 119160
ccttcagcat gacaaaggta gggacatggg cactactact ggaaaaattc aagataaagt 119220
gatccctact cacattgtct catgcttctg ttttgcagga agaaagcaaa cctgtgcaaa 119280
```

-continued

```
tgatgtgtat gaacaatagc tttaatgtgg ccacactgcc tgcagagaaa atgaagatcc 119340
tggagctccc atatgccagc ggagatctga gcatgttggt gctgttgcct gatgaggttt 119400
ctggcctgga gcgggtacgg ccctggcagg ggaagccaac tagttcggag ttcagtggga 119460
acttctgact gctttcagac ctttggctgt cctctcaccc cctggctgtg ctgtgctggc 119520
caggcagggg agcacaacag tggcccaggt gcttctaggt gctcaggcag aggttggcct 119580
ctaaggagag ccctagcctc aatgttatta aacaaagagt gtagctaaca aaacaaaggt 119640
aaaggagcct agggctgctg tagtcctgca gcaggggatg ttggtatatg caagttatct 119700
ccatcaagta ctagagacag atatgctagc aggatttctt tttttacttt gaagaaattt 119760
caattcccag agatcaagta gagttcaaac actgttacca agtcataggg accaattctg 119820
ttgatgaccg ttaatagatt tttttcatga gtcacccctc caaataatta aatataattt 119880
tttttttgta aatatgaggg atattttaaa tgatcatttc tcattgaatg tagaaaaaaa 119940
taggaaaaat ataacaagaa aacaaacagc atttctgaga ggttagctgc aaacatctgc 120000
aaatgagcaa aaatttgatt tgacataatc aaaaaactgat ttttcagaaa agcatttgat 120060
ctgttggaag aattttcaga tgacaaagtt ttggagagct tcatcaagac agatgatatg 120120
taggctatag tcaggaagaa gcacaaggga taaacaaata gatttaagct taagcgtcac 120180
ttctgttttg cacacaaata aatgaaataa atagcaacaa gtggtattaa tacagttggt 120240
atggccacca tactcctgct ttatgcattt cattgtctct tctctttgca gattgagaag 120300
acaattaact ttgacaaact cagagagtgg actagtacca atgcaatggc aaagaagagc 120360
atgaaagtgt acctgccccg catgaagatc gaggaaaaat ataacctcac atctatatta 120420
atggccttgg gaatgactga cctgttcagc cgttcagcca atctgactgg catctcttca 120480
gtagataacc tgatgatatc tgatgctgtc catggggtgt tcatggaagt caatgaagag 120540
ggcactgagg cgacaggttc aacaggggca attggaaaca tcaagcattc ccttgagtta 120600
gaagagttta gggctgacca tccattcctc ttcttcatca gatacaaccc aaccaatgct 120660
attctattct ttggtagata ttggtcgccc taaagagaga aagagctgga aataatgctt 120720
accttcccct cagaaatcaa acctctttac tgtagtattg tagcataatc tcaatgcaat 120780
attttatcca agtggaaagc cttcaatatc tagggagaca ttcttgaaga agcatgtgaa 120840
atttcagatc tttatatgca ggaatttatt ctcagcttag attcaggatt catatccaag 120900
gtgtacatat tcccaatgtg cttgaataac ttgggaaaca gggccagtgc tttggggttt 120960
tttttgtttg tttgtttttt gtttttttgg tttggtttgt ttttttctgg ttggttgttt 121020
tttttttttg tgtgtgtgtg tgagattctg ccattgttat tgagaatctg gtttctctat 121080
aggagttctc tgaaataaac acagctttca ggaaaatcct ggtcctttcc attgaattag 121140
ctgggcagtc atcctagaac tgatgcctgg acaacttgca gatgaaattt ttaacttcag 121200
cagaccattt gtcttccagt aatccatttg gacttattcg tgctgcgtaa cattttttct 121260
gagggagcat acagaaagtc taccatttct tcttaaatca tctccaaaca aaacatcttc 121320
ctgattgata ttatttccca ttttcatccc agtgacatgt cactgatttt gtgaatgtta 121380
attaatggtc tttctattta ttctaataaa agcttcgcaa acaaaacatg tcattaccta 121440
ttctgggtta ctgtactaca caacctgaaa aatacgatat agcgggtaat aattattgac 121500
agaggtgact aagctggtat gtggatccta ttttcaaaat cagaatgtac ccatatatga 121560
ggtcactaaa tattttaaga ttaaaaaaaa aaaaaacaac tgggtttaat caaggtaaac 121620
```

-continued

```
cctatagctc ctactcttca attgagcttc tcccaataca gcataccaaa taacaaaatt 121680
ttttgaattt actgaatttc cagagaactt ttacagaaat cctctaaggg tcctcagtaa 121740
atacatgaag gtgatgtgta caagatagaa ttttaaaata tgagaaaggt attaaaaggt 121800
agactgcttc agctttctca tgctgacaag aatcacatga agaaatcttt ctattgcctc 121860
atgtgatatt cctctcgaga tgttgtatgc tatttcacgg tctttagagg aaagggtctt 121920
taggttatat attatccaat tataatggtt actagtgtta atgacagttt tctgctagga 121980
tacacatgca gaattgcaaa ttacagtatt ggtactgaaa atgtagcgat acttcagtaa 122040
ttcagagctg cctcaaacac atgccatgtc agcattaact ataacttgaa atgatgacat 122100
tagcagcagt gaaacacgtt tcatacccac taaaaatggg agaaatgcga ttactggtct 122160
tcccaagagg gtcagaagga ttaggtacag tttgcacaag gattcaagta aaaaaaagta 122220
tttcaagagc tatgaaattt caagttttac tgtgtacatc atgttatttc cctcttacag 122280
ctgaaatcag tcaatacagt tttgctacaa ctaaaaccaa ccaaccaaac aaacggcaaa 122340
ggaaaaaagg caggactggt aaaatattgt cctgagcagc agagtgtgta aggttactaa 122400
gcagttataa tactgtgttg gaactgaaat atgcagctat gtcactctgc actttctagg 122460
tacaataaca gtaaaagtac ccacatttac tatggaggta tttaatatat agcgtaaact 122520
aaaaaaacag ctattcaatt gtttgatctt tttaaagcaa aagatgaaga aaatcaaggc 122580
agaaatgata aatgaatttc aaaaactata caaaagaggg tattcaaggc acagagtcca 122640
cctaatgtct taactgtgaa atggaagcat ttgacttgtt ttaaaaaggc cattaggtgt 122700
cactaagggt aaaaagttac gtttatcagc tttcagaaag aggatggcat tccaaaggtg 122760
cctctgagct ctgaagccca gcaagggata agagaaatga atcccaagtc cagctattgt 122820
ccaaaagtcc tttttgttcc ctgataccat gactgaagtt gtcatgtcaa gacattgcct 122880
tctgtctgtt cactacacct catgttctct cagtgctgtg ttcttagaga ggcagtactg 122940
ctagtggtcc gcggaatgaa aacagccagg tgtaatcaca ctcttttgaa tgcctcatga 123000
gaagtgctct ctggactaag tgtaactttc cttctcacat catttggaga agggaccatc 123060
acagaatcat ttggagacca cctgcatcta ttctgcactt ctctccacat ttgcctatcg 123120
tcttctaagc aaaccgaatc tatggctgaa gttacaagac tctgcatgtg gtgtcacagt 123180
caccagaggc agaggactca agagaatatc ctggtccaga gctactctgg gatctcaaaa 123240
gtcacttggg aaagcacagc atgttgaact agactttggt gtatttttcc aatctttatc 123300
agtctacaaa atatcaactg gacatggagc agtggttcac tttggtgttt cctgtggctc 123360
atgatctaag attcttcagt ctggaaaata aactgcagag attactgttg aggagcagca 123420
agtgtcagtc tgctcagcaa gggaaggaga ctgagggcaa gggaaggaga ccgtgccagt 123480
aaggctagaa gggcccgata agggatcaag tgctaaattt tccaatatta tagccatagt 123540
ttagtgattt ccagagaaat atgtagtgat gtggtaggcc aaagatcaaa ccagaaggcc 123600
ccagaatggc aacaggtgat gatccctgtg gcacattctc tatcttgaag taaaacagca 123660
tggatccata taaatacatt cttgctcaac agcagaaata acaaacagta ttgcttactt 123720
ctacgaatat cctaacaaaa catgtagatc acaatgccac tgaacctttg tatggatgga 123780
atctgtgcaa tctgccatga ctaaagctct gtccaaaact gcacaactta gggtgcccag 123840
cttctgaagg gatgtgaaat tatctgtgct atctcctttt cccttcttgt gttagctcca 123900
gtaaactcta ttttaagaaa taccttacag tttctgattg tcttctttac tggtatccaa 123960
agggactcct atgcattaca gggtcctcca gcacagtgag gttcttggcc tggtgcaggc 124020
```

```
atgcaaagta gcttaggcac gggtcacaat caagatactc agtttaatgc ttctcccaag 124080
tgatgggatg ctaaaatctt acatgatttt aaaaggaaag tgttcaaact gtggaagaga 124140
aatccactga caaataagaa agatacagaa aataaagtta gctatagaag acatggaaca 124200
ggaaataatg ttagaactct gagggcaaga gtaagcctta acagtaatga caagcctcac 124260
tggaggagct cttccacata cgttgttctc atgggcccag gagtctgtac tggaaattgg 124320
cacacagttt gggtaccggg ggcgatcttt gtgagatgaa gccctgaact gccctgggtc 124380
agctgcaggt gtctctgtaa tggatgaaaa caactcactg tgcaccagat tttcagctaa 124440
taagaaaagc acatggcatc tctgctcaaa cagaatcata gaattgctca ggttggaaaa 124500
gaccttaaag gtcatcgagt ccaactgcaa cctaaccaac taccctaact ctaacaaccc 124560
tcctctaaat catgtccctg agcaccacat ccaaacagtt tttaaacaca tccagggatg 124620
gtgaatcaat cacatccctg ggagcctat tccagtgctt aacaacactt tctgtaaaga 124680
agtttttcct gatatccaac ataaacttac cctggcacaa cttaaggcca aatttaatta 124740
gaaaatgtag cagcactgca atgtagcaaa tgtaattacg aaaaggtggt agctgctagg 124800
gacagaggac atgcaaatag acccaaaaga taaagactag aaacagaaaa aggggacatg 124860
tgagaggtat gtttggagaa acataacaga ggagatattt gaaaggagat cttgggagca 124920
caggcaaaga cacaatcctg ggaggaggtg ctccatgcta gaggatgtac ctctaaggca 124980
ccgcagccat gggcaaccaa cacaggtcag cgtcatcctg gtgagactgt atcccacaag 125040
cagctaacac tggagtaggg acagccccga agaactgcag cccaggcagc acactagagc 125100
agagaaatct agttagcagc aaccactggc agacagaaat gattatatag attacatact 125160
gaccctagcc tcttacactg cctactgcat cactgaaagg actgggaaga agagagtgca 125220
ataacgtagc tgaaactagg aggaaggcaa ggagaactga agctgactag ggaaaagggg 125280
gattaaaggt ttaagtgtct attccatagt ttgctggttt gtttttgtc aattcctgaa 125340
tcagtaattt ttatgttaat tagcaaaaaa ttacaaacac tccccaagtc aggactgtta 125400
cctacaacag aagctcagat cagctgagcc ttagtctttt ggtccctccc tagggaatgc 125460
tgtatgtgtc tctctctcca ggcctgctca aaattgacct cagacccaaa cttttgctga 125520
atctccagta ccacctcttt tgctcctaac tagataacaa agccctgagc gctttgcttt 125580
tagcaaagcc tttaagtgcc attaccaact gcacctggag cctttaccta cccctatgga 125640
cccaggctct atatttaagc tctgccctga accttcactt ctttcctgtc ctaagttaga 125700
tgtactagta tggtgtgtac tatgtctcca gttcaaacac agctgtgccc atacctggcc 125760
aaggactcct agtatgacct gggctgtgcc ttgctgctaa ggacctgctg ggtgattgct 125820
ggacctgatc ctaatcctga attaagaaat gatttcttgg cttgactgga tgtgccctgt 125880
ggtatgatac tgccttatga tttggactct tgtttgcagc tgtgcaaatc cctaaggagc 125940
ccagtctctg gccacctgga atcttgtcac taccaaactt cctgagggac tggtcttgct 126000
ctgggttctg atctctggac agtactcacc ctttactcag cccaggctcc cagttaagcc 126060
cctttccacc ctgccaggct ctccgctcca tccctagcag ggctctcat gacagtgtga 126120
ccccccctta ctcaggtcag ggccacttgt gccacgttcc tttcctgtct tctgtccctg 126180
ccttggctct aaagcagtgt gctaccatcc acaaccactg catctctcta aagtaagcct 126240
ctcctgagcc caagtctctg taacgaggaa ggatgcactt tgctcagaag gatgcgaggc 126300
tgcttctgag ctctgagggc actgacctcc catgaggtac accccatacc caggaccaca 126360
```

-continued

```
attcagcctg ctggaaccat caactcctgc tggagtaagg ccatagcaag accagcatcc 126420
acctccctgc agccctgccc tgcccagata ttgggcctgc tgatctcagg atgcagactt 126480
gcttctcagc ttgacctaag cattgccctg tctttatgga cccacctggt tagcaagttc 126540
agtgcagaag gaggctgttg gcatctagct aattttccac ccacattact gtctgctgac 126600
tcattctacg tctctcccat cttgttacaa taataatttg ggagatcata ttgaaggtct 126660
taataaagtc aaggcatgtg atattctctg ctttgccttt gtttctagaa taagccactt 126720
catcatagaa gatgaaaatg ctgatcagca gagatctgtg cttgataaat ccatgctggc 126780
ttttcctatc accttatatt ccttcatatg ccttgagaca cccaaggagg ccttggatca 126840
gagctgtctg tagcagtcct aactggtata caattagttg tacaacaggt agtgatccgc 126900
ataatagttg gcgtgagaaa gtgggcctgt gctgtgtcaa gcatagagtt tgggttccag 126960
tcctgttctg catggcacat atgcctgagc agctgggtaa tctctgcatt ccaattggaa 127020
ggcaggggcc tgtaggcagt tcccacttgg catgggtgat tgtaccacct gtgtcctcat 127080
ctgtgaagca tcatgttttc attcaaatat ccttttgttt gacagtagaa atgaacagaa 127140
ttgttttttt ttcctaagca aattctgcaa gagctctgaa gaacaaggtg tcagtgaact 127200
tctagctcca tagataggac ttgcatcaca tgtcatgcct tgattggagg tctatccgat 127260
actgaacaac ttgtggttcc ctgagggaat gtaagattac tgatactact ctctctttat 127320
gttagctaca ataaatggta ggttaagcaa tagatacaga gtttgagtgc ctttcttaca 127380
agcatcatag tgaacaaatc cactggtgat ctaccttttc aataactaca gagaattgta 127440
atctcttgga ttctcctcct tccccgttct gaaaatgtgt tctttttttc caaatcagaa 127500
accttcctca accaccctga ctattctttg gacattgttt tgttcttgct cctaaatagg 127560
ctttataatt tttgtaagtg aaaggctttg catgcaggtg aggctacaac tcattcagta 127620
acaatgagga agactgtcag attttgggga aaattctccc acccaacctt ttgctagcca 127680
gtaagatgta atcactgaat gtcatgccac aaagaccata ccaacatcag accacatatc 127740
tacaggaagc tttaaggaat cattgactgt acagtgaagg gtaaatcaaa ttaaaatgaa 127800
tgtgaggtct gatacgagat atcctcatgg gaatcaagag caaagacaaa tagtttttca 127860
cagtcttgtc atgatctgtc acagaccaag gcagcacagc aggcaacaat gttggtctct 127920
tcagaatggc acagcaccgc tgcagaaaaa tgccaggtgg actatgaact cacatccaaa 127980
ggagcttgac ctgatacctg attttcttca aacaggggaa acaacacaat cccacaaaac 128040
agctcagaga gaaaccatca ctgatggcta cagcaccaag gtatgcaatg gcaatccatt 128100
cgacattcat ctgtgacctg agcaaaatga tttatctctc catgaatggt tgcttctttc 128160
cctcatgaaa aggcaatttc cacactcaca atatgcaaca aagacaaaca gagaacaatt 128220
aatgtgctcc ttcctaatgt taaaattgta gtggcaaaga ggagaacaaa atctcaagtt 128280
ctgagtaggt tttagtgatt ggataagagg ctttgacctg tgagctcacc tggacttcat 128340
atccttttgg ataaaaagtg cttttataac tttcaggtct ccgagtcttt attcatgaga 128400
ctgttggttt agggacagac ccacaatgaa atgcctggca taggaaaggg cagcagagcc 128460
ttagctgacc ttttcttggg acaagcattg tcaaacaatg tgtgacaaaa ctatttgtac 128520
tgctttgcac agctgtgctg ggcagggcaa tccattgcca cctatcccag gtaaccttcc 128580
aactgcaaga agattgttgc ttactctctc tagaccccca agtcaaacca actatgcagg 128640
tatgctgaca acactatgat gacagcctgt tctgatcaag atctcatttg ttcatggaca 128700
atttttgttg cttgcagctg gtcttccatt gggaaagagt gtagtatatc cttctcatct 128760
```

gacagaaaag cagaaattct catgctccac acttaatcta cattgtttta aaccaccggc 128820
tacttcttgg agaggaaaaa tggcttttat aagactcaca aaacaaagct ctgcaagtca 128880
aatgcataca aaactgttct gtaggtctgg aatcaggaca ctatgtggaa gtcaaataga 128940
gcagctttaa aaagcctttg ggatcattct catcttatat ttgcagcacg atactatgac 129000
agtgataact gacataactg catcaatttc cttgatattt tatttgtctt aaagtacaag 129060
acatagagat ggacgtaaag atggacatat gactcaggtc tggacaggtc cgtggtccat 129120
gtatgataaa agagatgaag ggaaggagaa ttgagactgt ctaagaaggg cttcagggac 129180
gttctgaagg cagatttgac tgaatcagat gtactgtcca agtctcatat gtagcaatgg 129240
aaggctgata ttggagaaat ataaagaaat ggctgtgaac tcaaagtgac cctgaacaga 129300
aaagggatat ggagttaaaa taatgtcaca gaactgaggt ttatatgata taccatgggc 129360
tgcagagggt cagagtgctc caccatgggc ctctcttggg ctgcagggaa cttctgttct 129420
acacctggaa cacctcctgc cctcctccgc actgacctca gtgtcatcag ggctgtttct 129480
ctcacatttt ctcactcacc tctcccaact accattgtac agcagttgtt cttacatatt 129540
gctcctcctg aggtacatct agcatcgatc actggctcag ctctggccag tggcagctcc 129600
cttttgagga cacgggacag ctgctgggct ctgttcacag aggccactcc ggcagacctc 129660
cactaccaca acttgtagtg taaatccact acaactttct gagctacaga aatgaaatgg 129720
agaccctctc tgctatggga tacaaaagag gaaacgtggc gtttagctct ggctcactgg 129780
tacacccaac cacagggtga gaagcagcct gttgttattc actactctta ggacagatta 129840
tggtgaattg ttaataaaag catttcttca taacatccaa aggaggaaat acactaaatt 129900
atatttttta ttaattaatt acacatgctt aattatatat ggcatggttg ctttggaaga 129960
atcttgtcct tactgaccag atctgctgtt tgctgagaca aaatggctga caattttggc 130020
catggtggat accttccccc ttttctgtag cattaggaca gaagttattc tggagcctgt 130080
ctgacaagtt agacttgata cctttaagta tttggaagtg tgcttttcat gctggatgtc 130140
atctccagaa cctccctgtc tggtaagcag ttccctgcct tagtaagagc cgaaacggtc 130200
tctcttttcc ttgttatctc accaggatat tacaatgtga caggactatc tgaactatgc 130260
caacctgcaa attccaaata tatatatata tataagatat ctatacacaa attattagtg 130320
tttgattgac accagatgac agagaagtgc atctgagaaa acctattccc aatctccttt 130380
ctctttctgc agactgacat gcatttcata ggtagagata acatttactg ggaagcacat 130440
ctatcatcac aaaaagcagg caagattttc agactttctt agtggctgaa atagaagcaa 130500
aagacgtgat taaaaacaaa atgaaacaaa aaaaatcagt tgatacctgt ggtgtagaca 130560
tccagcaaaa aaatattatt tgcactacca tcttgtctta agtcctcaga cttggcaagg 130620
agaatgtaga tttccacagt atatatgttt tcacaaaagg aaggagagaa acaaaagaaa 130680
atggcactga ctaaacttca gctagtggta taggaaagta attctgctta acagagattg 130740
cagtgatctc tatgtatgtc ctgaagaatt atgttgtact tttttccccc atttttaaat 130800
caaacagtgc tttacagagg tcagaatggt ttctttactg tttgtcaatt ctattatttc 130860
aatacagaac aatagcttct ataactgaaa tatatttgct attgtatatt atgattgtcc 130920
ctcgaaccat gaacactcct ccagctgaat ttcacaattc ctctgtcatc tgccaggcca 130980
ttaagttatt catggaagat ctttgaggaa cactgcaagt tcatatcata aacacatttg 131040
aaattgagta ttgttttgca ttgtatggag ctatgttttg ctgtatcctc agaataaaag 131100

-continued

```
tttgttataa agcattcaca cccataaaaa gatagattta aatattccaa ctataggaaa 131160
gaaagtgtgt ctgctcttca ctctagtctc agttggctcc ttcacatgca cgcttcttta 131220
tttctcctat tttgtcaaga aaataatagg tcaagtcttg ttctcattta tgtcctgtct 131280
agcgtggctc agatgcacat tgtacataca agaaggatca aatgaaacag acttctggtc 131340
tgttactaca accatagtaa taagcacact aactaataat tgctaattat gttttccatc 131400
tccaaggttc ccacattttt ctgttttctt aaagatccca ttatctggtt gtaactgaag 131460
ctcaatggaa catgagcaat atttcccagt cttctctccc atccaacagt cctgatggat 131520
tagcagaaca ggcagaaaac acattgttac ccagaattaa aaactaatat ttgctctcca 131580
ttcaatccaa aatggaccta ttgaaactaa aatctaaccc aatcccatta aatgatttct 131640
atggtgtcaa aggtcaaact tctgaaggga acctgtgggt gggtcacaat tcagactata 131700
tattccccag ggctcagcca gtgtctgtac atacagctag aaagctgtat tgcctttagc 131760
agtcaagctc gaaaggtaag caactctctg gaattacctt ctctctatat tagctcttac 131820
ttgcacctaa actttaaaaa attaacaatt attgtgctat gtgttgtatc tttaagggtg 131880
aagtacctgc gtgatacccc ctataaaaac ttctcacctg tgtatgcatt ctgcactatt 131940
ttattatgtg taaaagcttt gtgtttgttt tcaggaggct tattctttgt gcttaaaata 132000
tgtttttaat ttcagaacat cttatcctgt cgttcactat ctgatatgct ttgcagtttg 132060
cttgattaac ttctagccct acagagtgca cagagagcaa aatcatggtg ttcagtgaat 132120
tctggggagt tattttaatg tgaaaattct ctagaagttt aattcctgca aagtgcagct 132180
gctgatcact acacaagata aaaatgtggg gggtgcataa acgtatattc ttacaataat 132240
agatacatgt gaacttatat acagaaaaga aaatgagaaa aatgtgtgtg tgtatactca 132300
cacacgtggt cagtaaaaac ttttgagggg tttaatacag aaaatccaat cctgaggccc 132360
cagcactcag tacgcatata aagggctggg ctctgaagga cttctgactt tcacagatta 132420
tataaatctc aggaaagcaa ctagattcat gctggctcca aaagctgtgc tttatataag 132480
cacactggct atacaatagt tgtacagttc agctctttat aatagaaaca gacagaacaa 132540
gtataaatct tctattggtc tatgtcatga acaagaattc attcagtggc tctgttttat 132600
agtaaacatt gctattttat catgtctgca tttctcttct gtctgaatgt caccactaaa 132660
atttaactcc acagaaagtt tatactacag tacacatgca tatctttgag caaagcaaac 132720
catacctgaa agtgcaatag agcagaatat gaattacatg cgtgtctttc tcctagacta 132780
catgacccca tataaattac attccttatc tattctgcca tcaccaaaac aaaggtaaaa 132840
atacttttga agatctactc atagcaagta gtgtgcaaca aacagatatt tctctacatt 132900
tatttttagg gaataaaaat aagaaataaa atagtcagca agcctctgct ttctcatata 132960
tctgtccaaa cctaaagttt actgaaattt gctctttgaa tttccagttt tgcaagccta 133020
tcagattgtg ttttaatcag aggtactgaa aagtatcaat gaattctagc tttcactgaa 133080
caaaaatatg tagaggcaac tggcttctgg gacagtttgc tacccaaaag acaactgaat 133140
gcaaatacat aaatagattt atgaatatgg ttttgaacat gcacatgaga ggtggatata 133200
gcaacagaca cattaccaca gaattacttt aaaactactt gttaacattt aattgcctaa 133260
aaactgctcg taatttactg ttgtagccta ccatagagta ccctgcatgg tactatgtac 133320
agcattccat ccttacattt tcactgttct gctgtttgct ctagacaact cagagttcac 133380
catgggctcc atcggtgcag caagcatgga attttgtttt gatgtattca aggagctcaa 133440
agtccaccat gccaatgaga acatcttcta ctgccccatt gccatcatgt cagctctagc 133500
```

-continued

```
catggtatac ctgggtgcaa aagacagcac caggacacaa ataaataagg tgagcctaca 133560
gttaaagatt aaaacctttg ccctgctcaa tggagccaca gcacttaatt gtatgataat 133620
gtcccttgga aactgcatag ctcagaggct gaaaatctga aaccagagtt atctaaaagt 133680
gtggccacct ccaactccca gagtgttacc caaatgcact agctagaaat cttgaaactg 133740
gattgcataa cttctttttg tcataaccat tatttcagct actattattt tcaattacag 133800
gttgttcact ttgataaact tccaggattc ggagacagta ttgaagctca ggtacagaaa 133860
taatttcacc tccttctcta tgtccctttc ctctgagaag caaaatacag cagatgaagc 133920
aatctcttaa ctgttccaag ccctctctga tgagcagcta gtgctctgca tccagcagtt 133980
gggagaacac tgttcataag aacagagaaa aagaaggaag taacagggga ttcagaacaa 134040
acagaagata aaactcagga caaaaatacc gtgtgaatga ggaaacttgt ggatatttgt 134100
acgcttaagc aagacagcta gatgattctg gataaatggg tctggttgga aaagaaggaa 134160
agcctggctg atctgctgga gctagattat tgcagcaggt aggcaggagt tccctagaga 134220
aaagtatgag ggaattacag aagaaaaaca gcacaaaatt gtaaatattg gaaaaggacc 134280
acatcagtgt agttactagc agtaagacag acaggatgaa aaatagtttt gtaaacagaa 134340
gtatctaact actttactct gttcatacac tacgtaaaac ctactaagta ataaaactag 134400
aataacaaca tctttctttc tctttgtatt cagtgtggca catctgtaaa cgttcactct 134460
tcacttagag acatcctcaa ccaaatcacc aaaccaaatg atgtttattc gttcagcctt 134520
gccagtagac tttatgctga agagagatac ccaatcctgc cagtaagttg ctctaaaatc 134580
tgatctgagt gtatttccat gccaaagctc taccattctg taatgcaaaa acagtcagag 134640
ttccacatgt ttcactaaga aaatttcttt ttctcttgtt tttacaaatg aaagagagga 134700
caaataacat ttctctatca ccgacctgaa actctacagt cttcagagaa tgaatggctt 134760
gctaaaagaa tgtcaaatct tactatacag ctatttcata ttacactact aaatacacta 134820
taaggcatag catgtagtaa tacagtgtaa aatagctttt tacactacta tattattaat 134880
atctgttaat tccagtcttg catttcacat ttgcaaaacg ttttgaaatt cgtatctgaa 134940
agctgaatac tcttgcttta caggaatact tgcagtgtgt gaaggaactg tatagaggag 135000
gcttggaacc tatcaacttt caaacagctg cagatcaagc cagagagctc atcaattcct 135060
gggtagaaag tcagacaaat ggtaaggtag aacatgcttt gtacatagtg agagttggtt 135120
caccctaata ctgagaacct ggatatagct cagccagcgt gctttgcgtt caagcttacc 135180
agagctgttg tatgcctgtt aagcagggca tacagtcatg aggctcttga aaaatcttaa 135240
cagacaaagg gcaatggaaa atcggagtta agggatggta gggataaaat gcatagaaag 135300
aggtaccaca attttgattt ttgccctaat gcctctctgc gtggttcctc aatttttcta 135360
cttcattcct catctcctca gagcattcct ttccctcatg cttgaaacac agatgaaaga 135420
ctgtgaattc taactgagat gaaaacatcc acaaccacac aacctctggt gtggagtcac 135480
attctgtgaa ggcaaaaact aggccacgta atctatgtgt gcaagctacg tgtaagctat 135540
gtgtgtgaca ggacaatgtg aggaacatac tatgtgcaca aggactgcag aataaacagg 135600
agcaaagttt ttgaagaaaa cagagtaaaa tcctgttttc ctcttttgtt acattcttta 135660
catatatctc aaatttcctc tttggttaga agcaagtaat atttatgttt cttggtactg 135720
tttgggttga agaccattct gggataagag aaattccagt ggttcttccc ctaatcataa 135780
aatgtacagg tttagttttt ttgtaacaca gaaatctctt catcttttat cttttgttgt 135840
```

```
gattctttat agagagagaa acaagactta ctgacaatag cagcaagaaa atcaatcttg 135900
gaagaacaag attgcagttg caaaaacaaa ccaatgtcct tgcccctaca tcctcttccc 135960
cataaattct acattctcta tctaccttgt gcttgccaac atgatatacg taaactctct 136020
tttcgtattc attcttaaag gaattatcag aaatgtcctt cagccaagct ccgtggattc 136080
tcaaactgca atggttctgg ttaatgccat tgtcttcaaa ggactgtggg agaaagcatt 136140
taaggatgaa gacacacaag caatgccttt cagagtgact gaggtatatg ggcatacctt 136200
agagatgtaa tctagaattt atgaagagag tagacatgtt gttatatgaa cactgcatta 136260
gcgtatctgc tcatttgtct gcatctcttt cagacactgt gttaaaagca gggaattttc 136320
cttatgtctc tctcatcaca atattcctga cattgcaaag ctcctgagaa ataacttcag 136380
attcccactt ttcctaggaa ggtcttcctg gatgagaaca atcaatcatc ttaactgtaa 136440
ctagatattt ctgcatctaa gaataatctt tgttaaaact atattctctc tctctttttt 136500
ttttttttt ggttctccag caagaaagca aacctgtgca gatgatgtac cagattggtt 136560
tatttagagt ggcatcaatg gcttctgaga aaatgaagat cctggagctt ccatttgcca 136620
gtgggacaat gagcatgttg gtgctgttgc ctgatgaagt ctcaggcctt gagcaggtat 136680
ggccctagaa gttggcttca gaatattaaa aacacatgga aatttagctg ttgtaaagct 136740
cttttcaaca cagttatcct aaaacattta accagcacaa atttcatcat gattcaatat 136800
gtgattgttg catagaagtg tagatttgtc ccactgggtc ctgcaatagc ccatgctgag 136860
catggcttgc tgaaagaact gctttagagg gtgaaaagtt tgacacagca gacaagatga 136920
ttctcaccta agcagctgtt actgtagtgg cttgaactct aaaggtcttg tatctccatt 136980
cctgtgcact gaggagcttc ttggaaagtt catataaggt ttactagttc taactattat 137040
ctcatttggt ggcactcaat gtgctttgtt cacgtcttca taaattaatc tatctaaaaa 137100
ttggatgtgg ttaaagcaat ttcagaaata acatgtacat aatgtacaat tattgatatg 137160
aacagaacac aggcatagca tattgtaatt aggaggactg tagttatttt gaataggaaa 137220
cacaatgtaa taaatgagaa ttcattgaaa tgttagtatg ctaactcaat ctaaattata 137280
aagataaaga ggcatttaat cacagctaga tttccatcac ttgtgacaga caggcatatg 137340
aatgattatg tacagctcta ggaaaaaaag tatgtaggaa aactagtaca ttttgattag 137400
aaagtctgaa aatgaggtgc cttgatcaaa gagaatacgt gtgtttgaga aaaaaaaagt 137460
ttggatagag gtggtaagag agaatatatt gaaatggtgt ttctacaaac tgccatggcc 137520
agatttgtgt aagagacatt cagtaagtag gcaaggaaag aaatattact aggtacaaag 137580
caacattagt aataccaaaa gaaaccaatt attccagatg ccaatctcgt aatagggtta 137640
agagatttcc acccctctag tagtcaccag tgcaaccagt aactttgcta atttacattt 137700
tctttttta aatggcagat atagctttga actgagtgat catgaactgg tactgtgtaa 137760
ataagatgga agcatacttg ggagctaaac ttctagtttt taaaaactca aattctcttg 137820
aaagatcagt tcccagtcta gtaacagctg atagtttaag tatcagtaat tggctaccat 137880
taacaactgg ctcctgagag gtcttaaatg tagagacagc tttaaactca aaagcacaga 137940
gtgattttta gaatagattt cccaagcaaa gaaaataaac agggaggagc tttaagggag 138000
tagccatctc attattatta ttatttaaag aaatggcagc aaggctataa aagaaaaata 138060
agacagagca gagaagaaag agtcatggta tgcttttcta tcttagcaaa attaatctct 138120
acatgcctag gaaaaagcca tgacaagagc aatcagttca aaggtgtat gcaaaaaaac 138180
acataatagt aactagtact gcattgccag gaaggaagtt atgtcgccat tccatggatc 138240
```

```
tcattctcat ttccttgcag cttgagagta taatcaactt tgaaaaactg actgaatgga 138300
ccagttctaa tgttatggaa gagaggaaga tcaaagtgta cttacctcgc atgaagatgg 138360
aggaaaaata caacctcaca tctgtcttaa tggctatggg cattactgac gtgtttagct 138420
cttcagccaa tctgtctggc atctcctcag cagagagcct gaagatatct caagctgtcc 138480
atgcagcaca tgcagaaatc aatgaagcag gcagagaggt ggtagggtca gcagaggctg 138540
gagtggatgc tgcaagcgtc tctgaagaat ttagggctga ccatccattc ctcttctgta 138600
tcaagcacat cgcaaccaac gccgttctct tctttggcag atgtgtttcc ccttaaaaag 138660
aagaaagctg aaaaactctg tcccttccaa caagacccag agcactgtag tatcaggggt 138720
aaaatgaaaa gtatgttatc tgctgcatcc agacttcata aaagctggag cttaatctag 138780
aaaaaaaatc agaaagaaat tacactgtga gaacaggtgc aattcacttt tcctttacac 138840
agagtaatac tggtaactca tggatgaagg cttaagggaa tgaaattgga ctcacagtac 138900
tgagtcatca cactgaaaaa tgcaacctga tacatcagca gaaggtttat gggggaaaaa 138960
tgcagccttc caattaagcc agatatctgt atgaccaagc tgctccagaa ttagtcactc 139020
aaaatctctc agattaaatt atcaactgtc accaaccatt cctatgctga caaggcaatt 139080
gcttgttctc tgtgttcctg atactacaag gctcttcctg acttcctaaa gatgcattat 139140
aaaaatctta taattcacat ttctccctaa actttgactc aatcatggta tgttggcaaa 139200
tatggtatat tactattcaa attgttttcc ttgtacccat atgtaatggg tcttgtgaat 139260
gtgctctttt gttcctttaa tcataataaa aacatgttta agcaaacact tttcacttgt 139320
agtatttgaa gtacagcaag gttgtgtagc agggaaagaa tgacatgcag aggaataagt 139380
atggacacac aggctagcag cgactgtaga acaagtacta atgggtgaga agttgaacaa 139440
gagtccccta cagcaactta atctaataag ctagtggtct acatcagcta aaagagcata 139500
gtgagggatg aaattggttc tcctttctaa gcatcacctg ggacaactca tctggagcag 139560
tgtgtccaat ctgccgctgc cctgatcctg gctggggtga tgggacagac cttggctgcc 139620
actgagacat ctgagacact gagatctgtc tcaactcaga tttacccaag aacagatcat 139680
tgccaacaga acaaaatctc aaacttatgg ctagtgatga cagcagtcag ttgtcccatc 139740
tgtgacccac caaggctggc atgctggaat gagcaggctt tggtggcttg tagttactgg 139800
acagcaccac tgacatgggc aggggaaaaa ctgagcatgg tgtaaatcac tgcctcaaag 139860
ccacttctct gtgcctgcac catgcttgaa agctcttcta caggagctgg gtttgttcaa 139920
gaaagcttct gtttctccca tctgcttctt gtaccttcac agggacagag ttagaagggt 139980
acagccatgg ctggaagggg ctgactttca aatgtgccta attttccttt ggttgctgct 140040
gcagctgcag aagaaggggt tcagaagcca agagctttga gataaggatg cctaacctat 140100
gttgaagaca tttgtgctga cacctcaggc cccaggatag gacaactgct ggattgtggc 140160
taacccacta gctacagaac ctaatttata ttaccagatt aggaagagca aaagaacatg 140220
tatttataac aggaggtctt ctgtgcttct ctactaaaag gtgctgtgaa ggagcccaca 140280
gtgcagcagt gtatgaggcc tgaaagaggc cgcagcacac gaagagccct ggtaggagca 140340
gcacacagag gggcaggagg gctgggggaa ctgccaccca tggggacctg tgtgaagcag 140400
tgcactcctg aggggtggac tgcgtgggaa aggaaaagaa agcaaacaga cctgtgatga 140460
actgtcacac agactgcaga gtgacagagg agggcttgag gcagtgcgct tactgcaggg 140520
agtggcgctc cttcctcaca gcagcgctaa cagcttggca ccaatattca gtagtctgtg 140580
```

-continued

```
gtgatgcttt ttccagtttc accacacagc atttcgcttg ttctacttgt tttagctttc 140640
cccctccaca agataacaca tactttgcca gtcagtccct aagaccttag cctaacagtt 140700
agcaaacagg atcttgcaaa agaaggaaga taacatgaca ccaccttcac tggtgtataa 140760
atagttcaaa tactttcctt cactttcccg taaattagtt gattgcaggt caggagataa 140820
caggggaact tactgcaaga gagaaaatga tgtttaatat tgtcttggac tttctggtgg 140880
tctgggcatg aaaatggagt actcaaaatc ctcaggacgt ttatttttca cctgatttat 140940
tcccaaactg cactatttct aggccattgg agttcttatc aattaaatta tactttggct 141000
ctctgctatc tcactccctt tcatcttcag catcactttc agcacaatta caggagaaga 141060
cttagactca gagctttagg actcatcata agaggctttc attgctctgt caccacaccc 141120
catatagatc tgtagtatac cacacatgtg aagaagcaca gtacattagt gcattacaga 141180
gagacaaaac cacacctatt tgtgtgcctg cagtcttaca ccagcaggaa gataattaac 141240
gtaatgaatt tctataaaaa tgagagaata tggcccctgg gtcctactgc ttgttctagt 141300
cctgattctt caaacgtaag aatgcaagta aaattactca cttgaacaaa gtcagcaatt 141360
tgcaagaact gatattctga agttcaagta attagagtga tttccagtac ttctggctgg 141420
aacgggcagc tgaaaatcac ctggtccagc accttgctca aagcaggact atcttcaaag 141480
ccatatcaga tagctccaga ccttccctag tcaagtgttg cctatctgca tggttggaga 141540
acccacagcc ttctgattaa tttgatttta aacataaatt caaatgtcac tagcgtagca 141600
gtagtgaaag ccattcaact ggctttactt tctcttacca aatgagagtt agctgcaggt 141660
gaaaataagc cctgccagtt ctcatttttt ctcccacagc ccacaaagct ctcactgtct 141720
gtcctcactt gtaatacttt tgaaccaaca tctacagatt atctctgtaa atcccaagca 141780
gtacctagtc accacgtgaa caacaaattc ctacatttaa caatatttaa gagcaaaggc 141840
cagaccatat gtagctgcac actacacatt tttagaccca atagtataat ttatactttg 141900
actccatgtt gctgccatgt ggataacaat gcgcaatcat ttgtacctgg cttccttttc 141960
taactagtat actcttaaac gtcacaagat aaagactcta gttctgtata gtctagctga 142020
cttgtgacaa gagcaaacac tcacaatttc atggtactcc tgaggaaaaa aaggatccca 142080
aactaatttt gagcttttac atattttttt ttaacctaca gagcaccttg ctacttctgc 142140
tgaatgttag caatagcaac ccacagtctg aaatcaatgc aatgaacttc tactatgggt 142200
accatactga tgacaggaat agtgcaagtc cttacactgg aaggctgact ccttagtcac 142260
ataggtaaaa tttagaaatt gcagctctga taagagatca gtatgggaaa gggaaaataa 142320
tggggtgcca gatgagtgca ccttcctgaa aggaaggcag atatatggga attaaaggtg 142380
gacaagggat gctgtggagg taccatcaac tttcacaggg ctgtatgtaa aagcagctct 142440
ctttcctgtt gattctccgc tgcctcattt cttctgggca aagtttgtta ctctccagta 142500
acgtcccttc ctcaaactgt tacctaatcc caccctcatt gccttctctg ttttgctctg 142560
tccttcagca gtctctacct gcttcttaag gtagtgaagt aagagggcag ttctggagtc 142620
aagctctgtt tctatgaggg taaaggccag ggagagaaag gtttgggagt gtgaggagag 142680
cctttttcct gtgttgttca agtacttagt ccaagctgct ttcagctgca tctgcagaag 142740
atggggaatg gagggtgatc aatgccattc ctccagccac agagcaaggg ctttgcctct 142800
ccttgcatac agtatactag ctttccttag tcaaatgttt cctctgtgct gcagagtcca 142860
aggtaaagag gctttgtcta cagctaggtc tatgttccta gagaaacaat tagcaactgc 142920
aaaatcaaga ggtactaaga aagcctctga agctataccc aggggtctgg caaatgaagg 142980
```

```
gggacagatc aagaagaaag aagagtctag agcagtttaa gggaataatg ccactagttt 143040
taagccacac atctggtggt aagcttttaa ctttgaaaga gacagaaatc tcaagataca 143100
ccagcccaaa atataatgga gccataaagg tctgcacgta gctgaatccc aactggaaag 143160
aacagcttca aagagcttgg aagtgctgag gtgaagaaga gcatgtgatc attagatttc 143220
aaaagaaggt cctcagcaca ataaccagaa agttcacctt tctgtgggac aaaagatgcg 143280
tccctcacaa aggctggggg aacaaaatct ttgcatctca ttttgcctga gaggagaagg 143340
aaatacaaga tcatcttgtt ttacttggtg tgtatcacat cattaatttc tatttggtca 143400
ctactatgca gaacttgcta acttgaacca tgtaaaaagc acactaggtc tcaagagact 143460
aaaatgcttc ttgcaacagg cagagtgtga gagatggaag gatggaaaaa tcttgcagtg 143520
atgaaggcac tgataagaga tgttgaaatg atactaacaa atggcactct atctttccca 143580
agatctttgt cagcatgaag ggaaaattct attccaagct ctctttgagg ggttaccatg 143640
ttccaggata aagacttgct gcatacacaa gcgcacttag tcaggtcact cagatcagtc 143700
tcatgctaaa aagtgtgaaa atagaaatac aaataagggg ccaagcagat tactgaacag 143760
caaagattgc cagtacgtgt ccacaatgag tatttggaca tttcactgcc gaaacttctg 143820
aaaatatcaa ctgccttatg aaactctggt tattccaccg cacaggagta tttgtggttg 143880
agctgcatga agaaatagca agtgtttaaa ctgatttctt aaaagagagc ctttcctcta 143940
catgctgctc ttgcacatcc atgcgtggct cctcttcagg agcaggaatt ggttttctga 144000
ttcagcagtt gtgtagctga cgtagttata ccctttgaga gatttcttca gaaaaatgac 144060
atgtttaggc taaagtgcat gtaatccaca catacaccat tactcacaat gaagtactat 144120
gcagcatgaa attcaggcta ttcttcttca tatttttggt tttaattgct accttggtta 144180
cttaaaaaat gctcaccatc tgattcatgc aaaggaaaac tgcacactgg tagatgtgag 144240
aacagcacgc atactcactt ccagataaac taatctctac tcagatatcg agatcattgc 144300
ttctccagaa gtgttgcact ggtcatcaga actgagtatc tcaggaaaag cactgtcttt 144360
tctaattacg gcatctaagc taaagcacac agcggtaata gtgcagtatg acaaattatg 144420
ccagtgttca attcatgtgc caaatctcac cacgcctttg cgttctgcag gtgtggagca 144480
aaatgcctca gtgatattta gacaggaaca ccaccacacc tcttaacaac tcataaattc 144540
taaatgctat tggagtatgt cagcaaagat tgcttggcaa aggttgcaaa tgtacatgta 144600
atatgtacgc tttagatagc tatctacact gtttcaaaat aaagacgcgt gtgttctcac 144660
tcaaagcttt aaagggaaat aagatactca aagaaataat ctcttttgaa ctttaaaagc 144720
tatttgagac ttcacgatga tacaaactta tcccacataa aaatcttagg acataaaatc 144780
cattacaacc attccagctg agacatatac accattgtta cgctttaatt tacaaggtca 144840
ggacaagctc ttgctgcatt ctgtgacaaa agggctcctt tgcacaccaa aatccatgca 144900
cccactccaa gcacctgatc actgatcacc attaccatca cttcagtctc cgtgctccca 144960
ttccccatac tgttttggct cttgccaatt acaggattgt tatgaaacta aatgttaagc 145020
tgccctccca caggattcca acattctcag gtttcaaaac cattgtcttc cccacccctc 145080
ttatctcctg aagtccttat aatggtttgg acatttaaag tcctttcatg tttaaaactt 145140
actggcctgc tctggctgag acaaaaacac gagcagaatg ctctgttggc tgaaccagaa 145200
accattcccc cccagataaa taaacagcac ttttactggt aaaaaaagat attagaagat 145260
gccaaagaaa tggagtagct tttcttcaag cataattttt ttcttttcaa ataccaaaca 145320
```

-continued

```
ccttaggttt gaattacatt agattttcaa gaattacaaa gggttcgtag ttaaaacagc 145380
atacgtacat gaaaaccagc catggcaagt ttcacacaaa tactgtgtga aagcagaagc 145440
taccaaacct tcctctcaaa accctcaagt acatttagat cactttataa atgatctatg 145500
tagacagcaa gtatttaacc tactcctgat cccaggtacc aatgaactga gcaacatact 145560
gtgtaggaaa gttgcactga cttgtgctaa gttgcacgga aactgaagga aaacaaaatg 145620
tgcttatata gctgagatct ggccagggtg cctggtgtgc tgccaatatt tgtcctgcca 145680
aaatggaaac atgaatgacc acagtgaatg aactacaggc ttacttccca caggaaggat 145740
actaccaata caaacataag actttgagca tgttggagtg ttgacttagt agagagtggg 145800
agtgagggaa ccgctgctcc tgagtcagcc tcagcaccgc ccattgaact ctgtacctcc 145860
tagccttggt aacttcacag gatgctggaa aatattatca agtcatcaca ttgatttatt 145920
gaatatcttc cttttagatt ttagttgctt tgtatgtatt tttttttcca ctaataacca 145980
gccatgctat tcaaaaggca tttttaaaag gcaacgttaa caccctgtac aaacaccatc 146040
ctctcattca ttcaaatccc acatttctgc atatatggaa catgtcagtc acttcttgta 146100
acagagcaag tactatgact agtcagcaaa ttaaattcat ccctgcttta aaaacagaaa 146160
atccaagtaa ctgctccaag ggatgaagtt tatttagtgt atctatcatt tgttctacaa 146220
cacagttaat tttgcaaaga tgactcaaat catttaaagc tttggaaatc atttaaggcc 146280
aatgtaaaca gattacaact ttcccaggcg caatggaagc aattaattct gcagcacacc 146340
tctcctacac tactatactc tggaaaacgt aacagatgca tctaattata acccacactg 146400
aaacatgctg tctttatgta gctatgaatt caaaacagct gaggggcagg aaagaaccat 146460
cctcctaaag ctatgtggct gctcacctgt aggaaagcaa cttcagcaaa gctttgagtt 146520
cccaggttac actgatgcag aagcttcacc actggcaagg tgctccttgt gtgagcaacc 146580
tattctgctc tataaaacat ttagcagata atcccatatc tcagtcctca gtacaagaga 146640
ctctgtgcca gccacttctg tacgaaataa gcccacacgt actttcatag acctcagggc 146700
agaagaaaag tttcagaaag cagtttgtgc tgaggagata gaccttgggg gtgagtcttt 146760
ctccatattg aggcggaatc cctcaaagac aagcagccct tatccaggtg ttcaaggtga 146820
tattttcaac agagcaggga ggtaaagaat gaaataaagg gcagagttac ataggatttt 146880
tcagtcagag gtgagagctg agatggacag gacaatgagg taaggacagt gtgactgtga 146940
ggagaattag cgatggaaat gcttcactag ccaaggcaag aagaaaaaga gtattcaata 147000
gaatatcaat ttctggggaa agaattcatc tctgaagggc tacatagggc aaatagctgc 147060
tttcaactta gaacagggaa actgaggcag cagcaaaaaa aaaaaaaaaa gtctaatctg 147120
aaacccacat caggttctac tgttgttgca gtgataagaa aagtgtctga tgagtgtttc 147180
tcaaccttcg ttatctcaca gtgaaaacat tttcctggtt atacagtttt agaatcctcc 147240
aatattacca aaaaatcatt ttactaaaaa tggaatccca caagaaatga ctaatttttt 147300
atctgtagga aacggacaat agaaaaactc ataaatatga tgtcactgtc ctttcgctgt 147360
ctcttccttg gaaattgttt ctattagagg aatcataagt aggtcagcta ctgcattttt 147420
ttaccctcca aattgcaaaa gaaatgttgt ttccagcagt gatggttcaa gttgtaacta 147480
gcctgttgcc acaaaaatgt ttatagaaat atttctgcag tcagttttgt aaggttcttg 147540
tatggtatca ctctcaccgt cacttcacat cctactctga gatgattcag ttcttccata 147600
gggatgtggc cttcagggca aaataaattg cagagtcatg agtcataaga acctttgaag 147660
aacaggccag gcagactata aattcagcct acccatcatc tgaactgcat aaaccttgga 147720
```

```
cagacccaga gcagcagtct tcctccctgc acaaaacaag gtactgtaat tatttctaga 147780
gattatttat ttcacctact cttggatgat gtcgatctgt tgacaaatgc atagaaaaaa 147840
aaggcagaag gaatctgaat agaaaacaat aaatacttga ggaagaaatt tactaagatg 147900
gcacaggcaa ggtctagaag gggtaagtct cagaaatatg caggaagagt ggtttattct 147960
atgtagttct cactggcaaa catgtatatc atagcagagt aagaaccatt gtgtttgctt 148020
aagttagatc atttgttcat gtgctcttca attcttgtgt acgtcaagac acagtcagta 148080
catctttatt ttatggctat tctgtatcaa ccagaatagc tcccactaca tacctagggc 148140
tctcagcttc aactgcaatg caaataacaa agagcagcac ctgtgttcta ccaataagga 148200
aatttgtctt gcagaactgg gaagctatga ttcggactag caccataaga cagagtttcc 148260
agaaattttt gaaagttaaa aatggaattc aggatactta gcacacagta gttagagagc 148320
tgcttgtcta gtgcttcaat attttcttgt atcctaaagg aatggaatat ttgttcacta 148380
cagttacgag ctccaaaagg ctcttgcacc agtagtcata agaaacaatc tctcagcatc 148440
ttctagccct cgcaccagtg agtagcatta tcatatgtca ctccaagatg ctgtaaagga 148500
cagtgcaata aacgtcctga tgaacaaata caaaatgaaa tatgaggctg ctttttctat 148560
atcacttgag tatggttagt gttgttggtg aaacgggatg cactatactt aatataactt 148620
tttagtagct aatcttcctc attttccata aagatatctc tcttctttcc atctgtaagt 148680
tccttaccat atcattatat tgcttacata gaattcacca tatagttata aattgcatgc 148740
tttttctttt tagtataaca ctgtaaccat cctgtttcga tgaattttct tttgtttctc 148800
ctggctgtcc cttgcatgga tatctgtctt tctaagtgaa cttctgctga accaaggaga 148860
gttcattcat gcactacaaa cagacgtagt tggcagaaat gaatattgta ccagtactga 148920
caggtcagaa tgctttcatt cagtttcctg aggtcagagg agagctgaag aaaatacctg 148980
gcacagtcta gattttgcct ttgaacatac actgccagtg agcctcagtc atacaaagga 149040
tcactgtgct gcactggcat tcttccacag tcaataagtg ttaaaaatac ttttagaaag 149100
cctacaaatc ataaaataaa cttcaaatac tgaaagggag cctgcagaca tatagcaaac 149160
acaattaatt cttagctaat aacatctttt gtccctttct gcgcaggttc agaacaatgg 149220
aagctttaaa taaagcaaac acaagctttg ctcttgactt tttcaaacat gagtgtcagg 149280
aagatgacaa caagaacatt ttgttctccc ctctcagtat ttcatctgcc ctggctactg 149340
tgtatctggg agccaaaggc aacactgcag atcagatggc aaaggtgagt ctgagaagag 149400
ttgatctact ggagtaacat tctctatgat agaaatttag catgatgcat caaaggaaaa 149460
ccttatgcag gtcaaaagat acagtctaca gtagcttctg taagcaggcc cacaccaaat 149520
gggagcagtg gcattagtga cattgtctcc ttttaaatgt cattggaaga aagaagagct 149580
cttaatccca aagctcaata acttgagcac tcaccagtga gagggagact cggattctcc 149640
acctgccttg ctccagaaaa ttctcatttt ctgtctcatc tctctggaaa tggccctatg 149700
cagaaagacc ctccactgta tctctagtaa gttttgtgct ttgctaacat aaatctacaa 149760
acccacaagg tcagagaaga aacacagtca gggtgataat acaacccctt cttttgagta 149820
cgtactttac aagaaaaatc acctactgaa gttcctaaac tctgtgcaaa gttcatagct 149880
tcaaaaggca gcaatgagaa cagccccagt gcaaacatgg ttacctagca tgtactgcgg 149940
gaggggctga tgaactggca tctgctaagg cagaagaagc tgctccacct gctaaggcag 150000
caatccaact actgagctac aggacaaatg aggaccagca gggtcacaaa gaaaggagag 150060
```

-continued atcttctgtc aggaagaagg gaaaacaaaa caaaacagaa ggcttttgaa aaatgttcca 150120
aggttagatg tacacctctg tagcctgggt aaggtgcaca tgcccagagg aaggcattta 150180
gggtatcaat ttgctcccag tgtttacctg ctttctgaca tgtaccaggc tctccatttt 150240
acacccatgc tttggcagtt tccacctgca gataactggc ccgtcccagg tattacccta 150300
tgagtacaag agccgatttg aagcaggcaa gttcctctag aaataccaga tatatgagaa 150360
ttctgcttgc agccctcatc ttagtgtgct caagacatcc tgtacacatg ggctcaaaag 150420
taaaatctgt ctttgtctct cttcatcacc agtcccatga cattactgaa agtttttact 150480
gaaacagcaa attttctatc attgcattta ttactgcaat ttccactgca ggtactctac 150540
ttcaacgaag ctgaaggagc cagaaacgtc accacaacca taagaatgca agtctattcc 150600
agaacagatg agcgcctatc aaatcaccgt gcctgtttcc agaaggtata taaccaagtc 150660
taatgatcat agaatcatag aatggcctgg gttgaaaagg accacaatga tcatctagtt 150720
tcaatccccc tgctatgtgc agggtcacca accactagac caggctgtcc agagccacat 150780
ccagcctggc cttgaatgcc tccagggatg gggcatccac aacctctttg ggcaacctgt 150840
tccagtgcct catgatcaag ctacagtcat gctaacacct tcccttgctt ttattttctc 150900
tctctgtttg ccttcctcaa atgcagggta cacaactgat tagtacagca tcctgtgata 150960
ccttcacctt atgcaatact taagacatgc ttcccatttg taggtagaat tgcaaaattt 151020
aacctcaaat ttgcaaaatt tgaaatttaa tgatgggact attctctatc agtggacctc 151080
ttgatcttct cccttcagct ttgagatttc tctctttttt ttttctcttt cttttttttcc 151140 cctttcctct tctttctttc ttctttttct ttttctttct ttctctcttt caatctttca 151200
ttccttcatt cttttctttt taactactac tgttcaatta gttattgcta gttattcagg 151260
aacatgttct ttgaacaggc acagtcccta tctcagaaca aatcagaaca acaaaactac 151320
tctcccacac attggattgc agcatcaaca caacaacaac aacaacagaa aaaaacagcc 151380
agagaagtaa cttttacaga ctatccatgc ttgatacatt tcagaaatta gtttctattt 151440
catttgaaag tttagtggaa taaattggca tgttggaatt tcctaaggta gaccttgcaa 151500
taaatcttaa agaaatggga attattgtat tcccgagata tttctttgac agactggcag 151560
gcatcttttg ttaaaataga cataatttaa gagagcagaa aatttggaag tcaaactctg 151620
agtgagtaag gtagtttttc ctcactgaca atgcagccac tgtggtaaaa agttcctctc 151680
cctactcttt cccatcattc ttttttcttt ttgtgagtaa atcatttccc tgaagtctgt 151740
ccacaaaacc cctgtggcag caagttttga taaatgggaa cttgggtcta cattccacag 151800
ctacggtggg aagactaatt ttggggacta cgccaacaaa ccatttatgt tgcacgaaca 151860
ggagatggat tgtttctcat gagtaatgct tgtctgaact gtaagaatta tggagcgctc 151920
taggcaggga aaagaaactg ttctaatagc ttagaaattt agatagctgt tcatgcttct 151980
gattttcttg cagtaacaag atgaatacaa cacaggtcca gtttcttagt ccactaattc 152040
acagcttcat ttccttaagc tggtttgaca gtttgagtcc acattcatat aattctgtta 152100
cataaatata aagaatttac tgcaattact acaacaaaaa gcatttgcaa aatattatta 152160
tttagaggta ggttaaaaaa gttagaggca aacttaccat gtaattaact ttcataaatc 152220
ttatcaggag tcacacagcc aggtcttcat gtatagttta gcaattacat tctgtctctc 152280
tctctgtatg tacttcattt tgcaacctcc atttaaaagt ccttaaacat tctaaacagt 152340
tcaagctttt actacttgca tcccagggct cttacagtgt ctatagcata tctgaaactt 152400
ttagtaattt cacatcattc ttttaatatc tgtctgagtt agtacacatc ttgcattgca 152460

-continued

```
gtaaaggcaa caccacctga atagcagtag tttacataga gctgcatgag gaaagaattt 152520
agaaattttg aactgtttta cagaaaaaaa aaaaatgtat aacccttatt tccttgtctc 152580
caagacagaa ataggcaaat caggtaatat ccatgctggg tttaaagcac tcaacttgga 152640
aatcaaccaa cccactaaaa gttacttgct tagaagcgtc aaccagttat atggagaaaa 152700
gtcactgcct ttcagtaagg taggtaggcc atttattcat gttatcctgt gtgtgtcaga 152760
ctttatgatc tatctatgac aacaaaccat aaattatatg ctttcaaata ttttcattac 152820
atctgcaaat tgtgtaatta tctttaacat acttcctgtg aggttcttct tgagaattta 152880
gatatcatga cttttatagg atgtatattt aatttgtgtg attcacagtt gtggctacgc 152940
aaaaacattt aaattatgta tttccaaata aaatcaatac tatgttcttt tgacaatgct 153000
gtgcttgtag cctacacaat ttttatgcat tctctccaat cggctatagt tatttattgg 153060
cattcacact ggcaggcaac aaacataaga cagatgtcta tcttgcactg caggaatact 153120
tacagttaac caagaaatac tacagtgcag aaccacaatc agttgacttt gtgggagcag 153180
caaatgcaat cagaagagag atcaattcca cggttgaaca ccagactgaa ggtaagctct 153240
agcatctcct ctcccagttc tgaaggaagc agttttagtc ttgaacaatt tctctgtgcc 153300
caaaggcagg taaacaattt aactcagaaa ggaaaatcag aacagttttg ctgaagtaat 153360
catctgctgg caagcccttt ctagaattat ctttcaccat ttgaaaggga gaggaatgtg 153420
gtttcctcta taaatcaagg ttgtcatgta tttatgaata atctcaagct agaagtatgc 153480
caaatcagca ctctaaattt ccttgtctta tgacttcaga aactacgcca gcatttactc 153540
tgaaacagta aagctgcaca aatatgtaaa cgttctttgt ttttctctag gtaaaataaa 153600
aagtctgctg cctcctggat ccatagattc actcaccagg ctagtcctgg taaatgcgct 153660
ctatttcaaa ggaaactggg caacaaagtt tgatgctgaa gataccaggc aaaggccttt 153720
cagaataaat acggtatggt aacatactgc cttatatacc agactgcagg ttgaaaaagc 153780
agtgaaaaag atggaggaga taaattcctg tcattcttta aagccacata gcactaaaat 153840
tagtatattt aaaacatacg ttatatcctt cttagcacat cttcagtaca aagaccgcat 153900
acatatgcta gcacccaagg cacaaataaa attatcagaa gccagcttga aacaaacttc 153960
catacacctc ttaaagcagg aaaaacatag atgtgaatag aactgtatga actagttcta 154020
tatattttca tttttaacca tacaatgaat tggagtggaa cagagcttcc agtaaatacg 154080
tgtcatccta gctggctaag ataaccttcc cagcctccca gtgcattccc agaagagagg 154140
ggccctctgt agatcctaca gcttctctta gagccacagg gatgtacctc catgctactt 154200
caatgtagtc tttactgttc tgagtataaa tagcaagctt ttcatttgat ttgttgcagc 154260
atacaactaa accagtgcca ataatgcacc tgagtgataa atttaattgg acctacatag 154320
aatcagccca gattgatgtt cttgagcttc catatgtcaa taatgaactc agtatgttca 154380
tcctgctacc acgggatatc actggcctac aaaaggtaaa gggtaacttt aaactcaaat 154440
tgcgtgagaa acaacgtttt catgcatatc catggcaaag caatcctgtt tctaggaagg 154500
aaggtatcga taaggctaaa ggaaaaacaa accccaaact tgcccaaatg ttatgaagct 154560
gaacctttc aatgttttgt ttggttttct ttttaactcc tggcacgtgg cacctcgtgc 154620
ttcctcatgt tgatcagtgc tggaaataag tagcccgaat ccaacaagat agatctaatt 154680
ccagctgaag aacaacgagg acagaaagat agttctgctg actgtctgta ctgattcgga 154740
cagatattat tacattaaaa agaaaagcac aaactggaca ccctccacta ctttctgtga 154800
```

-continued

```
tgtttagagc taatatacat gtacactgcc accttctgta aacacactga acctgacttc 154860
agatagtgaa ctactgtgaa attctcattt acattagtgg gtgttttgta gaaaaaaaaa 154920
aaaaaagtta ttttcactaa attctaagac acacagaaaa cagaaatgtg agcagcaagt 154980
caaatagact attgttactt gacagtgacg ttgttttaca aatatttaat ccctctatat 155040
tccctgatga ttactaagaa cagttcaaat actgcactaa catgctgtag agcaaaacac 155100
tccttcctag tagaaaatat ttcagagttg gcatttcact aatggtttct gtacttgaaa 155160
agtacaattt tttttgctac aaaaaaaagc tacagaattt ttgtagtttg aaaagttctt 155220
aaataagaat ataaaagaaa taacccctag ggaacagttt tttgaacact ctgtaatttt 155280
ctggttctct tttcaattaa ctgcagctaa taaatgaatt gactttcgaa aaattgtctg 155340
catggaccag tccagaatta atggagaaaa tgaaaatgga agtgtatctg cccaggttca 155400
cagtagaaga gaaatacgac ctgaaatcta ctttgagcaa gatgggaata gaagacgctt 155460
tcactgaagg tcaagctgat ttcaggggaa tgtcagagaa cgctgacctg tttttgtcac 155520
aggtttttca caagtgttat gtggaagtca atgaagaagg cacagaggca gcggctgcca 155580
gttcagcatc tctagcgtca cgaacccttg gtgctacagt tatttttgta gcagatcacc 155640
cttttctctt cattatcaga cacaacaaga ccaagtgcat ccttttcttg ggaaggttct 155700
gctcccccta gaaaatcagc tattaataaa caagccctta caacaacgat gaacacaatg 155760
tatgccatga agaacacctt gacagacttt gcactttacc attttcctgt actattgaca 155820
atctctttta gaagagagct caaattaaaa acatgaattc aaacctctga ttccttttcc 155880
tctgcaaaga atcctagcat cgtatactgc actgtagaac actgaactgc acgctgaaca 155940
acatggatgt gtcttttcag tgctgtccaa accagaactg ctacaatgca gaacagacta 156000
ggctgatcta aacagtacct tctgacccag ttcctttcac acgtaagaag aaaagaaaca 156060
ggagaaactc attcctgcat acagctgttt catctcttca aagccagctg tcccaggcca 156120
gctcaatcac agccttgtca gttttaaatc agcttcacaa catagcatgg ctggtaatga 156180
aacaaaagtg caaaatcctc tgtgttgctg atactggtgg tttgctcttg cacacaaagg 156240
agctaacaca tgtactttct aatctctgtc cctcataaac tagcaaatac caaacaatac 156300
agaaccagag taaagtaaaa tacatacctt gaaatgcttt cttttgtcat aacctttaat 156360
tcattcaacg ctgttgcagc ccagcactgc actgctttac ttgcctttta ctttgccaca 156420
tattttgctg cttggagcaa gtgggagaat aaagtctgtt atgttaactc cctaagtgct 156480
gtctaaaaga ttacatgcaa attctcctct acatattcac tgctttcaca gcttttactc 156540
ctaaagggga ggaattccta atcagtcatg cacatctaag aacacaggtg atgctcctgt 156600
ttctctgaat tcagaacagg gaggaaagga ctgggtctct taacagcact tgcacacaca 156660
ctgacagcat ctcactagaa acatcccttc ccagaaaggt aggatacctt tttcctggca 156720
gagggaagag cgctgactga tagtgagtcc tttctgtatt attccacgtg accaactgtg 156780
gccaggctcc cttttggctc tgcttcccaa atgggaagga acgtagggaa gggccaatgg 156840
caaccaaatt agagggtgag tcttgcattg aggaacacca ttttcccacc gtaagtagca 156900
cagcactggg gcagactgcc cagaaaaaaa ttgaggattt cccattcttc aaagggctgt 156960
agctgaccta atttaccagt gggtctgctc caggcatgag ctggactatg gaaataccca 157020
taaaccagct tgtgtcttgt ttctatcaac atccattcta ccttaccacc tcaatttctc 157080
atcctctctg gcacccttac agcttgacaa gcaggggcag ttagcttgct tgcttgctct 157140
caagcatatt tctttgagac ttggaatctc cctagcttgt actttcccat caatcaatca 157200
```

```
ctcagtggac ctttcttcta ccctgatttt ttgacaactc ctctcattgt actaaagtca 157260
ccacttgttt agtttctggc atttcttcat tgccttgcat aatactgatt tctataactt 157320
ttcagaagac ttgacccgct ctgttcttgt aatcaagctt acagcaaaat gcttggcaca 157380
ccatacagtt tccttccctt cctcctcctt ccttccctgt ccccctagact cttacagata 157440
ttgccactac cttccccttc tcttaccacc aaagagctgc tctgctgtct tctgggacag 157500
cagagtgaca actattgtga catatttatc cctgttgtat tgttttcact ccctccttgc 157560
tcaagctctg ccagtggggc cgtttcagtt cttgcccacc tccatggcat gcaagtactg 157620
cacactaact cagtactctg cagtgcttct ctgaagcgtt tcccagccat ggatgcaatg 157680
agattctttc accaacacaa gaagcaaggt attcaacctt acaccttcaa tggctttgcc 157740
tctgcctatg ctcctaatga tcttcactct gaagcttgac tctcagagtc tcattcagtc 157800
agtaagctcc tgacatttta tgctgatgca tcttactcat agaatcatag aatggcttgg 157860
gttagaagat catctagtcc caagcctcct gccaaccact aaatcaggca ctacatcagg 157920
ctgcccaggg ccccatccag cctggcctcg aacatctcca gatctccagg gatggggcat 157980
ccacagcttc tctggggaga ggttccagca cttcaccacc ttctcagtga aaactttcct 158040
caacatctaa tctaactcta ccttatttta gttttaaaac attccccctt aacctatcac 158100
taccttccca tgtgaaaagt tgatttccct ccttacttac aagcttcttc taggtacttg 158160
aaggctgcta tcaggtctcc cctgatcctt cacttcttca gactgagcaa gccaagcttc 158220
ctcagccgat cttcagagaa gaggtcttcc agttctctaa ccatcttcat ggccctgctc 158280
tggacttgtt ccaaaggtcc acatctttcc tgtgctgggt gcctcagacc tggacacagt 158340
actccagatg gggcctcatt tgggcagaac agagggggga caatcacctc cctctccctg 158400
ctggtcaccc ttcttttgat gcagcccggg atattgttgg cctttcaggc ttcaagagca 158460
cgctgctggc tcatgttaag ttcttcatct gccaggatcc ctaagtcctt ctcagtaggg 158520
ctactctcga tgaattctta tcctagtatg gatacatatc tgggattgtc tcaacacaag 158580
tgcaacacct agcacttggc cttgttgaac ctcattatgt tcacatggac ccaatcctca 158640
agcctgccca ggtcgctatt aaaaaaaaca agtgtcatgg cttcacaagg ctggaaagtt 158700
ggatcaggcc tacaatacct gctaacatcc agaaaccaaa accatgcatt ctggctctgt 158760
aatcatttta ctagatttat ttagtttaaa caacaggcca gttgtcttca caacaacaga 158820
agatcactga aatgagtgag tgacttgttt tactgtcctc tcagtagaca attgtggtgt 158880
aacagttaaa atgagattat gatccacatt gttcctttga aacgcctaaa actaaaacat 158940
aacatgatga acaaggaaga caaaactgta tgagatcttt ttgtgattca ttagaagctt 159000
tgagtaggcg ggaacagtgt tgacatagga gagaaggaaa aggaagtgca aactgtacta 159060
tatttctaaa tttattcact gcataacaca caggcacaga acctgactga ggacaagact 159120
caggtcttct ctctcacggg accacaggta aacatttaaa ccaatttaaa taactttttt 159180
gatgttttta aatggttatc tatagcttgt atgacaatgt aagtatatta aaacacacca 159240
gagttattct gtagtcggga gcataattga tcacaagaag gaaaatcttg tcaggacagt 159300
agctgtctta ctaattaaaa tgttcagttt gataaaggag tctcatactt caggtaaagc 159360
aaaggccatt ttcattctgc cttgtatgag gtcaggccag ggactcagag gagcagagta 159420
aaacagacag atttctatcc tgatgctcat ttggtcaggt tctccaagga gaggaagtca 159480
ctctgttggt acagatttgg tgtagactgg ataacgactg ccagaaaaac tgaagtggtt 159540
```

-continued

```
tggtaaccaa aatcttgata aatatctgtg gacttcagag attgtcctgc aatttctgca 159600
gtgccattca ataaatataa atctttcttt acataataat aactactaca acaacaacat 159660
tttccagtcc ctctatcaga aacaacatc aagaaggcac tactgaacag gtaagttaaa 159720
gtttggaatg ctcatagctt atatgcatag gtatttgcca gtttctgggg aaaataaaat 159780
tgcaagaata taaagaagag attgtagtta gacttcgtga ataaaatggt aacactctaa 159840
aagcaaataa caactttgcc atacattata ttatctgaaa tgggtgacta gccagaaaaa 159900
ttccataagc ctaagagtta cacctaaata cattctcagt atcagctcct aattctatct 159960
agatccaaaa tgaggtagtg aaaagttcaa atgtcccatg tacaaaaaac tacttaaact 160020
tccctaggaa cattactttg ataatgagtt aagaatgaaa atgaacaaaa tatgcagctt 160080
acaaatccac acacttttga aaaccaaagg cagaaagaaa cacaaataaa agggcagatc 160140
tataaaagag gacatatcta taatcataga gaaatatgag atggataaca aaaacctaaa 160200
agaaactgct gctcccagca ggtggcacat ggtatgtgta gaacatataa cgtacaacta 160260
ggctattagt ttcaaaaggt acctacgtgc tccgttgcaa atgtaacatg taaatgtaaa 160320
atgtaaatgc aaatgtaact aatatgcact acatacatca ttttagacac tcaaatacta 160380
caattctgtc tgttgcctct ttccaggctg tagcaatgga acaggtctcg gcatcaattg 160440
gcaactttac agttgatctt ttcaacaagc tgaatgagac caacagggac aaaaacattt 160500
tcttttcccc ttggagcata tcatctgctc tcgccctgac atatctggct gcaaaaggca 160560
gtacagcaag agagatggca gaggtaagta gctctgtgaa gctatgatgc tcaacactgc 160620
ccagcactgc tgttgagatg ccctgctccg ttgtcatagg gaaaaactac atttgagttt 160680
gcacaaatgc attgctattg ctgagtgcaa tggctgtgga agggatttca gccttgtagt 160740
gcacagacag aagcactgtg atgatgctca caggcaggag caatactatt ccttgttact 160800
gtaggggatt tacatatact agagctccag tgtccctctg attagatcag aagatagcac 160860
agtgtgttat cataaggatc caaacaagac aaccatttta tctcttttag gttttaggtc 160920
atgcaaactc tttcatgtca gtttcttacc tttggaaacc ctgtttgcag gttcttcatt 160980
tcactgaagc tgtgcgagct gaaagctctt ctgtggccag accttctcgg gggagaccaa 161040
aaagaagaag aatggtatct attaaacatg aaatcccaag ataagagttc aaatgtctgg 161100
atatagtttt taagagtcca ccatttcttg tttgcagctc tctttatgtt taaagtataa 161160
aacccaatat acttcgcatc acatccaatt tcagttccct tcactcattc agactcaaaa 161220
gtatagaagc acaagtcact ggtataatct gaaaggattg caatatggta aatcagttaa 161280
tcaaatcata aaaggagccc tgcaaactgc agtggtggtg aatttggaaa gataaaaagt 161340
aagagagagg aacagaaatt cttcccccac atctacccct tagcgtttca aaaacttcat 161400
gccaaaaatg caactggtaa atgtacagtt tctctttcca aggaccctga gcatgagcaa 161460
gctgaaaaca tccactctgg attcaaagag ctcctgacag ccttcaacaa acccagaaac 161520
aactactcgc tgagaagtgc caaccgtatc tatgtggaaa aaacctacgc attgctgcct 161580
gtaagttgaa tggttttatg tcaaagaaga aaaagaaaaa aaaagaaaag aaaagaaaag 161640
aaaaaaagaa aaaaaagttt tgcattgtat tcacttacca ttaatagaac agatctgaag 161700
ctgtccataa atgctgcaaa tgatgagtct tggcttccag tgataaactt cattggaaaa 161760
tacaatttgg tcttctccca gtatataaga atgcacttgg ctgtaatgca ggactccttt 161820
tcatgtaata cagctttatc actaggaacc tcagtacata caattgaaaa tgagatatta 161880
aaatacacat atccagggga tttgcacagt cttccttcct tctccaaata aaaatgggaa 161940
```

```
cgagagaata agagtatttc ctttggttat ttcctaacca ttaactcact gctcaataga 162000
gagcaaaatg ctagatcctg caattgcctg tgtgcaaaaa gttaacaaga agtccagtag 162060
ctaacaaatt actttttgga ctataaaaat actgtacaat acagaatgtt tccttctttc 162120
gttctttttg tatgccattt tccagacata tctacagctc agtaagaaat actataaggc 162180
agagccacag aaggttaact ttaagacagc accggaacaa tccagaaagg aaatcaacac 162240
ctgggtggaa aaacaaaccg agagtaagtt gagctcaact ccaacatcct tcctcttccc 162300
actgttccct tcgggaccct gttcccactc ctgtgactgt ggcatccagg tcatgccctc 162360
tggtgtgggc agtagatggc tgtctgcttc cagctgcttg ccttgagact gtggcgtttt 162420
ttcaggcagg agccaattgc tgtcagctag ccaggagaac tgggcaacaa acagcaaaca 162480
gactaactgg tttatgtcag ggaagtaatc cagggagtag ggcactgagg cttgcacttt 162540
ttcactaagg agttgaactg agtggataaa gaatcaacac attccctcac tgtgttacac 162600
tggagtaaag cctgactttt ctgatttcaa aaggtaaaat aaagaatttg ctgagttcgg 162660
atgatgtgaa agccaccact aggttgatct tggtcaatgc catttacttc aaggcagaat 162720
gggaagtgaa atttcaggca gaaaaaacat ctatacaacc cttccgactg agcaaggtaa 162780
gctcctctgg tgtcctcctt aaaacaagca gactggagac tgcacccact accatctttt 162840
atttcatcca tcctttaggc attccttggt aaacagactc tctgaaaagt tgtttacagc 162900
aaaacatgtc agttgtcagc tcaccaacat ttatggaaca ttaagatgct gctcaggcaa 162960
aggataacta gatccagatg gaacacagtt tccaaaaatg ctagggtcaa ttaaagcctt 163020
tttgcaagac tgaggtataa gagctacatt gtaaaaatca gatattaaga gtccatcctt 163080
cctgcacagg aactacatgc tatgctatgg acgagtgcag tacccgcgcc tctgtgctgc 163140
acaatccggc tgtgaataca gctgctaaag tatggatgca gcagcacagc tccactggat 163200
gggtgcatgg ccgagtgaga ctagaagtaa tgttgccaga gaggagatca caaaaaggct 163260
gcacaacatt tatcctctca caccatagct gtttcattgc tgtaatgttg ggtgcctgta 163320
tgccatgaat gctccatccc cctaattctt gaagatattt ctgactccct tcctctctcc 163380
tctgtgggtt gatgtgcatg ttctggggaa aagagaacat cagttagctc agtccccagc 163440
aaaatactct gggaaaagag ccaagatcag caatattgtc cagtcaagaa aagccttgga 163500
aaaagaatgt caaatctctg ttacaaaagc tgcttatgaa agtttcctct ttacaaggaa 163560
ttcctttttt caaggaataa ttttaaccga taaataaata ccttacagaa caagtccaag 163620
cccgtgaaga tgatgtatat gagagataca tttccagttc ttatcatgga aaaaatgaac 163680
ttcaaaatga ttgagcttcc atacgtgaaa cgtgaactca gtatgttcat cctacttcct 163740
gacgacatca aagatggtac tacgggtctt gagcaggtaa aaagttctgc tacatccatt 163800
ctgtatcgcc actcagtcat cagaacaaaa aggacaggct gatgaccata cggccctttc 163860
tttctttggc agttcattcg gcagaagtag cgcacaaaaa cttgcagcat tatgtctcac 163920
atttgctttg cagcctgttc tctggtcatc agtaaaagca atttatattt catattttca 163980
gctgaatgtt aaatacgcca tttaaaaatc tgtttaaatc attaaaaaaa aaaagacaat 164040
cataattaat tggtttatcc ttgcaattat caaattcctc tcatttctta aacaacagct 164100
ggaaagagaa ctcacctacg agaggctgtc agaatgggct gattcaaaga tgatgacaga 164160
aactcttgtg gatctgcacc tgcctaagtt ctcactggag gacagaattg acctccgtga 164220
tactctgaga aacatgggaa tgacaactgc cttcacaacc aatgctgatt tcagagggat 164280
```

gactgataag aaggatttgg ctatttccaa agtcattcac cagtcttttg ttgcagttga 164340
tgagaaaggc actgaggcag ctgctgctac agctgtaatt atatcattca caacttcagt 164400
tatcaatcat gttctgaaat ttaaggttga tcaccctttc cacttcttca tcagacataa 164460
caaatccaaa acaatcctgt tttttggcag attctgctgc ccagtagaat aaattattcc 164520
tcactcctag agggatccaa agttcacttt tcaaaggaaa aaatgtgaac tgtagtatta 164580
aaagctcagc cttcaatcat atagccataa gtactggaag tctatgtctt tttccttaag 164640
taaggcagca cccagacacc accacgcgcc tcgaagactg tctctctact gctcctttcc 164700
attatgctca tgaaattgcc ttttatagaa agcaaatgct tgaggtacaa ttgctagcct 164760
ctgttcacct tgcgttttgt ccttatttct ctaaactctc aagactgagg ttgataagta 164820
tcccaaccag caaaaaagac caagaaaact acaacaatgt gccttattgc tacctcttac 164880
tgaaatgtga cctaaacaat tcaaatctgc ttcccgtttt cattaacata attatatgtt 164940
tcctggctaa catctgcacg gtctccttgc tacctggatc attgataagt gtatgatttg 165000
taacttacga gtgcctttca gctaagatag tcccggtatt gacagaaaca ccagtaacat 165060
ttttatggat gcttcacttc attattttgc catgatctac atttaaacaa taaatgaatt 165120
tggaactgtg tttatgctat gcaagattct gactcacgta gctcttttac agcatcctgt 165180
ataatgggtg gctgacacat atttccattc ttgttatttc aaaccaacca tcacatcacc 165240
gctaacgaca aagtgctgag gcactctaat aaaccagggt cttactccca ctagatttca 165300
tacaacactg aaaacactgt cgttcaacgt gttatcgtag acatatacta gacacaccaa 165360
ttcaaatcaa agcctgtgat aacagagtta aggcatttgc ccagtcttgt tcaacagctt 165420
caccaatagt ctagataaag ggatagagtg aatcctcaac aagtttgctg acaatatgaa 165480
gctgggagga gtggttgata caccagaagg ctgtgctgcc actcactgag acccagacag 165540
gttgtagagt tgggtggata gaaacccaat gagcttctac aagaacaagc atagggtgct 165600
gcagctgggg aggaataact gcatgcatca ctacagatca gaggctagcc tgctggaaaa 165660
aaacctctga agagaataag ctgggtgtct tggtagacaa cagattggcc atgagccaac 165720
agtgtgccca tgtggcccag gtggccaatg gtatcctggg gtgaattaat aagagcgtgg 165780
ccagcaagtt gagagaggtg attctcccca tctactctgc actggtgagg ccacatctgg 165840
agtactatgt ccagttctgg gctcctcagt taaaggaaga cagggaactg ctgaggagag 165900
tccagtggag gactgccaag ttgattaggg acctggagca tctcccatac aaagaaaggt 165960
tgagagaccg cagactattc agctcagaga agaaaagact gaggggtgga tctcatcatt 166020
gtttataaat atctaaagta caggagtcaa atgaatggac ccagactgtt ttcagtggtg 166080
tgcagcacaa gggggcaatg gctaaaaact gcagtgcaga acgttctata caaacatgag 166140
gaagtacttc tttattttga gagtgacaga gcactggaac aggcagccca gagaggttgt 166200
ggagtctcct tctctagaga tatttaagat ctgcctggat gctttcctgt gcaacctgcc 166260
gtagggaact gctttagcag gggttggact ggatgatctc caagaggtcc cttccaactt 166320
ctatgattct gtgatctgaa cttgctttca ctgtaagcat tcagtttccc attgttgacc 166380
actgcttatt gcactatcag cgccccatgg acctactgag aaagctcatt ttcttctgca 166440
ttatgataca caagaaataa aagtctgacc agagcaaata gcccagaaga gtggcttcca 166500
aacatccaat gctgtatcag caacatccat ttcttccatt agcttaggag ggcagtagct 166560
gtgctatctt atgcctataa ggaattggat aaagttttgt agccattatg atgcccacct 166620
accacacgtc acaggacatt atttcaagca acaagatctg aatgctggag ggaagtactt 166680
tagaaatata tactcctagc aaaattccac ctgtaactac agctcactct atgcctcaac 166740
aaaaggtaga ctatttggaa atatatctcc acccaacaaa gtatatatac gccgccttct 166800
ctgtacactg tgctgcttct aaactcagtg ccctccctca cctgtaaccc ccagctcagg 166860
gttcagctgt ctgtcactga ggacccactt tggttcagcc cagctgcatg ctactgactc 166920
agctttgcaa agaattgcac attgtaaatt gtataagtgt ggaaaagcac acaagtgaaa 166980
actacacaat ataagtaaag taaaaacaca aagaagttac tgtcaggatg gaatagtcag 167040
catagcaagg actcgagagg attgcacgta ggggtgtcaa acttcaatta aaaaaaagtt 167100
aagaattgga attctccagc ttgttcaggt ccttctgaat ggcagcaaaa ccctctggtg 167160
tatcatccac ccctccaaat tttgtattgt ctgcaaattt ggtgaaggtg aactctatct 167220
cagcatcctg gtcattaatg aatgtgtaaa tagtactgac actggtgtta accgctggag 167280
tacaccacta gtgacttcac cttcagctgg acttcatacc actgatcaca gctctctggg 167340
cctggctggg ctcacttatc taacccatcg tttgtcagcc tggccataag gatatcacag 167400
gaaaaagtgt taaatgctgt ttctaaagtt aaggcaaaca acatttagta ttctcccctc 167460
atcaaagaga ctagctgcct catggtagaa ggcaatcagg ctggctaagc atgacttccc 167520
cttcatatat caatcctgac tactctcaat ctccttctta ctcttcatga gtttcacagt 167580
agtgtccaac tctgtggtag cctgacctcg cagcaagcag aaatggcaga gagagtacag 167640
aataataaag acaaggaatg ttacagtgct ggtgtatttt tagtactcaa ggcttggatg 167700
cagaaaaaaa ccagcaacaa aacaacctat tttagaacta aaatgcaaat gtaccaatat 167760
tttttaaggt ttttatttca ccatcagtaa ctggaacaag aaaatccctt ttaaaatatt 167820
atttatactc cagtcactta caggtctatt gcaaccactg tgatacttat tctcctttcc 167880
tctcttgtag gacaaggctg aatgggactt cccacggagt aaaaaactgt aactggactt 167940
aatctagcag tgattttaaa ttgtgctgct tgttaaccag gcataaatgc ctagatgtac 168000
caaactatag agtaaactga tcacaggtat aggagtacaa cagcagaata gaaagataca 168060
gcctcacatc cacactgaga aaggtgagga tgaaagatga attcatgaga aagcccgaga 168120
aaagtgactt gctttatcag aaaaatttta tgaccatttg tcagagagca acctatttgt 168180
ggccagcagg ggttttgatg ctgcaacaca ttgtttctac cattctgttt gcagtaagcc 168240
actctttcct cttctccacg tggcacagca aaaccaagag cacctttttct ttcccatgtt 168300
ttctcccctt tgaaactcta ctccctctta ctaaacagga tcttgcagca gataccatag 168360
agtgtccaca cagtttgggc acccttttgt aattttcctg tatttttgcc caatctttgt 168420
agtttgtagt acagtaatta ttgctattaa ctgctttctt acctctccta aatattcagc 168480
ccaacaggta acagcagttt cagatatgta gcaggaacat ttcttaacca cataactaaa 168540
cataatagca ttcgatagat ttctgaagaa agaaaatgag attgatattc caggtaggaa 168600
aaatgtgcac acttagagag agagcatgtg aaaaaagata ggtatacatg tcactcctga 168660
aaccttgtcc tgtgtatgta tcagtcacat tcaaagtgaa tagcaccata aaaatttagt 168720
tctagttcta gatatggttt tgtactcctc atacaaatgc ttttgcacat aggttgactg 168780
catgctgata actggtttac tttccagtgt cataactgtg agcagagggc actcctaagg 168840
caattctgag taaccaaaca tgtactagaa aatatataca atgattgcaa aggaaactga 168900
tcaatgcatt tcatccaagc cacgcagata aaaactggaa ttgctaatta cattggttaa 168960
aataaaatgc ctgtgtacag ataactgtct tgcattatat ctttactgat ctgattccat 169020

-continued ataacatgct acttcgactc tctactacaa aacaacaagc agtttcagta aatcaaataa 169080
ttacaagcag aacttccaag cagcttggca gcttttcgtg agtggcccaa actccctccc 169140
ttcatagaag ataataagct tggcacagtg cagggcctgt aggttatcta aagcatcttc 169200
acctcctctg ctaggaggaa atgcattctc ttaaagcacc acccaccagt tcgaataagt 169260
accatgctca cgtagacttc atcacttgct ttaggtgact gtgggaatac agtctgagtc 169320
tccttgagga tctgactgct gagacataaa aggattaagg gtaaaatatc acaacataag 169380
ggctttgtgt gacctgacaa ccacaagtat tcaaatcttt ccactctgaa atttgacagc 169440
aggatgaatg acactaacag cctacttctg tactcctttt cagctaaatc tttgagatta 169500
gtttctctta attccctagt tcatagagta aaaagaaaag gaaactgtaa aattatttca 169560
acgtgtccct tgtcaatgca ctgcaactct attcttttct gcaattccta catacttgca 169620
gacaaagatt gaggagggca ccactgggaa aaaggcatac caggcttcat gtttcaggac 169680
acacaccaac taacagtggt tttgaattgg cctctctacc ctcatctctc taattctgaa 169740
agccagtgac ggagagaaga aatgggaata aatgagggaa caggcatatt aatacaagaa 169800
gaggatgttg ggaagagaag ggaggtgcaa ccatttctac atttccaaaa gtattcgttg 169860
cctcacagac cgccacagat cctgactgaa gaaacatctt aactcttccc tctctcacag 169920
gatttcaggt agtgtaaata ttcttatcta aataaccagc tttattttga cagtcttaaa 169980
aattcatata aattttccag aatggagagg gtaaatggta acttaaatgt catgcaggga 170040
aatggagcac tcaagtcttc atacaaactg cagcctttag gaaaacactg cacaaagggc 170100
acagtgttca ggatgcacat ccagactggg caaaacctgt gcagcacata gagagcacaa 170160
gagtttcctc acttgcaggc agggtgccct aatcaccagg ctaccagctg atttaggatc 170220
agaggactga acacagaacg cagatgataa tgcactccta ctgatcctgg agttgaacac 170280
acgtgactgc atgactccat aacacagtgt tttagacaat cagcactgtc caagccactg 170340
ctttattcgt gttaaataac tactggatca gcacccagcc ttttcctttc ctgaatgacc 170400
aaagtggcta ttagacaggc agtgctgata caaacacaca tgctctctca agccctagaa 170460
atgcttgatt gctgtgtgca aattcagttt tgacacgctc tggcaatagt ggagatacta 170520
gtttgaaatt ctttaagcaa aaacattcag ctgagcccag ttctctagtt atgctctggg 170580
agtatctggc tgatcagctc ctccaggcac agcagtaaga aataccaggc ttaaggtaaa 170640
atgcttaagg tatgagctag gctgcagggc attcacctct gaagcacacc tgagaatgat 170700
ccaaagctgt tttggagcac tgggaagctt tgatatccaa atttaagaat cccaaaagct 170760
ccagctatct ctaagactga acagcagctg gttttgagga ctgctgcttt tgatttcagc 170820
atgcaaattg tgagtgaagc tggactgaaa attccactca ttctcattga cctaaggcaa 170880
gtctttcact tgatgcaatc ctgcaccgac aatggaaatt tctgcattta tcctaatatt 170940
tgtcaacagt actaaattca tctaaaatat gttagttaga accacgaacc tattctggat 171000
ccagctatga aaaattactt taaccctggg gtttctatgt ttttgttatt atctttgatt 171060
ttgtcccata aagagggaag cagaaagaga atgggaaatc tgcaggttct gataaaccag 171120
cacgaaagta gaacagagct gttgcttaaa atgggaactg tttggagttg tatgtaagac 171180
acaagagctt acttgaaaaa cagtcattaa caaatccagc tacagttgac aaatgcaggc 171240
ctacgctcac aaagatcaaa taacaatcta cagatctcca tcagccttct aaagcatgtg 171300
gcaaatggca tgaattcgca atagttcttt cagcagaaaa taatgcagtt taaggaagta 171360
ggaataaaag ctcagcgcag cacagtggga aatatttcta tttcgctccc tcagaatgga 171420
aggataattc taagaaactt aagtaaatgc tttttaagaa caagtttggt ttgggaaaac 171480
gttcctaaaa tagtgtttgt ctgatgatga ataagcgaaa cggctgaaac aagaatataa 171540
gcatttaaca gtgatgggaa agggagaaat agcgtaggtc ttaaaaaggg acttgctatc 171600
tgactgtacg tggcgttttg gccattacag agccatccca tcagcgtgtg tacaagggtg 171660
caggcaatct cctaccagca acttcccatt ttgttagatg ttgtgaagat gcagtcatca 171720
cctccctctg ctaatcattc gtctcaggct gtattgatgg agtgtctttc agcatcaacc 171780
aacagcttca ccctggacct ttacaaaaag ctggatgtaa cttccaaagg acaaaacatt 171840
ttctttgctc cttggagtat tgcaactgct ctcgctatgg tctatctggg tgcaaaaggt 171900
gacacagcaa cccagatggc taaggtaagt tctgaactta gcagtgtatc acttaaagct 171960
ggctcccacg tgacttgcat tattcacctg cctacgtgga acaaaaagga gcaacatgag 172020
agaacagtga tccgccatca tgttgggtgc aagaaaaaac actgcatgca gtcctgcagg 172080
acactgttgt tccaacttat ttccaagagc cccttctct gctaccacct ctacctttag 172140
cttaaaattg ttctggcaga gtgaagctat ggacattaga gactgtcttc tcattctcca 172200
cacccagtta gtaagtcctc tgaacccaag cttggctgca cagcagcagc agcaacatct 172260
ttgcttgtga catggttagt ccataaataa ggtaatacac ccatgaagaa gggaaggttt 172320
agattggatg tcaggcggaa gtttttcaca gagaatggtg aggtgctgga acaggctgcc 172380
cacagaggct gtggatgccc cttccctgga ggtgttcaag gccaggttgg atgtggccct 172440
gggcagcccg gtctagtatt aaatgtggag gttggtggcc ctgcctatgg aaagggattg 172500
gagcttcatg atccttgggg tcccttccaa cccaagccac tctacgattc tatgaataat 172560
ggggatatac tagaaatgaa aatatgatat catttataac cacttttgca aaactttcgg 172620
tgatgtactc ctagattata tgcatttaca taaatgcatt tatctgtgta atgtactgta 172680
gagttgtaca ttggtgcctc aatagtaaga ctacaaacca tcctatgttg tttgttctgc 172740
ctgataacaa tctgaaaata aattccacat tgctaagcat gaattgacca tttctccaaa 172800
tcaatccatg tctgagcaat cacattgatc tgttattaag tagtaaatga ctaaaattaa 172860
tataactatg atacggttat agaatctaaa tctagaccga ggtcttgttc tctataactt 172920
taatagacta acatttgtac gatggctaaa ttatcctaag tagaaaacta acatcattac 172980
gtaacactag agcacttcta tcttcacaaa acaaactgtc cttaagaaaa tttatcactg 173040
ccacaggttc ttcattttaa ccagactgca agagaagaaa gtccttctga gatgacagca 173100
ccttctctgc ggagcccaaa gagaagagac atggtattta ttttgacaag gctcacagaa 173160
acaaatctcg gagaatggga cagcacaact gccttaaccc tctgaaattt gtctgtctat 173220
acctactgtc ctattgcagt aagaactata cataaaaaat gtgaacaagc aggtaatatt 173280
actgtaaaac tcacgaactc agaacttcaa agcagaacag agacaccaga agcattctga 173340
ttgtctttta cactttgtta cttgctttta gctgctctat ggcaatagga atacctaata 173400
ttttactaac ttcaggattt tttttttttt ctgggctgta aaacagccat tgccttcaca 173460
tctgactcca gtcctgctct cttaaactct gttccacctt tgctatgcat gcacacatca 173520
ggcaaacaaa attcccctgt aagctaacac acactgattc acccttgctc atcagctccc 173580
cagagacttg acagcaggag gaactgcaca gaactcctta cgcctcaaag gtctgtcaac 173640
tcaaacaagc tgcaattctt tagcacagaa actaagaaag ctcaaagaaa ccaagttaga 173700
aaaactggaa ataaaaagga gcagttacat cattctccat ctagatggcc gtggattaat 173760

-continued atttaagata aatcattatg tccacattga ttttagctat tcactgcctt tctaagttgc 173820
acagcaaggt ctgcctgatg tagccttcca gacatttctc tccattacct cttcactatg 173880
tacccattgc cttgcaaaac ctatctacta tcctgttctc taccaagttc ttccccacat 173940
gtcctttctg aaagcctgta cctctgcctg tgtgaaaaaa taccagagga aggaatgcct 174000
cctcaccaat cttatgacaa gcccccatgc atcagcagca aagaatctcg gtgtctcaca 174060
tgtagcgcat ggtacatgcc atggagcagg aaattatact gaagcagctt atccctacac 174120
tacgaaagca acagctgaca agcaagctcc tgctccctaa aaccatcacc aaggacattc 174180
tggacaggtt ccttccaaca tccaagcagt aacagcaaaa ttcacatcaa atagaaaatt 174240
cgaatcaact caattacatg acatcagtat ctgtctgaac agagtagctc ctcaaaagct 174300
gcaatgttgc cttaatgatt tttgtgataa tcaaaattag gcttgactgt gactggaatg 174360
agatgaccca atatcctggg tgcaccatct gaggacagct gatgtcctca aaggtgtaag 174420
cagctccgca gaatcaaatc ataaccccac agacataaaa caatgtatcc agttacacac 174480
agtgctgcaa aagtaccaga tacccgaaga agagctccat ccctgcacac actttttaaa 174540
ttaaaatgac ctggggattt taaataacca tagaaagtgt aatgcttcag ccaaaaatat 174600
ttcaatacta attggtgcct ctttccaagg gtcttgagta tgaggaaact gaaaacatcc 174660
actccggctt caaagaactc ctgtctgcca tcagcaaacc tagaaacact tacttgctga 174720
aaagtgctaa ccaactgttt gaggacaaaa cctacccatt actgcctgtg agttgaacgt 174780
ttctgcttaa gaatgttttg acaaagagta tttgacgtac atatttgaca atcataattt 174840
tccaaatgtt ctgcctttta aatctactgc agcctttaaa actgtaagag ttctacagtt 174900
gaactacaga aagctcctgt ctcttttgag cctatttctt gttagcatca ctgttggttc 174960
acttctcctc taaaggaagc ttctccatat cagtggtcat cttcctcccc cttctcacta 175020
tctattacat tctagcattt ctgagattgg aggccagagc tatatagaaa agtcacacca 175080
tacctttaca gagcggcata ttaacgttct cccttttatt acactgtcat ttccttcaac 175140
ttttcacatc atatttgctt gtttgactat tactgggcag attatttttt tttttcatgc 175200
aactgtccat tagaacttca atacctcttt tctaaagcaa taatcatcct tattagtatg 175260
ctttgctgga tcattttcag atgtttcaat attgatactg taatctattt ccttcttctc 175320
ttagtttcta gccttttaaa caagatcttt ctctgtagtc ccacggatac tcagcttctt 175380
caaaagcctt tggtgagaag tcttccaaaa tgccttttgg caatcctaat tggctgtagt 175440
ggtttgacct tctcatttgc aagcttcttt acaccttcaa aaacctccaa aagattcatg 175500
atgtaggact tattgttaca aaatgctgtt ccaacacatc atgcttacct acgtgcccag 175560
taggcctgct tatccatttg ccctgtacag actcatgagc ttgtaattct gtgtatcttt 175620
gaaatctttt taagaaatgg cactgtatta atcatcctcc agtttcttgg aaggtgctgt 175680
taaatgaggt tagcgttctt tcatcttgga gttaagtttc agtctcctga gtaatttctc 175740
agtcattaaa ttcaatcagc cttactgaat gcttgttgct catgttctgc ataattttgt 175800
gtaaccgtgg tttaagacta atcagggaat ttcctgccgg gaatctccat gaacagtttc 175860
atagaagaca gtaatgtaaa agtcagttct agtttattct accataacat tcccttcata 175920
tctgaccctc tactgacctc acaaactctt ggcagcttga ctctgaagca aatcttaaaa 175980
cattgtttca actgtccttg aagctattct ttcttcttgt actgaactct gtcataaaac 176040
ataaaaatgt acttcaagtc agtctgagaa atcaaaaata atttaaaaaa atgtgtagaa 176100
tgtttatctc ataggatttc aaaattacaa atttgcatgt tggatttaaa acacaaaact 176160

-continued ttcaagcatc attttttgtg aaacacaaat actgaatttt tgatcagtcc ttgcttatta 176220
tttaacacag aatcataatc acagaatcat agaatggcct gggttgaaaa ggaccacaat 176280
gatcatcgag tttcaacccc tctgctatat gcagggtcaa caaccagcag accaggctgc 176340
ccagagccac atccagcctg gcctggaatg cctccaggga tgggcatcca caacctcctt 176400
gggcaacctg ttccagtgtg tcaccaccct ctgtgtgaaa aacttcctcc taatatctaa 176460
cctaaacctc ccctgtctca gtttaaaaac cattcccccct tgtcctatca ctgtccaccc 176520
tcataaacag tcattccccc tccagtttat acactccttt caaatattgg aaggccacaa 176580
tgaggtctcc ctggagcttt ctcttctcca agctaaacaa gtccagtccc ctcaaccctt 176640
cttcatagga gaggtgctcc agccctctga tcatcttagc agccatcatc acagaatgta 176700
tcagaatttg ttttacgggt tatctagttt caaatgaatt acattttctt ccagtatgta 176760
ttagtatgta ttgcatgatc tgttgagatg atctttttct actatttttg tgcttaaatt 176820
taactatata agcatacatt ttccaattct atccttcaga aatttttaca actgatcaca 176880
aggtactacc aagcaaagcc acaagctgta aactttaaga cagatgcgga acaagccaga 176940
gcacagatca attcctgggt tgaaaacgaa actgagagta agtatcgctc tgatggcttt 177000
ttcttttctc acttcaaaat catttgcatt tccacttgaa ttgctcttgc agtaagggat 177060
ccataaagga tggaaactgt ggggaaatga tgaacaaatt gcagttaaat gtcttgaaga 177120
aagccaacca ccaaaactaa ctgctgcccc ttgcaaagtt tttcccttga tttttcatgt 177180
catagtctct tctgaagtat ttctgttcat aaggaagcag agtggatact acatggctcc 177240
actctgatca gtgaaggttt tacttctgca agcttcaact ggttgcagcc aactccagag 177300
aacttccacg ctttacacac ttcttaacat cttttactac taaaactgaa ataaatatgg 177360
tttaaaaaac agtgatgctt caaaagccat ttatgtatgt acgctgtgaa aaatgcacag 177420
ggaaaaaaaa tctctgagtg taaacacttt tgttagatag ctaggcatag agaaagcaca 177480
tctgaaattg gtgagttgtg cattcgcagc gaattaacag tcctatctat ttgattttta 177540
agggaagatc cagaatctgc tacctgcagg atctcttgat tctgacactg tattggtctt 177600
agtaaatgct atttacttca aaggaaactg ggaaaagagg tttctggaaa aagacacatc 177660
cgagatgccc ttcagattaa gcaaggtaaa ttccttcaaa atgtctatta tggcagagca 177720
agaatcctct aaatatttca cctgcatttc acatcccagt acaacactac ttacagcagt 177780
agcagatggt ataaactctg agaacagcaa cagtgaaaat aaatcagcag tctcatttat 177840
acagatgcat gagattagga ttttcagtta agttagtagc ttcttggcac caaaacagtt 177900
gaaaacacca tggttaagca gcttaaggac aagagaaagt ttctctaagt actgagatat 177960
cattttcaga aggaattgag ctaattctga gagcagtact tcgacaccta ggtctctttt 178020
catgcttttc agacagaggc tgtataatgt gagctcaagt agcctaagtg ttctttccta 178080
atgccctggc cattgcgtaa aacctcacgt ggaattctca agagggtttg tcattttagc 178140
cagatgcgta tggatgatgt gttcagcatg cattgtgggc acgactgagc ttacagtatc 178200
tcagtgattg tgcatggaca atttacagta gctgacagca tgcatacttt cggcttgtgt 178260
caaaggtgag caaaaagaat tttcattcag aacacgttgt ttgacatgag attacgagtg 178320
caaacacctt ttgtatgtct ggtgatgtga agcaattgtg tcgatactgt ggctgtgtta 178380
tctgaaacct actacattgc atgcgcagtt ttaggacctg taatagtaca cggtgcacag 178440
aaagggtttc attcacagag tggctgatag caaagcctgc aaacagataa gcttttgcac 178500

-continued ttgtgtaaca atggaaaaga gagagtggat atatcagtga aggtctctga gcataataca 178560
gcgtaagagt tcagatgatt actgtctaac gcgatttcag ttggtaatcc aaacctctac 178620
agtttgggaa agagaaaaaa caagcagagg tcacagcaaa tatggtccat aggtaaattc 178680
aatcaatcag tgctgtccgg aagcatacaa aagagttgat gacatccaga gaatgaaagt 178740
cagcattttt ttcccctccc aatcaacaca ttcactcaag aaatgtaaag ttttggggaa 178800
aacttgaaac atacaaagta gtttcttgtt taccaaagct aactctttca aaagagtgag 178860
aaatacattg catgtaatta tgttatcagg tggtgtctgt gctttttttt tctttttttt 178920
cttttcttct gaagatccct ttgactttga aacaggagaa atggcactgg gaaagaataa 178980
tgccaagtct tatacttgtt tacaattttt ttttgccttc agttcaacaa agcaagtaat 179040
ctttaccatt caccttaagg aataagtaca actaatcttt ttcttttctg ttcttttta 179100 acatctgaat catttcacag accaagacta aagcagtaca gatgatgttt ctcagagata 179160
catttttgat gctccatgaa caaacaatga aattcaaaat tattgagctg ccgtacgcgg 179220
aaaatgaact cagcatgttc gtactcctac cagatgacat cagtgataac actactggtc 179280
tggagctggt aaaactgaca tactgcatca cacgcactac aaagcactaa cagaaataga 179340
tgaaaacagt gaggaagaat gaacttcaaa tgacacaatg actgctcagc ctaggtttca 179400
gggcatctat taatgatgca aaaatacaaa tctacctgag gatacaccta aaaaagtatg 179460
cccactctac tctcttagcc tattcggtgc ctccttttct acctccagaa tagcagaata 179520
acgaaagcaa gaatcaaatc taaaccactg tgccccagaa ttaatcttct gagggcaaca 179580
ctaaccagtt ttatgtcatc cgcagtccag atttccacct gatactttgt aacgaggctt 179640
ttcaaactcg gggctgactt accttgaccc atgaggtatc agcagccact catgaccgtg 179700
ccaggattag ttcctgaatc taaatacatc agagcttcag aatctaaata catcagggca 179760
aatatctttt tatttgctct tgaggtccca tgcattccac ttacttacca ctactaagag 179820
aaatgcctta caaattcaca cataccaagc acttattaat gtggttaagt tggacactgc 179880
ataaaagcaa cacttctcat atccacctcc aaaataatga attattctga aggttcactc 179940
tacacctcac tgcatttaag gaaacagata gaagtacagg tcactcagca ctatgcagga 180000
tcacatccta agaatatgca gcacatttca gctgtactca cagctggtag ttggaccttt 180060
taaatctaga gcattagaca ccaatgtatg catgccttct tttttctgtt gcattatgac 180120
tatattctta taaaattcat tgcaggtaga aagagagctg acccacgaaa aattagctga 180180
atggtccaac tcagcccgta tgatgaaagt cgaagtggaa ctgtacctgc ccaagttgaa 180240
gattgaagaa aattatgatc ttacatccac tttgagcaac atggggatac aaaatgcttt 180300
tgaccctgtt caggctgatt tcacaaggat gtcagcaaag aaggacttct tcctatcaaa 180360
agttattcac aaagcttttg tggaggtcaa tgaagaaggt accgaggcag cagctgccac 180420
aggtgtcctg gtgttgaggt caagaacacc tagagtaact ttcaaagccg accacccttt 180480
tctcttcttc atcagacaca acaaatccaa aaccatcctc ttctttggca gactatgctc 180540
accttagtca gagtcactcc ctgctctaca gagcaggaga tgctggcttg ccagctcaag 180600
ggcagagctt gatactcctg ctgcagctga gggactaaga cctgcactct ttcagactac 180660
acattccaca gcccaaggca aagcttcaac tactccagat agccatagca gtgcctgtag 180720
atgcatttga ttccttcctc ttgcagcagt agatacaaac acatggcact atcttcgttc 180780
tcacaagtag agcacctgat tcaggtgtgc atcttcaccc ttccaccctg ccataattag 180840
cccctgctcc tctgtagctc ttgactagtt ctttttgtta cagaggcaca cacagcccaa 180900

-continued gcttaagtct ttaccagttc acttccattc tactgattgc ctgaaagaca taacaagcac 180960
acactcccac gtgggctatt tcctcgcacg gagttacagg tgtgacagaa gagcctgacc 181020
catgctgctg actttataca aagcagcacc tgcttcaaaa atagcagtac tgataataaa 181080
caacccctcg tagcttgatg gtgctttctg tcagctctac caggagggga aggcagaagg 181140
ggaaatcaag cagcgacaag aggctcgcgg aggtagcgac ctccgagcta aaatggccgc 181200
ctcccactgc tgcagcgagt gctcagggcc gctttccgca gctgagctcc agccctctcc 181260
cccacgatgg gcggcccgtg gctaggcaaa aacttccggg aggagggcgg ggcagaggcc 181320
aggggaaagc tggtgctcgg ctgggtgagt gtggagggtc tgtgttgttg ttttctgcgg 181380
gaaacacgca ttggtttttt gaggggagac ggtagcgttt ccctcgcggc ggcgctctga 181440
gcggtttcgg cgggcgcggc cgccgggcgt tgaccgggtg ctggaggcgg gaggggcccc 181500
gcagagttcc gcaccgctgg aatccatccc tgtcatccag ccctgcctct gtgggttttg 181560
tggcaaacag gcggaaatcg atggagaggt gcgagcttca gcctgttctg agtcacaggg 181620
agagagcttg gccaattgtc ctgcgcccag ccttattgga gctgtaaggt gcacgggatt 181680
aaatcgctcc tgcttcaggc agaatggaag gactgtttca gtccaagttt tcttttcatc 181740
agtgttttta tggctatggg cagaaggaaa catgagtaca gctgcagctg ttgaacgtag 181800
ccaagctcct accaagaatt tgtcttagag gaaacatgcc tgaggaaact tgctgctacc 181860
gcttgtttga gatgatgaat cattaataca aagtaggcgt tggctctgta ttttctagca 181920
acgtaccaac accaggcact gccttagggg aaaaaaaaca aaccaccttt actactagtt 181980
gatatcctgc gatgtctgct ggcacttatc tgtaacttac tccacgttct ggcactcgtt 182040
gctccttcct gtaggtatgt agtataactt cggattagtt agctacctgc tcggctgacg 182100
tatgtgaagt ctgacaagca ctgagctacg tatgtgccat gaagttccca ataaaccgtt 182160
tactttattg cgtctgtttc catcgtgtag acaataaaag gcaaactgca gtggactttg 182220
attttgtacc acagcaggaa accccagtaa tctgtaatgc tgaccagata aatttcgttt 182280
gaatattgta gatcgagtca ttcagttgga ttctggcaga ctgactgcta ggtctagaac 182340
acaagtgaag taatcttgaa gggaatactg aagacacaca gactttgaga aggtgagttt 182400
ataattctgc cattctgata cctttctgct ttggttttcc tgtaaagcaa ataactgtct 182460
ctgtggagcc aaaggagact tattctacca agtcctagta tgctcatctc aaaaaatata 182520
gtattattta ctccatgaag aagaccaatg actttttcctc actacaagaa agacattgag 182580
gtcttggagt gtttccagag aagggcaaga aagccgtgaa gggtctggag cacaagtctt 182640
actattgagt ggctgagggg gctgggattg tacagcctga agaagaggag gctcagagga 182700
gactttatca ctctgtacag tgacctgaaa ggaggttgta gttggcctct tttcctgggt 182760
aacagcaata ggatgagagg ggatggtctc aagttgtgtc aaaggaggtt cagatgggat 182820
attatgaaca atttattttc cgagtggtga ggcactggca cagactgccc aggaaggtgg 182880
tggagtcacg tctctggagg catttaagaa acatgtaaat atggcactga gggatgtggg 182940
ttagtggaca tggtgggaat gggttgacag ttgtactaga tgatcttata tttgctttat 183000
ggtttatatt gagaaatgta aaagacagaa ataggttgtc agtttgtgat caaataaatt 183060
taagccaatc ttcatttttt tttttctcct aggctttgaa ccatggatag cctcagtgca 183120
gcaaattcca cttttgctct tgacctttta aatgagctgc gtgagaaaag cagcacaaag 183180
aatctattct tttctccttt tagtatttct tctgctttgt ctatgatttt actgggttca 183240

-continued

```
aaaggggaca ctgaagccca gatagcaaag gtatgtatcc aaacgtaatg tattggattt 183300
gatgcatata tcatctactt aatgatatat gaactacaga tctgagatct gtattacagt 183360
ctgtgacctc taattgctga attgttacag tcattctggc ctcagaggtc agaagtcttc 183420
cttaggtatg tacataagca gaacctattt ctattgagtt tatgtatagg acttactgca 183480
gtgtgaaatt aagagattcc tgttttttgg ggtgtgtgtg ggtttttgtt tgtgatacgg 183540
agatcttcct tttatatgtc attaacaggc acctggaatt tctttttttt tttacttaca 183600
tatttgtata tttagagcta tagatgaatc tccagttaca taaaataatt tactctgtaa 183660
tctttttggg cttaatatca gactttgcat acttcaaaaa tgtagccaga taatcaaggg 183720
aaaaaaaatc caacatacaa gcatgtcatg ttaaacagtc ccagatttta ggaaacaaac 183780
aaaaaaatga tcagttgctt gttcagtgta atagcttttg ttttcacaac ctgtaatctc 183840
aatcctggaa catccagaag aaagaagtga tacagggcta agaacatagc tctgaagttc 183900
cagagaatac cccagcaaag attcaatggg gcaaagctgc gtggccagtg aagagtaaaa 183960
ttcataatgt aaacttgcaa ttaaattacc aggagagcag ttaaggagtg cagtggtggg 184020
cctgttgtgt gacagtaggg tcaaatctat cattaactgc agtgcagttt attctacgtt 184080
cactaaggtg cgtgcctgcc tctctctttc tggtattgta atttggagta gatcatcaat 184140
actttttcat ttgtagctat ggtagtagtg atgaggctga atgaggatga agctgatgtg 184200
ttgttttaat gggaatttaa atatttgctt gtgttgacat cggctccagc agcctatttc 184260
ctgttatcgc ttgaaggatc gggtttgcat ctaaggtatt aaataagatg ctttggtgct 184320
attataatca gtgtgaaaaa ttatggaaag ttgttttttt ttatttaatc ttcaggctcc 184380
tttgtttctg gattttaaca gttttgctag gttttatagg gtggagatta taaatcctca 184440
gttctctaag aagtactgtg tacagcatta agaaaagggc agaatgtgtc tgcactcaga 184500
cttctttgga ggctggatgg gttccttaga aagcagggag ataaaccagg taacctccat 184560
agcttccttc caacctcaac cattgtgtga tcctctaatg cttggacaaa atgaagataa 184620
ataccactca cttttcagca acgtaatttc ttgcttatac aacatctgtg tggatacatt 184680
gtacgtgact tgtgtaatga aaaatctgct ggcttcaagt ctcaaaactc atttaaaaac 184740
agaacaattg tgctgatgca agtgtgtcag agattacgtg gactccacag aaggtatttg 184800
tctctctgca ggtgctttct ttgaacaaag ctgaggatgc tcacaatggg tatcagtcgc 184860
ttctctctga aattaacaac cctgacacca aatacatcct cagaactgct aaccgacttt 184920
atggagaaaa gacatttgag tttctctcag taagtaaaca ttaaatttgg gtgttgtgaa 184980
gtataatgta cttgctagct attccccttg aaggttagat aaaggctttg ggttttactc 185040
tccaaatttt tctaggctga gacttacaac ctgagagtct atgcaaaaag caggatgtga 185100
acagaatgga gaagctactt ttagattata tgaatgcaca actggtgcaa gaccatgaaa 185160
aaaaactaaa tcttctaggt ttcttggtcc acttttggtg ggttctagga tcaaatgaat 185220
gacaaatctc cttgcctttg ataacctgta gctatgatga aaacaactgt tactgctgtc 185280
cagcatgggc agaacttttc ttttttctta attaaacaat ccagagaaca tgctgagagg 185340
agtatgtgac tcttaatatt ttccttataa gtatatatac acaagagggc acaggtacgt 185400
tgcatataca ttacatatac attataacat tgtatgttct ctcactcaag caaaaagaac 185460
aaacggaaga aacaaaaaga aacaacccag acaatcattt ctcagttgag tactgtagaa 185520
tgttctggtg tattaaagaa gacatttgac ttcttaataa caaagaggaa gataattcct 185580
agctcagatg gctaataaaa caactgataa gaacatgtca gacaaaacct gaatggcttt 185640
```

-continued atatcaagct gggggaagag aggatataga tttttctcag tgtacttaaa aacatctgtg 185700
gctgaatgtc agtaaaatgc attgctaaaa agctgtttta aatgttcatg gcagtcattt 185760
atagaatcga gtcagaaatt ctaccatgct gggctagaac agactgactt caaaaatgct 185820
tcagaggatt ccagaaagca aataaatggc tgggtggaag agaagactga aggtgagtgt 185880
tctgcagaac tccctgctgt atgtaatgtc agccaggact tgcataaaca gctctgtcaa 185940
ggtgtaatac tgtcattttt aaagcaaaca caaacctcag ccattgtgct ctgtctctgg 186000
ttggggcata attcccatat ctgatctatc gttaatacat attagatact ctgtattgca 186060
acagttgctt acgtaccact gttcaatttg tgttttctaa aggtaaaatt caaaaattgt 186120
tggcagaggg aattattaac tcaatgacca aacttgtgtt ggtgaatgcc atctacttca 186180
aaggcaactg ggaagagaag tttgacaaag agcgcacaaa agaaatgcca tttaaaatta 186240
acaaggtacg ctacgttaat atgctgacaa tacaaaggtc tttgtaatac agaagacaaa 186300
aattgttcaa gcagatttac ctaaggtagt ctgcatggag ctccctatgc cctgtcccct 186360
tagtatgaac actctctttg tttagtttct gttaagtttc acataattac taaaaacttt 186420
aatatcacat atttatttta tactctctct ttttttcct ttactctttt tgtttgtgtt 186480
tcagttggtg aacttgacta tgtcagtgta aaatctgcat gggcaaaaaa cattcatagg 186540
ttccaggcag aaaagaactt ccgtgtgtgc agaaatgtct gaatatagca gtcatcttca 186600
gtcagaatgc ttttctttct gctgtgtttc taccactaaa ttgatagaaa tgaaatgagg 186660
tgaagaaaaa aaaaaccact ctcctttgaa ggcctccatg cttgactttc ttttgcttct 186720
aaaagtgcag cagggcaatc gaggaggact ttatgtacta tcattaatag gctacggctg 186780 cccttagag gtcaatttca aactctggat gtccacccag gtgtcgtgag agtgaactgc 186840
taatgtgaat tgcttaagaa ctcacctgct taaaataacc acaatgcaaa attgaagctc 186900
tagtgcctaa tttcaaactt cagtgttgaa atatatacag gaatgcttga aactgctaat 186960
accacttttc aaacagggaa taataatatt gctcttgcca tactgtatgc tatagcactt 187020
agaaaccact gcactgactt ggttcctgtt aggaagggag gtttttatc agtttcccac 187080 agagatgtca cacaaaaccc aagcttacat tctgcttaga gtttttcct ctccctcctc 187140 aggaggcaaa tccagtgctg tttctctggg tacgaggctc agcctagttc tgagattacc 187200
ctttcctttg cagacacaca tttatttttg aagactgcag tttttgggat gcagatggct 187260
attggaacaa gttgtaagat gtgagactgg ggaatgctgc cttggctcat caagtaacac 187320
gctgttagat gtgcaaccac aaacctcttc ccttacaaaa ctaagtggct taaatttcta 187380
ttttcatcct attgatgact agtcactgat gagctacaga agtcaatgag taggctcaaa 187440
taagcaatga aaaatccaaa gggcaaagct gaagttttaa gctagttatt ttacagtctg 187500
tccaggagta gttacttaaa cataccagta gtcttctgag cattctgtga catctatttt 187560
atctgtgact tttgcacttt gttgtgactc actggatgat tctagcatgc agtgtgggct 187620
tttctttgct tatccatcat tttcatgtgt cactgattgc tgttgcaaaa tcatttccga 187680
catattctgt tctcagagtt catggcagtc atttatagaa ttgagtcaga aattcactgt 187740
ctcaatggtc tttcctttaa aaagaaaaaa cggtgaaggt aaggggaaga agggatttag 187800
actccacaga aaaggaggaa aataatgtag acaaaagtaa ctgatgctcc atgcaaaaat 187860
ggagagagat gggggagaaa ctggtagtaa gaagacaaaa gattaacctc tccatgtgcc 187920
ttttaacaat tcaaagtgat gctaatactt tcctagcatt tttagtggct tagtaaaata 187980

-continued

```
tttttgttgc cctacgtcag agtaattaga gacacatgga gtgaaatgaa aatatcgaag 188040
ttgaagttat tttgtattta tttaaagcaa ggaatacagg ctctgcttat taccaacttt 188100
gtttagagct tgtcactact tctaaagtga gcaaatatgt attcttgctc ctttacccta 188160
aagcaaattt cacagatatc tccaattaac aattaaatct cagggatcct tacttctcat 188220
ctcttgcttt acgaaagagt gactgtgcta tactatgtta tgcagtgtac ttagttctct 188280
gtgcagtcaa atagtaaaaa gccctaagta actagatgcc tgcttcatgt attaggactg 188340
tcatgccagc ccagtagtaa ctcttagtgt ctctttcatt ttagaatgaa accaaacctg 188400
tgcagatgat gttcagaaaa ggtaaataca acatgaccta tattggagac ttggagacca 188460
aaatccttga gatcccttac attggtaatg aactcagtat gatcgttcta ctccctgatg 188520
caatccagga tgaatctact ggcttggaaa aggtaagtta ttgagctcag tgcaaagaca 188580
gtttgtgtcc tgccttggaa gagagtttgg tgctgcacat ggattcacag ttcagtttca 188640
gagctattat atcattgatg ctcaagactg actgaaatgc tccttgtgtt tctgccccta 188700
aagtggcatg ccatctatta ctactggcca agctatgtgc tgctgtgcta agaggctctg 188760
aaagaggcct catcagaagc tgtagttatg gtgaagccat agtatgatga gcaccaaatg 188820
agagggaatt tggggcagct cttaggaagt ccttaccaga atttctacag tttgtcccat 188880
aggtcatctt agtgaagacc tggcagattg tcactgcccc tctacttgga aacacgctca 188940
cagaatagtc caggttccct tccgttgtga tgatagaata caagtcatgc tctggcctct 189000
tgtttttttt tctaatgctg attttaattt aaaaagtgtt gtaagcaggt tttgtcacca 189060
gcccgtgagc tgaaagatcc tgaaaggctg aagaactggg ttcagtttgt ttggggcctt 189120
gtcagcagtt ctcccgtgcc tttactccct atatataaaa taaggttttt acaatctgat 189180
aatgttttat aaactgaact ttactgtatc taccacgaaa aagaaaacac caaacaagaa 189240
ttgacctcag ctgaagctgt agtctctagt aagtagaaac ctgtagtgac ttgtgctttt 189300
gacttgggat cctgtaagct cctgaaaaag atgcatattg catgtatgtg tttacataac 189360
acacatacac agacaaaagt agagattagt gcaaaactgt cactattctt attttaatta 189420
cctaatgttg ggttatgttt cgttgctttt tttgttttaa gctggaaaga gaacttacat 189480
acgagaagct gatggattgg atcaatcctg aaatgatgga cagtacagaa gtgaggctgt 189540
ctttacccag atttaaactg gaagaaaatt atgatctgaa acccatcctg agcaacatgg 189600
gaatgcgtga tgcgtttgac ttacggatgg cgaacttctc aggaatctcc tctggtaacg 189660
agcttgtgct ctctgaagtg gttcacaagt ccttcgtgga ggtcaacgaa gaaggcactg 189720
aagcagcagc tgccacagca ggagtgatgg tgctccgttg tgctatgatc gttcccgact 189780
tcactgccga tcatcccttc ctcttcttca tccggcacaa caaaacttcc agtattttgt 189840
tctgtggcag atattgctct ccctaagaag agagacagaa gagctaccat taacgcagta 189900
atgtgatttc ttttaggata gaactgctct tttgcactaa ctgcttattt ccactgtgcc 189960
tgaatcccct tatctggttg tcattttggg cttgcgtaga gtaacaaagc cacttacaca 190020
tacacagcag ctaccacttg aaacagctgc cttacacttt gcacctaagt ggagttgttt 190080
tcttgctggc ccaagaaaga tgaacatccc acttgctcag tgaacttcca cctgtcttat 190140
attttctatt gcactttgct tttgtgtggc caccaggtag caaggtgaca aagagaaaag 190200
aagtggattt tgtttctgac tatagtggaa gatatcttat gctctgctcc ccatttttct 190260
tcctctcccc acttattttt aactttttct ttaatgtttt gataatagag ggagatgaaa 190320
ggaggctttg gcgacctatt tgtaagagtt actaagcatc tgcactagac agaggtttta 190380
```

-continued

```
ttataactgg atagcactta cacaaggatg ggaataaaag tatgtctgta acaaatgacc 190440
ttagaggttt tcatggagta cggattctta tcttaacacc acatgtgcca cctgggaata 190500
ttagctatca ctcacctact tcattagtct tttaaaaaaa gaatgttttt aaaaacaaac 190560
aaacaaaaaa aaacccatag atgcctatgt agtatttaag tgacagagct ttatttttgt 190620
ttttcagtct ttatatgttt ttttcctatt ctgggtttgt aaagcatctt tgttaatctg 190680
aatgccaaag gtttcttaac gcagtgattt acgtgttttg ctgttcttga aagaataaac 190740
aaatttgttg tgagtgctgt gggcattgcc cataaatttt gtggggtttt ttttttttcat 190800
ggctactgta aagaaaacaa gcaatcaact ttcgtgtagc ttatgcagaa ttcattgctt 190860
aacagaggct tttctgaatg ctgcaagacc aagatgctta cctggattac gatggagttt 190920
aggtttttac cttcgaagga ttcatagcaa ggagtctttg aggcaaaggc tcaagggatt 190980
ttaaagacta tctggttcca actccctgct gtgggcatgg ctgcccaggg ctccctcctc 191040
cctggccttc gacacctcca aggatggggc acccacagct tccctgggca gctgtgccag 191100
tgcctcacca acctccaagt gaaaaagatc cccctgacat ctaattgaaa gttcctttca 191160
tttattttaa agccattccc tcttattcca tcactatcag accaaggctc cctttatgta 191220
ttggaaggcc acaacaaggt ccccttggag tcttctcgag gctgaacaag ctaagtgctt 191280
gtttccagat ggggtactgc tgctgtgggt gcaactcctt ggccccaggc caaggagtgt 191340
gccatgcctc agatgcagcg attagtcacc atttggggtg aggaagctgc caaagtgctg 191400
cctgtcagac cgatgctcag tcagggctga gagcagcagt gggtagaagg gaagtgggca 191460
gcctctgctc ccagtgcatt gtctgggaag ggggtggtag caagatgaaa agtagaaatt 191520
tttctgaccc ttcctacgtg tccaggctgc tgctggagtg tattcatggt gctatgctta 191580
aagtgaaagc aaaagcgtgc ttgtctaatt tgcttctttt ctaaattgaa aaggaaagta 191640
atcacattaa cgtctaccat aaagcagaga gaagctgcca gaaagcttga gagaagctag 191700
aagcagccat atctacaaat cccagtgcaa acaagaagga gggatcccag ctgcacaagc 191760
aggaaggcag gaaggtttta cagcactgtc tgccgccagc ctttgcgtaa ccatctgccc 191820
gccccagcat tgcacctttc aacccactcc cagagacctc acagctccca gtggtcctag 191880
ctccagctta ctgctggctg ctctcctcct ggtttgatcc tccctagcag ctgccaagca 191940
tcacaggagg taagtgtgtg cttgctgtgc ctctgcattt tgcagcctga aatgaatcca 192000
gcccttggaa ctcgcactag ggcatcgagg agtgctttct gaagccttca ctgaaacttt 192060
tatttttcag ctgcagccat ggagagcctg agcaatgcca acagcaggtt tgcacttgat 192120
ctcttccgaa aggttaatga gacgaaccca tcaggaaaca ttttcttctc ccctctcagt 192180
atttctactg ctctggccat ggtcctcctc gggtccagag gtaatacaga gacacaggtg 192240
ctgaaggtca gcagcatttt cgcttgtttt attaaaatta aatgttgttc agttttagag 192300
acaaggcaag gggaggaggg cgttatttgc gtgagcttgg ggcaaggttc ctgtcactcc 192360
tgctgactct tccccccctgc tgccacctgc ctgctgcact ccagagccct cctcttgtgc 192420
tcactgatag cccttctttc tcacttcatt tgggttaatt gatgaatctg gaaactaatt 192480
tcactgattt atcagtctta atttaaaatc gattagcatc tccagcagca agtctttact 192540
agagcttgtg ataggacatg ggggaacagc attaaacaaa aagggaagat ttaggcaaga 192600
tatttgttag aggaagtttt tccactgaga aagtggtgag gtggtggcac agctgcccag 192660
ggaagctgag ggtgccccat ccctggaggt gttcaagacc aggttggatg gggccctggg 192720
```

-continued

```
cagcctgagc tggtgggtgg ctgccctgcc cacagcaagg cagtggaact gggtgggctt 192780
taagttgaat tccagcccaa ccccattcta tgattctatg agccttttcc acagagaact 192840
attgttttgc aatgtataca tacataatgg tatacatagt aatgctaagt gtatcttata 192900
aataaaaaat aaaatataga gctgtattat tctaaggctg acaactgtta caatacatgg 192960
tgatgttacc caagacccag tgttatagca gccaagcacc cagtatttct gaggagcaga 193020
actcacgtgt ccattctcat ggtatcctta ggttgagcag cagaggttaa atgaaaatgg 193080
tgtggctcct ttactggggg ctttgttgtg gacccagctc atcaatcctt tcccactctc 193140
cacaacagca gttgcaaact gcaaattctc atgtaggtag cagtgccaat tccctctcag 193200
actcatgttc aaaagggacc ctgcctcttt tttaatttgc aaggcaaaca cctgctagtg 193260
caaggggaag tatgaaagaa ttgtcgctgt agttcctatt aacttatttg ccctatgatt 193320
aagttcacct ttgtattccg aactttagga agaacttgtt tagaccatta actgctgcca 193380
ttctttgtga aaagactata aaactgaatc actgcttgta gaaacagact ttgaacatac 193440
attccttata actcaactgt cagccccacc caggaagaat ctactgagag cagaaataat 193500
gcaagagaag catagggaag ttggagatag aaggttggga tgaatggttg gactgggtga 193560
tcctgtgtgt cttttccaac ttcagtgatt ctatgattct aaggtgtttc agcacagtaa 193620
ccttctgtaa tgcacattcc catggtataa tgtttaattg atgagaacat cagttaatta 193680
aggagatgat gactgatgag tgtgaagggt gtttataagc atgcagaaat ccatttctgg 193740
gatcataatc ctaccttaag ttggaatcat agagtacacc acggtggagg ggatccatga 193800
ggatccagct ccacacagca ccacccacta tggtagatcc tgctgcccaa cctgcacacc 193860
ttggctagtc agcttccctt caggtatctg tatgcacgct ttcatattat aacagctttt 193920
aattttaagg tgatagttgt ctgtagaagc acttatattt tcataaaacc aaaggttata 193980
gctctcacat tttcctaaca cctcaccttc cctgagtgct cagacaagct cagtagtcca 194040
cggaggaaaa acatgcagac agcaccctat taggactctg gatcacaatt aacagcttca 194100
gctgtggcta actgtattca gctactgctt tacaagtgac atggctggca cagcactaag 194160
ggacagtttc acttgttctt tgatggttac agctttcagc ttctttctgc ttttgttttt 194220
caacttaact accaaacaaa taccatacag atatgctgca tgttctctat aaatacagca 194280
ttagcagtag ttagctcatc tctttcattt cagacgtttc attttgatga agttgaaaat 194340
atacactcaa gattccgggc tctgactgca gacatcaaca gaagggattc ttcctgtctc 194400
ctacggattg ccaaccggct ttatggagag aagtcctaca gctttctgcc ggtatgggta 194460
cacagaccat agctgtgtgg tggaacctgg ggggaggctt tgtaacttca tcatctgttg 194520
ctctcctgcc tccagaacgc gccccatagc aaaaatatca caccagcaag tccagatgtc 194580
aaaactatct ttctgcatca ataagcagca tagctcaggt gttgctgtct ttataggaat 194640
gcagccattt gagtatttga ggtaaaaaca tgactagaca tctaaaagtt accaggcagt 194700
cagtacgagt gttgtacaca tgcctataga tgcagaaatg catatgcatc tggacatcct 194760
aaaggatacg cctagaggat attacataac aaatcccttt ctttgatagt tcagttctgc 194820
tgctttgggg ctcaagagaa attgcaagcc atgtaggttc ttagcttaga gtacagatta 194880
gcaatgcccc attcctctgt ctgttgtttt ttaggctttt cattgctcta gtactatatt 194940
acttaaaaca tttttgaaaa catttctctg gggggagatt gccatcatgt ctcaacagca 195000
tgcctcttta caagggaact gtacctctgc atctatttag gtactgctat ttttatccct 195060
ctccagctct ttctgggagt ttttgttttc ttagtcaagc tt                    195102
```

```
<210> SEQ ID NO 2
<211> LENGTH: 285
<212> TYPE: DNA
<213> ORGANISM: SV40

<400> SEQUENCE: 2

aaagtctaga gtcggggcgg ccggccgctt cgagcagaca tgataagata cattgatgag     60

tttggacaaa ccacaactag aatgcagtga aaaaaatgct ttatttgtga aatttgtgat    120

gctattgctt tatttgtaac cattataagc tgcaataaac aagttaacaa caacaattgc    180

attcatttta tgtttcaggt tcagggggag gtgtgggagg ttttttaaag caagtaaaac    240

ctctacaaat gtggtaaaat cgataaggat ccgtcgagcg gccgc                    285


<210> SEQ ID NO 3
<211> LENGTH: 498
<212> TYPE: DNA
<213> ORGANISM: Artificial
<220> FEATURE:
<223> OTHER INFORMATION: Human interferon alpha2b codon optimized for
      avian expression
<220> FEATURE:
<221> NAME/KEY: misc_feature
<222> LOCATION: (1)..(498)

<400> SEQUENCE: 3

tgcgatctgc ctcagaccca cagcctgggc agcaggagga ccctgatgct gctggctcag     60

atgaggagaa tcagcctgtt tagctgcctg aaggataggc acgattttgg ctttcctcaa    120

gaggagtttg gcaaccagtt tcagaaggct gagaccatcc ctgtgctgca cgagatgatc    180

cagcagatct ttaacctgtt tagcaccaag gatagcagcg ctgcttggga tgagaccctg    240

ctggataagt tttacaccga gctgtaccag cagctgaacg atctggaggc ttgcgtgatc    300

cagggcgtgg gcgtgaccga gacccctctg atgaaggagg atagcatcct ggctgtgagg    360

aagtactttc agaggatcac cctgtacctg aaggagaaga agtacagccc ctgcgcttgg    420

gaagtcgtga gggctgagat catgaggagc tttagcctga gcaccaacct gcaagagagc    480

ttgaggtcta aggagtaa                                                  498
```